US011834504B2

United States Patent
Reschke et al.

(10) Patent No.: US 11,834,504 B2
(45) Date of Patent: Dec. 5, 2023

(54) DARPIN BASED MULTI-SPECIFIC T-CELL ENGAGERS

(71) Applicant: MOLECULAR PARTNERS AG, Schlieren (CH)

(72) Inventors: Nina Reschke, Schlieren (CH); Sebastian Grimm, Schlieren (CH); Christian Reichen, Schlieren (CH); Bernd Schlereth, Schlieren (CH); Victor Levitsky, Schlieren (CH); Matteo Bianchi, Schlieren (CH)

(73) Assignee: MOLECULAR PARTNERS AG, Schlieren (CH)

( * ) Notice: Subject to any disclaimer, the term of this patent is extended or adjusted under 35 U.S.C. 154(b) by 0 days.

(21) Appl. No.: 17/654,209

(22) Filed: Mar. 9, 2022

(65) Prior Publication Data

US 2023/0056271 A1    Feb. 23, 2023

Related U.S. Application Data

(60) Provisional application No. 63/265,184, filed on Dec. 9, 2021, provisional application No. 63/172,973, filed on Apr. 9, 2021, provisional application No. 63/158,539, filed on Mar. 9, 2021.

(51) Int. Cl.
*C07K 16/28* (2006.01)
*A61P 35/00* (2006.01)

(52) U.S. Cl.
CPC .......... *C07K 16/2809* (2013.01); *A61P 35/00* (2018.01); *C07K 16/28* (2013.01); *C07K 16/2803* (2013.01); *C07K 16/2866* (2013.01); *C07K 16/2875* (2013.01); *C07K 2317/31* (2013.01); *C07K 2318/00* (2013.01); *C07K 2319/00* (2013.01)

(58) Field of Classification Search
CPC .......... C07K 16/2809; C07K 16/28; C07K 2317/31; C07K 2318/00; A61P 35/00
See application file for complete search history.

(56) References Cited

U.S. PATENT DOCUMENTS

| | | |
|---|---|---|
| 7,417,130 B2 | 8/2008 | Stumpp et al. |
| 8,710,187 B2 | 4/2014 | Binz et al. |
| 8,722,618 B2 | 5/2014 | Jacobs et al. |
| 8,846,577 B2 | 9/2014 | Steiner et al. |
| 8,901,076 B2 | 12/2014 | Binz et al. |
| 9,163,070 B2 | 10/2015 | Baumann |
| 9,221,892 B2 | 12/2015 | Binz |
| 9,284,361 B2 | 3/2016 | Steiner et al. |
| 9,365,629 B2 | 6/2016 | Parmeggiani et al. |
| 9,458,211 B1 | 10/2016 | Bakker et al. |
| 9,822,181 B2 | 11/2017 | Bonvini et al. |
| 10,370,414 B2 | 8/2019 | Fiedler et al. |
| 10,717,772 B2 | 7/2020 | Metz et al. |
| 11,453,708 B2 | 9/2022 | Tresch et al. |
| 2008/0206201 A1 | 8/2008 | Beier et al. |
| 2013/0296221 A1 | 11/2013 | Binz |
| 2015/0284463 A1 | 10/2015 | Tamaskovic et al. |
| 2020/0095309 A1* | 3/2020 | Peters ............ C07K 16/22 |
| 2020/0385488 A1 | 12/2020 | Reichen et al. |
| 2021/0347835 A1 | 11/2021 | Amstutz et al. |
| 2021/0395318 A1 | 12/2021 | Rigamonti et al. |
| 2022/0064234 A1 | 3/2022 | Binz et al. |
| 2022/0106707 A1 | 4/2022 | Levitsky et al. |
| 2022/0242973 A1 | 8/2022 | Fiedler et al. |
| 2022/0298212 A1 | 9/2022 | Reichen et al. |

FOREIGN PATENT DOCUMENTS

| | | |
|---|---|---|
| WO | 2002/020565 A2 | 3/2002 |
| WO | 2010/060748 A1 | 6/2010 |
| WO | 2011/135067 A1 | 11/2011 |
| WO | 2012/069654 A1 | 5/2012 |
| WO | 2012/069655 A2 | 5/2012 |
| WO | 2014/001442 A1 | 1/2014 |
| WO | 2014/083208 A1 | 6/2014 |
| WO | 2014/167022 A1 | 10/2014 |
| WO | 2014/191574 A1 | 12/2014 |
| WO | 2016/156596 A1 | 10/2016 |
| WO | 2018/054971 A1 | 3/2018 |
| WO | 2020/245171 A1 | 12/2020 |

(Continued)

OTHER PUBLICATIONS

Anonymous, "Molecular Partners: Pioneering a new class of drugs with a broad portfolio and global partnerships," (Nov. 1, 2020), 36 pages.
Balakrishnan et al., "Multispecific Targeting with Synthetic Ankyrin Repeat Motif Chimeric Antigen Receptors," Clinical Cancer Research, 2019, 25(24):7506-7516.
Binz et al., "Designing repeat proteins: well-expressed, soluble and stable proteins from combinatorial libraries of consensus ankyrin repeat proteins," J Mol Biol, 2003, 332:489-503.
Binz et al., "High addinity binders selected from designed ankyrin repeat protein libraries," Nat Biotechnol, 2004, 22:575-582.
Binz et al., "Design and characterization of MP0250, a tri-specific anti-HGF/anti-VEGF DARPin drug candidate," MABS, 2017, 9(8):1262-1269.

(Continued)

*Primary Examiner* — Daniel E Kolker
*Assistant Examiner* — Brittney E Donoghue
(74) *Attorney, Agent, or Firm* — FINNEGAN, HENDERSON, FARABOW, GARRETT & DUNNER, LLP

(57) ABSTRACT

The present invention relates to recombinant multi-specific proteins comprising binding agents with binding specificity for different targets, such as, e.g. CD3, CD33, CD123 and CD70. In addition, the invention relates to nucleic acids encoding such multi-specific proteins, pharmaceutical compositions comprising such proteins or nucleic acids, and the use of such binding proteins, nucleic acids or pharmaceutical compositions in methods for treating or diagnosing diseases, such as cancer, e.g. acute myeloid leukaemia (AML), in a mammal, including a human.

21 Claims, 102 Drawing Sheets

Specification includes a Sequence Listing.

(56) References Cited

FOREIGN PATENT DOCUMENTS

| | | |
|---|---|---|
| WO | 2020/245746 A1 | 12/2020 |
| WO | 2021/116470 A2 | 6/2021 |
| WO | 2021/229076 A1 | 11/2021 |
| WO | 2022/129428 A1 | 6/2022 |
| WO | 2022/130300 A1 | 6/2022 |
| WO | 2022/190008 A1 | 9/2022 |
| WO | 2022/190010 A1 | 9/2022 |
| WO | 2022/190018 A1 | 9/2022 |
| WO | 2022/215032 A1 | 10/2022 |

OTHER PUBLICATIONS

Bortoletto et al., "Optimizing anti-CD3 affinity for effective T cell targeting against tumor cells," Eur J Immunol, 2002, 32(11):3102-3107.
Cadwell et al., "Randomization of Genes by PCR Mutagenesis," PCR Methods Appl, 1992, 2:28-33.
"CD137 (4-1BB) binding domain alternative 10 SEQ ID 54," Geneseq, (Feb. 4, 2021), Database accession No. BIS35209, 1 page.
"DARPin protein #24 ankyrin repeat domain, SEQ ID 24," Geneseq, (Feb. 4, 2021), Database accession No. BIS20816, 1 page.
Ellerman, "Bispecific T-cell engagers: Towards understanding variables influencing the in vitro potency and tumor selectivity and their modulation to enhance their efficacy and safety," Methods, 2019, 154:102-117.
Hanes et al., "In vitro selection and evolution of functional proteins by using ribosome display," PNAS, 1997, 94:4937-4942.
International Search Report and Written Opinion of International Application No. PCT/IB2022/052126, dated Jun. 28, 2022, 7 pages.
Junttila et al., "Antitumor Efficacy of a Bispecific Antibody That Targets HER2 and Activates T Cells," Cancer Res, 2014, 19:5561-5571.
Kjer-Nielsen et al., "Crystal structure of the human T cell receptor CD3εγ heterodimer complexed to the therapeutic mAb OKT3," PNAS, 2004, 101(20):7675-7680.
Labrijn et al., "Bispecific antibodies: a mechanistic review of the pipeline," Nat Rev Drug Discov, 2019, 18(8):585-608.
Li et al., "Highlights of 2019 Protein Engineering Summit (PEGS) in Boston, USA: Advancing Antibody-Based Cancer Therapies to the Clinic," Antibody Therapeutics, 2019, 2(4):79-87.
Main et al., "Design of Stable α-Helical Arrays from an Idealized TPR Motif," Structure, 2003, 11(5):497-508.
Mandikian et al., "Relative Target Affinities of T Cell-Dependent Bispecific Antibodies Determine Biodistribution in a Solid Tumor Mouse Model," Mol Cancer Ther, 2018, 17(4):776-785.
Serum albumin binding designed ankyrin repeat domain protein, SEQ ID 42., Geneseq, (Jan. 26, 2017), Database accession No. BDK44105, 1 page.
Shimabukuro-Vornhagen et al., "Cytokine release syndrome," J Immunother Cancer, 2018, 6(1):56, 14pags.
Steiner et al., "Efficient Selection of DARPins with Sub-nanomolar Affinities using SRP Phage Display," J Mol Biol, 2008, 382(5):1211-1227.
Steiner et al., Supplementary Material of "Efficient Selection of DARPins with Sub-nanomolar Affinities using SRP Phage Display," J Mol Biol, 2008, 382(5), 17 pages.
Stemmer, "Rapid evolution of a protein in vitro by DNA shuffling," Nature, 1994, 370:389-391.
Stumpp et al., "DARPins: A new generation of protein therapeutics," Drug Discov Today, 13, 2008, 13(15-16):695-701.
Tanaka et al., "Structural basis for recognition of 2',5'-linked oligoadenylates by human ribonuclease L," EMBO J, 2004, 23(30):3929-3938.
Vafa et al., "Perspective: Designing T-Cell Engagers With Better Therapeutic Windows," Frontiers in Oncology, 2020, 10:446, 7 pages.
Venugopal et al., "An Update on the Clinical Evaluation of Antibody-Based Therapeutics in Acute Myeloid Leukemia," Current Hematologic Malignancy Reports, 2021, 16(1):89-96.
Weiner et al., "Human neutrophil interactions of a bispecific monoclonal antibody targeting tumor and human Fcγ RIII," Cancer Immunol Immunother, 1996, 42(3):141-150.
Weiner et al., "Phase I Trial of 2B1, a Bispecific Monoclonal Antibody Targeting c-erbB-2 and FcγRIII", Cancer Res, 1995, 55(20):4586-4593.
Winer et al., "Novel therapy in Acute myeloid leukemia (AML): moving toward targeted approaches," Ther Adv Hematol, 2019, 10, 18 pages.
Wu et al., "T cell engaging bispecific antibody (T-BsAb): from technology to therapeutics," Pharmacol Ther, 2018, 182:161-175.
Williams et al., "Design of Bioactive Peptides Based on Antibody Hypervariable Region Structures," J Biol Chem, 1991, 266:5182-5190.
Yang et al., "A common pathway for T lymphocyte activation involving both the CD3-Ti complex and CD2 sheep erythrocyte receptor determinants," J Immunol, 1986, 137:1097-1100.
Zaccolo et al., "An Approach to Random Mutagenesis of DNA Using Mixtures of Triphosphate Derivatives of Nucleoside Analogues," J Mol Biol, 1996, 255:589-603.
Zahnd et al., "Ribosome display: selecting and evolving proteins in vitro that specifically bind to a target," Nat Methods, 2007, 4(3):269-279.
Amstutz et al., "Intracellular Kinase Inhibitors Selected from Combinatorial Libraries of Designed Ankyrin Repeat Proteins," JBC (2005) vol. 280 No. 26, 24715-24722.
Amstutz et al., "Rapid selection of specific MAP kinase-binders from designed ankyrin repeat protein libraries," Protein Engineering, Design & Selection (2006) 19(5), 219-229.
Bandeiras et al., "Structure of wild-type Plk-1 kinase domain in complex with a selective DARPin," Acta Cryst (2008) D64, 339-353.
Binz et al., "Crystal Structure of a Consensus-Designed Ankyrin Repeat Protein: Implications for Stability," Proteins: Structure, Function, and Bioinformatics (2006) 65:280-284.
Binz et al., "Design and characterization of MP0250, a tri-specific anti-HGF/anti-VEGF DARPin® drug candidate," mAbs (2017) vol. 9 No. 8, 1262-1269.
Binz et al., "Designed Repeat Proteins—Molecules with Antibody-like Binding Properties," BIOforum Europe Apr. 2005 (GIT VERLAG Gmbh & Co. KG, Darmstadt), 34-36.
Binz et al., "Engineered proteins as specific binding reagents," Current Opinion in Biotechnology (2005) 16, 459-469.
Binz et al., "Engineering novel binding proteins from nonimmunoglobulin domains," Nature Biotechnology (2005) 23(10), 1257-1268.
Binz et al., "High-affinity binders selected from designed ankyrin repeat protein libraries," Nature Biotechnology (2004) 22(5), 575-582.
Binz, "Designing Repeat Proteins: Well-expressed, Soluble and Stable Proteins from Combinatorial Libraries of Consensus Ankyrin Repeat Proteins," J Mol Biol (2003) 332, 489-503.
Boersma et al., "DARPins and other repeat protein scaffolds: advances in engineering and applications," Curr Opin Biotechnol (2011) 22(6), 849-857.
Boersma, "Advances in the Application of Designed Ankyrin Repeat Proteins (DARPins) as Research Tools and Protein Therapeutics," Methods Mol Biol (2018) 1798, 307-327.
Eggel et al., "DARPins as Bispecific Receptor Antagonists Analyzed for Immunoglobulin E Receptor Blockage," J Mol Biol (2009) 393, 598-607.
Fiedler et al., " MP0250, a VEGF and HGF neutralizing DARPin® molecule shows high anti-tumor efficacy in mouse xenograft and patient-derived tumor models", Oncotarget 2017, 98371-98383 (incl. Supplement).
Forrer et al., "A novel strategy to design binding molecules harnessing the modular nature of repeat proteins," FEBS Letters (2003) 539, 2-6.
Forrer et al., "Consensus Design of Repeat Proteins," ChemBioChem (2004) 5, 183-189.

(56) References Cited

OTHER PUBLICATIONS

Hanes et al., "In vitro selection and evolution of functional proteins by using ribosome display," Proc Natl Acad Sci USA (1997) 94(10), 4937-4942.
He et al., "Ribosome display: cell-free protein display technology," Brief Funct Genomic Proteomic (2002) 1(2), 204-212.
Interlandi et al., " Characterization and Further Stabilization of Designed Ankyrin Repeat Proteins by Combining Molecular Dynamics Simulations and Experiments," J Mol Biol (2008) 375(3), 837-854.
Kawe et al., "Isolation of Intracellular Proteinase Inhibitors Derived from Designed Ankyrin Repeat Proteins by Genetic Screening," J Biol Chem (2006) 281, 40252-40263.
Kohl et al., "Designed to be stable: Crystal structure of a consensus ankyrin repeat protein," PNAS (2003) 100(4), 1700-1705.
Kramer et al., "Structural Determinants for Improved Stability of Designed Ankyrin Repeat Proteins with a Redesigned C-Capping Module," J Mol Biol (2010) 404, 381-391.
Plückthun, "Designed ankyrin repeat proteins (DARPins): binding proteins for research, diagnostics, and therapy," Annu Rev Pharmacol Toxicol (2015) 55, 489-511.
Rothenberger et al., "Ensovibep, a novel trispecific DARPin candidate that protects against SARS-COV-2 variants," bioRxiv preprint (2021), 76 pages.
Sennhauser et al., "Chaperone-Assisted Crystallography with DARPins," Structure (2008) 16, 1443-1453.
Steiner et al., "Efficient Selection of DARPins with Sub-nanomolar Affinities using SRP Phage Display," J Mol Biol 2008, 382(5), 1211-1227 (incl. Supplement).
Steiner et al., "Half-life extension using serum albumin-binding DARPin® domains", PEDS (2017), 1-9.
Stumpp et al., "Beyond Antibodies: The DARPin(R) Drug Platform," BioDrugs (2020), 11 pages.
Stumpp et al., "DARPins: A new generation of protein therapeutics," Drug Discovery Today (2008) 13(15-16), 695-701.
Stumpp et al., "DARPins: A true alternative to antibodies," Curr Opin Drug Discov Devel. (2007) 10(2) 153-159.
Stumpp et al., "Designing Repeat Proteins: Modular Leucine-rich Repeat Protein Libraries Based on the Mammalian Ribonuclease Inhibitor Family," J Mol Biol (2003) 332, 471-487.
Theurillat et al., "Designed ankyrin repeat proteins: a novel tool for testing epidermal growth factor receptor 2 expression in breast cancer," Modern Pathology (2010), 1-9.
Veesler et al., "Crystal Structure and Function of a DARPin Neutralizing Inhibitor of Lactococcal Phage TP901-1," J Biol Chem (2009) 284(44), 30718-30726.
Walser et al., "Highly potent anti-SARS-COV-2 multivalent DARPin therapeutic candidates," BioRxiv preprint, Aug. 26, 2020, 39 pages.
Walser et al., "Highly potent anti-SARS-COV-2 multivalent DARPin therapeutic candidates," BioRxiv preprint, Nov. 20, 2020, 46 pages.
Zahnd et al., "Efficient Tumor Targeting with High-Affinity Designed Ankyrin Repeat Proteins: Effects of Affinity and Molecular Size," Cancer Res (2010) 70(4), 1595-1605 (incl. Supplement).
Zahnd et al., "Ribosome display: selecting and evolving proteins in vitro that specifically bind to a target," Nature Methods (2007) 4(3), 269-279.
Zahnd et al., "Selection and Characterization of Her2 Binding-designed Ankyrin Repeat Proteins," J Biol Chem (2006) 281(46), 35167-35175.

* cited by examiner

A. Mean vs actual time, DARPin® protein #51
B. Mean vs actual time, DARPin® protein #50
C. Mean vs actual time, DARPin® protein #54
D. Mean vs actual time, DARPin® protein #53
E. Mean vs actual time, DARPin® protein #55

DARPIN BASED MULTI-SPECIFIC T-CELL ENGAGERS

CROSS-REFERENCE TO RELATED APPLICATIONS

The present application claims the benefit of priority to U.S. 63/158,539, filed on Mar. 9, 2021; U.S. 63/172,973, filed on Apr. 9, 2021; and U.S. 63/265,184, filed on Dec. 9, 2021. The disclosures of these patent applications are incorporated herein for all purposes by reference in their entirety.

SEQUENCE LISTING

The instant application contains a Sequence Listing which has been submitted electronically in ASCII format and is hereby incorporated by reference in its entirety. The sequence listing file, created on Mar. 9, 2022, is named SequenceListing.txt and 338,733 bytes in size.

FIELD OF THE DISCLOSURE

The present invention relates to recombinant multi-specific proteins comprising binding agents with binding specificity for different targets, such as, e.g., CD3, CD33, CD70 and CD123. In addition, the invention relates to nucleic acids encoding such multi-specific proteins, pharmaceutical compositions comprising such proteins or nucleic acids, and the use of such binding proteins, nucleic acids or pharmaceutical compositions in methods for treating or diagnosing diseases, such as cancer, e.g., acute myeloid leukemia (AML), in a mammal, including a human.

BACKGROUND

Acute myeloid leukemia (AML) is a heterogeneous and complex malignant disease characterized by rapid cellular proliferation, an aggressive clinical course and generally high mortality rates. AML. Treatment resistance remains a leading cause of acute leukemia related deaths (Winer & Stone, Ther Adv Hematol; 2019; 10). While standard protocols employing chemotherapy are still the main therapeutic approach applied worldwide, recent advances in immunotherapy have provided effective treatment options for chemotherapy resistant AML. Such immunotherapy approaches include monoclonal antibodies, bispecific antibodies and chimeric antigen receptor-expressing T cells (CAR-T cells).

Monoclonal antibody-based therapy mainly includes anti-CD33 or anti-CD123 antibodies, either as monotherapy or conjugated with cytotoxic agents (Winer & Stone, Ther Adv Hematol; 2019; 10). However, these drugs have shown either significant adverse effects or low efficacy. For example, treatment with gemtuzumab ozogamicin, a humanized, anti-CD33 monoclonal antibody conjugated to the antibiotic calicheamicin, has resulted in significant hematologic and hepatic toxicity, while treatment with talcotuzumab, a humanized, anti-CD123 monoclonal antibody, failed to provide effective therapeutic benefit. Currently, another human, monoclonal antibody targeting CD70 is under clinical trials (cusatuzumab) and although initial findings seem to be promising, experts still express concerns regarding its potential safety profile (see, e.g.: www.clinicaltrialsarena.com/comment/argenxs-cusatuzumab-in-previously-untreated-aml-draws-varied-expert-forecasts).

CAR-T cell therapy is an approach which has strongly affected the management of lymphoid malignancies. While there has been great interest in applying this technology also to AML, in practice this has proven challenging. As for monoclonal antibodies, CD33 and CD123 have been considered among the most promising targets for CAR-T cell therapy in AML. However, pre-clinical models for these targets showed broad side effects on non-AML cells (on-target/off-tumor toxicity), and cytokine release syndrome (CRS) is another recognized side effect.

T cell-directed killing of tumor cells using bispecific antibodies is another, recent therapeutic tool which has been utilized for the treatment of various cancer types, including AML. These T cell engager (TCE) bispecific antibodies comprise two different variable regions, one binding to the T cell receptor complex subunit CD3 and the other binding to a tumor cell surface antigen. Binding of a TCE to these two targets provides a functional connection between the cells, resulting in T cell activation and cytotoxic activity against the tumor cells, bypassing the normal TCR-MHC interaction (Ellerman, Methods; 154:102-117 (2019)). AMG330 is a bispecific antibody against CD3 and CD33 that can cause T cell cytotoxicity against AML cells. Similarly, flotetuzumab is a dual-affinity retargeting antibody (DART®), which employs two independent polypeptides, fusing the heavy chain variable domain of one antibody to the light chain variable domain of another antibody, to connect CD3 on T cells and CD123 on AML cells.

However, such antibody-based TCE therapeutics present various disadvantages, such as high production costs and the inability to target multiple tumor surface markers, and they can cause severe side effects, such as cytokine release syndrome (CRS) (Shimabukuro-Vornhagen et al, J Immunother Cancer; 6(1):56 (2018); Labrjin et al, Nat Rev Drug Discov; 18(8):585-608 (2019)) and/or on-target/off-tumor toxicities (Weiner et al, Cancer Res.; 55 (20): 4586-4593 (1995); Weiner et al, Cancer Immunol. Immunother.; 42 (3); 141-150 (1996)). Antibody-based T cell engagers often display more than 1000-fold higher affinity for CD3, as compared to the natural TCR-MHC interaction (Wu et al, Pharmacol Ther; 182:161-75 (2018); WO2014/167022; Junntila et al, Cancer Res.; 19:5561-71 (2014); Yang et al, J Immunol August; 15 (137):1097-100 (1986)). This high affinity has been correlated with lower efficiency of T cell activation and tumor cell killing (Bortoletto et al, Eur. J. Immunol. 32; 11: 3102-3107 (2002); Ellerman, Methods; 154:102-117(2019); Mandikian et al, Mol. Cancer Ther.; 17 (4): 776 LP-785 (2018); Vafa et al, Frontiers in Oncology; 10: 446 (2020)). Furthermore, downregulation of the tumor surface marker targeted by the TCE can lead to resistance of the tumor to the TCE therapy.

Acute myeloid leukemia (AML) is a type of cancer that in many ways exemplifies the challenges for cancer therapy and the shortcomings of currently available cancer therapies, as discussed above. For AML, the medical need due to high mortality remains high, and the treatment of relapsed or refractory AML continues to be therapeutically challenging. Currently, a plethora of antibody drug conjugates (ADCs) and targeted T-cell engager therapies have entered clinical development in AML, but those therapies are often accompanied by dose-limiting toxicities. The biggest challenges seem to be limited target specificity and hyperstimulation of the immune system, leading, for example, to myelotoxicities and cytokine release syndrome (CRS), respectively. Furthermore, resistance to targeted cancer therapies may evolve due to downregulation of individual targets in the tumor cells. Thus, novel approaches or drug molecules are needed to address these challenges for cancer therapy and the shortcomings of currently available cancer therapies, as exemplified in AML.

Therefore, there remains a need for new molecules, such as immune cell engagers, e.g., TCE proteins, with beneficial properties addressing one or more shortcomings of previously described therapeutic proteins. Such new molecules may be useful for therapeutic approaches for the treatment of neoplastic diseases, e.g., acute myeloid leukemia.

SUMMARY

The present invention provides recombinant proteins comprising a first binding agent that specifically binds to a protein expressed on the surface of an immune cell, and at least two binding agents that specifically bind to a tumor-associated antigen, wherein said two binding agents specifically bind to different tumor-associated antigens. In addition, the invention provides nucleic acids encoding such binding proteins and pharmaceutical compositions comprising such binding proteins or nucleic acids. The invention also provides the use of such binding proteins, nucleic acids or pharmaceutical compositions in methods for localized activation of immune cells, such as T cells, in a tumor environment, and for treating diseases, such as acute myeloid leukemia, in a mammal, including a human.

Recombinant proteins of the invention target at least two different tumor-associated antigens (TAAs). The recombinant proteins of the invention may display substantially increased tumor specificity by avidity gain when the at least two TAAs are simultaneously present in the tumor cells. Also due to such avidity gain, the multi-specific proteins of the invention may have a larger potency window as compared to the respective single target-specific controls. Furthermore, proteins of the invention may induce significantly less cytokine release as compared to current therapeutic molecules, indicating an improved therapeutic window. Also, by targeting at least two different TAAs, proteins of the invention may be more resistant to development of tumor resistance due to target downregulation.

In one aspect the invention provides such a recombinant protein, wherein said recombinant protein comprises a first binding agent that specifically binds to a protein expressed on the surface of an immune cell, and at least two binding agents that specifically bind to a tumor-associated antigen, wherein said two binding agents specifically bind to different tumor-associated antigens. In one aspect the invention provides such a recombinant protein, wherein said recombinant protein is capable of binding simultaneously to said protein expressed on the surface of an immune cell and to said two different tumor-associated antigens.

In one aspect the invention provides such a recombinant protein, wherein said tumor-associated antigens specifically bound by said two binding agents are co-expressed in a tumor cell.

In one aspect the invention provides such a recombinant protein, wherein said recombinant protein comprises a first binding agent that specifically binds to a protein expressed on the surface of an immune cell, and at least three binding agents that specifically bind to a tumor-associated antigen, wherein said three binding agents specifically bind to different tumor-associated antigens. In one aspect the invention provides such a recombinant protein, wherein said recombinant protein is capable of binding simultaneously to said protein expressed on the surface of an immune cell and to said three different tumor-associated antigens.

In one aspect the invention provides such a recombinant protein, wherein said tumor-associated antigens specifically bound by said three binding agents are co-expressed in a tumor cell.

In one aspect the invention provides such a recombinant protein wherein, said tumor cell is a tumor cell from a liquid tumor, preferably wherein said liquid tumor is leukemia, more preferably wherein said leukemia is acute myeloid leukemia (AML).

In one aspect the invention provides such a recombinant protein, wherein said recombinant protein is capable of binding with a lower dissociation constant ($K_D$) to a surface displaying said tumor-associated antigens, when compared to a recombinant protein comprising only one of said binding agents that specifically bind to a tumor-associated antigen.

In one aspect the invention provides such a recombinant protein, wherein said surface displaying said tumor-associated antigens is the surface of said tumor cell.

In one aspect the invention provides such a recombinant protein, wherein said immune cell is a T cell.

In one aspect the invention provides such a recombinant protein, wherein said protein expressed on the surface of an immune cell is a protein that is part of the T-cell receptor complex, preferably said part of the T-cell receptor complex is CD3.

In one aspect the invention provides such a recombinant protein, wherein said first binding agent is an antibody, an antibody mimetic, a scaffold protein, a repeat protein, or a designed repeat domain.

In one aspect the invention provides such a recombinant protein, wherein said first binding agent is a designed ankyrin repeat domain with binding specificity for said protein expressed on the surface of an immune cell.

In one aspect the invention provides such a recombinant protein, wherein said first binding agent is a designed ankyrin repeat domain with binding specificity for CD3.

In one aspect the invention provides such a recombinant protein, wherein said ankyrin repeat domain with binding specificity for CD3 comprises an amino acid sequence that is at least 85% identical to anyone of the amino acid sequences of SEQ ID NOs: 1 to 5, preferably of SEQ ID NO: 2. The invention further provides such a recombinant protein, wherein said ankyrin repeat domain with binding specificity for CD3 comprises an amino acid sequence that is at least 85% identical to the amino acid sequence of SEQ ID NO: 3.

In one aspect the invention provides such a recombinant protein, wherein said binding agents that specifically bind to a tumor-associated antigen are selected from the group consisting of (i) a second binding agent that specifically binds to a first tumor-associated antigen (TAA1), (ii) a third binding agent that specifically binds to a second tumor-associated antigen (TAA2), and (iii) and a fourth binding agent that specifically binds to a third tumor-associated antigen (TAA3).

In one aspect the invention provides such a recombinant protein, wherein said second binding agent is an antibody, an antibody mimetic, a scaffold protein, a repeat protein, or a designed repeat domain.

In one aspect the invention provides such a recombinant protein, wherein said second binding agent is a designed ankyrin repeat domain with binding specificity for said TAA1, preferably wherein TAA1 is CD33.

In one aspect the invention provides such a recombinant protein, wherein said ankyrin repeat domain with binding specificity for CD33 comprises an amino acid sequence that is at least 85% identical to anyone of the amino acid sequences of SEQ ID NOs: 15, and 67 to 70. The invention further provides such a recombinant protein, wherein said ankyrin repeat domain with binding specificity for CD33 comprises an amino acid sequence that is at least 85% identical to anyone of the amino acid sequences of SEQ ID NOs: 15, 67 to 70, and 111 to 112, preferably SEQ ID NO: 111.

In one aspect the invention provides such a recombinant protein, wherein said third binding agent is an antibody, an antibody mimetic, a scaffold protein, a repeat protein, or a designed repeat domain.

In one aspect the invention provides such a recombinant protein, wherein said third binding agent is a designed ankyrin repeat domain with binding specificity for said TAA2, preferably wherein TAA2 is CD123.

In one aspect the invention provides such a recombinant protein, wherein said ankyrin repeat domain with binding specificity for CD123 comprises an amino acid sequence that is at least 85% identical to anyone of the amino acid sequences of SEQ ID NOs: 6, and 65 to 66. The invention further provides such a recombinant protein, wherein said ankyrin repeat domain with binding specificity for CD123 comprises an amino acid sequence that is at least 85% identical to anyone of the amino acid sequences of SEQ ID NOs: 6, 65 to 66, and 102 to 106, preferably SEQ ID NO: 105.

In one aspect the invention provides such a recombinant protein, wherein said fourth binding agent is a designed ankyrin repeat domain with binding specificity for said TAA3, preferably wherein TAA3 is CD70.

In one aspect the invention provides such a recombinant protein, wherein said ankyrin repeat domain with binding specificity for CD70 comprises an amino acid sequence that is at least 85% identical to the amino acid sequence of SEQ ID NO: 64. The invention further provides such a recombinant protein, wherein said ankyrin repeat domain with binding specificity for CD70 comprises an amino acid sequence that is at least 85% identical to anyone of the amino acid sequences of SEQ ID NOs: 64, and 107 to 110, preferably SEQ ID NO: 109.

In one aspect the invention provides such a recombinant protein, wherein said ankyrin repeat domain with binding specificity for CD3 comprises an amino acid sequence that is at least 85% identical to anyone of the amino acid sequences of SEQ ID NOs: 1 to 5, preferably SEQ ID NO: 2; wherein said ankyrin repeat domain with binding specificity for CD33 comprises an amino acid sequence that is at least 85% identical to anyone of the amino acid sequences of SEQ ID NOs: 15, 67 to 70; and wherein said ankyrin repeat domain with binding specificity for CD123 comprises an amino acid sequence that is at least 85% identical to anyone of the amino acid sequences of SEQ ID NO: 6, 65 to 66. The invention further provides such a recombinant protein, wherein said ankyrin repeat domain with binding specificity for CD3 comprises an amino acid sequence that is at least 85% identical to anyone of the amino acid sequences of SEQ ID NOs: 1 to 5, preferably SEQ ID NO: 3; wherein said ankyrin repeat domain with binding specificity for CD33 comprises an amino acid sequence that is at least 85% identical to anyone of the amino acid sequences of SEQ ID NOs: 15, 67 to 70, and 111 to 112, preferably SEQ ID NO: 111; and wherein said ankyrin repeat domain with binding specificity for CD123 comprises an amino acid sequence that is at least 85% identical to anyone of the amino acid sequences of SEQ ID NO: 6, 65 to 66, and 102 to 106, preferably SEQ ID NO: 105.

In one aspect the invention provides such a recombinant protein, wherein said ankyrin repeat domain with binding specificity for CD3 comprises an amino acid sequence that is at least 85% identical to anyone of the amino acid sequences of SEQ ID NOs: 1 to 5, preferably SEQ ID NO: 2; wherein said ankyrin repeat domain with binding specificity for CD33 comprises an amino acid sequence that is at least 85% identical to anyone of the amino acid sequences of SEQ ID NOs: 15, 67 to 70; and wherein said ankyrin repeat domain with binding specificity for CD70 comprises an amino acid sequence that is at least 85% identical to the amino acid sequence of SEQ ID NO: 64. The invention further provides such a recombinant protein, wherein said ankyrin repeat domain with binding specificity for CD3 comprises an amino acid sequence that is at least 85% identical to anyone of the amino acid sequences of SEQ ID NOs: 1 to 5, preferably SEQ ID NO: 3; wherein said ankyrin repeat domain with binding specificity for CD33 comprises an amino acid sequence that is at least 85% identical to anyone of the amino acid sequences of SEQ ID NOs: 15, 67 to 70 and 111 to 112, preferably SEQ ID NO: 111; and wherein said ankyrin repeat domain with binding specificity for CD70 comprises an amino acid sequence that is at least 85% identical to the amino acid sequence of any one of SEQ ID NO: 64 and 107 to 110, preferably SEQ ID NO: 109.

In one aspect the invention provides such a recombinant protein, wherein said ankyrin repeat domain with binding specificity for CD3 comprises an amino acid sequence that is at least 85% identical to anyone of the amino acid sequences of SEQ ID NOs: 1 to 5, preferably SEQ ID NO: 2; wherein said ankyrin repeat domain with binding specificity for CD123 comprises an amino acid sequence that is at least 85% identical to anyone of the amino acid sequences of SEQ ID NO: 6, 65 to 66; and wherein said ankyrin repeat domain with binding specificity for CD70 comprises an amino acid sequence that is at least 85% identical to the amino acid sequence of SEQ ID NO: 64. The invention further provides such a recombinant protein, wherein said ankyrin repeat domain with binding specificity for CD3 comprises an amino acid sequence that is at least 85% identical to anyone of the amino acid sequences of SEQ ID NOs: 1 to 5, preferably SEQ ID NO: 3; wherein said ankyrin repeat domain with binding specificity for CD123 comprises an amino acid sequence that is at least 85% identical to anyone of the amino acid sequences of SEQ ID NO: 6, 65 to 66; and 102 to 106, preferably SEQ ID NO: 105; and wherein said ankyrin repeat domain with binding specificity for CD70 comprises an amino acid sequence that is at least 85% identical to the amino acid sequence of any one of SEQ ID NO: 64 and 107 to 110, preferably SEQ ID NO: 109.

In one aspect the invention provides such a recombinant protein, wherein said ankyrin repeat domain with binding specificity for CD3 comprises an amino acid sequence that is at least 85% identical to anyone of the amino acid sequences of SEQ ID NOs: 1 to 5, preferably SEQ ID NO: 2; wherein said ankyrin repeat domain with binding specificity for CD33 comprises an amino acid sequence that is at least 85% identical to anyone of the amino acid sequences of SEQ ID NOs: 15, 67 to 70; wherein said ankyrin repeat domain with binding specificity for CD123 comprises an amino acid sequence that is at least 85% identical to anyone of the amino acid sequences of SEQ ID NO: 6, 65 to 66; and wherein said ankyrin repeat domain with binding specificity for CD70 comprises an amino acid sequence that is at least 85% identical to the amino acid sequence of SEQ ID NO: 64. The invention further provides such a recombinant protein, wherein said ankyrin repeat domain with binding specificity for CD3 comprises an amino acid sequence that is at least 85% identical to anyone of the amino acid sequences of SEQ ID NOs: 1 to 5, preferably SEQ ID NO: 3; wherein said ankyrin repeat domain with binding specificity for CD33 comprises an amino acid sequence that is at least 85% identical to anyone of the amino acid sequences of SEQ ID NOs: 15, 67 to 70 and 111 to 112, preferably SEQ ID NO: 111; wherein said ankyrin repeat domain with binding specificity for CD123 comprises an amino acid sequence that is at least 85% identical to anyone of the amino acid sequences of SEQ ID NO: 6, 65 to 66 and 102 to 106, preferably SEQ ID NO: 105; and wherein said ankyrin repeat domain with binding specificity for CD70 comprises an amino acid sequence that is at least 85% identical to the amino acid sequence of any one of SEQ ID NO: 64 and 107 to 110, preferably SEQ ID NO: 109.

In one aspect the invention provides such a recombinant protein, wherein said first, second and/or third binding agents are covalently linked with a peptide linker.

In one aspect the invention provides such a recombinant protein, wherein said protein comprises a polypeptide having an amino acid sequence that is at least 80% identical to any one of the amino acid sequences of SEQ ID NOs: 7 to 10 and 58 to 62, preferably wherein said protein comprises a polypeptide having the amino acid sequence of any one of SEQ ID NOs: 7 to 10 and 58 to 62. The invention further provides such a recombinant protein, wherein said protein comprises a polypeptide having an amino acid sequence that is at least 80% identical to any one of the amino acid sequences of SEQ ID NOs: 11 to 14, 78 to 86 and 95 to 101, preferably wherein said protein comprises a polypeptide having the amino acid sequence of anyone of the amino acid sequences of SEQ ID NOs: 11 to 14, 78 to 86 and 95 to 101. The invention further provides such a recombinant protein, wherein said protein comprises a polypeptide having an amino acid sequence that is at least 80% identical to any one of the amino acid sequences of SEQ ID NOs: 95 to 101, preferably SEQ ID NO: 95 or SEQ ID NO: 96. The invention further provides such a recombinant protein, wherein said protein comprises a polypeptide having the amino acid sequence of anyone of the amino acid sequences of SEQ ID NOs: 95 to 101, preferably SEQ ID NO: 95 or SEQ ID NO: 96.

In one aspect the invention provides such a recombinant protein, wherein said protein binds human CD3 in PBS with a dissociation constant ($K_D$) below $10^{-6}$M.

In one aspect the invention provides such a recombinant protein, wherein said protein binds human CD33 in PBS with a dissociation constant ($K_D$) below $10^{-7}$M.

In one aspect the invention provides such a recombinant protein, wherein said protein binds human CD123 in PBS with a dissociation constant ($K_D$) below $10^{-7}$M.

In one aspect the invention provides such a recombinant protein, wherein said protein binds human CD70 in PBS with a dissociation constant ($K_D$) below $10^{-7}$M.

In one aspect the invention provides such a recombinant protein, wherein said binding protein binds human CD3 with an $EC_{50}$ ranging from 1 to 400 nM.

In one aspect the invention provides such a recombinant protein, wherein said protein further comprises a half-life extending moiety, preferably wherein said half-life extending moiety is a binding agent that specifically binds to human serum albumin.

In one aspect the invention provides such a recombinant protein, wherein said half-life extending moiety is a designed ankyrin repeat domain with binding specificity for human serum albumin.

In one aspect the invention provides such a recombinant protein, wherein said ankyrin repeat domain with binding specificity for human serum albumin comprises an amino acid sequence that is at least 85% identical to the amino acid sequence of any one of SEQ ID NOs: 34 to 36.

In one aspect the invention provides such a recombinant protein, wherein said recombinant protein binds human serum albumin in PBS with a dissociation constant ($K_D$) below $10^{-7}$M.

In one aspect the invention further provides a nucleic acid encoding such a recombinant protein.

In one aspect the invention further provides a pharmaceutical composition comprising such a recombinant protein or the nucleic acid encoding such a recombinant protein, and a pharmaceutically acceptable carrier and/or diluent.

In one aspect the invention further provides a method of treating a medical condition, the method comprising the step of administering to a patient in need thereof a therapeutically effective amount of such a recombinant protein, or of a pharmaceutical composition comprising said recombinant protein.

In one aspect the invention provides a method of treating a medical condition, wherein said medical condition is a cancer, preferably a liquid tumor, more preferably leukemia, even more preferably acute myeloid leukemia.

In one aspect, the invention provides the recombinant protein defined herein or a pharmaceutical composition comprising said recombinant protein, for use in therapy.

In one aspect, the invention provides the recombinant protein defined herein or a pharmaceutical composition comprising said recombinant protein for use in treating cancer, preferably for use in treating a liquid tumor.

In one aspect, the invention provides the recombinant protein defined herein or a pharmaceutical composition comprising said recombinant protein for use in treating cancer, wherein said cancer is leukemia, preferably wherein said cancer is acute myeloid leukemia.

BRIEF DESCRIPTION OF THE FIGURES

FIG. 1.

FIG. 3 (A-C). Short term T cell activation measured by activation marker CD25. Pan-T and MOLM-13 cells were incubated at an E:T ratio of 1:1 and T-cell activation assessed by FACS after 24 hours co-culture in the presence of serial dilutions of indicated molecules. Activated T-cells were gated as living CD8+/CD25+ cells. Shown known benchmark T cell engagers, AMG330 with binding specificity for CD33 and flotetuzumab with binding specificity for CD123 and selected recombinant proteins (without half-life extension) binding to MOLM-13 cells.

FIG. 5 (A-C). Short Term Target Cell Killing (LDH). Pan-T and Molm-13 cells were incubated at an E:T ratio of 5:1 and tumor cell killing was assessed by LDH release in the supernatant after 48 hours of co-culture in the presence of serial dilutions of indicated molecules. Shown are benchmark control molecule (known benchmark T cell engager, AMG330 with binding specificity for CD33 and flotetuzumab with binding specificity for CD123) and multi-specific recombinant proteins with two or three tumor specific binding domains.

FIG. 20 (A-C).

FIG. 22 (A-B). Short Term Target Cell Killing (LDH). Pan-T and Molm-13 cells were incubated at an E:T ratio of 5:1 and tumor cell killing was assessed by LDH release in the supernatant after 48 hours of co-culture in the presence of serial dilutions of indicated molecules. Shown are benchmark control molecules (known benchmark T cell engager, AMG330 with binding specificity for CD33 and flotetuzumab with binding specificity for CD123) and selected ankyrin repeat proteins DARPin® protein 7, DARPin® protein 8, DARPin® protein 9 and DARPin® protein 10 without (FIG. 22A) or DARPin® protein 11, DARPin® protein 12, DARPin® protein 13 and DARPin® protein 14 with (FIG. 22B) half-life extension (HLE).

FIG. 23 (A-B). Short term T cell activation measured by activation marker CD25. Pan-T and Molm-13 cells were incubated at an E:T ratio of 1:1 and T-cell activation assessed by FACS after 24 hours co-culture in the presence of serial dilutions of indicated molecules. Activated T-cells were gated as living CD8+/CD25+ cells. Shown are benchmark control molecule (known benchmark T cell engager, AMG330 with binding specificity for CD33) and selected ankyrin repeat proteins DARPin® protein 7, DARPin® protein 8, DARPin® protein 9 and DARPin® protein 10 without (FIG. 23A) or DARPin® protein 11, DARPin® protein 12, DARPin® protein 13 and DARPin® protein 14 with (FIG. 23B) half-life extension (HLE).

(FIG. 24A) Without half-life extension, T-cell activation induced by DARPin® protein 8 and DARPin® protein 9 is comparable to benchmark molecules, whereas DARPin® protein 10 and DARPin® protein 7 show lower potencies. (FIG. 24B) Half-life extended proteins show 3-20-fold reduction in potency compared to the corresponding non-HLE molecules shown in (A). Pan-T cells from 4 different donors were tested, one representative donor is shown here. (*Negative control: a designed ankyrin repeat protein with binding specificity for CD33 and CD123 only, with or without half-life extension respectively).

FIG. 26 (A-B). Long-term T-cell activation. Pan-T and Molm-13 cells were incubated at an E:T ratio of 1:1 and T-cell activation assessed by FACS after 5 days co-culture in the presence of serial dilutions of indicated molecules. Activated T-cells were gated as living CD8+/CD25+ cells. Shown are benchmark control molecules (known benchmark T cell engagers AMG330 with binding specificity for CD33 and flotetuzumab with binding specificity for CD123) and selected ankyrin repeat proteins DARPin® protein 7, DARPin® protein 8, DARPin® protein 9 and DARPin® protein 10 without or DARPin® protein 11, DARPin® protein 12, DARPin® protein 13 and DARPin® protein 14 with half-life extension (HLE).

FIG. 27 (A-B). Long-term T-cell proliferation. Pan-T and Molm-13 cells were incubated at an E:T ratio of 1:1 and T-cell proliferation assessed by FACS after 5 days co-culture in the presence of serial dilutions of indicated molecules. Proliferating T-cells were gated as CellTrace Violet positive cells showing at least one cell division. Shown are two benchmark control molecules (known benchmark T cell engagers, AMG330 with binding specificity for CD33 and flotetuzumab with binding specificity for CD123) and selected ankyrin repeat proteins DARPin® protein 7, DARPin® protein 8, DARPin® protein 9 and DARPin® protein 10 without or DARPin® protein 11, DARPin® protein 12, DARPin® protein 13 and DARPin® protein 14 with half-life extension (HLE).

FIG. 51 (A-E).

FIG. 52 (A-D).

FIG. 53 (A-B).

FIG. 5A. Potency Titration curves (T cell activation) of selected multi-specific DARPin® proteins targeting CD123-CD33-CD70 on AML patient BMMC tumor cells compared to Flotetuzumab.

FIG. 58 (A-B).

FIG. 59 (A-L). Autologous killing of patient derived AML cells vs release of cytokines (IFN-g, TNFα, IL-2) after 2 days incubation. Cell killing is shown as % viable cells by the black squares/curves, and concentration of cytokines by the black circles/curve.

FIG. 60 (A-L). Autologous killing of patient derived AML cells vs release of cytokines (IFN-g, TNFα, IL-2) after 5 days incubation. Cell killing is shown as % viable cells by the black squares/curves, and concentration of cytokines by the black circles/curve.

FIG. 61 (A-L). Allogenic killing of patient derived AML cells in the presence of human Pan-T cells (E:T ratio 4:1) vs release of cytokines (IFN-g, TNFα, IL-2) after 2 days incubation. Cell killing is shown as % viable cells by the black squares/curves, and concentration of cytokines by the black circles/curve.

FIG. 62 (A-H): Cytokine release in whole blood from 2 healthy donors spiked with Molm13 cells.

FIG. 69 (A-B). Cytokine and chemokine release in mouse tumor environment after treatment.

DETAILED DESCRIPTION OF THE INVENTION

Figure 1A:
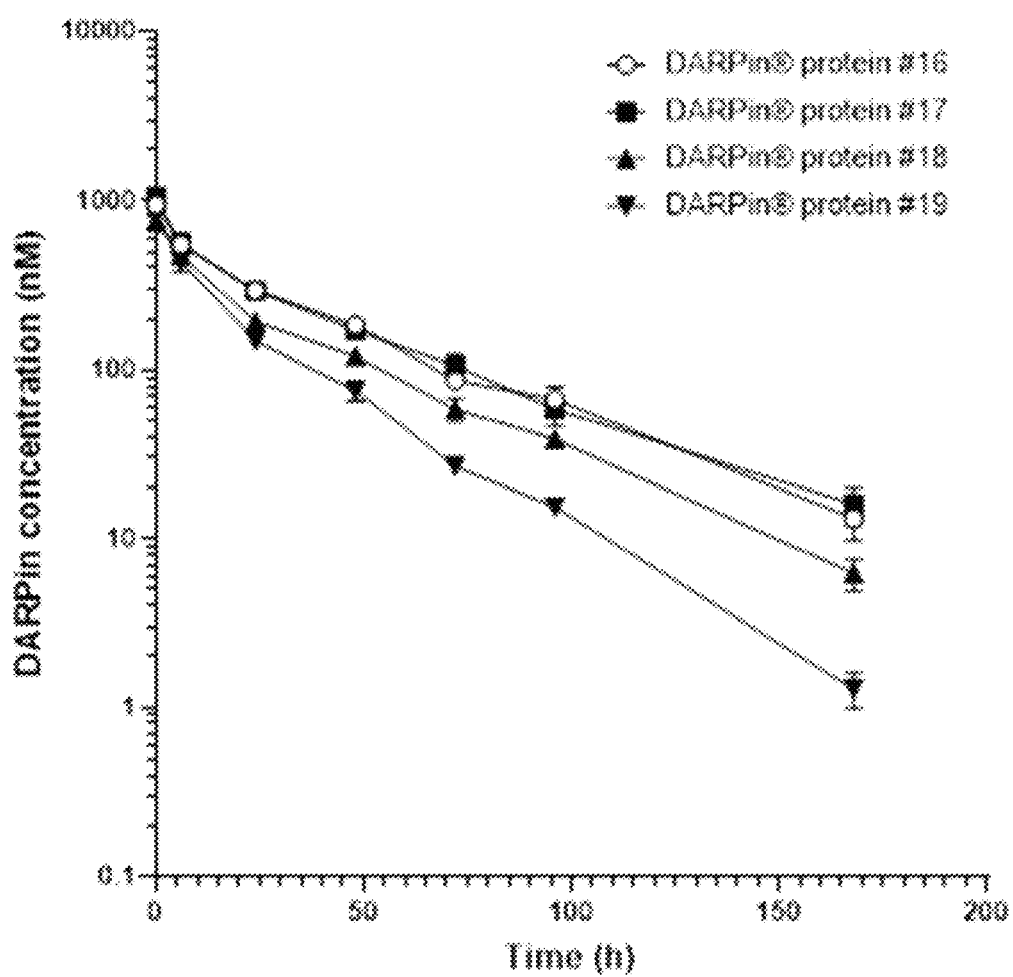
FIG. 1A. Pharmacokinetic analysis of exemplary CD3 specific designed ankyrin repeat proteins in female BALB/c mice. The figure shows the group mean serum concentration-time profiles of DARPin® protein #16, DARPin® protein #17, DARPin® protein #18 and DARPin® protein #19 in female BALB/c mice (mean+/−max/min, N=3 per group), following single intravenous bolus administration of 1 mg/kg.

Disclosed herein are recombinant proteins comprising a first binding agent that specifically binds to a protein expressed on the surface of an immune cell, and at least two binding agents that specifically bind to a tumor-associated antigen, wherein said two binding agents specifically bind to different tumor-associated antigens.

More particularly, disclosed herein are recombinant proteins comprising designed ankyrin repeat domains with binding specificity for different targets such as CD3, CD33, CD123 and CD70. Also disclosed are nucleic acids encoding the binding proteins, pharmaceutical compositions comprising the binding proteins or nucleic acids, and methods of using the binding proteins, nucleic acids, or pharmaceutical compositions. Designed ankyrin repeat protein libraries (WO2002/020565; Binz et al., Nat. Biotechnol. 22, 575-582, 2004; Stumpp et al., Drug Discov. Today 13, 695-701, 2008) can be used for the selection of target-specific designed ankyrin repeat domains that bind to their target with high affinity. Such target-specific designed ankyrin repeat domains in turn can be used as valuable components of recombinant binding proteins for the treatment of diseases. Designed ankyrin repeat proteins are a class of binding molecules which have the potential to overcome limitations of monoclonal antibodies, hence allowing novel therapeutic approaches. Such ankyrin repeat proteins may comprise a single designed ankyrin repeat domain, or may comprise a combination of two or more designed ankyrin repeat domains with the same or different target specificities (Stumpp et al., Drug Discov. Today 13, 695-701, 2008; U.S. Pat. No. 9,458,211). Ankyrin repeat proteins comprising only a single designed ankyrin repeat domain are small proteins (14 kDa) which can be selected to bind a given target protein with high affinity and specificity. These characteristics, and the possibility of combining two or more designed ankyrin repeat domains in one protein, make designed ankyrin repeat proteins ideal agonistic, antagonistic and/or inhibitory drug candidates. Furthermore, such ankyrin repeat proteins can be engineered to carry various effector functions, e.g. cytotoxic agents or half-life extending agents, enabling completely new drug formats. Taken together, designed ankyrin repeat proteins are an example of the next generation of protein therapeutics with the potential to surpass existing antibody drugs.

DARPin® is a trademark owned by Molecular Partners AG, Switzerland.

Molecules expressed on the surface of tumor cells, such as, e.g., CD33, CD123 and CD70, are potential targets for anti-cancer therapy, particularly if they are expressed on tumor cells but not, or much less, on healthy cells. As an example, CD33, CD123 and CD70 are expressed on the surface of AML blasts and leukemic stem cells, but they are not, or much less, expressed simultaneously on the surface of healthy cells, including hematopoietic stem cells.

In one aspect the invention provides a recombinant protein comprising (1) a first binding agent that specifically binds to a protein expressed on the surface of an immune cell, and (2) at least two binding agents that specifically bind to a tumor-associated antigen, wherein said two binding agents specifically bind to different tumor-associated antigens.

In one aspect the invention provides a recombinant protein comprising (1) a first binding agent that specifically binds to a protein expressed on the surface of an immune cell, and (2) at least two binding agents that specifically bind to a tumor-associated antigen, wherein said two binding agents specifically bind to different tumor-associated antigens, and wherein said recombinant protein is capable of binding simultaneously to said protein expressed on the surface of an immune cell and to said two different tumor-associated antigens.

In one aspect the invention provides a recombinant protein comprising (1) a first binding agent that specifically binds to a protein expressed on the surface of an immune cell, and (2) at least three binding agents that specifically bind to a tumor-associated antigen, wherein said three binding agents specifically bind to different tumor-associated antigens.

In one aspect the invention provides a recombinant protein comprising (1) a first binding agent that specifically binds to a protein expressed on the surface of an immune cell, and (2) at least three binding agents that specifically bind to a tumor-associated antigen, wherein said three binding agents specifically bind to different tumor-associated antigens, and wherein said recombinant protein is capable of binding simultaneously to said protein expressed on the surface of an immune cell and to said three different tumor-associated antigens.

In one aspect said tumor associated antigens are co-expressed in a tumor cell. In one aspect said tumor cell is a tumor cell from a liquid tumor. In another aspect, said tumor cell is a liquid tumor cell from a leukemia. In one aspect said leukemia is acute myeloid leukemia (AML).

In one aspect the invention provides a recombinant protein, wherein said recombinant protein is capable of binding with a lower dissociation constant ($K_D$) to a surface displaying said tumor-associated antigens, when compared to a recombinant protein comprising only one of said binding agents that specifically bind to a tumor-associated antigen.

In one aspect the invention provides a recombinant protein, wherein said surface displaying said tumor associated antigens is the surface of said tumor cell.

In one aspect the invention provides a recombinant protein, wherein said lower dissociation constant ($K_D$) is at least about 2-fold lower, at least about 4-fold lower, at least about 10-fold lower, at least about 20-fold lower, at least about 40-fold lower or at least about 100-fold lower than the corresponding dissociation constant of said recombinant protein comprising only one of said binding agents that specifically bind to a tumor-associated antigen.

In one aspect the invention provides a recombinant protein, wherein said immune cell is a T cell.

In one aspect the invention provides a recombinant protein, wherein said T-cell is a CD8+ cytotoxic T-cell.

In one aspect the invention provides a recombinant protein, wherein said protein expressed on the surface of an immune cell is a protein that is part of the T-cell receptor complex.

In one aspect the invention provides a recombinant protein, wherein said protein that is part of the T-cell receptor complex is CD3.

In one aspect the invention provides a recombinant protein, wherein said first binding agent is an antibody, an antibody mimetic, a scaffold protein, a repeat protein, or a designed repeat domain.

In one aspect the invention provides a recombinant protein, wherein said first binding agent is a designed ankyrin repeat domain with binding specificity for said protein expressed on the surface of an immune cell.

In one aspect the invention provides a recombinant protein, wherein said first binding agent is a designed ankyrin repeat domain with binding specificity for CD3.

In one aspect the invention provides a recombinant protein, wherein said ankyrin repeat domain with binding specificity for CD3 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to any one of the amino acid sequences of SEQ ID NOs: 1 to 5, preferably SEQ ID NO: 2 or 3, and wherein A at the second last position of SEQ ID NO: 1 to 4 is optionally substituted by L, and/or A at the last position of SEQ ID NOs: 1 to 4 is optionally substituted by N; or wherein L at the second last position of SEQ ID NO: 5 is optionally substituted by A, and/or N at the last position of SEQ ID NO: 5 is optionally substituted by A.

In one aspect the invention provides a recombinant protein, wherein said ankyrin repeat domain with binding specificity for CD3 comprises the amino acid sequences of SEQ ID NOs: 1 to 5, preferably SEQ ID NO: 2 or 3, and wherein A at the second last position of SEQ ID NOs: 1 to 4 is optionally substituted by L, and/or A at the last position of SEQ ID NOs: 1 to 4 is optionally substituted by N; or wherein L at the second last position of SEQ ID NO: 5 is optionally substituted by A, and/or N at the last position of SEQ ID NO: 5 is optionally substituted by A.

In one aspect the invention provides a recombinant protein, wherein said ankyrin repeat domain with binding specificity for CD3 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 2, and wherein A at the second last position of SEQ ID NO: 2 is optionally substituted by L, and/or A at the last position of SEQ ID NO: 2 is optionally substituted by N.

In one aspect the invention provides a recombinant protein, wherein said ankyrin repeat domain with binding specificity for CD3 comprises the amino acid sequence of SEQ ID NO: 2, and wherein A at the second last position of SEQ ID NO: 2 is optionally substituted by L, and/or A at the last position of SEQ ID NO: 2 is optionally substituted by N.

In one aspect the invention provides a recombinant protein, wherein said ankyrin repeat domain with binding specificity for CD3 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 3, and wherein A at the second last position of SEQ ID NO: 3 is optionally substituted by L, and/or A at the last position of SEQ ID NO: 3 is optionally substituted by N.

In one aspect the invention provides a recombinant protein, wherein said ankyrin repeat domain with binding specificity for CD3 comprises the amino acid sequence of SEQ ID NO: 3, and wherein A at the second last position of SEQ ID NO: 3 is optionally substituted by L, and/or A at the last position of SEQ ID NO: 3 is optionally substituted by N.

In one aspect the invention provides a recombinant protein, wherein said binding agents that specifically bind to a tumor-associated antigen are selected from the group consisting of (i) a second binding agent that specifically binds to a first tumor-associated antigen (TAA1), (ii) a third binding agent that specifically binds to a second tumor-associated antigen (TAA2), and (iii) and a fourth binding agent that specifically binds to a third tumor-associated antigen (TAA3).

In one aspect the invention provides a recombinant protein, wherein said binding agents that specifically bind to a tumor-associated antigen are selected from the group consisting of (i) a second binding agent that specifically binds to a first tumor-associated antigen (TAA1), (ii) a third binding agent that specifically binds to a second tumor-associated antigen (TAA2), and (iii) and a fourth binding agent that specifically binds to a third tumor-associated antigen (TAA3), and wherein said selected binding agents are capable of binding simultaneously to their respective tumor-associated antigen targets.

In one aspect the invention provides a recombinant protein, wherein said wherein said second binding agent is an antibody, an antibody mimetic, a scaffold protein, a repeat protein, or a designed repeat domain. In one aspect the invention provides a recombinant protein, wherein said second binding agent is a designed ankyrin repeat domain with binding specificity for said TAA1.

In one aspect the invention provides a recombinant protein, wherein said TAA1 is CD33.

In one aspect the invention provides a recombinant protein, wherein said second binding agent is a designed ankyrin repeat domain with binding specificity for CD33.

In one aspect the invention provides a recombinant protein, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70, and 111 to 112, and wherein A at the second last position of SEQ ID NOs: 15, 67 to 70, and 111 to 112 is optionally substituted by L, and/or A at the last position of SEQ ID NOs:15, 67 to 70, and 111 to 112 is optionally substituted by N.

In one aspect the invention provides a recombinant protein, wherein said ankyrin repeat domain with binding specificity for CD33 comprises anyone of the amino acid sequences of SEQ ID NOs: 15, 67 to 70 and 111 to 112, and wherein A at the second last position of SEQ ID NOs: 15, 67 to 70, and 111 to 112 is optionally substituted by L, and/or A at the last position of SEQ ID NOs: 15, 67 to 70, and 111 to 112 is optionally substituted by N.

In one aspect the invention provides a recombinant protein, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 15, and wherein A at the second last position of SEQ ID NO: 15 is optionally substituted by L, and/or A at the last position of SEQ ID NO: 15 is optionally substituted by N.

In one aspect the invention provides a recombinant protein wherein said ankyrin repeat domain with binding specificity for CD33 comprises the amino acid sequence of SEQ ID NO: 15, and wherein A at the second last position of SEQ ID NO: 15 is optionally substituted by L, and/or A at the last position of SEQ ID NO: 15 is optionally substituted by N.

In one aspect the invention provides a recombinant protein, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 67, and wherein A at the second last position of SEQ ID NO: 67 is optionally substituted by L, and/or A at the last position of SEQ ID NO: 67 is optionally substituted by N.

In one aspect the invention provides a recombinant protein wherein said ankyrin repeat domain with binding specificity for CD33 comprises the amino acid sequence of SEQ ID NO: 67, and wherein A at the second last position of SEQ ID NO: 67 is optionally substituted by L, and/or A at the last position of SEQ ID NO: 67 is optionally substituted by N.

In one aspect the invention provides a recombinant protein, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 68, and wherein A at the second last position of SEQ ID NO: 68 is optionally substituted by L, and/or A at the last position of SEQ ID NO: 68 is optionally substituted by N.

In one aspect the invention provides a recombinant protein wherein said ankyrin repeat domain with binding specificity for CD33 comprises the amino acid sequence of SEQ ID NO: 68, and wherein A at the second last position of SEQ ID NO: 68 is optionally substituted by L, and/or A at the last position of SEQ ID NO: 68 is optionally substituted by N.

In one aspect the invention provides a recombinant protein, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 69, and wherein A at the second last position of SEQ ID NO: 69 is optionally substituted by L, and/or A at the last position of SEQ ID NO: 69 is optionally substituted by N.

In one aspect the invention provides a recombinant protein wherein said ankyrin repeat domain with binding specificity for CD33 comprises the amino acid sequence of SEQ ID NO: 69, and wherein A at the second last position of SEQ ID NO: 69 is optionally substituted by L, and/or A at the last position of SEQ ID NO: 70 is optionally substituted by N.

In one aspect the invention provides a recombinant protein, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 13, and wherein A at the second last position of SEQ ID NO: 70 is optionally substituted by L, and/or A at the last position of SEQ ID NO: 70 is optionally substituted by N.

In one aspect the invention provides a recombinant protein wherein said ankyrin repeat domain with binding specificity for CD33 comprises the amino acid sequence of SEQ ID NO: 70, and wherein A at the second last position of SEQ ID NO: 70 is optionally substituted by L, and/or A at the last position of SEQ ID NO: 70 is optionally substituted by N.

In one aspect the invention provides a recombinant protein, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 111, and wherein A at the second last position of SEQ ID NO: 111 is optionally substituted by L, and/or A at the last position of SEQ ID NO: 111 is optionally substituted by N.

In one aspect the invention provides a recombinant protein wherein said ankyrin repeat domain with binding specificity for CD33 comprises the amino acid sequence of SEQ ID NO: 111, and wherein A at the second last position of SEQ ID NO: 111 is optionally substituted by L, and/or A at the last position of SEQ ID NO: 111 is optionally substituted by N.

In one aspect the invention provides a recombinant protein, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 112, and wherein A at the second last position of SEQ ID NO: 112 is optionally substituted by L, and/or A at the last position of SEQ ID NO: 112 is optionally substituted by N.

In one aspect the invention provides a recombinant protein wherein said ankyrin repeat domain with binding specificity for CD33 comprises the amino acid sequence of SEQ ID NO: 112, and wherein A at the second last position of SEQ ID NO: 112 is optionally substituted by L, and/or A at the last position of SEQ ID NO: 112 is optionally substituted by N.

In one aspect the invention provides a recombinant protein wherein said first binding agent is an antibody, an antibody mimetic, a scaffold protein, a repeat protein, or a designed repeat domain, and wherein said second binding agent is an antibody, an antibody mimetic, a scaffold protein, a repeat protein, or a designed repeat domain.

In one aspect the invention provides a recombinant protein wherein said first binding agent is a designed ankyrin repeat domain with binding specificity for said protein expressed on the surface of an immune cell, and wherein said second binding agent is an antibody, an antibody mimetic, a scaffold protein, a repeat protein, or a designed repeat domain.

In one aspect the invention provides a recombinant protein, wherein said first binding agent is a designed ankyrin repeat domain with binding specificity for CD3, and wherein said second binding agent is an antibody, an antibody mimetic, a scaffold protein, a repeat protein, or a designed repeat domain.

In one aspect the invention provides a recombinant protein, wherein said ankyrin repeat domain with binding specificity for CD3 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to any one of the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N, or wherein L at the second last position of SEQ ID NO: 5 is optionally substituted by A, and/or N at the last position of SEQ ID NO: 5 is optionally substituted by A; and wherein said second binding agent is an antibody, an antibody mimetic, a scaffold protein, a repeat protein, or a designed repeat domain.

In one aspect the invention provides a recombinant protein, wherein said ankyrin repeat domain with binding specificity for CD3 comprises the amino acid sequence of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N, or wherein L at the second last position of SEQ ID NO: 5 is optionally substituted by A, and/or N at the last position of SEQ ID NO: 5 is optionally substituted by A; and wherein said second binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain. and wherein said second binding agent is a designed ankyrin repeat domain with binding specificity for CD33.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical anyone of the amino acid sequences of SEQ ID NOs: 15, 67 to 70 and 111 to 112.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises anyone of the amino acid sequences of SEQ ID NOs: 15, 67 to 70 and 111 to 112.

In one aspect the invention provides a recombinant protein wherein said first binding agent is an antibody, an antibody mimetic, a scaffold protein, a repeat protein, or a designed repeat domain, and wherein said third binding agent is an antibody, an antibody mimetic, a scaffold protein, a repeat protein, or a designed repeat domain.

In one aspect the invention provides a recombinant protein wherein said first binding agent is a designed ankyrin repeat domain with binding specificity for said protein expressed on the surface of an immune cell, and wherein said third binding agent is an antibody, an antibody mimetic, a scaffold protein, a repeat protein, or a designed repeat domain.

In one aspect the invention provides a recombinant protein, wherein said first binding agent is a designed ankyrin repeat domain with binding specificity for CD3, and wherein said third binding agent is an antibody, an antibody mimetic, a scaffold protein, a repeat protein, or a designed repeat domain.

In one aspect the invention provides a recombinant protein, wherein said ankyrin repeat domain with binding specificity for CD3 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to any one of the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N, or wherein L at the second last position of SEQ ID NO: 5 is optionally substituted by A, and/or N at the last position of SEQ ID NO: 5 is optionally substituted by A; and wherein said third binding agent is an antibody, an antibody mimetic, a scaffold protein, a repeat protein, or a designed repeat domain.

In one aspect the invention provides a recombinant protein, wherein said ankyrin repeat domain with binding specificity for CD3 comprises the amino acid sequence of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N, or wherein L at the second last position of SEQ ID NO: 5 is optionally substituted by A, and/or N at the last position of SEQ ID NO: 5 is optionally substituted by A; and wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain. and wherein said third binding agent is a designed ankyrin repeat domain with binding specificity for CD123.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 6, 65 to 66 and 102 to 106, and wherein A at the second last position of SEQ ID NOs: 6, 65 to 66 and 102 to 106 is optionally substituted by L, and/or A at the last position of SEQ ID NOs: 6, 65 to 66 and 102 to 106 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises anyone of the amino acid sequences of SEQ ID NOs: 6, 65 to 66 and 102 to 106, and wherein A at the second last position of SEQ ID NOs: 6, 65 to 66 and 102 to 106 is optionally substituted by L, and/or A at the last position of SEQ ID NOs: 6, 65 to 66 and 102 to 106 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 6, and wherein A at the second last position of SEQ ID NO: 6 is optionally substituted by L, and/or A at the last position of SEQ ID NO: 6 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 6, and wherein A at the second last position of SEQ ID NO: 6 is optionally substituted by L, and/or A at the last position of SEQ ID NO: 6 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 65, and wherein A at the second last position of SEQ ID NO: 65 is optionally substituted by L, and/or A at the last position of SEQ ID NO: 65 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 65, and wherein A at the second last position of SEQ ID NO: 65 is optionally substituted by L, and/or A at the last position of SEQ ID NO: 65 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 66, and wherein A at the second last position of SEQ ID NO: 66 is optionally substituted by L, and/or A at the last position of SEQ ID NO: 66 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 66, and wherein A at the second last position of SEQ ID NO: 66 is optionally substituted by L, and/or A at the last position of SEQ ID NO: 66 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 102, and wherein A at the second last position of SEQ ID NO: 102 is optionally substituted by L, and/or A at the last position of SEQ ID NO: 102 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 102, and wherein A at the second last position of SEQ ID NO: 102 is optionally substituted by L, and/or A at the last position of SEQ ID NO: 102 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 103, and wherein A at the second last position of SEQ ID NO: 103 is optionally substituted by L, and/or A at the last position of SEQ ID NO: 103 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 103, and wherein A at the second last position of SEQ ID NO: 103 is optionally substituted by L, and/or A at the last position of SEQ ID NO: 103 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 104, and wherein A at the second last position of SEQ ID NO: 104 is optionally substituted by L, and/or A at the last position of SEQ ID NO: 104 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 104, and wherein A at the second last position of SEQ ID NO: 104 is optionally substituted by L, and/or A at the last position of SEQ ID NO: 104 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 105, and wherein A at the second last position of SEQ ID NO: 105 is optionally substituted by L, and/or A at the last position of SEQ ID NO: 105 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 105, and wherein A at the second last position of SEQ ID NO: 105 is optionally substituted by L, and/or A at the last position of SEQ ID NO: 105 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 106, and wherein A at the second last position of SEQ ID NO: 106 is optionally substituted by L, and/or A at the last position of SEQ ID NO: 106 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 106, and wherein A at the second last position of SEQ ID NO: 106 is optionally substituted by L, and/or A at the last position of SEQ ID NO: 106 is optionally substituted by N.

In one aspect the invention provides a recombinant protein wherein said first binding agent is an antibody, an antibody mimetic, a scaffold protein, a repeat protein, or a designed repeat domain, and wherein said second binding agent is an antibody, an antibody mimetic, a scaffold protein, a repeat protein, or a designed repeat domain, wherein said third binding agent is an antibody, an antibody mimetic, a scaffold protein, a repeat protein, or a designed repeat domain.

In one aspect the invention provides a recombinant protein wherein said first binding agent is a designed ankyrin repeat domain with binding specificity for said protein expressed on the surface of an immune cell, and wherein said second binding agent is an antibody, an antibody mimetic, a scaffold protein, a repeat protein, or a designed repeat domain, wherein said third binding agent is an antibody, an antibody mimetic, a scaffold protein, a repeat protein, or a designed repeat domain.

In one aspect the invention provides a recombinant protein, wherein said first binding agent is a designed ankyrin repeat domain with binding specificity for CD3, and wherein said second binding agent is an antibody, an antibody mimetic, a scaffold protein, a repeat protein, or a designed repeat domain, wherein said third binding agent is an antibody, an antibody mimetic, a scaffold protein, a repeat protein, or a designed repeat domain.

In one aspect the invention provides a recombinant protein, wherein said ankyrin repeat domain with binding specificity for CD3 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to any one of the amino acid sequence of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N, or wherein L at the second last position of SEQ ID NO: 5 is optionally substituted by A, and/or N at the last position of SEQ ID NO: 5 is optionally substituted by A; and wherein said second binding agent is an antibody, an antibody mimetic, a scaffold protein, a repeat protein, or a designed repeat domain; and wherein said third binding agent is an antibody, an antibody mimetic, a scaffold protein, a repeat protein, or a designed repeat domain.

In one aspect the invention provides a recombinant protein, wherein said ankyrin repeat domain with binding specificity for CD3 comprises the amino acid sequence of SEQ ID NOs: 1 to 5, and wherein A at the second last position of SEQ ID NOs: 1 to 4 is optionally substituted by L, and/or A at the last position of SEQ ID NO: 6 is optionally substituted by N, or wherein L at the second last position of SEQ ID NO: 5 is optionally substituted by A, and/or N at the last position of SEQ ID NO: 5 is optionally substituted by A; and wherein said second binding agent is an antibody, an antibody mimetic, a scaffold protein, a repeat protein, or a designed repeat domain; and wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain and wherein said second binding agent is a designed ankyrin repeat domain with binding specificity for CD33, wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112; and wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain; and wherein said ankyrin repeat domain with binding specificity for CD33 comprises anyone of the amino acid sequences of SEQ ID NOs: 15, 67 to 70 and 111 to 112; and wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain; and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 15; and wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain; and wherein said ankyrin repeat domain with binding specificity for CD33 comprises the amino acid sequence of SEQ ID NO: 15; and wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 67, wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises the amino acid sequence of SEQ ID NO: 67, wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 68, wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises the amino acid sequence of SEQ ID NO: 68, wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 69, wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises the amino acid sequence of SEQ ID NO: 69, wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 70, wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises the amino acid sequence of SEQ ID NO: 70, wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain; and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 111; and wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain; and wherein said ankyrin repeat domain with binding specificity for CD33 comprises the amino acid sequence of SEQ ID NO: 111; and wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain; and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 112; and wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain; and wherein said ankyrin repeat domain with binding specificity for CD33 comprises the amino acid sequence of SEQ ID NO: 112; and wherein said third binding agent is an antibody, an antibody mimetic, a scaffold protein, a repeat protein, or a designed repeat domain.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said third binding agent is a designed ankyrin repeat domain with binding specificity for CD123.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 6, 65 to 66 and 102 to 106.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises anyone of the amino acid sequences of SEQ ID NOs: 6, 65 to 66 and 102 to 106.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 6.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 6.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 65.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 65.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 66.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 66.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 102.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 102.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 103.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 103.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 104.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 104.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 105.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 105.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NO: 106.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD123 comprises the amino acid sequence of SEQ ID NO: 106.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said fourth binding agent is a designed ankyrin repeat domain with binding specificity for CD70.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 64 and 107 to 110.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD70 comprises anyone of the amino acid sequences of SEQ ID NOs: 64 and 107 to 110.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NOs: 64.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD70 comprises the amino acid sequence of SEQ ID NO: 64.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NOs: 107.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD70 comprises the amino acid sequence of SEQ ID NO: 107.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NOs: 108.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD70 comprises the amino acid sequence of SEQ ID NO: 108.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NOs: 109.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD70 comprises the amino acid sequence of SEQ ID NO: 109.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence SEQ ID NOs: 110.

In one aspect the invention provides a recombinant protein, wherein said first binding agent is an antibody, an antibody mimetic, a scaffold protein, a repeat protein, or a designed repeat domain, wherein said second binding agent is an antibody, an antibody mimetic, a scaffold protein, a repeat protein, or a designed repeat domain, and wherein said ankyrin repeat domain with binding specificity for CD70 comprises the amino acid sequence of SEQ ID NO: 110.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences SEQ ID NOs: 6, 65 to 66 and 102 to 106.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises anyone of the amino acid sequences of SEQ ID NOs: 15, 67 to 70 and 111 to 112, and wherein said ankyrin repeat domain with binding specificity for CD123 comprises anyone of the amino acid sequences SEQ ID NOs: 6, 65 to 66 and 102 to 106.

In one aspect the invention provides a recombinant protein wherein said first binding agent is a designed ankyrin repeat domain with binding specificity for said protein expressed on the surface of an immune cell, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 6, 65 to 66 and 102 to 106.

In one aspect the invention provides a recombinant protein, wherein said first binding agent is a designed ankyrin repeat domain with binding specificity for CD3, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 6, 65 to 66 and 102 to 106.

In one aspect the invention provides a recombinant protein, wherein said ankyrin repeat domain with binding specificity for CD3 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to any one of the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 6, 65 to 66 and 102 to 106.

In one aspect the invention provides a recombinant protein, wherein said ankyrin repeat domain with binding specificity for CD3 comprises the amino acid sequence of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N, or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 6, 65 to 66 and 102 to 106.

In one aspect the invention provides a recombinant protein wherein said first binding agent is a designed ankyrin repeat domain with binding specificity for said protein expressed on the surface of an immune cell, and wherein said ankyrin repeat domain with binding specificity for CD33 comprises anyone of the amino acid sequences of SEQ ID NOs: 15, 67 to 70 and 111 to 112, and wherein said ankyrin repeat domain with binding specificity for CD123 comprises anyone of the amino acid sequences of SEQ ID NO: 6, 65 to 66 and 102 to 106.

In one aspect the invention provides a recombinant protein, wherein said first binding agent is a designed ankyrin repeat domain with binding specificity for CD3, and wherein said ankyrin repeat domain with binding specificity for CD33 comprises anyone of the amino acid sequences of SEQ ID NOs: 15, 67 to 70 and 111 to 112, and wherein said ankyrin repeat domain with binding specificity for CD123 comprises anyone of the amino acid sequences of SEQ ID NOs: 6, 65 to 66 and 102 to 106.

In one aspect the invention provides a recombinant protein, wherein said ankyrin repeat domain with binding specificity for CD3 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to any one of the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises anyone of the amino acid sequences of SEQ ID NOs: 15, 67 to 70 and 111 to 112, and wherein said ankyrin repeat domain with binding specificity for CD123 comprises anyone of the amino acid sequences of SEQ ID NO: 6, 65 to 66 and 102 to 106.

In one aspect the invention provides a recombinant protein, wherein said ankyrin repeat domain with binding specificity for CD3 comprises the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises anyone of the amino acid sequences of SEQ ID NOs: 15, 67 to 70 and 111 to 112, and wherein said ankyrin repeat domain with binding specificity for CD123 comprises anyone of the amino acid sequences of SEQ ID NOs: 6, 65 to 66 and 102 to 106.

In one aspect the invention provides a recombinant protein, wherein said ankyrin repeat domain with binding specificity for CD3 comprises the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises anyone of the amino acid sequences of SEQ ID NOs: 15, 67 to 70 and 111 to 112, and wherein A at the second last position of SEQ ID NOs: 15, 67 to 70 and 111 to 112 is optionally substituted by L, and/or A at the last position of SEQ ID NOs: 15, 67 to 70 and 111 to 112 is optionally substituted by N, and wherein said ankyrin repeat domain with binding specificity for CD123 comprises anyone of the amino acid sequences SEQ ID NOs: 6, 65 to 66 and 102 to 106, wherein A at the second last position of SEQ ID NOs: 6, 65 to 66 and 102 to 106 is optionally substituted by L, and/or A at the last position of SEQ ID NOs: 6, 65 to 66 and 102 to 106 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 64 and 107 to 110.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises anyone of the amino acid sequences of SEQ ID NOs: 15, 67 to 70 and 111 to 112, and wherein said ankyrin repeat domain with binding specificity for CD70 comprises anyone of the amino acid sequences of SEQ ID NOs: 64 and 107 to 110.

In one aspect the invention provides a recombinant protein wherein said first binding agent is a designed ankyrin repeat domain with binding specificity for said protein expressed on the surface of an immune cell, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 64 and 107 to 110.

In one aspect the invention provides a recombinant protein, wherein said first binding agent is a designed ankyrin repeat domain with binding specificity for CD3, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 64 and 107 to 110.

In one aspect the invention provides a recombinant protein, wherein said ankyrin repeat domain with binding specificity for CD3 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to any one of the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 64 and 107 to 110.

In one aspect the invention provides a recombinant protein, wherein said ankyrin repeat domain with binding specificity for CD3 comprises the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N, or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 64 and 107 to 110.

In one aspect the invention provides a recombinant protein wherein said first binding agent is a designed ankyrin repeat domain with binding specificity for said protein expressed on the surface of an immune cell, and wherein said ankyrin repeat domain with binding specificity for CD33 comprises anyone of the amino acid sequences of SEQ ID NOs: 15, 67 to 70 and 111 to 112 and wherein said ankyrin repeat domain with binding specificity for CD70 comprises anyone of the amino acid sequences of SEQ ID NOs: 64 and 107 to 110.

In one aspect the invention provides a recombinant protein, wherein said first binding agent is a designed ankyrin repeat domain with binding specificity for CD3, and wherein said ankyrin repeat domain with binding specificity for CD33 comprises anyone of the amino acid sequences of SEQ ID NOs: 15, 67 to 70 and 111 to 112, and wherein said ankyrin repeat domain with binding specificity for CD70 comprises anyone of the amino acid sequences of the amino acid sequences of SEQ ID NOs: 64 and 107 to 110.

In one aspect the invention provides a recombinant protein, wherein said ankyrin repeat domain with binding specificity for CD3 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to any one of the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises anyone of the amino acid sequences of SEQ ID NOs: 15, 67 to 70 and 111 to 112, and wherein said ankyrin repeat domain with binding specificity for CD70 comprises anyone of the amino acid sequences of SEQ ID NOs: 64 and 107 to 110.

In one aspect the invention provides a recombinant protein, wherein said ankyrin repeat domain with binding specificity for CD3 comprises the amino acid sequences of SEQ ID Nos: 1 to 5, and wherein A at the second last position of SEQ ID Nos: 1 to 4 is optionally substituted by L, and/or A at the last position of SEQ ID Nos: 1 to 4 is optionally substituted by N or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises anyone of the amino acid sequences of SEQ ID Nos: 15, 67 to 70 and 111 to 112, and wherein said ankyrin repeat domain with binding specificity for CD70 comprises anyone of the amino acid sequences of SEQ ID NOs: 64 and 107 to 110.

In one aspect the invention provides a recombinant protein, wherein said ankyrin repeat domain with binding specificity for CD3 comprises the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises the amino acid sequences of SEQ ID NOs: 15, 67 to 70 and 111 to 112 and wherein A at the second last position of SEQ ID NOs: 15, 67 to 70 and 111 to 112 is optionally substituted by L, and/or A at the last position of SEQ ID NOs: 15, 65 to 70 and 111 to 112 is optionally substituted by N, and wherein said ankyrin repeat domain with binding specificity for CD70 comprises the amino acid sequences SEQ ID NOs: 64 and 107 to 110 and wherein A at the second last position of SEQ ID NOs: 64 is optionally substituted by L, and/or A at the last position of SEQ ID NOs: 64 and 107 to 110 is optionally substituted by N.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 6, 65 to 66 and 102 to 106, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to any one of the amino acid sequences of SEQ ID NOs: 64 and 107 to 108.

In one aspect the invention provides a recombinant protein, wherein said first binding agent is an antibody, an antibody mimetic, a scaffold protein, a repeat protein, or a designed repeat domain, and wherein said ankyrin repeat domain with binding specificity for CD33 comprises anyone of the amino acid sequences of SEQ ID NOs: 15, 67 to 70 and 111 to 112, and wherein said ankyrin repeat domain with binding specificity for CD123 comprises anyone of the amino acid sequences of SEQ ID NOs: 6, 65 to 66 and 102 to 106, and wherein said ankyrin repeat domain with binding specificity for CD70 comprises any one of the amino acid sequences of SEQ ID NOs: 64 and 107 to 110.

In one aspect the invention provides a recombinant protein wherein said first binding agent is a designed ankyrin repeat domain with binding specificity for said protein expressed on the surface of an immune cell, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID Nos: 15, 67 to 70 and 111 to 112, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 6, 65 to 66 and 102 to 106, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 64 and 107 to 110.

In one aspect the invention provides a recombinant protein, wherein said first binding agent is a designed ankyrin repeat domain with binding specificity for CD3, and wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 6, 65 to 66 and 102 to 106, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 64 and 107 to 110.

In one aspect the invention provides a recombinant protein, wherein said ankyrin repeat domain with binding specificity for CD3 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to any one of the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 6, 65 to 66 and 102 to 106, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 64 and 107 to 110.

In one aspect the invention provides a recombinant protein, wherein said ankyrin repeat domain with binding specificity for CD3 comprises the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N, or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 15, 67 to 70 and 111 to 112, and wherein said ankyrin repeat domain with binding specificity for CD123 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 6, 65 to 66 and 102 to 106, and wherein said ankyrin repeat domain with binding specificity for CD70 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 64 and 107 to 110.

In one aspect the invention provides a recombinant protein wherein said first binding agent is a designed ankyrin repeat domain with binding specificity for said protein expressed on the surface of an immune cell, and wherein said ankyrin repeat domain with binding specificity for CD33 comprises anyone of the amino acid sequences of SEQ ID NOs: 15, 67 to 70 and 111 to 112, and wherein said ankyrin repeat domain with binding specificity for CD123 comprises anyone of the amino acid sequences of SEQ ID NOs: 6, 65 to 66 and 102 to 106, and wherein said ankyrin repeat domain with binding specificity for CD70 comprises anyone of the amino acid sequences of SEQ ID NOs: 64 and 107 to 110.

In one aspect the invention provides a recombinant protein, wherein said first binding agent is a designed ankyrin repeat domain with binding specificity for CD3, and wherein said ankyrin repeat domain with binding specificity for CD33 comprises anyone of the amino acid sequences of SEQ ID NOs: 15, 67 to 70 and 111 to 112, and wherein said ankyrin repeat domain with binding specificity for CD123 comprises anyone of the amino acid sequences of the amino acid sequences of SEQ ID NOs: 6, 65 to 66 and 102 to 106, and wherein said ankyrin repeat domain with binding specificity for CD70 comprises anyone of the amino acid sequences of SEQ ID NO: 64 and 107 to 110.

In one aspect the invention provides a recombinant protein, wherein said ankyrin repeat domain with binding specificity for CD3 comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to any one of the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises anyone of the amino acid sequences of SEQ ID NOs: 15, 67 to 70 and 111 to 112, and wherein said ankyrin repeat domain with binding specificity for CD123 comprises anyone of the amino acid sequences of SEQ ID NO: 6, 65 to 66 and 102 to 106, and wherein said ankyrin repeat domain with binding specificity for CD70 comprises anyone of the amino acid sequences of SEQ ID NOs: 64 and 107 to 110.

In one aspect the invention provides a recombinant protein, wherein said ankyrin repeat domain with binding specificity for CD3 comprises the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises anyone of the amino acid sequences SEQ ID NOs: 15, 67 to 70 and 111 to 112, and wherein said ankyrin repeat domain with binding specificity for CD123 comprises anyone of the amino acid sequences of SEQ ID NOs: 6, 65 to 66 and 102 to 106, and wherein said ankyrin repeat domain with binding specificity for CD70 comprises anyone of the amino acid sequences of SEQ ID NOs: 64 and 107 to 110.

In one aspect the invention provides a recombinant protein, wherein said ankyrin repeat domain with binding specificity for CD3 comprises the amino acid sequences of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N or wherein L at the second last position of SEQ ID NO: 5 is optionally substituted by A, and/or N at the last position of SEQ ID NO: 5 is optionally substituted by A, wherein said ankyrin repeat domain with binding specificity for CD33 comprises anyone of the amino acid sequences of SEQ ID NOs: 15, 67 to 70 and 111 to 112, and wherein A at the second last position of SEQ ID NOs: 1 5, 67 to 70 and 111 to 112 is optionally substituted by L, and/or A at the last position of SEQ ID Nos: 15, 67 to 70 and 111 to 112 is optionally substituted by N, and wherein said ankyrin repeat domain with binding specificity for CD123 comprises anyone of the amino acid sequences of SEQ ID NOs: 6, 65 to 66 and 102 to 106 and wherein A at the second last position of SEQ ID NOs: 6, 65 to 66 and 102 to 106 is optionally substituted by L, and/or A at the last position of SEQ ID NOs: 6, 65 to 66 and 102 to 106 is optionally substituted by N, and wherein said ankyrin repeat domain with binding specificity for CD70 comprises anyone of the amino acid sequences of SEQ ID NOs: 64 and 107 to 110 and wherein A at the second last position of SEQ ID NOs: 64 and 107 to 110 is optionally substituted by L, and/or A at the last position of SEQ ID NOs: 64 and 107 to 110 is optionally substituted by N.

In one aspect the invention provides a recombinant protein, wherein said recombinant protein comprises said first, second and third binding agents, and wherein said recombinant protein is capable of binding the respective targets of said first, second and third binding agents simultaneously.

In one aspect the invention provides a recombinant protein, wherein said recombinant protein comprises said first, second and third binding agents, and wherein said first, second and third binding agents are arranged, from the N-terminus to the C-terminus, according to the following formula: (third binding agent)-(second binding agent)-(first binding agent).

In one aspect the invention provides a recombinant protein, wherein said first, second and third binding agents are arranged, from the N-terminus to the C-terminus, according to the following formula: (second binding agent)-(third binding agent)-(first binding agent).

In one aspect the invention provides a recombinant protein, and wherein said first, second and third binding agents are arranged, from the N-terminus to the C-terminus, according to the following formula: (first binding agent)-(second binding agent)-(third binding agent).

In one aspect the invention provides a recombinant protein, wherein said first, second and third binding agents are arranged, from the N-terminus to the C-terminus, according to the following formula: (first binding agent)-(third binding agent)-(second binding agent).

In one aspect the invention provides a recombinant protein, wherein said recombinant protein comprises said first, second and fourth binding agents, and wherein said recombinant protein is capable of binding the respective targets of said first, second and fourth binding agents simultaneously.

In one aspect the invention provides a recombinant protein, wherein said recombinant protein comprises said first, second and fourth binding agents, and wherein said first, second and fourth binding agents are arranged, from the N-terminus to the C-terminus, according to the following formula: (fourth binding agent)-(second binding agent)-(first binding agent).

In one aspect the invention provides a recombinant protein, wherein said first, second and fourth binding agents are arranged, from the N-terminus to the C-terminus, according to the following formula: (second binding agent)-(fourth binding agent)-(first binding agent).

In one aspect the invention provides a recombinant protein, wherein said first, second and fourth binding agents are arranged, from the N-terminus to the C-terminus, according to the following formula: (first binding agent)-(second binding agent)-(fourth binding agent).

In one aspect the invention provides a recombinant protein, wherein said first, second and fourth binding agents are arranged, from the N-terminus to the C-terminus, according to the following formula: (first binding agent)-(fourth binding agent)-(second binding agent).

In one aspect the invention provides a recombinant protein, wherein said recombinant protein comprises said first, third and fourth binding agents, and wherein said recombinant protein is capable of binding the respective targets of said first, third and fourth binding agents simultaneously.

In one aspect the invention provides a recombinant protein, wherein said recombinant protein comprises said first, third and fourth binding agents, and wherein said first, third and fourth binding agents are arranged, from the N-terminus to the C-terminus, according to the following formula: (fourth binding agent)-(third binding agent)-(first binding agent).

In one aspect the invention provides a recombinant protein, wherein said first, third and fourth binding agents are arranged, from the N-terminus to the C-terminus, according to the following formula: (third binding agent)-(fourth binding agent)-(first binding agent).

In one aspect the invention provides a recombinant protein, wherein said first, third and fourth binding agents are arranged, from the N-terminus to the C-terminus, according to the following formula: (first binding agent)-(third binding agent)-(fourth binding agent).

In one aspect the invention provides a recombinant protein, wherein said first, third and fourth binding agents are arranged, from the N-terminus to the C-terminus, according to the following formula: (first binding agent)-(fourth binding agent)-(third binding agent).

In one aspect the invention provides a recombinant protein, wherein said recombinant protein comprises said first, second, third and fourth binding agents, and wherein said recombinant protein is capable of binding the respective targets of said first, second, third and fourth binding agents simultaneously.

In one aspect the invention provides a recombinant protein, wherein said recombinant protein comprises said first, second, third and fourth binding agents, and wherein said first, second, third and fourth binding agents are arranged, from the N-terminus to the C-terminus, according to the following formula: (fourth binding agent)-(third binding agent)-(second binding agent)-(first binding agent).

In one aspect the invention provides a recombinant protein, wherein said recombinant protein comprises said first, second, third and fourth binding agents, and wherein said first, second, third and fourth binding agents are arranged, from the N-terminus to the C-terminus, according to the following formula: (second binding agent)-(third binding agent)-(fourth binding agent)-(first binding agent).

In one aspect the invention provides a recombinant protein, wherein said first, second, third and/or fourth binding agents are covalently linked with a peptide linker.

In one aspect the invention provides a recombinant protein comprising a peptide linker, wherein said peptide linker is a proline-threonine-rich peptide linker.

In one aspect the invention provides a recombinant protein comprising a peptide linker, wherein the amino acid sequence of said peptide linker has a length from 1 to 50 amino acids. In one aspect the invention provides a recombinant protein comprising a peptide linker, wherein the amino acid sequence of said peptide linker has a length from 1 to 30 amino acids.

In one aspect the invention provides a recombinant protein, wherein A at the second last position of any one of SEQ ID NOs: 1, 2, 3, 4, 6, 15, 64 to 70 and 102 to 112 is optionally substituted by L, and/or A at the last position of any one of SEQ ID NOs: 1, 2, 3, 4, 6, 15, 64 to 70 and 102 to 112 is optionally substituted by N; or wherein L at the second last position of SEQ ID NO: 5 is optionally substituted by A, and/or N at the last position of SEQ ID NO: 5 is optionally substituted by A.

In one aspect the invention provides a recombinant protein, wherein any of said first, second or third ankyrin repeat domains additionally comprises a G, a S or a GS at the N-terminus.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to any one of the amino acid sequences of SEQ ID NOs: 7 to 10 and 58 to 62, preferably wherein said protein comprises a polypeptide having the amino acid sequence of any one of SEQ ID NOs: 7 to 10 and 58 to 62.

In one aspect the invention provides a recombinant protein comprising a polypeptide consisting of an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to any one of the amino acid sequences of SEQ ID NOs: 7 to 10 and 58 to 62. In one aspect the invention provides a recombinant protein comprising a polypeptide consisting of an amino acid sequence of any one of SEQ ID NOs: 7 to 10 and 58 to 62.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 7, preferably wherein said protein comprises a polypeptide having the amino acid sequence of SEQ ID NO: 7.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 8, preferably wherein said protein comprises a polypeptide having the amino acid sequence of SEQ ID NO: 8.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 9, preferably wherein said protein comprises a polypeptide having the amino acid sequence of SEQ ID NO: 9.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 10, preferably wherein said protein comprises a polypeptide having the amino acid sequence of SEQ ID NO: 10.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 58, preferably wherein said protein comprises a polypeptide having the amino acid sequence of SEQ ID NO: 58.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 59, preferably wherein said protein comprises a polypeptide having the amino acid sequence of SEQ ID NO: 59.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 60, preferably wherein said protein comprises a polypeptide having the amino acid sequence of SEQ ID NO: 60.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 61, preferably wherein said protein comprises a polypeptide having the amino acid sequence of SEQ ID NO: 61.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 62, preferably wherein said protein comprises a polypeptide having the amino acid sequence of SEQ ID NO: 62.

In one aspect the invention provides a recombinant protein wherein said protein binds human CD3 in PBS with a dissociation constant ($K_D$) of or below about $10^{-6}$M, or of or below about $5 \times 10^{-7}$M.

In one aspect the invention provides a recombinant protein comprising a first binding agent that specifically binds to a protein expressed on the surface of an immune cell, a second binding agent that specifically binds to a first tumor-associated antigen, and a third binding agent that specifically binds to a second tumor-associated antigen, wherein said first binding protein binds to human CD3 in PBS with a dissociation constant ($K_D$) of or below about $10^{-6}$M, or of or below about $5 \times 10^{-7}$M. Thus, in one aspect, said binding protein binds human CD3 in PBS with a dissociation constant ($K_D$) of or below about $10^{-6}$M. In another aspect, said binding protein binds human CD3 in PBS with a dissociation constant ($K_D$) of or below about $5 \times 10^{-7}$M.

In one aspect, said recombinant protein comprises a first binding agent that specifically binds to a protein expressed on the surface of an immune cell, wherein said binding protein binds human CD3 in PBS with a dissociation constant ($K_D$) of or below about $10^{-6}$M, and wherein said ankyrin repeat domain comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with any one of SEQ ID NOs: 1 to 5, wherein A at the second last position of SEQ ID NOs: 1 to 4 is optionally substituted by L, and/or A at the last position of SEQ ID NOs: 1 to 4 is optionally substituted by N; or wherein L at the second last position of SEQ ID NO: 5 is optionally substituted by A, and/or N at the last position of SEQ ID NO: 5 is optionally substituted by A. In another aspect, said recombinant binding protein comprises an ankyrin repeat domain with binding specificity for CD3, wherein said binding protein binds human CD3 in PBS with a dissociation constant (KD) of or below about $5 \times 10^{-7}$M, and wherein said ankyrin repeat domain comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with any one of SEQ ID NOs:1 to 5, wherein A at the second last position of SEQ ID NOs: 1 to 5 is optionally substituted by L, and/or A at the last position of SEQ ID NOs: 1 to 4 is optionally substituted by N; or wherein L at the second last position of SEQ ID NO: 5 is optionally substituted by A, and/or N at the last position of SEQ ID NO: 5 is optionally substituted by A. Thus, in one aspect, said protein binds human CD3 in PBS with a dissociation constant ($K_D$) below about $5 \times 10^{-7}$M, and said ankyrin repeat domain comprises an amino acid sequence with at least 80% amino acid sequence identity with any one of SEQ ID NOs: 1 to 5. In one aspect, said binding protein binds human CD3 in PBS with a dissociation constant ($K_D$) below about $5 \times 10^{-7}$M, and said ankyrin repeat domain comprises an amino acid sequence with at least 90% amino acid sequence identity with any one of SEQ ID NOs: 1 to 5. In another aspect, said protein binds human CD3 in PBS with a dissociation constant ($K_D$) below about $5 \times 10^{-7}$M, and said ankyrin repeat domain comprises an amino acid sequence with at least 93% amino acid sequence identity with any one of SEQ ID NOs: 1 to 5; and in a further aspect, said binding protein binds human CD3 in PBS with a dissociation constant ($K_D$) below about $5 \times 10^{-7}$M, and said ankyrin repeat domain comprises an amino acid sequence with at least 95% amino acid sequence identity with any one of SEQ ID NOs: 1 to 5. In one aspect, said protein binds human CD3 in PBS with a dissociation constant ($K_D$) below about $5 \times 10^{-7}$M, and said ankyrin repeat domain comprises an amino acid sequence with at least 98% amino acid sequence identity with any one of SEQ ID NOs: 1 to 5; and in one aspect, said binding protein binds human CD3 in PBS with a dissociation constant ($K_D$) below about $5 \times 10^{-7}$M, and said ankyrin repeat domain comprises the amino acid sequence of any one of SEQ ID NOs: 1 to 5. Thus, in one aspect, said recombinant protein comprises first binding agent that specifically binds to a protein expressed on the surface of an immune cell, wherein said binding protein binds human CD3 in PBS with a dissociation constant ($K_D$) of or below about $5 \times 10^{-7}$M, and wherein said ankyrin repeat domain comprises the amino acid sequence of any one of SEQ ID NOs: 1 to 5, wherein A at the second last position of SEQ ID NOs: 1 to 4 is optionally substituted by L, and/or A at the last position of SEQ ID NOs:1 to 4 is optionally substituted by N; or wherein L at the second last position of SEQ ID NO: 5 is optionally substituted by A, and/or N at the last position of SEQ ID NO: 5 is optionally substituted by A.

In one aspect the invention provides a recombinant protein comprising a first binding agent that specifically binds to a protein expressed on the surface of an immune cell, a second binding agent that specifically binds to a first tumor-associated antigen, a third binding agent that specifically binds to a second tumor-associated antigen and a fourth binding agent that specifically binds to a third tumor-associated antigen, wherein said binding protein binds to human CD3 in PBS with a dissociation constant ($K_D$) of or below about $10^{-6}$M, or of or below about $5 \times 10^{-7}$M. Thus, in one aspect, said binding protein binds human CD3 in PBS with a dissociation constant ($K_D$) of or below about $10^{-6}$M. In another aspect, said binding protein binds human CD3 in PBS with a dissociation constant ($K_D$) of or below about $5 \times 10^{-7}$M.

In one aspect, said recombinant protein comprises a first binding agent that specifically binds to a protein expressed on the surface of an immune cell, wherein said binding protein binds human CD3 in PBS with a dissociation constant (KD) of or below about $10^{-6}$M, and wherein said ankyrin repeat domain comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with any one of SEQ ID NOs: 1 to 5, wherein A at the second last position of SEQ ID NOs: 1 to 4 is optionally substituted by L, and/or A at the last position of SEQ ID NOs:1 to 4 is optionally substituted by N; or wherein L at the second last position of SEQ ID NO: 5 is optionally substituted by A, and/or N at the last position of SEQ ID NO: 5 is optionally substituted by A. In another aspect, said recombinant binding protein comprises an ankyrin repeat domain with binding specificity for CD3, wherein said binding protein binds human CD3 in PBS with a dissociation constant (KD) of or below about $5\times10^{-7}$M, and wherein said ankyrin repeat domain comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with any one of SEQ ID NOs:1 to 5, wherein A at the second last position of SEQ ID NOs: 1 to 4 is optionally substituted by L, and/or A at the last position of SEQ ID NOs:1 to 4 is optionally substituted by N; or wherein L at the second last position of SEQ ID NO: 5 is optionally substituted by A, and/or N at the last position of SEQ ID NO: 5 is optionally substituted by A. Thus, in one aspect, said protein binds human CD3 in PBS with a dissociation constant (KD) below about $5\times10^{-7}$M, and said ankyrin repeat domain comprises an amino acid sequence with at least 80% amino acid sequence identity with any one of SEQ ID NOs: 1 to 5. In one aspect, said binding protein binds human CD3 in PBS with a dissociation constant ($K_D$) below about $5\times10^{-7}$M, and said ankyrin repeat domain comprises an amino acid sequence with at least 90% amino acid sequence identity with any one of SEQ ID NOs: 1 to 5. In another aspect, said protein binds human CD3 in PBS with a dissociation constant ($K_D$) below about $5\times10^{-7}$M, and said ankyrin repeat domain comprises an amino acid sequence with at least 93% amino acid sequence identity with any one of SEQ ID NOs: 1 to 5; and in a further aspect, said binding protein binds human CD3 in PBS with a dissociation constant ($K_D$) below about $5\times10^{-7}$M, and said ankyrin repeat domain comprises an amino acid sequence with at least 95% amino acid sequence identity with any one of SEQ ID NOs:1 to 5. In one aspect, said protein binds human CD3 in PBS with a dissociation constant ($K_D$) below about $5\times10^{-7}$M, and said ankyrin repeat domain comprises an amino acid sequence with at least 98% amino acid sequence identity with any one of SEQ ID NOs: 1 to 5; and in one aspect, said binding protein binds human CD3 in PBS with a dissociation constant ($K_D$) below about $5\times10^{-7}$M, and said ankyrin repeat domain comprises the amino acid sequence of any one of SEQ ID NOs:1 to 5. Thus, in one aspect, said recombinant protein comprises first binding agent that specifically binds to a protein expressed on the surface of an immune cell, wherein said binding protein binds human CD3 in PBS with a dissociation constant ($K_D$) of or below about $5\times10^{-7}$M, and wherein said ankyrin repeat domain comprises the amino acid sequence of any one of SEQ ID NOs: 1 to 5, wherein A at the second last position of SEQ ID NOs: 1 to 4 is optionally substituted by L, and/or A at the last position of SEQ ID NOs:1 to 4 is optionally substituted by N; or wherein L at the second last position of SEQ ID NO: 5 is optionally substituted by A, and/or N at the last position of SEQ ID NO: 5 is optionally substituted by A. In one aspect the invention provides a recombinant protein comprising a first binding agent with binding specificity for CD3, a second binding agent with binding specificity for CD33 and a third binding agent with binding specificity for CD123, wherein said protein binds human CD33 in PBS with a dissociation constant (KD) of or below about $10^{-6}$M, or of or below about $10^{-7}$M, or of or below about $10^{-8}$M, or of or below about $10\times10^{-9}$M.

In one aspect the invention provides a recombinant protein comprising a first binding agent with binding specificity for CD3, a second binding agent with binding specificity for CD33 and a third binding agent with binding specificity for CD123, wherein said protein binds human CD33 in PBS with a dissociation constant ($K_D$) of or below about $10^{-6}$M, and wherein said second binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NO: 15, 67 to 70 and 111 to 112, wherein A at the second last position of SEQ ID NO:15, 67 to 70 and 111 to 112 is optionally substituted by L, and/or A at the last position of SEQ ID NO: 15, 67 to 70 and 111 to 112 is optionally substituted by N.

In one aspect the invention provides a recombinant protein comprising a first binding agent with binding specificity for CD3, a second binding agent with binding specificity for CD33 and a third binding agent with binding specificity for CD123, wherein said protein binds human CD33 in PBS with a dissociation constant ($K_D$) of or below about $10^{-7}$M, and wherein said second binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NO: 15, 67 to 70 and 111 to 112 wherein A at the second last position of SEQ ID NO:15, 67 to 70 and 111 to 112 is optionally substituted by L, and/or A at the last position of SEQ ID NO: 15, 67 to 70 and 111 and 112 is optionally substituted by N.

In one aspect the invention provides a recombinant protein comprising a first binding agent with binding specificity for CD3, a second binding agent with binding specificity for CD33 and a third binding agent with binding specificity for CD123, wherein said protein binds human CD33 in PBS with a dissociation constant ($K_D$) of or below about $10^{-8}$M, and wherein said second binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NO: 15, 67 to 70 and 111 to 112, wherein A at the second last position of SEQ ID NO:15, 67 to 70 and 111 and 112 is optionally substituted by L, and/or A at the last position of SEQ ID NO: 15, 67 to 70 and 111 and 112 is optionally substituted by N.

In one aspect the invention provides a recombinant protein comprising a first binding agent with binding specificity for CD3, a second binding agent with binding specificity for CD33 and a third binding agent with binding specificity for CD123, wherein said protein binds human CD33 in PBS with a dissociation constant ($K_D$) of or below about $10^{-9}$M, and wherein said second binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NO: 15, 67 to 70 and 111 to 112, wherein A at the second last position of SEQ ID NO: 15, 67 to 70 and 111 to 112 is optionally substituted by L, and/or A at the last position of SEQ ID NO: 15, 67 to 70 and 111 to 112 is optionally substituted by N.

In one aspect the invention provides a recombinant protein comprising a first binding agent with binding specificity for CD3, a second binding agent with binding specificity for CD33 and a third binding agent with binding specificity for CD123, wherein said protein binds human CD33 in PBS with a dissociation constant ($K_D$) of or below about $10^{-10}$M, and wherein said second binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NO: 15, 67 to 70 and 111 to 112, wherein A at the second last position of SEQ ID NO: 15, 67 to 70 and 111 to 112 is optionally substituted by L, and/or A at the last position of SEQ ID NO: 15, 67 to 70 and 111 to 112 is optionally substituted by N.

In one aspect the invention provides a recombinant protein comprising a first binding agent with binding specificity for CD3, a second binding agent with binding specificity for CD33 and a third binding agent with binding specificity for CD123, wherein said protein binds human CD123 in PBS with a dissociation constant ($K_D$) of or below about $10^{-6}$M, or of or below about $10^{-7}$M, or of or below about $10^{-8}$M, or of or below about $10^{-9}$M, or of or below about $10^{-10}$M.

In one aspect the invention provides a recombinant protein comprising a first binding agent with binding specificity for CD3, a second binding agent with binding specificity for CD33 and a third binding agent with binding specificity for CD123, wherein said protein binds human CD123 in PBS with a dissociation constant ($K_D$) of or below about $10^{-6}$M, and wherein said third binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NO: 6, 65 to 66 and 102 to 106, wherein A at the second last position of SEQ ID NO: 6, 65 to 66 and 102 to 106 is optionally substituted by L, and/or A at the last position of SEQ ID NO: 6, 65 to 66 and 102 to 106 is optionally substituted by N.

In one aspect the invention provides a recombinant protein comprising a first binding agent with binding specificity for CD3, a second binding agent with binding specificity for CD33 and a third binding agent with binding specificity for CD123, wherein said protein binds human CD123 in PBS with a dissociation constant ($K_D$) of or below about $10^{-7}$M, and wherein said third binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NO: 6, 65 to 66 and 102 to 106, wherein A at the second last position of SEQ ID NO: 6, 65 to 66 and 102 to 106 is optionally substituted by L, and/or A at the last position of SEQ ID NO: 6, 65 to 66 and 102 to 106 is optionally substituted by N.

In one aspect the invention provides a recombinant protein comprising a first binding agent with binding specificity for CD3, a second binding agent with binding specificity for CD33 and a third binding agent with binding specificity for CD123, wherein said protein binds human CD123 in PBS with a dissociation constant ($K_D$) of or below about $10^{-8}$M, and wherein said third binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NO: 6, 65 to 66 and 102 to 106, wherein A at the second last position of SEQ ID NO: 6, 65 to 66 and 102 to 106 is optionally substituted by L, and/or A at the last position of SEQ ID NO: 6, 65 to 66 and 102 to 106 is optionally substituted by N.

In one aspect the invention provides a recombinant protein comprising a first binding agent with binding specificity for CD3, a second binding agent with binding specificity for CD33 and a third binding agent with binding specificity for CD123, wherein said protein binds human CD123 in PBS with a dissociation constant ($K_D$) of or below about $10^{-9}$M, and wherein said third binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NO: 6, 65 to 66 and 102 to 106, wherein A at the second last position of SEQ ID NO: 6, 65 to 66 and 102 to 106 is optionally substituted by L, and/or A at the last position of SEQ ID NO: 6, 65 to 66 and 102 to 106 is optionally substituted by N.

In one aspect the invention provides a recombinant protein comprising a first binding agent with binding specificity for CD3, a second binding agent with binding specificity for CD33 and a third binding agent with binding specificity for CD123, wherein said protein binds human CD123 in PBS with a dissociation constant ($K_D$) of or below about $10^{-10}$M, and wherein said third binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NO: 6, 65 to 66 and 102 to 106, wherein A at the second last position of SEQ ID NO: 6, 65 to 66 and 102 to 106 is optionally substituted by L, and/or A at the last position of SEQ ID NO: 6, 65 to 66 and 102 to 106 is optionally substituted by N.

In one aspect the invention provides a recombinant protein comprising a first binding agent with binding specificity for CD3, a second binding agent with binding specificity for CD33 and a fourth binding agent with binding specificity for CD70, wherein said protein binds human CD70 in PBS with a dissociation constant ($K_D$) of or below about $10^{-6}$M, or of or below about $10^{-7}$M, or of or below about $10^{-8}$M, or of or below about $10^{-9}$M, or of or below about $10^{-10}$M.

In one aspect the invention provides a recombinant protein comprising a first binding agent with binding specificity for CD3, a second binding agent with binding specificity for CD33 and a fourth binding agent with binding specificity for CD70, wherein said protein binds human CD70 in PBS with a dissociation constant ($K_D$) of or below about $10^{-6}$M, and wherein said fourth binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs:64 and 107 to 110, wherein A at the second last position of SEQ ID NOs: 64 and 107 to 110 is optionally substituted by L, and/or A at the last position of SEQ ID NOs: 64 and 107 to 110 is optionally substituted by N.

In one aspect the invention provides a recombinant protein comprising a first binding agent with binding specificity for CD3, a second binding agent with binding specificity for CD33 and a fourth binding agent with binding specificity for CD70, wherein said protein binds human CD70 in PBS with a dissociation constant ($K_D$) of or below about $10^{-7}$M, and wherein said fourth binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs: 64 and 107 to 110, wherein A at the second last position of SEQ ID NOs: 64 and 107 to 110 is optionally substituted by L, and/or A at the last position of SEQ ID NOs:64 and 107 to 110 is optionally substituted by N.

In one aspect the invention provides a recombinant protein comprising a first binding agent with binding specificity for CD3, a second binding agent with binding specificity for CD33 and a fourth binding agent with binding specificity for CD70, wherein said protein binds human CD70 in PBS with a dissociation constant ($K_D$) of or below about $10^{-8}$M, and wherein said fourth binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs:64 and 107 to 110, wherein A at the second last position of SEQ ID NOs:64 and 107 to 110 is optionally substituted by L, and/or A at the last position of SEQ ID NOs: 64 and 107 to 110 is optionally substituted by N.

In one aspect the invention provides a recombinant protein comprising a first binding agent with binding specificity for CD3, a second binding agent with binding specificity for CD33 and a fourth binding agent with binding specificity for CD70, wherein said protein binds human CD70 in PBS with a dissociation constant ($K_D$) of or below about $10^{-9}$M, and wherein said fourth binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs: 64 and 107 to 110, wherein A at the second last position of SEQ ID NOs: 64 and 107 to 110 is optionally substituted by L, and/or A at the last position of SEQ ID NOs: 64 and 107 to 110 is optionally substituted by N.

In one aspect the invention provides a recombinant protein comprising a first binding agent with binding specificity for CD3, a second binding agent with binding specificity for CD33 and a fourth binding agent with binding specificity for CD70, wherein said protein binds human CD70 in PBS with a dissociation constant ($K_D$) of or below about $10^{-10}$M, and wherein said second binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs: 64, and 107 to 110 wherein A at the second last position of SEQ ID NOs:64 and 107 to 110 is optionally substituted by L, and/or A at the last position of SEQ ID NOs: 64 and 107 to 110 is optionally substituted by N.

In one aspect the invention provides a recombinant protein comprising a first binding agent with binding specificity for CD3, a second binding agent with binding specificity for CD33, a third binding agent with binding specificity for CD123, and a fourth binding agent with binding specificity for CD70, wherein said protein binds human CD33 in PBS with a dissociation constant ($K_D$) of or below about $10^{-6}$M, or of or below about $10^{-7}$M, or of or below about $10^{-8}$M, or of or below about $10 \times 10^{-9}$M.

In one aspect the invention provides a recombinant protein comprising a first binding agent with binding specificity for CD3, a second binding agent with binding specificity for CD33, a third binding agent with binding specificity for CD123, and a fourth binding agent with binding specificity for CD70, wherein said protein binds human CD33 in PBS with a dissociation constant ($K_D$) of or below about $10^{-6}$M, and wherein said second binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs:15, 67 to 70 and 111 to 112, wherein A at the second last position of SEQ ID NOs:15, 67 to 70 and 111 to 112 is optionally substituted by L, and/or A at the last position of SEQ ID NOs: 16, 67 to 70 and 111 to 112 is optionally substituted by N.

In one aspect the invention provides a recombinant protein comprising a first binding agent with binding specificity for CD3, a second binding agent with binding specificity for CD33, a third binding agent with binding specificity for CD123, and a fourth binding agent with binding specificity for CD70, wherein said protein binds human CD33 in PBS with a dissociation constant ($K_D$) of or below about $10^{-7}$M, and wherein said second binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs: 15, 67 to 70 and 111 to 112, wherein A at the second last position of SEQ ID NOs: 15, 67 to 70 and 111 to 112 is optionally substituted by L, and/or A at the last position of SEQ ID NOs: 15, 67 to 70 and 111 to 112 is optionally substituted by N.

In one aspect the invention provides a recombinant protein comprising a first binding agent with binding specificity for CD3, a second binding agent with binding specificity for CD33, a third binding agent with binding specificity for CD123, and a fourth binding agent with binding specificity for CD70, wherein said protein binds human CD33 in PBS with a dissociation constant ($K_D$) of or below about $10^{-8}$M, and wherein said second binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs: 15, 67 to 70 and 111 to 112, wherein A at the second last position of SEQ ID NOs:15, 67 to 70 and 111 to 112 is optionally substituted by L, and/or A at the last position of SEQ ID NOs: 15, 67 to 70 and 111 to 112 is optionally substituted by N.

In one aspect the invention provides a recombinant protein comprising a first binding agent with binding specificity for CD3, a second binding agent with binding specificity for CD33, a third binding agent with binding specificity for CD123, and a fourth binding agent with binding specificity for CD70, wherein said protein binds human CD33 in PBS with a dissociation constant ($K_D$) of or below about $10 \times 10^{-9}$M, and wherein said second binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs:15, 67 to 70 and 111 to 112, wherein A at the second last position of SEQ ID NOs: 15, 67 to 70 and 111 to 112 is optionally substituted by L, and/or A at the last position of SEQ ID NOs: 15, 67 to 70 and 111 to 112 is optionally substituted by N.

In one aspect the invention provides a recombinant protein comprising a first binding agent with binding specificity for CD3, a second binding agent with binding specificity for CD33, a third binding agent with binding specificity for CD123, and a fourth binding agent with binding specificity for CD70, wherein said protein binds human CD33 in PBS with a dissociation constant ($K_D$) of or below about $10 \times 10^{-9}$ M, and wherein said second binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs:15, 67 to 70 and 111 to 112, wherein A at the second last position of SEQ ID NOs: 15, 67 to 70 and 111 to 112 is optionally substituted by L, and/or A at the last position of SEQ ID NOs:15, 67 to 70 and 111 to 112 is optionally substituted by N.

In one aspect the invention provides a recombinant protein comprising a first binding agent with binding specificity for CD3, a second binding agent with binding specificity for CD33 a third binding agent with binding specificity for CD123, and a fourth binding agent with binding specificity for CD70, wherein said protein binds human CD123 in PBS with a dissociation constant ($K_D$) of or below about $10^{-6}$M, or of or below about $10^{-7}$M, or of or below about $10^{-8}$M, or of or below about $10\times10^{-9}$M.

In one aspect the invention provides a recombinant protein comprising a first binding agent with binding specificity for CD3, a second binding agent with binding specificity for CD33, a third binding agent with binding specificity for CD123, and a fourth binding agent with binding specificity for CD70, wherein said protein binds human CD123 in PBS with a dissociation constant ($K_D$) of or below about $10^{-6}$M, and wherein said third binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs:6, 65 to 66 and 102 to 106, wherein A at the second last position of SEQ ID NOs: 6, 65 to 66 and 102 to 106 is optionally substituted by L, and/or A at the last position of SEQ ID NOs: 6, 65 to 66 and 102 to 106 is optionally substituted by N.

In one aspect the invention provides a recombinant protein comprising a first binding agent with binding specificity for CD3, a second binding agent with binding specificity for CD33, a third binding agent with binding specificity for CD123, and a fourth binding agent with binding specificity for CD70, wherein said protein binds human CD123 in PBS with a dissociation constant ($K_D$) of or below about $10^{-7}$M, and wherein said third binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs: 6, 65 to 66 and 102 to 106, wherein A at the second last position of SEQ ID NOs: 6, 65 to 66 and 102 to 106 is optionally substituted by L, and/or A at the last position of SEQ ID NOs: 6, 65 to 66 and 102 to 106 is optionally substituted by N.

In one aspect the invention provides a recombinant protein comprising a first binding agent with binding specificity for CD3, a second binding agent with binding specificity for CD33, third binding agent with binding specificity for CD123, and a fourth binding agent with binding specificity for CD70, wherein said protein binds human CD123 in PBS with a dissociation constant ($K_D$) of or below about $10^{-8}$M, and wherein said third binding agent comprises an amino acid sequence with at least 80%, 81%, 82%, 83%, 84%, 85%, 86%, 87%, 88%, 89%, 90%, 9M), 92%, 93%, 94%, 95%, 96%, 97%, 98%, 99%, 100% amino acid sequence identity with anyone of SEQ ID NOs:6, 65 to 66 and 102 to 106, wherein A at the second last position of SEQ ID NOs: 6, 65 to 66 and 102 to 106 is optionally substituted by L, and/or A at the last position of SEQ ID NOs:6, 65 to 66 and 102 to 106 is optionally substituted by N.

In one aspect the invention provides a recombinant protein comprising a first binding agent with binding specificity for CD3, a second binding agent with binding specificity for CD33, third binding agent with binding specificity for CD123, and a fourth binding agent with binding specificity for CD70, wherein said protein binds human CD123 in PBS with a dissociation constant ($K_D$) of or below about $10\times10^{-9}$M, and wherein said third binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs: 6, 65 to 66 and 102 to 106, wherein A at the second last position of SEQ ID NOs: 6, 65 to 66 and 102 to 106 is optionally substituted by L, and/or A at the last position of SEQ ID NOs: 6, 65 to 66 and 102 to 106 is optionally substituted by N.

In one aspect the invention provides a recombinant protein comprising a first binding agent with binding specificity for CD3, a second binding agent with binding specificity for CD33, a third binding agent with binding specificity for CD123, and a fourth binding agent with binding specificity for CD70, wherein said protein binds human CD70 in PBS with a dissociation constant ($K_D$) of or below about $10^{-6}$M, or of or below about $10^{-7}$M, or of or below about $10^{-8}$M, or of or below about $10^{-9}$M, or of or below about $10^{-10}$M.

In one aspect the invention provides a recombinant protein comprising a first binding agent with binding specificity for CD3, a second binding agent with binding specificity for CD33, a third binding agent with binding specificity for CD123, and a fourth binding agent with binding specificity for CD70, wherein said protein binds human CD70 in PBS with a dissociation constant ($K_D$) of or below about $10^{-6}$M, and wherein said fourth binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs: 64 and 107 to 110, wherein A at the second last position of SEQ ID NOs: 64 and 107 to 110 is optionally substituted by L, and/or A at the last position of SEQ ID NOs: 64 and 107 to 110 is optionally substituted by N.

In one aspect the invention provides a recombinant protein comprising a first binding agent with binding specificity for CD3, a second binding agent with binding specificity for CD33, a third binding agent with binding specificity for CD123, and a fourth binding agent with binding specificity for CD70, wherein said protein binds human CD70 in PBS with a dissociation constant ($K_D$) of or below about $10^{-7}$M, and wherein said fourth binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID Nos: 64 and 107 to 110, wherein A at the second last position of SEQ ID NOs: 64 and 107 to 110 is optionally substituted by L, and/or A at the last position of SEQ ID NOs: 64 and 107 to 110 is optionally substituted by N.

In one aspect the invention provides a recombinant protein comprising a first binding agent with binding specificity for CD3, a second binding agent with binding specificity for CD33, a third binding agent with binding specificity for CD123 and a fourth binding agent with binding specificity for CD70, wherein said protein binds human CD70 in PBS with a dissociation constant ($K_D$) of or below about $10^{-8}$M, and wherein said fourth binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs: 64 and 107 to 110 wherein A at the second last position of SEQ ID NOs:64 and 107 to 110 is optionally substituted by L, and/or A at the last position of SEQ ID NO: 64 and 107 to 110 is optionally substituted by N.

In one aspect the invention provides a recombinant protein comprising a first binding agent with binding specificity for CD3, a second binding agent with binding specificity for CD33, a third binding agent with binding specificity for CD123, and a fourth binding agent with binding specificity for CD70, wherein said protein binds human CD70 in PBS with a dissociation constant ($K_D$) of or below about $10^{-9}$M, and wherein said fourth binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with anyone of SEQ ID NOs: 64 and 107 to 110, wherein A at the second last position of SEQ ID NOs:64 and 107 to 110 is optionally substituted by L, and/or A at the last position of SEQ ID NOs: 64 and 107 to 110 is optionally substituted by N.

In one aspect the invention provides a recombinant protein comprising a first binding agent with binding specificity for CD3, a second binding agent with binding specificity for CD33, a third binding agent with binding specificity for CD123, and a fourth binding agent with binding specificity for CD70, wherein said protein binds human CD70 in PBS with a dissociation constant ($K_D$) of or below about $10^{-10}$M, and wherein said fourth binding agent comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with an one of SEQ ID Nos:64 and 107 to 110, wherein A at the second last position of SEQ ID NOs: 64 and 107 to 110 is optionally substituted by L, and/or A at the last position of SEQ ID NOs: 64 and 107 to 110 is optionally substituted by N.

A typical and preferred determination of dissociation constants ($K_D$) of the inventive recombinant binding proteins by Surface Plasmon Resonance (SPR) analysis is described in Example 4. Thus, in one aspect said binding specificity for CD3, CD33, CD123 or CD70 of the inventive recombinant binding proteins is determined in PBS by Surface Plasmon Resonance (SPR). In one aspect said binding specificity of the inventive recombinant binding proteins is determined in PBS by Surface Plasmon Resonance (SPR) as described in Example 3.

In one aspect the invention provides a recombinant protein comprising a first binding agent that specifically binds to a protein expressed on the surface of an immune cell, a second binding agent that specifically binds to a first tumor-associated antigen, a third binding agent that specifically binds to a second tumor-associated antigen and/or a fourth binding antigen that specifically binds to a third tumor-associated antigen, wherein said protein binds human CD3 with an $EC_{50}$ of less 10 nM.

In one aspect the invention provides a recombinant protein comprising a first binding agent that specifically binds to a protein expressed on the surface of an immune cell, a second binding agent that specifically binds to a first tumor-associated antigen (TAA1), and a third binding agent that specifically binds to a second tumor-associated antigen (TAA2) and/or a fourth binding agent that specifically binds to a third tumor-associated antigen (TAA3), wherein said protein binds human CD3 with an EC50 ranging from about 1 to about 400 nM, preferably wherein said protein binds human CD3 with an EC50 ranging from about 1 to about 10 nM.

A typical and preferred determination of CD3 binding on T cells (EC50) of the inventive recombinant binding proteins with binding specificity for CD3 by using Mirrorball laser scanning imaging cytometry is described in Example 4 (with primary human T cells). Thus, in one aspect said CD3 binding (EC50) of the inventive recombinant binding proteins is determined on primary human T cells by Mirrorball laser scanning imaging cytometry as described in Example 4.

In one aspect, said recombinant protein comprises an ankyrin repeat domain with binding specificity for CD3, wherein said binding protein binds human CD3 on T cells with an $EC_{50}$ ranging from about 1 to about 10 nM, and wherein said binding protein comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity with any one of SEQ ID NOs: 1 to 5, and wherein A at the second last position of SEQ ID NOs: 1 to 4 is optionally substituted by L, and/or A at the last position of SEQ ID NOs: 1 to 4 is optionally substituted by N; or wherein L at the second last position of SEQ ID NO: 5 is optionally substituted by A, and/or N at the last position of SEQ ID NO: 5 is optionally substituted by A. Thus, in one aspect, said protein binds human CD3 on T cells with an $EC_{50}$ ranging from about 1 to about 10 nM, and said ankyrin repeat domain comprises an amino acid sequence with at least 80% amino acid sequence identity with any one of SEQ ID NOs: 1 to 5. In one aspect, said protein binds human CD3 on T cells with an EC50 ranging from about 1 to about 10 nM, and said ankyrin repeat domain comprises an amino acid sequence with at least 90% amino acid sequence identity with any one of SEQ ID NOs: 1 to 5. In another aspect, said protein binds human CD3 on T cells with an EC50 ranging from about 1 to about 10 nM, and said ankyrin repeat domain comprises an amino acid sequence with at least 93% amino acid sequence identity with any one of SEQ ID NOs: 1 to 5; and in a further aspect, said protein binds human CD3 on T cells with an $EC_{50}$ ranging from about 1 to about 10 nM, and said ankyrin repeat domain comprises an amino acid sequence with at least 95% amino acid sequence identity with any one of SEQ ID NOs: 1 to 5. In one aspect, said protein binds human CD3 on T cells with an $EC_{50}$ ranging from about 1 to about 10 nM, and said ankyrin repeat domain comprises an amino acid sequence with at least 98% amino acid sequence identity with any one of SEQ ID NOs: 1 to 5; and in one aspect, said protein binds human CD3 on T cells with an $EC_{50}$ ranging from about 1 to about 10 nM, and said ankyrin repeat domain comprises the amino acid sequence of any one of SEQ ID NOs: 1 to 5. Thus, in one aspect, said recombinant protein comprises an ankyrin repeat domain with binding specificity for CD3, wherein said protein binds human CD3 on T cells with an $EC_{50}$ ranging from about 1 to about 10 nM, and wherein said ankyrin repeat domain comprises the amino acid sequence of any one of SEQ ID NOs: 1 to 5, wherein A at the second last position of SEQ ID NOs: 1 to 5 is optionally substituted by L, and/or A at the last position of SEQ ID NOs:1 to 5 is optionally substituted by N.

In one aspect the invention provides a recombinant protein comprising (i) a first binding agent that specifically binds to a protein expressed on the surface of an immune cell, and (ii) a second binding agent that specifically binds to a first tumor-associated antigen (TAA1), a third binding agent that specifically binds to a second tumor-associated antigen (TAA2), and/or a fourth binding agent that specifically binds to a third tumor-associated antigen (TAA3), and wherein said recombinant protein further comprises a half-life extending moiety. Thus, in one aspect said protein further comprises a half-life extending moiety, wherein said half-life extending moiety is a binding agent that specifically binds to human serum albumin. In one aspect said binding agent that specifically binds to human serum albumin is a designed ankyrin repeat domain with binding specificity for human serum albumin. In one aspect said designed ankyrin repeat domain with binding specificity for human serum albumin comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of any one of SEQ ID NOs: 34 to 36. In one aspect said designed ankyrin repeat domain with binding specificity for human serum albumin comprises the amino acid sequence of any one of SEQ ID NOs: 34 to 36.

In one aspect the invention provides a recombinant protein comprising (i) a first binding agent that specifically binds to a protein expressed on the surface of an immune cell, wherein said first binding agent is a designed ankyrin repeat domain with binding specificity for said protein expressed on the surface of an immune cell, preferably a designed ankyrin repeat domain with binding specificity for CD3, and (ii) a second binding agent that specifically binds to a first tumor-associated antigen (TAA1), wherein said second binding agent is a designed ankyrin repeat domain with binding specificity for said TAA1, preferably TAA1 being CD33, a third binding agent that specifically binds to a second tumor-associated antigen (TAA2), wherein said third binding agent is a designed ankyrin repeat domain with binding specificity for said TAA2, preferably TAA2 being CD123, and/or a fourth binding agent that specifically binds to a third tumor-associated antigen (TAA3), wherein said fourth binding agent is a designed ankyrin repeat domain with binding specificity for said TAA3, preferably TAA3 being CD70, and wherein said recombinant protein further comprises a half-life extending moiety. Thus, in one aspect said recombinant protein further comprises a half-life extending moiety, wherein said half-life extending moiety is a binding agent that specifically binds to human serum albumin. In one aspect said binding agent that specifically binds to human serum albumin is a designed ankyrin repeat domain with binding specificity for human serum albumin. In one aspect said designed ankyrin repeat domain with binding specificity for human serum albumin comprises an amino acid sequence that is at least 85% identical, such as at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of any one of SEQ ID NOs: 34 to 36. In one aspect said designed ankyrin repeat domain with binding specificity for human serum albumin comprises the amino acid sequence of any one of SEQ ID NOs: 34 to 36.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 11 to 14, 78 to 86 and 95 to 101, preferably wherein said protein comprises a polypeptide having the amino acid sequence of anyone of SEQ ID NOs: 11 to 14, 78 to 86 and 95 to 101.

In one aspect the invention provides a recombinant protein comprising a polypeptide consisting of an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to anyone of the amino acid sequences of SEQ ID NOs: 11 to 14, 78 to 86 and 95 to 101. In one aspect the invention provides a recombinant protein comprising a polypeptide consisting of an amino acid sequence of anyone of SEQ ID NOs: 11 to 14, 78 to 86 and 95 to 101.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 11, preferably wherein said protein comprises a polypeptide having the amino acid sequence of SEQ ID NO: 11.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 12, preferably wherein said protein comprises a polypeptide having the amino acid sequence of SEQ ID NO: 12.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 13, preferably wherein said protein comprises a polypeptide having the amino acid sequence of SEQ ID NO: 13.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 14, preferably wherein said protein comprises a polypeptide having the amino acid sequence of SEQ ID NO: 14.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO:

78, preferably wherein said protein comprises a polypeptide having the amino acid sequence of SEQ ID NO: 78.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 79, preferably wherein said protein comprises a polypeptide having the amino acid sequence of SEQ ID NO: 79.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 80, preferably wherein said protein comprises a polypeptide having the amino acid sequence of SEQ ID NO: 80.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 81, preferably wherein said protein comprises a polypeptide having the amino acid sequence of SEQ ID NO: 81.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 82, preferably wherein said protein comprises a polypeptide having the amino acid sequence of SEQ ID NO: 82.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 83, preferably wherein said protein comprises a polypeptide having the amino acid sequence of SEQ ID NO: 83.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 84, preferably wherein said protein comprises a polypeptide having the amino acid sequence of SEQ ID NO: 84.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 85, preferably wherein said protein comprises a polypeptide having the amino acid sequence of SEQ ID NO: 85.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 86, preferably wherein said protein comprises a polypeptide having the amino acid sequence of SEQ ID NO: 86.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 95, preferably wherein said protein comprises a polypeptide having the amino acid sequence of SEQ ID NO: 95.

In one aspect, the invention provides a recombinant protein comprising a first ankyrin repeat domain, a second ankyrin repeat domain, a third ankyrin repeat domain, a fourth ankyrin repeat domain, a fifth ankyrin repeat domain and a sixth ankyrin repeat domain, wherein said first ankyrin repeat domain specifically binds to human serum albumin in PBS with a dissociation constant ($K_D$) of or below $10^{-7}$M, wherein said second ankyrin repeat domain specifically binds to human serum albumin in PBS with a dissociation constant ($K_D$) of or below $10^{-7}$M, wherein said third ankyrin repeat domain specifically binds to human CD33 in PBS with a dissociation constant ($K_D$) of or below $10^{-7}$M, wherein said fourth ankyrin repeat domain specifically binds to human CD123 in PBS with a dissociation constant ($K_D$) of or below $10^{-7}$M, wherein said fifth ankyrin repeat domain specifically binds to human CD70 in PBS with a dissociation constant ($K_D$) of or below $10^{-7}$M, wherein said sixth ankyrin repeat domain specifically binds to human CD3 in PBS with a dissociation constant ($K_D$) of or below $10^{-6}$M, wherein said first, second, third, fourth, fifth and sixth ankyrin repeat domains are arranged, from the N-terminus to the C-terminus, according to the following formula: (first ankyrin repeat domain)-(second ankyrin repeat domain)-(third ankyrin repeat domain)-(fourth ankyrin repeat domain)-(fifth ankyrin repeat domain)-sixth ankyrin repeat domain). In one embodiment, each of said first, second, third, fourth, fifth and sixth ankyrin repeat domain specifically binds to its target (as recited above) in PBS with a dissociation constant ($K_D$) between $10^{-6}$M and $10^{-12}$M. In one embodiment, said recombinant protein binds human CD3 with an $EC_{50}$ ranging from 1 to 400 nM. In one embodiment, said recombinant protein binds Molm-13 tumor cells with an $EC_{50}$ of or below 1 nM. In one embodiment, said recombinant protein is capable of binding to CD3, CD33, CD123 and CD70 simultaneously. In one embodiment, said recombinant protein comprises a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to the amino acid sequence of SEQ ID NO: 95. In one embodiment, said recombinant protein comprises the amino acid sequence of SEQ ID NO: 95. In one embodiment, said recombinant protein further comprises at its N-terminus, a G, an S, or a GS, preferably a GS.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 96, preferably wherein said protein comprises a polypeptide having the amino acid sequence of SEQ ID NO: 96.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 97, preferably wherein said protein comprises a polypeptide having the amino acid sequence of SEQ ID NO: 97.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 98, preferably wherein said protein comprises a polypeptide having the amino acid sequence of SEQ ID NO: 98.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 99, preferably wherein said protein comprises a polypeptide having the amino acid sequence of SEQ ID NO: 99.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 100, preferably wherein said protein comprises a polypeptide having the amino acid sequence of SEQ ID NO: 100.

In one aspect, the invention provides a recombinant protein comprising a first ankyrin repeat domain, a second ankyrin repeat domain, a third ankyrin repeat domain, a fourth ankyrin repeat domain, a fifth ankyrin repeat domain and a sixth ankyrin repeat domain, wherein said first ankyrin repeat domain specifically binds to human serum albumin in PBS with a dissociation constant ($K_D$) of or below $10^{-7}$M, wherein said second ankyrin repeat domain specifically binds to human serum albumin in PBS with a dissociation constant ($K_D$) of or below $10^{-7}$M, wherein said third ankyrin repeat domain specifically binds to human CD33 in PBS with a dissociation constant ($K_D$) of or below $10^{-7}$M, wherein said fourth ankyrin repeat domain specifically binds to human CD123 in PBS with a dissociation constant ($K_D$) of or below $10^{-7}$M, wherein said fifth ankyrin repeat domain specifically binds to human CD70 in PBS with a dissociation constant ($K_D$) of or below $10^{-7}$M, wherein said sixth ankyrin repeat domain specifically binds to human CD3 in PBS with a dissociation constant ($K_D$) of or below $10^{-6}$M, wherein said first, second, third, fourth, fifth and sixth ankyrin repeat domains are arranged, from the N-terminus to the C-terminus, according to the following formula: (first ankyrin repeat domain)-(second ankyrin repeat domain)-(fifth ankyrin repeat domain)-(fourth ankyrin repeat domain)-(third ankyrin repeat domain)-sixth ankyrin repeat domain). In one embodiment, each of said first, second, third, fourth, fifth and sixth ankyrin repeat domain specifically binds to its target (as recited above) in PBS with a dissociation constant ($K_D$) between $10^{-6}$M and $10^{-12}$M. In one embodiment, said recombinant protein binds human CD3 with an $EC_{50}$ ranging from 1 to 400 nM. In one embodiment, said recombinant protein binds Molm-13 tumor cells with an $EC_{50}$ of or below 1 nM. In one embodiment, said recombinant protein is capable of binding to CD3, CD33, CD123 and CD70 simultaneously. In one embodiment, said recombinant protein comprises a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to the amino acid sequence of SEQ ID NO: 96. In another embodiment, said recombinant protein comprises a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to the amino acid sequence of SEQ ID NO: 97. In another embodiment, said recombinant protein comprises a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to the amino acid sequence of SEQ ID NO: 98. In another embodiment, said recombinant protein comprises a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to the amino acid sequence of SEQ ID NO: 99. In another embodiment, said recombinant protein comprises a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to the amino acid sequence of SEQ ID NO: 100. In one embodiment, said recombinant protein comprises the amino acid sequence of SEQ ID NO: 96. In one embodiment, said recombinant protein comprises the amino acid sequence of SEQ ID NO: 97. In one embodiment, said recombinant protein comprises the amino acid sequence of SEQ ID NO: 98. In one embodiment, said recombinant protein comprises the amino acid sequence of SEQ ID NO: 99. In one embodiment, said recombinant protein comprises the amino acid sequence of SEQ ID NO: 100. In one embodiment, said recombinant protein further comprises at its N-terminus, a G, an S, or a GS, preferably a GS.

In one aspect the invention provides a recombinant protein comprising a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identical to the amino acid sequence of SEQ ID NO: 101, preferably wherein said protein comprises a polypeptide having the amino acid sequence of SEQ ID NO: 101.

In one aspect, the invention provides a recombinant protein comprising a first ankyrin repeat domain, a second ankyrin repeat domain, a third ankyrin repeat domain, a fourth ankyrin repeat domain, a fifth ankyrin repeat domain and a sixth ankyrin repeat domain, wherein said first ankyrin repeat domain specifically binds to human serum albumin in PBS with a dissociation constant ($K_D$) of or below $10^{-7}$M, wherein said second ankyrin repeat domain specifically binds to human serum albumin in PBS with a dissociation constant ($K_D$) of or below $10^{-7}$M, wherein said third ankyrin repeat domain specifically binds to human CD33 in PBS with a dissociation constant ($K_D$) of or below $10^{-7}$M, wherein said fourth ankyrin repeat domain specifically binds to human CD123 in PBS with a dissociation constant ($K_D$) of or below $10^{-7}$M, wherein said fifth ankyrin repeat domain specifically binds to human CD70 in PBS with a dissociation constant ($K_D$) of or below $10^{-7}$M, wherein said sixth ankyrin repeat domain specifically binds to human CD3 in PBS with a dissociation constant ($K_D$) of or below $10^{-6}$M, wherein said first, second, third, fourth, fifth and sixth ankyrin repeat domains are arranged, from the N-terminus to the C-terminus, according to the following formula: (first ankyrin repeat domain)-(second ankyrin repeat domain)-(fifth ankyrin repeat domain)-(third ankyrin repeat domain)-(fourth ankyrin repeat domain)-sixth ankyrin repeat domain). In one embodiment, each of said first, second, third, fourth, fifth and sixth ankyrin repeat domain specifically binds to its target (as recited above) in PBS with a dissociation constant ($K_D$) between $10^{-6}$M and $10^{-12}$M. In one embodiment, said recombinant protein binds human CD3 with an $EC_{50}$ ranging from 1 to 400 nM. In one embodiment, said recombinant protein binds Molm-13 tumor cells with an $EC_{50}$ of or below 1 nM. In one embodiment, said recombinant protein is capable of binding to CD3, CD33, CD123 and CD70 simultaneously. In one embodiment, said recombinant protein comprises a polypeptide having an amino acid sequence that is at least 80% identical, such as at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to the amino acid sequence of SEQ ID NO: 101. In one embodiment, said recombinant protein comprises the amino acid sequence of SEQ ID NO: 101. In one embodiment, said recombinant protein further comprises at its N-terminus, a G, an S, or a GS, preferably a GS.

The repeat domains, preferably ankyrin repeat domains, of the recombinant binding protein disclosed herein preferably comprise a N-terminal and/or a C-terminal capping module (thereafter also referred to as capping repeats or capping units). Capping modules are located at the N- and/or C-terminal end of an ankyrin repeat domain, typically forming tight tertiary interactions (i.e., tertiary structure interactions) with the ankyrin repeat module(s) in between, thereby providing a cap that shields the hydrophobic core of the ankyrin repeat domain at the side from exposure to the solvent. The N- and/or C-terminal capping modules may be derived from a capping unit or other structural unit found in a naturally occurring repeat protein adjacent to a repeat unit. Examples of capping sequences are described in International Patent Publication Nos. WO 2002/020565 and WO 2012/069655, in U.S. Patent Publication No. US2013/0296221, and by Interlandi et al., J Mol Biol. 2008 Jan. 18; 375(3):837-54. Examples of N-terminal capping modules (i.e., N-terminal capping repeats) are SEQ ID NOs: 16-22 and examples of C-terminal capping modules (i.e., C-terminal capping repeats) are SEQ ID NOs: 23-23.

In an exemplary aspect, the N-terminal capping module comprises the amino acid sequence of any one of SEQ ID NOs: 16 to 21, wherein up to 9, up to 8, up to 7, up to 6, up to 5, up to 4, up to 3, up to 2 or up to 1 amino acid(s) of any one of SEQ ID NOs: 16 to 21 are optionally exchanged by any amino acids.

In an exemplary aspect, the C-terminal capping module comprises the amino acid sequence of any one of SEQ ID NO: 23 to 31, wherein up to 9, up to 8, up to 7, up to 6, up to 5, up to 4, up to 3, up to 2 or up to 1 amino acid(s) of any one of SEQ ID NOs: 23 to 31 are optionally exchanged by any amino acids.

Advantageously, in some aspects, certain amino acid residues in the N-terminal capping module and/or the C-terminal capping module of the designed ankyrin repeat domain herein provided are altered, resulting in improved pharmacokinetic properties, including a prolonged terminal half-life, of the designed ankyrin repeat domain and of the recombinant binding proteins comprising the designed ankyrin repeat domain. The altered amino acid residues are mostly surface exposed residues. Preferably, the altered amino acids residues are the amino acid residues at positions 8 and 15 of an N terminal capping module, wherein the amino acid at position 8 is Q and the amino acid at position 15 is L and wherein the position numbers correspond to the positions in SEQ ID NO: 16, and the amino acid residues at positions 14 and 18 of a C-terminal capping module, wherein the amino acid at position 14 is R and the amino acid at position 18 is Q and wherein the position numbers correspond to the positions in SEQ ID NO: 16.

For example, an N-terminal capping module with altered amino acid residues can comprise the following sequence: DLGxxLLQAAxxGQLDxVRxLxxxGADVNA (SEQ ID NO: 22), wherein "x" denotes any amino acid.

For example, a C-terminal capping module with altered amino acid residues can comprise the following sequence: xDxxGxTPADxAARxGHQxIAxVLQxAA (SEQ ID NO: 32), wherein "x" denotes any amino acid.

Accordingly, in one aspect, the ankyrin repeat domain with binding specificity for CD3 of the invention comprises an N-terminal capping module having the amino acid sequence of SEQ ID NO: 22, wherein "x" denotes any amino acid. Alternatively, or additionally, the ankyrin repeat domain with binding specificity for CD3 of the invention may comprise a C-terminal capping module having the amino acid sequence of SEQ ID NO: 32, wherein "x" denotes any amino acid.

Furthermore, a binding domain of the invention may optionally further comprise a "G," an "S," or a "GS" sequence at its N-terminus. Accordingly, in some aspects, a binding protein provided herein (i) comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any one of SEQ ID NOs: 1 to 6, 15, 64 to 70 and (ii) further comprises at its N-terminus, a G, an S, or a GS. In an exemplary aspect, binding protein comprises an amino acid sequence that is at least 90% identical to any one of SEQ ID NOs: 1 to 6, 15, 64 to 70 and further comprises at its N-terminus, a G, an S, or a GS. In an exemplary aspect, said binding protein comprises an amino acid sequence that is at least 95% identical to any one of SEQ ID NOs: 1 to 6, 15, 64 to 70, and further comprises at its N-terminus, a G, an S, or a GS. In an exemplary aspect, said binding protein comprises the amino acid sequence of any one of SEQ ID NOs: 1 to 6, 15, 64 to 70 and further comprises at its N-terminus, a G, an S, or a GS.

In one aspect, the recombinant binding protein of the invention further comprises a polypeptide tag. A polypeptide tag is an amino acid sequence attached to a polypeptide/protein, wherein said amino acid sequence is useful for the purification, detection, or targeting of said polypeptide/protein, or wherein said amino acid sequence improves the physicochemical behavior of the polypeptide/protein, or wherein said amino acid sequence possesses an effector function. The individual polypeptide tags of a binding protein may be connected to other parts of the binding protein directly or via a peptide linker. Polypeptide tags are all well known in the art and are fully available to the person skilled in the art. Examples of polypeptide tags are small polypeptide sequences, for example, His, HA, myc, FLAG, or Strep-tags, or polypeptides such as enzymes (for example alkaline phosphatase), which allow the detection of said polypeptide/protein, or polypeptides which can be used for targeting (such as immunoglobulins or fragments thereof) and/or as effector molecules.

In one aspect, the recombinant binding protein of the invention further comprises a peptide linker. A peptide linker is an amino acid sequence, which is able to link, for example, two protein domains, a polypeptide tag and a protein domain, a protein domain and a non-proteinaceous compound or polymer such as polyethylene glycol, a protein domain and a biologically active molecule, a protein domain and a localizer, or two sequence tags. Peptide linkers are known to the person skilled in the art. A list of examples is provided in the description of patent application WO2002/020565. In one aspect, peptide linkers for use in the present invention have a length from 1 to 50 amino acids. In another aspect, peptide linkers for use in the present invention have a length from 1 to 30 amino acids. Particular examples of peptide linkers are glycine-serine-linkers and proline-threonine rich linkers of variable lengths. Examples of a glycine-serine-linker are the amino acid sequence GS and the amino acid sequence of SEQ ID NO: 63, and an example of a proline-threonine rich linker is the amino acid sequence of SEQ ID NO: 37.

In the context of the present invention a proline-threonine rich linker comprises at least 20% proline residues and at least 20% threonine residues in its amino acid sequence.

In another aspect, the invention relates to a nucleic acid encoding the amino acid sequence of an ankyrin repeat domain or a recombinant protein of the present invention. In one aspect, the invention relates to a nucleic acid encoding the amino acid sequence of a recombinant protein of the present invention. In one aspect, the invention relates to a nucleic acid encoding an amino acid sequence selected from the group consisting of SEQ ID NO: 7 to 10, and 58 to 62. In one aspect, the invention relates to a nucleic acid encoding the amino acid sequence of SEQ ID NO: 7. In one aspect, the invention relates to a nucleic acid encoding the amino acid sequence of SEQ ID NO: 8. In one aspect, the invention relates to a nucleic acid encoding the amino acid sequence of SEQ ID NO: 9. In one aspect, the invention relates to a nucleic acid encoding the amino acid sequence of SEQ ID NO: 10. In one aspect, the invention relates to a nucleic acid encoding the amino acid sequence of SEQ ID NO: 58. In one aspect, the invention relates to a nucleic acid encoding the amino acid sequence of SEQ ID NO: 59. In one aspect, the invention relates to a nucleic acid encoding the amino acid sequence of SEQ ID NO: 60. In one aspect, the invention relates to a nucleic acid encoding the amino acid sequence of SEQ ID NO: 61. In one aspect, the invention relates to a nucleic acid encoding the amino acid sequence of SEQ ID NO: 62. Furthermore, the invention relates to vectors comprising any nucleic acid of the invention. Nucleic acids are well known to the skilled person in the art. In the examples, nucleic acids were used to produce designed ankyrin repeat domains or recombinant binding proteins of the invention in *E. coli*. Examples nucleic acids of the invention are provided by SEQ ID NOs: 52 to 55 and 90 to 94 which encode the amino acid sequences of SEQ ID NOs: 7 to 10 and 58 to 62, respectively.

In another aspect, the invention relates to a nucleic acid encoding the amino acid sequence of an ankyrin repeat domain or a recombinant protein of the present invention. In one aspect, the invention relates to a nucleic acid encoding the amino acid sequence of a recombinant protein of the present invention. In one aspect, the invention relates to a nucleic acid encoding an amino acid sequence selected from the group consisting of SEQ ID NO: 11 to 14, 78 to 86 and 95 to 101. In one aspect, the invention relates to a nucleic acid encoding the amino acid sequence of SEQ ID NO: 11. In one aspect, the invention relates to a nucleic acid encoding the amino acid sequence of SEQ ID NO: 12. In one aspect, the invention relates to a nucleic acid encoding the amino acid sequence of SEQ ID NO: 13. In one aspect, the invention relates to a nucleic acid encoding the amino acid sequence of SEQ ID NO: 14. In one aspect, the invention relates to a nucleic acid encoding the amino acid sequence of SEQ ID NO: 78. In one aspect, the invention relates to a nucleic acid encoding the amino acid sequence of SEQ ID NO: 79. In one aspect, the invention relates to a nucleic acid encoding the amino acid sequence of SEQ ID NO: 80. In one aspect, the invention relates to a nucleic acid encoding the amino acid sequence of SEQ ID NO: 81. In one aspect, the invention relates to a nucleic acid encoding the amino acid sequence of SEQ ID NO: 82. In one aspect, the invention relates to a nucleic acid encoding the amino acid sequence of SEQ ID NO: 83. In one aspect, the invention relates to a nucleic acid encoding the amino acid sequence of SEQ ID NO: 84. In one aspect, the invention relates to a nucleic acid encoding the amino acid sequence of SEQ ID NO: 85. In one aspect, the invention relates to a nucleic acid encoding the amino acid sequence of SEQ ID NO: 86. In one aspect, the invention relates to a nucleic acid encoding the amino acid sequence of SEQ ID NO: 95. In one embodiment, said nucleic acid encoding the amino acid sequence of SEQ ID NO: 95 is the nucleic acid of SEQ ID NO: 118. In one aspect, the invention relates to a nucleic acid encoding the amino acid sequence of SEQ ID NO: 96. In one embodiment, said nucleic acid encoding the amino acid sequence of SEQ ID NO: 96 is the nucleic acid of SEQ ID NO: 119. In one aspect, the invention relates to a nucleic acid encoding the amino acid sequence of SEQ ID NO: 97. In one embodiment, said nucleic acid encoding the amino acid sequence of SEQ ID NO: 97 is the nucleic acid of SEQ ID NO: 120. In one aspect, the invention relates to a nucleic acid encoding the amino acid sequence of SEQ ID NO: 98. In one embodiment, said nucleic acid encoding the amino acid sequence of SEQ ID NO: 98 is the nucleic acid of SEQ ID NO: 121. In one aspect, the invention relates to a nucleic acid encoding the amino acid sequence of SEQ ID NO: 99. In one embodiment, said nucleic acid encoding the amino acid sequence of SEQ ID NO: 99 is the nucleic acid of SEQ ID NO: 122. In one aspect, the invention relates to a nucleic acid encoding the amino acid sequence of SEQ ID NO: 100. In one embodiment, said nucleic acid encoding the amino acid sequence of SEQ ID NO: 100 is the nucleic acid of SEQ ID NO: 123. In one aspect, the invention relates to a nucleic acid encoding the amino acid sequence of SEQ ID NO: 101. In one embodiment, said nucleic acid encoding the amino acid sequence of SEQ ID NO: 101 is the nucleic acid of SEQ ID NO: 124. Furthermore, the invention relates to vectors comprising any nucleic acid of the invention. Nucleic acids are well known to the skilled person in the art. In the examples, nucleic acids were used to produce designed ankyrin repeat domains or recombinant binding proteins of the invention in E. coli. Examples nucleic acids of the invention are provided by SEQ ID NOs: 118 to 124 and which encode the amino acid sequences of SEQ ID NOs: 95 to 101, respectively.

In one aspect, the invention relates to a pharmaceutical composition comprising a recombinant binding protein and/or a designed ankyrin repeat domain of the present invention, and/or a nucleic acid encoding a recombinant binding protein and/or a designed ankyrin repeat domain of the present invention, and optionally a pharmaceutically acceptable carrier and/or diluent.

In one aspect, the invention relates to a pharmaceutical composition comprising a recombinant binding protein or a nucleic acid encoding a recombinant binding protein of the present invention, and optionally a pharmaceutically acceptable carrier and/or diluent.

Pharmaceutically acceptable carriers and/or diluents are known to the person skilled in the art and are explained in more detail below.

A pharmaceutical composition comprises a recombinant binding protein, and/or a designed ankyrin repeat domain, and/or a nucleic acid, preferably a recombinant binding protein and/or a nucleic acid, as described herein and a pharmaceutically acceptable carrier, excipient or stabilizer, for example as described in Remington's Pharmaceutical Sciences 16th edition, Osol, A. Ed., 1980.

Suitable carriers, diluents, excipients or stabilizers known to one of skill in the art include, for example, saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. A pharmaceutical composition may also be a combination formulation, comprising an additional active agent, such as an anti-cancer agent or an anti-angiogenic agent, or an additional bioactive compound. The compositions to be used for in vivo administration must be aseptic or sterile. This is readily accomplished by filtration through sterile filtration membranes.

One aspect of the present invention relates to the use of a recombinant protein of the present invention comprising an first ankyrin repeat domain with binding specificity for CD3, a second ankyrin repeat domain with binding specificity for TAA1, preferably CD33, a third ankyrin repeat domain with binding specificity for TAA2, preferably CD123 and/or a fourth repeat domain with binding specificity for TAA3, preferably CD70 and further comprising an ankyrin repeat domain with binding specificity for human serum albumin for manufacturing a pharmaceutical composition, wherein said recombinant protein exhibits an increased terminal half-life, preferably an increased terminal half-life of at least about 5%, preferably at least about 10%, about 15%, about 20%, about 25%, about 30%, about 35%, about 40%, about 45%, about 50%, about 60%, about 70%, about 80%, about 90%, about 100%, about 150%, about 200%, or about 250%, compared to a corresponding recombinant protein comprising said first, second and third ankyrin repeat domain but not said ankyrin repeat domain with binding specificity for serum albumin.

In one aspect, a pharmaceutical composition comprises at least one recombinant protein as described herein and a detergent such as nonionic detergent, a buffer such as phosphate buffer, and a sugar such as sucrose. In one aspect, such a composition comprises recombinant binding proteins as described above and PBS.

In another aspect, the invention provides a method of tumor-localized activation of T cells in a mammal, including a human, the method comprising the step of administering to said mammal the recombinant protein of the invention, the nucleic acid of the invention or the pharmaceutical composition of the invention.

In another aspect, the invention provides a method of treating a medical condition, the method comprising the step of administering to a patient in need thereof a therapeutically effective amount of the recombinant protein of the invention, the nucleic acid of the invention or the pharmaceutical composition of the invention.

In another aspect, the invention provides a method of treating a medical condition, the method comprising the step of administering to a patient in need thereof a therapeutically effective amount of the inventive recombinant protein further comprising a binding agent with binding specificity for a disease-associated antigen, a nucleic acid encoding said binding protein or a pharmaceutical composition comprising said binding protein.

In one aspect, the invention relates to a pharmaceutical composition, a recombinant protein, or a nucleic acid according to the present invention for use in the treatment of a disease. For that purpose, the pharmaceutical composition, the nucleic acid or the recombinant binding protein according to the present invention is administered, to a patient in need thereof, in a therapeutically effective amount. Administration may include topical administration, oral administration, and parenteral administration. The typical route of administration is parenteral administration. In parental administration, the pharmaceutical composition of this invention will be formulated in a unit dosage injectable form such as a solution, suspension or emulsion, in association with the pharmaceutically acceptable excipients as defined above. The dosage and mode of administration will depend on the individual to be treated and the particular disease.

Further, any of the above-mentioned pharmaceutical composition, nucleic acid or recombinant protein is considered for use in the treatment of a disorder.

In one aspect, said recombinant binding protein or such other pharmaceutical composition described herein is applied intravenously. For parenteral application, the recombinant protein or said pharmaceutical composition can be injected as bolus injection or by slow infusion at a therapeutically effective amount.

In one aspect, the invention relates to the use of the recombinant protein of the invention, the nucleic acid of the invention or the pharmaceutical composition of the invention, as medicament for the treatment of a disease. In one aspect, the invention relates to the use of the recombinant protein of the invention, the nucleic acid of the invention or the pharmaceutical composition of the invention for manufacturing of a medicament. In one aspect, the invention relates to the use of the recombinant protein of the invention, the nucleic acid of the invention or the pharmaceutical composition of the invention, for manufacturing of a medicament for the treatment of a disease. In one aspect, the invention relates to a process for the manufacturing of a medicament for the treatment of a disease, wherein the recombinant protein of the invention, the nucleic acid of the invention or the pharmaceutical composition of the invention is an active ingredient of the medicament. In one aspect, the invention relates to a method of treatment of a disease using the recombinant protein of the invention, the nucleic acid of the invention or the pharmaceutical composition of the invention.

In one aspect the invention further provides a use of such a recombinant protein for treating a medical condition of a subject in need thereof.

As used herein, said medical condition or disease is a cancer, preferably a liquid tumor, more preferably leukemia, even more preferably acute myeloid leukemia (AML).

The recombinant protein of the present invention, nucleic acid of the invention or a pharmaceutical composition of the invention can also be used in combination with one or more other therapies known in the art. The term "use in combination with", as used herein, shall refer to a co-administration, which is carried out under a given regimen. This includes synchronous administration of the different compounds as well as time-shifted administration of the different compounds (e.g., compound A is given once and compound B is given several times thereafter, or vice versa, or both compounds are given synchronously and one of the two is also given at later stages).

In one aspect, the invention relates to a kit comprising the recombinant protein of the invention. In one aspect, the invention relates to a kit comprising a nucleic acid encoding the recombinant protein of the invention. In one aspect, the invention relates to a kit comprising the pharmaceutical composition of the invention. In one aspect, the invention relates to a kit comprising the recombinant protein of the invention, and/or the nucleic acid of the invention, and/or the pharmaceutical composition of the invention. In one aspect, the invention relates to a kit comprising a recombinant protein of the invention, said recombinant protein comprising anyone of the SEQ ID NOs: 7 to 10 and 58 to 62 and/or a nucleic acid encoding said recombinant protein comprising anyone of the SEQ ID NOs: 52 to 55 and 90 to 94, and/or a pharmaceutical composition comprising a recombinant protein comprising anyone of the SEQ ID NOs: 7 to 10 and 58 to 62. In one aspect, the invention relates to a kit comprising the recombinant protein comprising any one of the amino acid sequences of SEQ ID NOs: 7 to 10 and 58 to 62 and/or a nucleic acid encoding said recombinant protein, and/or a pharmaceutical composition comprising the recombinant protein.

In one aspect, the invention relates to a kit comprising the recombinant protein of the invention. In one aspect, the invention relates to a kit comprising a nucleic acid encoding the recombinant protein of the invention. In one aspect, the invention relates to a kit comprising the pharmaceutical composition of the invention. In one aspect, the invention relates to a kit comprising the recombinant protein of the invention, and/or the nucleic acid of the invention, and/or the pharmaceutical composition of the invention. In one aspect, the invention relates to a kit comprising a recombinant protein of the invention, said recombinant protein comprising anyone of the SEQ ID NOs: 11 to 14, 78 to 82 and 95 to 101 and/or a nucleic acid encoding said recombinant protein comprising anyone of the SEQ ID NOs: 118 to 124, and/or a pharmaceutical composition comprising a recombinant protein comprising anyone of the SEQ ID NOs: 11 to 14, 78 to 82 and 95 to 101. In one aspect, the invention relates to a kit comprising the recombinant protein comprising any one of the amino acid sequences of SEQ ID NOs: 11 to 14, 78 to 82 and 95 to 101 and/or a nucleic acid encoding said recombinant protein, and/or a pharmaceutical composition comprising the recombinant protein.

In one aspect, the invention relates to a method for producing a recombinant protein of the present invention. In one aspect, the invention relates to a method for producing a recombinant binding protein, for example a recombinant protein comprising the amino acid sequence of SEQ ID NOs: 7 to 10 and 58 to 62, the method comprising the steps of (i) expressing said recombinant binding protein in a suitable host cell (e.g., bacteria), and (ii) purifying said recombinant binding protein (e.g., using chromatography). Said method may comprise additional steps. Such a method of producing a recombinant binding protein of the present invention is described in Example 1.

In one aspect, the invention relates to a method for producing a recombinant protein of the present invention. In one aspect, the invention relates to a method for producing a recombinant binding protein, for example a recombinant protein comprising the amino acid sequence of SEQ ID NOs: 11 to 14, 78 to 82 and 95 to 101, the method comprising the steps of (i) expressing said recombinant binding protein in a suitable host cell (e.g., bacteria), and (ii) purifying said recombinant binding protein (e.g., using chromatography). Said method may comprise additional steps. Such a method of producing a recombinant binding protein of the present invention is described in Example 1.

All of the amino acid sequences described herein may be substituted by one or more amino acids. In some aspects, up to 15, up to 14, up to 13, up to 12, up to 11, up to 10, up to 9, up to 8, up to 7, up to 6, up to 5, up to 4, up to 3, up to 2, or up to 1 substitution is made in any of the amino acid sequences described herein.

In some aspects, the amino acid substitution(s) are all made in framework positions. In some aspects, the amino acid substitution(s) are all made in non-randomized positions. The location of randomized positions in a designed ankyrin repeat domain is disclosed, e.g., in Binz et al., Nature Biotech. 22(5): 575-582 (2004).

In some aspects, amino acid substitution(s) made to the binding agents do not change the KD value by more than about 1000-fold, more than about 100-fold, or more than about 10-fold, compared to the KD value of the unsubstituted binding agents. For example, in some aspects, the amino acid substitution(s) do not change the $K_D$ value by more than about 1000-fold, more than about 300-fold, more than about 100-fold, more than about 50-fold, more than about 25-fold, more than about 10-fold, or more than about 5-fold, compared to the $K_D$ value of the binding agent comprising any of the sequences of SEQ ID NOs:7 to 10 and 58 to 62.

In certain aspects, the amino acid substitution in the binding moiety is a conservative substitution according to Table 1 below.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |

TABLE 1-continued

Amino Acid Substitutions

| Original Residue | Conservative Substitutions | Exemplary Substitutions |
|---|---|---|
| Lys (K) | Arg | Arg; Gln; Asn |
| Met (M) | Leu | Leu; Phe; Ile |
| Phe (F) | Tyr | Leu; Val; Ile; Ala; Tyr |

When the binding agent is an ankyrin repeat domain, in some aspects, the substitution may be made outside the structural core residues of the ankyrin repeat domain, e.g., in the beta loops that connect the alpha-helices. In other aspects, the substitution may be made within the structural core residues of the ankyrin repeat domain. For example, the ankyrin domain may comprise the consensus sequence: xDxxGxTPLHLAxxxGxxxIVxVLLxxGADVNA, wherein "x" denotes any amino acid (preferably not cysteine, glycine, or proline); or xDxxGxTPLH-LAAxxGHLEIVEVLLKzGADVNA, wherein "x" denotes any amino acid (preferably not cysteine, glycine, or proline), and "z" is selected from the group consisting of asparagine, histidine, or tyrosine. In one aspect, the substitution is made to residues designated as "x". In another aspects, the substitution is made outside the residues designated as "x".

The invention is not restricted to the particular aspects described in the Examples. This specification refers to a number of amino acid sequences, nucleic acid sequences and SEQ ID NOs that are disclosed in the appended Sequence Listing, which is herewith incorporated by reference in its entirety.

Definitions

Unless defined otherwise herein, all technical and scientific terms used herein shall have the meanings that are commonly understood by those of ordinary skill in the art to which the present invention belongs. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry described herein are those well-known and commonly used in the art.

The terms "comprising", "having", "including" and "containing" are to be construed as open-ended terms unless otherwise noted. If aspects of the invention are described as "comprising" a feature, aspects also are contemplated "consisting of" or "consisting essentially of" the feature. The use of any and all examples, or exemplary language (e.g., "such as") provided herein, is intended merely to better illustrate the disclosure and does not pose a limitation on the scope of the disclosure unless otherwise claimed. No language in the specification should be construed as indicating any non-claimed element as essential to the practice of the disclosure. Other than in the operating examples, or where otherwise indicated, all numbers expressing quantities of ingredients or reaction conditions used herein should be understood as modified in all instances by the term "about" as that term would be interpreted by the person skilled in the relevant art. The term "about" as used herein is equivalent to ±10% of a given numerical value, unless otherwise stated.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

In the context of the present invention the term "protein" refers to a molecule comprising a polypeptide, wherein at least part of the polypeptide has, or is able to acquire, a defined three-dimensional arrangement by forming secondary, tertiary, and/or quaternary structures within a single polypeptide chain and/or between multiple polypeptide chains. If a protein comprises two or more polypeptide chains, the individual polypeptide chains may be linked non-covalently or covalently, e.g., by a disulfide bond between two polypeptides. A part of a protein, which individually has, or is able to acquire, a defined three-dimensional arrangement by forming secondary and/or tertiary structure, is termed "protein domain". Such protein domains are well known to the practitioner skilled in the art.

The term "recombinant" as used in recombinant protein, recombinant polypeptide and the like, means that said protein or polypeptide is produced by the use of recombinant DNA technologies well known to the practitioner skilled in the art. For example, a recombinant DNA molecule (e.g., produced by gene synthesis) encoding a polypeptide can be cloned into a bacterial expression plasmid (e.g., pQE30, QIAgen), yeast expression plasmid, mammalian expression plasmid, or plant expression plasmid, or a DNA enabling in vitro expression. If, for example, such a recombinant bacterial expression plasmid is inserted into appropriate bacteria (e.g., *Escherichia coli*), these bacteria can produce the polypeptide(s) encoded by this recombinant DNA. The correspondingly produced polypeptide or protein is called a recombinant polypeptide or recombinant protein.

In the context of the present invention, the term "binding protein" refers to a protein comprising a binding domain. A binding protein may also comprise two, three, four, five or more binding domains. Preferably, said binding protein is a recombinant binding protein. Binding proteins of the instant invention comprise an ankyrin repeat domain with binding specificity for CD3, an ankyrin repeat domain with binding specificity for CD33 and an ankyrin repeat domain with binding specificity for CD123.

Furthermore, any such binding protein may comprise additional polypeptides (such as e.g., polypeptide tags, peptide linkers, fusion to other proteinaceous domains with binding specificity, cytokines, hormones, or antagonists), or chemical modifications (such as coupling to polyethyleneglycol, toxins (e.g., DM1 from Immunogen), small molecules, antibiotics and alike) well known to the person skilled in the art. A binding protein of the instant invention may comprise a localizer molecule.

The term "binding domain" means a protein domain exhibiting binding specificity for a target. Preferably, said binding domain is a recombinant binding domain.

The term "target" refers to an individual molecule such as a nucleic acid molecule, a polypeptide or protein, a carbohydrate, or any other naturally occurring molecule, including any part of such individual molecule, or to complexes of two or more such molecules, or to a whole cell or a tissue sample, or to any non-natural compound. Preferably, a target is a naturally occurring or non-natural polypeptide or protein, or a polypeptide or protein containing chemical modifications, for example, naturally occurring or non-natural phosphorylation, acetylation, or methylation. In the context of the present invention, T cells are targets of CD3-specific binding proteins and localizer target proteins and cells and tissues are targets of localizers.

In the context of the present invention, the term "polypeptide" relates to a molecule consisting of a chain of multiple, i.e., two or more, amino acids linked via peptide bonds. Preferably, a polypeptide consists of more than eight amino acids linked via peptide bonds. The term "polypeptide" also includes multiple chains of amino acids, linked together by S—S bridges of cysteines. Polypeptides are well-known to the person skilled in the art.

Patent application WO2002/020565 and Forrer et al., 2003 (Forrer, P., Stumpp, M. T., Binz, H. K., Plückthun, A., 2003. FEBS Letters 539, 2-6), contain a general description of repeat protein features and repeat domain features, techniques and applications. The term "repeat protein" refers to a protein comprising one or more repeat domains. Preferably, a repeat protein comprises one, two, three, four, five or six repeat domains. Furthermore, said repeat protein may comprise additional non-repeat protein domains, polypeptide tags and/or peptide linkers. The repeat domains can be binding domains.

The term "repeat domain" refers to a protein domain comprising two or more consecutive repeat modules as structural units, wherein said repeat modules have structural and sequence homology. Preferably, a repeat domain further comprises an N-terminal and/or a C-terminal capping module. For clarity, a capping module can be a repeat module. Such repeat domains, repeat modules, and capping modules, sequence motives, as well as structural homology and sequence homology are well known to the practitioner in the art from examples of ankyrin repeat domains (WO2002/020565), leucine-rich repeat domains (WO2002/020565), tetratricopeptide repeat domains (Main, E. R., Xiong, Y., Cocco, M. J., D'Andrea, L., Regan, L., Structure 11(5), 497-508, 2003), and armadillo repeat domains (WO2009/040338). It is further well known to the practitioner in the art, that such repeat domains are different from proteins comprising repeated amino acid sequences, where every repeated amino acid sequence is able to form an individual domain (for example FN3 domains of Fibronectin).

The term "ankyrin repeat domain" refers to a repeat domain comprising two or more consecutive ankyrin modules as structural units. Ankyrin repeat domains may be modularly assembled into larger ankyrin repeat proteins, optionally with half-life extension domains, using standard recombinant DNA repeat technologies (see, e.g., Forrer, P., et al., FEBS letters 539, 2-6, 2003, WO2002/020565, WO2016/156596, WO2018/054971).

The term "designed" as used in designed repeat protein, designed repeat domain and the like refers to the property that such repeat proteins and repeat domains, respectively, are man-made and do not occur in nature. The binding proteins of the instant invention are designed repeat proteins and they comprise at least one designed ankyrin repeat domain. Preferably, the designed repeat domain is a designed ankyrin repeat domain.

The term "target interaction residues" refers to amino acid residues of a repeat module, which contribute to the direct interaction with a target.

The term "framework residues" refers to amino acid residues of a repeat module, which contribute to the folding topology, i.e. which contribute to the fold of said repeat module or which contribute to the interaction with a neighboring module. Such contribution may be the interaction with other residues in the repeat module, or the influence on the polypeptide backbone conformation as found in α-helices or □-sheets, or the participation in amino acid stretches forming linear polypeptides or loops. Such framework and target interaction residues may be identified by analysis of the structural data obtained by physicochemical methods, such as X-ray crystallography, NMR and/or CD spectroscopy, or by comparison with known and related structural information well known to practitioners in structural biology and/or bioinformatics.

The term "repeat modules" refers to the repeated amino acid sequence and structural units of the designed repeat domains, which are originally derived from the repeat units of naturally occurring repeat proteins. Each repeat module comprised in a repeat domain is derived from one or more repeat units of a family or subfamily of naturally occurring repeat proteins, e.g., the family of ankyrin repeat proteins. Furthermore, each repeat module comprised in a repeat domain may comprise a "repeat sequence motif" deduced from homologous repeat modules obtained from repeat domains selected on a target, e.g., as described in Example 1, and having the same target specificity.

Accordingly, the term "ankyrin repeat module" refers to a repeat module, which is originally derived from the repeat units of naturally occurring ankyrin repeat proteins. Ankyrin repeat proteins are well known to the person skilled in the art. Designed ankyrin repeat proteins have been described previously; see, e.g., International Patent Publication Nos. WO2002/020565, WO2010/060748, WO2011/135067, WO2012/069654, WO2012/069655, WO2014/001442, WO2014/191574, WO2014/083208, WO2016/156596, and WO2018/054971, all of which are incorporated by reference in their entireties. Typically, an ankyrin repeat module comprises about 31 to 33 amino acid residues that form two alpha helices, separated by loops.

Repeat modules may comprise positions with amino acid residues which have not been randomized in a library for the purpose of selecting target-specific repeat domains ("non-randomized positions") and positions with amino acid residues which have been randomized in the library for the purpose of selecting target-specific repeat domains ("randomized positions"). The non-randomized positions comprise framework residues. The randomized positions comprise target interaction residues. "Have been randomized" means that two or more amino acids were allowed at an amino acid position of a repeat module, for example, wherein any of the usual twenty naturally occurring amino acids were allowed, or wherein most of the twenty naturally occurring amino acids were allowed, such as amino acids other than cysteine, or amino acids other than glycine, cysteine and proline.

The term "repeat sequence motif" refers to an amino acid sequence, which is deduced from one or more repeat modules. Preferably, said repeat modules are from repeat domains having binding specificity for the same target. Such repeat sequence motifs comprise framework residue positions and target interaction residue positions. Said framework residue positions correspond to the positions of framework residues of the repeat modules. Likewise, said target interaction residue positions correspond to the positions of target interaction residues of the repeat modules. Repeat sequence motifs comprise non-randomized positions and randomized positions.

The term "repeat unit" refers to amino acid sequences comprising sequence motifs of one or more naturally occurring proteins, wherein said "repeat units" are found in multiple copies, and exhibit a defined folding topology common to all said motifs determining the fold of the protein. Examples of such repeat units include leucine-rich repeat units, ankyrin repeat units, armadillo repeat units, tetratricopeptide repeat units, HEAT repeat units, and leucine-rich variant repeat units.

The term "has binding specificity for a target", "specifically binding to a target", "binding to a target with high specificity", "specific for a target", "target specificity", or "specifically binds" and the like means that a binding protein or binding domain binds in PBS to a target with a lower dissociation constant (i.e., it binds with higher affinity) than it binds to an unrelated protein such as the *E. coli* maltose binding protein (MBP). Preferably, the dissociation constant ("$K_D$") in PBS for the target is at least 102; more preferably, at least 103; more preferably, at least 104; or more preferably, at least 105 times lower than the corresponding dissociation constant for MBP. Methods to determine dissociation constants of protein-protein interactions, such as surface plasmon resonance (SPR) based technologies (e.g., SPR equilibrium analysis) or isothermal titration calorimetry (ITC) are well known to the person skilled in the art. The measured $K_D$ values of a particular protein-protein interaction can vary if measured under different conditions (e.g., salt concentration, pH). Thus, measurements of $K_D$ values are preferably made with standardized solutions of protein and a standardized buffer, such as PBS. A typical and preferred determination of dissociation constants ($K_D$) of the inventive recombinant binding proteins with binding specificity for CD3, CD33 and CD123 by Surface Plasmon Resonance (SPR) analysis is described in Example 4. A variety of assay formats may be used to select or characterize a binding moiety that specifically binds a drug molecule of interest. For example, solid-phase ELISA immunoassay, immunoprecipitation, BIAcore™ (GE Healthcare, Piscataway, N.J.), fluorescence-activated cell sorting (FACS), Octet™ (ForteBio, Inc., Menlo Park, Calif.) and Western blot analysis are among many assays that may be used to identify a binding moiety that specifically binds to a target drug molecule. Typically, a specific or selective binding will be at least twice the background signal or noise and more typically more than 10 times the background signal. More particularly, a binding agent is said to "specifically bind" a target when the equilibrium dissociation constant ($K_D$) value is <1 µM, such as <500 nM, <100 nM, <10 nM, <1 nM, <100 pM or <10 pM.

The term "binding agent" refers to any molecule capable of specifically binding a target molecule. Binding agents include, for example, antibodies, antibody fragments, aptamers, peptides (e.g., Williams et al., J Biol Chem 266:5182-5190 (1991)), antibody mimics, repeat proteins, e.g., designed ankyrin repeat proteins, receptor proteins and any other naturally occurring interaction partners of the target molecule, and can comprise natural proteins and proteins modified or genetically engineered, e.g., to include non-natural residues and/or to lack natural residues.

The term "PBS" means a phosphate buffered water solution containing 137 mM NaCl, 10 mM phosphate and 2.7 mM KCl and having a pH of 7.4.

The term "tumor associated antigen" or TAA as used herein refers to antigens found on tumor cells that are not qualitatively different in structure from antigens found on normal cells. However, tumor associated antigens are found on the surface of tumor cells in greater numbers than on the surface of most healthy cells. Tumor associated antigens can be specific to a tumor type but can also be expressed in several tumor types. For example, the TAA MUC1 has been associated with colon, breast, ovarian, lung and pancreatic cancers.

The term "mouse serum albumin" refers to UniProt accession number P07724, the term "cynomolgus monkey serum albumin" (i.e. *Macaca fascicularis*) refers to UniProt accession number A2V9Z4, and the term "human serum albumin" refers to UniProt accession number P02768.

Preferably, clearance, and/or exposure, and/or terminal half-life are assessed in a mammal, more preferably mouse and/or cynomolgus monkey, more preferably cynomolgus monkey. Preferably, when measuring the clearance, and/or exposure, and/or terminal half-life in mouse, the evaluation is done considering the data up to 48 h post-injection. More preferably, the evaluation of terminal half-life in mouse is calculated from 24 h to 48 h. Preferably, when measuring the clearance, and/or exposure, and/or terminal half-life in cynomolgus monkey, the evaluation is done considering the data up to day 7 post-injection. More preferably, the evaluation of terminal half-life in cynomolgus monkey is calculated from day 1 to day 5. The person skilled in the art further is able to identify effects such as target-mediated clearance and consider them when calculating the terminal half-life. The term "terminal half-life" of a drug such as a recombinant binding protein of the invention refers to the time required to reach half the plasma concentration of the drug applied to a mammal after reaching pseudo-equilibrium (for example calculated from 24 hours to 48 hours in mouse or calculated from day 1 to day 5 in cynomolgus monkey). Terminal half-life is not defined as the time required to eliminate half the dose of the drug administered to the mammal. The term terminal half-life is well known to the person skilled in the art. Preferably, pharmacokinetic comparison is done at any dose, more preferably at equivalent dose (i.e., same mg/kg dose) or equimolar dose (i.e., same mol/kg dose), more preferably at equimolar dose (i.e., same mol/kg dose). It is understood by the person skilled in the art that equivalent and/or equimolar dosing in animals is subject to experimental dose variations of at least about 20%, more preferably about 30%, about 40%, about 50%, about 60%, about 70%, about 80%, about 90%, or about 100%. Preferably, a dose used for pharmacokinetic measurement is selected from about 0.001 to about 1000 mg/kg, more preferably about 0.01 to about 100 mg/kg, more preferably about 0.1 to about 50 mg/kg, more preferably about 0.5 to about 10 mg/kg.

The term "CD3" or "Cluster of Differentiation 3" refers to a multimeric protein complex composed of four distinct polypeptide chains, epsilon (ε), gamma (γ) and zeta (ζ) that assemble as three pairs (εγ, εδ, ζζ). The CD3 complex serves as a T cell co-receptor that associates non-covalently with the T cell receptor. It may refer to any form of CD3, as well as to variants, isoforms, and species homologs thereof that retain at least a part of the activity of CD3. Accordingly, a binding protein, as defined and disclosed herein, may also bind CD3 from species other than human. In other cases, a binding protein may be completely specific for the human CD3 and may not exhibit species or other types of cross-reactivity. Unless indicated differently, such as by specific reference to human CD3, CD3 includes all mammalian species of native sequence CD3, e.g., human, canine, feline, equine and bovine. The amino acid sequences of human CD3 gamma, delta and zeta chains are shown in NCBI (www.ncbi.nlm.nih.gov/) Ref. Seq. NP_000064.1, NP_000723.1 and NP_932170.1 respectively.

The term "CD3-expressing cells" as used herein refers to any cells expressing CD3 (cluster of differentiation 3) on the cell surface, including, but not limited, to T cells such as cytotoxic T cells (CD8+ T cells) and T helper cells (CD4+ T cells).

The term "CD33" refers to myeloid cell surface antigen CD33, which is a sialic-acid-binding immunoglobulin-like lectin (Siglec) that plays a role in mediating cell-cell interactions and in maintaining immune cells in a resting state. The amino acid sequence of human CD33 (hCD33) is shown in UniProt (www.uniprot.org) Ref. No. P20138.

The term "CD70" refers to the CD70 antigen, which is a cytokine that functions as the ligand for CD27. The CD70-CD27 pathway plays an important role in the generation and maintenance of T cell immunity, in particular during antiviral responses. The amino acid sequence of human CD70 (hCD70) is shown in UniProt (www.uniprot.org) Ref. No. P32970.

The term "CD123" refers to the interleukin-3 receptor subunit alpha. This is a receptor for interleukin-3. The amino acid sequence of human CD123 (hCD123) is shown in UniProt (www.uniprot.org) Ref. No. P26951.

The term "tumor-localized activation of T cells" means that T cells are activated preferentially in tumor tissue as compared to a non-tumor tissue.

Furthermore, the term "peptide" also encompasses peptides modified by, e.g., glycosylation, and proteins comprising two or more polypeptide chains, each of length of 4 to 600 amino acids long, cross-linked by, e.g., disulfide bonds, such as, e.g., insulin and immunoglobulins. The term "chemical or biochemical agent" is intended to include any naturally occurring or synthetic compound that may be administered to a recipient. In a preferred aspect, the localizer is a target-specific ankyrin repeat domain.

The term "medical condition" (or disorder or disease) includes autoimmune disorders, inflammatory disorders, retinopathies (particularly proliferative retinopathies), neurodegenerative disorders, infections, metabolic diseases, and neoplastic diseases. Any of the recombinant binding proteins described herein may be used for the preparation of a medicament for the treatment of such a disorder, particularly a disorder such as a neoplastic disease. A "medical condition" may be one that is characterized by inappropriate cell proliferation. A medical condition may be a hyperproliferative condition. The invention particularly relates to a method of treating a medical condition, the method comprising the step of administering, to a patient in need of such treatment, a therapeutically effective amount of a recombinant binding protein or said pharmaceutical composition of the invention. In a preferred aspect said medical condition is a neoplastic disease. The term "neoplastic disease", as used herein, refers to an abnormal state or condition of cells or tissue characterized by rapidly proliferating cell growth or neoplasm. In one aspect said medical condition is a malignant neoplastic disease. In one aspect said medical condition is a cancer, preferably leukemia, more preferably acute myeloid leukemia.

The term "therapeutically effective amount" means an amount that is sufficient to produce a desired effect on a patient.

The term "antibody" means not only intact antibody molecules, but also any fragments and variants of antibody molecules that retain immunogen-binding ability. Such fragments and variants are also well known in the art and are regularly employed both in vitro and in vivo. Accordingly, the term "antibody" encompasses intact immunoglobulin molecules, antibody fragments such as, e.g., Fab, Fab', F(ab')2, and single chain V region fragments (scFv), bispecific antibodies, chimeric antibodies, antibody fusion polypeptides, and unconventional antibodies.

The terms "cancer" and "cancerous" are used herein to refer to or describe the physiological condition in mammals that is typically characterized by unregulated cell growth. Cancer encompasses solid tumors and liquid tumors, as well as primary tumors and metastases. A "tumor" comprises one or more cancerous cells. Solid tumors typically also comprise tumor stroma. Examples of cancer include, but are not limited to, primary and metastatic carcinoma, lymphoma, blastoma, sarcoma, and leukemia, and any other epithelial and lymphoid malignancies. More particular examples of such cancers include brain cancer, bladder cancer, breast cancer, ovarian cancer, clear cell kidney cancer, head/neck squamous cell carcinoma, lung adenocarcinoma, lung squamous cell carcinoma, malignant melanoma, non-small-cell lung cancer (NSCLC), ovarian cancer, pancreatic cancer, prostate cancer, renal cell carcinoma, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myelodysplastic syndrome (MDS), non-Hodgkin's lymphoma (NHL), Squamous Cell Carcinoma of the Head and Neck (SCCHN), chronic myelogenous leukemia (CML), small lymphocytic lymphoma (SLL), malignant mesothelioma, colorectal cancer, or gastric cancer.

EXAMPLES

Starting materials and reagents disclosed below are known to those skilled in the art, are commercially available and/or can be prepared using well-known techniques.

Materials

Chemicals were purchased from Sigma-Aldrich (USA). Oligonucleotides were from Microsynth (Switzerland). Unless stated otherwise, DNA polymerases, restriction enzymes and buffers were from New England Biolabs (USA) or Fermentas/Thermo Fisher Scientific (USA). Inducible E. coli expression strains were used for cloning and protein production, e.g. E. coli XL1-blue (Stratagene, USA) or BL21 (Novagen, USA). If appropriate, proteins were frequently produced with an N-terminal His-tag (such as SEQ ID NO: 33) for ease of purification. Two benchmark T-cell engagers were generated and used as controls in various experiments described in the Examples. These benchmark T-cell engagers were similar to AMG330 and flotetuzumab, respectively, and are called AMG330 or AMG330-similar, and flotetuzumab or flotetuzumab-similar, throughout the Examples, Figure Legends and Figures.

Molecular Biology

Unless stated otherwise, methods are performed according to known protocols (see, e.g., Sambrook J., Fritsch E. F. and Maniatis T., Molecular Cloning: A Laboratory Manual, Cold Spring Harbor Laboratory 1989, New York).

Designed Ankyrin Repeat Protein Libraries

Methods to generate designed ankyrin repeat protein libraries have been described, e.g. in U.S. Pat. No. 7,417,130; Binz et al., J. Mol. Biol. 332, 489-503, 2003; Binz et al. 2004, loc. cit. By such methods designed ankyrin repeat protein libraries having randomized ankyrin repeat modules and/or randomized capping modules can be constructed. For example, such libraries could accordingly be assembled based on a fixed N-terminal capping module (e.g. the N-terminal capping module of SEQ ID NO: 16, 17, 18, 19, 20 or 21) or a randomized N-terminal capping module according to SEQ ID NO: 22, and a fixed C-terminal capping module (e.g. the C-terminal capping module of SEQ ID NO: 23, 24, 25, 26, 27, 28, 29, 30 or 31) or a randomized C-terminal capping module according to SEQ ID NO: 32. Preferably, such libraries are assembled to not have any of the amino acids C, G, M, N (in front of a G residue) and P at randomized positions of repeat or capping modules.

Furthermore, such randomized modules in such libraries may comprise additional polypeptide loop insertions with randomized amino acid positions. Examples of such polypeptide loop insertions are complement determining region (CDR) loop libraries of antibodies or de novo generated peptide libraries. For example, such a loop insertion could be designed using the structure of the N-terminal ankyrin repeat domain of human ribonuclease L (Tanaka, N., Nakanishi, M, Kusakabe, Y, Goto, Y., Kitade, Y, Nakamura, K. T., EMBO J. 23(30), 3929-3938, 2004) as guidance. In analogy to this ankyrin repeat domain where ten amino acids are inserted in the beta-turn present close to the boarder of two ankyrin repeats, ankyrin repeat proteins libraries may contain randomized loops (with fixed and randomized positions) of variable length (e.g. 1 to 20 amino acids) inserted in one or more beta-turns of an ankyrin repeat domain.

Any such N-terminal capping module of an ankyrin repeat protein library preferably possesses the RILLAA, RILLKA or RELLKA motif (e.g. present from position 21 to 26 in SEQ ID NO: 1) and any such C-terminal capping module of an ankyrin repeat protein library preferably possesses the KLN, KLA or KAA motif (e.g. present at the last three amino acids in SEQ ID NO:). SEQ ID NOs: 16, 17, 18, 19, 20, or 21 provide examples of N-terminal capping modules comprising the RILLAA, RILLKA or RELLKA motif, and SEQ ID NOs: 23, 24, 25, 26, 27, 28, 29, 30 or 31 provide examples of C-terminal capping modules comprising the KLN, KLA or KAA motif.

The design of such an ankyrin repeat protein library may be guided by known structures of an ankyrin repeat domain interacting with a target. Examples of such structures, identified by their Protein Data Bank (PDB) unique accession or identification codes (PDB-IDs), are 1WDY, 3V31, 3V30, 3V2X, 3V20, 3UXG, 3TWQ-3TWX, 1N11, 1S70 and 2ZGD.

Examples of designed ankyrin repeat protein libraries, such as N2C and N3C designed ankyrin repeat protein libraries, have been described (U.S. Pat. No. 7,417,130; Binz et al. 2003, loc. cit.; Binz et al. 2004, loc. cit.). The digit in N2C and N3C describes the number of randomized repeat modules present between the N-terminal and C-terminal capping modules.

The nomenclature used to define the positions inside the repeat units and modules is based on Binz et al. 2004, loc. cit. with the modification that borders of the ankyrin repeat modules and ankyrin repeat units are shifted by one amino acid position. For example, position 1 of an ankyrin repeat module of Binz et al. 2004 (loc. cit.) corresponds to position 2 of an ankyrin repeat module of the current disclosure and consequently position 33 of an ankyrin repeat module of Binz et al. 2004, loc. cit. corresponds to position 1 of a following ankyrin repeat module of the current disclosure.

All the DNA sequences were confirmed by sequencing, and the calculated molecular weight of selected proteins was confirmed by mass spectrometry.

Example 1: Selection of Binding Proteins Comprising an Ankyrin Repeat Domain with Binding Specificity for CD3, CD33, CD70 or CD123

A. Selection of Binding Proteins Comprising an Ankyrin Repeat Domain with Binding Specificity for CD3

Using ribosome display (Hanes, J. and Plückthun, A., PNAS 94, 4937-42, 1997), many ankyrin repeat proteins with binding specificity for human scCD3 were selected from DARPin® libraries similar as described by Binz et al.

2004 (loc. cit.). The binding of the selected clones towards recombinant human CD3 target was assessed by crude extract Homogeneous Time Resolved Fluorescence (HTRF), indicating that hundreds of human scCD3-specific binding proteins were successfully selected. For example, the ankyrin repeat domain of SEQ ID NO: 2 constitutes an amino acid sequence of a selected binding protein comprising an ankyrin repeat domain with binding specificity for scCD3.

Human Recombinant CD3 Target Preparation

The target format chosen is based on single chain format, consisting of the human CD3ε and CD3γ heterodimer linked by a 26 amino acid linker (scCD3cy) and a C-terminal Avi-tag for site-directed biotinylation. The target protein contains only the CD3 extracellular domain, lacking the C-terminal cysteine "knobs" and the entire transmembrane and cytoplasmic regions.

The extracellular domain of human scCD3εγ (SEQ ID NO: 38_scCD3εγ_Avi-Bio) was expressed in a single-chain format similar as described previously (Kjer-Nielsen et al., *PNAS*, 2004, 101 (20):7675-7680) in *Escherichia coli*, followed by refolding from inclusion bodies and purified by preparative size exclusion chromatography (SEC). The material was up-concentrated in 10 mM Tris-HCl, 50 mM NaCl, pH 8.0 to 3.4 mg/ml and in vitro biotinylated using recombinant BirA. To isolate functional target material, the material was re-purified using an OKT3-loaded column (GE HiTrap NHS-activated HP column). The final material was monomeric on size exclusion and stored at the final concentration of 0.39 mg/ml in 10 mM Tris, 100 mM NaCl, pH 8.0, 10% glycerol.

An overview of the recombinant human scCD3 target preparation process is described in Dunstone et al., Acta Crystallographica 2004.

Selection of CD3-Specific Ankyrin Repeat Proteins by Ribosome Display

The selection of CD3-specific ankyrin repeat proteins was performed by ribosome display (Hanes and Plükthun, loc. cit.) using part of the extracellular domain of CD3 (SEQ ID NO: 38) as target protein, libraries of ankyrin repeat proteins as described above, and established protocols (see, e.g., Zahnd, C., Amstutz, P. and Plükthun, A., *Nat. Methods* 4, 69-79, 2007). The number of reverse transcription (RT)-PCR cycles after each selection round was constantly reduced from 45 to 28, adjusting to the yield due to enrichment of binders. The first four rounds of selection employed standard ribosome display selection, using decreasing target concentration (400 nM, 133 nM, 45 nM and 15 nM, respectively) and increasing washing stringency to increase selection pressure from round 1 to round 4 (Binz et al. 2004, loc. cit.). In rounds 2-4, mRNA was recovered by competitive elution using excess of CD3 binding antibody OKT3 (in each round, competitor excess was constantly increased from 35-fold to 300-fold).

Selected Clones Activate T-Cells in a Bivalent Format

Individual ankyrin repeat protein clones binding to CD3 target were selected by ribosome display and were cloned into derivatives of the pQE30 (Qiagen) expression vector, transformed into *E. coli* XL1-Blue (Stratagene), plated on LB-agar (containing 1% glucose and 50 μg/ml ampicillin) and then incubated overnight at 37° C. The expression vector, a Jun leucine-zipper construct with both His- and Myc-tag and a CD3-specific ankyrin repeat domain, was used for screening in a bivalent format (with regard to the CD3-specific binding domain), which allowed testing for functionality by cross-linking of T-cells. Single colonies were picked into a 96 well plate (each clone in a single well) containing 160 μl growth medium (TB containing 1% glucose and 50 μg/ml ampicillin) and incubated overnight at 37° C., shaking at 800 rpm. 150 μl of fresh TB medium containing 50 μg/ml ampicillin was inoculated with 8.5 μl of the overnight culture in a fresh 96 well plate. After incubation for 120 minutes at 37° C. and 850 rpm, expression was induced with IPTG (0.5 mM final concentration) and continued for 4 hours. Cells were harvested and the pellets were frozen at −20° C. overnight before resuspension in 8.5 μl μl B-PERII (Thermo Scientific) and incubation for one hour at room temperature with shaking (600 rpm). Then, 160 μl PBS was added and cell debris was removed by centrifugation (3220 g for 15 min), and stored at −20° C. for further usage.

In a first step, a T-cell activation screen was performed using BK112 CD8+ monoclonal T-cells. The extract of each lysed clone was applied as a 1:20 dilution (final concentration) in PBSB (PBS pH 7.4 supplemented with 12% (w/v) FBS) to an anti-penta-His-antibody (Qiagen) coated 96 well plate, and incubated at 4° C. overnight. Plates were washed five times wish PBS before 100 μl of 100,000 BK112 T cells were added per well, cultured in T-cell assay medium RPMI-1640+10% FBS+1% L-glutamine+1% Pen Strep+200 IU IL2. 0.1 μg/100 μL of Golgi Stop were added and plates were centrifuged at 20 g for 3 minutes at RT before incubation of 4-5 hours at 37° C. in the CO$_2$-incubator. Cells were centrifuged at 350 g for 5 minutes at 4° C. and decanted. Cells were stained for surface CD8 expression before preserving the cells using BD Cytofix, incubated overnight at 4° C. Cells were washed with 1×PBS+2% FBS and stained for intracellular IFNγ by adding 50 μl of IFNγ-APC antibody in Cell perm (BD) and incubation for 30 min at 4° C. Cells were washed again in PBS and analyzed using a Cytometer FACS Canto II from BD.

Selected Clones Show Binding to CD3 (Shown by HTRF and OKT3 Competition) and Functionality in the Bispecific Format Identified functional designed ankyrin repeat domains hits were subcloned into derivatives of the pQE30 (Qiagen) expression vector containing an N-terminal His-tag, a Tumor Associated Antigen (TAA)-specific ankyrin repeat domain and a CD3-specific ankyrin repeat domain, in order to create a T cell engager (TCE) construct. Constructs were expressed in *E. coli* cells and purified using their His-tag according to standard protocols. 25 ml of stationary overnight cultures (TB, 1% glucose, 50 μg/ml of ampicillin; 37° C.) were used to inoculate 500 ml cultures (TB, 50 μg/ml ampicillin, 37° C.). At an absorbance of 1.0 to 1.5 at 600 nm, the cultures were induced with 0.5 mM IPTG and incubated at 37° C. for 4-5 h while shaking. The cultures were centrifuged and the resulting pellets were re-suspended in 25 ml of TBS500 (50 mM Tris-HCl, 500 mM NaCl, pH 8) and lysed (sonication). Following the lysis, the samples were mixed with 50 KU DNase/ml and incubated for 15 minutes prior to a heat-treatment step for 30 minutes at 62.5° C., centrifuged and the supernatant was collected and filtrated. Triton X100 (1% (v/v) final concentration) and imidazole (20 mM final concentration) were added to the homogenate. Proteins were purified over a Ni-nitrilotriacetic (Ni-NTA) acid column followed by a size exclusion chromatography on an AKTAxpress™ system according to standard protocols and resins known to the person skilled in the art.

In a first step, binding to recombinant protein was tested using an HTRF assay. Titration of the ankyrin repeat protein (5-640 nM) in PBS-TC (PBS supplemented with 0.1% (w/v) Casein and 0.1% Tween20, pH 7.4) was performed against 48 nM (final concentration) of human biotinylated scCD3εγ, 1:100 (final concentration) of anti-6His-D2 HTRF antibody- FRET acceptor conjugate (Cisbio) and 1:100 (final concentration) of anti-strep-Tb antibody FRET donor conjugate (Cisbio) in a well of a 384-well plate and incubated for 120 minutes at RT. The HTRF was read-out on a Tecan M1000 using a 340 nm excitation wavelength and a 665±10 nm emission filter. Several candidates showed dose dependent binding and were used for further evaluation. For all these constructs, binding signals were at background level when competed with 20-fold excess of CD3 binding antibody (OKT3 variant containing a human Fc region—final concentration 2.4 mM), which binds to a conformational epitope of CD3ε (Kjer-Nielsen et al., PNAS, 2004, 101 (20):7675-7680). Dose-dependent in vitro T-cell activation was confirmed using a BK112 T-cell activation assay (BK112 CD8 monoclonal T-cells which were pre-activated with CD3/CD28 Dynabeads), in presence of TAA1 expressing tumor cells. Intracellular IFNγ levels were measured on CD8+ or CD4+ T-cells after 5 hours of incubation of BK112 and SKOV3 cells (E:T=1:10) in presence of 1-100,000 pM of bispecific TCE constructs. The most potent construct showed EC50 values of 0.5 nM and 0.4 nM for CD4+ and CD8+ cells, respectively.

Affinity Maturation and Rational Design of Selected CD3-Specific Ankyrin Repeat Proteins Several rounds of affinity maturation combined with rational design were applied on the parental low affinity binding CD3-specific ankyrin repeat protein (named precursor A), and resulted in four higher affinity CD3-specific ankyrin repeat proteins (named precursor B, C and D). These precursor molecules were then finally engineered into CD3-specific ankyrin repeat proteins e.g. DARPin® protein #2.

Affinity maturation was performed on one of the parental CD3-specific ankyrin repeat proteins (precursor A), which was chosen taking into consideration, both its sufficient binding ability to the CD3 target and its ability to efficiently activate T-cells in vitro), by introducing diversity using error-prone PCR and DNA I shuffling as described by Zahnd et al., Nat Methods, 2007, 4: 269-279. In short: Three rounds of ribosome display were conducted using different concentrations of dNTP-analogues (mutagenesis kit from Jena Biosciences, using 5-10 μM 8-oxo-dGTP and dPTP) to introduce approximately 1-2 mutations per CD3-specific ankyrin repeat protein/round with increasing selection pressures (washing steps were increased from round 1 (3×15 min), to 3×30 min (round 2), to 3×45 min (round 3)), while the target concentration was kept constant at 5 nM. In a second step, DNA pools were DNA-shuffled and back-crossed using parental clones in one or two rounds of ribosome display using as described previously (Cadwell & Joyce, PCR Methods Appl, 1992, 2:28-33; Stemmer, Nature, 1994 370:389-391; Zaccolo et al, J Mol Biol 1996, 255: 589-603) using a DNAse I incubation time of 90 seconds and DNA polymerase HotStarTaq DNA Polymerase (Qiagen). Affinity matured CD3-specific ankyrin repeat protein pools were subcloned into derivatives of the pQE30 (Qiagen) expression vector, finally containing an N-terminal His-Flag-tag, an HSA binding ankyrin repeat domain for half-life extension, a TAA1-binding ankyrin repeat domain and a CD3-specific ankyrin repeat domain, and expressed and screened for binding to recombinant scCD3εγ by HTRF as described before. A lead clone was selected (precursor B, generated after 5 rounds of affinity maturation including 3 rounds of error-prone PCR using in all steps 10 μM dNTP analogues and two rounds of DNA-shuffling and back-crossing).

In the same process, several potential beneficial mutations for increased T-cell activation were identified by % of IFNγ+ T-cell in a BK112 assay, including N-cap mutations in positions 5 and 20, $1^{st}$ internal repeat mutations in positions 2 and 4, $2^{nd}$ internal repeat mutations in position 2, 5 and 20, and C-cap mutations in positions 1 and 18. A combination of these mutations—while keeping N- and the C-cap framework mutations to a minimum in order to maintain thermal stability—resulted in a set of designed variants, which were tested again in the same format for improved T-cell activation. Thereby, a new further matured variant (precursor C) was generated with higher T-cell activation potency compared to parental and initially matured ones.

In order to increase CD3 affinity and T-cell activation potency even further, a second affinity maturation was performed on the precursor C clone, similar to what has been described above. In short: Four rounds of ribosome display were performed. In the first three rounds, mutations were introduced by error-prone PCR with 7.5 μM of dNTP analogues. In round one and three, an off-rate selection was applied using either the further matured clone itself or a non-biotinylated CD3 target protein for competition. 1 nM target was used in round 1 and 2, whereas 5 nM was applied in less stringent rounds 3 and 4. CD3 variants were screened in a trispecific format, including an HSA-binding domain and a TAA1 binding ankyrin repeat domain, using an off-rate HTRF assay with 250-fold access of the further matured clone as competitor. A total of 3×96 clones with highest remaining HTRF signal after competition were sequenced. Identified beneficial mutations for improved binding (including N-cap position 16, first internal repeat positions 1, 12, 18, 19, 26, 30 and 33, second internal repeat positions 2, 3, 7, 20, 21, 26 and 32, and C-cap positions 9, 11 and 18) or for reduced domain interactions (including N-cap positions 11, 18, 19 26, and C-cap positions 3, 19 and 22) were tested first as individual or paired mutations on purified proteins variants for BK112 T-cell activation. Most beneficial variants were then recombined in a second step and variants were screened for highest T-cell activation, which resulted in the identification of precursor D.

In a last step, the variants e.g. DARPin® protein #6, were generated based on CD3-specific ankyrin repeat protein precursor A, B, C and D, respectively, in order to improve serum half-life and biophysical properties. Thereby, N-cap mutations in positions 23 and/or 26 were introduced while some of the framework mutations were removed (in positions 19, 18).

Affinity matured ankyrin repeat domains with binding specificity for human CD3 were cloned into a pQE (QIAgen, Germany) based expression vector providing an N-terminal His-tag (SEQ ID NO: 33) to facilitate simple protein purification as described below. For example, expression vectors encoding the following ankyrin repeat proteins were constructed:

DARPin® protein #1 (SEQ ID NO: 1 with a His-tag (SEQ ID NO: 33) fused to its N terminus)

DARPin® protein #2 (SEQ ID NO: 2 with a His-tag (SEQ ID NO: 33) fused to its N terminus)

DARPin® protein #3 (SEQ ID NO: 3 with a His-tag (SEQ ID NO: 33) fused to its N terminus)

DARPin® protein #4 (SEQ ID NO: 4 with a His-tag (SEQ ID NO: 33) fused to its N terminus)

High Level and Soluble Expression of CD3-Specific Ankyrin Repeat Proteins

Figure 19:
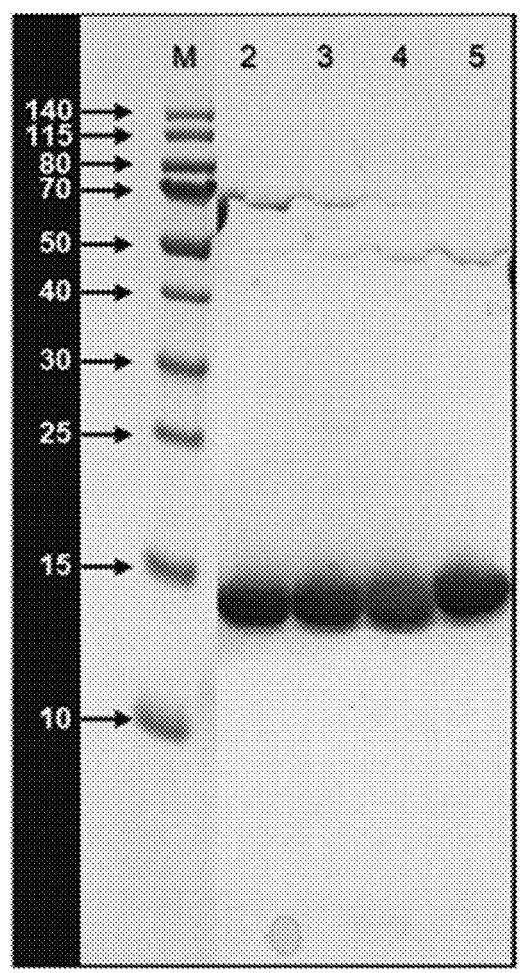
FIG. 19: SDS-PAGE gel analysis of the purification of four selected ankyrin repeat proteins with binding specificity for human CD3, DARPin® protein #1, DARPin® protein #2, DARPin® protein #3 and DARPin® protein #4. M corresponds to a protein size marker (reduced SDS-PAGE, NuPAGE 4-12%, Bis Tris (invitrogen) gel; 5 μg/lane; MES-buffer; Instant blue staining). The molecular weights (kDa) of the marker proteins are indicated. Lane 1: protein size marker; Lane 2: purified DARPin® protein #1; Lane 3: purified DARPin® protein #2, Lane 4: purified DARPin® protein #3, Lane 5: purified DARPin® protein #4.

For In-Depth Analyses, the Selected Clones Showing Specific CD3 Binding, Either as Monovalent or in combination with TAAs and/or HSA binding ankyrin repeat domains were expressed in E. coli cells and purified using their His-tag followed by a size exclusion chromatography on an ÄKTAxpress™ system according to standard protocols and resins known to the person skilled in the art. The proteins were monomeric and soluble when concentrated to 10 mg/ml in TBS pH 8.0 (50 mM Tris, 500 mM NaCl) or PBS pH 7.4 for monovalent and multivalent constructs, respectively. A representative example of such SDS-PAGE analysis is shown in FIG. 19.

B. Selection of Binding Proteins Comprising an Ankyrin Repeat Domain with Binding Specificity for CD33.

Using ribosome display (Hanes, J. and Plükthun, A., PNAS 94, 4937-42, 1997), many ankyrin repeat proteins with binding specificity for human CD33 (hCD33) were selected from DARPin® libraries similar as described by Binz et al. 2004 (loc. cit.). The binding of the selected clones toward recombinant human CD33 targets (full-length and splice variant of ECD of CD33) was assessed by crude extract Homogeneous Time Resolved Fluorescence (HTRF), indicating that hundreds of hCD33-specific binding proteins were successfully selected. For example, the ankyrin repeat domains of SEQ ID NOs: 15 and 67-70 constitute amino acid sequences of selected binding proteins comprising an ankyrin repeat domain with binding specificity for hCD33.

Selection of CD33-Specific Ankyrin Repeat Proteins by Ribosome Display

The selection of hCD33-specific ankyrin repeat proteins was performed by ribosome display (Hanes and Plükthun, loc. cit.) using the biotinylated extracellular domain of human CD33 (SEQ ID NO: 87) as target protein, libraries of ankyrin repeat proteins as described above, and established protocols (See, e.g., Zahnd, C., Amstutz, P. and Plükthun, A., Nat. Methods 4, 69-79, 2007). CD33 targets (Evitria) contained a C-terminal Fc Tag and an Avi tag and were biotinylated using the enzyme BirA-GST. Two different forms of CD33 has been used for selection: Full-length ECD of CD33 covering both variable and constant domain of CD33 by using residues 18-259 and a splice variant of CD33, covering only the constant domain of CD33 by using residues 120-259. In total four rounds of standard ribosome selections were employed, using decreasing target concentration and increasing washing stringency to increase selection pressure from round 1 to round 4 (Binz et al. 2004, loc. cit.). A deselection strategy was applied in each round by using Streptavidin and Neutravidin Beads in conjunctions with biotinylated non-CD33 Fc domain. The number of reverse transcription (RT)-PCR cycles after each selection round was constantly reduced from 45 to 28 adjusting to the yield due to enrichment of binders.

To enrich high affinity CD33-specific ankyrin repeat proteins, the output from the fourth round of standard ribosome display selection (above) was subjected to an off-rate selection round with increased selection stringency (Zahnd, 2007, loc. cit.). A final standard selection round was performed after the off-rate selection round to amplify and recover the off-rate selected binding proteins. In these last two selection rounds, the number of RT-PCR cycles was 30 and 35, respectively.

In total three different selection approaches have been conducted as described above with the following differences: In the first approach, selections were performed only against the ECD of the full-length CD33 protein. In a second approach, targets of full-length CD33 and splice variant were alternated in each round. In the third approach, a competitive elution step was applied using the condition of the first approach by adding HIM-3-4 CD33 binding antibody (BD Pharmingen™). From each approach, binders against full-length CD33 and/or its splice variant were generated.

Selected Clones Bind Specifically to Human and Cyno CD33 as Shown by Crude Extract HTRF Individual selected ankyrin repeat proteins specifically binding to hCD33 in solution were identified by a Homogeneous Time Resolved Fluorescence (HTRF) assay using crude extracts of ankyrin repeat protein-expressing *Escherichia coli* cells using standard protocols. Ankyrin repeat protein clones selected by ribosome display were cloned into derivatives of the pQE30 (Qiagen) expression vector (pMPAG06), transformed into *E. coli* XL1-Blue (Stratagene), plated on LB-agar (containing 1% glucose and 50 μg/ml ampicillin) and then incubated overnight at 37° C. Single colonies were picked into a 96 well plate (each clone in a single well) containing 160 μl growth medium (TB containing 1% glucose and 50 μg/ml ampicillin) and incubated overnight at 37° C., shaking at 800 rpm. 900 μl of fresh TB medium containing 50 μg/ml ampicillin was inoculated with 50 μl of the overnight culture in a fresh 96-deep-well plate. After incubation for 120 minutes at 37° C. and 700 rpm, expression was induced with IPTG (0.5 mM final concentration) and continued for 4 hours. Cells were harvested and the pellets were frozen at −20° C. overnight before resuspension in 50 μl μl B-PERII (Thermo Scientific) and incubation for 15 minutes at room temperature with shaking (900 rpm). Then, 950 μl PBS was added and cell debris was removed by centrifugation (3220 g for 15 min).

The extract of each lysed clone was applied as a 1:900 dilution (final concentration) in PBSTB (PBS supplemented with 0.1% Tween 20® and 0.2% (w/v) BSA, pH 7.4) together with 12 nM (final concentration) biotinylated hCD33, 1:200 (final concentration) of anti-strep-D2 HTRF antibody-FRET acceptor conjugate (Cisbio) and 1:200 (final concentration) of anti-6His-Tb antibody FRET donor conjugate (Cisbio) to a well of 384 well plate and incubated for 90 minutes at RT. The HTRF was read-out on a Tecan M1000 using a 340 nm excitation wavelength and a 665±10 nm emission filter. Screening of several hundred clones by such a crude cell extract HTRF revealed ankyrin repeat domains with specificity for hCD33. An amino acid sequence of a selected ankyrin repeat domain that specifically bind to hCD33 are provided in SEQ ID NO: 15.

DARPin® protein #15 (SEQ ID NO: 15);

Similarly, individual selected ankyrin repeat proteins specifically binding to hCD33 in solution were identified by a Homogeneous Time Resolved Fluorescence (HTRF) assay using crude extracts of ankyrin repeat protein-expressing *Escherichia coli* cells using standard protocols. Ankyrin repeat protein clones selected by ribosome display were cloned into derivatives of the pQE30 (Qiagen) expression vector (pMPDV045), which contains a C-terminal CD3 binding designed ankyrin repeat protein followed by a Flag tag, transformed into *E. coli* XL1-Blue (Stratagene), plated on LB-agar (containing 1% glucose and 50 μg/ml ampicillin) and then incubated overnight at 37° C. Single colonies were picked into a 96 well plate (each clone in a single well) containing 160 μl growth medium (TB containing 1% glucose and 50 μg/ml ampicillin) and incubated overnight at 37° C., shaking at 800 rpm. 150 μl of fresh TB medium containing 50 μg/ml ampicillin was inoculated with 8.5 μl of the overnight culture in a fresh 96-well plate. After incubation for 120 minutes at 37° C. and 700 rpm, expression was induced with IPTG (0.5 mM final concentration) and continued for 4 hours. Cells were harvested and the pellets were frozen at −20° C. overnight before resuspension in 8 μl μl B-PERII (Thermo Scientific) and incubation for 1 hour at room temperature with shaking (900 rpm). Then, 160 µl PBS was added and cell debris was removed by centrifugation (3220 g for 15 min).

The extract of each lysed clone was applied as a 1:1000 dilution (final concentration) in PBSTB (PBS supplemented with 0.1% Tween 20® and 0.2% (w/v) BSA, pH 7.4) together with 6 nM (final concentration) biotinylated hCD33 (full-length or splice variant of ECD CD33), 1:400 (final concentration) of anti-strep-Tb HTRF antibody-FRET donor conjugate (Cisbio) and 1:400 (final concentration) of anti-6His-D2 antibody FRET acceptor conjugate (Cisbio) to a well of 384 well plate and incubated for 60 minutes at RT. The HTRF was read-out on a Tecan M1000 using a 340 nm excitation wavelength and a 665±10 nm emission filter. Screening of several hundred clones by such a crude cell extract HTRF revealed ankyrin repeat domains with specificity for hCD33. Amino acid sequences of selected ankyrin repeat domains that specifically bind to hCD33 are provided in SEQ ID NO: 68 for DARPin® protein #37 and SEQ ID NO:69 for DARPin® protein #38.

Engineering of Additional Ankyrin Repeat Proteins with Binding Specificity for hCD33

SEQ ID NOs: 67 and 70 are engineered based on the sequence of SEQ ID NOs: 68 and 69 respectively.

For DARPin® protein #37 and DARPin® protein #38, the sequence was modified in order to reduce the amount of aromatic residues and change the surface charges. In both N-terminal capping modules, the RILLAA motiv was replaced by RILLKA and Aspartate (position18) was replaced by Leucine. In both C-terminal capping modules, Gluatmate (position18) was replaced by Glutamine. For DARPin® protein #12, an additional Phenylalanine (position 14) was replaced by a Valine in the N-terminal capping module. For DARPin® protein #37, an additional Tryptophane (position 7) was replaced by a Valine in the N-terminal capping module, and the EDIA motive in the second internal repeat (position 18-21) was replaced by LEIV. Engineered variants did not alter T-cell killing (assessed in combination with other TAAs and CD3 binding DARPin molecule) compared to parental version by more than factor two measured in a standard LDH killing assay after 48 h of incubation using PanT and MOLM-13 cells at a ratio or 5:1.

Expression of CD33-Specific Ankyrin Repeat Proteins

For further analysis, the selected clones showing specific human CD33 binding in the crude cell extract HTRF, as described above, were expressed in E. coli cells and purified using their His-tag according to standard protocols. 0.11 ml of stationary overnight cultures (TB, 1% glucose, 50 mg/l of ampicillin; 37° C.) were used to inoculate 0.99 ml cultures in 96-deep-well plate (TB, 50 mg/l ampicillin, 37° C.). After 2 hours incubation at 37° C. (700 rpm), the cultures were induced with 0.5 mM IPTG and incubated at 37° C. for 6 h with shaking (900 rpm). Cells were harvested and the pellets were frozen at −20° C. overnight before resuspensions in 50 µl B-PERII (Thermo Scientific) supplemented with DNAse I (200 Units/ml) and Lysozyme (0.4 mg/ml) and incubation for one hour at room temperature with shaking (900 rpm). Then, 60 µl low salt sodium phosphate buffer was added and cell debris was removed by centrifugation (3220 g for 15 min). In total, eight individual expressions were pooled, before removal of cell debris by centrifugation (3'200 g for 60 min at 4° C.). Supernatant was filtered using a Multi-Screen filter plate (Millipore) before purification using a 96-well Thermo HisPur cobalt spin plates and rebuffering the proteins solution using 96-well Thermo Zeba spin desalting plate in PBS. Purified proteins were soluble and monomeric in PBS using a standard Sephadex 150/5 column on an Agilent 1200 HPLC system.

Generation of Affinity Matured CD33 Specific Binding Proteins, DARPin® Protein #72 (SEQ ID NO: 111) and DARPin® Protein #73 (SEQ ID NO:112), Originating from DARPin® Protein #36 (SEQ ID NO:67)

In further development of the initially identified CD33 specific binding proteins, new variants with very high affinity to and/or very low off-rate from target protein were generated using affinity maturation. Thereby, one initially identified CD33 specific binding protein DARPin® protein #36 (the "parental" binding protein) was selected as a suitable starting point for affinity maturation. The affinity maturation procedure entailed saturation mutagenesis of each randomized position of the ankyrin repeat domain used as a starting point. Sequences generated by the affinity maturation procedure were screened for lower off-rates by competition HTRF. In short: Single amino acid point mutations variants were generated by standard QuikChange PCR on parental plasmid (pMCHE1190) using primers with a single NNK degenerated codon to introduce all 20 amino acids at a potential binding position. Crude extract (CE) of proteins variants (containing finally an N-terminal His-tag, followed by the CD33 specific binding domain) were generated from standard E. coli expression cultures. Diluted CE's were incubated with the biotinylated target before addition of excess of non-tagged parental CD33 binding protein (DARPin® protein #36) and measurement of HTRF signal over time. Beneficial mutations, identified based on higher HTRF signals compared to parental clone, were combined in the binding proteins by protein engineering.

Engineered CD33 specific hits were subcloned into derivatives of the pQE30 (Qiagen) expression vector, one vector containing finally an N-terminal His-tag, followed by the CD33 specific binding domain of SEQ ID NO: 111 or 112 and a C-terminal CD3 binding domain of SEQ ID NO:3, and one vector containing finally an N-terminal His-tag, followed by the CD33 specific binding domain of SEQ ID NO: 111 or 112, to express proteins in a bivalent (2D) and monovalent format (1 D), respectively. All constructs were expressed in E. coli cells and purified using their His-tag according to standard protocols.

C. Selection of Binding Proteins Comprising an Ankyrin Repeat Domain with Binding Specificity for CD123.

Using ribosome display (Hanes, J. and Plükthun, A., PNAS 94, 4937-42, 1997), many ankyrin repeat proteins with binding specificity for human CD123 (hCD123) and cyno CD123 (cCD123) were selected from DARPin® libraries similar as described by Binz et al. 2004 (loc. cit.). The binding of the selected clones toward recombinant human and cyno CD123 target was assessed by crude extract Homogeneous Time Resolved Fluorescence (HTRF), indicating that hundreds of hCD123-specific binding proteins were successfully selected. For example, the ankyrin repeat domains of SEQ ID NOs: 6 and 65 to 66 constitute amino acid sequences of selected binding proteins comprising an ankyrin repeat domain with binding specificity for hCD123 and cCD123.

Selection of CD123-Specific Ankyrin Repeat Proteins by Ribosome Display

The selection of hCD123-specific ankyrin repeat proteins (e.g. SEQ ID NO: 6) was performed by ribosome display (Hanes and Plükthun, loc. cit.) using the biotinylated extracellular domains of human (uniprot ID 26951) and cyno CD123 (uniprot ID G8F3K3) as a target protein, libraries of ankyrin repeat proteins as described above, and established protocols (See, e.g., Zahnd, C., Amstutz, P. and Plükthun, A., Nat. Methods 4, 69-79, 2007). All target molecules were produced in an Fc format. In total four rounds of standard ribosome selections were employed, using decreasing target concentration and increasing washing stringency to increase selection pressure from round 1 to round 4 (Binz et al. 2004, loc. cit.). Specifically, cyno target was used in round 1, 2, and 4, and human CD123 in round 3. A deselection strategy was applied from round two on using an excess of non-CD123-Fc protein. The number of reverse transcription (RT)-PCR cycles after each selection round was constantly reduced from 45 to 31 adjusting to the yield due to enrichment of binders.

The selection of hCD123-specific ankyrin repeat proteins (SEQ ID NOs: 65 to 66) was performed by ribosome display (Hanes and Plükthun, loc. cit.) using the biotinylated extracellular domains of human CD123 (SEQ ID NO: 88) as target protein, libraries of ankyrin repeat proteins as described above, and established protocols (See, e.g., Zahnd, C., Amstutz, P. and Plükthun, A., Nat. Methods 4, 69-79, 2007). CD123 target (Evitria) contained a C-terminal Fc Tag and an Avi tag and was biotinylated using the enzyme BirA-GST. In total four rounds of standard ribosome selections were employed, using decreasing target concentration and increasing washing stringency to increase selection pressure from round 1 to round 4 (Binz et al. 2004, loc. cit.). A deselection strategy was applied in each round by using Streptavidin and Neutravidin Beads. The number of reverse transcription (RT)-PCR cycles after each selection round was constantly reduced from 45 to 28 adjusting to the yield due to enrichment of binders.

To enrich high affinity CD123-specific ankyrin repeat proteins, the output from the fourth round of standard ribosome display selection (above) was subjected to an off-rate selection round with increased selection stringency (Zahnd, 2007, loc. cit.). A final standard selection round was performed after the off-rate selection round to amplify and recover the off-rate selected binding proteins. In round 5 and 6 the number of RT-PCR cycles was 30 and 35, respectively.

Additional, two additional selection approaches were conducted next to standard approach (as described above) to expand the potential epitope space by applying either a competitive elution step using a CD123-binding T cell engager (U.S. Pat. No. 9,822,181B2-7G3 epitope), or by co-incubation of hCD123-specific ankyrin repeat proteins (with an epitope different to antibody 7G3) with the CD123 target before running the selection. From each of the applied approaches, binders against CD123 were generated.

Selected Clones Bind Specifically to Human CD123 as Shown by Crude Extract HTRF

Individual selected ankyrin repeat proteins specifically binding to hCD123 in solution were identified by a Homogeneous Time Resolved Fluorescence (HTRF) assay using crude extracts of ankyrin repeat protein-expressing *Escherichia coli* cells using standard protocols. Ankyrin repeat protein clones selected by ribosome display were cloned into derivatives of the pQE30 (Qiagen) expression vector (pMPDV045), which contains a C-terminal CD3 binding designed ankyrin repeat protein followed by a Flag tag, transformed into *E. coli*XL1-Blue (Stratagene), plated on LB-agar (containing 1% glucose and 50 μg/ml ampicillin) and then incubated overnight at 37° C. Single colonies were picked into a 96 well plate (each clone in a single well) containing 160 μl growth medium (TB containing 1% glucose and 50 μg/ml ampicillin) and incubated overnight at 37° C., shaking at 800 rpm. 150 μl of fresh TB medium containing 50 μg/ml ampicillin was inoculated with 8.5 μl of the overnight culture in a fresh 96-well plate. After incubation for 120 minutes at 37° C. and 700 rpm, expression was induced with IPTG (0.5 mM final concentration) and continued for 4 hours. Cells were harvested and the pellets were frozen at −20° C. overnight before resuspension in 8 μl μl B-PERII (Thermo Scientific) and incubation for 1 hour at room temperature with shaking (900 rpm). Then, 160 μl PBS was added and cell debris was removed by centrifugation (3220 g for 15 min).

The extract of each lysed clone was applied as a 1:500 dilution (final concentration) in PBSTB (PBS supplemented with 0.1% Tween 20® and 0.2% (w/v) BSA, pH 7.4) together with 6 nM (final concentration) biotinylated human or cyno CD123, 1:300 (final concentration) of anti-6His-D2 HTRF antibody-FRET acceptor conjugate (Cisbio) and 1:300 (final concentration) of anti-strep-Tb antibody FRET donor conjugate (Cisbio) to a well of 384 well plate and incubated for 120 minutes at RT. The HTRF was read-out on a Tecan M1000 using a 340 nm excitation wavelength and a 665±10 nm emission filter. Screening of several hundred clones by such a crude cell extract HTRF revealed ankyrin repeat domains with specificity for human and cyno CD123. Amino acid sequences of selected ankyrin repeat domains that specifically bind to human and cyno CD123 are provided in SEQ ID NO: 6, 102 and 103.

DARPin® protein #6 (SEQ ID NO: 6);
DARPin® protein #63 (SEQ ID NO: 102)
DARPin® protein #64 (SEQ ID NO: 103)

Alternatively, the extract of each lysed clone was applied as a 1:1000 dilution (final concentration) in PBSTB (PBS supplemented with 0.1% Tween 20® and 0.2% (w/v) BSA, pH 7.4) together with 4 nM (final concentration) biotinylated hCD123, 1:400 (final concentration) of anti-strep-Tb HTRF antibody-FRET donor conjugate (Cisbio) and 1:400 (final concentration) of anti-6His-D2 antibody FRET acceptor conjugate (Cisbio) to a well of 384 well plate and incubated for 60 minutes at RT. The HTRF was read-out on a Tecan M1000 using a 340 nm excitation wavelength and a 665±10 nm emission filter. Screening of several hundred clones by such a crude cell extract HTRF revealed ankyrin repeat domains with specificity for hCD123. An amino acid sequences of a selected ankyrin repeat domain that specifically bind to hCD123 is provided in SEQ ID NO: 66.

DARPin® protein #35 (SEQ ID NO: 66).

Engineering of Additional Ankyrin Repeat Proteins with Binding Specificity for hCD123

SEQ ID NO: 65 is further engineered based on the sequence of SEQ ID NO: 66.

DARPin® protein #35 (SEQ ID NO: 66) was modified in order to change the surface charges. In the N-terminal capping module, Aspartate (position18) was replaced by Leucine and in the C-terminal capping module, Glutamate (position18) was replaced by Glutamine. Engineered variants did reduce T-cell killing (assessed in combination with a CD3 binding DARPin molecule) compared to parental measured in a standard LDH killing assay after 48 h of incubation using PanT and MOLM-13 cells at a ratio or 5:1.

Expression of CD123-Specific Ankyrin Repeat Proteins

For further analysis, the selected clones showing specific human CD123 binding in the crude cell extract HTRF, as described above, were expressed in *E. coli* cells and purified using their His-tag according to standard protocols. 0.11 ml of stationary overnight cultures (TB, 1% glucose, 50 mg/l of ampicillin; 37° C.) were used to inoculate 0.99 ml cultures in 96-deep-well plate (TB, 50 mg/l ampicillin, 37° C.). After 2 hours incubation at 37° C. (700 rpm), the cultures were induced with 0.5 mM IPTG and incubated at 37° C. for 6 h with shaking (900 rpm). Cells were harvested and the pellets were frozen at −20° C. overnight before resuspensions in 50 µl B-PERII (Thermo Scientific) supplemented with DNAase I (200 Units/ml) and Lysozyme (0.4 mg/ml) and incubation for one hour at room temperature with shaking (900 rpm). Then, 60 µl low salt sodium phosphate buffer was added and cell debris was removed by centrifugation (3220 g for 15 min). In total, eight individual expressions were pooled, before removal of cell debris by centrifugation (3,200 g for 60 min at 4° C.). Supernatant was filtered using a Multi-Screen filter plate (Millipore) before purification using a 96-well Thermo HisPur cobalt spin plates and rebuffering the proteins solution using 96-well Thermo Zeba spin desalting plate in PBS. Purified proteins were soluble and monomeric in PBS using a standard Sephadex 150/5 column on an Agilent 1200 HPLC system.

Generation of Affinity Matured CD123 Specific Binding Proteins DARPin® Protein #66 and DARPin® Protein #67 Originating from DARPin® Protein #34

In further development of the initially identified CD123 specific binding proteins, variants with very high affinity to and/or very low off-rate from target protein were generated using affinity maturation. Thereby, one initially identified binding protein DARPin® protein #34 (SEQ ID NO:65, the "parental" binding protein) was selected as a suitable starting point for affinity maturation. The affinity maturation procedure entailed saturation mutagenesis of each randomized position of the ankyrin repeat domain used as a starting point. Sequences generated by the affinity maturation procedure were screened for lower off-rates by competition HTRF. In short: In short: Single amino acid point mutations variants were generated by standard QuikChange PCR on parental plasmid using primers with a single NNK degenerated codon to introduce all 20 amino acids at a potential binding position. Crude extract (CE) of protein variants (containing finally an N-terminal His-tag, followed by the CD123 specific binding domain of SEQ ID NO: 105 or 106) were generated from standard E. coli expression cultures. Diluted CE's were incubated with the biotinylated target before addition of excess of non-tagged parental CD123 specific binding domain of SEQ ID NO: 65 and measurement of HTRF signal over time. Beneficial mutations identified based on higher HTRF signals compared to parental protein, were combined in the binding proteins by protein engineering.

In a first step, engineered CD123 specific hits were subcloned into derivatives of the pQE30 (Qiagen) expression vector, containing finally an N-terminal His-tag, followed by the CD123 specific binding domain of SEQ ID NO: 105 or 106 and a C-terminal CD3 specific binding domain of SEQ ID NO: 3. The constructs were expressed in E. coli cells and purified using their His-tag according to standard protocols.

D. Selection of Binding Proteins Comprising an Ankyrin Repeat Domain with Binding Specificity for CD70.

Using ribosome display (Hanes, J. and Plükthun, A., PNAS 94, 4937-42, 1997), many ankyrin repeat proteins with binding specificity for human CD70 (hCD70) were selected from DARPin® libraries similar as described by Binz et al. 2004 (loc. cit.). The binding of the selected clones toward recombinant human CD70 target was assessed by crude extract Homogeneous Time Resolved Fluorescence (HTRF), indicating that hundreds of hCD70-specific binding proteins were successfully selected. For example, the ankyrin repeat domains of SEQ ID NO: 64 constitutes an amino acid sequence of a selected binding proteins comprising an ankyrin repeat domain with binding specificity for hCD70.

Selection of CD70-Specific Ankyrin Repeat Proteins by Ribosome Display

The selection of hCD70-specific ankyrin repeat proteins was performed by ribosome display (Hanes and Plükthun, loc. cit.) using the biotinylated extracellular domain of human CD70 (SEQ ID NO: 89) as target protein, libraries of ankyrin repeat proteins as described above, and established protocols (See, e.g., Zahnd, C., Amstutz, P. and Plükthun, A., Nat. Methods 4, 69-79, 2007). CD70 target (ACROBiosystems) contained a C-terminal Fc Tag and was chemically biotinylated using 5 fold excess of Biotin. In total four rounds of standard ribosome selections were employed, using decreasing target concentration and increasing washing stringency to increase selection pressure from round 1 to round 4 (Binz et al. 2004, loc. cit.). A deselection strategy was applied in each round by using Streptavidin and Neutravidin Beads. The number of reverse transcription (RT)-PCR cycles after each selection round was constantly reduced from 45 to 28 adjusting to the yield due to enrichment of binders.

To enrich high affinity CD70-specific ankyrin repeat proteins, the output from the fourth round of standard ribosome display selection (above) was subjected to an off-rate selection round with increased selection stringency (Zahnd, 2007, loc. cit.). A final standard selection round was performed after the off-rate selection round to amplify and recover the off-rate selected binding proteins. In round 5 and 6 the number of RT-PCR cycles was 30 and 35, respectively.

Selected Clones Bind Specifically to Human CD70 as Shown by Crude Extract HTRF

Individual selected ankyrin repeat proteins specifically binding to hCD70 in solution were identified by a Homogeneous Time Resolved Fluorescence (HTRF) assay using crude extracts of ankyrin repeat protein-expressing Escherichia coli cells using standard protocols. Ankyrin repeat protein clones selected by ribosome display were cloned into derivatives of the pQE30 (Qiagen) expression vector (pMPDV25), transformed into E. coliXL1-Blue (Stratagene), plated on LB-agar (containing 1% glucose and 50 µg/ml ampicillin) and then incubated overnight at 37° C. Single colonies were picked into a 96 well plate (each clone in a single well) containing 160 µl growth medium (TB containing 1% glucose and 50 µg/ml ampicillin) and incubated overnight at 37° C., shaking at 800 rpm. 150 µl of fresh TB medium containing 50 µg/ml ampicillin was inoculated with 8.5 µl of the overnight culture in a fresh 96-well plate. After incubation for 120 minutes at 37° C. and 700 rpm, expression was induced with IPTG (0.5 mM final concentration) and continued for 4 hours. Cells were harvested and the pellets were frozen at −20° C. overnight before resuspension in 8 µl µl B-PERII (Thermo Scientific) and incubation for 1 hour at room temperature with shaking (900 rpm). Then, 160 µl PBS was added and cell debris was removed by centrifugation (3220 g for 15 min).

The extract of each lysed clone was applied as a 1:2000 dilution (final concentration) in PBSTB (PBS supplemented with 0.1% Tween 20® and 0.2% (w/v) BSA, pH 7.4) together with 2 nM (final concentration) biotinylated hCD70, 1:400 (final concentration) of anti-strep-Tb HTRF antibody-FRET donor conjugate (Cisbio) and 1:400 (final concentration) of anti-6His-D2 antibody FRET acceptor conjugate (Cisbio) to a well of 384 well plate and incubated for 60 minutes at RT. The HTRF was read-out on a Tecan M1000 using a 340 nm excitation wavelength and a 665±10 nm emission filter. Screening of several hundred clones by such a crude cell extract HTRF revealed ankyrin repeat domains with specificity for hCD70. Amino acid sequences of selected ankyrin repeat domains that specifically bind to hCD70 are provided in SEQ ID NO: 107 and 108:

DARPin® protein #68 (SEQ ID NO: 107);
DARPin® protein #69 (SEQ ID NO: 108);

Engineering of Additional Ankyrin Repeat Proteins with Binding Specificity for hCD70

SEQ ID NO: 64 is engineered based on the sequence of a selected designed ankyrin repeat domain of the previous step, namely DARPin® protein #69 (SEQ ID NO: 108).

This selected sequence was modified in order to change the surface charges. The N-terminal capping module, the RILLAA motif was replaced by RILLKA and Aspartate (position18) was replaced by Leucine. Additionally, for the C-terminal capping module was modified replacing Serine (position 16) by Glycine and Glutamate (position18) by Glutamine.

Expression of CD70-Specific Ankyrin Repeat Proteins

For further analysis, the selected clones showing specific human CD70 binding in the crude cell extract HTRF, as described above, were expressed in *E. coli* cells and purified using their His-tag according to standard protocols. 0.11 ml of stationary overnight cultures (TB, 1% glucose, 50 mg/l of ampicillin; 37° C.) were used to inoculate 0.99 ml cultures in 96-deep-well plate (TB, 50 mg/l ampicillin, 37° C.). After 2 hours incubation at 37° C. (700 rpm), the cultures were induced with 0.5 mM IPTG and incubated at 37° C. for 6 h with shaking (900 rpm). Cells were harvested and the pellets were frozen at −20° C. overnight before resuspensions in 50 µl B-PERII (Thermo Scientific) supplemented with DNAase I (200 Units/ml) and Lysozyme (0.4 mg/ml) and incubation for one hour at room temperature with shaking (900 rpm). Then, 60 µl low salt sodium phosphate buffer was added and cell debris was removed by centrifugation (3220 g for 15 min). In total, eight individual expressions were pooled, before removal of cell debris by centrifugation (3'200 g for 60 min at 4° C.). Supernatant was filtered using a Multi-Screen filter plate (Millipore) before purification using a 96-well Thermo HisPur cobalt spin plates and rebuffering the proteins solution using 96-well Thermo Zeba spin desalting plate in PBS. Purified proteins were soluble and monomeric in PBS using a standard Sephadex 150/5 column on an Agilent 1200 HPLC system.

Generation of Affinity Matured CD70-Specific Ankyrin Repeat Proteins DARPin® Protein #70 (SEQ ID NO:109) and DARPin® Protein #71 (SEQ ID NO:110), Originating from Parental Proteins DARPin® Protein #69 (SEQ ID NO:108) and DARPin® Protein #68 (SEQ ID NO 107) Respectively.

In a further development of the initially identified CD70-specific binding proteins, binding domains with very high affinity to and/or very low off-rate from target protein were generated using affinity maturation. Thereby, two initially identified binding proteins (the "parental" binding proteins DARPin® protein #68 and DARPin® protein #69) were selected as a suitable starting point for affinity maturation. The affinity maturation procedure entailed saturation mutagenesis of each randomized position of the ankyrin repeat domain used as a starting point. Sequences generated by the affinity maturation procedure were screened for lower off-rates by competition HTRF. In short: Crude extracts of ankyrin repeat proteins, containing an N-terminal His-tag were incubated with the biotinylated target before addition of excess of non-tagged parental CD70-specific binding proteins and measurement of HTRF signal over time. Beneficial mutations, identified based on higher HTRF signals compared to parental clone, were combined in the binding proteins by protein engineering.

In a first step, engineered CD70-specific binding domains were subcloned into derivatives of the pQE30 (Qiagen) expression vector pMPTLO847, containing finally an N-terminal His-tag, followed by the CD70 specific binding domain (SEQ ID NOs: 109 or 110) and a C-terminal CD3-specific binding domain (SEQ ID NO: 3). Constructs were expressed in *E. coli* cells and purified using their His-tag according to standard protocols. Proteins were tested for dose-dependent in vitro T-cell activation and killing assay using primary T-cells isolated from healthy donor PBMCs and Molm-13-N1 tumor cells (E:T ratio of 5:1). Assay incubation of co-culture for 48 h and analysis by Flow Cytometry and LDH release. DARPin® protein #70 (SEQ ID NO:109) and DARPin® protein #71 (SEQ ID NO:110) were selected based on improved EC50 values compared to parental binding proteins of approximately 7-fold and 31-fold, respectively; and monomericity of >95% measured by analytical size exclusion chromatography. In a second step, CD70 specific binding proteins DARPin® protein #70 (SEQ ID NO:109) and DARPin® protein #71 (SEQ ID NO:110) were subcloned into derivatives of the pQE30 (Qiagen) expression vector pMPDV025, containing a N-terminal His-tag and expressed as monovalent designed ankyrin repeat proteins in *E. coli*, purified and characterized according to standard protocols.

Example 2: Pharmacokinetic Analysis of Recombinant Proteins in Female BALB/c Mice A. Pharmacokinetic Analysis of CD3 Specific Ankyrin Repeat Proteins in Female BALB/c Mice In order to determine whether a CD3-specific ankyrin repeat domain of the invention can have an appropriate serum half-life in vivo for it to be useful for the development of therapeutic agents, the pharmacokinetic profiles of DARPin® protein #1, DARPin® protein #2, DARPin® protein #3 and DARPin® protein #4 were analyzed in mice. For that, DARPin constructs were subcloned and expressed as described above into derivatives of the pQE30 (Qiagen) expression vector, containing an N-terminal His-tag, an HSA binding ankyrin repeat domain for half-life extension, followed by one of the CD3 specific binding domains. For example, expression vectors encoding the following ankyrin repeat proteins were constructed:

DARPin® protein #16 (SEQ ID NO: 39 with a His-tag (SEQ ID NO: 33) fused to its N terminus);
DARPin® protein #17 (SEQ ID NO: 40 with a His-tag (SEQ ID NO: 33) fused to its N terminus);
DARPin® protein #18 (SEQ ID NO: 41 with a His-tag (SEQ ID NO: 33) fused to its N terminus);
DARPin® protein #19 (SEQ ID NO: 42 with a His-tag (SEQ ID NO: 33) fused to its N terminus);

In Vivo Administration and Sample Collection

DARPin® protein #16, DARPin® protein #17, DARPin® protein #18 and DARPin® protein #19, formatted with a human serum albumin specific ankyrin repeat domain, were administered as a single intravenous bolus injection into the tail vein of 6 mice for each ankyrin repeat fusion protein. The target dose level was 1 mg/kg with an application volume of 5 mL/kg. Ankyrin repeat fusion proteins were formulated in phosphate-buffered saline (PBS) solution.

Mice were split into 2 groups with equal numbers of animals. Four serum samples were collected from each mouse. Blood samples for pharmacokinetic investigations were collected from the saphenous vein at 5 min, 4 h, 24 h, 48 h, 76 h, 96 h and 168 h post compound administration. Blood was kept at room temperature to allow clotting followed by centrifugation and collection of serum.

Bioanalytics by ELISA to Measure Ankyrin Repeat Proteins in Serum Samples

One hundred µl per well of 10 nM polyclonal goat anti-rabbit IgG antibody (Ab18) in PBS was coated onto a NUNC Maxisorb ELISA plate overnight at 4° C. After washing with 300 µl PBST (PBS supplemented with 0.1% Tween20) per well five times, the wells were blocked with 300 µl PBST supplemented with 0.25% Casein (PBST-C) for 1 h at room temperature (RT) on a Heidolph Titramax 1000 shaker (450 rpm). Plates were washed as described above. 100 µl 5 nmol/L rabbit anti-DARPin® 1-1-1 antibody in PBST-C was added and the plates were incubated at RT (22° C.) with orbital shaking (450 rpm) for 1 h. Plates were washed as described above.

One hundred µl of diluted serum samples (1:20-1:312500 in 1:5 dilution steps) or ankyrin repeat protein standard curve samples (0 and 50-0.0008 nmol/L in 1:3 dilution steps) were applied for 2 h, at RT, shaking at 450 rpm. Plates were washed as described above.

Wells were then incubated with 100 µl murine anti-RGS-His-HRP IgG (Ab06, 1:2000 in PBST-C) and incubated for 1 h, at RT, 450 rpm. Plates were washed as described above.

Maximum serum concentrations (Cmax) and the times of their occurrence (Tmax) were obtained directly from the serum concentration-time profiles. The area under the serum concentration-time curve (AUCinf) was determined by the linear trapezoidal formula up to the last sampling point (Tlast) and extrapolation to infinity assuming mono-exponential decrease of the terminal phase. The extrapolation up to infinity was performed using Clast/$\lambda z$, where $\lambda z$ denotes the terminal rate constant estimated by log linear regression and Clast denotes the concentration estimated at Tlast by means of the terminal log-linear regression. Total serum clearance (Cl_pred) and the apparent terminal half-life were calculated as follows: Cl_pred=i.v. dose/AUCinf and t½=ln2/$\lambda z$. The steady-state volume of distribution Vss was determined by: Vss=i.v. dose·AUMCinf/(AUCinf)2. AUMCinf denotes the total area under the first moment of drug concentration-time curve extrapolated to infinity using the same extrapolation procedure as described for calculation of AUCinf. To calculate PK parameters based on concentrations given in nmol/L dose values given as mg/kg were converted to nmol/kg by using the molecular weight of the ankyrin repeat proteins. Table 2a shows the summary of pharmacokinetic characteristics of the four tested ankyrin repeat proteins DARPin® protein #16, DARPin® protein #17, DARPin® protein #18 and DARPin® protein #19 following single intravenous administration of 1 mg/kg.

TABLE 2a

Pharmacokinetic parameters for four exemplary HSA/CD3 specific ankyrin repeat proteins

| parameter | unit | DARPin® protein #16 | DARPin® protein #17 | DARPin® protein #18 | DARPin® protein #19 |
| --- | --- | --- | --- | --- | --- |
| AUCINF_D_pred | (h*nmol*kg)/(L*mg) | 26470 | 26814 | 18688 | 14155 |
| AUClast | h*(nmol/L) | 25857 | 26060 | 18420 | 14115 |
| Cmax | nmol/L | 949 | 1042 | 761 | 820 |
| Tmax | h | 0.083 | 0.083 | 0.083 | 0.083 |
| Cl_pred | L/(h*kg) | 0.00127 | 0.00126 | 0.00179 | 0.00237 |
| HL_Lambda_z (half life) | h | 32.3 | 34.3 | 29.0 | 21.0 |
| Vss_pred | L/kg | 0.0515 | 0.0515 | 0.0618 | 0.0547 |
| AUC_% Extrap_pred | (%) | 2 | 3 | 1 | 0 |
| AUC_% Back_Ext_pred | (%) | 0 | 0 | 0 | 0 |

The ELISA was developed using 100 µl/well TMB substrate solution for 5 minutes and stopped by the addition of 100 µl 1 mol/L $H_2SO_4$. The difference between the absorbance at 450 nm and the absorbance at 620 nm was calculated. Samples were measured in duplicate on two different plates. FIG. 1A shows the serum concentrations of DARPin® protein #16, DARPin® protein #17, DARPin® protein #18 and DARPin® protein #19 as a function of time after the single intravenous administration into mice. The traces indicate roughly mono-exponential elimination of the compounds.

Pharmacokinetic Analysis

Pharmacokinetic data analysis was performed at Molecular Partners using Version 7.0 of the WinNonlin program as part of Phoenix 64, Pharsight, N.C. Calculation of the pharmacokinetic parameters based on the mean concentration-time data of the animals dosed via intravenous bolus injection was performed with non-compartmental analysis (NCA model 200-202, IV bolus, linear trapezoidal linear interpolation). The following pharmacokinetic parameters were calculated: AUCinf, AUClast, AUC_% extrapol, Cmax, Tmax, Cl_pred, Vss_pred, t½

B. Pharmacokinetic Analysis of Multi-Specific Recombinant Proteins in Female BALB/c Mice In order to determine whether multi-specific recombinant binding proteins of the invention can have an appropriate serum half-life in vivo for it to be useful for the development of therapeutic agents, the pharmacokinetic profiles of DARPin® protein #29 and DARPin® protein #31 (in a half-life extended format) were analyzed in mice. For that, DARPin constructs were subcloned and expressed as described above into derivatives of the pQE30 (Qiagen) expression vector, containing an N-terminal His-tag, an (one or two, as described in previous examples) HSA binding ankyrin repeat domain for half-life extension, followed by the tumor-associated binding domains and a CD3 binding domain or containing an N-terminal His-tag, tumor-associated binding domains, and a CD3 binding domain, followed by an (one or two, as described in previous examples) HSA binding ankyrin repeat domain for half-life extension. For example, expression vectors encoding the following ankyrin repeat proteins were constructed:

DARPin® protein #50 (SEQ ID NO: 81 with a His-tag (SEQ ID N033) fused to its N terminus);

DARPin® protein #53 (SEQ ID NO:84 with a His-tag (SEQ ID NO:33) fused to its N terminus);
DARPin® protein #51 (SEQ ID NO:82 with a His-tag (SEQ ID NO:33) fused to its N terminus);
DARPin® protein #54 (SEQ ID NO:85 with a His-tag (SEQ ID NO:33) fused to its N terminus);
DARPin® protein #55 (SEQ ID NO:86 with a His-tag (SEQ ID NO:33) fused to its N terminus);

In Vivo Administration and Sample Collection

DARPin® protein #50, DARPin® protein #53, DARPin® protein #51, DARPin® protein #54 and DARPin® protein #55 formatted with a human serum albumin specific ankyrin repeat domain, were administered as a single intravenous bolus injection into the tail vein of 6 mice for each ankyrin repeat fusion protein. Ankyrin repeat proteins were formulated in phosphate-buffered saline (PBS) solution and dosed at 1 mg/kg with an application volume of 100 µl.

Mice were split into 2 groups with equal numbers of animals. Four serum samples were collected from each mouse. Blood samples for pharmacokinetic investigations were collected from the saphenous vein at 5 min, 4 h, 24 h, 48 h, 76 h, 96 h and 168 h post compound administration. Blood was kept at room temperature to allow clotting followed by centrifugation and collection of serum.

Bioanalytics by ELISA to Measure Ankyrin Repeat Proteins in Serum Samples

One hundred µl per well of 10 nM polyclonal goat anti-rabbit IgG antibody (Ab18) in PBS was coated onto a NUNC Maxisorb ELISA plate overnight at 4° C. After washing with 300 µl PBST (PBS supplemented with 0.1% Tween20) per well five times, the wells were blocked with 300 µl PBST supplemented with 0.25% Casein (PBST-C) for 1 h at room temperature (RT) on a Heidolph Titramax 1000 shaker (450 rpm). Plates were washed as described above. 100 µl 5 nmol/L rabbit anti-DARPin® 1-1-1 antibody in PBST-C was added and the plates were incubated at RT (22° C.) with orbital shaking (450 rpm) for 1 h. Plates were washed as described above.

One hundred µl of diluted serum samples (1:20-1:312500 in 1:5 dilution steps) or ankyrin repeat protein standard curve samples (0 and 50-0.0008 nmol/L in 1:3 dilution steps) were applied for 2 h, at RT, shaking at 450 rpm. Plates were washed as described above.

Figure 1B:
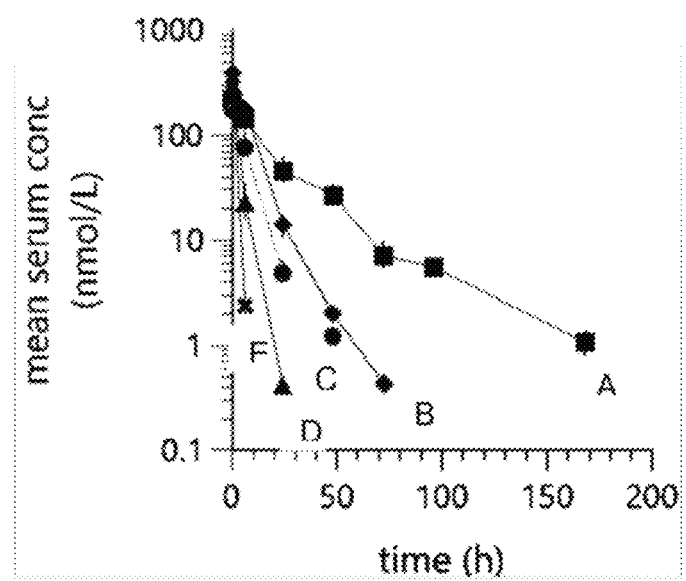
FIG. 1B. Pharmacokinetic analysis of exemplary specific designed ankyrin repeat proteins in female BALB/c mice. The figure shows the group mean serum concentration-time profiles of DARPin® protein #51, DARPin® protein #50, DARPin® protein #54, DARPin® protein #54 and DARPin® protein #55 in female BALB/c mice (mean+/−max/min, N=3 per group), following single intravenous bolus administration of 1 mg/kg.

Wells were then incubated with 100 µl murine anti-RGS-His-HRP IgG (Ab06, 1:2000 in PBST-C) and incubated for 1 h, at RT, 450 rpm. Plates were washed as described above. The ELISA was developed using 100 µl/well TMB substrate solution for 5 minutes and stopped by the addition of 100 µl 1 mol/L $H_2SO_4$. The difference between the absorbance at 450 nm and the absorbance at 620 nm was calculated. Samples were measured in duplicate on two different plates. FIG. 1B shows the serum concentrations of DARPin® protein #50, DARPin® protein #53, DARPin® protein #51, DARPin® protein #54 and DARPin® protein #55 as a function of time after the single intravenous administration into mice. The traces indicate roughly mono-exponential elimination of the compounds.

Pharmacokinetic Analysis

Pharmacokinetic data analysis was performed at Molecular Partners using Version 7.0 of the WinNonlin program as part of Phoenix 64, Pharsight, N.C. Calculation of the pharmacokinetic parameters based on the mean concentration-time data of the animals dosed via intravenous bolus injection was performed with non-compartmental analysis (NCA model 200-202, IV bolus, linear trapezoidal linear interpolation). The following pharmacokinetic parameters were calculated: AUCinf, AUC_% extrapol, Cmax, Tmax, CI_pred, Vss_pred, t½. Maximum serum concentrations (Cmax) and the times of their occurrence (Tmax) were obtained directly from the serum concentration-time profiles. The area under the serum concentration-time curve (AUCinf) was determined by the linear trapezoidal formula up to the last sampling point (Tlast) and extrapolation to infinity assuming mono-exponential decrease of the terminal phase. The extrapolation up to infinity was performed using Clast/λz, where λz denotes the terminal rate constant estimated by log linear regression and Clast denotes the concentration estimated at Tlast by means of the terminal log-linear regression. Total serum clearance (CI_pred) and the apparent terminal half-life were calculated as follows: CI_pred=i.v. dose/AUCinf and t½=ln2/λz. The steady-state volume of distribution Vss was determined by: Vss=i.v. dose·AUMCinf/(AUCinf)2. AUMCinf denotes the total area under the first moment of drug concentration-time curve extrapolated to infinity using the same extrapolation procedure as described for calculation of AUCinf. To calculate PK parameters based on concentrations given in nmol/L dose values given as mg/kg were converted to nmol/kg by using the molecular weight of the ankyrin repeat proteins. Table 2b shows the summary of pharmacokinetic characteristics of the five tested ankyrin repeat proteins DARPin® protein #50, DARPin® protein #53, DARPin® protein #51, DARPin® protein #54 and DARPin® protein #55 following single intravenous administration of 1 mg/kg.

TABLE 2b

Pharmacokinetic parameters for five exemplary multi-specific recombinant proteins

| parameter | unit | DARPin® protein #50 | DARPin® protein #53 | DARPin® protein #51 | DARPin® protein #54 | DARPin® protein #55 |
| --- | --- | --- | --- | --- | --- | --- |
| AUCINF_D_pred | (h*nmol*kg)/(L*mg) | 3688 | 1187 | 4505 | 1577 | 923 |
| Cmax | nmol/L | 390 | 298 | 221 | 175 | 300 |
| Tmax | h | 0.083 | 0.083 | 0.083 | 0.083 | 0.083 |
| CI_pred | L/(h*kg) | 0.00448 | 0.0111 | 0.00293 | 0.00698 | 0.0143 |
| Vss_pred | L/kg | 0.028 | 0.018 | 0.075 | 0.041 | 0.002 |
| HL_Lambda_z (half-life) | h | 9.6 | 3.1 | 26.6 | 7.2 | 0.85 |
| AUC_% Extrap_pred | (%) | 0 | 0 | 1 | 1 | 0 |
| AUC_% Back_Ext_pred | (%) | 1 | 2 | 0 | 1 | 3 |

As it can be seen in the Table 2b above and FIG. 1, DARPin® protein #51 shows the longest half-life followed by DARPin® protein #50, DARPin® protein #54 and DARPin® protein #53, while DARPin® protein #55, which is half-life extended at the C-terminus, shows the shortest half-life.

Additionally, the pharmacokinetic profiles of DARPin® protein #56 (SEQ ID NO:95), DARPin® protein #57 (SEQ ID NO:96), DARPin® protein #58 (SEQ ID NO:97), DARPin® protein #59 (SEQ ID NO:98), DARPin® protein #60 (SEQ ID NO:99) and DARPin® protein #61 (SEQ ID NO:100) were analyzed in mice, following the same experimental set up as for DARPin® protein #50, DARPin® protein #53, DARPin® protein #51, DARPin® protein #54 and DARPin® protein #55.

Table 2c shows the summary of pharmacokinetic characteristics of the six tested ankyrin repeat proteins DARPin® protein #56, DARPin® protein #57, DARPin® protein #58, DARPin® protein #59, DARPin® protein #60 and DARPin® protein #61 following single intravenous administration of 1 mg/kg.

a NLC chip (BioRad) to a level of around 700-1400 resonance units (RU). The interaction of ankyrin repeat protein and human CD3 was then measured by injecting 300 μl running buffer (PBS, pH 7.4 containing 0.005% Tween 20®) containing serial dilutions of ankyrin repeat proteins covering a concentration range between 64 nM and 4 nM for multi-trace SPR measurements, followed by a running buffer flow for at least 10 minutes at a constant flow rate of 60 μl/min (off-rate measurement). The regeneration was performed using 30 μl of 10 mM Glycine pH 2. The signals (i.e. resonance unit (RU) values) of the interspots and a reference injection (i.e. injection of running buffer only) were subtracted from the RU traces obtained after injection of ankyrin repeat protein (double-referencing). While binding was too weak for DARPin® protein #7, binding parameters ($K_D$, on-rate, off-rate) against CD3 were determined for affinity matured constructs. On-rates ($k_{on}$) and dissociation constants ($K_D$) are given only as approximation because binding equilibrium was not appropriately reached even at highest samples concentration, leading to non-optimal fits for on-rates.

TABLE 2c

Pharmacokinetic parameters for six exemplary multi-specific recombinant proteins

| parameter | unit | DARPin® protein #56 | DARPin® protein #57 | DARPin® protein #58 | DARPin® protein #59 | DARPin® protein #60 | DARPin® protein #61 |
|---|---|---|---|---|---|---|---|
| AUCINF_D_pred | (h*nmol*kg)/(L*mg) | 2408 | 2341 | 3812 | 2426 | 3858 | 3201 |
| AUClast | h*(nmol/L) | 2392 | 2329 | 3776 | 2413 | 3834 | 3189 |
| Cmax | nmol/L | 283 | 251 | 258 | 290 | 247 | 227 |
| Tmax | h | 0.083 | 0.083 | 0.083 | 0.083 | 0.083 | 0.083 |
| CL_pred | L/(h*kg) | 0.00456 | 0.00487 | 0.00294 | 0.00462 | 0.00280 | 0.00337 |
| Vss_pred | L/kg | 0.0375 | 0.0424 | 0.0478 | 0.0350 | 0.0437 | 0.0420 |
| HL_Lambda_z (half-life) | h | 11.4 | 10.5 | 14.9 | 10.9 | 13.5 | 12.6 |
| AUC_% Extrap_pred | (%) | 1 | 1 | 1 | 1 | 1 | 1 |
| AUC_% Back_Ext_pred | (%) | 1 | 1 | 1 | 1 | 1 | 1 |

As it can be seen in the Table 2c above, DARPin® protein #58 shows the longest half-life followed by DARPin® protein #60, DARPin® protein #61, DARPin® protein #56 and DARPin® protein #59, while DARPin® protein #57 shows the shortest half-life.

Example 3: Determination of Dissociation Constants ($K_D$) of Multi-Specific Recombinant Ankyrin Repeat Proteins A. Determination of Dissociation Constants ($K_D$) of Multi-Specific Recombinant Ankyrin Repeat Proteins with Binding Specificity for Human CD3 by Surface Plasmon Resonance (SPR) Analysis The binding affinities of four purified ankyrin repeat proteins on recombinant human CD3 target were analyzed using a ProteOn instrument (BioRad) and the measurement was performed according standard procedures known to the person skilled in the art. For that, DARPin® protein #7, DARPin® protein #8 and DARPin® protein #9 and DARPin® protein #10 of the invention were subcloned and expressed as described above into derivatives of the pQE30 (Qiagen) expression vector, containing an N-terminal His-tag, CD33 and CD123 binding ankyrin repeat domains, followed by one of the four CD3 specific ankyrin repeat protein constructs.

Figure 2A:
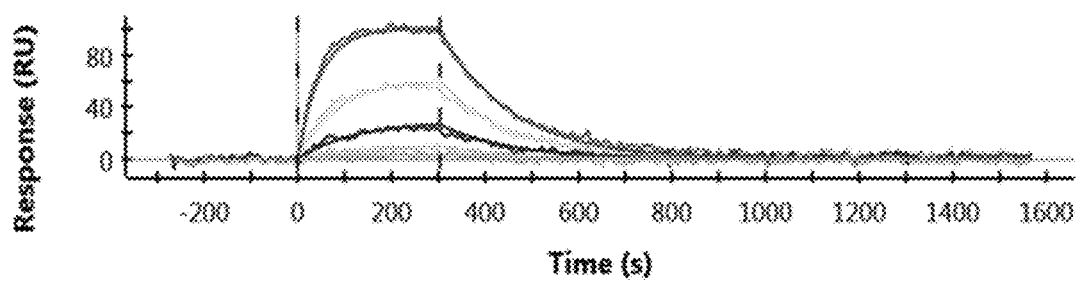
FIG. 2 (A-D). Surface Plasmon Resonance (SPR) analysis of ankyrin repeat protein binding to human CD3, exemplified by DARPin® protein #53 (FIG. 2A), DARPin® protein #54 (FIG. 2B) and DARPin® protein #9 (C). Various concentrations of the purified ankyrin repeat proteins were applied to a GLC chip with immobilized human CD3 for on-rate and off-rate measurements. The obtained SPR trace analyses were used to determine the ankyrin repeat protein CD3 interaction. RU, Resonance Units; s, time in seconds. Similarly, SPR analyses were performed to analyze binding of multi-domain DARPin® protein #56 and DARPin® protein #57 to various target proteins, and binding affinities were determined (see Example 3). KD values of the binding interactions of DARPin® protein #56 and DARPin® protein #57 with human CD33, CD123, CD70, CD3 and serum albumin (SA) are shown in FIG. 2D.
Figure 2B:
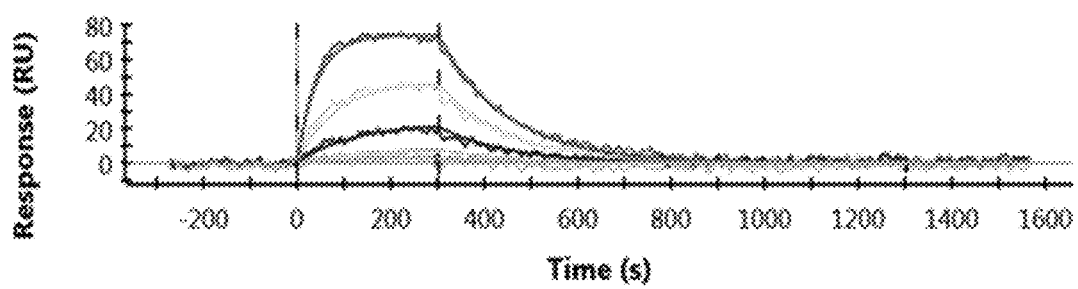
Figure 2C:
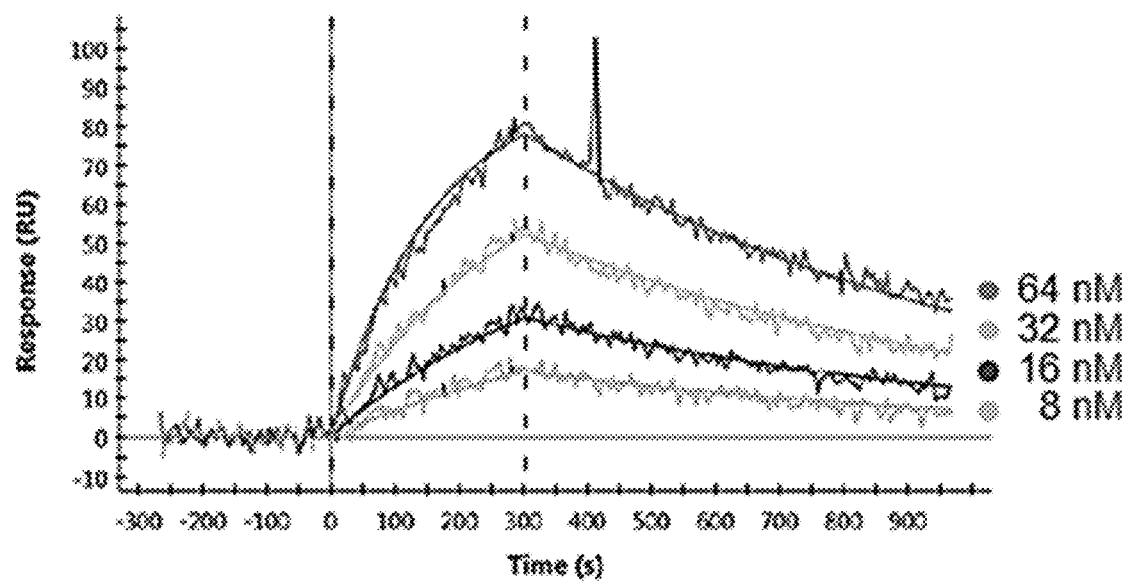

Briefly, biotinylated human scCD3εγ was diluted in PBST (PBS, pH 7.4 containing 0.005% Tween 20®) and coated on As representative example, FIG. 2C shows SPR traces obtained for DARPin® protein #9 formatted with CD33 and CD123-binding designed ankyrin repeat domains. Dissociation constants (KO) were calculated from the estimated on- and off-rates using standard procedures known to the person skilled in the art. $K_D$ values of the binding interactions of selected ankyrin repeat proteins with human CD3 were determined to be in the range of 6-35 nM (see Table 3a).

TABLE 3a $K_D$ values of ankyrin repeat protein-human CD3 interactions

| DARPin® protein # | $K_D$ [nM] | $k_{on}$ [1/Ms] | $k_{off}$ [1/s] | number of measurements |
|---|---|---|---|---|
| DARPin® protein #8 | ~35 ± 15 nM | ~4.9E$^{+04}$ | 1.5E$^{-03}$ | n = 2 |
| DARPin® protein #9 | ~15 ± 2 nM | ~8.9E$^{+04}$ | 1.3E$^{-03}$ | n = 4 |
| DARPin® protein #10 | ~6 ± 2 nM | ~8.2E$^{+04}$ | 4.1E$^{-04}$ | n = 6 |

B. Determination of Dissociation Constants ($K_D$) of Recombinant Ankyrin Repeat Proteins with Binding Specificity for Human CD33 and CD123 by Surface Plasmon Resonance (SPR) Analysis.

The binding affinities of two purified ankyrin repeat proteins on recombinant human CD33 and CD123 target respectively were analyzed using a ProteOn instrument (BioRad) and the measurement was performed according standard procedures known to the person skilled in the art. For that, DARPin® protein #25 (with binding specificity for CD33 and CD3), DARPin® protein #26 (with binding specificity for CD123 and CD33) of the invention were subcloned and expressed as described above into derivatives of the pQE30 (Qiagen) expression vector, containing an N-terminal His-tag, CD33 or CD123 binding ankyrin repeat domains respectively, followed by one of the four CD3 specific ankyrin repeat protein constructs. The following steps were performed as described in A above. Briefly, biotinylated extracellular domains of human CD33 (provided by Speed BioSystems, Lot no cat #YCP2045) as target protein was used for the assessment of DARPin® protein #25 and biotinylated extracellular domains of human (uniprot ID 26951) for the assessment of DARPin® protein #26 accordingly. $K_D$ values of the binding interactions of selected ankyrin repeat proteins with human CD33 and CD123 are shown in the table below (see Table 3b).

TABLE 3b $K_D$ values of ankyrin repeat protein-human CD33 or human CD123 interactions

| DARPin® protein # | $K_D$ [nM] | $k_{on}$ [1/Ms] | $k_{off}$ [1/s] | number of measurements |
|---|---|---|---|---|
| DARPin® protein #25 | 7.3 ± 1.3 nM | $4.2E^{+06}$ | $3.04E^{-02}$ | n = 6 |
| DARPin® protein #26 | 9.5 ± 0.7 nM | $1.79E^{+06}$ | $1.7E^{-02}$ | n = 2 |

C. Determination of Dissociation Constants ($K_D$) of Multi-Specific Recombinant Ankyrin Repeat Proteins with Binding Specificity for Human CD33, CD123 and/or CD70 by Surface Plasmon Resonance (SPR) Analysis The binding affinities of 16 purified ankyrin repeat proteins on recombinant human CD33, CD123 and CD70 targets were analyzed using a ProteOn XPR36 instrument (BioRad) and the measurement was performed according standard procedures known to the person skilled in the art. For that, DARPin® protein #27, DARPin® protein #29, DARPin® protein #47 and DARPin® protein #48 and DARPin® protein #49, DARPin® protein #50, DARPin® protein #51, DARPin® protein #52, DARPin® protein #31, DARPin® protein #53, DARPin® protein #54, DARPin® protein #55, DARPin® protein #34, DARPin® protein #33, DARPin® protein #39 and DARPin® protein #36 were subcloned and expressed as described above into derivatives of the pQE30 (Qiagen) expression vector, containing an N-terminal His-tag, CD33, CD123 and/or CD70 binding ankyrin repeat domains, followed by a CD3 specific ankyrin repeat domain and for some constructs by a human serum albumin specific ankyrin repeat domain.

Briefly, biotinylated human CD70, CD123 and CD33 was diluted in PBST (PBS, pH 7.4 containing 0.005% Tween 20®) and coated on a GLC chip (BioRad) to a level of around 200, 460 and 450 resonance units (RU) respectively. HSA in NaOAc pH 5.0 was directly immobilized on the GLC chip to a level of 800 RU. Bio. CD70, bio. CD33 and bio. CD123 required to have Neutravidin coated first to a level of 6000 RU before the biotinylated targets could be applied. The interaction of the selected ankyrin repeat proteins and human CD70, CD123 and CD33 was then measured by injecting 300 µl running buffer (PBS, pH 7.4 containing 0.005% Tween 20®) containing serial dilutions of ankyrin repeat proteins covering a concentration range between 100 nM and 2.6 nM (100, 40, 16, 6.4 and 2.6 nM respectively) for multi-trace SPR measurements, with an association of 120 s and dissociation of 1200 s using a constant flow of 100 µl/min. The regeneration was performed using 30 µl of 4 mM Glycine pH 2. The signals (i.e. resonance unit (RU) values) of the interspots and a reference injection (i.e. injection of running buffer only) were subtracted from the RU traces obtained after injection of ankyrin repeat protein (double-referencing).

$K_D$ values of the binding interactions of selected ankyrin repeat proteins with human CD33, CD123 and CD70 are shown in the table below (see Table 3c).

TABLE 3c $K_D$ values of ankyrin repeat protein-human CD33, CD123 and CD70 interactions

| DARPin® protein # | $K_D$ [M] CD70 | $K_D$ [M] CD123 | $K_D$ [M] CD33 | $K_D$ [M] Human serum albumin |
|---|---|---|---|---|
| DARPin® protein #27 | nb | 1.9E−08 | 5.7E−09 | nb |
| DARPin® protein #47 | nb | 8.0E−09 | 5.4E−09 | 1.5E−08 |
| DARPin® protein #48 | nb | 5.1E−09 | 4.2E−09 | 1.1E−09 |
| DARPin® protein #49 | nb | 2.3E−08 | 6.8E−09 | 1.4E−08 |
| DARPin® protein #29 | 1.8E−10 | nb | 4.8E−09 | nb |
| DARPin® protein #50 | 8.1E−10 | nb | 7.5E−09 | 2.4E−08 |
| DARPin® protein #51 | 5.6E−10 | nb | 5.5E−09 | 1.3E−09 |
| DARPin® protein #52 | 2.7E−10 | nb | 5.7E−09 | 4.8E−08 |
| DARPin® protein #31 | 3.1E−10 | 1.0E−08 | 1.1E−08 | nb |
| DARPin® protein #53 | 7.0E−10 | 8.0E−09 | 1.2E−08 | 2.4E−08 |
| DARPin® protein #54 | 6.1E−10 | 3.3E−08 | 8.2E−09 | 1.2E−09 |
| DARPin® protein #55 | 3.8E−10 | 1.3E−08 | 9.6E−09 | 7.5E−09 |
| DARPin® protein #34 | nb | 8.6E−09 | nb | nb |
| DARPin® protein #33 | 1.8E−10 | nb | nb | nb |
| DARPin® protein #39 | nb | nb | 2.4E−08 | nb |
| DARPin® protein #36 | nb | nb | 6.7E−09 | nb |

*nb: no binding

Similarly, the binding affinities of two purified ankyrin repeat proteins on recombinant human CD3 target were analyzed as described before. Briefly, DARPin® protein #53, DARPin® protein #54 in NaOAc pH 4.5 was coated on a GLC chip (BioRad) to a level of around 790-1500 resonance units (RU). The interaction of ankyrin repeat protein and human CD3 was then measured by injecting 300 µl running buffer (PBS, pH 7.4 containing 0.005% Tween 20®) containing serial dilutions of human scCD3εγ (56.4 u M), was diluted in PBST (PBS, pH 7.4 containing 0.005% Tween 20®) and covering a concentration range between 300 nM and 19 nM for multi-trace SPR measurements, followed by a running buffer flow for at least 10 minutes at a constant flow rate of 60 µl/min (off-rate measurement).

The regeneration was performed using 30 µl of 10 mM Glycine pH 2. The signals (i.e. resonance unit (RU) values) of the interspots and a reference injection (i.e. injection of running buffer only) were subtracted from the RU traces obtained after injection of CD3 (double-referencing). Binding parameters (KD, on-rate, off-rate) against CD3 were determined by using a standard Langmuir fit model. As representative example, FIG. 2 (A-B) shows SPR traces obtained for DARPin® protein #53 (A) and DARPin® protein #54 (B)

TABLE 4a

K$_D$ values of ankyrin repeat protein-human CD3 interactions

| DARPin® protein # | K$_D$ [nM] | k$_{on}$ [1/Ms] | k$_{off}$ [1/s] |
|---|---|---|---|
| DARPin® protein #53 | 139 ± 26 | 4.8E+04 | 6.5E−03 |
| DARPin® protein #54 | 129 ± 14 | 5.2E+04 | 6.7E−03 |

D. Determination of Dissociation Constants (K$_D$) of Multi-Specific Recombinant Ankyrin Repeat Proteins with Binding Specificity for Human CD33, CD123 and CD70 by Surface Plasmon Resonance (SPR) Analysis The binding affinities of selected multispecific ankyrin repeat proteins on recombinant targets were analyzed using ProteOn (BioRad) and Bruker Sierra SPR-32 Pro instruments. The measurements were performed according to standard procedures known to the person skilled in the art. For that, DARPin® protein #56 and DARPin® protein #57 of the invention were subcloned and expressed as described above into derivatives of the pQE30 (Qiagen) expression vectors, containing an N-terminal His-tag, two human serum album specific binding domains and CD70, CD123 and CD33 specific binding domains, followed by one CD3 specific binding domain.

Briefly, human target CD70 (SEQ ID NO: 89; hCD70-Fc-trimer, ACRO Biosystems) was diluted in PBST (PBS, pH 7.4 containing 0.005% Tween 20®) and captured on a PAGD200L protein A/G sensorchip (XanTec bioanalytics GmbH) to a level of around 36 resonance units (RU) using a ProteOn (BioRad). The interaction of each tested ankyrin repeat protein and human CD70-Fc-trimer was then measured by injecting 400 µl running buffer (PBS, pH 7.4 containing 0.005% Tween 20®) containing three-fold serial dilutions of ankyrin repeat proteins covering a concentration range between 600 nM and 7.4 nM, followed by a running buffer flow for 2700 seconds at a constant flow rate of 100 µl/min (off-rate measurement). The regeneration was performed using 30 µl of 10 mM glycine pH 2 and hCD70-Fc-trimer was reinjected to prepare the surface for the next measurement. Each interaction was recorded in triplicates. The signals (i.e. resonance unit (RU) values) of the interspots and a reference injection (i.e. injection of running buffer only) were subtracted from the RU traces obtained injecting the ankyrin repeat protein (double-referencing). Dissociation constants (KD) were calculated from the globally fitted on- and off-rates using standard 1:1-Langmuir model.

Similarly, human target_hCD123 (SEQ ID NO: 88) was diluted in PBST (PBS, pH 7.4 containing 0.005% Tween 20®) and captured on a Bruker IgG Capture sensorchip to a level of around 177 resonance units (RU) using a Bruker Sierra SPR-32pro. The interaction of each tested ankyrin repeat protein and target_hCD123 was then measured by injecting 100 µl running buffer (PBS, pH 7.4 containing 0.005% Tween 20®) containing three-fold serial dilutions of ankyrin repeat proteins covering a concentration range between 200 nM and 91 pM, followed by a running buffer flow for at least 1500 seconds at a constant flow rate of 25 µl/min (off-rate measurement). The regeneration was performed using 8.3 µl of 10 mM glycine pH 2 and hCD123 was reinjected to prepare the surface for the next measurement. Each interaction was recorded in triplicates. The signals (i.e. resonance unit (RU) values) of empty surface and a reference injection (i.e. injection of running buffer only) were subtracted from the RU traces obtained injecting the ankyrin repeat protein (double-referencing). Dissociation constants (K$_D$) were calculated from the globally fitted on- and off-rates using standard 1:1-Langmuir model.

Figure 2D:
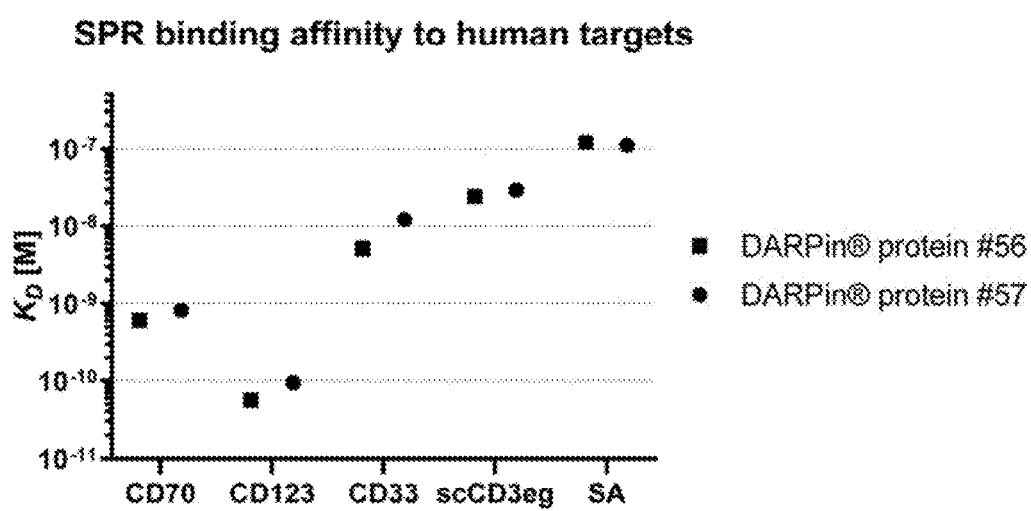

For measuring the interaction with human CD33, DARPin® protein #56 and DARPin® protein #57 were diluted in 10 mM NaOAc pH 4.0 and immobilized on an NHS/EDC activated HC200M sensorchip (XanTec bioanalytics GmbH) to a level of around 1000 resonance units (RU) (SMA555) or 1400 Rus (PSC466) using a ProteOn (BioRad). The surface was deactivated using Ethanolamine. The interaction of the tested proteins and human target hCD33 (SEQ ID NO:87) was then measured by injecting 400 µl running buffer (PBS, pH 7.4 containing 0.005% Tween 20®) containing three-fold serial dilutions of human target hCD33 covering a concentration range between 66.7 nM and 0.82 nM, followed by a running buffer flow for 500 seconds at a constant flow rate of 100 µl/min (off-rate measurement). After each measurement, a 10 min pause was introduced to allow for complete dissociation of the analyte. Each interaction was recorded in triplicates. The signals (i.e. resonance unit (RU) values) of the interspots and a reference injection (i.e. injection of running buffer only) were subtracted from the RU traces obtained injecting human hCD33 (double-referencing). Dissociation constants (K$_D$) were calculated from the globally fitted on- and off-rates using standard 1:1-Langmuir model. FIG. 2D shows SPR traces obtained for DARPin® protein #56 and DARPin® protein #57

K$_D$ values of the binding interactions of selected ankyrin repeat proteins with human CD33, CD123, CD70 and CD3 are shown in the table below (see Table 4b).

TABLE 4b

K$_D$ values of ankyrin repeat protein-human CD33, CD123 and CD70 interactions

| DARPin® protein # | K$_D$ [M] CD70 | K$_D$ [M] CD123 | K$_D$ [M] CD33 | K$_D$ [M] CD3 | K$_D$ [M] Human serum albumin (SA) |
|---|---|---|---|---|---|
| DARPin® protein #56 | 6.1E−10 | 5.6E−11 | 5.1E−09 | 2.4E−08 | 1.2E−07 |
| DARPin® protein #57 | 8.2E−10 | 9.4E−11 | 1.2E−08 | 2.9E−08 | 1.1E−07 |

Example 4: Determination of T Cell or Tumor Cell Binding

Determination of CD3 T Cell Binding of DARPin® Protein #11, DARPin® Protein #12, DARPin® Protein #13 and DARPin® Protein #14.

The determination of CD3 binding was performed with primary human T cells using Mirrorball laser scanning imaging cytometry. Therefore, primary T cells were isolated from human peripheral blood mononuclear cells (PBMCs) using a pan-T cell purification kit (Miltenyi Biotec). A titration of DARPin® protein #7, DARPin® protein #8 and DARPin® protein #9 and DARPin® protein #10, formatted into a trispecific format (including CD33 and CD123 binding ankyrin repeat domains), DARPin® protein #11, DARPin® protein #12, DARPin® protein #13 and DARPin® protein #14 UN tetraspecific format (including an additional ankyrin repeat domain binding specifically to human serum albumin) were incubated with 50,000 pan-T cells per well in presence of 600 µM human serum albumin (to mimic physiological serum concentration) for 30 minutes at 4° C.

Two benchmark T-cell engagers, AMG330 and flotetuzumab were applied as controls, targeting CD33 or CD123. After washing, CD3 binding was detected by 1:100-diluted anti-penta-His Alexa Fluor 488 antibody (Qiagen). After 30 min incubation at 4° C., cells were washed and resuspended in Cytofix fixation buffer (BD Biosciences) and counterstained by 5 μM DRAQ5 (Abcam) for 15 min at RT. Median of mean fluorescence intensities of Alexa Fluor 488 binding on far-red counterstained cells were measured by Mirrorball using Cellista software (SPT Labtech) and data was plotted using GraphPad Prism 8.

Figure 20A:
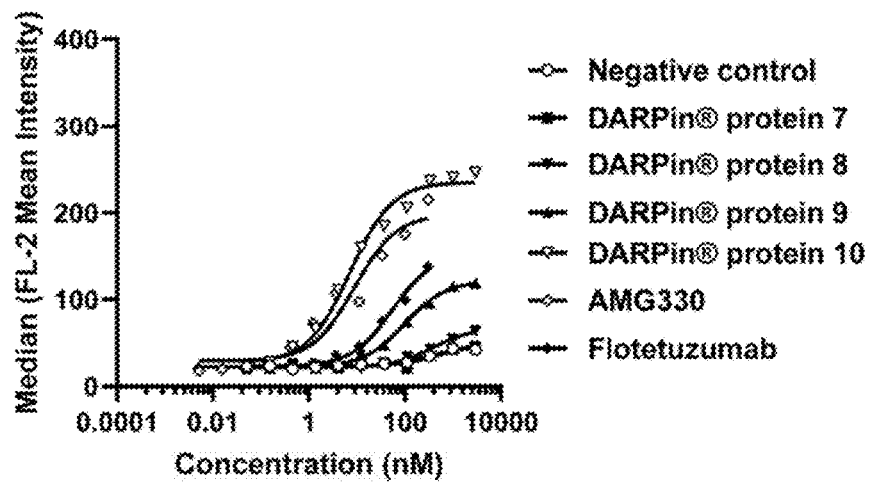
FIG. 20A and FIG. 20B. CD3 binding of exemplified ankyrin repeat proteins to T cells. Binding to CD3 on Pan-T cells was assessed by Mirrorball. Shown are benchmark control molecules (known benchmark T cell engagers, AMG330 with binding specificity for CD33 and flotetuzumab with binding specificity for CD123) and selected ankyrin repeat proteins, DARPin® protein 7, DARPin® protein 8, DARPin® protein 9 and DARPin® protein 10 without (FIG. 20A) or DARPin® protein 11, DARPin® protein 12, DARPin® protein 13 and DARPin® protein 14 (FIG. 20B) with half-life extension (HLE). Half-life extended proteins (B) show similar binding compared to the corresponding non-HLE molecules shown in (A). Pan-T cells from 5 different donors were tested, one representative donor is shown here. (*Negative control: a designed ankyrin repeat protein with binding specificity for CD33 and CD123 only, with or without half-life extension respectively).
Figure 20B:
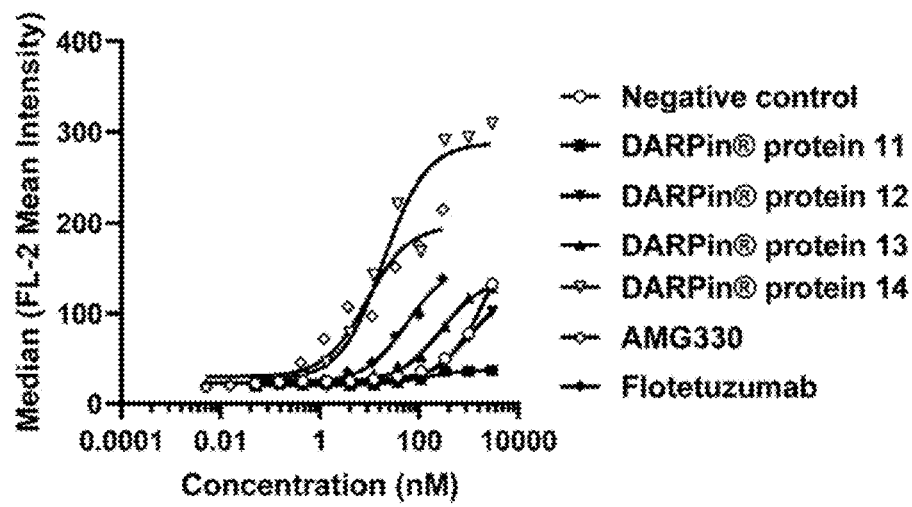

As shown in FIGS. 20A and B, DARPin® proteins show a broad range of affinities from no binding detectable for DARPin® protein 7 to binding as good as benchmark molecules for DARPin® protein 10 (known benchmark T cell engagers, AMG330 with binding specificity for CD33 and flotetuzumab with binding specificity for CD123). The CD3 binding to T cells is aligned with CD3 affinity measured by SPR. The presence of an additional HSA binding domain (see FIG. 3B) had only a minor impact on binding to T cells. Table 5a shows the CD3 binding affinity of the four exemplary ankyrin repeat proteins, as represented by their $EC_{50}$ values.

TABLE 5a $EC_{50}$ values of CD123-CD33-CD3-specific DARPin® proteins

| DARPin® protein # | $EC_{50}$ [nM] |
| --- | --- |
| #7 | Too low-not calculated |
| #8 | 250-400 nM |
| #9 | 50-100 nM |
| #10 | 5-15 nM |

Determination of T Cell Binding of DARPin® Protein #27, DARPin® Protein #28 and DARPin® Protein #29 and DARPin® Protein #30.

The determination of T cell binding was performed with primary human T cells using Mirrorball laser scanning imaging cytometry. Therefore, primary T cells were isolated from human peripheral blood mononuclear cells (PBMCs) using a pan-T cell purification kit (Miltenyi Biotec). A titration of DARPin® protein #27, DARPin® protein #28 and DARPin® protein #29 and DARPin® protein #30 were incubated with 50,000 pan-T cells per well in presence of 600 μM human serum albumin (to mimic physiological serum concentration) for 30 minutes at 4° C. Two benchmark T-cell engagers, AMG330 and flotetuzumab were applied as controls, targeting CD33 or CD123. After washing, CD3 binding was detected by 1:100-diluted anti-penta-His Alexa Fluor 488 antibody (Qiagen). After 30 min incubation at 4° C., cells were washed and resuspended in Cytofix fixation buffer (BD Biosciences) and counterstained by 5 μM DRAQ5 (Abcam) for 15 min at RT. Median of mean fluorescence intensities of Alexa Fluor 488 binding on far-red counterstained cells were measured by Mirrorball using Cellista software (SPT Labtech) and data was plotted using GraphPad Prism 8.

Table 5b shows the binding affinity of the four exemplary ankyrin repeat proteins, as represented by their $EC_{50}$ values.

TABLE 5b $EC_{50}$ values of multi-specific DARPin® proteins

| DARPin® protein # | $EC_{50}$ [nM] |
| --- | --- |
| #27 | 6.518 nM |
| #28 | 1.413 nM |
| #29 | 1.972 nM |
| #30 | 1.802 nM |

Determination of Tumor Cell Binding of Multispecific Binding Proteins.

Figure 20C:
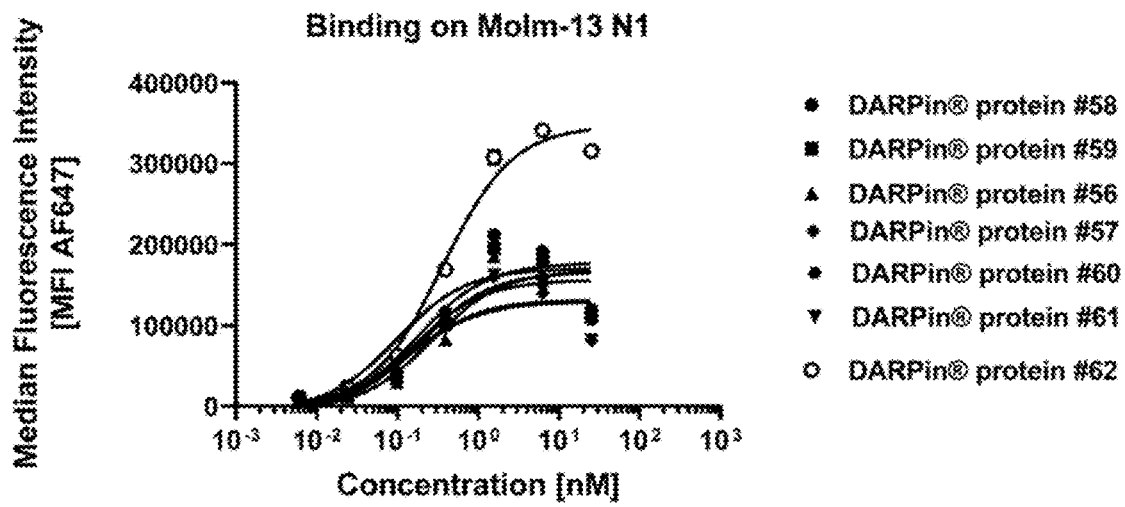
FIG. 20C shows tumor cell binding of selected multispecific binding proteins DARPin® protein #56, DARPin® protein #57, DARPin® protein #58, DARPin® protein #59, DARPin® protein #60, DARPin® protein #61 and DARPin® protein #62 on Molm-13 N1 cells.

The determination of binding of several multispecific proteins to tumor cells was performed by Fluorescence Activated Cell Sorting (FACS) flow cytometry. Therefore, tumor cells (Molm-13 N1), were seeded at 100,000 cells per well in a 96 well plate. DARPin® protein #56, DARPin® protein #57, DARPin® protein #58, DARPin® protein #59, DARPin® protein #60, DARPin® protein #61 and DARPin® protein #62 were titrated down starting at 100 nM in 1:5 dilution ratio. Tumor cells were resuspended with diluted DARPin® proteins and incubated 60 minutes at 4° C. The assay was performed in PBS including 2% fetal bovine serum and human serum albumin 20 uM (HSA). After washing twice with Phosphate Buffer saline (PBS), DARPin® protein specific tumor cell binding was detected by adding unlabelled primary anti-rabbit DARPin® antibody (anti-rabbit 1-1-1 antibody, CePower) at 2 ug/ml. An incubation step of at least 30 minutes at 4° C. followed. Afterwards, cells were washed with PBS and a secondary anti-rabbit antibody labelled with Alexa Fluor 647 antibody (ThermoFisher) at 2 ug/ml was added. The same incubation conditions applied. Finally, the cells were washed twice and resuspended in Cytofix fixation buffer (BD Biosciences) for 15 min at room temperature (RT). Median fluorescence intensities (MFI) of Alexa Fluor 647 DARPin® labelled cells were measured by Attune N×T (Thermo Fisher) using FlowJo software for analyses and GraphPad Prism 8 for data plotting. FIG. 20C shows titration curves of selected DARPin® proteins targeting CD123, CD33 and CD70 on Molm-13 N1 cells.

Table 5c shows the binding affinity of the seven exemplary multispecific binding proteins, as represented by their $EC_{50}$ values.

TABLE 5c $EC_{50}$ values of multi-specific DARPin® proteins

| DARPin® protein # | $EC_{50}$ [nM] |
| --- | --- |
| #58 | 0.17 |
| #59 | 0.19 |
| #56 | 0.26 |
| #57 | 0.13 |
| #60 | 0.16 |
| #61 | 0.13 |
| #62 | 0.36 |

Example 5: Assessment of Potency and Specificity of Multi-Specific Recombinant Proteins with In Vitro Short-Term T Cell Activation Assay A. Assessment of Potency and Specificity of Multi-Specific Recombinant Proteins on Molm-13 Target Cells in Co-Culture with Human PanT Cells.

Specificity and potency of the previously described recombinant multi-specific ankyrin repeat proteins were assessed in an in vitro short-term T cell activation assay by FACS, measuring CD25 activation marker on CD8+ T cells.

Therefore, 50,000 purified pan-T effector cells and 50,000 Molm-13 target cells per well were co-incubated (E:T ratio 1:1) with serial dilutions of selected DARPin® proteins or control benchmark molecules in duplicates in presence of 600 µM human serum albumin for 24 hours at 37° C. Cell were washed and stained with 1:1,000 Live/Dead Aqua (Thermo Fisher), 1:250 mouse anti-human CD8 Pacific Blue (BD), and 1:100 mouse anti-human-CD25 PerCP-Cy5.5 (eBiosciences) antibodies for 30 min at 4° C. After washing and fixation, cells were analyzed on a FACS Canto II (BD) machine. T cell activation was assessed by measuring CD25+ cells on Live/Dead-negative and CD8+ gated T cells. FACS data was analyzed using FlowJo software and data was plotted using GraphPad Prism 8.

Figure 3A:
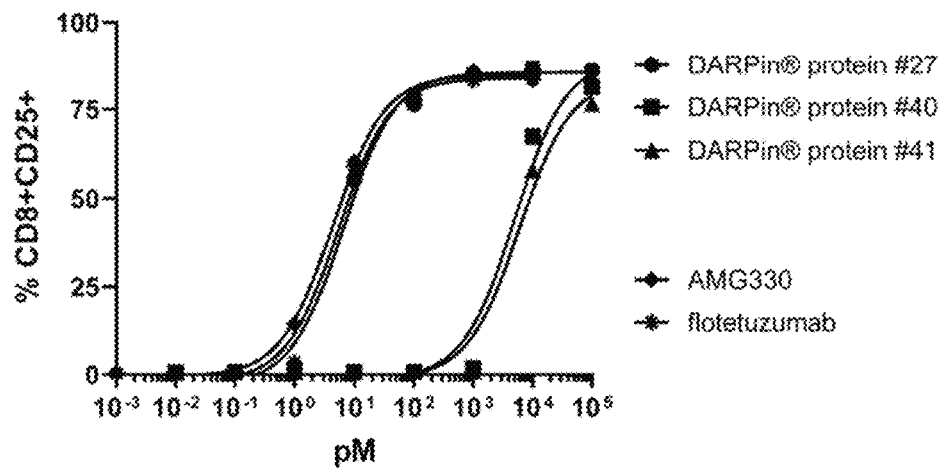
(FIG. 3A) two tumor antigen specific binding domains, with binding specificity for CD123 and CD33, DARPin® protein #27, compared to proteins with only one tumor antigen specific binding domain (DARPin® protein 40 and DARPin® protein 41).
Figure 3B:
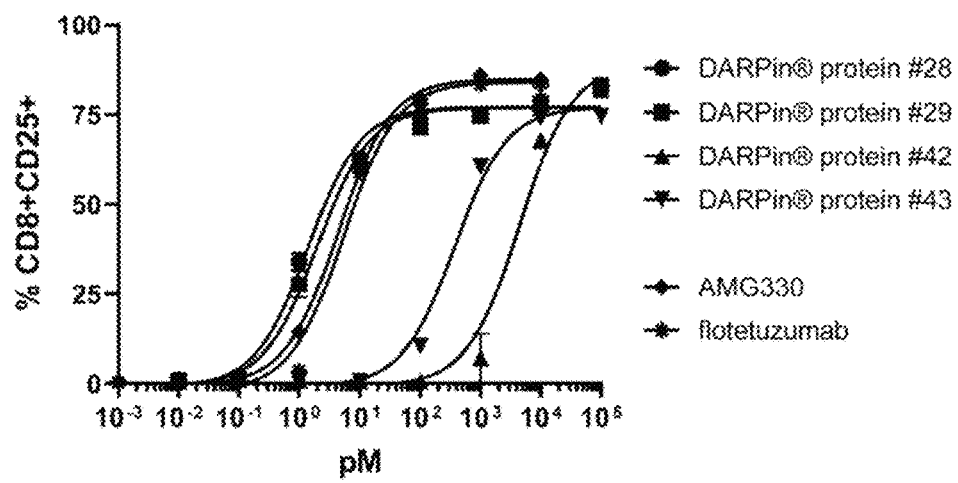
(FIG. 3B) two tumor antigen specific binding domains with binding specificity for CD70 and CD33, DARPin® protein #28 and DARPin® protein #29, compared to proteins with only one tumor antigen specific binding domain (DARPin® protein 42 and DARPin® protein 43).
Figure 3C:
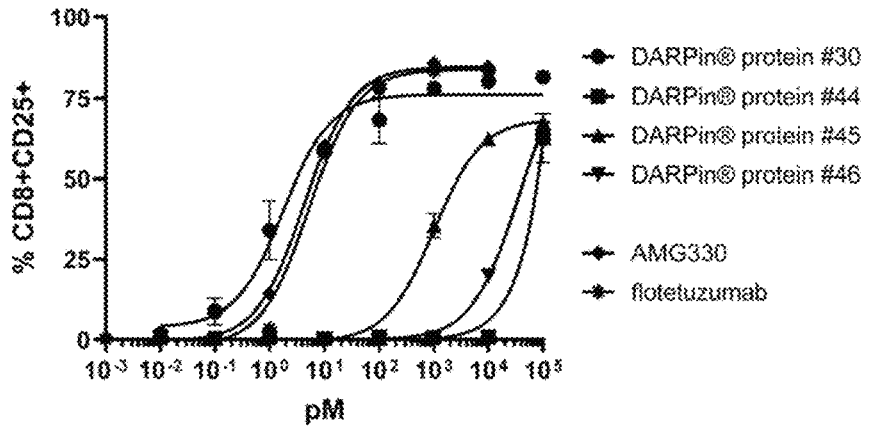
(FIG. 3C) three tumor antigen specific binding domains with binding specificity for CD70, CD123 and CD33, DARPin® protein #30, compared to proteins with only one tumor antigen specific binding domain (DARPin® protein 44, DARPin® protein 45 and DARPin® protein 46).

As shown in FIG. 3, (A) DARPin® protein #27, (B) DARPin® protein #28, (C) DARPin® protein #29 and (D)DARPin® protein #30 induced specific short-term T-cell activation comparable to benchmark molecules (known benchmark T cell engagers, AMG330 with binding specificity for CD33 and flotetuzumab with binding specificity for CD123). Furthermore, DARPin® protein #27, DARPin® protein #28, DARPin® protein #29 and DARPin® protein #30 the T cell activation of shows a clear avidity gain when compared to single targeting control recombinant proteins DARPin® protein #40 (with binding specificity for CD33), DARPin® protein #41 (with binding specificity for CD123), DARPin® protein #42 (with binding specificity for CD33), DARPin® protein #43 (with binding specificity for CD70), DARPin® protein #44 (with binding specificity for CD33), DARPin® protein #45 (with binding specificity for CD70), and DARPin® protein #46 (with binding specificity for CD123).

Figure 4A:
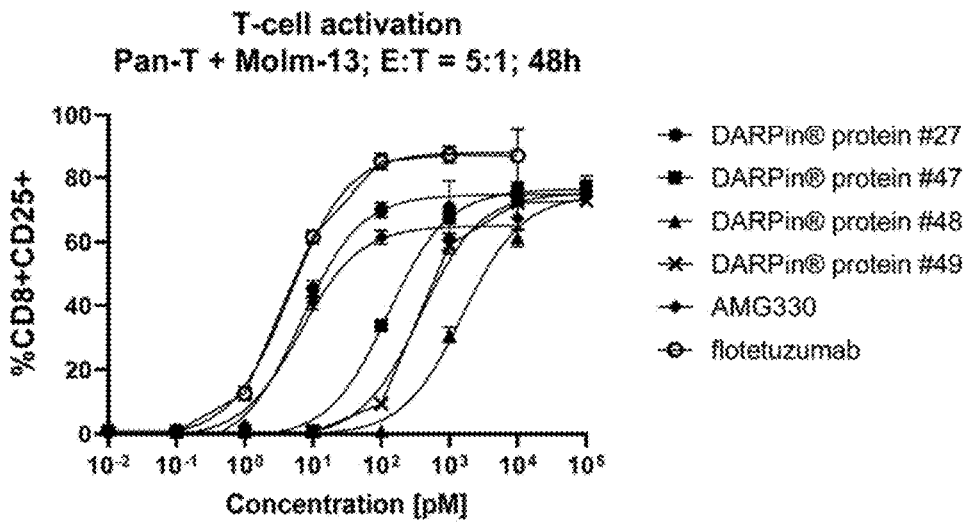
(FIG. 4A) DARPin® protein #27 compared to a similar protein with two tumor antigen specific binding domains and one half-life extending domain, located at the N-terminus (DARPin® protein #47), to a similar protein with two half-life extending domains located at the N-terminus (DARPin® protein #48) and to a similar protein with one half-life extending domain located at the C-terminus (DARPin® protein #49), (FIG. 4B) DARPin® protein #29 compared to a similar protein with two tumor antigen specific binding domains and one half-life extending domain, located at the N-terminus (DARPin® protein #50), to a similar protein with two half-life extending domains located at the N-terminus (DARPin® protein #51) and to a similar protein with one half-life extending domain located at the C-terminus (DARPin® protein #52), (FIG. 4C) DARPin® protein #31 compared to a similar protein with three tumor antigen specific binding domains and one half-life extending domain, located at the N-terminus (DARPin® protein #53), compared to a similar protein with two half-life extending domains located at the N-terminus (DARPin® protein #54) and to a similar protein with one half-life extending domain located at the C-terminus (DARPin® protein #55).
Figure 4B:
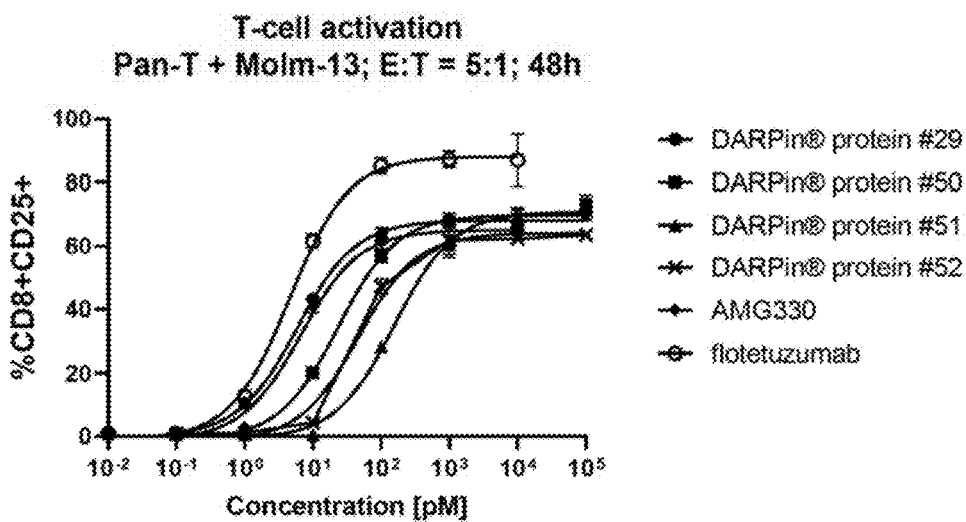
FIG. 4 (A-C). Short term T cell activation measured by activation marker CD25. Pan-T and MOLM-13 cells were incubated at an E:T ratio of 1:1 and T-cell activation assessed by FACS after 24 hours co-culture in the presence of serial dilutions of indicated molecules. Activated T-cells were gated as living CD8+/CD25+ cells. Shown known benchmark T cell engagers, AMG330 with binding specificity for CD33 and flotetuzumab with binding specificity for CD123 and selected recombinant proteins binding to MOLM-13 cells.
Figure 4C:
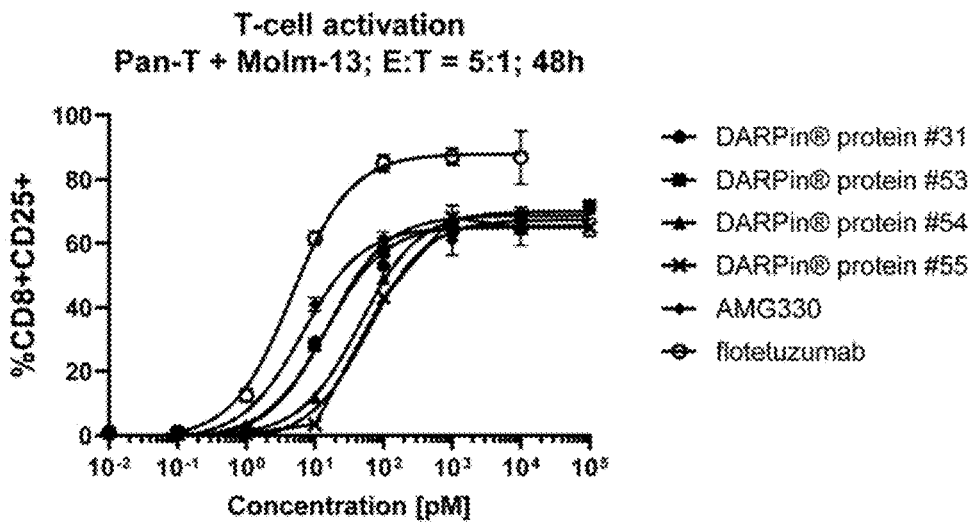

Additionally, several multi-specific recombinant proteins were tested in a similar assay having this time a half-life extending binding domain, where the influence of said half-life extension on the molecule& potency was assessed. (A) DARPin® protein #27 compared to half-life formatted DARPin® protein #47 with two tumor antigen specific binding domains (CD123 and CD33 respectively) and one half-life extending domain, located at the N-terminus, to a similar protein with two half-life extending domains located at the N-terminus (DARPin® protein #48) and to a similar protein with one half-life extending domain located at the C-terminus (DARPin® protein #49); (B) DARPin® protein #29 compared to half-life formatted DARPin® protein #50, with two tumor antigen specific binding domains (CD70 and CD33 respectively) and one half-life extending domain located at the N-terminus, to a similar protein with two half-life extending domains located at the N-terminus (DARPin® protein #51) and to a similar protein with one half-life extending domain located at the C-terminus (DARPin® protein #52); DARPin® protein 31 compared to half-life formatted DARPin® protein #53 with three tumor antigen specific binding domains (CD70, CD123 and CD33 respectively) and one half-life extending domain located at the N-terminus, to a similar protein with two half-life extending domains located at the N-terminus (DARPin® protein #54) and to a similar protein with one half-life extending domain located at the C-terminus (DARPin® protein #55). As it can be seen in FIG. 4, the addition of a half-life extension binding domain leads to potency loss by at least 20 fold in the case of DARPin® protein #27, by at 4 fold for DARPin® protein #29 and to minor potency loss below factor 10 for DARPin® protein #31.

Moreover, specificity and potency of multi-specific ankyrin repeat protein, DARPin® protein #8 with binding specificity for CD3, CD33 and CD123 was assessed in an in vitro short-term T cell activation assay by FACS measuring CD25 activation marker on CD8+ T cells. Specificity and potency were compared both to known benchmark T cell engagers, AMG330 with binding specificity for CD33 and flotetuzumab with binding specificity for CD123, and to recombinant proteins with binding specificity for CD3 and CD33, DARPin® proteins #23, and with binding specificity for CD3 and CD123, DARPin® proteins #24, respectively.

Figure 21:
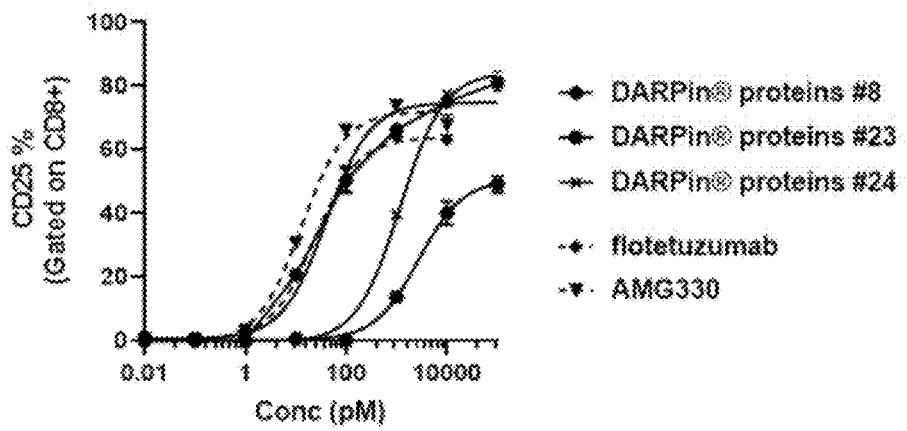
FIG. 21. Short term T cell activation measured by activation marker CD25. Pan-T and MOLM-13 cells were incubated at an E:T ratio of 1:1 and T-cell activation assessed by FACS after 24 hours co-culture in the presence of serial dilutions of indicated molecules. Activated T-cells were gated as living CD8+/CD25+ cells. Shown known benchmark T cell engagers, AMG330 with binding specificity for CD33 and flotetuzumab with binding specificity for CD123 and selected recombinant proteins, binding to MOLM-13 cells either with two tumor specific binding domains (DARPin® protein 8) or only one tumor specific binding domain (DARPin® protein 23 and DARPin® protein 24). T-cell activation induced by DARPin® protein 8 is comparable to benchmark molecules, whereas DARPin® protein 23 and DARPin® protein 24 showed lower potencies. Representative data are shown, using Pan-T cells from one donor.

Briefly, 50,000 purified pan-T effector cells and 50,000 MOLM-13 target cells per well were co-incubated (E:T ratio 1:1) with serial dilutions of recombinant proteins or control benchmark molecules (Flotetuzumab and AMG330) in duplicates in presence of 600 µM human serum albumin for 24 hours at 37° C. Cell were washed and stained with 1:1,000 Live/Dead Aqua (Thermo Fisher), 1:250 mouse anti-human CD8 Pacific Blue (BD), and 1:100 mouse anti-human-CD25 PerCP-Cy5.5 (eBiosciences) antibodies for 30 min at 4° C. After washing and fixation, cells were analyzed on a FACS Canto II (BD) machine. T cell activation was assessed by measuring CD25+ cells on Live/Dead-negative and CD8+ gated T cells. FACS data was analyzed using FlowJo software and data was plotted using Graph Pad Prism 8. As shown in FIG. 21, DARPin® proteins #8, with binding specificity for CD3, CD33 and CD123, thus binding two tumor specific targets on the MOLM-13, induced specific short-term T-cell activation comparable to benchmark molecules, while DARPin® proteins #23 and DARPin® proteins #24, each binding only to one of the tumor specific targets (CD33 or CD123) showed 10 to 100-fold reduction in potency.

In a similar experimental set up, DARPin® protein #56, DARPin® protein #57, DARPin® protein #58, DARPin® protein #59, DARPin® protein #60 and DARPin® protein #61 were also assessed by FACS measuring CD25 activation marker on CD8+ T cells. In brief, 80,000 purified pan-T effector cells and 20,000 Molm-13 or target cells per well were co-incubated (E:T ratio 4:1) with serial dilutions of the selected tested proteins in duplicates in presence of 20 µM human serum albumin for 48 hours at 37° C. After 48 hours, cells were washed and stained with 1:1,000 Live/Dead Green (Thermo Fisher), 1:400 mouse anti-human CD8 Pacific Blue (BD), and 1:100 mouse anti-human-CD25 PerCP-Cy5.5 (eBiosciences) antibodies for 30 min at 4° C. After washing and fixation, cells were analyzed on a FACS Canto II (BD) machine. T cell activation was assessed by measuring CD25+ cells on Live/Dead-negative and CD8+ gated T cells. FACS data was analyzed using FlowJo software and data was plotted using GraphPad Prism 8 (3-PL-fit).

Figure 51A:
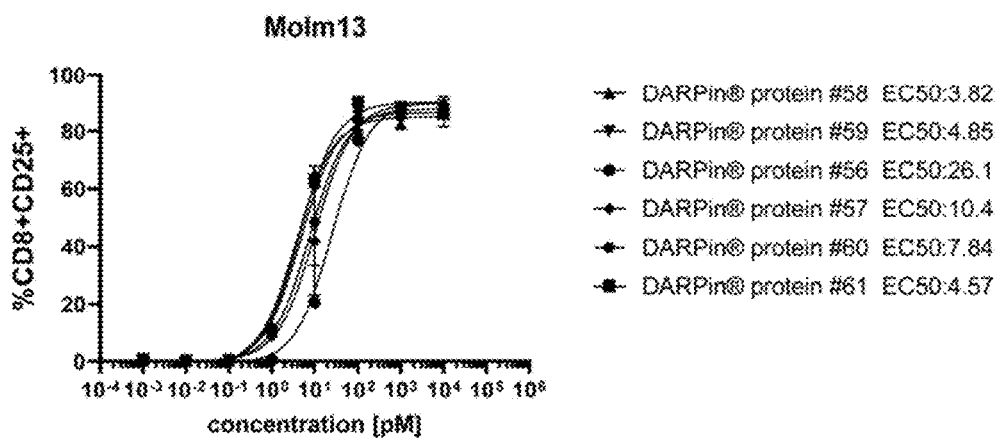
FIG. 51A. Potency Titration curve (Tcell activation) of DARPin® protein #56, DARPin® protein #57, DARPin® protein #58, DARPin® protein #59, DARPin® protein #60 and DARPin® protein #61, targeting CD123-CD33-CD70, on Molm13 tumor cells in co-culture with human PanTcells. EC50 values are shown in pM.

As shown in FIG. 51A tested DARPin proteins with binding specificity for CD3, CD33, CD123 and CD70 DARPin® protein #56 and DARPin® protein #57 induced potent Tcell activation as expected (EC50 on Molm-13 26.1 pM and 10.4 pM respectively). DARPin® protein #58, DARPin® protein #59, DARPin® protein #60 and DARPin® protein #61 displayed in FIG. 51A, show potency as expected, with roughly 5-fold differences amongst each other in terms of EC50 values.

Additionally, DARPin® protein #56 and DARPin® protein #57 were also tested (in the same experimental set up) in comparison to non-binding designed ankyrin repeat proteins, used as negative controls compounds. In brief, 100,000 purified pan-T effector cells and 20,000 Molm-13 target cells per well were co-incubated (E:T ratio 5:1 for PanT-cells) with serial dilutions of the selected proteins in duplicates in presence of 20 µM human serum albumin for 48 hours at 37° C. After 48 hours, cells were washed and stained with 1:1,000 Live/Dead Green (Thermo Fisher), 1:400 mouse anti-human CD8 Pacific Blue (BD), and 1:100 mouse anti-human-CD25 PerCP-Cy5.5 (eBiosciences) antibodies for 30 min at 4° C. After washing and fixation, cells were analyzed on a FACS Canto II (BD) machine. T cell activation was assessed by measuring CD25+ cells on Live/Dead-negative and CD8+ gated T cells. FACS data was analyzed using FlowJo software and data was plotted using GraphPad Prism 8 (3-PL-fit).

Figure 51B:
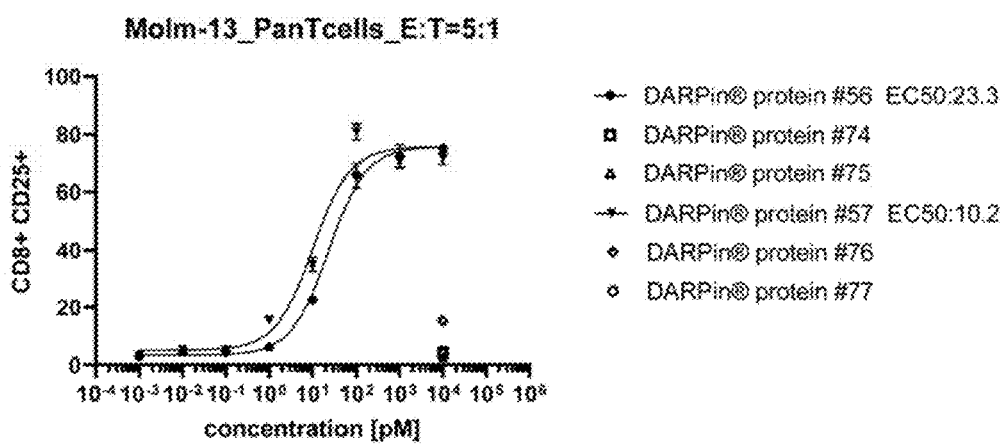
FIG. 51B. Potency Titration curve (Tcell activation) DARPin® protein #56 DARPin® protein #57 and targeting CD123-CD33-CD70, and corresponding negative controls, DARPin® protein #74, DARPin® protein #75, DARPin® protein #76, DARPin® protein #77, on Molm13 tumor cells in co-culture with human PanTcells. EC50 values are shown in pM.

As shown in FIG. 51B tested DARPin proteins with binding specificity for CD3, CD33, CD123 and CD70 DARPin® protein #56 and DARPin® protein #57 induced potent and specific Tcell activation (EC50 on Molm-13 23.3 pM respectively), as compared to their corresponding negative controls. Negative control proteins, each binding only to either the tumor specific targets or CD3 showed no upregulation of CD25 activation marker.

Figure 51C:
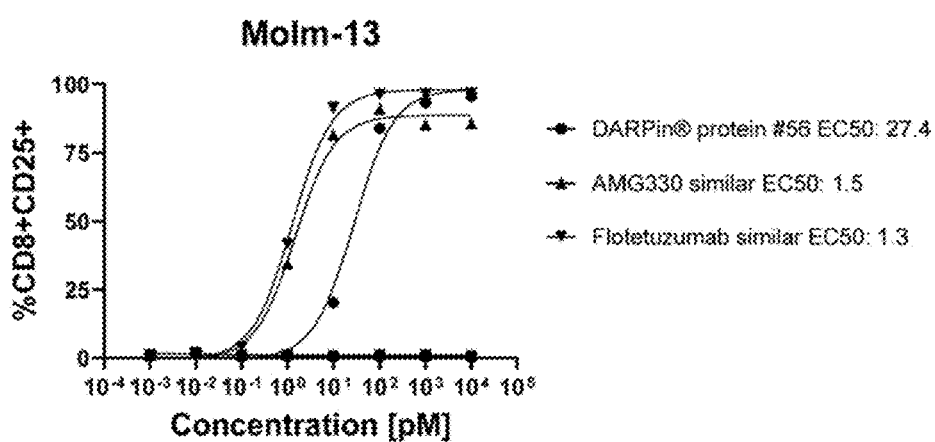
FIG. 51C. Potency Titration curve (Tcell activation) DARPin® protein #56 targeting CD123-CD33-CD70, and known benchmark control molecules AMG330-similar and flotetuzumab-similar, on Molm13 tumor cells in co-culture with human PanTcells. EC50 values are shown in pM.

DARPin® protein #56 was also assessed (in the same experimental set up) in comparison to known benchmark molecules flotetuzumab similar and AMG330 similar. As shown in FIG. 51C DARPin® protein #56 with binding specificity for CD3, CD33, CD123 and CD70 (thus binding 3 tumor specific targets) induced potent and specific Tcell activation.

B. Assessment of Potency and Specificity of Multi-Specific Recombinant Proteins on Molm13 CRISPR Knock-Out (KO) Target Cells in Co-Culture with Human PanT Cells.

Figure 51D:
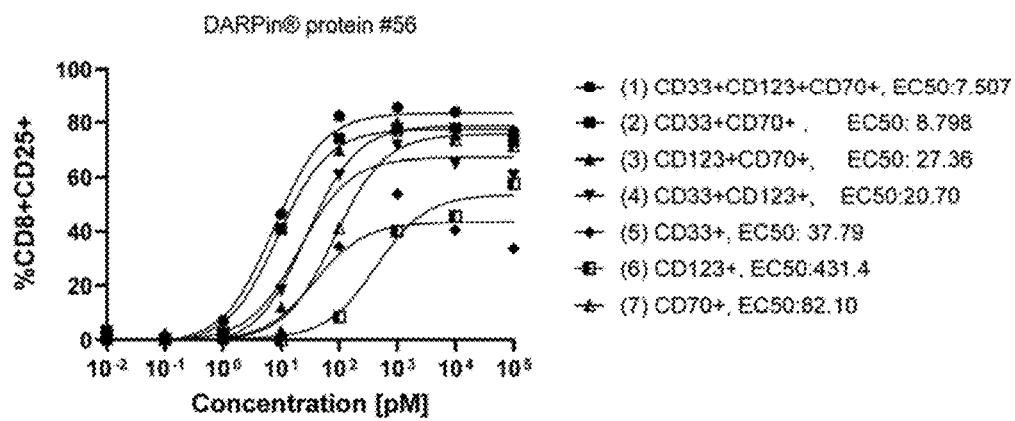
FIG. 51D. Potency Titration curves (Tcell activation) of DARPin® protein #56, targeting CD123-CD33-CD70, on Molm13 wildtype or various TAA knockout tumor cells. EC50 values are shown in pM.
Figure 51E:
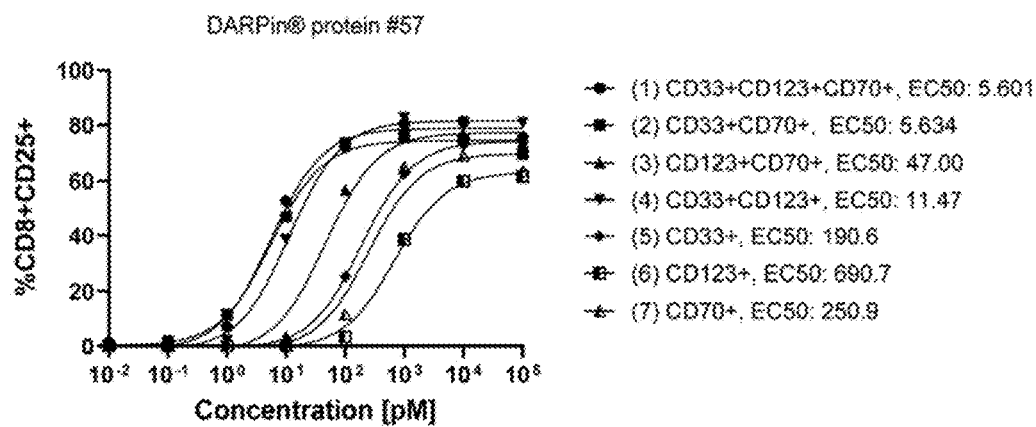
FIG. 51E. Potency Titration curves (Tcell activation) of DARPin® protein #57, targeting CD123-CD33-CD70, on Molm13 wildtype or various TAA knockout tumor cells. EC50 values are shown in pM.

Specificity and potency of DARPin® protein #56 and DARPin® protein #57 were assessed in an in vitro short-term T cell activation assay by FACS measuring CD25 activation marker on CD8+ T cells; in this assay Pan T cells were co-cultured with tumor cells consisted of Molm-13 cells with wildtype target expression for CD33, CD123 and CD70, and various knockout combinations (Molm13 CRISPR Knock-Out (KO) target cells) for the same targets (FIG. 51D and FIG. 51E).

For this reason, 100,000 purified pan-T effector cells and 20,000 target cells per well were co-incubated (E:T ratio 5:1) with serial dilutions of the selected proteins in duplicates in presence of 20 µM human serum albumin for 48 hours at 37° C. After 48 hours, cells were washed and stained with 1:1,000 Live/Dead Green (Thermo Fisher), 1:400 mouse anti-human CD8 Pacific Blue (BD), and 1:100 mouse anti-human-CD25 PerCP-Cy5.5 (eBiosciences) antibodies for 30 min at 4° C. After washing and fixation, cells were analyzed on a FACS Canto II (BD) machine. T cell activation was assessed by measuring CD25+ cells on Live/Dead-negative and CD8+ gated T cells. FACS data was analyzed using FlowJo software and data was plotted using GraphPad Prism 8 (3-PL-fit).

In FIGS. 51D and 51E potency (T cell activation) of DARPin® protein #56 and DARPin® protein #57 specific for CD33, CD123, CD70 and CD3 is shown in presence of Molm-13 tumor cells with various target knockout combinations. The highest potency is reached for both molecules shown, if all three targets are co-expressed (curve 1), and additionally when two targets are co-expressed (curves 2 to 4). Potency drops up to 10-100 fold upon co-culturing T cells with single target expressing tumor cells, such as CD33+, CD123+, CD70+(curves 5 to 7). DARPin® protein #56 shows similar EC50 values on CD33+ single expressing tumor cells, while being less efficacious, compared to DARPin® protein #57, which reaches comparable efficacy on all knockout cell lines.

Example 6: Assessment of Target-Specific Short-Term Tumor Cell Killing Induced by Recombinant Multi-Specific Ankyrin Repeat Proteins by LDH Cytotoxicity Assay A. Assessment of Potency and Specificity of Multi-Specific Recombinant Proteins on Molm-13 Target Cells in Co-Culture with Human PanT Cells.

Specificity and potency of multi specific recombinant proteins with binding specificity for two or three different tumor associated antigens, DARPin® protein #7 to #14, DARPin® protein #27, DARPin® protein #28, DARPin® protein #29, DARPin® protein #30 were assessed by an in-vitro short-term cytotoxicity assay by LDH release.

Effector and target cells were co-incubated in duplicates in 96-well plates with an E:T ratio of 5:1 in presence of 600 µM human serum albumin (to mimic physiological concentration). Untouched T cells were isolated from human PBMCs by using a pan-T cell isolation Kit (Miltenyi). 100,000 purified pan-T cells (effector cells) and 20,000 Molm-13 cells (target cells) per well were incubated with serial dilutions of selected the selected multi-specific recombinant proteins, control benchmark molecules or control containing 1% Triton X-100 for 48 hours at 37° C. After 48 h incubation, cells were spun down and 100 µl per well supernatant and 100 µl per well LDH reaction mixture (LDH detection kit; Roche Applied Science) were incubated for 30 minutes. Absorbance was measured at 492 nm-620 nm by TECAN infinite M1000Pro reader. After background correction, OD values were plotted using GraphPad Prism 8.

Figure 22A:
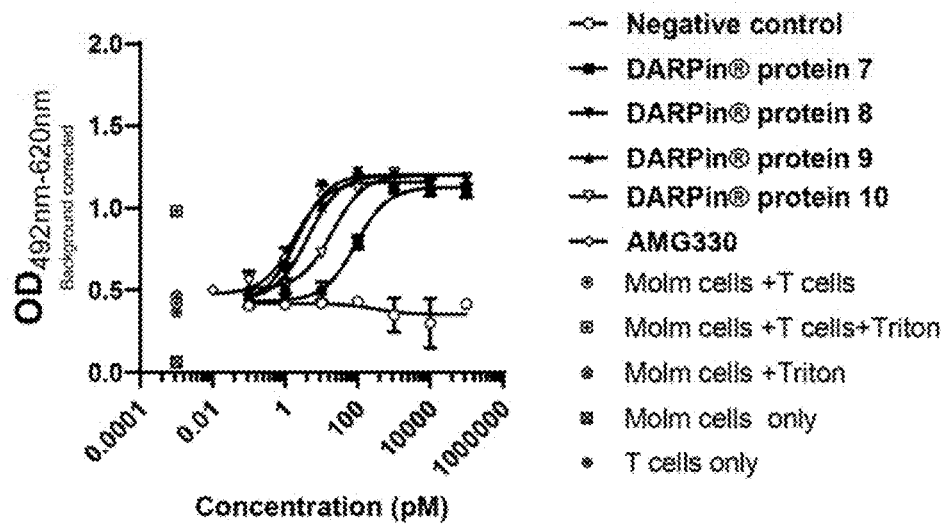
(FIG. 22A) For proteins without half-life extension, tumor cell killing induced by DARPin® protein 8 and DARPin® protein 9 is comparable to benchmark molecules, whereas DARPin® protein 10 and DARPin® protein 7 show lower potency in cytotoxicity.
Figure 22B:
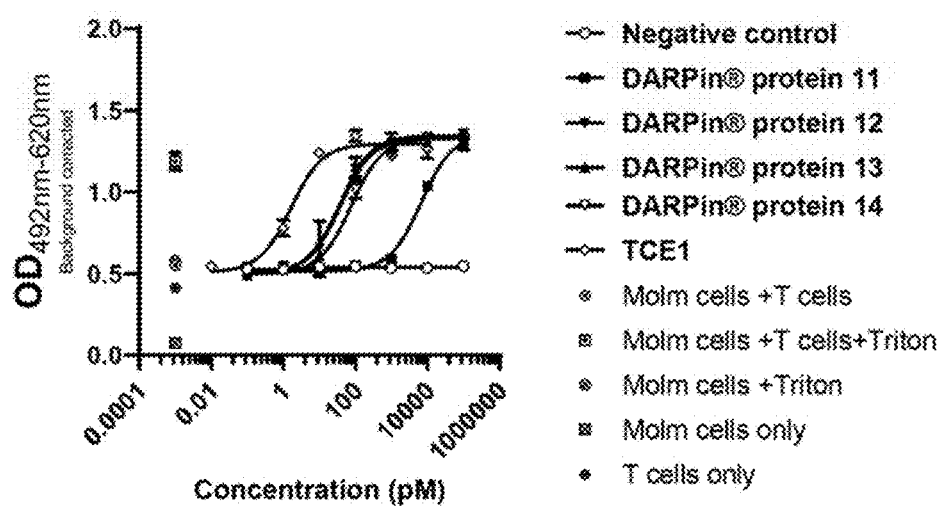
(FIG. 22B) Half-life extended proteins show 4-70-fold reduction in potency compared to the corresponding non-HLE molecules shown in (A). Pan-T cells from 5 different donors were tested, one representative donor is shown here. (*Negative control: a designed ankyrin repeat protein with binding specificity for CD33 and CD123, with or without half-life extension respectively).

As shown in FIG. 22A, for DARPin proteins without half-life extension, DARPin® protein #8 and DARPin® protein #9 induced tumor cell killing comparable to benchmark molecule (known benchmark T cell engager, AMG330 with binding specificity for CD33), whereas DARPin® protein #7 and DARPin® protein #10 show 10 to 100-fold reduction in potency. Half-life extended, DARPin® proteins #10-14, in FIG. 22B, show about 4 to 70-fold reduction in potency compared to the corresponding non-half-life extended molecules.

Figure 5A:
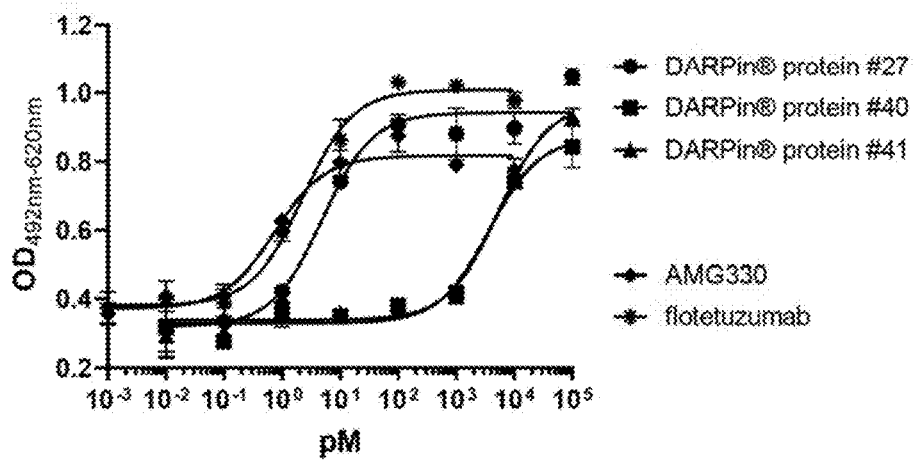
(FIG. 5A) two tumor antigen specific binding domains, with binding specificity for CD123 and CD33, DARPin® protein #27, compared to proteins with only one tumor antigen specific binding domain (DARPin® protein 40 and DARPin® protein 41).
Figure 5B:
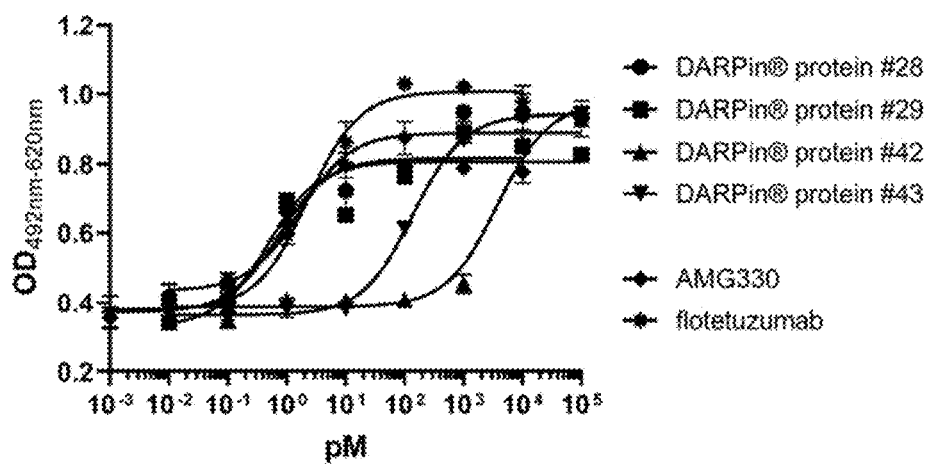
(FIG. 5B) two tumor antigen specific binding domains with binding specificity for CD70 and CD33, DARPin® protein #28 and DARPin® protein #29, compared to proteins with only one tumor antigen specific binding domain (DARPin® protein 42 and DARPin® protein 43).
Figure 5C:
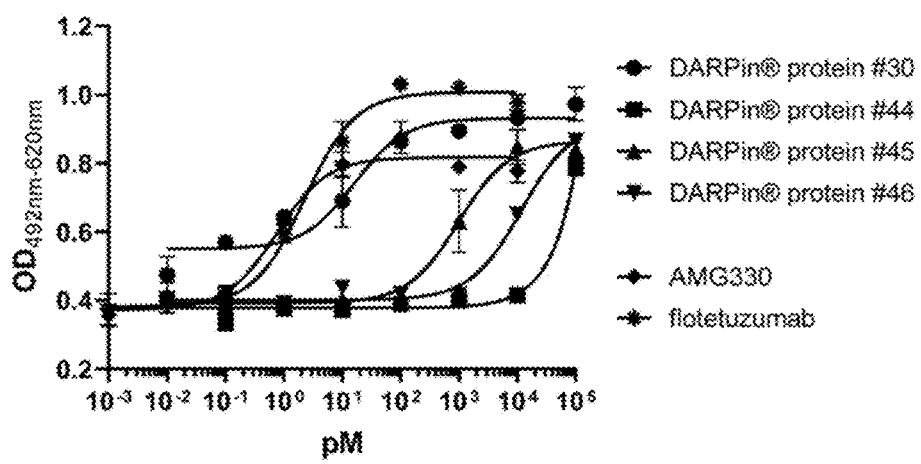
(FIG. 5C) three tumor antigen specific binding domains with binding specificity for CD70, CD123 and CD33, DARPin® protein #30, compared to proteins with only one tumor antigen specific binding domain (DARPin® protein 44, DARPin® protein 45, and DARPin® protein 46).

As shown in FIG. 5 DARPin® protein #27, DARPin® protein #28, DARPin® protein #29 and DARPin® protein #30 show target cell killing activity comparable to benchmark molecules AMG330 and flotetuzumab. Furthermore, they show a clear avidity gain when compared to single targeting control recombinant proteins DARPin® protein #40 (with binding specificity for CD33), DARPin® protein #41 (with binding specificity for CD123), DARPin® protein #42 (with binding specificity for CD33), DARPin® protein #43 (with binding specificity for CD70), DARPin® protein #44 (with binding specificity for CD33), DARPin® protein #45 (with binding specificity for CD70), and DARPin® protein #46 (with binding specificity for CD123).

Figure 6A:
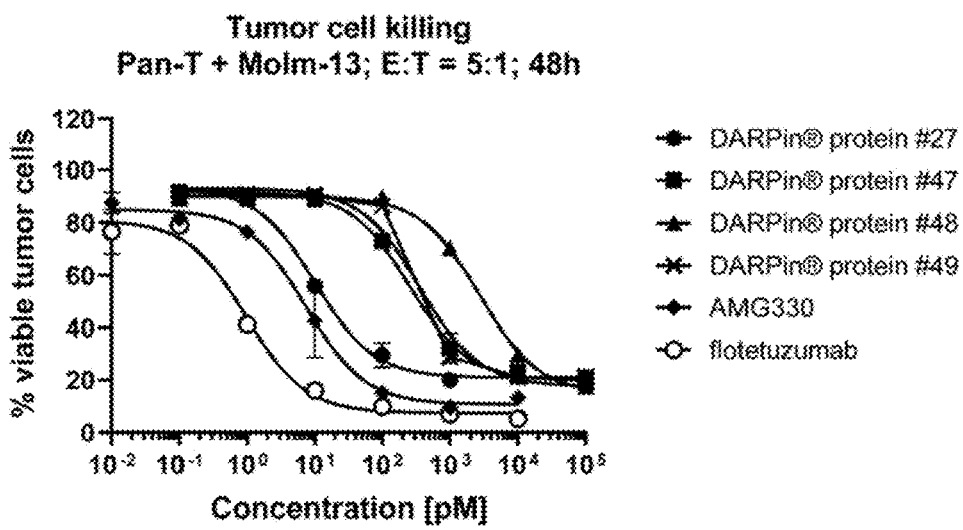
(FIG. 6A) DARPin® protein #27 compared to a similar protein with two tumor antigen specific binding domains and one half-life extending domain, located at the N-terminus (DARPin® protein #47), to a similar protein with two half-life extending domains located at the N-terminus (DARPin® protein #48) and to a similar protein with one half-life extending domain located at the C-terminus (DARPin® protein #49), (FIG. 6B) DARPin® protein #29 compared to a similar protein with two tumor antigen specific binding domains and one half-life extending domain, located at the N-terminus (DARPin® protein #50), to a similar protein with two half-life extending domains located at the N-terminus (DARPin® protein #51) and to a similar protein with one half-life extending domain located at the C-terminus (DARPin® protein #52), (FIG. 6C) DARPin® protein #31 compared to a similar protein with three tumor antigen specific binding domains and one half-life extending domain, located at the N-terminus (DARPin® protein #63), compared to a similar protein with two half-life extending domains located at the N-terminus (DARPin® protein #54) and to a similar protein with one half-life extending domain located at the C-terminus (DARPin® protein #55).
Figure 6B:
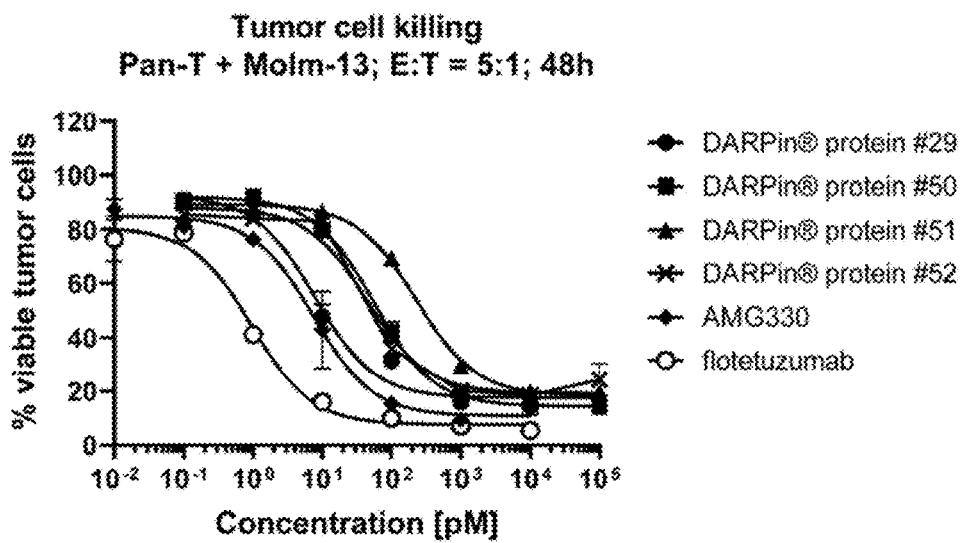
FIG. 6 (A-C). Short Term Target Cell Killing (LDH). Pan-T and Molm-13 cells were incubated at an E:T ratio of 5:1 and tumor cell killing was assessed by LDH release in the supernatant after 48 hours of co-culture in the presence of serial dilutions of indicated molecules. Shown are benchmark control molecule (known benchmark T cell engager, AMG330 with binding specificity for CD33 and flotetuzumab with binding specificity for CD123) and multi-specific recombinant proteins with two or three tumor specific binding domains.
Figure 6C:
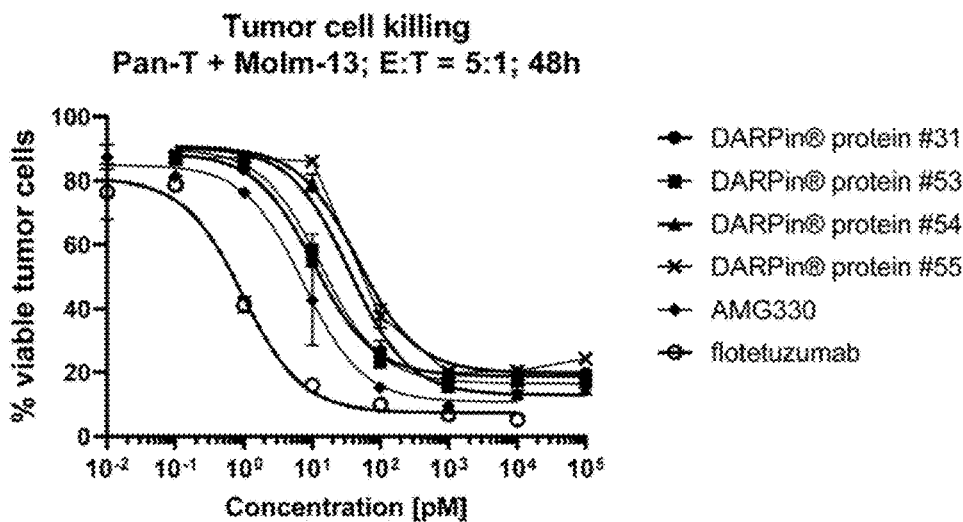

Additionally, multi-specific recombinant proteins were tested in a similar assay having this time a half-life extending binding domain, where the influence of said half-life extension on the molecules potency was assessed. DARPin® protein #47 with two tumor antigen specific binding domains (CD123 and CD33 respectively) and one half-life extending domain, located at the N-terminus was compared to a similar protein with two half-life extending domains located at the N-terminus (DARPin® protein #48) and to a similar protein with one half-life extending domain located at the C-terminus (DARPin® protein #49); DARPin® protein #50, with two tumor antigen specific binding domains (CD70 and CD33 respectively) and one half-life extending domain located at the N-terminus, compared to a similar protein with two half-life extending domains located at the N-terminus (DARPin® protein #51) and to a similar protein with one half-life extending domain located at the C-terminus (DARPin® protein #52); DARPin® protein #53 with three tumor antigen specific binding domains (CD70, CD123 and CD33 respectively) and one half-life extending domain located at the N-terminus, compared to a similar protein with two half-life extending domains located at the N-terminus (DARPin® protein #54) and to a similar protein with one half-life extending domain located at the C-terminus (DARPin® protein #55). As it can be seen in FIG. 6, the addition of a half-life extension binding domain leads to potency loss by at least 20 fold in the case of DARPin® protein #27, by at 4 fold for DARPin® protein #29 and to minor potency loss below factor 10 for DARPin® protein #31.

In the same experimental set up, DARPin® protein #56, DARPin® protein #57, DARPin® protein #58, DARPin® protein #59, DARPin® protein #60 and DARPin® protein #61 were also assessed.

Figure 52A:
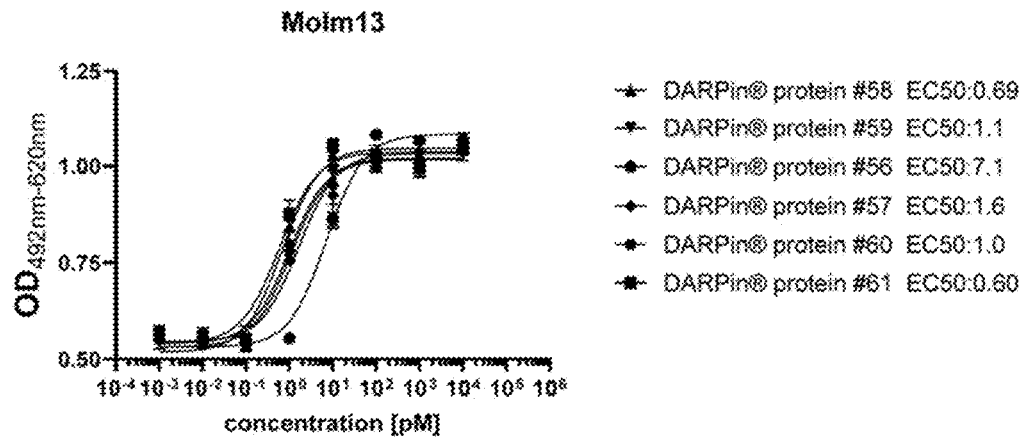
FIG. 52A. Potency Titration curve (cell killing) of DARPin® protein #56, DARPin® protein #57, DARPin® protein #58, DARPin® protein #59, DARPin® protein #60 and DARPin® protein #61, targeting CD123-CD33-CD70, on Molm13 tumor cells in co-culture with human PanTcells. EC50 values are shown in pM.

As shown in FIG. 52A tested proteins with binding specificity for CD3, CD33, CD123 and CD70 DARPin® protein #56 and DARPin® protein #57 induced potent Tumor cell killing as expected (EC50 on Molm-13. 7.1 pM and 1.6 pM respectively), while DARPin® protein #58, DARPin® protein #59, DARPin® protein #60 and DARPin® protein #61 displayed in FIG. 51A, show potency as expected, with 5-10 fold differences amongst each other in terms of EC50 values.

Figure 52B:
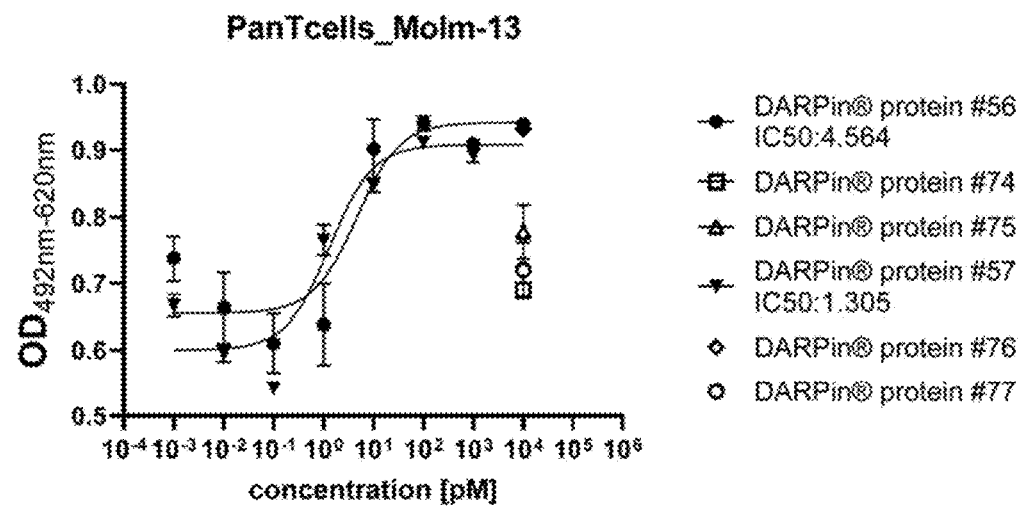
FIG. 52B. Potency Titration curve (cell killing) DARPin® protein #56 DARPin® protein #57 and targeting CD123-CD33-CD70, and corresponding negative controls, DARPin® protein #74, DARPin® protein #75, DARPin® protein #76, DARPin® protein #77, on Molm13 tumor cells in co-culture with human PanTcells. EC50 values are shown in pM.

DARPin® protein #56 and DARPin® protein #57 were also tested in comparison to non-binding designed ankyrin repeat proteins, used as negative control compounds. As shown in FIG. 52B tested proteins DARPin® protein #56 and DARPin® protein #57 show potent and specific tumor cell killing in presence of PanTcells (1050 on Molm-13 DARPin® protein #56: 4.6 pM, DARPin® protein #57: 1.3 pM), when compared to their corresponding negative controls. Negative control designed ankyrin repeat proteins bind only to either the tumor specific target (or CD3 barely lead to tumor cell killing at maximal concentration used, as expected.

Figure 52C:
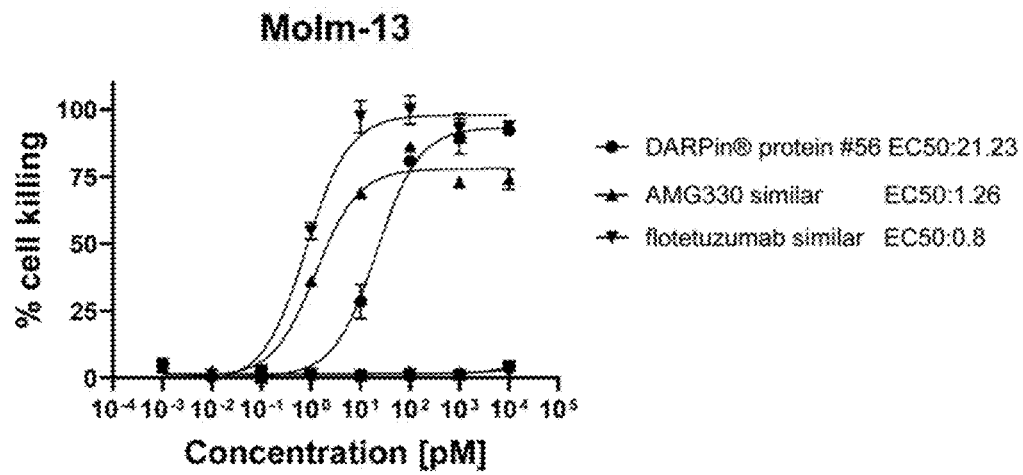
FIG. 52C. Potency Titration curve (cell killing) DARPin® protein #56 targeting CD123-CD33-CD70, and known benchmark control molecules AMG330-similar and flotetuzumab-similar, on Molm13 tumor cells in co-culture with human PanTcells. EC50 values are shown in pM.

Additionally, DARPin® protein #56 was assessed in comparison to known benchmark molecules flotetuzumab similar and AMG330 similar. As shown in FIG. 52C tested DARPin® protein #56 shows potent and specific tumor cell killing in presence of human PanTcells. Efficacy of flotetuzumab DARPin® protein #56 and are comparable, while EC50 values for DARPin® protein #56 are lower than flotetuzumab and AMG330 tested.

B. Assessment of Potency and Specificity of Multi-Specific Recombinant Proteins on Molm13 CRISPR Knock-Out (KO) Target Cells in Co-Culture with Human PanT Cells.

Figure 52D:
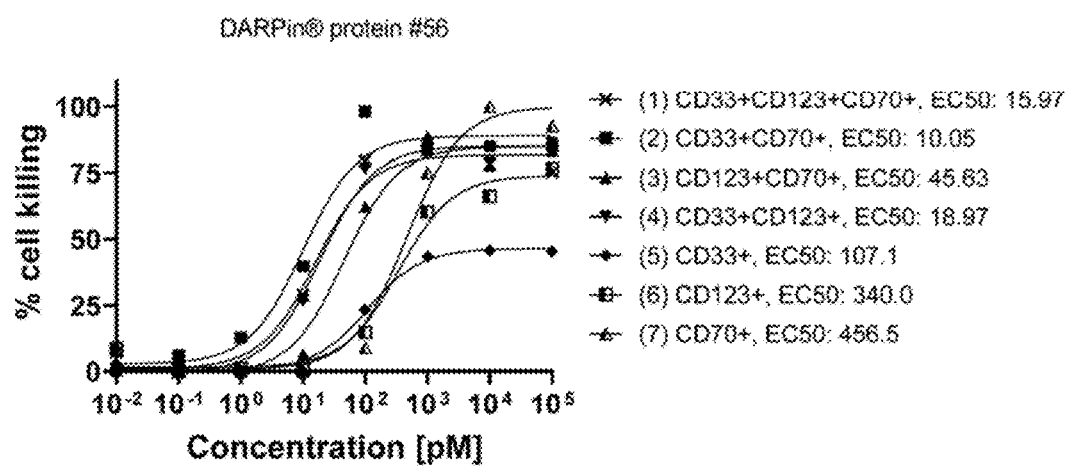
FIG. 52D. Potency Titration curves (cell killing) of DARPin® protein #56, targeting CD123-CD33-CD70, on Molm13 wildtype or various TAA knockout tumor cells. EC50 values are shown in pM.

Specificity and potency of DARPin® protein #56 was assessed in an in vitro short-term LDH cytotoxicity assay by measuring LDH release; in this assay Pan T cells were co-cultured with tumor cells consisted of Molm-13 cells with wildtype target expression for CD33, CD123 and CD70, and various knockout combinations (Molm13 CRISPR Knock-Out (KO) target cells) for the same targets (FIG. 52D).

For this reason, 100,000 purified pan-T cells (effector cells) and 20,000 Molm-13 KO cells (target cells) per well were incubated with serial dilutions of selected the selected multi-specific recombinant proteins, control benchmark molecules or control containing 1% Triton X-100 for 48 hours at 37° C. After 48 h incubation, cells were spun down and 100 µl per well supernatant and 100 µl per well LDH reaction mixture (LDH detection kit; Roche Applied Science) were incubated for 30 minutes. Absorbance was measured at 492 nm-620 nm by TECAN infinite M1000Pro reader. After background correction, OD values were plotted using GraphPad Prism 8. As shown in FIG. 52D, the highest potency for the tested protein is reached if all three targets are co-expressed (curve 1), and additionally when two targets are co-expressed (curves 2 to 4). Potency drops up to 10-100 fold upon co-culturing T cells with single target expressing Tumor cells, such as CD33+, CD123+, CD70+ (curves 5 to 7). Additionally, efficacy on CD33+ cells is also reduced with DARPin® protein #56.

Example 7: Assessment of Tumor Cell Killing by a Multi-Specific Recombinant Protein, Targeting Three Tumor Associated Antigens, DARPin® Protein #31

To analyse the activity of DARPin® protein #31 on tumor cell killing, effector cells (pan-T cells, 100.000 cells) and Molm13 tumor cells (20.000 cells) were seeded in a 96 well plate in a E:T ratio of 5:1. Pan-T cells were stained with Cell Trace Violet (CTV) before seeding to enable differentiation from tumor cells during FACS analysis. After 48 hours of co-culture in the presence of serial dilutions of indicated molecules, samples were analysed for tumor cell killing by flow cytometry. Cells were washed and stained with 1:1,000 Live/Dead Aqua (Thermo Fisher) and incubated for 30 min at 4° C. After washing and fixation, cells were analyzed on a FACS Canto II (BD) machine. Tumor cell killing was assessed by absolute count of remaining UDneg/CTVneg cells. FACS data was analyzed using FlowJo software and data was plotted using Graph Pad Prism 8.

Figure 7:
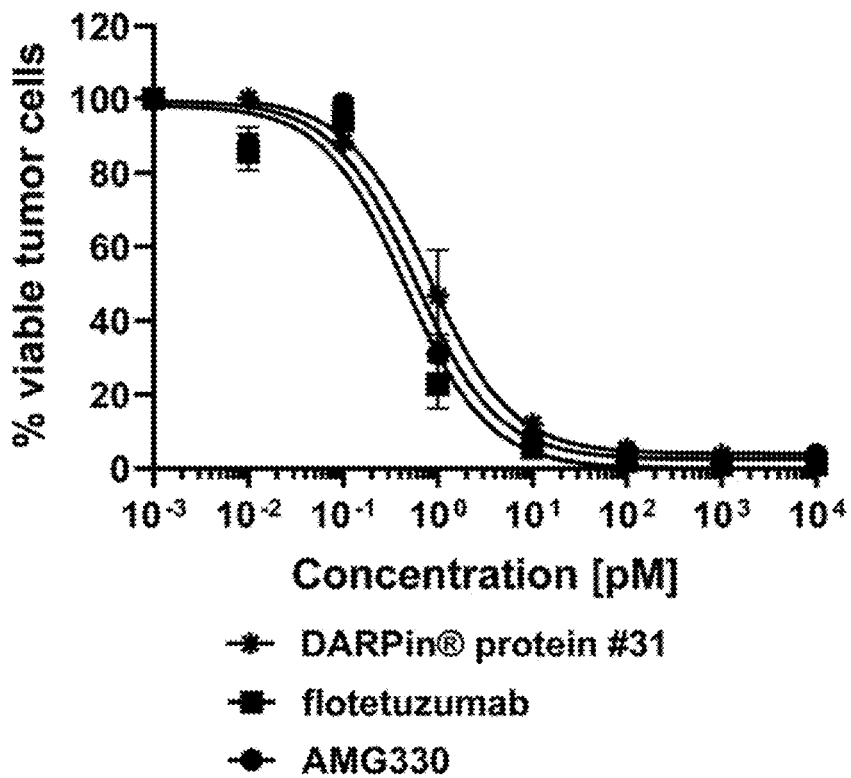
FIG. 7. Target Cell Killing. Shown are benchmark control molecules (known benchmark T cell engager, AMG330 with binding specificity for CD33 and flotetuzumab with binding specificity for CD123) and DARPin® protein #31. The data show that in a tumor cell killing assay DARPin® protein #5 exerts similar potency and efficacy when compared to clinical benchmarks.

FIG. 7 shows are benchmark control molecules (known benchmark T cell engager, AMG330 with binding specificity for CD33 and flotetuzumab with binding specificity for CD123) and DARPin® protein #31. The data show that in a tumor cell killing assay DARPin® protein #31 exerts similar potency and efficacy when compared to clinical benchmarks.

Figure 8:
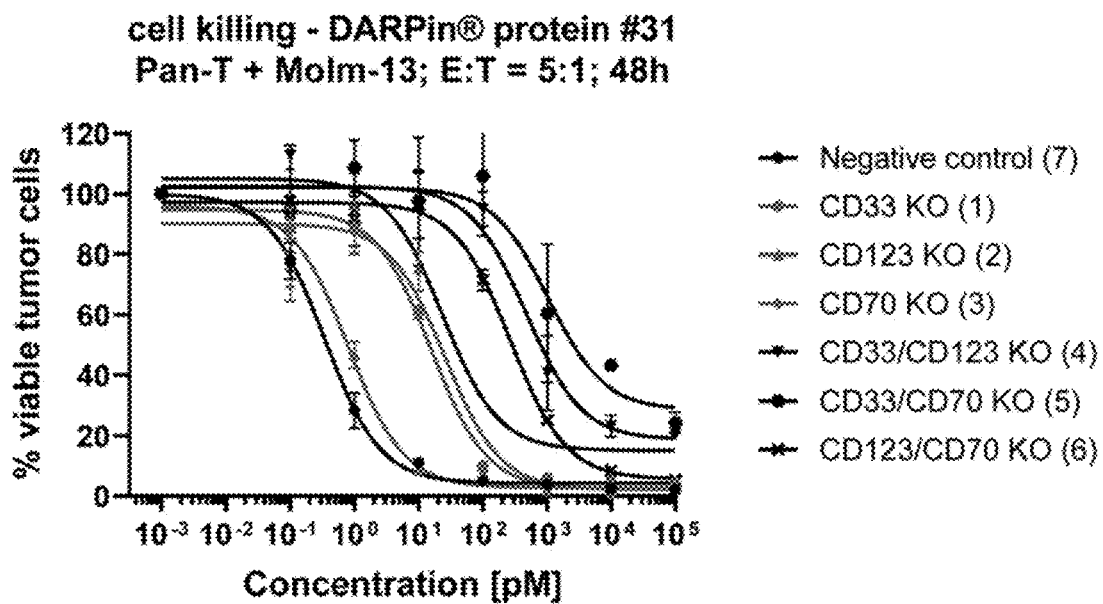
FIG. 8. Target Cell Killing. Curve 7 represents Molm13 parental cells expressing all three targets (CD70, CD123 and CD33). DARPin® protein #31 shows full potency. Curves 4-6 represent single KO cells meaning only two targets are still expressed. Here DARPin® protein #5 is still active suggesting the potential to counteract tumor heterogeneity. Curves 1-3 represent double KO cells meaning only one target is still expressed to mimic the healthy tissue compartment. Here, DARPin® protein #31 is significantly less active meaning an improved selectivity towards healthy tissue FIG. 9 (A-D). Levels of IFNγ. (Mean of three donors). Calculated mean concentration values of IFNγ for all three donors (D1-3) in the blood loop system. Plasma samples were collected from the blood loop system at 0 (zero), 2, 4, 8 and 24 hours. Calculated LLOQ is marked with a dotted line. Each point is the mean of three donors and the error bar SD. Flotetuzumab is presented in FIG. 9A, DARPin® protein #27 in FIG. 9B, DARPin® protein #29 in FIG. 9C, and DARPin® protein #31 in FIG. 9D. The data and values are >ULOQ.
Figure 9A:
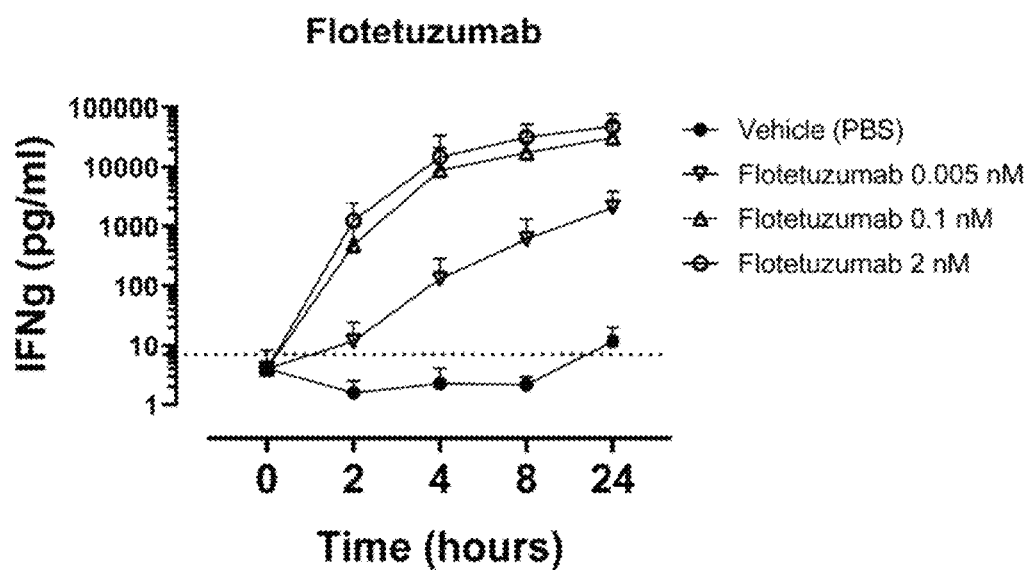
Figure 9B:
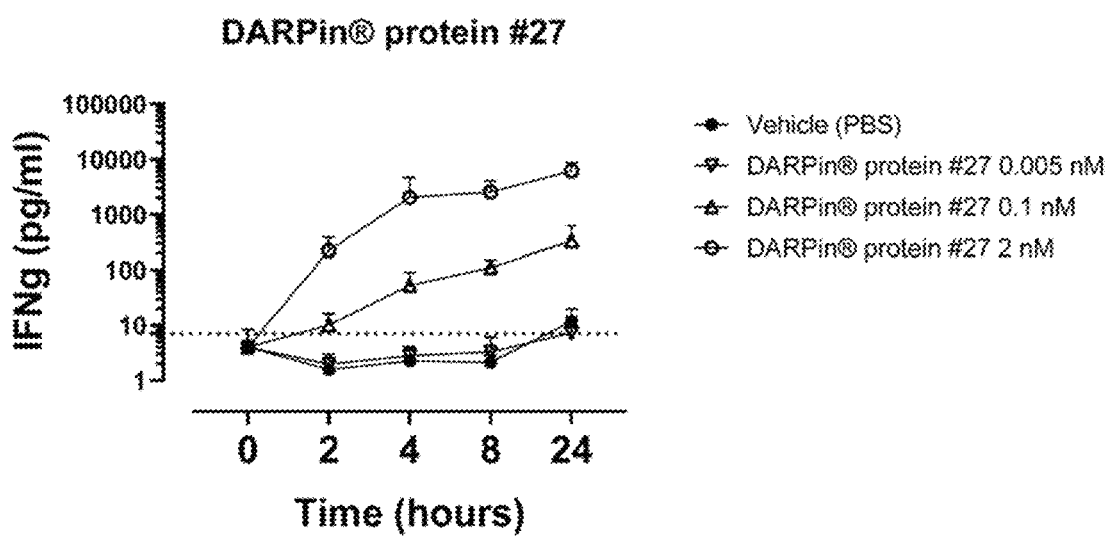
Figure 9C:
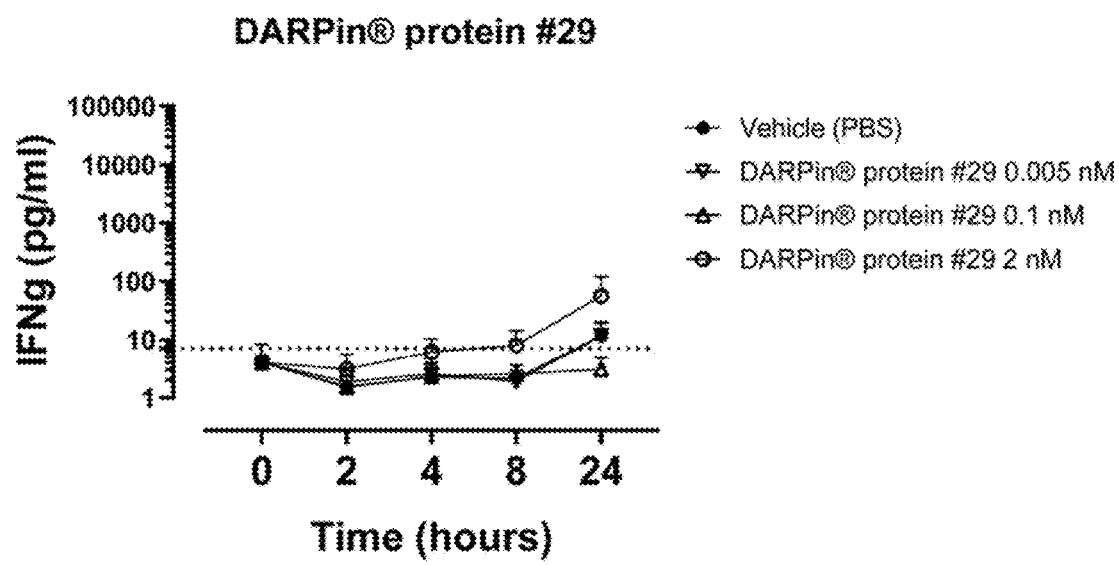
Figure 9D:
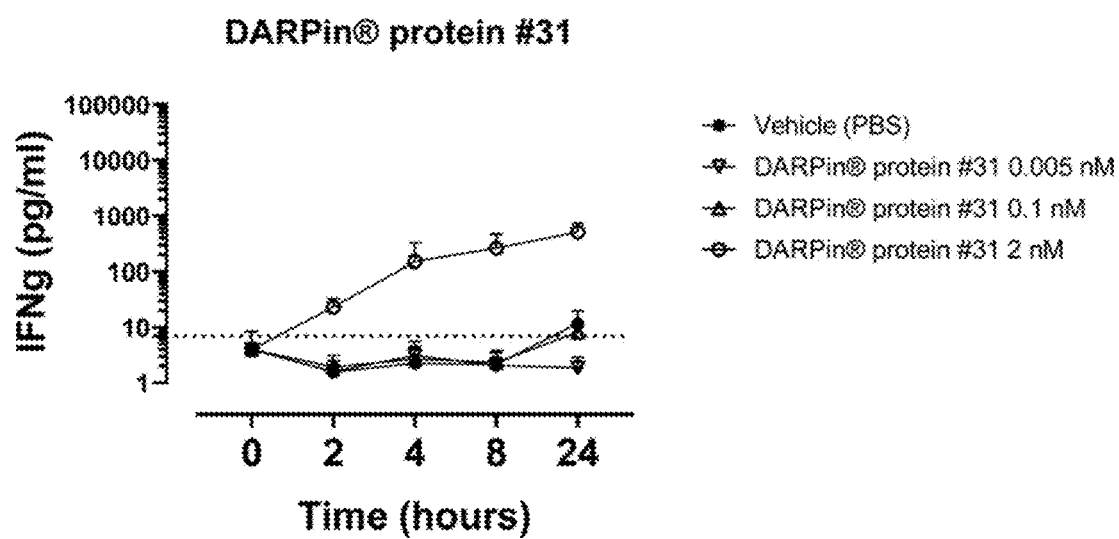
Figure 10A:
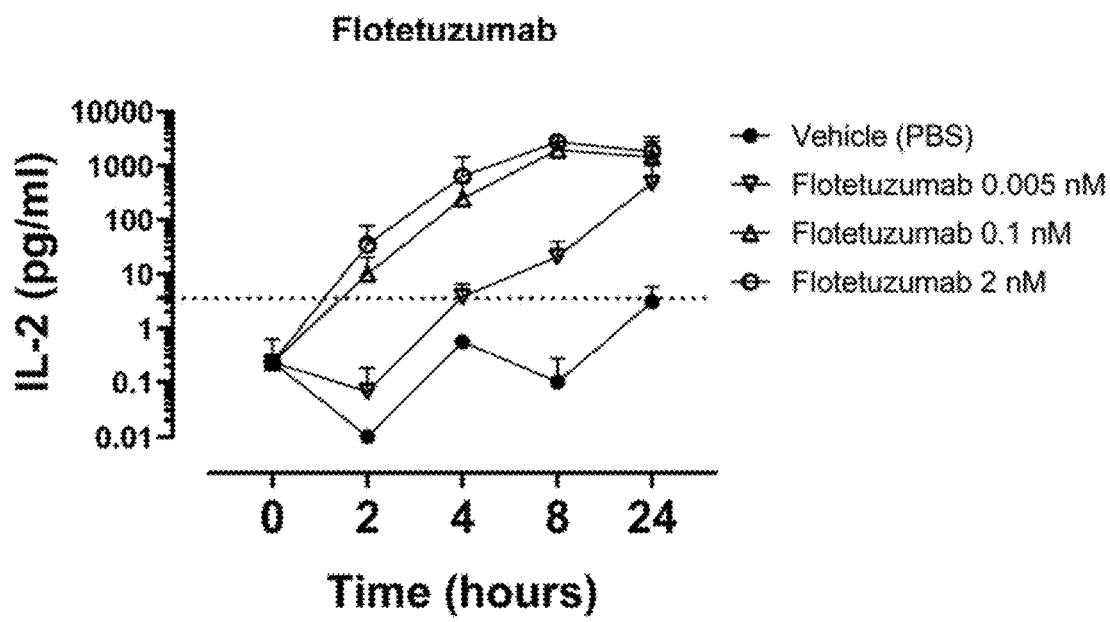
FIG. 10 (A-D). Levels of IL-2 (Mean of three donors). Calculated mean concentration values of IL-2 for all three donors (D1-3) in the blood loop system. Plasma samples were collected from the blood loop system at 0 (zero), 2, 4, 8 and 24 hours. Calculated LLOQ is marked with a dotted line. Each point is the mean of three donors and the error bar SD. Flotetuzumab is presented in FIG. 10A, DARPin® protein #27 in FIG. 10B, DARPin® protein #29 in FIG. 10C, and DARPin® protein #31 in FIG. 10D.
Figure 10B:
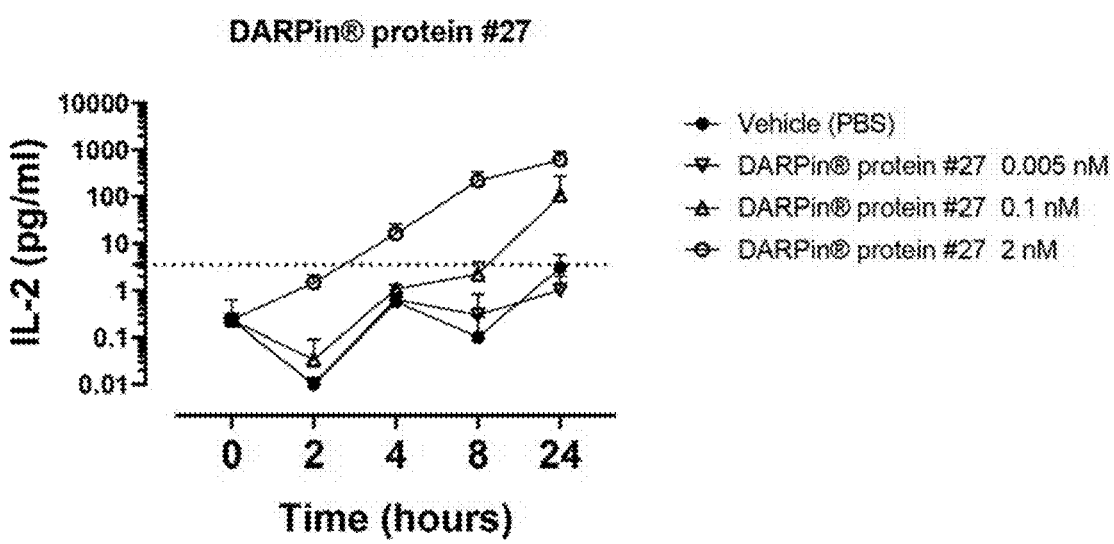
Figure 10C:
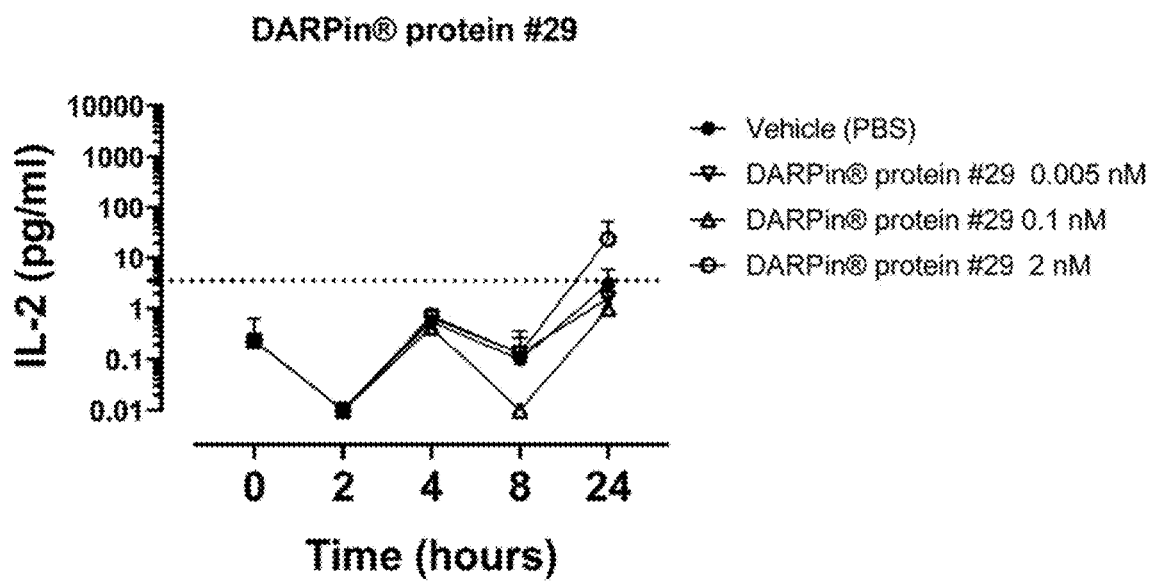
Figure 10D:
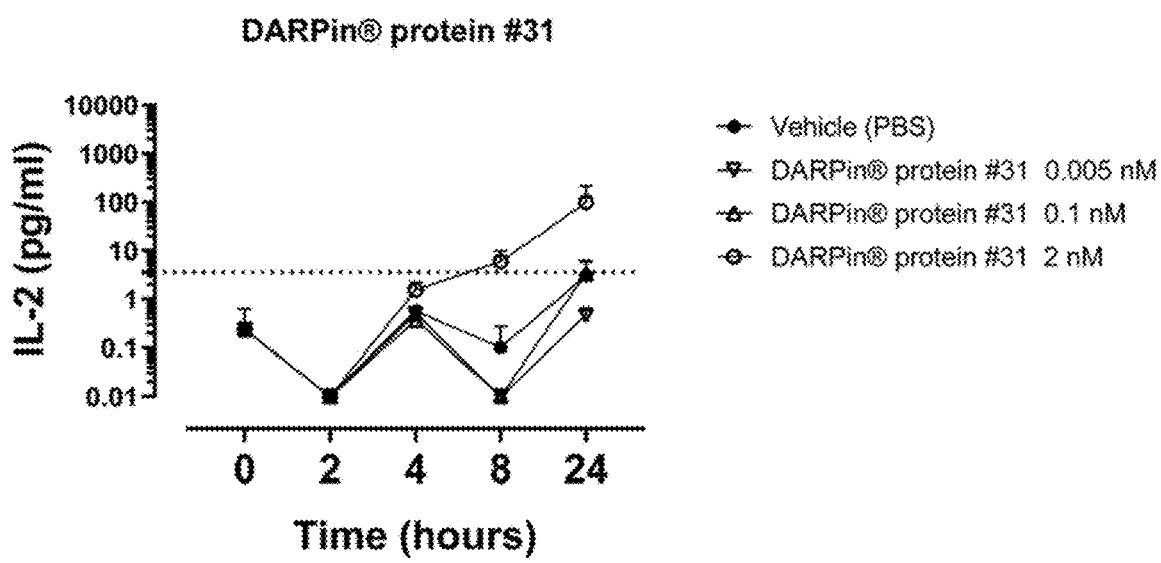
Figure 11A:
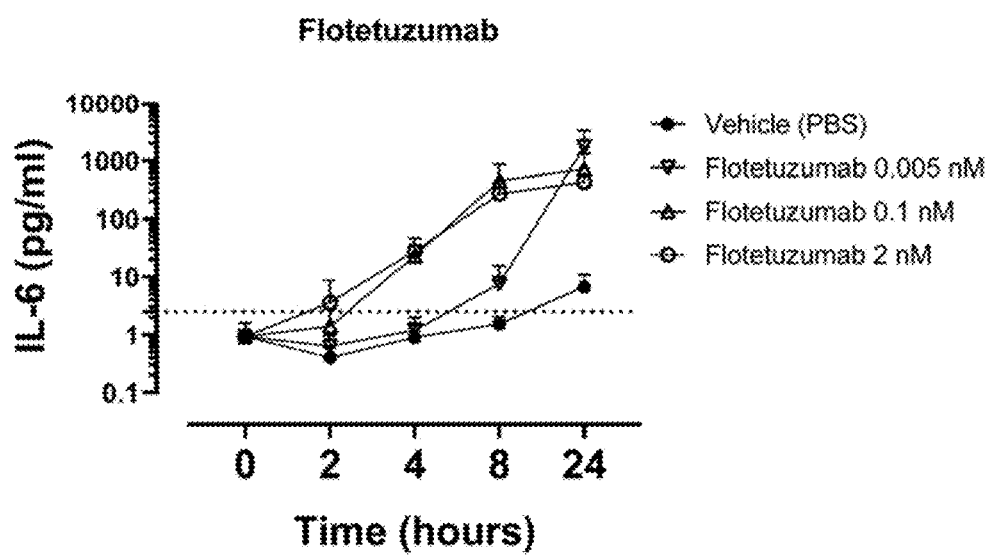
FIG. 11 (A-D). Levels of IL-6 (Mean of three donors). Calculated mean concentration values of IL-6 for all three donors (D1-3) in the blood loop system. Plasma samples were collected from the blood loop system at 0 (zero), 2, 4, 8 and 24 hours. Calculated LLOQ is marked with a dotted line. Each point is the mean of three donors and the error bar SD. Flotetuzumab is presented in FIG. 11A, DARPin® protein #27 in FIG. 11B, DARPin® protein #29 in FIG. 11C, and DARPin® protein #31 in FIG. 11D. The data and values are >ULOQ.
Figure 11B:
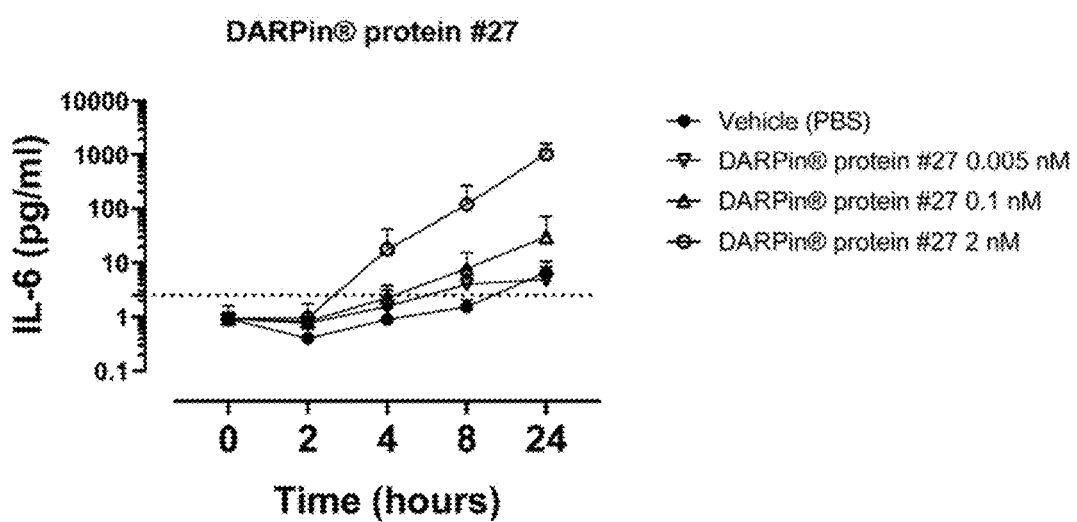
Figure 11C:
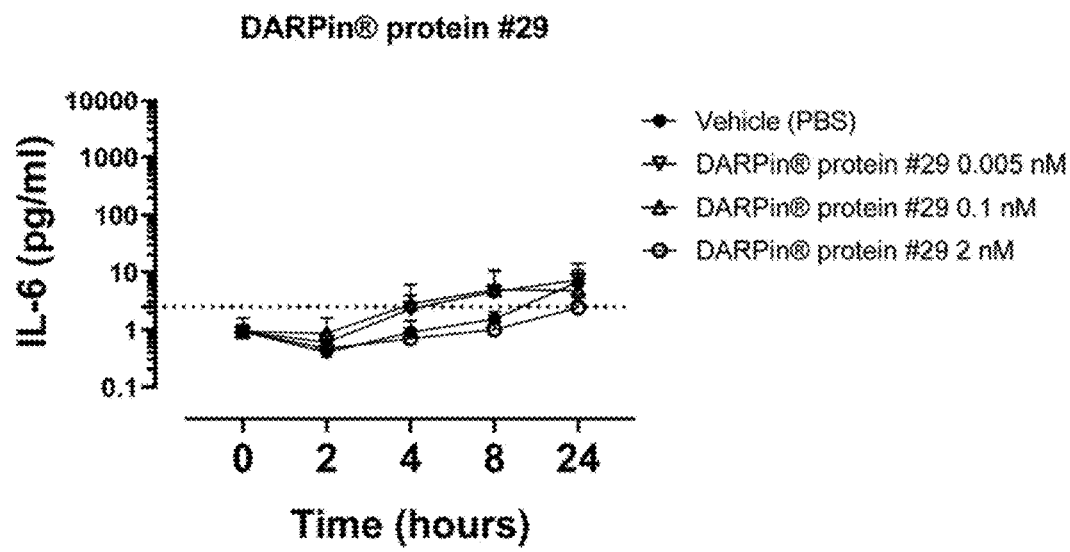
Figure 11D:
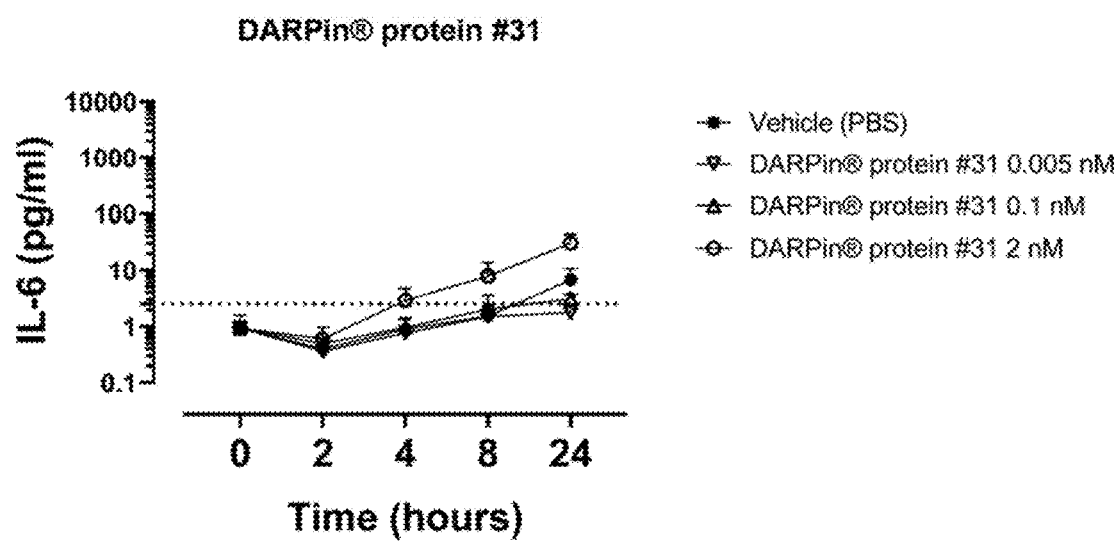
Figure 12A:
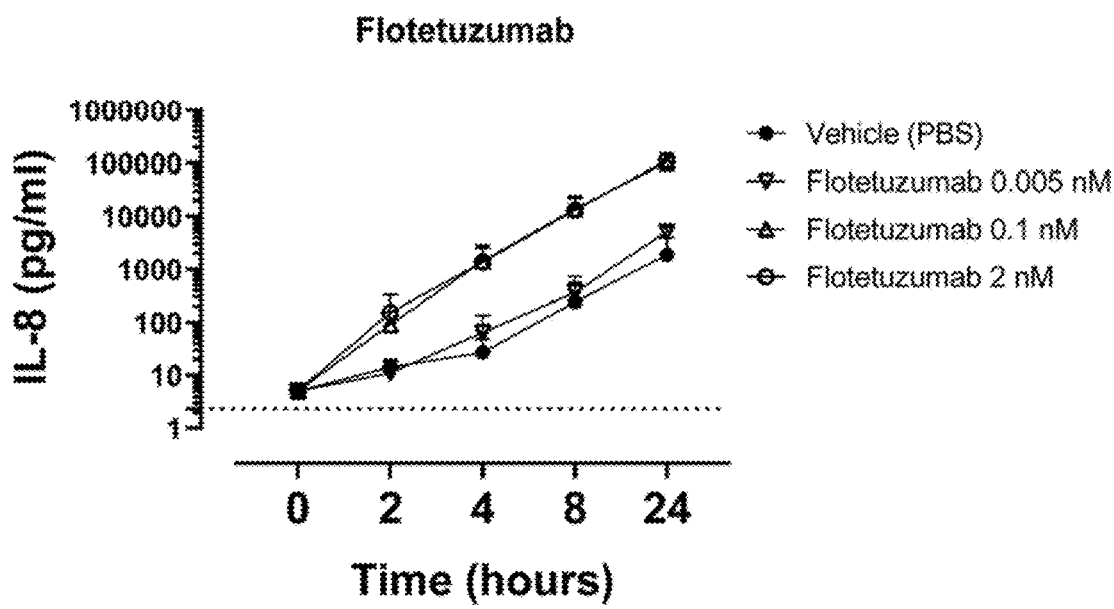
FIG. 12 (A-D). Levels of IL-8 (Mean of three donors). Calculated mean concentration values of IL-8 for all three donors (D1-3) in the blood loop system. Plasma samples were collected from the blood loop system at 0 (zero), 2, 4, 8 and 24 hours. Calculated LLOQ is marked with a dotted line. Each point is the mean of three donors and the error bar SD. Flotetuzumab is presented in FIG. 11A, DARPin® protein #27 in FIG. 11B, DARPin® protein #29 in FIG. 11C, and DARPin® protein #31 in FIG. 11D. The data and values are >ULOQ.
Figure 12B:
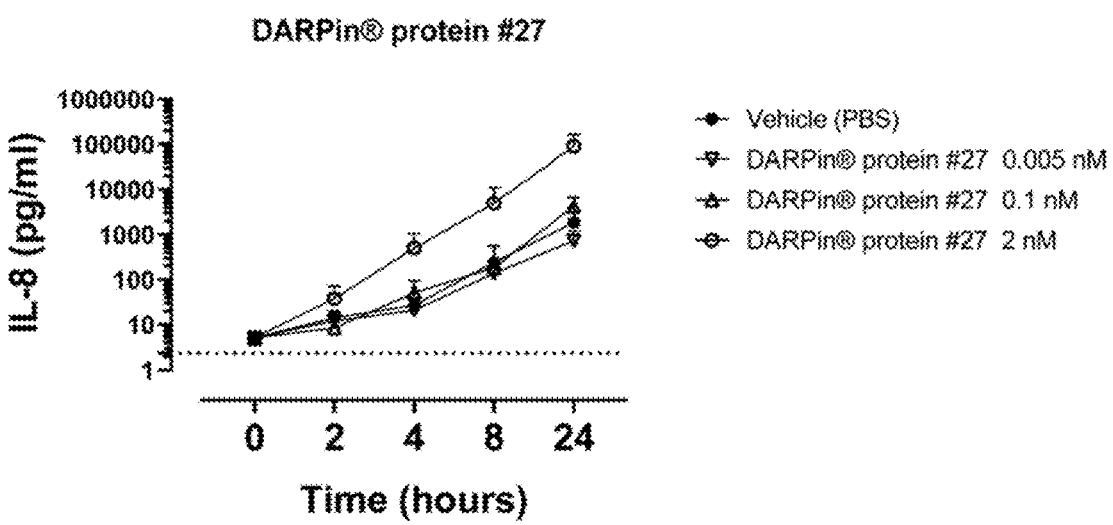
Figure 12C:
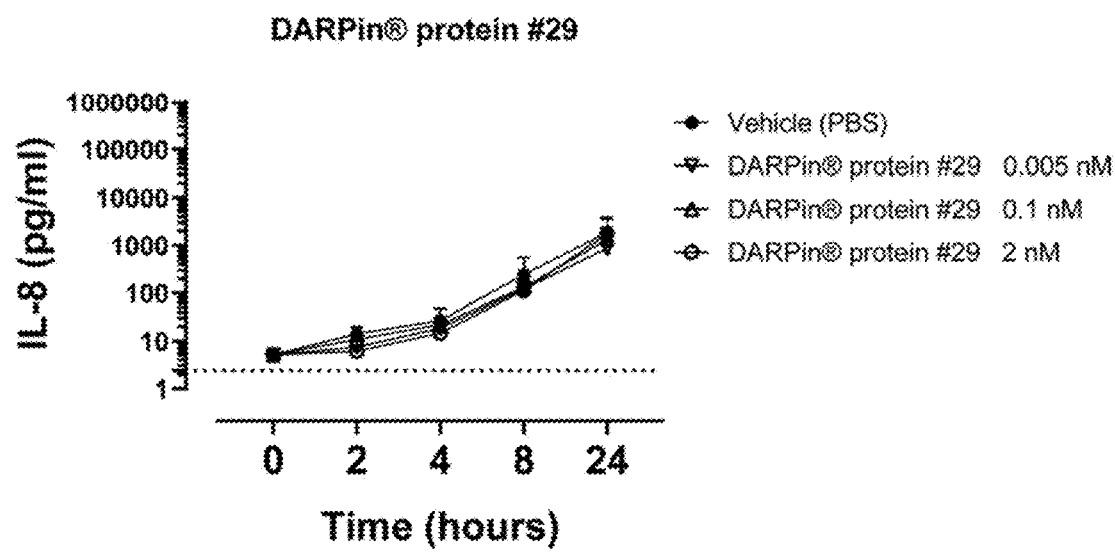
Figure 12D:
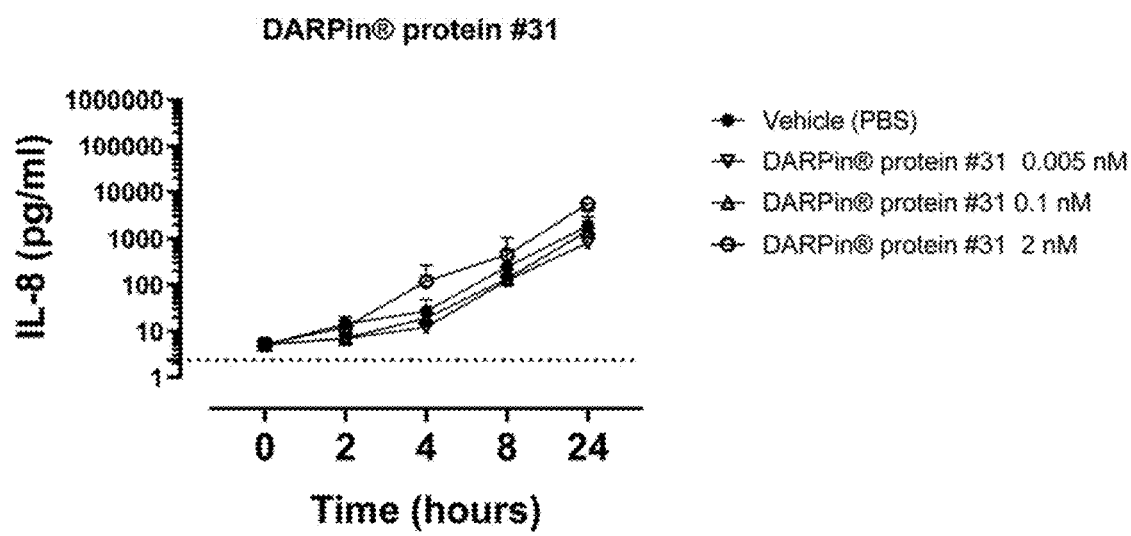
Figure 13A:
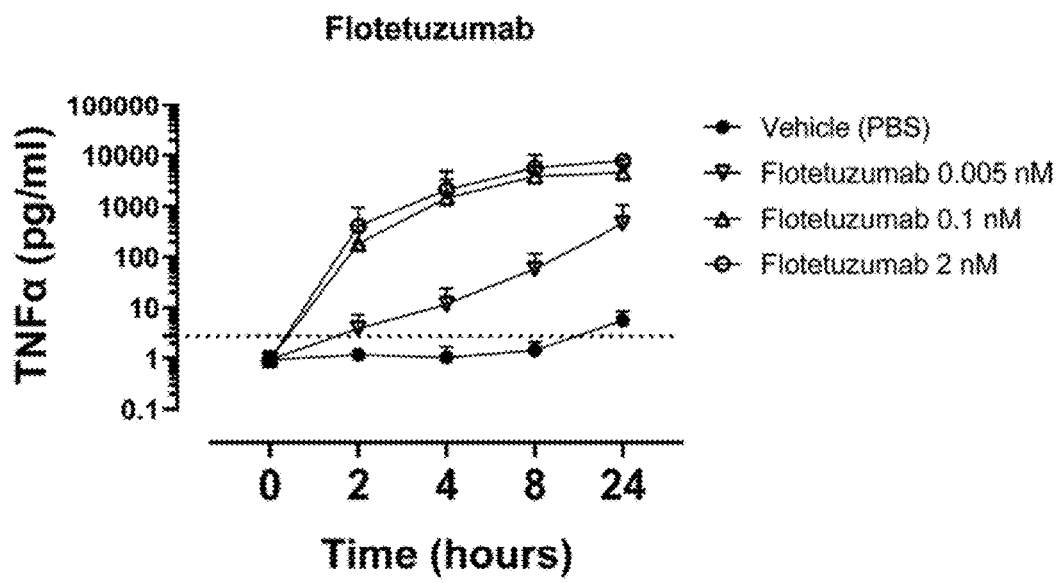
FIG. 13 (A-D). Levels of TNFα (Mean of three donors). Calculated mean concentration values of TNFα for all three donors (D1-3) in the blood loop system. Plasma samples were collected from the blood loop system at 0 (zero), 2, 4, 8 and 24 hours. Calculated LLOQ is marked with a dotted line. Each point is the mean of three donors and the error bar SD. Flotetuzumab is presented in FIG. 13A, DARPin® protein #27 in FIG. 13B, DARPin® protein #29 in FIG. 13C, and DARPin® protein #31 in FIG. 13D. The data and values are >ULOQ.
Figure 13B:
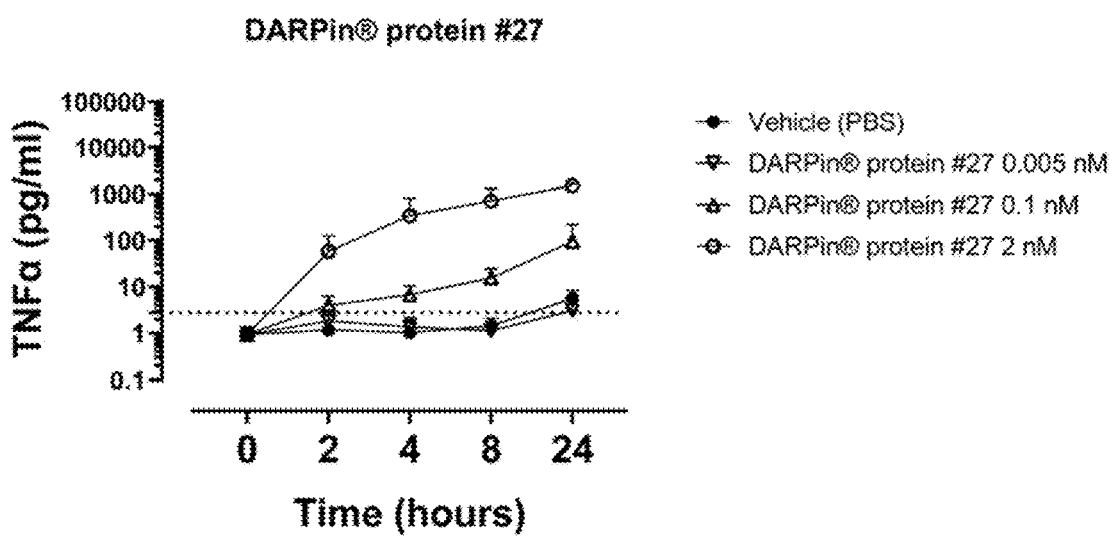
Figure 13C:
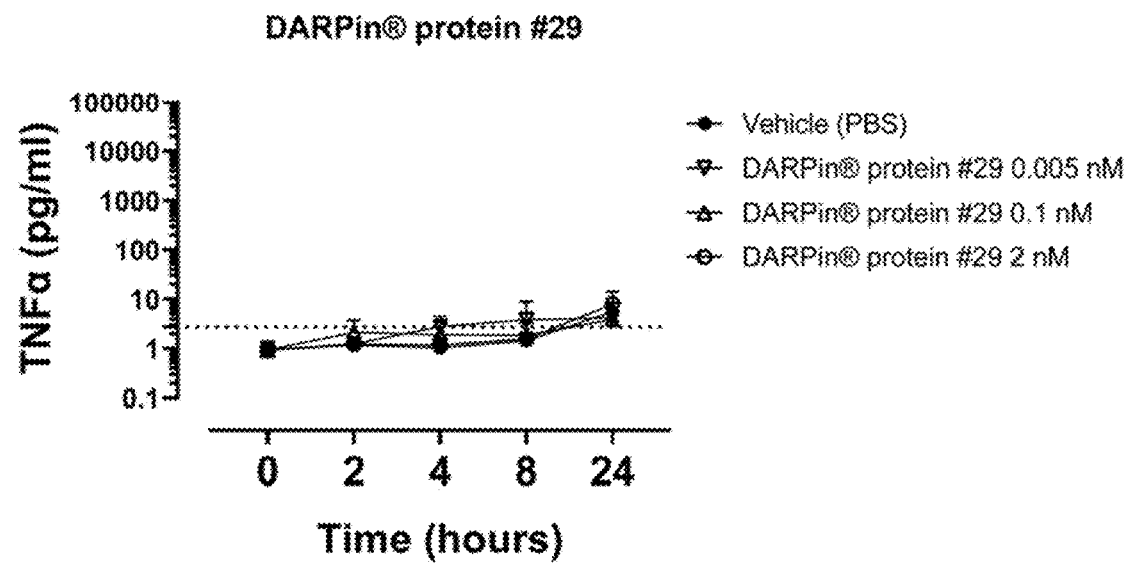
Figure 13D:
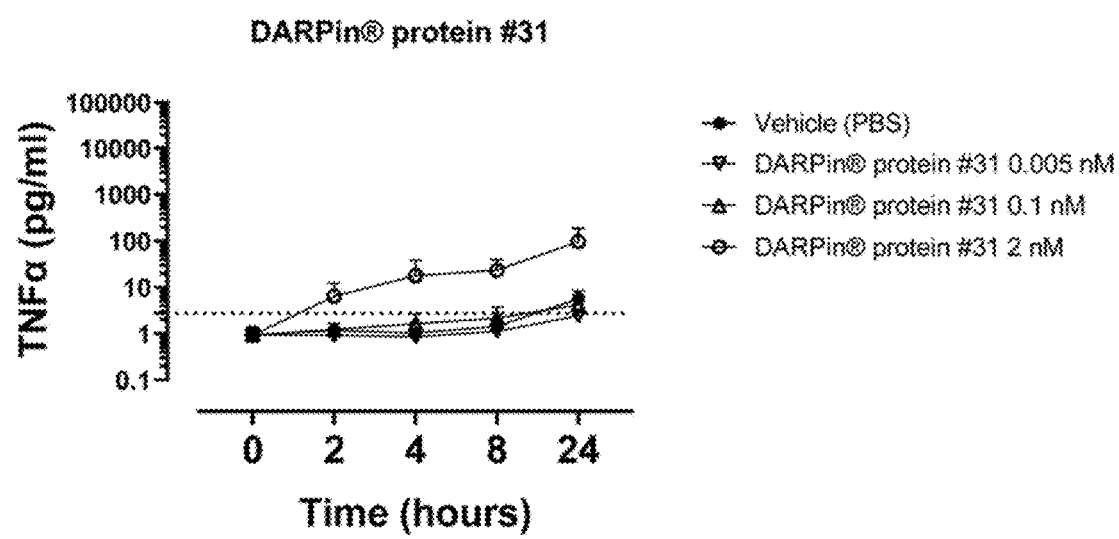
Figure 14A:
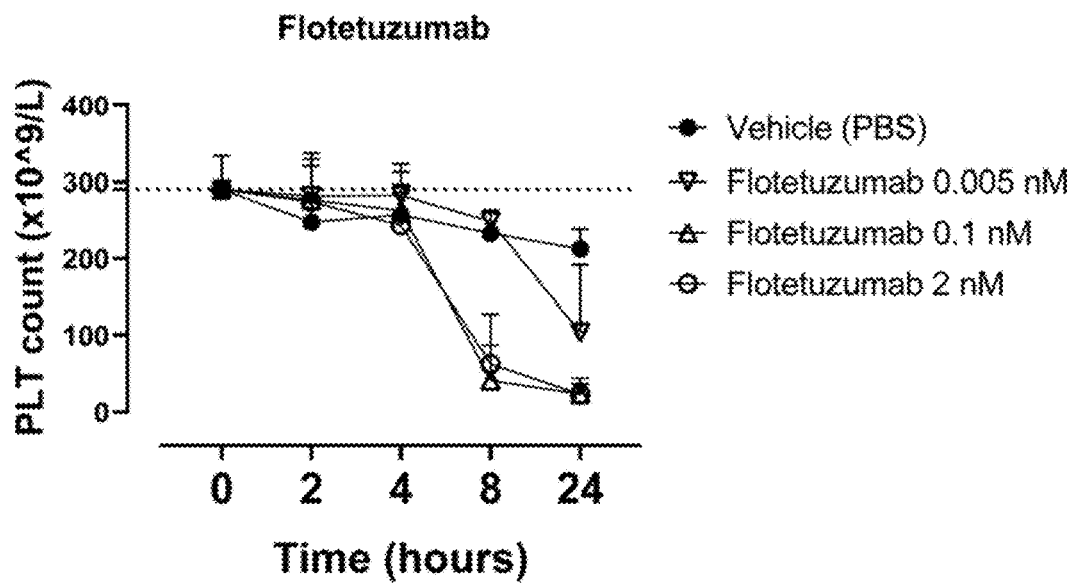
FIG. 14 (A-D). Platelet count. Blood was extracted from loops at time 0 (zero sample), 2, 4, 8 and 24 hours, PLT count was automatically counted using a Sysmex Hematology Analyzer. Each point represents the mean (and the error bar the SD) of three donors: Flotetuzumab in FIG. 14A, DARPin® protein #27 FIG. 14B, DARPin® protein #29 FIG. 14C, and DARPin® protein #31 FIG. 14D.
Figure 14B:
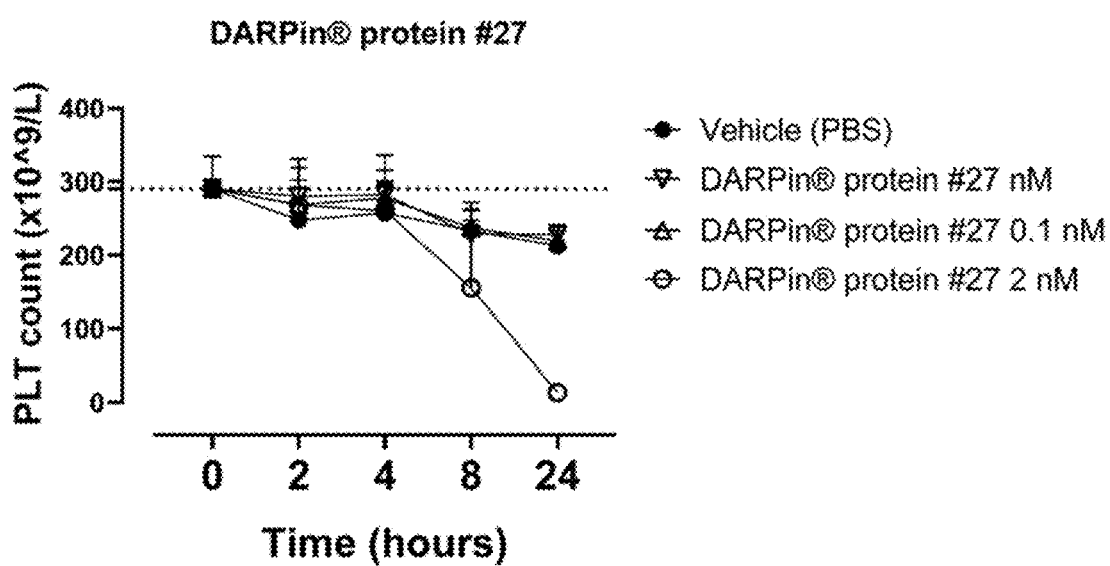
Figure 14C:
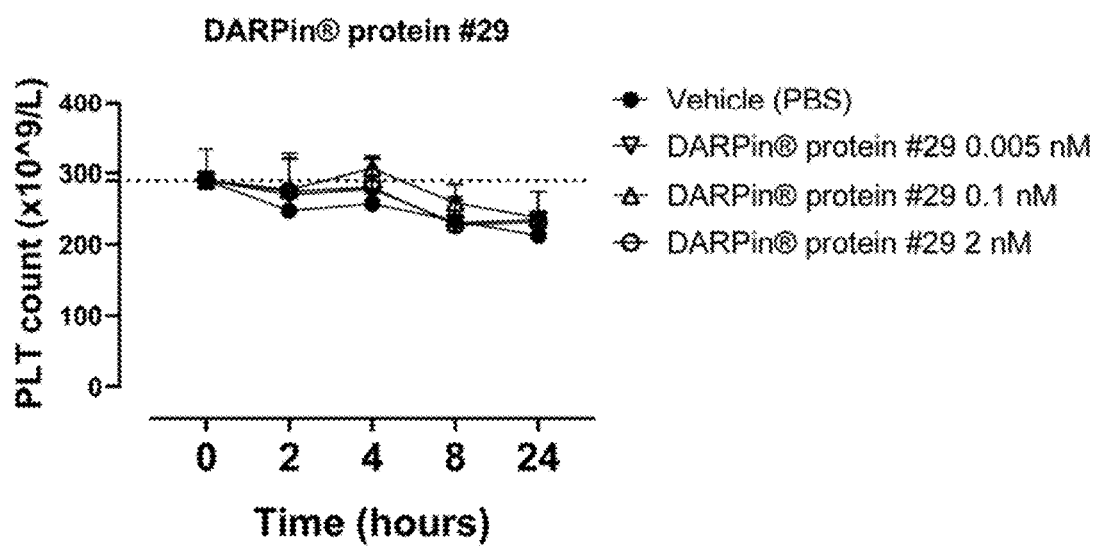
Figure 14D:
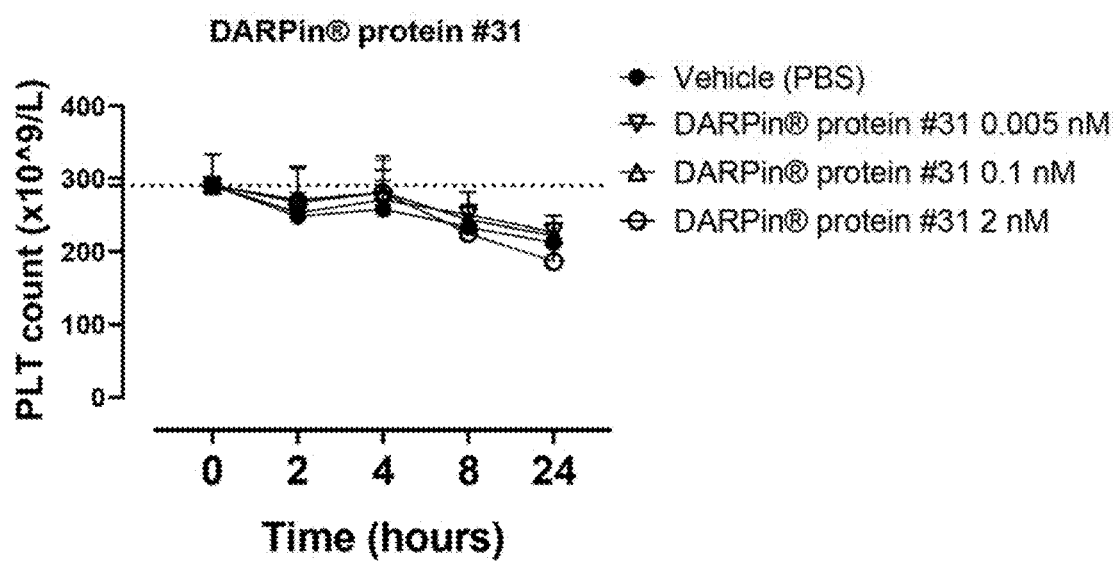

DARPin® protein #31 was also similarly tested on Molm13 CRISPR Knock-Out (KO) cells to investigate the functionality of the molecule. As it can be seen in FIG. 8 curve 7 represents Molm13 parental cells expressing all three targets (CD70, CD123 and CD33). DARPin® protein #31 shows full potency here. Curves 4-6 represent single KO cells meaning only two targets are still expressed. Here DARPin® protein #31 is still active suggesting the potential to counteract tumor heterogeneity. Curves 1-3 represent double KO cells meaning only one target is still expressed to mimic the healthy tissue compartment. Here, DARPin® protein #31 is significantly less active meaning an improved selectivity towards healthy tissue. In summary, FIG. 7 shows that DARPin® protein #31 has the potential to counteract tumor heterogeneity as well as to improve selectivity.

Example 8: Effect of Multi-Specific Binding Proteins on Cytokine Release in a Human Ex Vivo Whole Blood Loop Model The whole blood loop system is used to study interactions between blood and a drug sample, including the effect on cytokine release. The blood loop system uniquely includes both immune cells in the blood, immunoglobulins and intact complement and coagulation cascade systems (Fletcher, E. A. K., et al., Int Immunopharmacol, (2018) 54: p. 1-11). This system relies on fresh human whole blood that is kept in rotation to avoid clotting and it represents a model that mimics human blood circulation.

A. Recombinant binding proteins DARPin® #7, DARPin® #8, DARPin® #9 and DARPin® #10 have been evaluated at four different concentrations in the whole blood loop system, along with two known control benchmark T cell engagers, AMG330-similar and flotetuzumab-similar (AMG330 similar/flotetuzumab similar: 10 nM, 0.1 nM, 0.01 nM and 0.001 nM; DARPin® #7 to 10:10 nM, 1 nM, 0.1 nM and 0.01 nM).

In the whole blood loop system, cytokine release was analyzed at 0-hour, 4-hour, 8-hour, 24-hour and 48-hour timepoints. In this study, PBS was used as a negative control and AMG330 similar/and flotetuzumab similar as benchmark controls (T cell engager AMG330 with binding specificity for CD33 and flotetuzumab with binding specificity for CD123) for cytokine release.

The drug samples were prepared to obtain the following concentrations in the blood: AMG330 similar/flotetuzumab similar; 10 nM, 0.1 nM, 0.01 nM and 0.001 nM, DARPin® #7 to 10; 10 nM, 1 nM, 0.1 nM and 0.01 nM. Sterile PBS was used as vehicle as well as for dilution of test samples to obtain the final volume of 100 µl added to each loop. The remaining test sample solutions were discarded.

All materials in the loop system were surface heparinized. To prevent clotting, blood was set to rotate in plastic tubes in which the inside of the tubes was pre-coated with a unique heparin conjugate prior the run. The coating allows for blood to circulate without need for high anti-coagulant additions into the blood. Fresh whole blood was taken from two healthy volunteers (D1, D2). Immediately after blood acquisition, the blood was transferred to pre-coated plastic tubes to form the loops, followed by administration of the test items according to the following design:

1. Vehicle (PBS)
2. AMG330 similar 0.001 nM
3. AMG330 similar 0.01 nM
4. AMG330 similar 0.1 nM
5. AMG330 similar 10 nM
6. flotetuzumab similar 0.001 nM
7. flotetuzumab similar 0.01 nM
8. flotetuzumab similar 0.1 nM
9. flotetuzumab similar 10 nM
10. DARPin® #7 0.01 nM
11. DARPin® #7 0.1 nM
12. DARPin® #7 1 nM
13. DARPin® #7 10 nM
14. DARPin® #8 0.01 nM
15. DARPin® #8 0.1 nM
16. DARPin® #8 1 nM
17. DARPin® #8 10 nM
18. DARPin® #9 0.01 nM
19. DARPin® #9 0.1 nM
20. DARPin® #9 1 nM
21. DARPin® #9 10 nM
22. DARPin® #10 0.01 nM
23. DARPin® #10 0.1 nM
24. DARPin® #10 1 nM
25. DARPin® #10 10 nM Subsequently, the loops were set to rotate and for each donor, the set of 26 loops was divided onto two parallel rotating platforms.

Two healthy donors (males age 18 years) were recruited (no acute infection and no intake of NSAID or any kind of corticosteroids within 7 days from blood donation).

Fresh blood from each donor saved directly after blood collection (described as a zero-time point sample) was processed to plasma and included in cytokine analysis. Loops were sampled at 4 hour, 8 hour, 24 hour and 48 hour after addition of the test substances, and EDTA (concentration in blood: 10 mM) was added to each sample to stop reactions at sampling time point. Loops were sampled at 4 hour, 8 hour, 24 hour and 48 hour for cytokine release and flow cytometry analysis. Plasma samples were prepared by centrifugation, aliquoted and stored at ≤−60° C. until the analysis.

Cytokines (IFNγ, TNFα) were measured using the MULTI-ARRAY® technology from Meso Scale Discovery MSD (FIGS. 11 12). Samples for cytokine analysis were collected at zero, 4 hour, 8 hour, 24 hour and 48 hour time point. Blood samples were processed to plasma and stored at ≤−60° C. until the analysis, which in this study was done within 22 days from sample collection. Samples were diluted 1:4, 1:8, 1:16, 1:32 or 1:100 and run in duplicates according to the manufacturer's instructions.

Lower limit of detection (LLOD) was calculated by MSD software and defined as 2.5×SD above the zero calibrator (Standard-8). Upper limit of detection (ULOD) is calculated by MSD software from the signal value of the Standard-1. Lower and upper limit of quantifications (LLOQ and ULOQ) are verified by MSD and calculated from the standard curve and percentage recovery of diluent standards with precision of 20% and accuracy 80-120%. Three-levels of multi-analyte controls for IFNγ and TNFα from MSD (lot.no. A0000640; A0000641, A0000641) were used to evaluate precision and accuracy across multiple runs. Controls and test samples were run in duplicates. A typical acceptance criterion for controls is a CV <20%. In this study, all inter-run CV values were below 20%.

Cytokines were measured at the 0 (zero), 4-hour, 8-hour, 24-hour and 48-hour time point in the whole blood loop system. Concentrations of cytokines IFNγ, and TNFα in response to DARPin® #7 to 10 and controls are presented in FIGS. 27 and 28 as mean values of the two donors over time as well as raw mean concentration data for all values above 0 pg/ml calculated by MSD software. Cytokine production is described (arbitrary classification) as low for values ≤50 pg/ml; moderate for values between 50< and ≤500 pg/ml and high for values 500< and ≤5000 pg/ml.

Levels of IFNγ

Figure 27A:
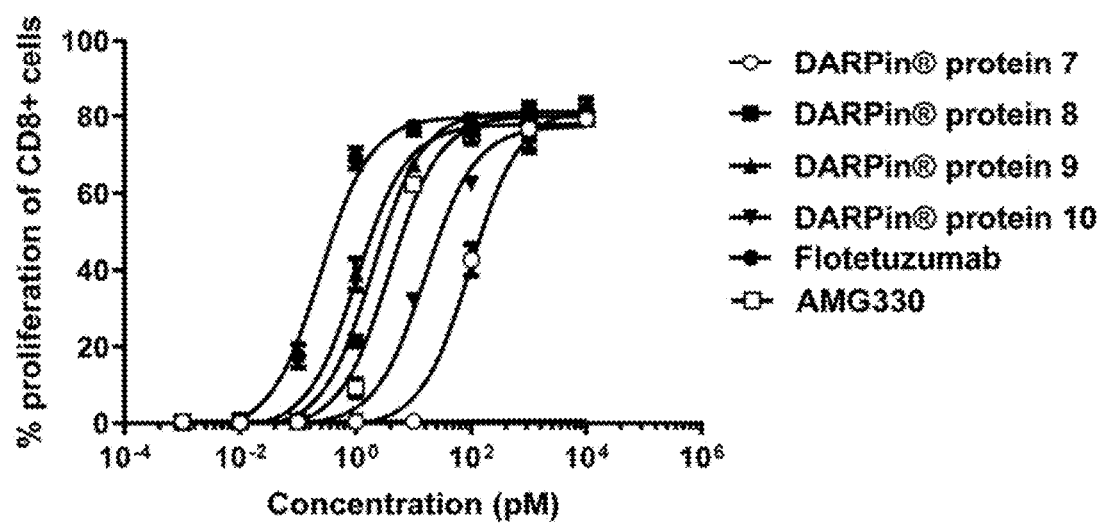
(FIG. 27A) Without half-life extension, T-cell proliferation induced by DARPin® protein 8 and DARPin® protein 9 is comparable to benchmark molecules, whereas DARPin® protein 7 and DARPin® protein 10 show >100-fold reduction in potency.
Figure 27B:
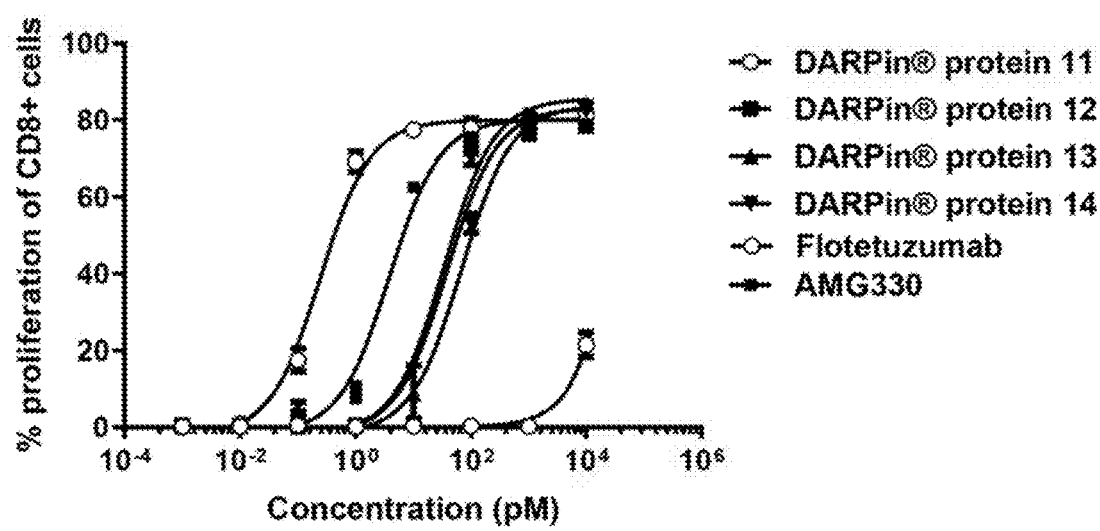
(FIG. 27B) Half-life extended DARPins show >30-fold reduction in potency compared to the corresponding non-HLE molecules shown in (A). Pan-T cells from 2 different donors were used, one representative donor is shown here FIG. 28 (A-F). Levels of IFNγ. Plasma samples were collected from the whole blood loop system at 0 (zero), 4 hours, 8 hours, 24 hours and 48 hours. Vehicle is a negative control. The mean of the two donors is presented over time for AMG330-similar (FIG. 28A), flotetuzumab-similar (FIG. 28B), DARPin® protein 7 (FIG. 28C), DARPin® protein 8 (FIG. 28D), DARPin® protein 9 (FIG. 28E) and DARPin® protein 10 (FIG. 28F). Zero values are not presented. The dotted line represents the lower limit of quantification (LLOQ). All values are below the upper limit of quantification (<ULOQ).
Figure 28A:
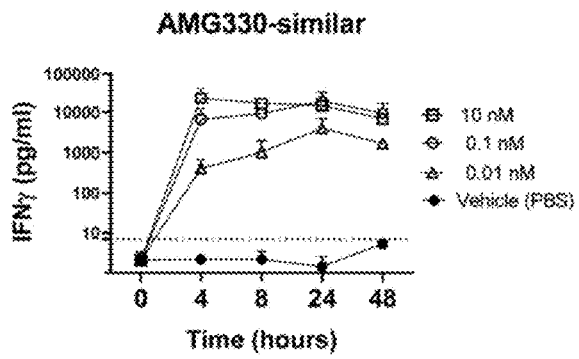
Figure 28B:
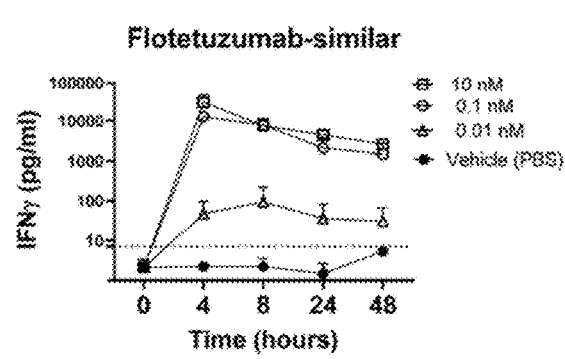
Figure 28C:
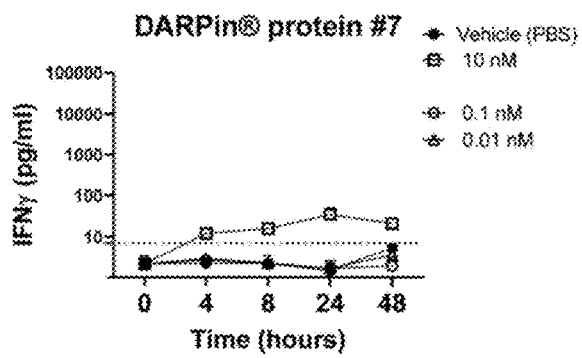
Figure 28D:
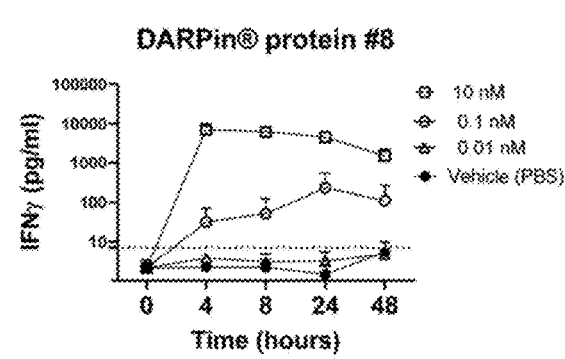
Figure 28E:
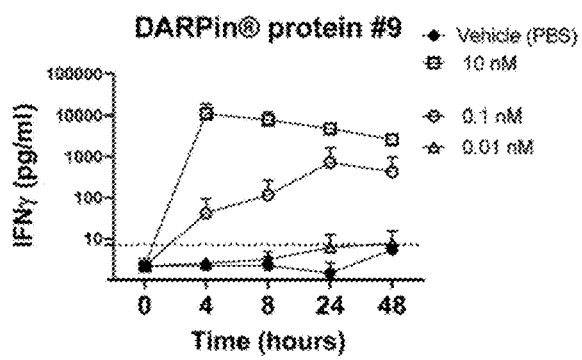
Figure 28F:
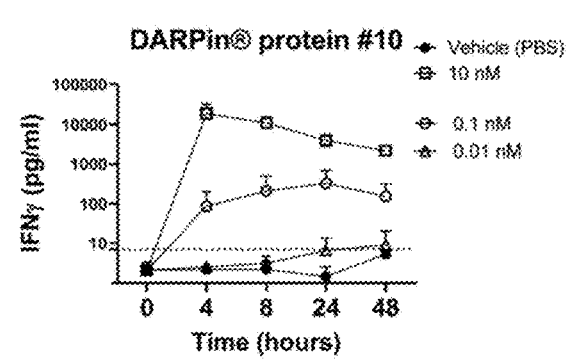
Figure 29A:
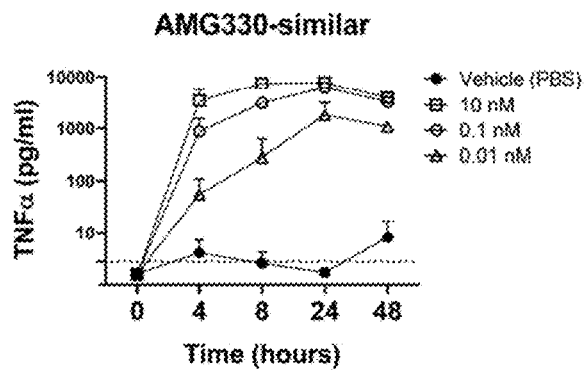
FIG. 29 (A-F). Levels of TNFα. Plasma samples were collected from the whole blood loop system at 0 (zero), 4 hours, 8 hours, 24 hours and 48 hours. Vehicle is a negative control. The mean of the two donors is presented over time for AMG330-similar (FIG. 29A), flotetuzumab-similar (FIG. 29B), DARPin® protein 7 (FIG. 29C), DARPin® protein 8 (FIG. 29D), DARPin® protein 9 (FIG. 29E) and DARPin® protein 10 (FIG. 29F). Zero values are not presented. The dotted line represents the LLOQ. All values are <ULOQ.
Figure 29B:
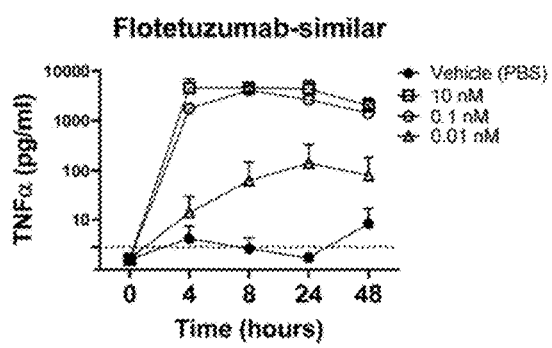
Figure 29C:
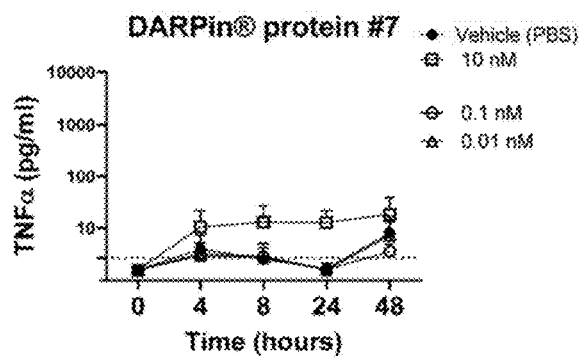
Figure 29D:
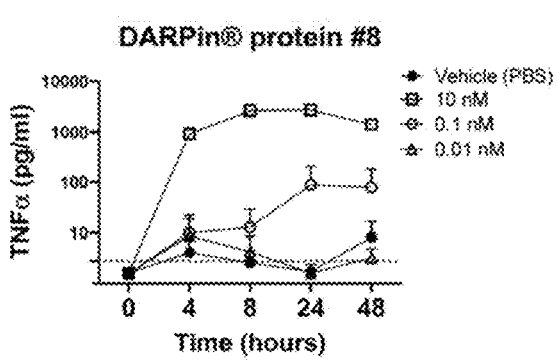
Figure 29E:
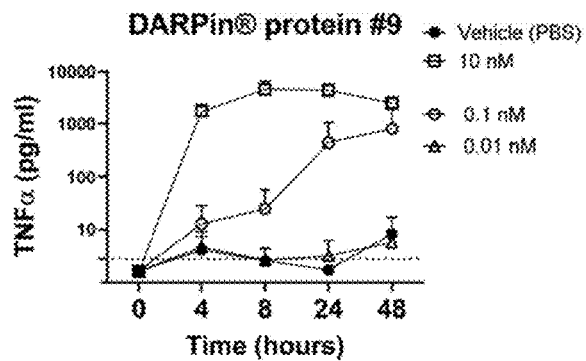
Figure 29F:
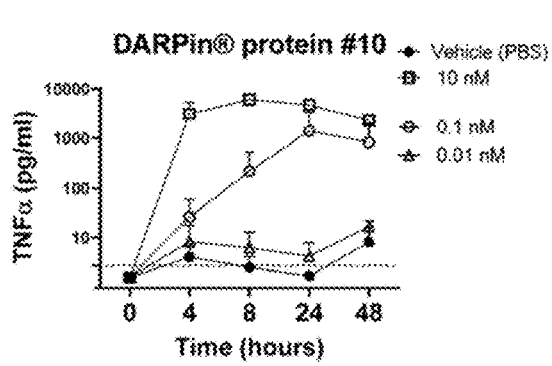
Figure 30A:
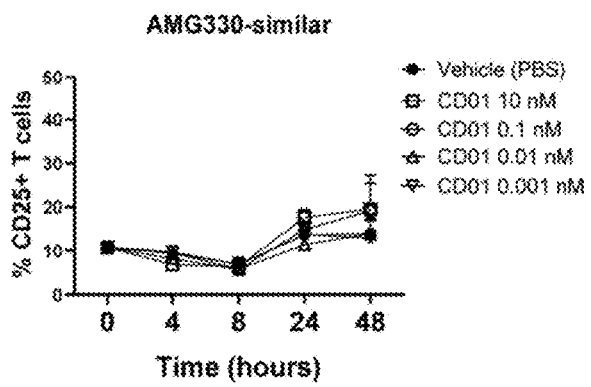
FIG. 30 (A-F). T cell activation (% CD25 positive cells). Blood cells were collected from the whole blood loop system at 0 (zero), 4 hours, 8 hours, 24 hours, 48 hours, stained with fluorophore-labelled antibodies and analyzed by flow cytometry. The % CD25 positive T cells are reported as mean of the two donors over time for AMG330-similar (FIG. 30A), flotetuzumab-similar (FIG. 30B), DARPin® protein 7 (FIG. 30C), DARPin® protein 8 (FIG. 30D), DARPin® protein 9 (FIG. 30E) and DARPin® protein 10 (FIG. 30F). Vehicle is a negative control.
Figure 30B:
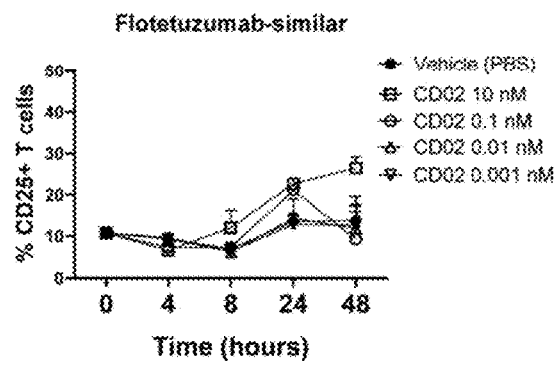
Figure 30C:
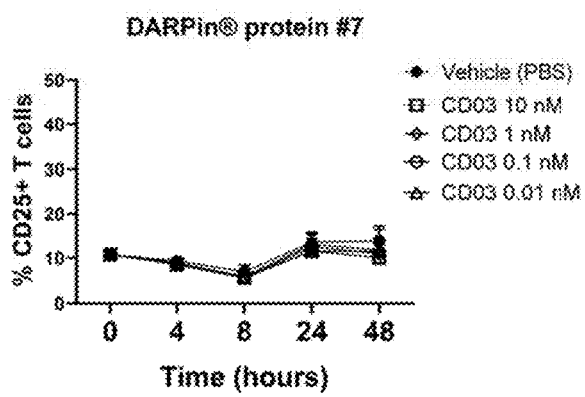
Figure 30D:
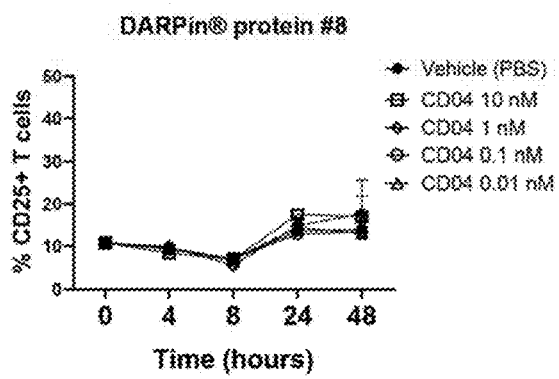
Figure 30E:
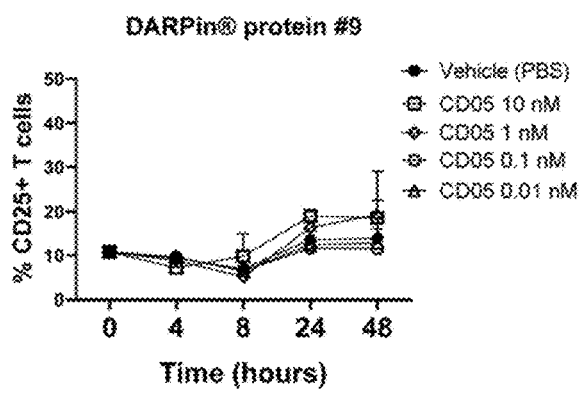
Figure 30F:
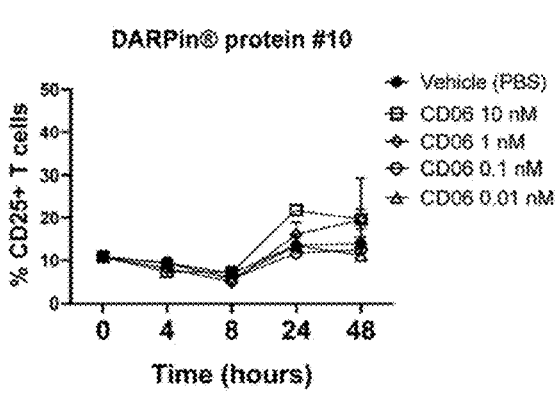
Figure 31A:
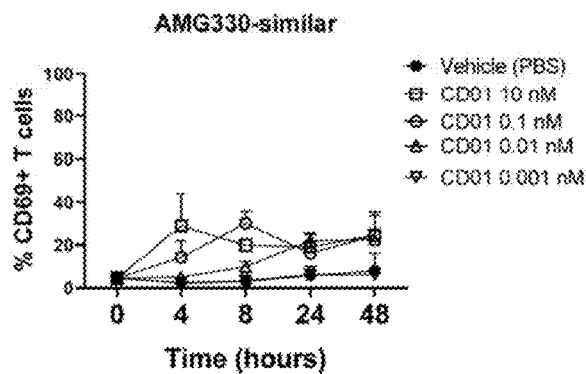
FIG. 31 (A-F). T cell activation (% CD69 positive cells). Blood cells were collected from the whole blood loop system at 0 (zero), 4 hours, 8 hours, 24 hours, 48 hours, stained with fluorophore-labelled antibodies and analyzed by flow cytometry. The % CD69 positive T cells are reported as mean of the two donors over time for AMG330-similar (FIG. 31A), flotetuzumab-similar (FIG. 31B), DARPin® protein 7 (FIG. 31C), DARPin® protein 8 (FIG. 31D), DARPin® protein 9 (FIG. 31E) and DARPin® protein 10 (FIG. 31F). Vehicle is a negative control.
Figure 31B:
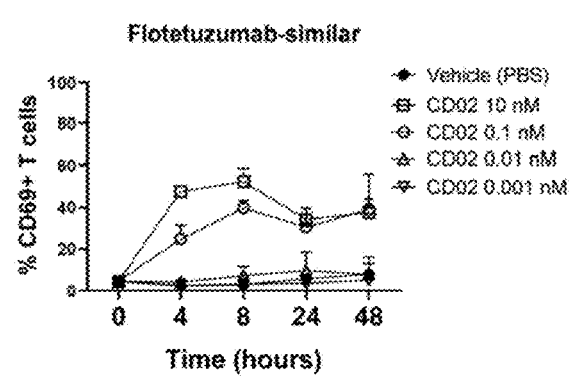
Figure 31C:
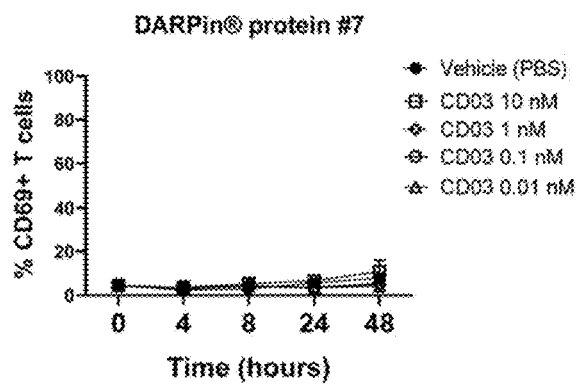
Figure 31D:
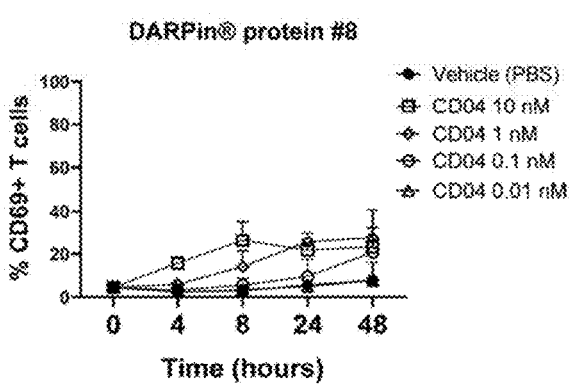
Figure 31E:
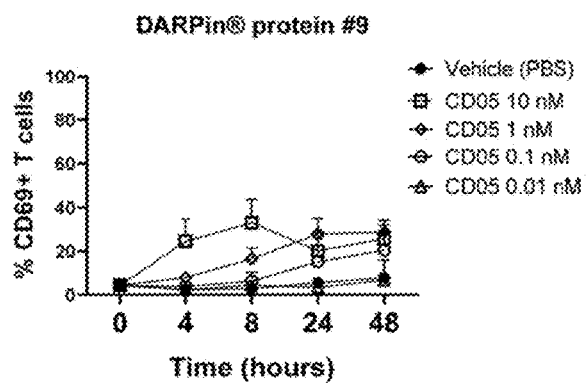
Figure 31F:
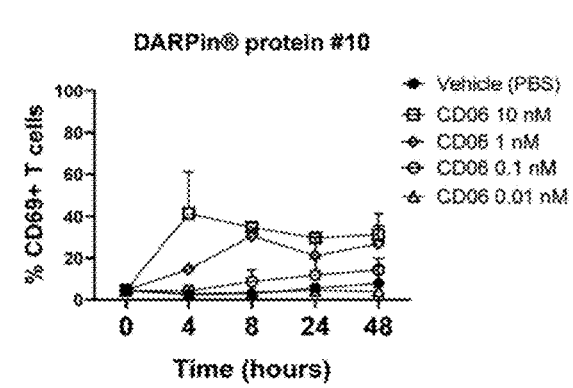
Figure 32A:
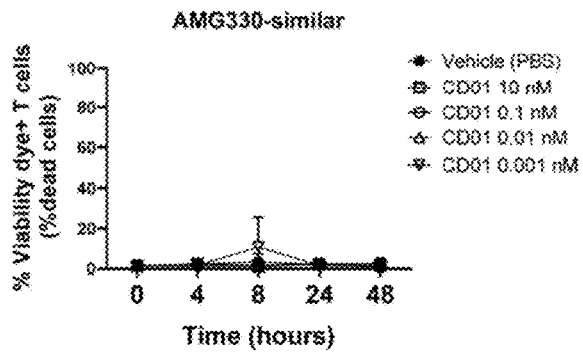
FIG. 32 (A-F). T cell viability (% dead cells of all CD3+). Blood cells were collected from the whole blood loop system at 0 (zero), 4 hours, 8 hours, 24 hours, 48 hours, stained with fluorophore-labelled antibodies and analyzed by flow cytometry. The % viability dye positive T cells (i.e. % dead cells) are reported as mean of the two donors over time for AMG330-similar (FIG. 32A), flotetuzumab-similar (FIG. 32B), DARPin® protein 7 (FIG. 32C), DARPin® protein 8 (FIG. 32D), DARPin® protein 9 (FIG. 32E) and DARPin® protein 10 (FIG. 32F). Vehicle is a negative control.
Figure 32B:
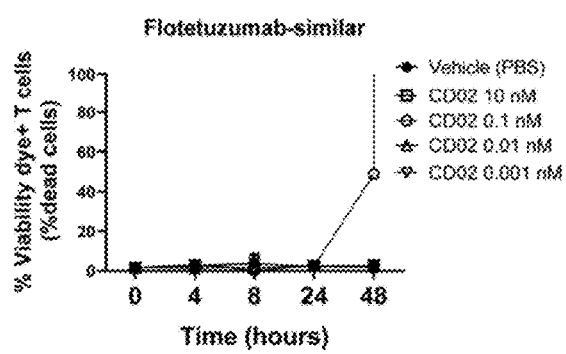
Figure 32C:
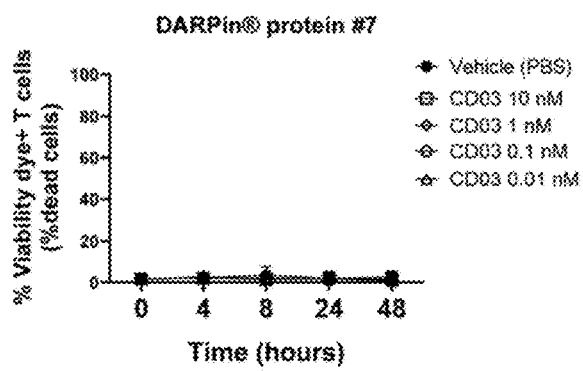
Figure 32D:
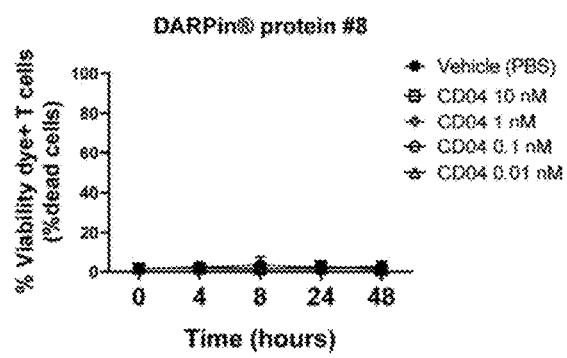
Figure 32E:
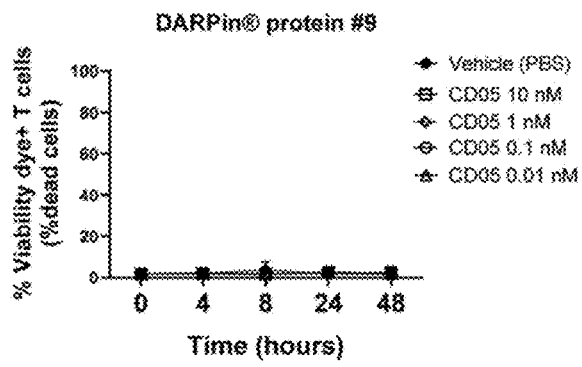
Figure 32F:
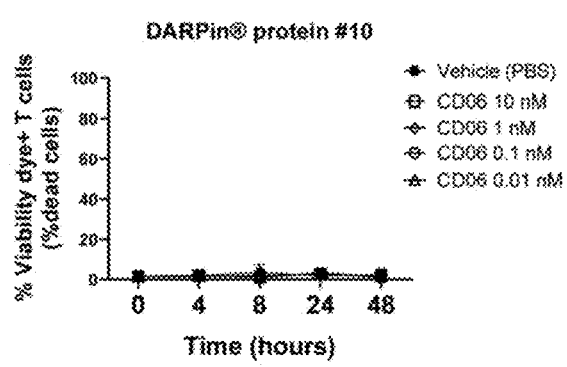
Figure 33A:
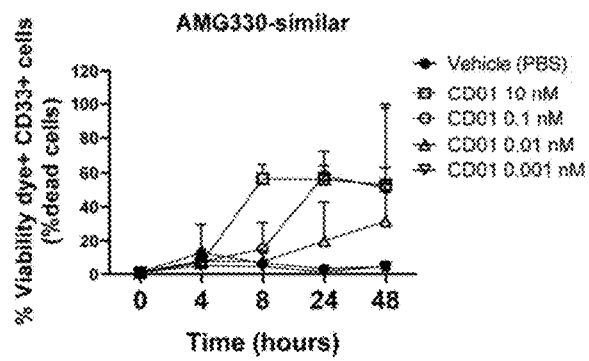
FIG. 33 (A-F). CD33+ cell viability (% dead cells of all CD33+). Blood cells were collected from the whole blood loop system at 0 (zero), 4 hours, 8 hours, 24 hours, 48 hours, stained with fluorophore-labelled antibodies and analyzed by flow cytometry. The % viability dye positive CD33+ cells (i.e. % dead cells) are reported as mean of the two donors over time for AMG330-similar (FIG. 33A), flotetuzumab-similar (FIG. 33B), DARPin® protein 7 (FIG. 33C), DARPin® protein 8 (FIG. 33D), DARPin® protein 9 (FIG. 33E) and DARPin® protein 10 (FIG. 33F). Vehicle is a negative control.
Figure 33B:
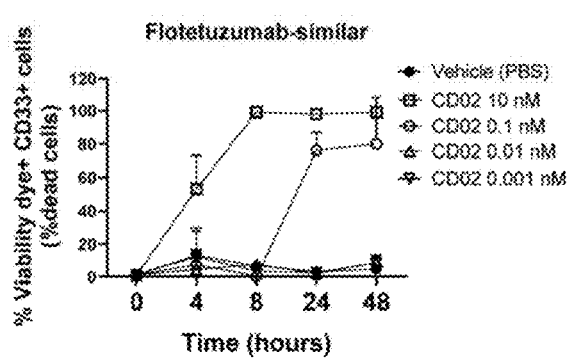
Figure 33C:
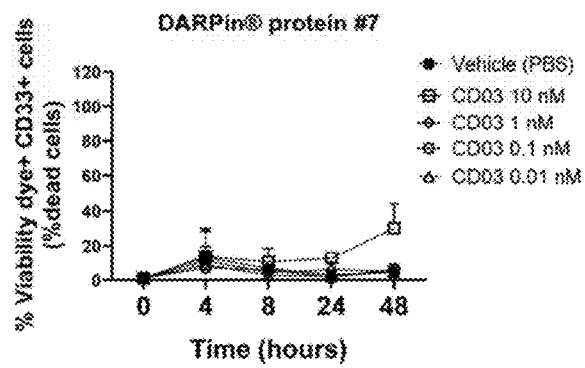
Figure 33D:
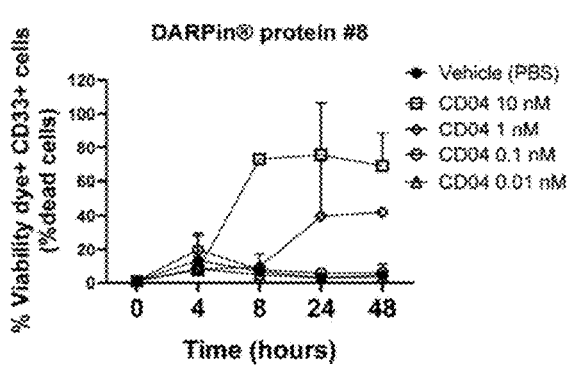
Figure 33E:
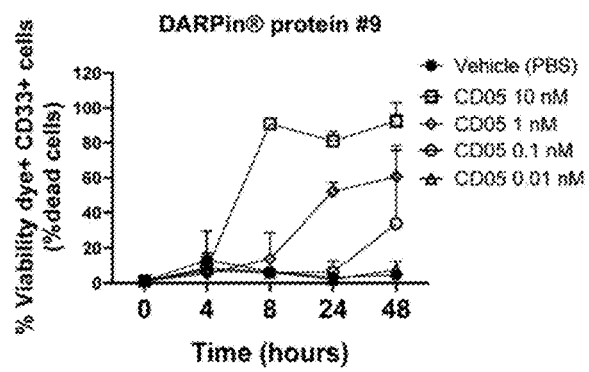
Figure 33F:
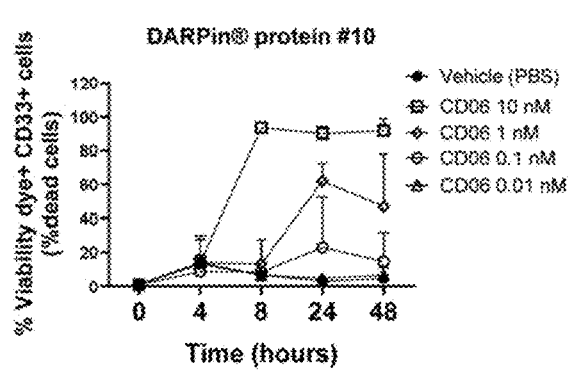
Figure 34A:
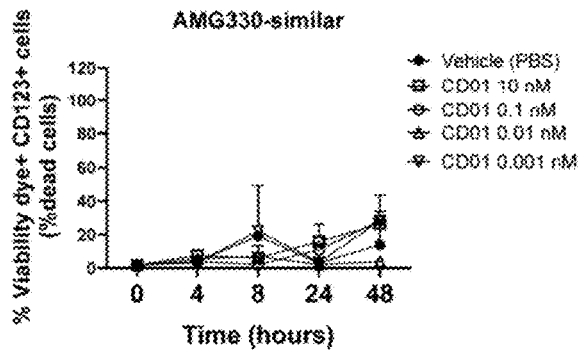
FIG. 34 (A-F). CD123+ cell viability (% dead cells of all CD123+). Blood cells were collected from the whole blood loop system at 0 (zero), 4 hours, 8 hours, 24 hours, 48 hours, stained with fluorophore-labelled antibodies and analyzed by flow cytometry. The % viability dye positive CD123+ cells (i.e. % dead cells) are reported as mean of the two donors over time for AMG330-similar (FIG. 34A), flotetuzumab-similar (FIG. 34B), DARPin® protein 7 (FIG. 34C), DARPin® protein 8 (FIG. 34D), DARPin® protein 9 (FIG. 34E) and DARPin® protein 10 (FIG. 34F). Vehicle is a negative control.
Figure 34B:
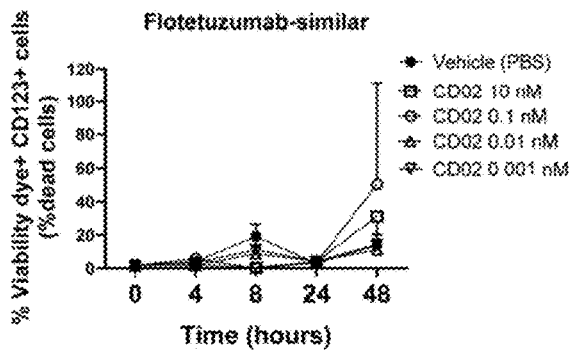
Figure 34C:
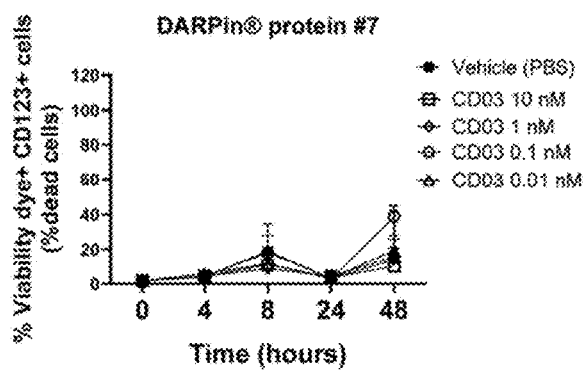
Figure 34D:
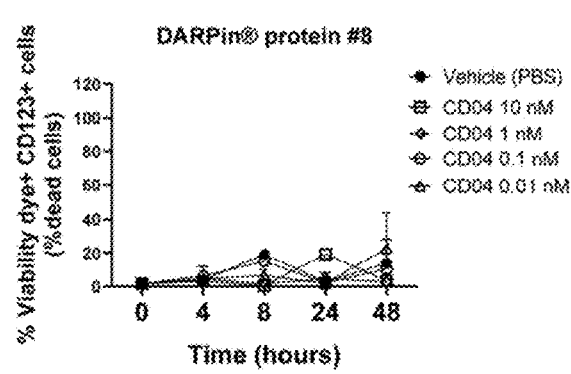
Figure 34E:
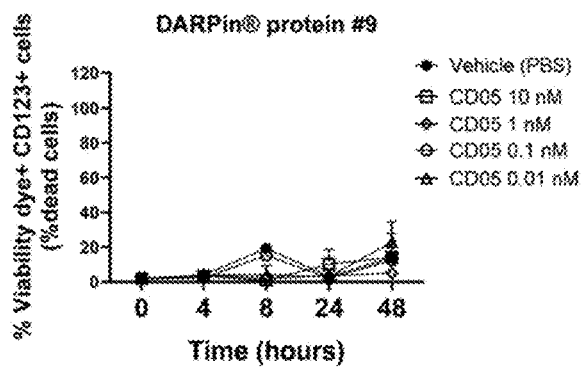
Figure 34F:
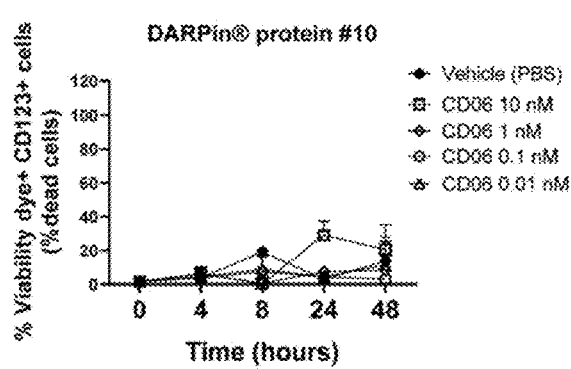
Figure 35A:
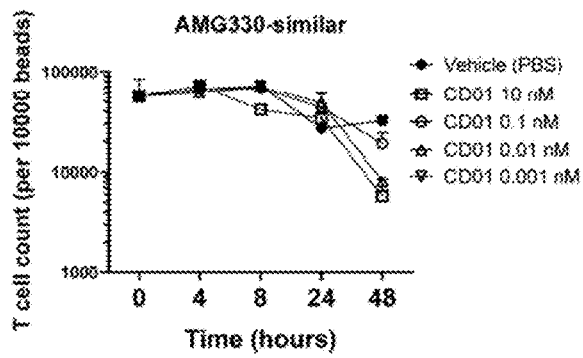
FIG. 35 (A-F). Cell counts of T cells (cells per 10000 beads). Blood cells were collected from the whole blood loop system at 0 (zero), 4 hours, 8 hours, 24 hours, 48 hours, stained with fluorophore-labelled antibodies and analyzed by flow cytometry. The cellular count per 10000 beads are reported as mean of the two donors over time for AMG330-similar (FIG. 35A), flotetuzumab-similar (FIG. 35B), DARPin® protein 7 (FIG. 35C), DARPin® protein 8 (FIG. 35D), DARPin® protein 9 (FIG. 35E) and DARPin® protein 10 (FIG. 35F). Vehicle is a negative control.
Figure 35B:
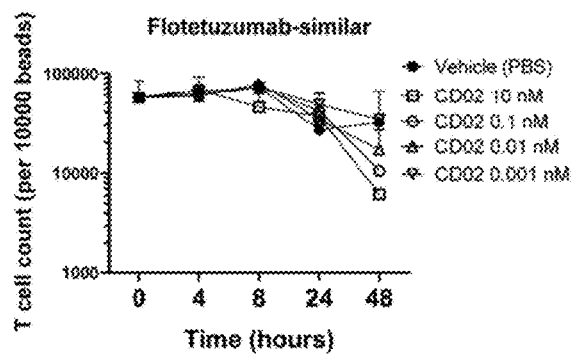
Figure 35C:
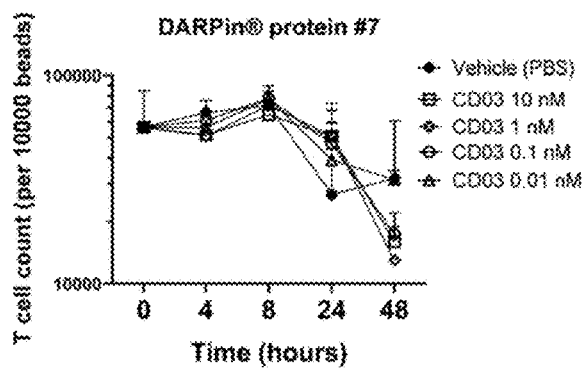
Figure 35D:
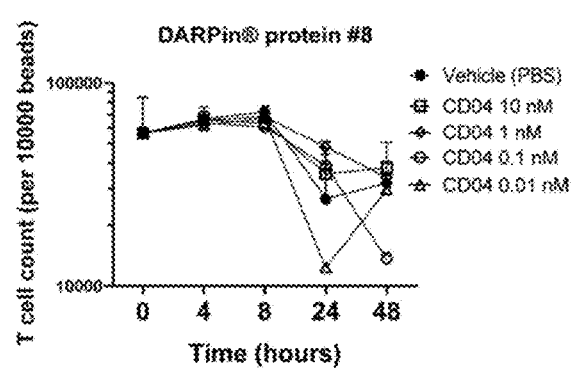
Figure 35E:
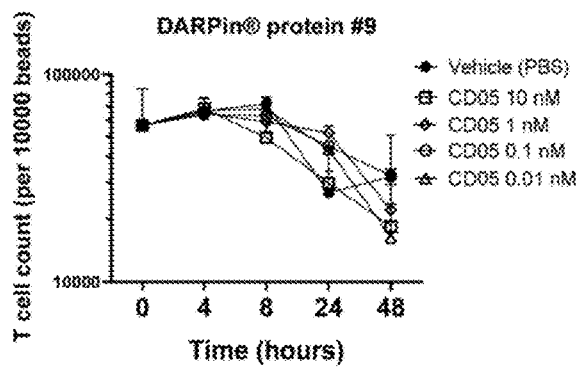
Figure 35F:
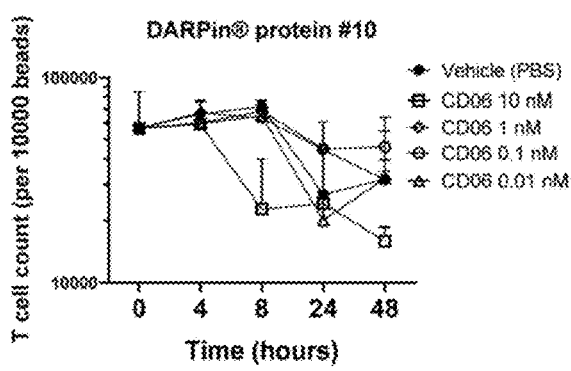
Figure 36A:
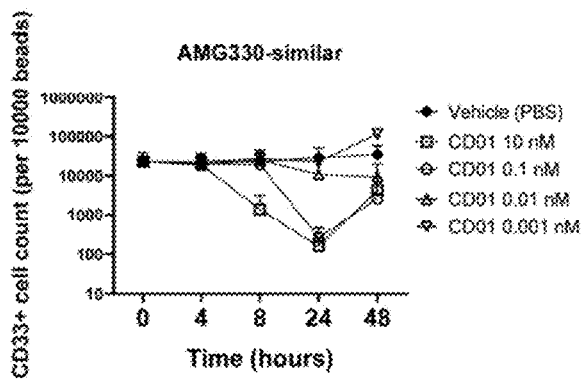
FIG. 36 (A-F). Cell counts of CD33+ cells (cells per 10000 beads). Blood cells were collected from the whole blood loop system at 0 (zero), 4 hours, 8 hours, 24 hours, 48 hours, stained with fluorophore-labelled antibodies and analyzed by flow cytometry. The cellular count per 10000 beads are reported as mean of the two donors over time for AMG330-similar (FIG. 36A), flotetuzumab-similar (FIG. 36B), DARPin® protein 7 (FIG. 36C), DARPin® protein 8 (FIG. 36D), DARPin® protein 9 (FIG. 36E) and DARPin® protein 10 (FIG. 36F). Vehicle is a negative control.
Figure 36B:
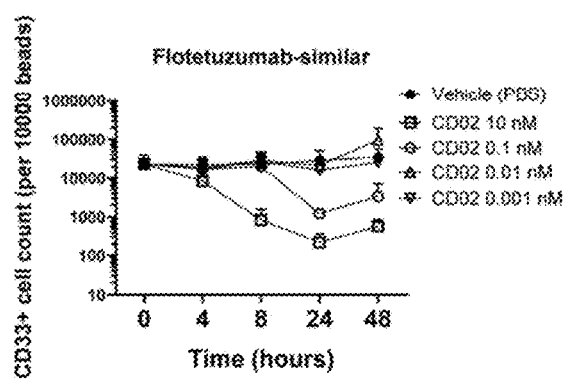
Figure 36C:
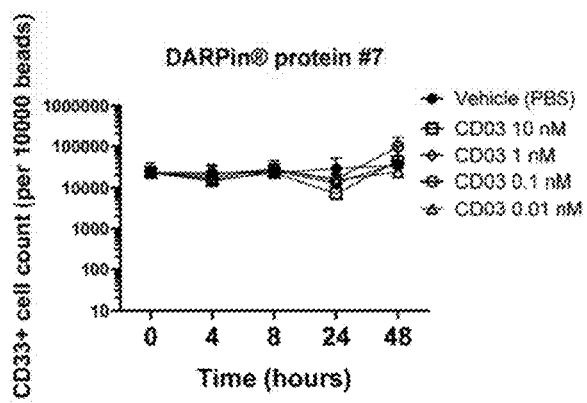
Figure 36D:
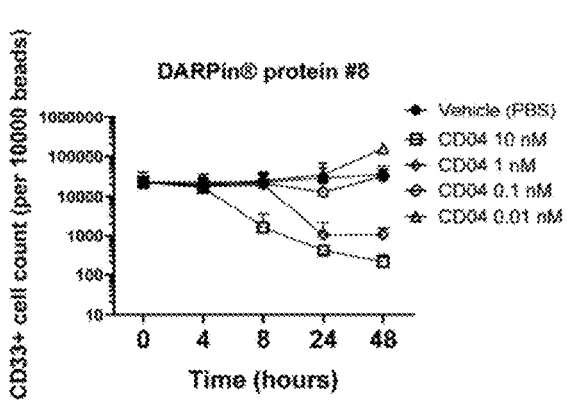
Figure 36E:
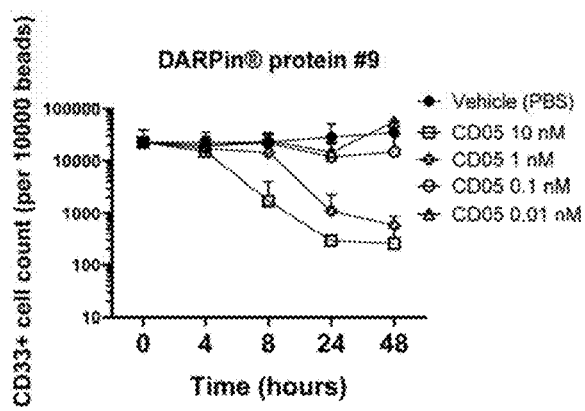
Figure 36F:
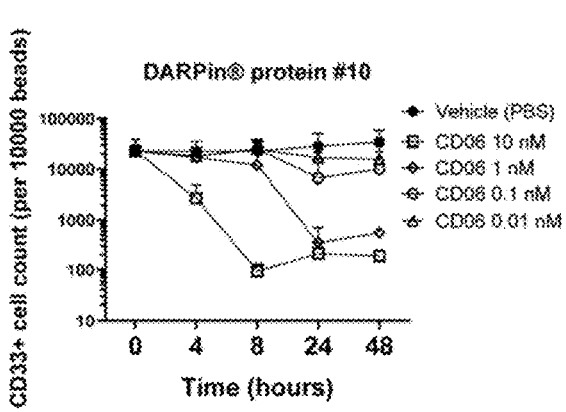
Figure 37A:
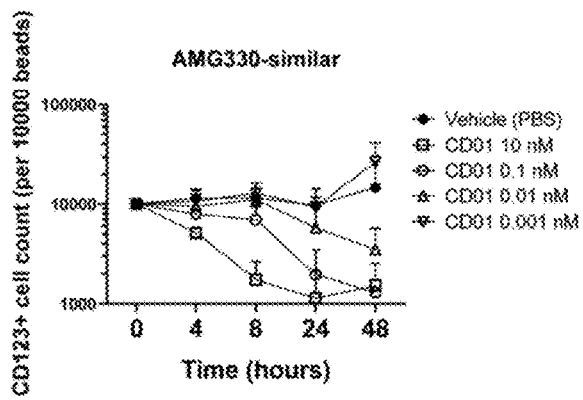
FIG. 37 (A-F). Cell counts of CD123+ cells (cells per 10000 beads). Blood cells were collected from the whole blood loop system at 0 (zero), 4 hours, 8 hours, 24 hours, 48 hours, stained with fluorophore-labelled antibodies and analyzed by flow cytometry. The cellular count per 10000 beads are reported as mean of the two donors over time for AMG330-similar (FIG. 37A), flotetuzumab-similar (FIG. 37B), DARPin® protein 7 (FIG. 37C), DARPin® protein 8 (FIG. 37D), DARPin® protein 9 (FIG. 37E) and DARPin® protein 10 (FIG. 37F). Vehicle is a negative control.
Figure 37B:
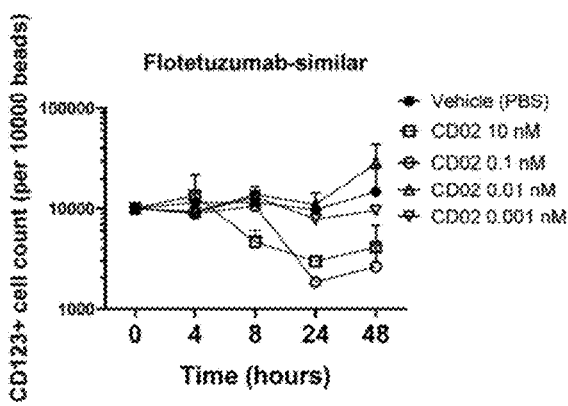
Figure 37C:
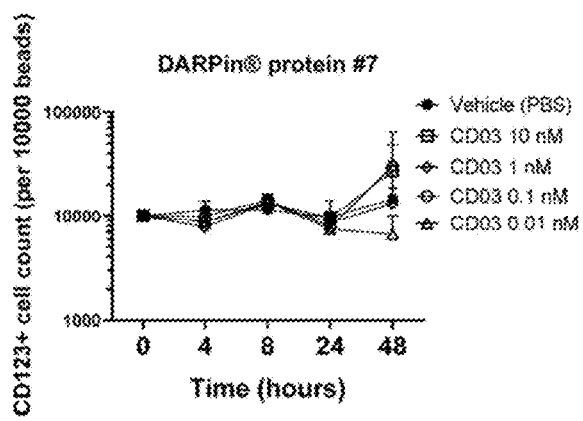
Figure 37D:
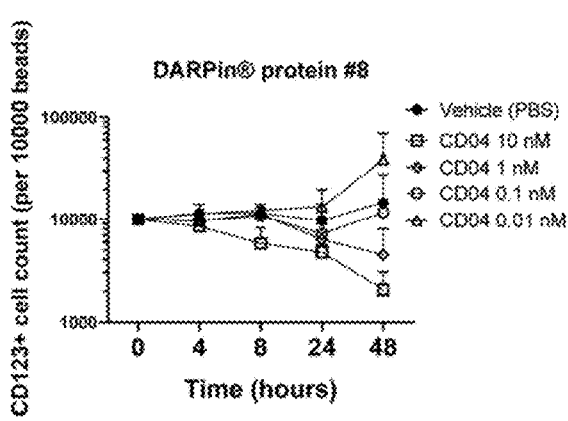
Figure 37E:
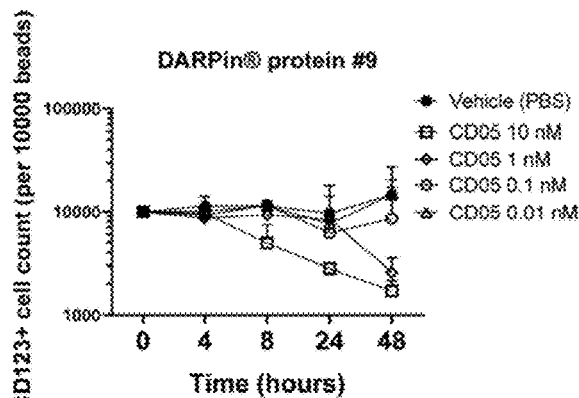
Figure 37F:
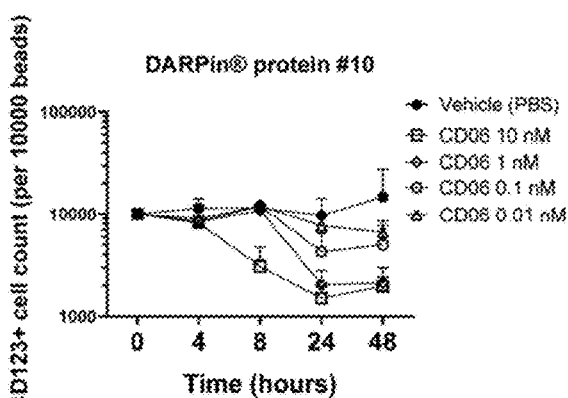

In the loop system, AMG330-similar and flotetuzumab-similar induced high levels of IFNγ at the two highest concentrations (10 nM and 0.1 nM), while at 0.01 nM the levels were moderate-to-high for AMG330-similar and low-moderate for flotetuzumab-similar. For both benchmark T cell engagers at the lowest concentration (0.001 nM) the IFNγ levels were low (FIG. 27). The IFNγ levels were low in the DARPin® #7 groups and only the highest concentration (10 nM) was noted above vehicle with a peak at 8 hours (average of 34.8 pg/ml). The IFNγ levels in loops with DARPin® #8-10 were high at 10 nM peaking after 4 hours (averages of 6758.6 pg/ml for DARPin® #8, 10988.6 pg/ml for DARPin® #9 and 18972.3 pg/ml for DARPin® #10), at 1 nM peaking after 24 hours (averages of 3914.4 pg/ml for DARPin® #8, 6482.0 pg/ml for DARPin® #9 and 4511.3 pg/ml for DARPin® #10) and low-to-high at 0.1 nM peaking after 24 hours (averages of 222.4 pg/ml for DARPin® #8, 710.1 pg/ml for DARPin® #9 and 326.4 pg/ml for DARPin® #10). At the lowest concentration of DARPin® #7 to 10 (0.01 nM) the IFNγ levels were low and comparable to vehicle at all four time points.

Levels of TNFα

Similar to IFNγ, high TNFα levels were noted in AMG330-similar and flotetuzumab-similar at 10 nM with a peak after 24 hours for AMG330-similar (average of 7680.9 pg/ml) and a peak after 4 hours for flotetuzumab-similar (average of 4594.1 pg/ml) (FIG. 28). At 0.1 nM the TNFα levels were high and for AMG330-similar the levels peaked after 24 hours (average of 6159.6 pg/ml) and for flotetuzumab-similar the TNFα levels peaked after 8 hours (average of 4077.3 pg/ml). At 0.01 nM the TNFα levels were moderate-to-high for AMG330-similar (with a peak after 24 hours of 1813.9 pg/ml on average), while for flotetuzumab-similar the levels were low-to-moderate (with a peak after 24 hours of 141.9 pg/ml. The TNFα levels in AMG330-similar and flotetuzumab-similar at 0.001 nM were low and comparable to the vehicle groups. The TNFα levels were low in all DARPin® #7 groups at all four time points, all were comparable to vehicle apart from the highest concentration that peaked after 48 hours with 18.5 pg/ml. The TNFα levels in loops with DARPin® #8-10 were moderate-to-high at 10 nM peaking after 24 hours for DARPin® #8 (average of 2732.8 pg/ml) and after 8 hours for DARPin® #9-10 (averages of 4671.9 pg/ml and 6026.4 pg/ml), respectively. At 1 nM the TNFα levels were moderate-to-high with a peak after 24 hours (averages of 2046.0 pg/ml for DARPin® #8, 3288.6 pg/ml for DARPin® #9 and 2522.7 pg/ml for DARPin® #10). At 0.1 nM of DARPin® #8-10 the TNFα levels were low-to-moderate at the 4 hour and 8 hour time points, while at 24-48 hours the levels were moderate-to-high (with a peak of 88.3 pg/ml for DARPin® #8 after 24 hours, a peak of 800.7 pg/ml for DARPin® #9 after 48 hours and a peak of 1382.8 pg/ml for DARPin® #10 after 24 hours). At the lowest concentration (0.01 nM) all DARPin® #8-10 groups were comparable to the vehicle group at all four time points.

Overall, increased levels of all cytokines (IFNγ, and TNFα) were observed in the known benchmark control groups (at 10 nM, 0.1 nM and 0.01 nM) and DARPin® #8-10 groups (at 10 nM, 1 nM and 0.1 nM) over vehicle at all four time points. No distinct cytokine release was observed in response to DARPin® #7 (at all concentrations), AMG330-similar and flotetuzumab-similar (at 0.001 nM) and DARPin® #8-10 (at 0.01 nM). This might suggest that a tenfold higher concentration of DARPin® #8-10 needs to be applied to match the cytokine release induced by the reference molecules AMG330-similar and flotetuzumab-similar. Moreover, this suggests a more manageable cytokine release with the DARPin® #8-10 compounds.

B. Recombinant binding proteins DARPin® protein #27, DARPin® protein #29 and DARPin® protein #31 have been evaluated at three different concentrations in the whole blood loop system, along with a known control benchmark T cell engager flotetuzumab In the whole blood loop system, cytokine release was analyzed at 0-hour, 2-hour, 4-hour, 8-hour and 24—a time-points. In this study, PBS was used as a negative control and flotetuzumab as benchmark, positive control (flotetuzumab with binding specificity for CD123) for cytokine release.

The drug samples and positive control were prepared to obtain the following concentrations in the blood:0.005 nM, 0.1 nM, and 2 nM. Sterile PBS was used as vehicle as well as for dilution of test samples to obtain the final volume of 100 µl added to each loop. The remaining test sample solutions were discarded.

All materials in the loop system were surface heparinized. To prevent clotting, blood was set to rotate in plastic tubes in which the inside of the tubes was pre-coated with a unique heparin conjugate prior the run. The coating allows for blood to circulate without need for high anti-coagulant additions into the blood. Fresh whole blood was taken from three healthy volunteers (D1-D3). Immediately after blood acquisition, the blood was transferred to pre-coated plastic tubes to form the loops, followed by administration of the test items according to the following design:
 1. Vehicle (PBS)
 2. Flotetuzumab 0.005 nM
 3. Flotetuzumab 0.1 nM
 4. Flotetuzumab 2 nM
 5. DARPin® protein #27 0.005 nM
 6. DARPin® protein #27 0.1 nM
 7. DARPin® protein #27 2 nM
 8. DARPin® protein #29 0.005 nM
 9. DARPin® protein #29 0.1 nM
 10. DARPin® protein #29 2 nM
 11. DARPin® protein #31 0.005 nM
 12. DARPin® protein #31 0.1 nM
 13. DARPin® protein #31 2 nM Subsequently, the loops were set to rotate and for each donor, the set of 26 loops was divided onto two parallel rotating platforms.

Three healthy donors (two females and one male aged 18 years) were recruited (no acute infection and no intake of NSAID or any kind of corticosteroids within 7 days from blood donation).

Fresh blood saved directly after blood collection (described as a zero-time point sample) was used for haematology measurements. Additionally, blood collected at the zero-time point was processed to plasma and included in cytokine analysis. Samples were extracted from each loop 2, 4, 8 and 24 hours after addition of the test substances, and EDTA (concentration in blood: 10 mM) was added to each sample to stop reactions at sampling time point. Loops were sampled at 2, 4, 8 and 24 hours for haematology and cytokine release analysis. Plasma samples were prepared by centrifugation, aliquoted and stored at ≤−60° C. until the analysis.

Cytokines (IFNγ, IL-2, IL-6, IL-8, TNFα) were measured using the MULTI-ARRAY® technology from Meso Scale Discovery (MSD). The levels of cytokines are displayed as mean values (FIG. 9, FIG. 10, FIG. 11, FIG. 12, FIG. 13) over time. Samples for cytokine analysis were collected at zero, 2-, 4-, 8- and 24-hour time-points. Blood samples were processed to plasma and stored at ≤−60° C. until the analysis, which in this study was done within 8 days from sample collection. Samples were diluted 1:4 (or 1:100) and run in duplicates according to the manufacturer's instructions.

Lower limit of detection (LLOD) was calculated by MSD software and defined as 2.5×SD above the zero calibrator (Standard-8). Upper limit of detection (ULOD) is calculated by MSD software from the signal value of the Standard-1. Lower and upper limit of quantifications (LLOQ and ULOQ) are verified by MSD and calculated from the standard curve and percentage recovery of diluent standards with precision of 20% and accuracy 80-120%. Data was defined as below LLOQ or above ULOQ if the measured mean concentration value of diluted plasma sample was below the LLOQ or above the ULOQ. Data was further transformed by the dilution factor (4× or 100×) to obtain calculated mean concentration values. Raw data corresponded to calculated mean concentration values of all samples. An acceptance criterion for replicates within the quantifiable range was set as a coefficient value (CV) ≤20%. All samples had CV values for replicates ≤20%.

Cytokines were measured at the 0- (zero), 2-, 4-, 8- and 24-hour time points in the whole blood loop system. Concentrations of cytokines IFNγ, IL-2, IL-6, IL-8 and TNFα in response to the drug samples are presented in FIG. 9, FIG. 10, FIG. 11, FIG. 12, FIG. 13 as mean values of the three donors over time. Cytokine production is described (arbitrary classification) as low for values ≤50 pg/ml; moderate for values between 50< and ≤500 pg/ml and high for values 500< and ≤5000 pg/ml.

Levels of IFNγ

IFNγ was induced at high levels (defined as >500 pg/ml) in samples with Flotetuzumab at 2 nM and 0.1 nM that increased over time from an average of 1243.8 to 48937.8 pg/ml at 2 nM and from 485.7 to 31335.2 pg/ml at 0.1 nM, while in samples with 0.005 nM Flotetuzumab, the IFNγ levels were low-to-high increasing over time from an average of 11.9 to 2064.8 pg/ml (FIG. 9). DARPin® protein #27 (at 2 nM) induced moderate-to-high levels of IFNγ that increased over time from an average of 233.5 to 6131.5 pg/ml (at 2 to 24 hours). At 0.1 nM of DARPin® protein #27, the levels of IFNγ increased over vehicle from low to moderate levels with an average of 10.2 to 334.3 pg/ml (at 2 to 24 hours). At 0.005 nM of DARPin® protein #27, the levels of IFNγ were low and similar to vehicle in all donors and at all four time-points. In samples with DARPin® protein #29, the levels of IFNγ were low and similar to vehicle at 0.005 nM and 0.1 nM, while at 2 nM the levels were slightly increased over vehicle from an average of 3.1 to 55.2 pg/ml at the 2 to 24-hour time-points. In samples with DARPin® protein #29 at 2 nM, the levels of IFNγ were increased over time from an average of 23.4 pg/ml at 2 hours to 511.0 pg/ml at 24-hours, while the levels were low and similar to vehicle at 0.1 nM and 0.005 nM and at all four time-points.

Levels of IL-2

The levels of IL-2 were low in samples with Flotetuzumab (at 0.005 nM) at 2 and 4 hours but increased gradually with time compared to vehicle at 8-24 hours with an average peak of 472.1 pg/ml at the 24-hour time-point (FIG. 10). At 0.1 nM and 2 nM, Flotetuzumab induced low-to-high levels of IL-2 with an average peak of 1951.6 pg/ml (at 0.1 nM) and 2756.6 pg/ml (at 2 nM) at the 8-hour time-point. The levels of IL-2 were low and similar to vehicle at 0.005 of DARPin® protein #27, while at 0.1 nM the levels were low, however, increased over vehicle at 24 hours in samples from D2 and D3 but not D1. At 2 nM of DARPin® protein #27, the levels of IL-2 increased from low at 2-4 hours to high at 8-24 hours with an average peak of 600.0 pg/ml at the 24-hour time-point. In samples with DARPin® protein #29, the levels of IL-2 were low at all concentrations and time-points except for the 24-hour time-point where the IL-2 levels were increased over vehicle in samples from D1 and D3 at 2 nM. In samples with DARPin® protein #31, the levels of IL-2 were low at all concentrations and time-points except for the highest concentration (2 nM) where the levels were increased over vehicle at the three later time-points with an average peak of 99.9 pg/ml at 24 hours.

Levels of IL-6

IL-6 was induced at low-to-high levels in samples with Flotetuzumab at 2 nM and 0.1 nM that increased over time from an average of 3.5 to 432.2 pg/ml at 2 nM and from 1.4 to 713.2 pg/ml at 0.1 nM, while in samples with 0.005 nM Flotetuzumab, the IL-6 levels were low and similar to vehicle at 2-4 hours and increased over vehicle at 8-24 hours with an average peak of 1744.4 pg/ml at 24 hours (FIG. 11). In samples with DARPin® protein #27 (at 2 nM) the IL-6 levels increased over vehicle at the three later time-points (4-24 hours), while at 0.005 and 0.1 nM the levels were low or similar to vehicle except for D3 at the 24-hour time-point where moderate levels were observed (77.6 pg/ml). The levels of IL-6 were low (defined as <50 pg/ml) or similar to vehicle at all concentrations of DARPin® protein #29 and DARPin® protein #31 at all four time-points.

Levels of IL-8

The levels of IL-8 increased from moderate-to-high over time in samples with 2 and 0.1 nM Flotetuzumab, while at 0.005 nM the levels were similar to vehicle in D1 at all four time-points and increased over vehicle in samples from D2 (at 24 hours) and D3 (at 4-24 hours) (FIG. 12). At 2 nM of DARPin® protein #27, the IL-8 levels were increased over vehicle with time for all three donors, while at 0.1 nM the IL-8 levels were increased over vehicle in samples from D2 (at 24 hours) and D3 (at 4-24 hours) but not D1. At 0.005 nM DARPin® protein #27 the levels of IL-8 were similar to vehicle at all four time-points. The levels of IL-8 were low and similar to vehicle in all samples with DARPin® protein #29, while in samples with DARPin® protein #31 the IL-8 levels were slightly increased over vehicle at the highest concentration (2 nM) and at 4-24 hours.

Levels of TNFα

TNFα was induced at moderate-to-high levels (defined as >500 pg/ml) in samples with Flotetuzumab at 2 nM and 0.1 nM that increased over time from an average of 412.1 to 7673.8 pg/ml at 2 nM and from 184.2 to 4689.8 pg/ml at 0.1 nM, while in samples with 0.005 nM Flotetuzumab, the TNFα levels increased from low-to-high over time from an average of 3.9 to 458.9 pg/ml (FIG. 13). DARPin® protein #1 (at 2 nM) induced moderate-to-high levels of TNFα that increased over time from an average of 57.8 to 1522.6 pg/ml (at 2 to 24 hours). At 0.1 nM of DARPin® protein #27, the levels of TNFα increased over vehicle from low to moderate levels with an average of 4.0 to 95.4 pg/ml (at 2 to 24 hours). At 0.005 nM of DARPin® protein #27, the levels of TNFα were low and similar to vehicle in all donors and at all four time-points. In samples with DARPin® protein #29, the levels of TNFα were low and similar to vehicle at all three concentrations and all four time-points. In samples with DARPin® protein #31 at 2 nM, the levels of TNFα were increased over time from low to moderate levels with an average of 6.5 pg/ml at 2 hours to 98.6 pg/ml at 24-hours, while the levels were low and similar to vehicle at 0.1 nM and 0.005 nM and at all four time-points.

Overall, the levels of IFNγ, IL-2, IL-6 and TNFα noted in the vehicle group at all four time points (2, 4, 8 and 24 hours) were generally similar to levels noted in zero-time point group. In contrast, there was a difference observed between zero and vehicle for IL-8 and this may indicate background levels of cytokine release from the donor in response to the vehicle in the system with active cascade systems. In conclusion, Flotetuzumab (0.005, 0.1 and 2 nM), DARPin® protein #27 (0.1 and 2 nM) and DARPin® protein #31 (at 2 nM) induced cytokine release that increased over time with a magnitude order of Flotetuzumab >DARPin® protein #27>DARPin® protein #31. In contrast, DARPin® protein

29 induced no or low levels of cytokines at all three concentrations and all four time-points.

C. Recombinant binding proteins DARPin® protein #58, DARPin® protein #59, DARPin® protein #57, DARPin® protein #60, DARPin® protein #61 and DARPin® protein #56, targeting CD70, CD123 and CD33. have been evaluated at three different concentrations in the whole blood loop system and compared with a half-life extended non-TAA (Ni2C) DARPin® protein #74 and Flotetuzumab-similar as a benchmark molecule.

In the whole blood loop system, cytokine release was analyzed at 0-hour, 2-hour, 4-hour, 8-hour and 24-hour timepoints. In this study, PBS was used as a negative control and Flotetuzumab-similar as benchmark positive control (Flotetuzumab with binding specificity for CD123) for cytokine release.

The drug samples and positive control were prepared to obtain the following concentrations in the blood: 0.005 nM, 0.1 nM, and 2 nM. Sterile PBS was used as vehicle as well as for dilution of test samples to obtain the final volume of 100 µl added to each loop. The remaining test sample solutions were discarded.

All materials in the loop system were surface heparinized. To prevent clotting, blood was set to rotate in plastic tubes in which the inside of the tubes was pre-coated with a unique heparin conjugate prior the run. The coating allows for blood to circulate without need for high anti-coagulant additions into the blood. Fresh whole blood was taken from three healthy volunteers (D1-D3). Immediately after blood acquisition, the blood was transferred to pre-coated plastic tubes to form the loops, followed by administration of the test items according to the following design:

TABLE 9a

| Test condition | Reagent/test item | Concentration |
| --- | --- | --- |
| 1 | Vehicle (PBS) | — |
| 2 | DARPin ® protein #58 low | 0.005 nM |
| 3 | DARPin ® protein #58 mid | 0.1 nM |
| 4 | DARPin ® protein #58. high | 2 nM |
| 5 | DARPin ® protein #59 low | 0.005 nM |
| 6 | DARPin ® protein #59 mid | 0.1 nM |
| 7 | DARPin ® protein #59 high | 2 nM |
| 8 | DARPin ® protein #57 low | 0.005 nM |
| 9 | DARPin ® protein #57 mid | 0.1 nM |
| 10 | DARPin ® protein #57 high | 2 nM |
| 11 | DARPin ® protein #60 low | 0.005 nM |
| 12 | DARPin ® protein #60 mid | 0.1 nM |
| 13 | DARPin ® protein #60 high | 2 nM |
| 14 | DARPin ® protein #56 low | 0.005 nM |
| 15 | DARPin ® protein #56 mid | 0.1 nM |
| 16 | DARPin ® protein #56 high | 2 nM |
| 17 | DARPin ® protein #61 low | 0.005 nM |
| 18 | DARPin ® protein #61 mid | 0.1 nM |
| 19 | DARPin ® protein #61 high | 2 nM |
| 20 | DARPin ® protein #74 low | 0.005 nM |
| 21 | DARPin ® protein #74 mid | 0.1 nM |
| 22 | DARPin ® protein #74 high | 2 nM |
| 23 | Flotetuzumab (MPEXT118) low | 0.005 nM |
| 24 | Flotetuzumab (MPEXT118) mid | 0.1 nM |
| 25 | Flotetuzumab (MPEXT118) high | 2 nM |

Subsequently, the loops were set to rotate and for each donor, the set of 26 loops was divided onto two parallel rotating platforms.

Three healthy donors (two females and one male aged 18 years) were recruited (no acute infection and no intake of NSAID or any kind of corticosteroids within 7 days from blood donation).

Fresh blood saved directly after blood collection (described as a zero-time point sample) was used for haematology measurements. Additionally, blood collected at the zero-time point was processed to plasma and included in cytokine analysis. Samples were extracted from each loop 2, 4, 8 and 24 hours after addition of the test substances, and EDTA (concentration in blood: 10 mM) was added to each sample to stop reactions at sampling time point. Loops were sampled at 2, 4, 8 and 24 hours for haematology and cytokine release analysis. Plasma samples were prepared by centrifugation, aliquoted and stored at ≤−60° C. until the analysis.

Cytokines (IFNγ, IL-2, IL-6, IL-8, TNFα) were measured using the MULTI-ARRAY® technology from Meso Scale Discovery (MSD). The levels of cytokines are displayed as mean values (FIG. 44, FIG. 45, FIG. 46, FIG. 47, FIG. 48) over time. Samples for cytokine analysis were collected at zero, 2-, 4-, 8- and 24-hour time-points. Blood samples were processed to plasma and stored at ≤−60° C. until the analysis, which in this study was done within 8 days from sample collection. Samples were diluted 1:4 (or 1:100) and run in duplicates according to the manufacturer's instructions.

Lower limit of detection (LLOD) was calculated by MSD software and defined as 2.5×SD above the zero calibrator (Standard-8). Upper limit of detection (ULOD) is calculated by MSD software from the signal value of the Standard-1. Lower and upper limit of quantifications (LLOQ and ULOQ) are verified by MSD and calculated from the standard curve and percentage recovery of diluent standards with precision of 20% and accuracy 80-120%. Data was defined as below LLOQ or above ULOQ if the measured mean concentration value of diluted plasma sample was below the LLOQ or above the ULOQ. Data was further transformed by the dilution factor (4× or 100×) to obtain calculated mean concentration values. Raw data corresponded to calculated mean concentration values of all samples. An acceptance criterion for replicates within the quantifiable range was set as a coefficient value (CV) ≤20%. All samples had CV values for replicates ≤20%.

Cytokine production is described (arbitrary classification) as low for values ≤50 pg/ml; moderate for values between 50< and ≤500 pg/ml and high for values 500< and ≤5000 pg/ml.

Overall, DARPin® protein #56 DARPin® protein #57 at the lowest concentration (0.005) did not induce increased IL-2, IL-8 or TNFα compared to vehicle. Furthermore, the lowest and medium concentrations of DARPin® protein #56 and DARPin® protein #60 induced IL-2 and IL-6 at a later time point than all other tested proteins at the same concentrations. DARPin® protein #60 at the highest concentration induced similar TNFα levels as most of the test items at 8 h and 24 h times points. By contrast, DARPin® protein #56 at the highest concentration induced lower TNFα values than all other test items. The CD3 and CD123 binding properties of flotetuzumab induced cell depletion and cytokine release as expected, whereas DARPin® protein #74 did not alter cell depletion and immune response remarkably compared to vehicle.

Example 9: Effect of Multi-Specific Binding
Proteins on T Cell Activation, Cell Viability, Blood
Platelet Counts and White Blood Cell Counts in a
Human Ex Vivo Whole Blood Loop Model A. Effect of Multi-Specific Binding Proteins on T Cell Activation and Cell Viability As with Example 8, in the whole blood loop system, T cell activation and cell viability in response to AMG330-similar/flotetuzumab-similar and DARPin® #7 to 10 were evaluated at 0 hour (pre-dose), 4 hour, 8 hour, 24 hour and 48 hour time-points. All samples preparation was carried out as described in example 10. Blood cells were stained with fluorescently labeled monoclonal antibodies (provided by Biolegend) to detect: myeloid cells (CD33+ and CD123+– antibodies used: CD33—PE/Cy7, CD123—PerCP/Cy5.5), T cells (CD3– antibody used: CD3—BV510), activation markers (CD69, CD25– antibodies used: CD69—BV421, CD25—APC) and viability dye that stains dead cells (Fixable viability dye eFluor 780). Cell counting beads were added in order to calculate a relative cell count over time for each loop. Samples for flow cytometry analysis were incubated with fluorescently labeled antibodies, Red blood cells lysed and washed. Samples were run on CytoFlex flow cytometer (Beckman Coulter) and data was analyzed by FlowJo v10 to present percentage of cell type positive for the activation markers and viability dye (% dead cells). Additionally, the zero sample for both donors were analyzed for CD33 and CD123 expression by T cells. In addition to the analysis of the blood samples collected from the loops, a zero-time point sample of each donor was incubated with the antibodies specific for Whole Blood Cells and without the activation markers. All controls were as expected. To compensate for spectral overlap of the fluorophores during flow cytometry a compensation was performed. Beads (cat.no. B22804, Beckman Coulter) were stained with antibodies with the same fluorophores as the ones included in the study and automatic compensation calculation was performed by the software (CytExpert by Beckman Coulter). The compensation settings were evaluated using single stained cells and optimized if necessary.

Flow cytometry analysis was performed on samples collected at 4 hour, 8 hour, 24 hour and 48 hour time points. Additionally, a zero time point sample was analyzed to determine cell activation status directly after blood collection. Surface markers (CD3, CD33+ and CD123+) were used to detect T cells and myeloid cells. Cell activation and viability were measured by the activation markers CD25, CD69 (activated) and a viability stain that bind dead cells. In addition, counting beads were included to analyze how cell counts changes over time for CD3+, CD33+ and CD123+ cells (FIG. 29-30).

T Cell Activation

The percentage of CD25+ T cells were similar in all groups (at 4 hour and 8 hour time-points) to the vehicle (with averages of 9.3% positive cells at 4 hours and 7.0% positive cells at 8 hours) (FIG. 29). At 24 hours and 48 hours, the percentage of CD25+ T cells had increased over vehicle in the groups of AMG330-similar/flotetuzumab-similar (at 10 nM and 0.1 nM) ranging from 15.4-28.4% positive T cells, while the two lowest concentrations of AMG330-similar/flotetuzumab-similar were similar to vehicle at the 24 and 48 hour time points (with averages of 13.5% at 24 hours and 13.9% at 48 hours). The percentage of CD25+ T cells in the DARPin® #7 groups were similar to vehicle at four time points. DARPin® #8-10 were similar to vehicle at 4 hours and 8 hours. At 24 hours and 48 hours the percentage of CD25% T cells had increased over vehicle ranging from 11.9-23.2% for DARPin® #8, 12.3-26.2% for DARPin® #9 and 12.4-26.5% for DARPin® #10. At the two lowest DARPin® #8-10 concentrations (0.1 nM and 0.01 nM) the percentage of CD25 positive T cells were similar to vehicle at all four time points.

T cells were activated to express CD69 by AMG330-similar at 10 nM (with a peak average of 28.9% positive T cells at 4 hours), at 0.1 nM (with a peak average of 30.0% positive T cells at 8 hours) and at 0.01 nM (with a peak average of 22.0% positive T cells at 24 hours) (FIG. 30). At 0.001 nM AMG330-similar group was similar to vehicle (with average of 2.5% at 4 hours, 3.0% at 8 hours, 5.6% at 24 hours and 7.9% at 48 hours). Flotetuzumab-similar induced CD69 expression at 10 nM (with a peak average of 52.2% positive T cells at 8 hours), at 0.1 nM (with a peak average of 39.7% positive T cells at 8 hours) and at 0.01 nM (with a peak average of 39.7% positive T cells at 24 hours). CD69 expression in the DARPin® #7 groups were similar to vehicle at all four time points. In the DARPin® #8-10 groups at 10 nM the CD69 expression peaked at 10 nM at 4 hours for DARPin® #10 (average of 41.4% positive T cells) and after 8 hours for DARPin® #8-9 at 10 nM (average of 26.4% for DARPin® #8 and 33.1% for DARPin® #9). At 1 nM and 0.1 nM the CD69 expression peaked at 24-48 hours in the DARPin® #8-10 groups with ranging averages of positive T cells from 14.4%-30.6% (FIG. 30). At 0.01 nM DARPin® #8-10 groups were similar to vehicle at all four time points.

Cell Viability

In addition to cell type markers and activation markers, a viability dye was included in the staining to assess the viability of target and effector cells (presented as % dead cells). Additionally, since the viability dye staining is dependent on the expression of the cell type markers, cell counts were reported to give a comprehensive picture of the viability and cells counts over time (FIG. 31-32).

The % viability dye positive T cells (i.e., % dead cells) were for all tested molecules <11.0% (FIG. 31). The number of T cells in all molecules were similar to vehicle (defined as <20% drop compared to the vehicle group) at 4 hours with the exception of DARPin® #7 (average drop of 20.8% at 1 nM and 19.2% at 10 nM). At 8 hours, T cell numbers dropped compared to vehicle at 10 nM (with an average drop of 33.3% for AMG330-similar, 26.3% for flotetuzumab-similar, 19.8% for DARPin® #9 and 63.6% for DARPin® #10), while all other groups were similar to vehicle at the 8 hour time point. After 24 hours, the T cell count in the vehicle group dropped and all groups were similar to vehicle except DARPin® #8 at 0.01 nM (average drop of 43.6% compared to vehicle). After 48 hours, T cell counts dropped with increasing molecule concentration (with average drop ranges of 15.5-86.5% for AMG330-similar, 45.4-83.0% for flotetuzumab-similar, 48.7-65.2% for DARPin® #7, 27.9-62.4% for DARPin® #9 and 20.7-58.9% for DARPin® #10), with the exception for DARPin® #8 where the largest drops were at the two lowest concentrations, at 0.1 nM (average drop of 63.9%) and 0.01 nM (average drop of 23.5%) compared to vehicle.

CD33+ myeloid cells stained positive for the viability dye (i.e. % dead cells) in the AMG330-similar group at 10 nM (with averages of 56.4% viability dye positive cells at 8 hours, 56.1% at 24 hours and 52.8% at 48 hours), at 0.1 nM (with averages of 15.3% viability dye positive cells at 8 hours, 58.0% at 24 hours and 51.1% at 48 hours) and at 0.01 nM (with averages of 19.8% viability dye positive cells at 24 hours and 31.5% at 48 hours) (FIG. 32). Flotetuzumab-similar killed CD33+ cells at 10 nM (with averages of 53.2% viability dye positive cells at 4 hours and >98.0% at 8-48 hours) and 0.1 nM (average of 76.3% at 24 hours and 80.1% at 48 hours). At the lower molecule concentrations (at 0.001 nM for AMG330-similar/flotetuzumab-similar, at 0.01 nM for DARPin® #8-10 and at 0.1 nM for DARPin®#7), the viability was similar to vehicle (<10% viability dye positive cells) at all four time points. At 4 hours, the percentage of viability dye positive cells were increased compared to vehicle in the DARPin® #7 group (with averages of 13.6% viability dye positive cells at 10 nM and 11.2% at 1 nM), DARPin® #8 groups (with averages of 19.7% at 0.1 nM) and DARPin® #10 groups (with averages of 14.0% at 10 nM, 13.9% at 1 nM and 14.2% at 0.01 nM). DARPin® #7 to 10 groups increased the percentage of viability dye positive cells compared to vehicle at 8-48 hours at 10 nM (with ranging averages of 10.5-30.2% for DARPin® #7, 73.1-69.1% for DARPin® #8, 90.9-92.6% for DARPin® #9 and 93.7-91.9% for DARPin® #10). At 1 nM DARPin® #8 induced viability positive cells at 24-48 hours (with ranging averages of 39.6-42.1%), DARPin® #9 at 8-48 hours (with averages of 13.7-60.7%) and DARPin® #10 at 8-24 hours (with averages ranging from 13.2-47.1%). Additionally, DARPin® #9 and DARPin® #10 increased the percentage of viability positive cells at 0.01 nM at 48 hours for DARPin® #9 (average of 33.9%) and at 24-48 hours for v10 (with averages of 22.9% and 14.7%, respectively).

Similarly, the cell counts of CD33+ cells dropped (>30% difference) compared to vehicle at the 4-8 hour time points at the highest molecule concentration (10 nM) in all tested groups except DARPin® #7 (FIG. 35). The second highest concentration (0.1 nM for AMG330-similar/flotetuzumab-similar and 1 nM for DARPin® #7 to 10) cause a drop of CD33+ cells at 8-24 hour time points for all tested groups. At the lower concentrations (0.01-0.001 nM for AMG330-similar/flotetuzumab-similar and 0.1-0.01 nM for DARPin® #7 to 10) the CD33+ cells are similar to the vehicle at the early time points and for some groups the cell counts dropped at the later time points.

The percentage viability dye positive CD123+ cells (i.e % dead cells) were similar to vehicle and on average <8.0% for all tested molecules at 4 hours and <20.0% at 8 hours. At 24 hours, the percentage of viability positive CD123+ cells increased compared to vehicle at the highest concentration of AMG330-similar, DARPin® #8, DARPin® #9 and DARPin® #10 (with ranging averages of 10.2-29.2% viability dye positive cells). At 48 hours the percentage of viability dye positive cells ranged from 3.0-50.3% in all groups, where some for groups were greater, and for some were less than the vehicle group (average of 13.9%) (FIG. 31-33).

The number of CD123+ cells dropped compared to vehicle in the AMG330-similar groups increasingly over time at 10 nM, (with average drop of 54.6% at 4 hours, 85.1% at 8 hours, 89.5% at 24 hours and 78.6% at 48 hours), at 0.1 nM (average drop of 40.3% at 8 hours, 81.5% at 24 hours and 86.6% at 48 hours) and at 0.01 nM (average drop of 49.3% at 24 hours and 72.4% at 48 hours) (FIG. 36). Flotetuzumab-similar induced a drop of CD123+ cells at 10 nM (with average drop of 60.2% at 8 hours, 65.2% at 24 hours and 42.4% at 48 hours 10 nM) and at 0.1 nM (average drop of 79.0% at 24 hours and 63.4% at 24 hours). At the lower concentrations of AMG330-similar (at 0.001 nM) and flotetuzumab-similar (0.01 nM and 0.001 nM) the counts were similar to vehicle at all four time points. In the DARPin® #7 groups the % CD123+ cells were similar to vehicle with the exception of the group with 1 nM at the 4 hour time point where a drop of 31.2% compared to vehicle was noted. DARPin® #8-10 decreased the number of CD123+ cells compared to the vehicle group with increasing molecule concentration and time point. DARPin® #8 at 10 nM (average drop of 50.4% at 8 hours, 47.7% at 24 hours and 72.9% at 48 hours) and at 1 nM (average drop of 38.1% at 24 hours and 68.1% at 48 hours). For DARPin® #9 CD123+ cells dropped compared to vehicle at 10 nM (average drop of 58.1% at 8 hours, 67.9% at 24 hours and 79.1% at 48 hours), at 1 nM (average drop of 29.6% at 24 hours and 76.2% at 48 hours) and at 0.1 nM (average drop of 34.4% at 24 hours and 48.6% at 48 hours). DARPin® #10 caused a CD123+ cell drop compared to vehicle at 10 nM (average drop of 31.3% at 4 hours, 72.3% at 8 hours, 81.3% at 24 hours and 76.3% at 48 hours), at 1 nM (average drop of 74.4% at 24 hours and 72.7 at 48 hours) and at 0.1 nM (average drop of 57.2% at 24 hours and 62.9%). At the lower concentrations of DARPin® #8 (at 0.1 and 0.01 nM), DARPin® #9 (0.01 nM) and DARPin® #10 (at 0.01 nM) the counts were similar to vehicle at all four time points.

B. Effect of Multi-Specific Binding Proteins on Blood Platelet Counts

As with Example 8, in the whole blood loop system, blood platelet counts (PLT (109/L), in response to recombinant binding proteins DARPin® protein #27, DARPin® protein #29 and DARPin® protein #31, were evaluated at 0 hour (pre-dose), 2 hour, 4 hour, 8 hour and 24 hour time-points. All samples preparation was carried out as described in example x and the measurements were performed by the Haematology Analyzer Sysmex XN-L350. The technical functions and reagent system of the instrument was monitored prior each run with XN-CHECK level 1 and level 2. XN-CHECK is a control blood designed specifically for the analyzer that allows effective and reliable internal and external quality control of the instrument. XN-CHECK level 2 covers the normal range of haematology parameters, while XN-CHECK level 1 is used for the abnormal low range of haematology parameters. A PLT count was measured as a means to check that micro-clots had not been formed, which can be a sign of cell/blood activation. In addition, presence of macroscopic blood clots was evaluated by visual inspection. If noted, haemolysis was graded visually.

Platelet Count

The donors presented a normal PLT range at the zero time point (i.e. values ranging between 150-400×109 cell/L) (FIG. 14). A PLT count decrease with >20% of zero time point is categorized as platelet aggregation (threshold determined based on measurement repeatability in the same conditions at 4 hour time point. Thresholds for time points exceeding 4 hours have not been determined). Macroscopic blood clots 1 mm) were observed in loops incubated with Flotetuzumab at 0.005 nM (at 24 hours for D1 and D3), at 0.1 nM (at 8 hours for D1-D2 and at 24 hours for D1-D3) and 2 nM (at 24 hours for D1-D3). In samples with DARPin® protein #27 at 2 nM (at 24 hours for D1-D3), while no macro-clots were observed in DARPin® protein #29 and DARPin® protein #31 samples at any time-point. A small microclot was observed at 8 hours in the vehicle sample from D1. The PLT levels in the vehicle group were similar (defined as levels 20% difference) to the zero time-point at 2 and 4 hours, while at 8 hours the PLT count decreased with 35.0% for D1 and at 24 hours the PLTs decreased with 37.9% for D1 and 24.9% for D2. In general, Flotetuzumab induced a decrease in PLT count at 8 and 24 hours increasingly with concentration. DARPin® protein #27 at the two highest concentrations (0.1 and 2 nM) reduced the PLT count at the two later time-points, while the PLT count in samples with DARPin® protein #29 and DARPin® protein #31 was similar to vehicle at all concentrations and time-points In response to Flotetuzumab, the PLT count decreased with 20% of the vehicle sample at 0.005 nM with the exception for D1 and D2 at 24 hours (a decrease of 65.1 and 85.8% compared to vehicle, respectively). At 0.1 nM, the PLT count was within 20% of the vehicle sample for each donor at 2 and 4 hours, while at 8 and 24 hours the PLT count had decreased for all three donors with an average decrease of 83.7 and 88.4%, respectively). At 2 nM, the PLT count decreased with >20% of vehicle in blood from all donors at the two later time-points (an average decrease of 75.1% at 8 hours and 88.9% at 24 hours). The PLT count decreased with 20% of the vehicle sample at all three concentrations of DARPin® protein #27, except for the highest concentration of 2 nM in blood from D1 (a decrease of 85.4% at 8 hours and 97.1% at 24 hours), D2 (a decrease of 94.7% at 24 hours) and D3 (a decrease of 90.4% at 24 hours). At all three concentrations of DARPin® protein #29 and DARPin® protein #31, the PLT count was within 20% of the vehicle sample for all three donors at all four time-points.

C. Effect of Multi-Specific Binding Proteins on Blood Platelet Counts and White Blood Cell Counts As with Example 8, in the whole blood loop system, blood platelet (PLT) and white blood cell (WBC) counts ($10^9$/L), in response to flotetuzumab-similar, DARPin® protein #58, DARPin® protein #59, DARPin® protein #57, DARPin® protein #60, DARPin® protein #61 and DARPin® protein #56, were evaluated at 0 hour (pre-dose), 2 hour, 4 hour, 8 hour and 24 hour time-points. All samples preparation was carried out as described in example 8 and the measurements were performed by the Haematology Analyzer Sysmex XN-L350. The technical functions and reagent system of the instrument was monitored prior each run with XN-CHECK level 1 and level 2. XN-CHECK is a control blood designed specifically for the analyzer that allows effective and reliable internal and external quality control of the instrument. XN-CHECK level 2 covers the normal range of haematology parameters, while XN-CHECK level 1 is used for the abnormal low range of haematology parameters. A PLT count was measured as a means to check that micro-clots had not been formed, which can be a sign of cell/blood activation. In addition, presence of macroscopic blood clots was evaluated by visual inspection.

Platelets in Zero and Vehicle Groups

All donors presented a normal PLT range at the zero-time point (i.e. values ranging between 150-400×$10^9$ cell/L) (FIG. 49). The PLT levels in the vehicle group were similar (defined as levels <20% difference) to the zero-time point sample for all donors. No macroscopic blood clots were observed in fresh blood incubated with vehicle but macroscopic blood clots were detected in several test items tested at 8 h and 24 hours (Table 9B).

TABLE 9b

| | Degrees of macroscopic blood clots | | | | | | | | | | | |
|---|---|---|---|---|---|---|---|---|---|---|---|---|
| | D 1 | | | | D 2 | | | | D 3 | | | |
| Vehicle | 2 h | 4 h | 8 h | 24 h | 2 h | 4 h | 8 h | 24 h | 2 h | 4 h | 8 h | 24 h |
| DARPin ®protein #58 low | | | | | | | | | | | | |
| DARPin ® protein #58 mid | | | | 2 | | | | 2 | | | | 2 |
| DARPin ® protein #58 high | | | | 2 | | | | 2 | | | | 3 |
| DARPin ® protein #59 low | | | | 2 | | | | | | | | 1 |
| DARPin ® protein #59 mid | | | 3 | 1 | | | | 2 | | | | 2 |
| DARPin ® protein #59 high | | | | 2 | | | | 3 | | | | 2 |
| DARPin ® protein #57 low | | | | | | | | | | | | |
| DARPin ® protein #57 mid | | | 2 | 1 | | | | 2 | | | | 2 |
| DARPin ® protein #57 high | | | 1 | 2 | | | | 2 | | | | 2 |
| DARPin ® protein #60 low | | | | | | | | | | | | |
| DARPin ® protein #60 mid | | | | 2 | | | | 3 | | | | 2 |
| DARPin ® protein #60 high | | | 2 | 2 | | | | 2 | | | | 2 |
| DARPin ® protein #56 low | | | | | | | | | | | | |
| DARPin ® protein #56 mid | | | | 1 | | | | 2 | | | | |
| DARPin ® protein #56 high | | | | 2 | | | | | | | | 2 |
| DARPin ® protein #61 low | | | | 2 | | | | | | | | |
| DARPin ® protein #61 mid | | | | 2 | | | | 2 | | | | 2 |

TABLE 9b-continued

| | Degrees of macroscopic blood clots | | | | | | | | | | | |
|---|---|---|---|---|---|---|---|---|---|---|---|---|
| | D 1 | | | | D 2 | | | | D 3 | | | |
| Vehicle | 2 h | 4 h | 8 h | 24 h | 2 h | 4 h | 8 h | 24 h | 2 h | 4 h | 8 h | 24 h |
| DARPin ® protein #61 high | | | 2 | | | 1 | 2 | | | | 2 | |
| DARPin ® protein #74 low | | | | | | | | | | | | |
| DARPin ® protein #74 mid | | | | | | | | | | | | |
| DARPin ® protein #74 high | | | | | | | | | | | | |
| Flotetuzumab low | | | 2 | | | | 3 | | | | 2 | |
| Flotetuzumab mid | | | 2 | | | | 2 | | | | 2 | |
| Flotetuzumab high | | | 3 | | | 2 | 3 | | | | 2 | |

Empty = no clots observed, 1 = small clot (<2 mm), 2 = medium sized clot (2-5 mm), 3 = big clot (>5 mm).
At 2 h, 4 h and 8 h only a portion of the blood is sampled and clots are possible even when not observed.
All donors presented a normal PLT range at the zero-time point (i.e. values ranging between 150-400 × 109 cells/L} (FIG. 49). The PLT levels in the vehicle group were similar (defined as levels <20% difference} to the zero time point sample for all donors. No macroscopic blood clots were observed in fresh blood incubated with vehicle (PBS) but macroscopic blood clots were detected in several test items tested at 8 h and 24 hours (Table 9b).

The WBC counts of all donors were within a normal range at the zero time point (i.e. values ranging between 4.0-11.0× $10^9$ cell/L). A variation of ±10% at the 4-hour time-point versus the zero time-point samples is judged normal (FIG. 50).

Overall, at all three concentrations, 0.005, 0.1 and 2 nM of the tested proteins, PLT and WBC counts were similar to the vehicle group until the 4 h time-point. After 4 hours, concentration-dependent decreases in PLT and WBC counts were detected over time, in general for all tested proteins in all donors compared with vehicle. DARPin® protein #56 and DARPin® protein #60 at 0.005 and 0.1 nM did, however, not induce noticeable decrease in WBC counts. Blood clots were firstly detected at 8 h for some tested proteins and at 24 h all tested proteins displayed blood clots at different concentrations. No blood clots were however observed in the vehicle samples, suggesting that clot formation was an effect of immune stimulation. No blood clots were detected for DARPin® protein #74 at any time point, displaying the limited immune activity by this control in protein.

Example 10: Determination of Combined Avidity of a Multi-Specific Binding Protein to Two Surface Ligands (CD33 and CD123)

In order to determine affinity and avidity of an exemplified, multi-specific designed ankyrin repeat proteins DARPin® protein #20 and DARPin® protein #27 (with binding specificity for CD3, CD33 and CD123) and its corresponding single-TAA target controls (DARPin® protein #21-with binding specificity for CD3 and CD123- and DARPin® protein #22-with binding specificity for CD3 and CD33; DARPin® protein #41-with binding specificity for CD3 and CD123- and DARPin® protein #40-with binding specificity for CD3 and CD33), a study utilizing the switchSENSE® technology (Dynamic Biosensors) was performed. SwitchSENSE® technology allows for high sensitivity in detecting both affinity constants (with a limit of detection of 10 fM) and binding kinetics (with detection limits of 1E3-1E8 1/Ms and 1E-6-1E0 1/s for association and dissociation rate constants respectively). (Langer et al; 2013. Protein analysis by time-resolved measurements with an electro-switchable DNA chip. Nat Commun 4: 2099).

The technique makes use of two different fluorophores making it possible to monitor two independent signals from two interactions at the same time and on the same sensor spot. Thereby affinity and avidity kinetics multi-specific binders and be measured simultaneously against two target molecules.

Materials and Methods

The designed ankyrin repeat proteins: DARPin® protein #20, DARPin® protein #21, DARPin® protein #22, DARPin® protein #27, DARPin® protein #40 and DARPin® protein #41 were tested in a concentration of 0.16 and 64 nM (in a buffer PE140 containing 10 mM Na2HPO4/NaH2PO4, 140 mM NaCl, 0.05% Tween20, 50 µM EDTA, 50 µM EGTA) for binding against two ligands hCD33 and hCD123, which both were immobilized simultaneously to DNA nanolevers, on the surface, at a pre-defined ratio (2:1, CD33:CD123) and 10% density (100:50) on an ADP-48-1-0 chip, where 100% density≈1000 receptors/µm2 (preincubated R1-B48-CD123 and G1-A48-CD33 (100 nM) diluted in cNL-48 (dark)). Briefly the following steps were performed:

Conjugation. Amine coupling of the two ligands (CD33 and CD123) to the DNA nanolever (A48, B48, respectively) and purification of the conjugates using the proFIRE® solution (Dynamic Biosensors GmbH) at 25° C.

Evaluation of all the combined affinity and avidity of all different proteins to both ligands attached on the surface of an ADP chip using a DRX+ instrument (dynamic BIOSENSORS).

Statistical analysis (repeatability from 2 to 5 times) including regeneration of the chip surface every concentration analyzed and long dissociation times and data were fitted using a bi-exponential global fit.

TABLE 6

| Sample Name | Coupled to sequence DNA | Detection channel | Subunits | MW (kDa) |
|---|---|---|---|---|
| CD33 (Ligand 1) | cNL-A48 | Green (G1) | — | 80 |
| CD123 (Ligand 2) | cNL-B48 | Red (R1) | — | 86 |
| DARPin ® protein #20 | — | — | αCD123-αCD33-αCD3_1 | |
| DARPin ® protein #22 | — | — | Ni2C-αCD33-αCD3 | |
| DARPin ® protein #21 | — | — | αCD123-Ni2C-αCD3 | |
| DARPin ® protein #27 | — | — | αCD123-aCD33-αCD3_1 | |
| DARPin ® protein #40 | — | — | Ni2C-αCD33-αCD3 | |
| DARPin ® protein #41 | — | — | αCD123-Ni2C-αCD3 | |

Results and Conclusions

Multi-specific recombinant protein DARPin® protein #20 showed a biphasic dissociation, representing two interactions on the chip: affinity (faster off rates) in the order of $1E^{-2}$ $s^{-1}$ and avidity (slower off rates where the analyte is interacting with both ligands) in the order of $1E^{-3}$ $s^{-1}$. In addition, the association rate for CD123 seems slightly higher ($1E^7$ $M^{-1}s^{-1}$), compared to CD33 ($1E^6$ $M^{-1}s^{-1}$). For both DARPin® protein #21 DARPin® protein #22 controls only binding interactions to one of the targets was observed. For example, DARPin® protein #21 interacts only with CD123, as expected, since it does not possess the CD33 subunit. Therefore, it shows a monophasic association and dissociation with a $k_{off}$ of $6E^2$ $s^{-1}$. No interaction between DARPin® protein #21 and CD33 is observed. Analogously, DARPin® protein #22 interacts only with CD33, as expected, since it does not possess the CD123 subunit. Therefore, it shows a monophasic association and dissociation with a $k_{off}$ of $1E^{-2}$ $s^{-1}$. No interaction between DARPin® protein #22 and CD123 is observed.

Overall, it is shown that designed ankyrin repeat proteins comprising both a CD33 specific and a CD123 specific binding domain (αCD33-αCD123) can bind to simultaneously to both targets attached to the surface of the chip, and they show affinity and avidity, while the designed ankyrin repeat proteins with either a CD33 specific binding domain or CD123 specific binding domain show only affinity to CD33 and CD123, respectively. Indeed, only for DARPin® protein #20 a biphasic dissociation, representing two interactions (populations) on the chip were observed: affinity ($2E^2$ $s^{-1}$, faster off rates) and avidity ($1E^3$ $s^{-1}$ slower off rates) was observed.

Figure 38A:
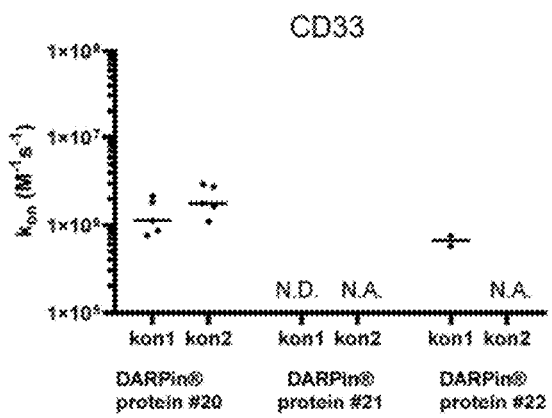
FIG. 38 (A-B). On rate (FIG. 38A) and off rate (FIG. 38B) constants for CD33 target, measured for selected recombinant proteins DARPin® protein 20, DARPin® protein 21 and DARPin® protein 22.
Figure 38B:
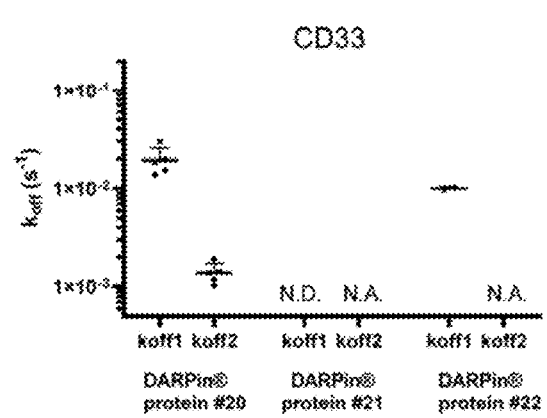
Figure 39A:
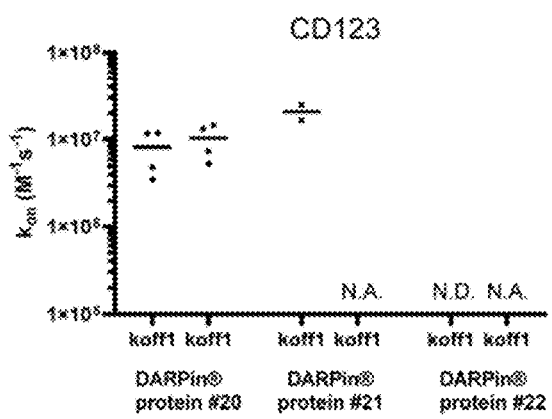
FIG. 39 (A-B). On rate (FIG. 39A) and off rate (FIG. 39B) constants for CD123 target, measured for selected recombinant proteins DARPin® protein 20, DARPin® protein 21 and DARPin® protein 22.
Figure 39B:
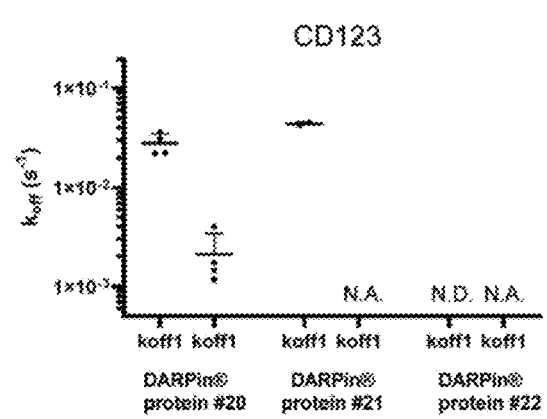
Figure 40:
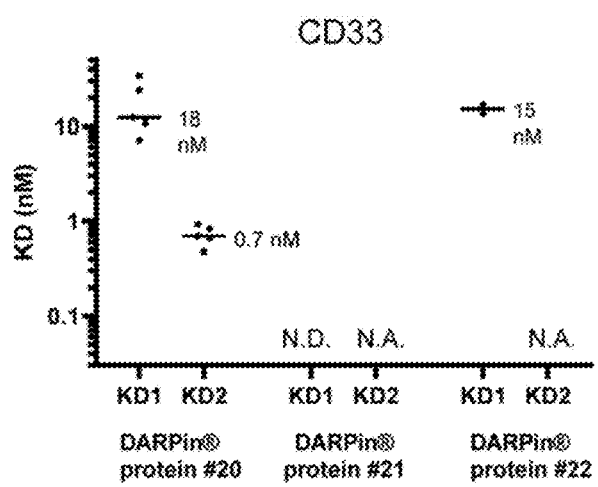
FIG. 40. $K_D$ values of recombinant proteins-human CD33 interactions.
Figure 41:
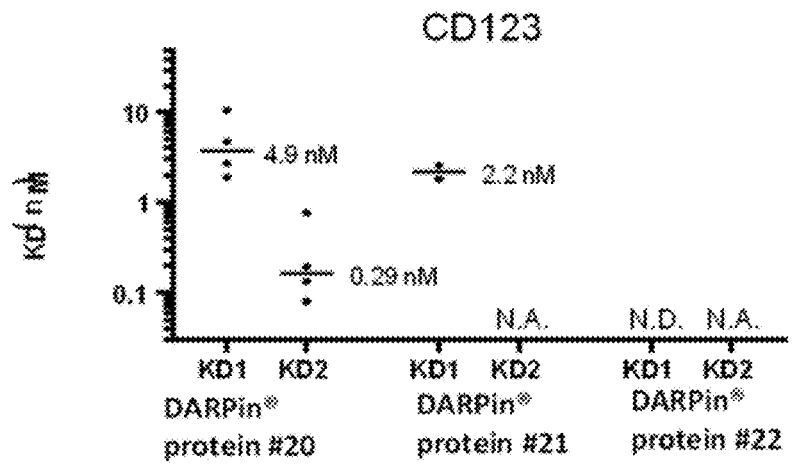
FIG. 41. $K_D$ values of recombinant proteins-human CD123 interactions.
Figure 42A:
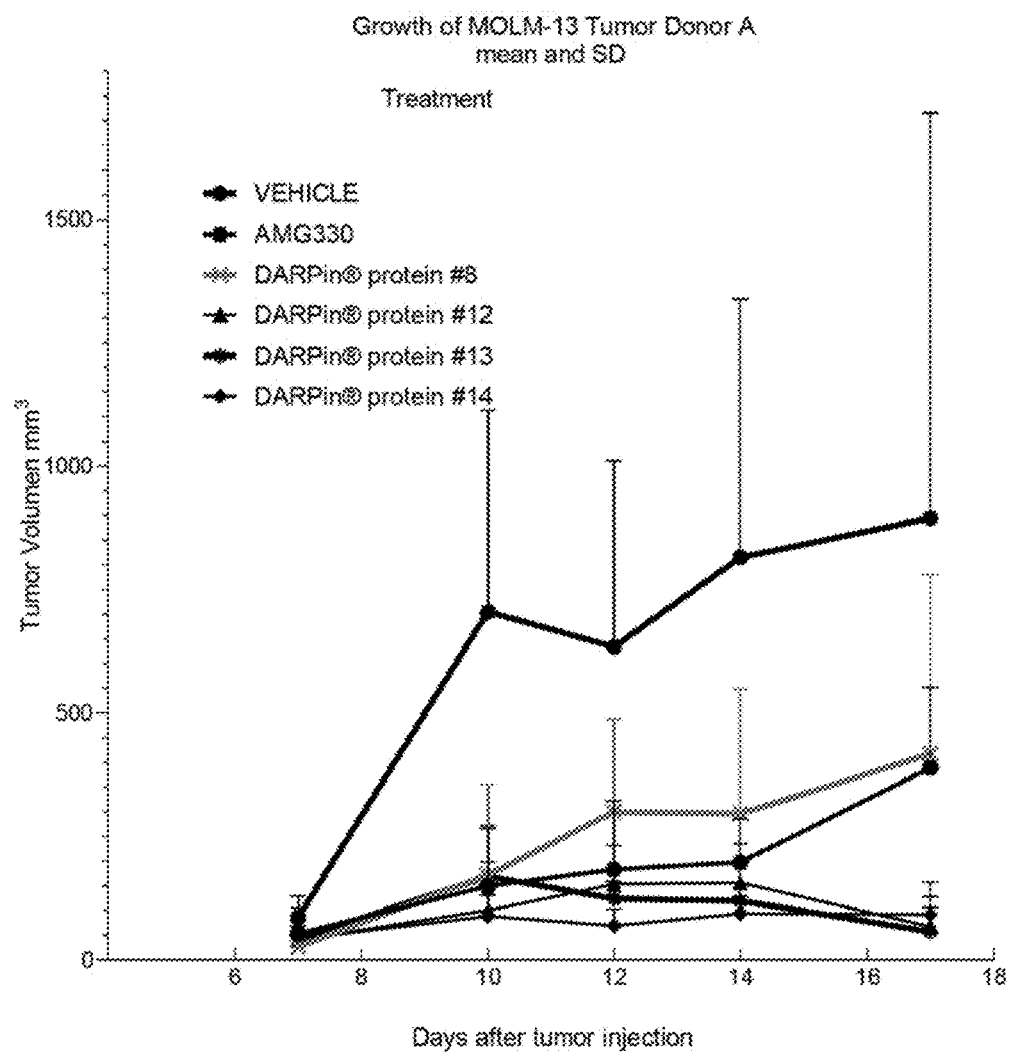
FIG. 42 (A-C). Mean and SD of tumor volume.
Figure 42B:
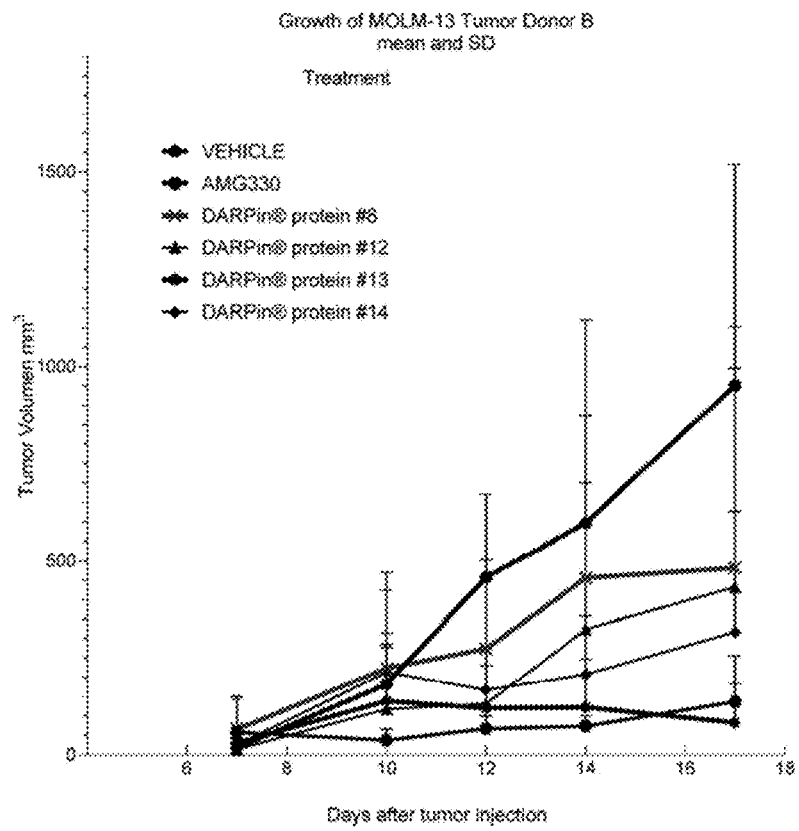
Figure 42C:
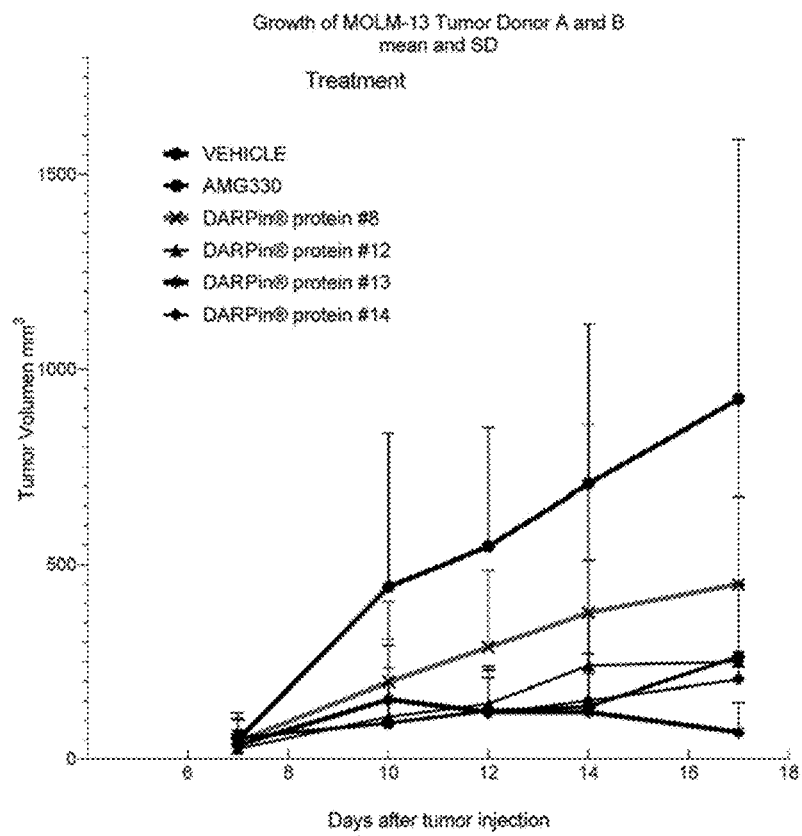
Figure 43A:
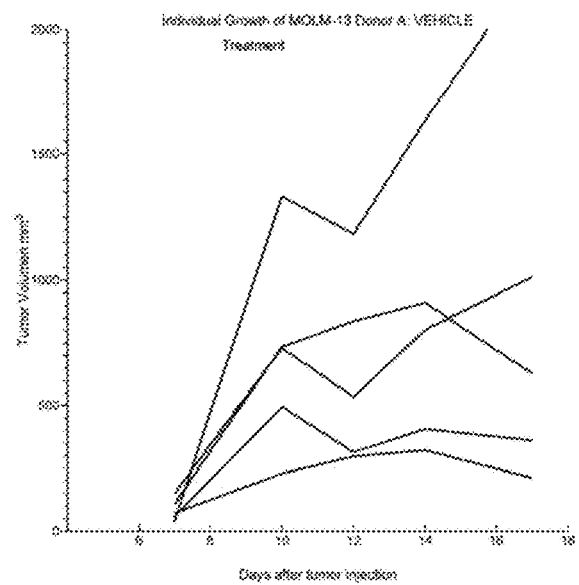
FIG. 43 (A-L). Single tumor growth curves.
Figure 43B:
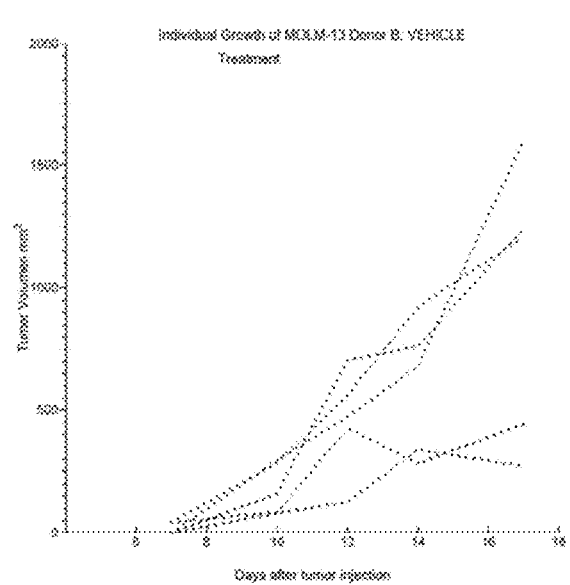
Figure 43C:
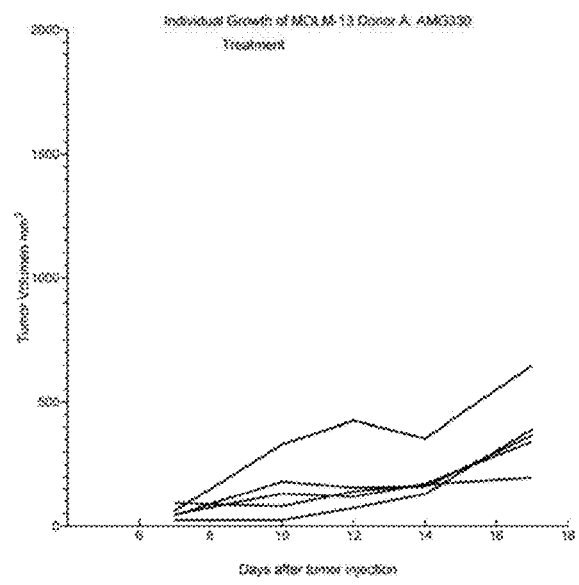
Figure 43D:
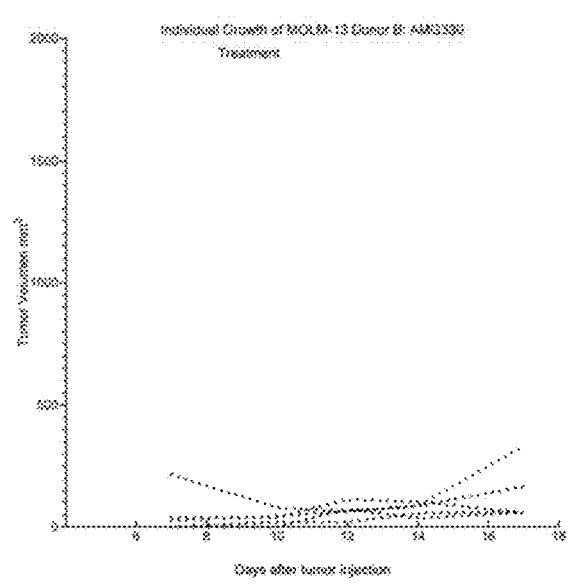
Figure 43E:
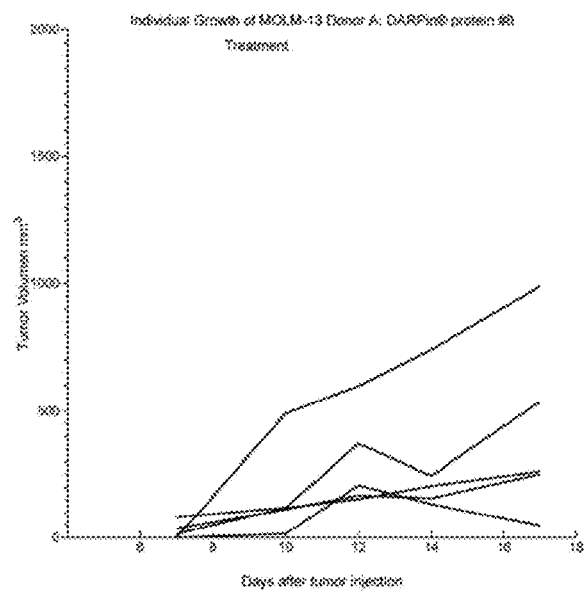
Figure 43F:
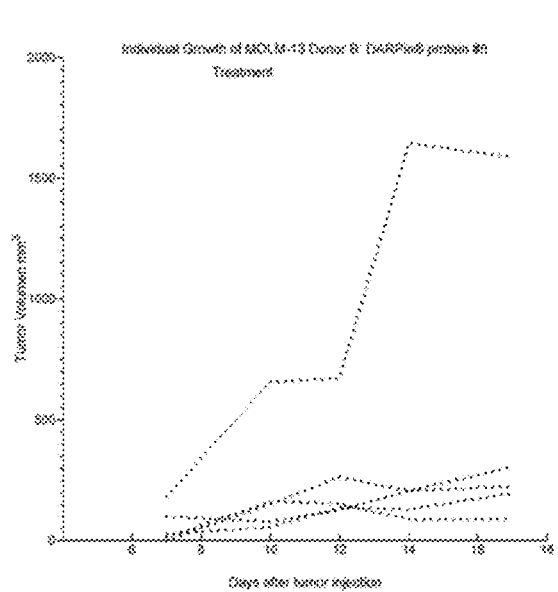
Figure 43G:
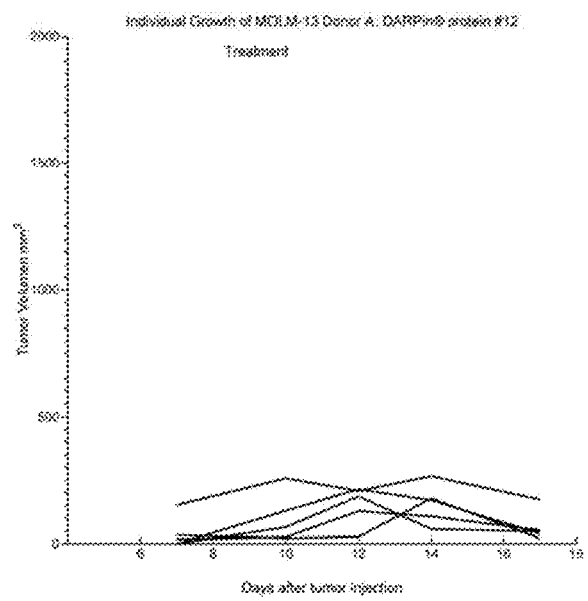
Figure 43H:
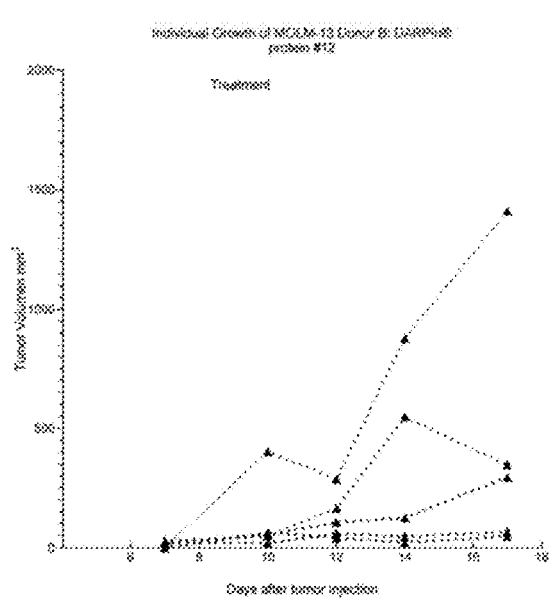
Figure 43I:
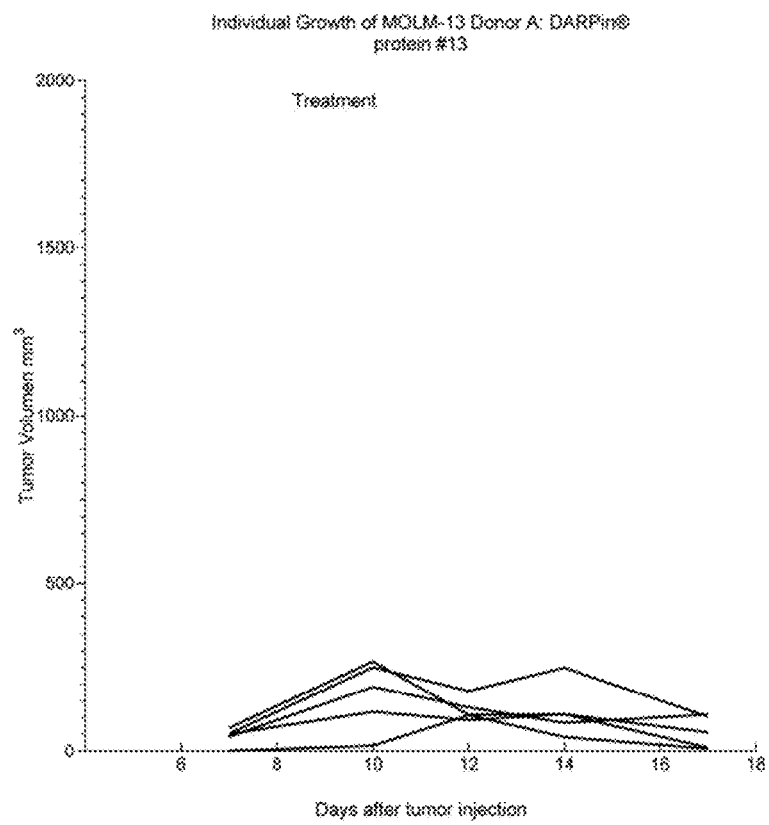
Figure 43J:
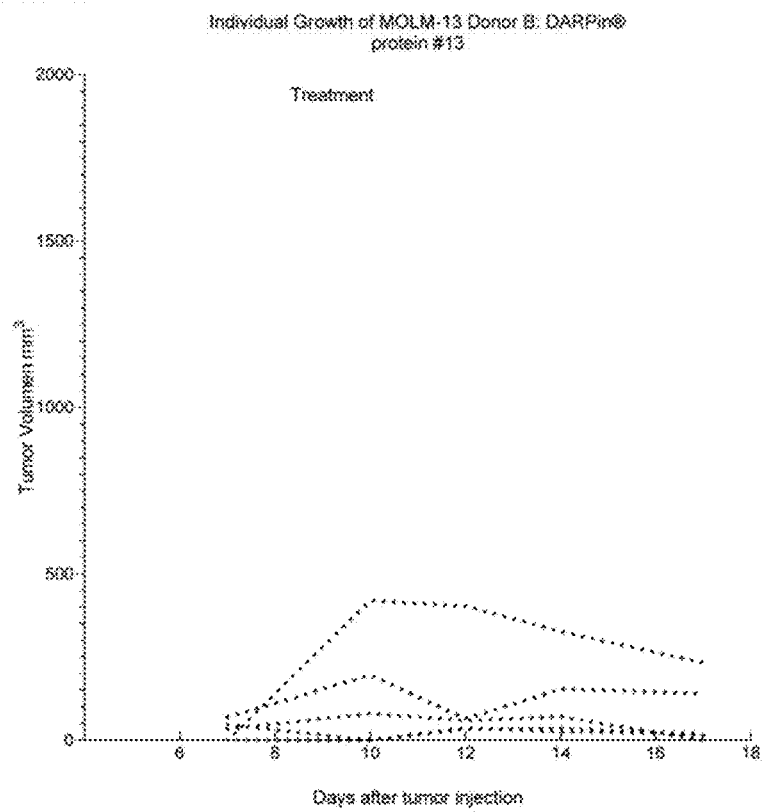
Figure 43K:
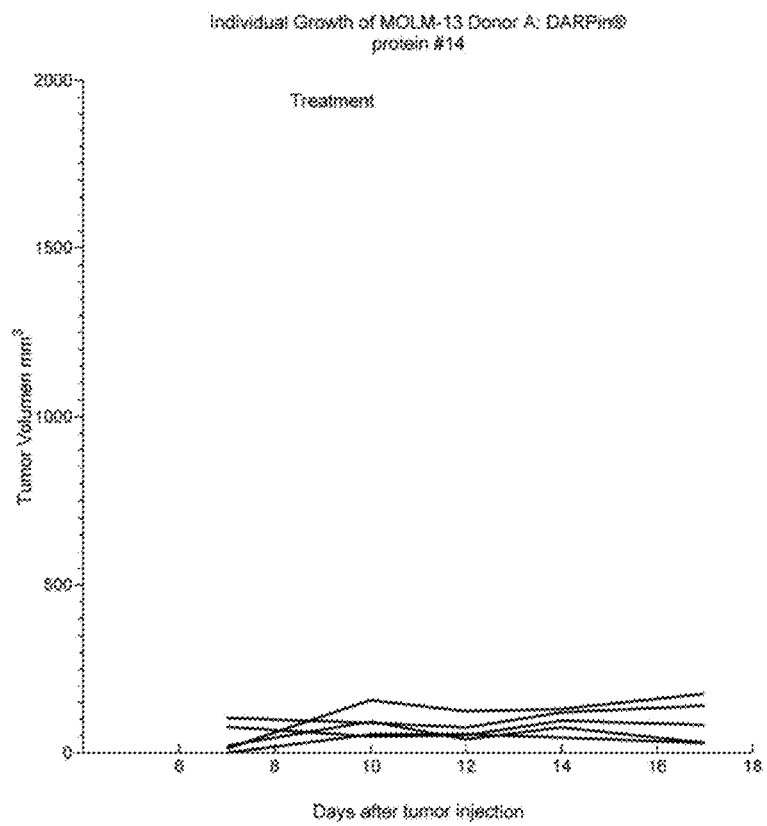
Figure 43L:
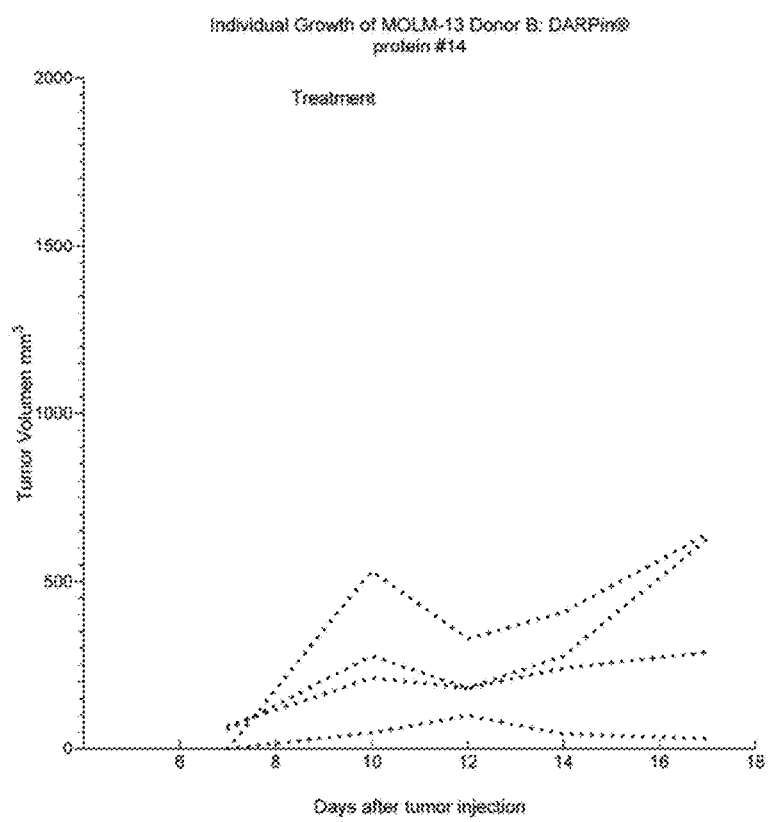
Figure 44A:
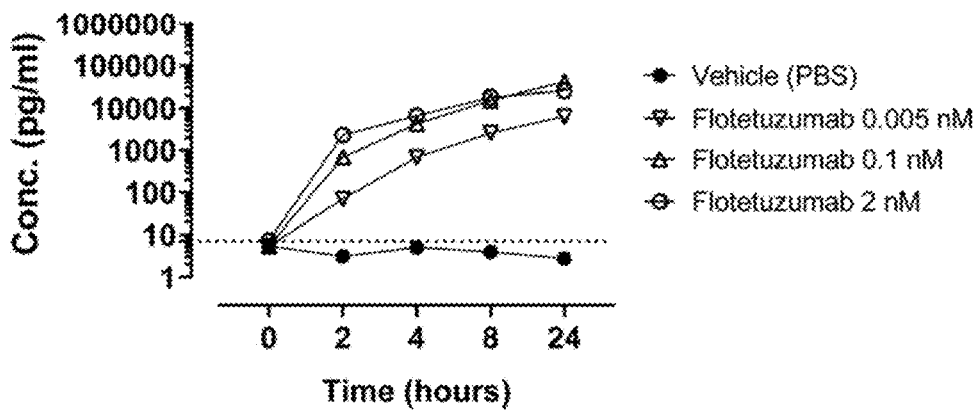
FIG. 44 (A-H): Levels of IFNγ. Calculated mean concentration values of IFNγ for all 3 donors in the blood loop system. Plasma samples were collected from the blood loop system at 0 (zero), 2, 4, 8 and 24 hours. Each point represents the mean (and the error bar the SD) of three donors: Flotetuzumab FIG. 44A, DARPin® protein #58 FIG. 44B, DARPin® protein #59 FIG. 44C, DARPin® protein #57 FIG. 44D, DARPin® protein #60 FIG. 44E, DARPin® protein #56 FIG. 44F, DARPin® protein #61 FIG. 44G, DARPin® protein #74 FIG. 44H. Calculated LLOQ is marked with a dotted line.
Figure 44B:
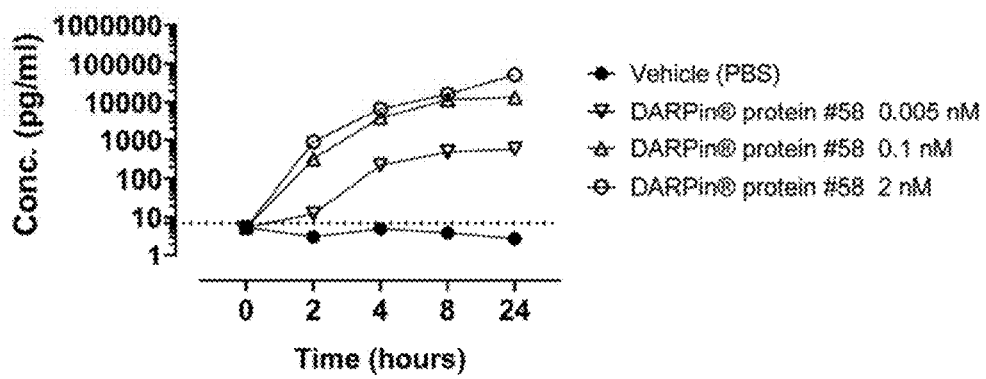
Figure 44C:
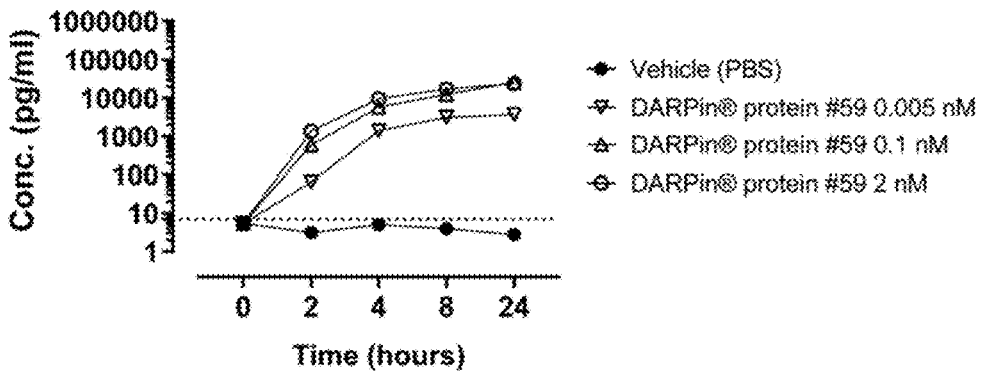
Figure 44D:
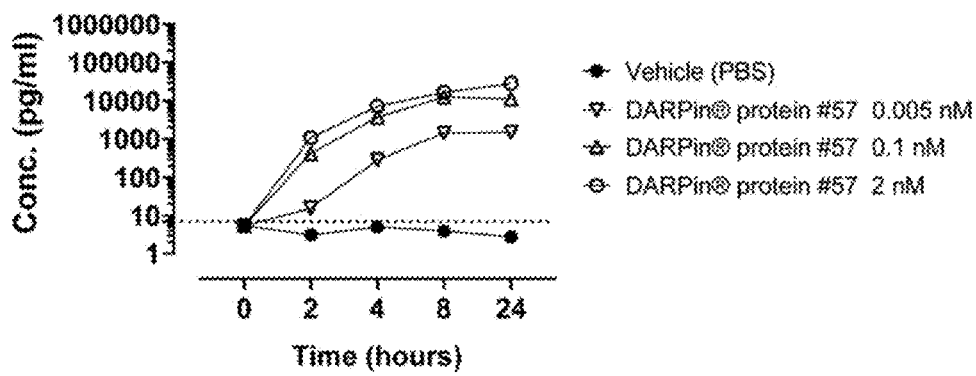
Figure 44E:
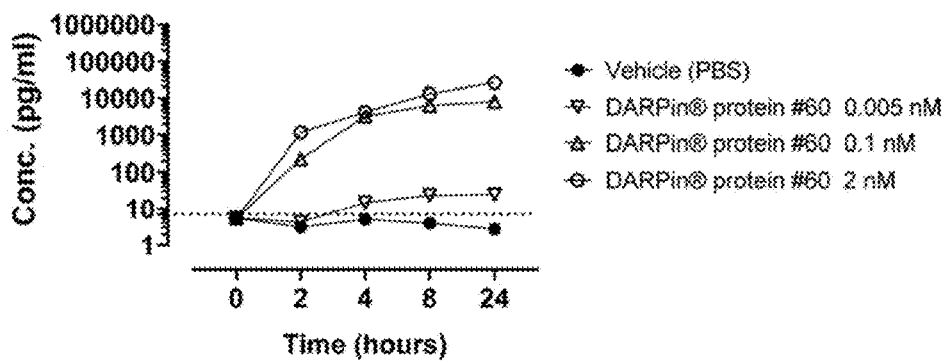
Figure 44F:
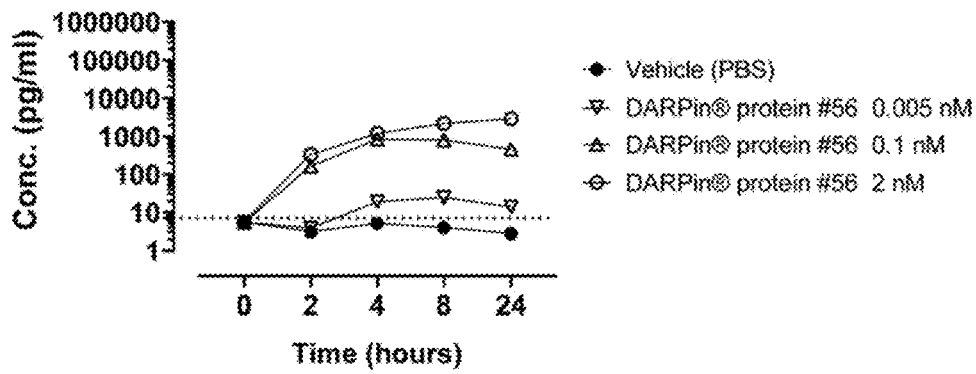
Figure 44G:
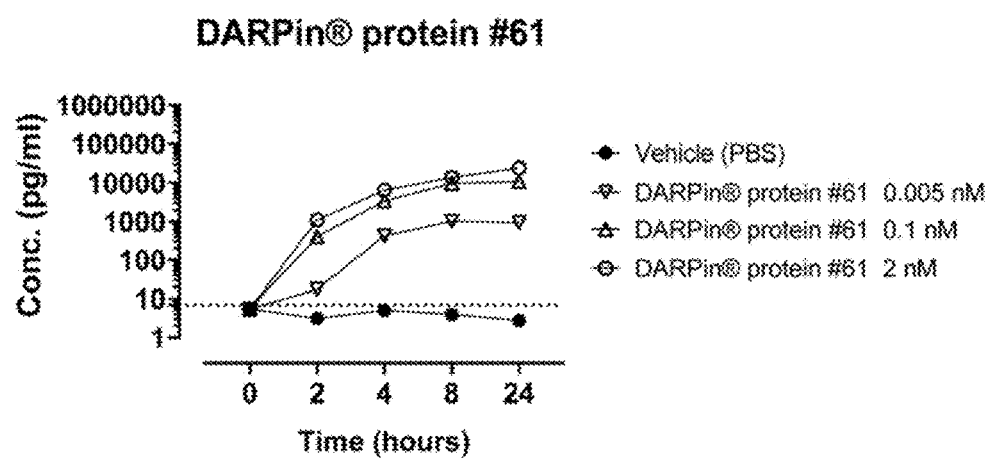
Figure 44H:
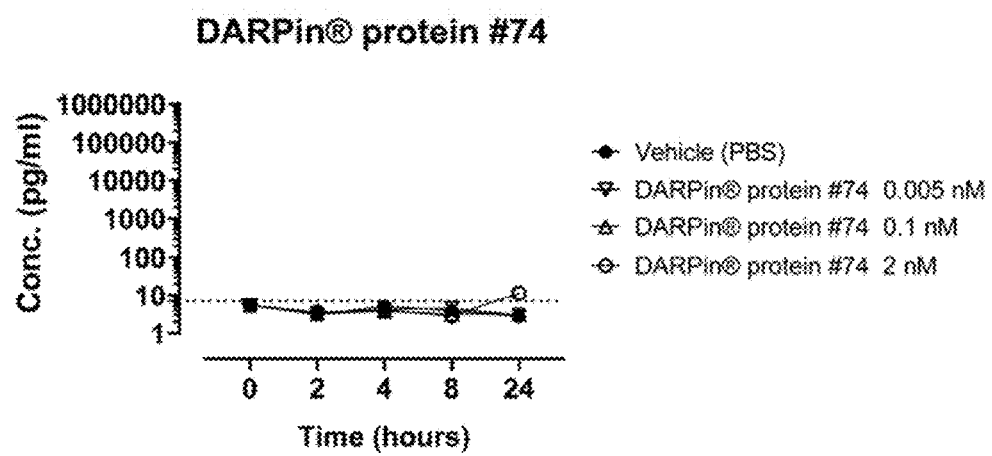
Figure 45A:
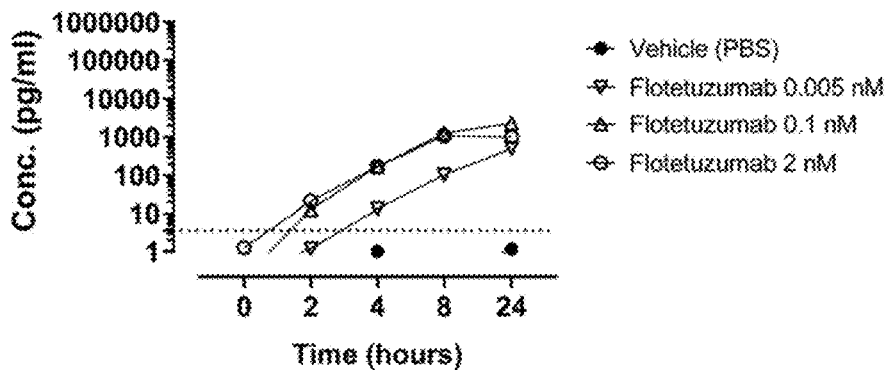
FIG. 45 (A-H): Levels of IL-2. Calculated mean concentration values of IL-2 for all 3 donors in the blood loop system. Plasma samples were collected from the blood loop system at 0 (zero), 2, 4, 8 and 24 hours. Each point represents the mean (and the error bar the SD) of three donors: Flotetuzumab FIG. 45A, DARPin® protein #58 FIG. 45B, DARPin® protein #59 FIG. 45C, DARPin® protein #57 FIG. 45D, DARPin® protein #60 FIG. 45E, DARPin® protein #56 FIG. 45F, DARPin® protein #61 FIG. 45G, DARPin® protein #74 FIG. 45H. Calculated LLOQ is marked with a dotted line.
Figure 45B:
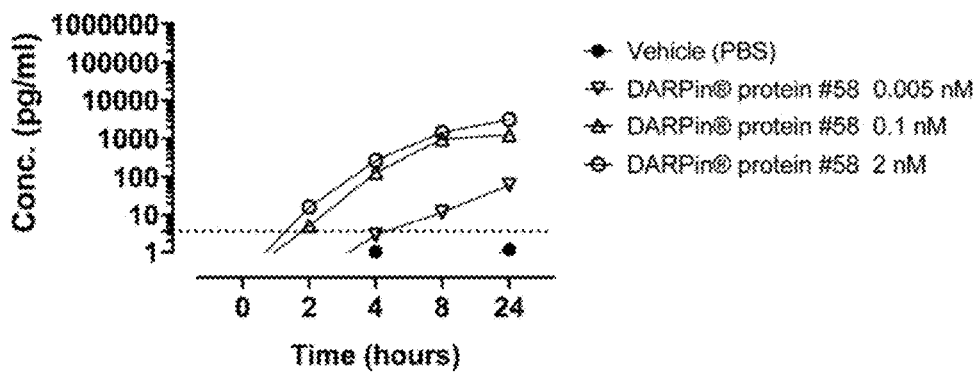
Figure 45C:
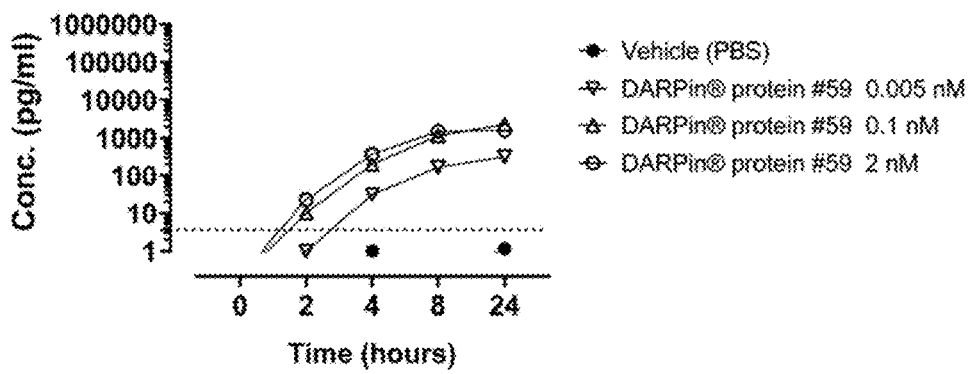
Figure 45D:
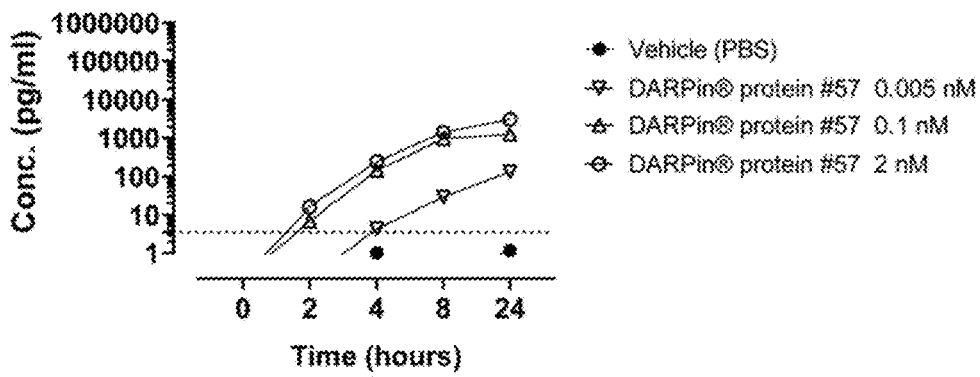
Figure 45E:
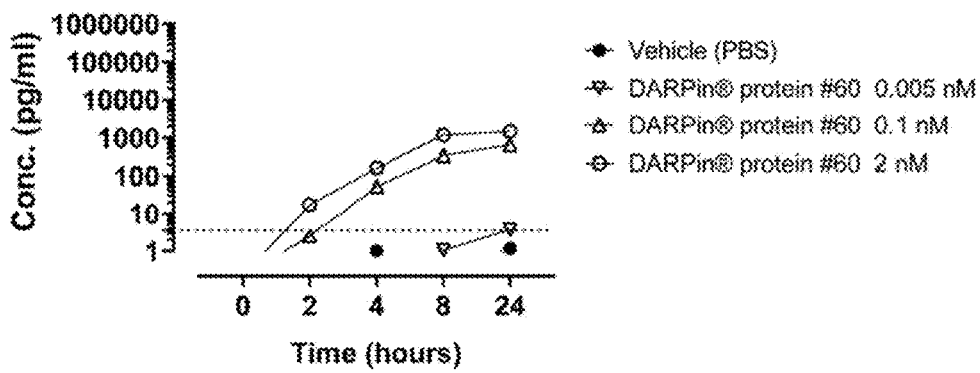
Figure 45F:
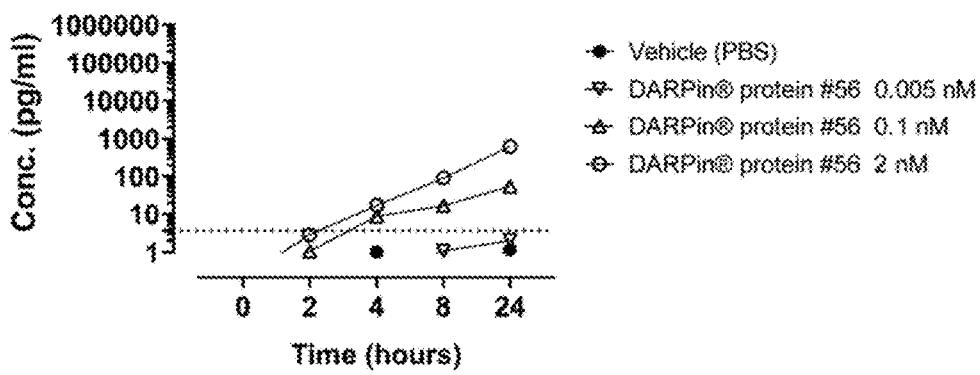
Figure 45G:
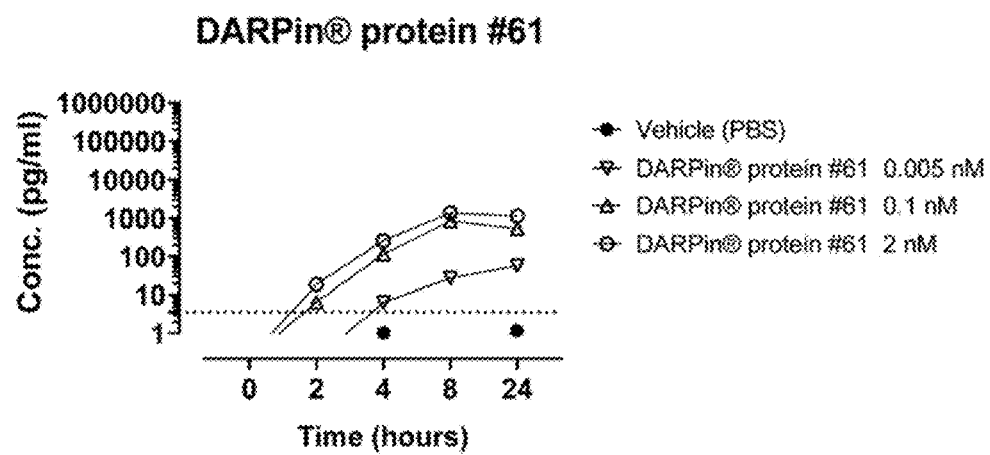
Figure 45H:
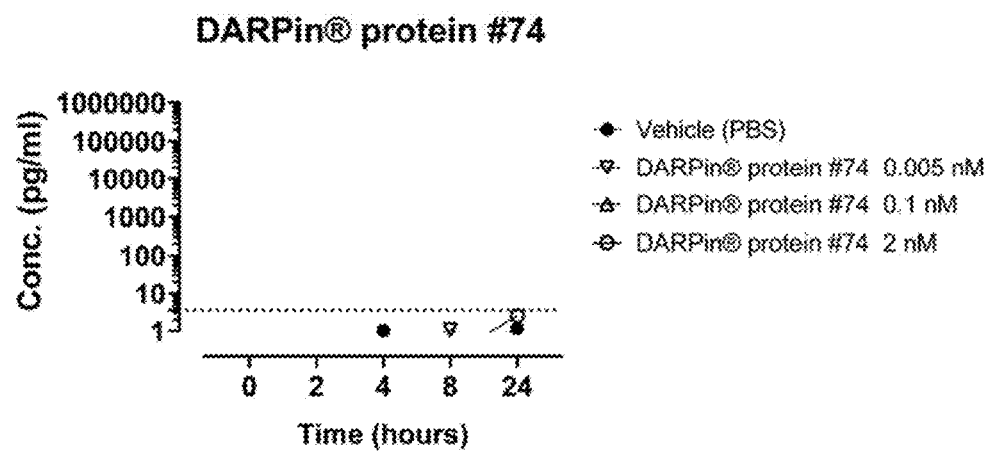
Figure 46A:
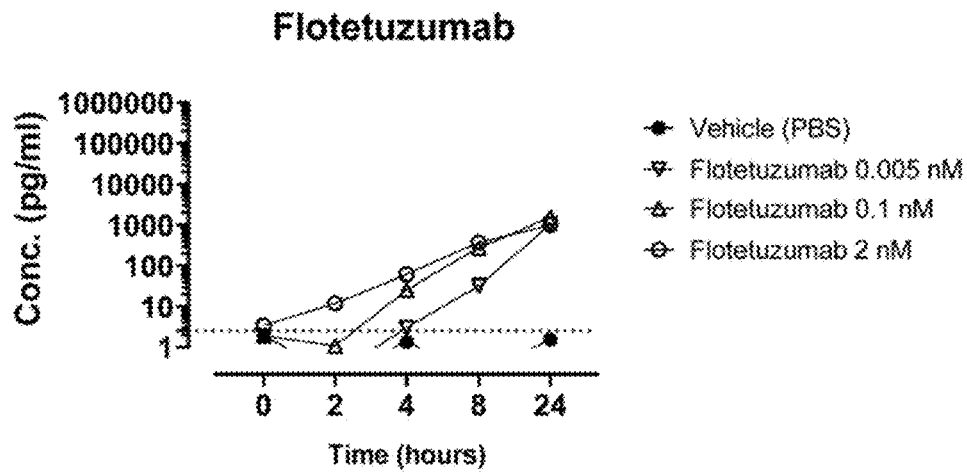
FIG. 46 (A-H): Levels of IL-6. Calculated mean concentration values of IL-6 for all 3 donors in the blood loop system. Plasma samples were collected from the blood loop system at 0 (zero), 2, 4, 8 and 24 hours. Each point represents the mean (and the error bar the SD) of three donors: Flotetuzumab FIG. 46A, DARPin® protein #58 FIG. 46B, DARPin® protein #59 FIG. 46C, DARPin® protein #57 FIG. 46D, DARPin® protein #60 FIG. 46E, DARPin® protein #56 FIG. 46F, DARPin® protein #61
FIG. 46G, DARPin® protein #74 FIG. 46H. Calculated LLOQ is marked with a dotted line.
Figure 46B:
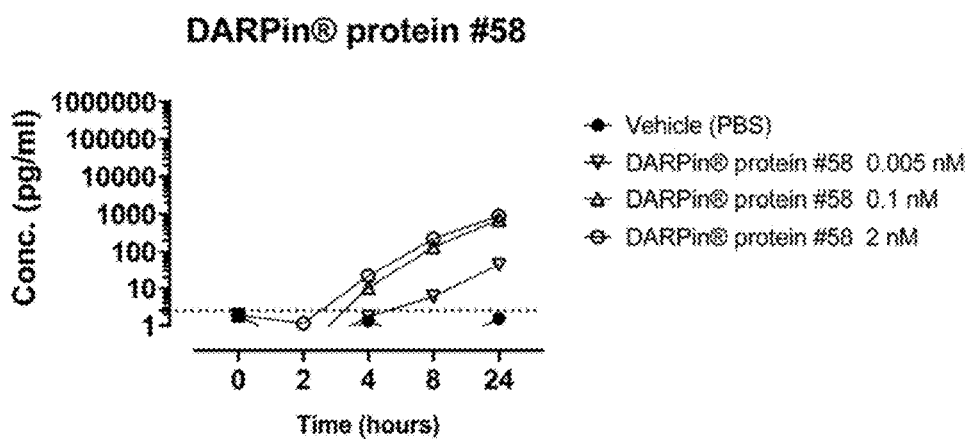
Figure 46C:
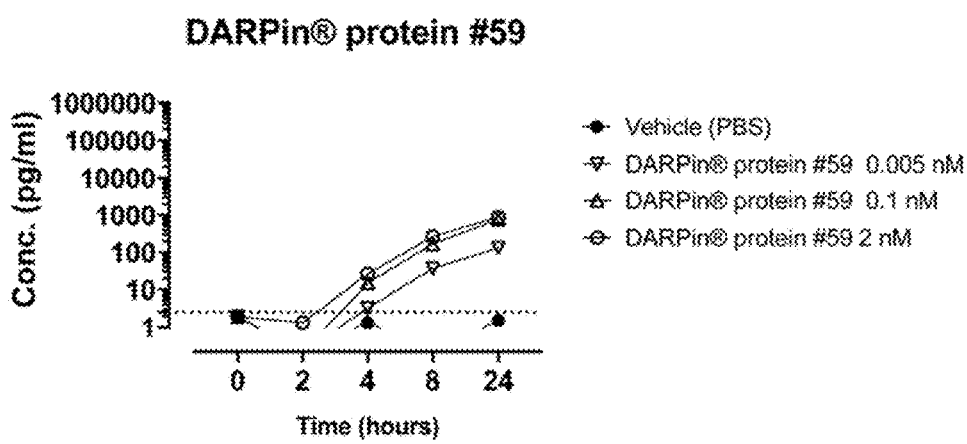
Figure 46D:
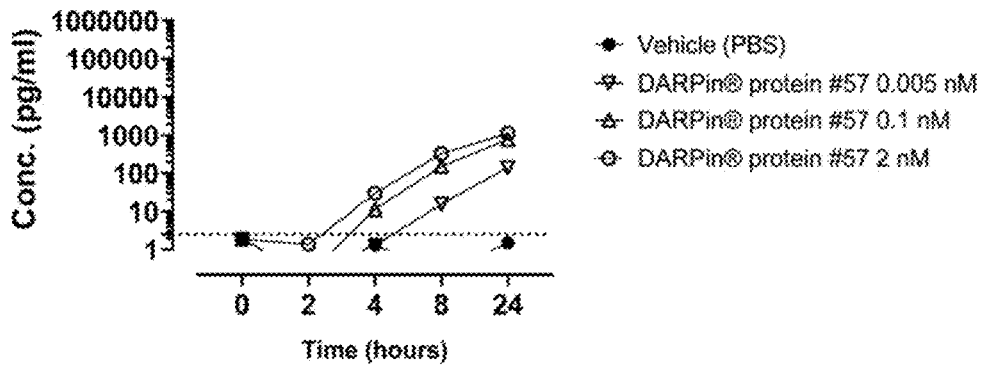
Figure 46E:
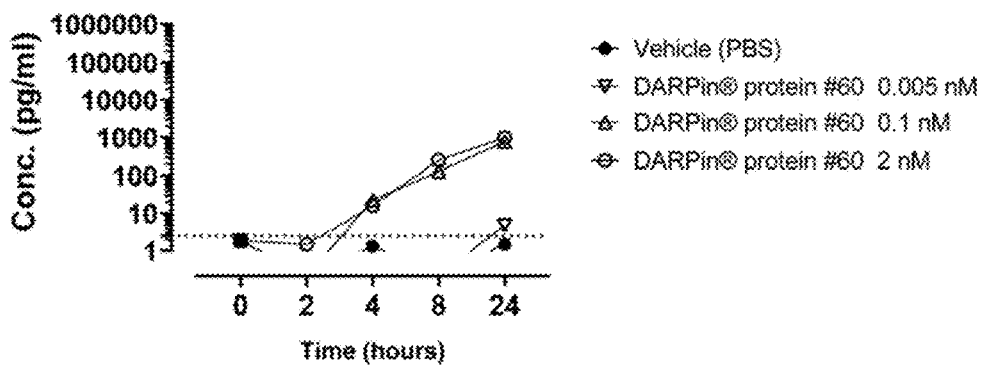
Figure 46F:
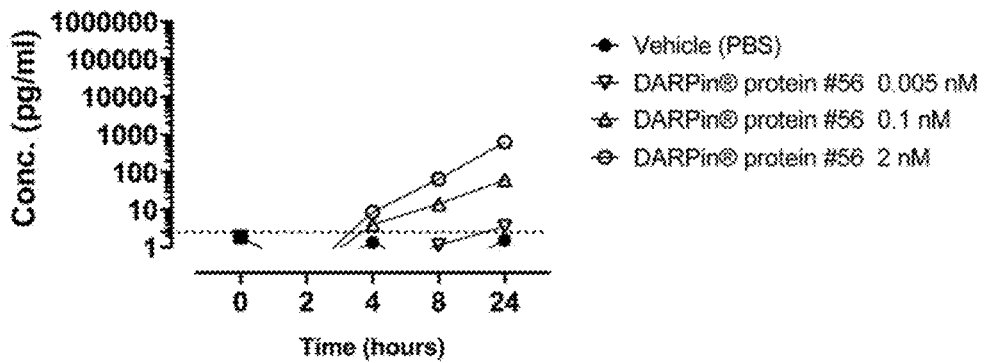
Figure 46G:
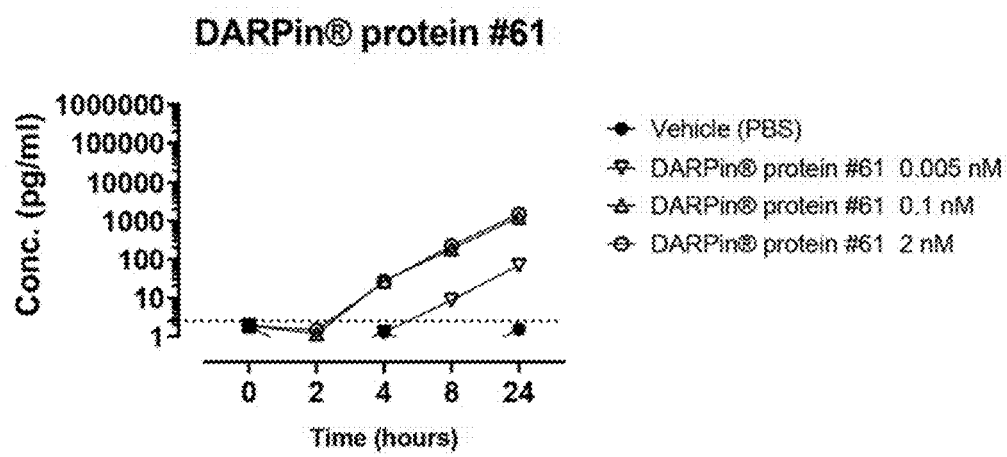
Figure 46H:
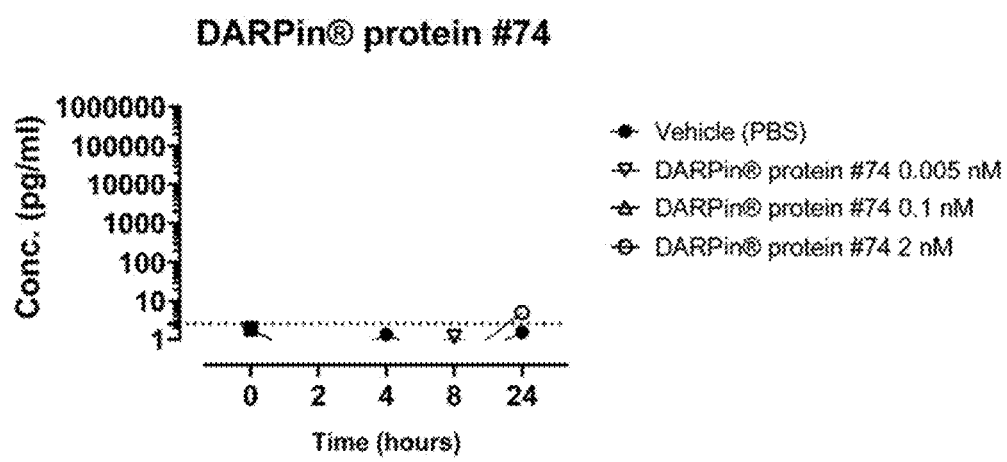
Figure 47A:
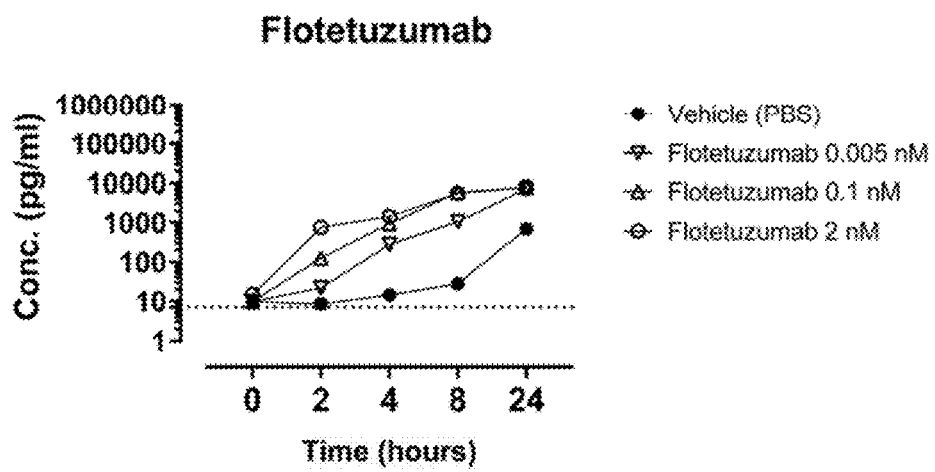
FIG. 47 (A-H): Levels of IL-8. Calculated mean concentration values of IL-8 for all 3 donors in the blood loop system. Plasma samples were collected from the blood loop system at 0 (zero), 2, 4, 8 and 24 hours. Each point represents the mean (and the error bar the SD) of three donors: Flotetuzumab FIG. 47A, DARPin® protein #58 FIG. 47B, DARPin® protein #59 FIG. 47C, DARPin® protein #57 FIG. 47D, DARPin® protein #60 FIG. 47E, DARPin® protein #56 FIG. 47F, DARPin® protein #61 FIG. 47G, DARPin® protein #74 FIG. 47H. Calculated LLOQ is marked with a dotted line.
Figure 47B:
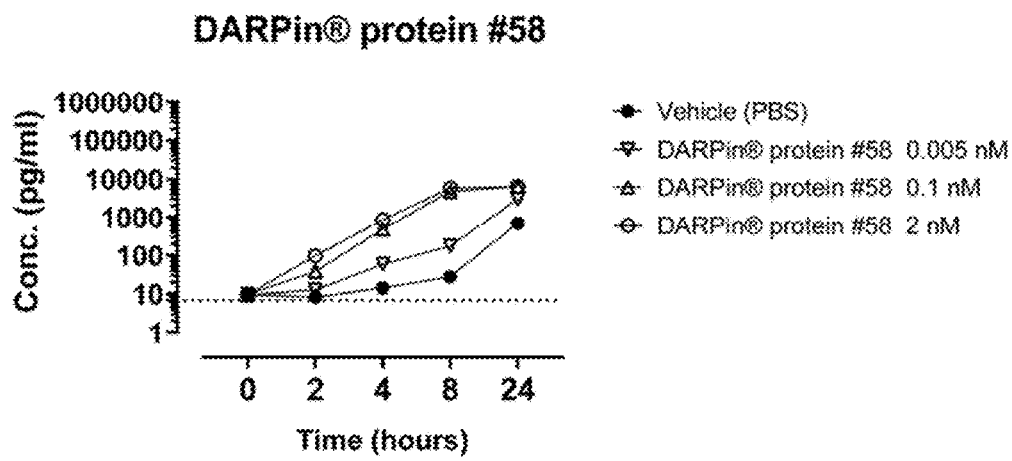
Figure 47C:
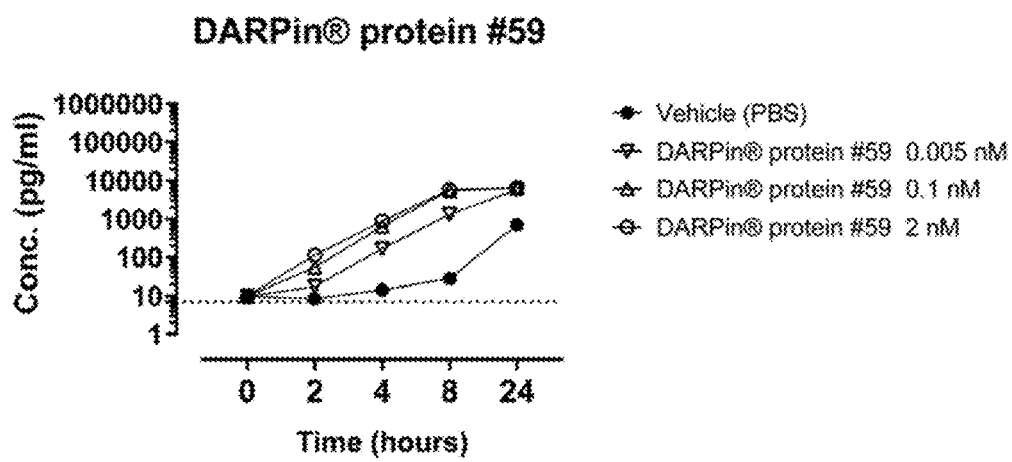
Figure 47D:
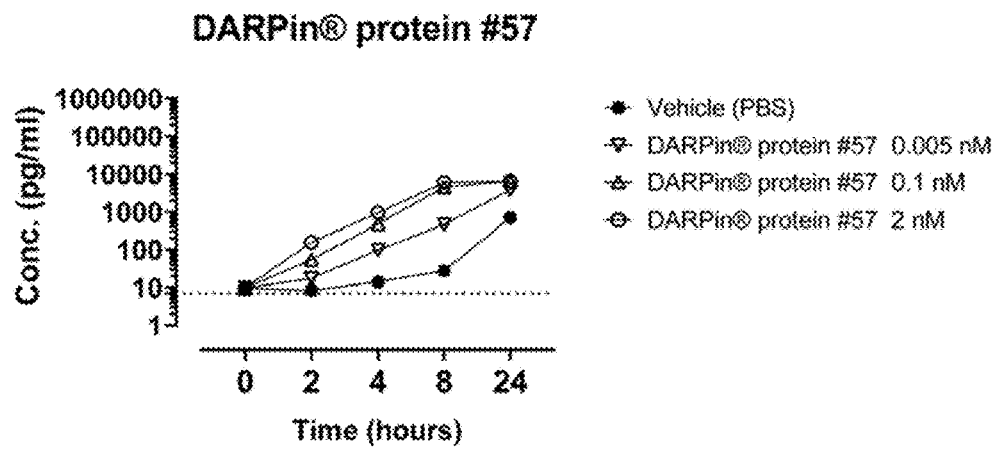
Figure 47E:
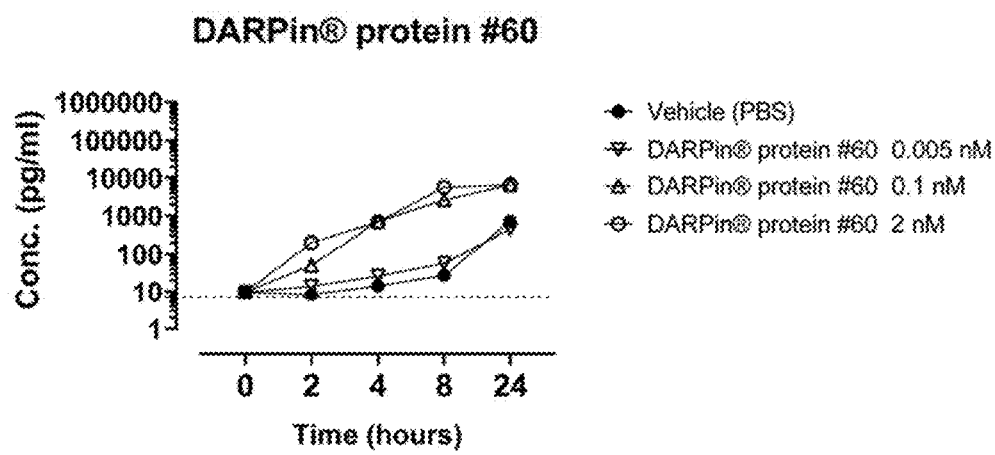
Figure 47F:
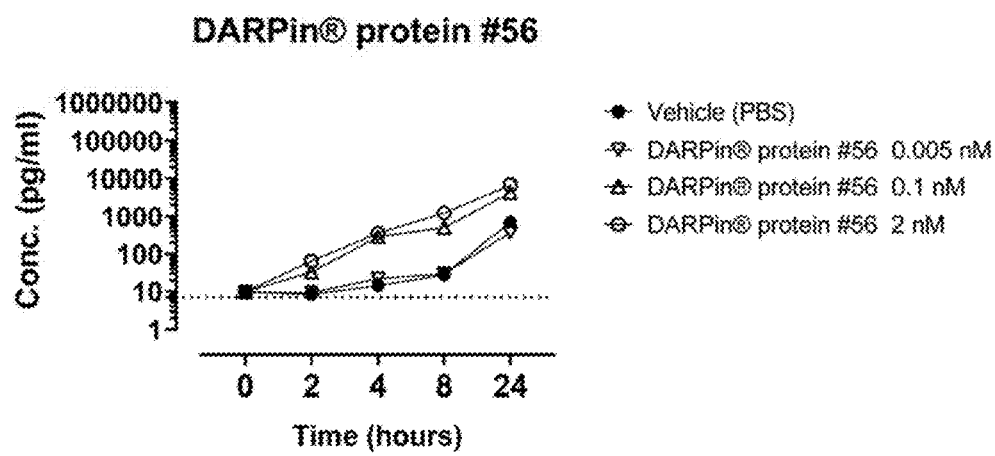
Figure 47G:
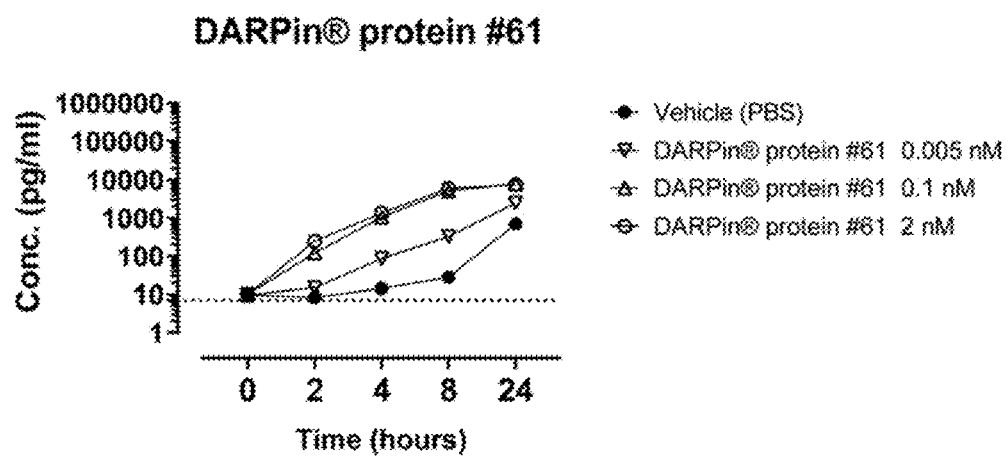
Figure 47H:
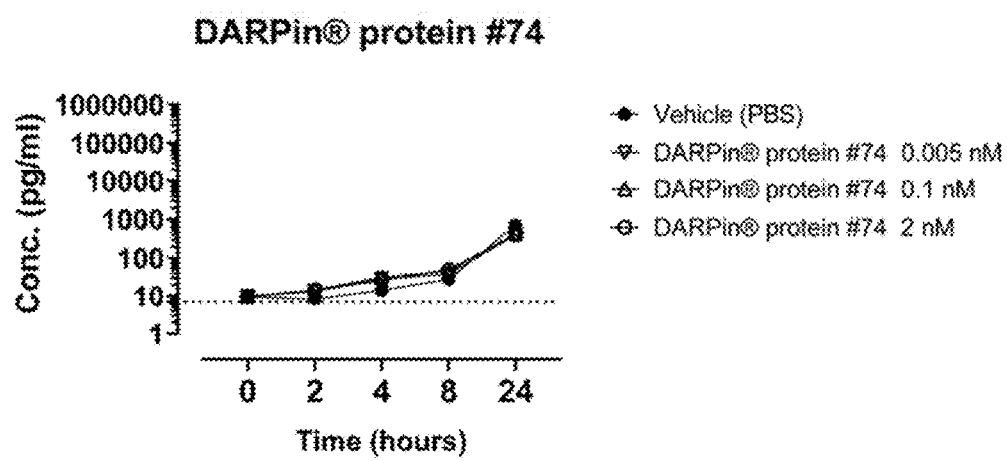
Figure 48A:
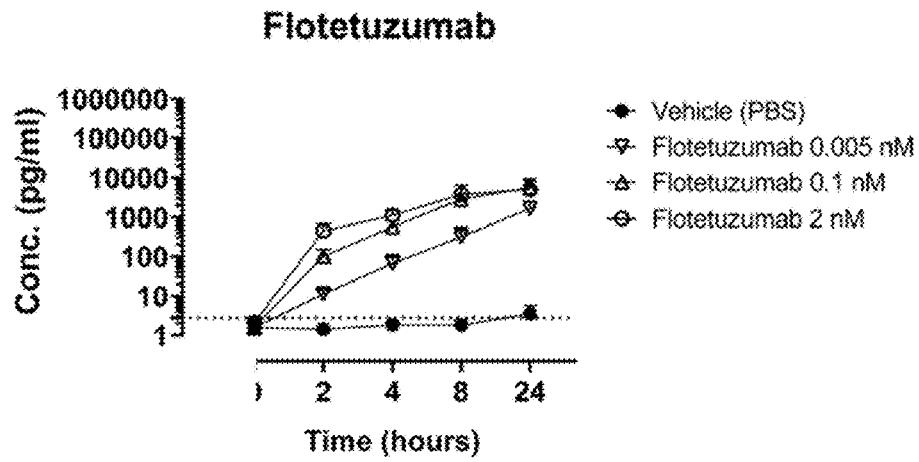
FIG. 48 (A-H). Levels of TNFα. Calculated mean concentration values of TNFα for all 3 donors in the blood loop system. Plasma samples were collected from the blood loop system at 0 (zero), 2, 4, 8 and 24 hours. Each point represents the mean (and the error bar the SD) of three donors: Flotetuzumab FIG. 48A, DARPin® protein #58 FIG. 48B, DARPin® protein #59 FIG. 48C, DARPin® protein #57 FIG. 48D, DARPin® protein #60 FIG. 48E, DARPin® protein #56 FIG. 48F, DARPin® protein #61 FIG. 48G, DARPin® protein #74 FIG. 44H. Calculated LLOQ is marked with a dotted line.
Figure 48B:
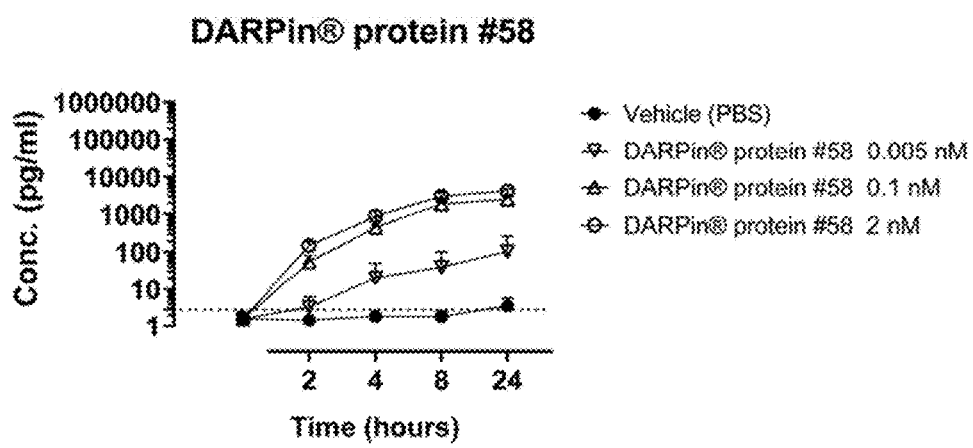
Figure 48C:
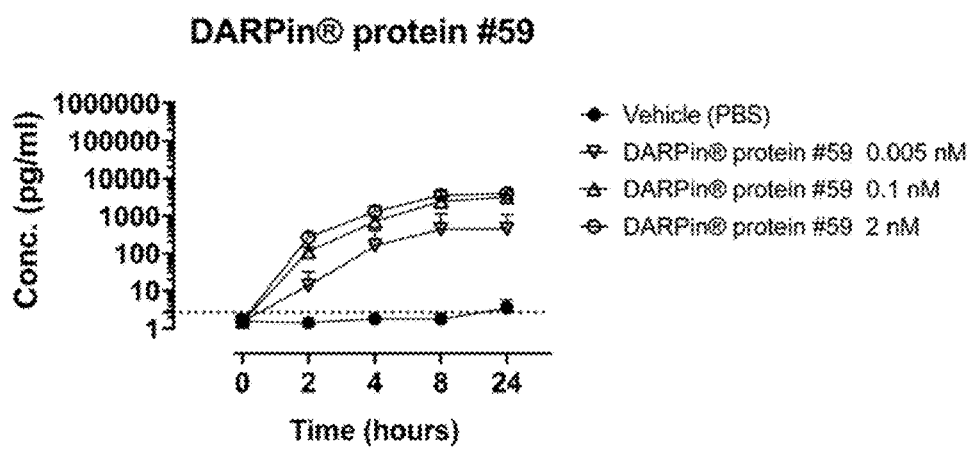
Figure 48D:
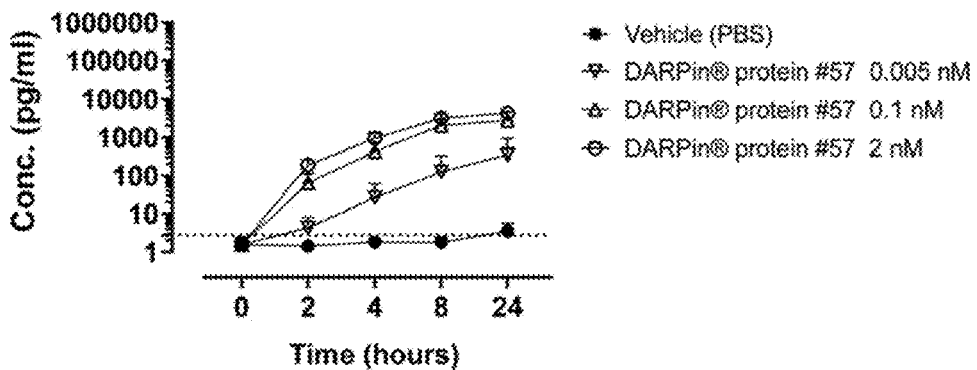
Figure 48E:
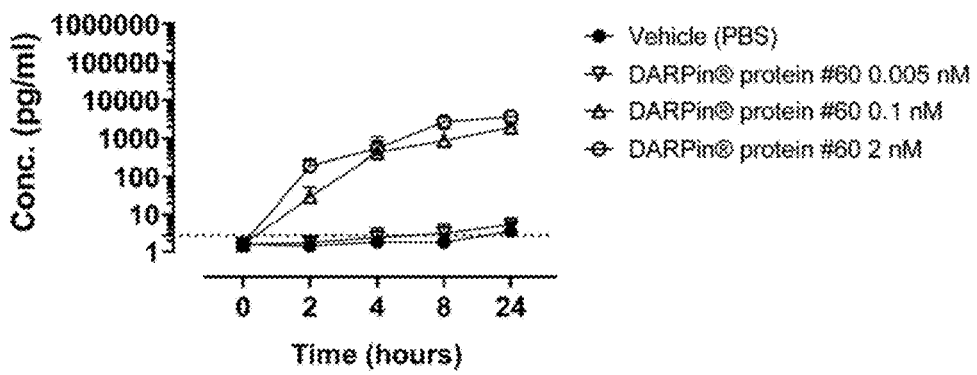
Figure 48F:
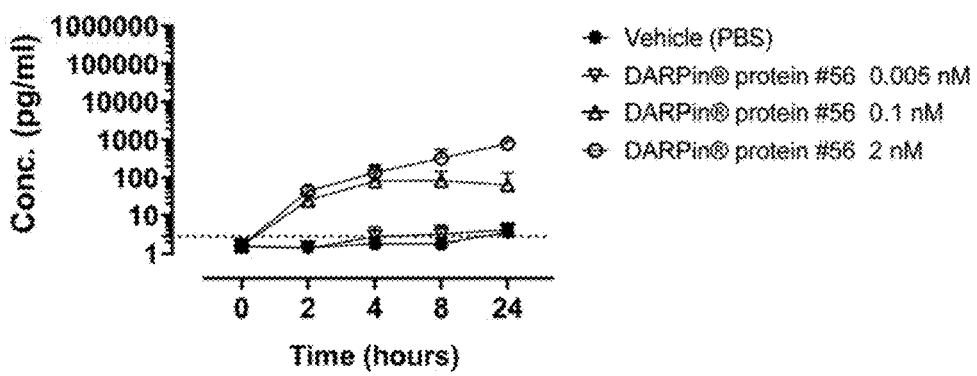
Figure 48G:
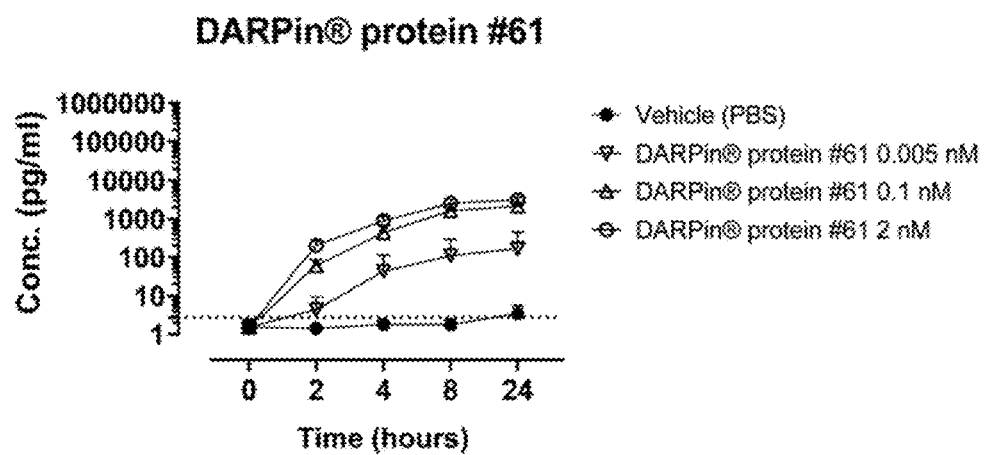
Figure 48H:
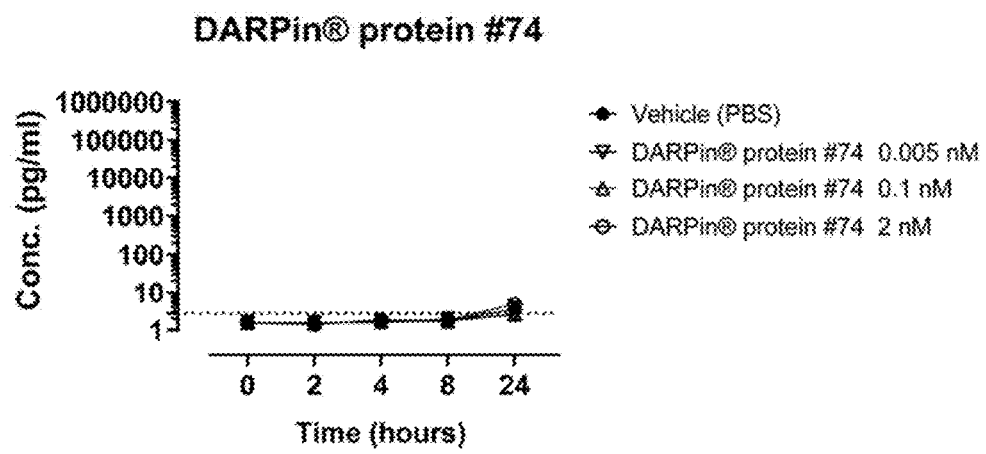
Figure 49A:
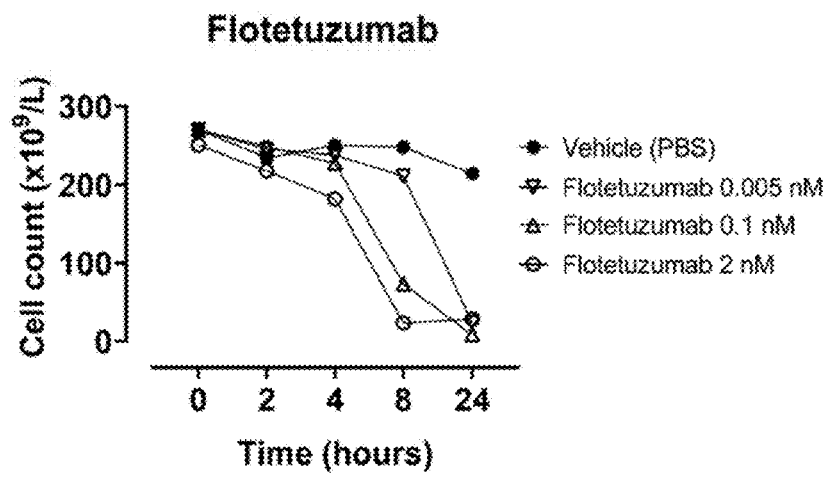
FIG. 49 (A-H). Platelet count. Blood samples were extracted from the blood loop system at time 0 (zero) and at 2-, 4-, 8- and 24 hours and platelets were automatically counted using a Sysmex XN-L350 Hematology (H). Each point represents the mean (and the error bar the SD) of three donors: Flotetuzumab FIG. 49A, DARPin® protein #58 FIG. 49B, DARPin® protein #59 FIG. 49C, DARPin® protein #57 FIG. 49D, DARPin® protein #60 FIG. 49E, DARPin® protein #56 FIG. 49F, DARPin® protein #61 FIG. 49G, DARPin® protein #74 FIG. 49H. Calculated LLOQ is marked with a dotted line.
Figure 49B:
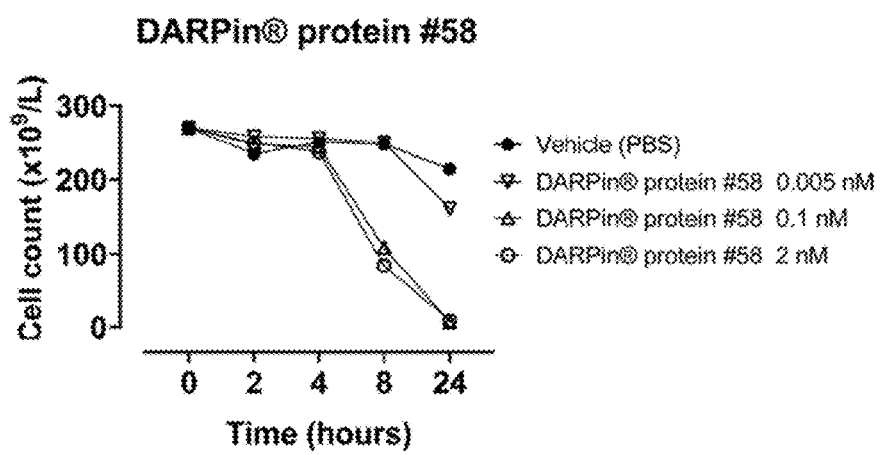
Figure 49C:
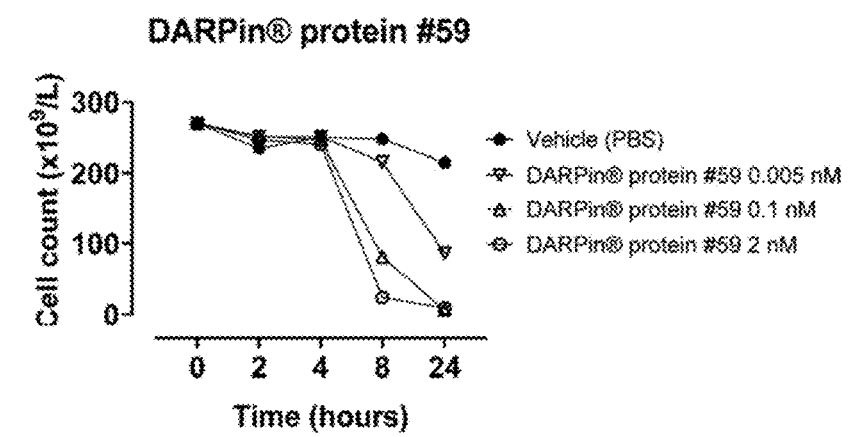
Figure 49D:
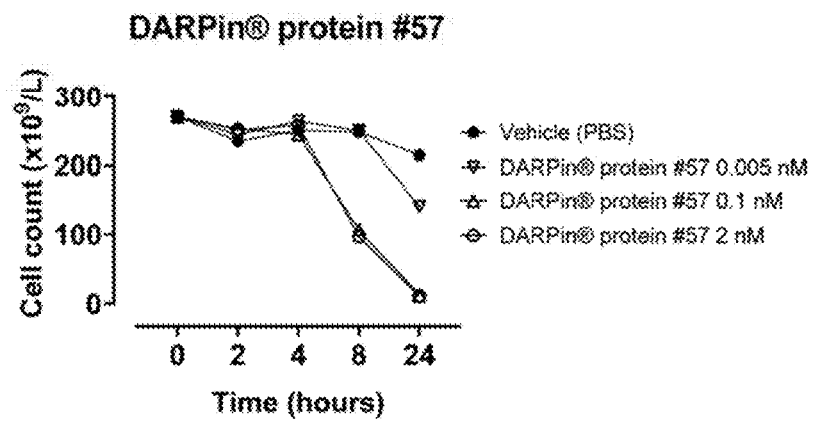
Figure 49E:
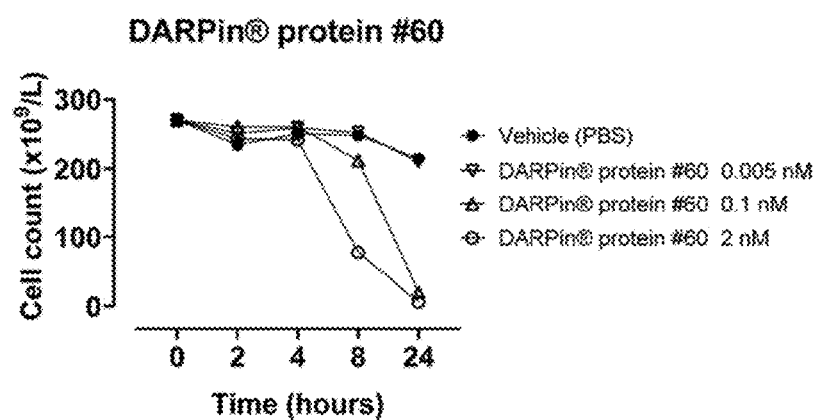
Figure 49F:
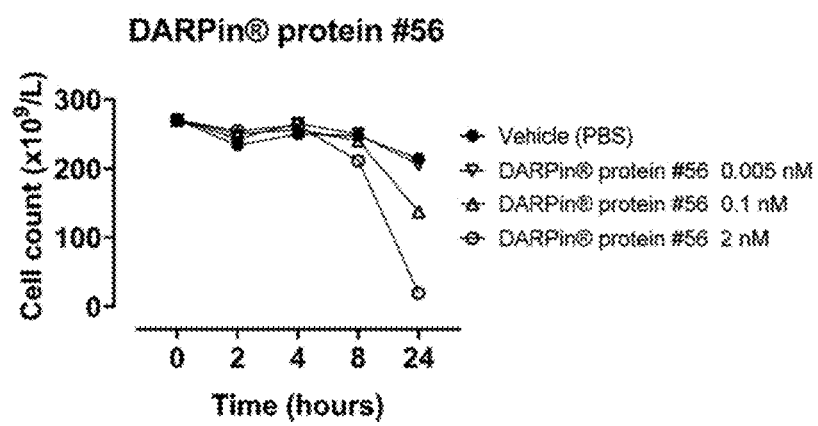
Figure 49G:
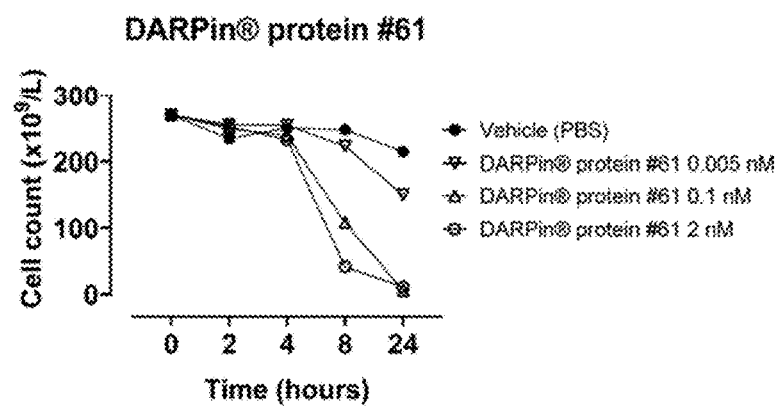
Figure 49H:
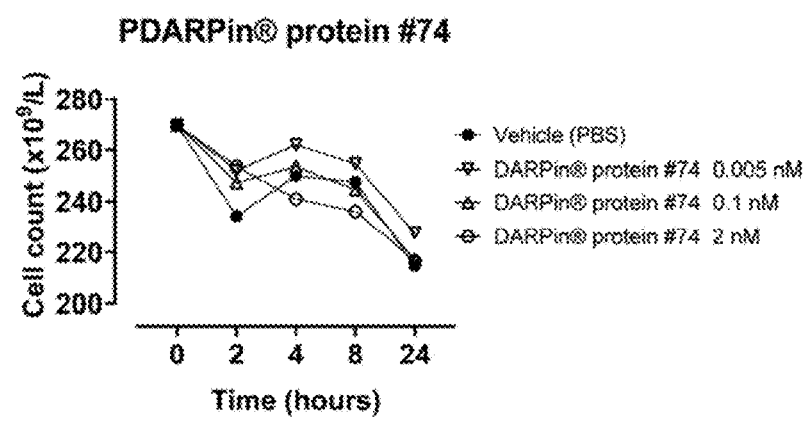
Figure 50A:
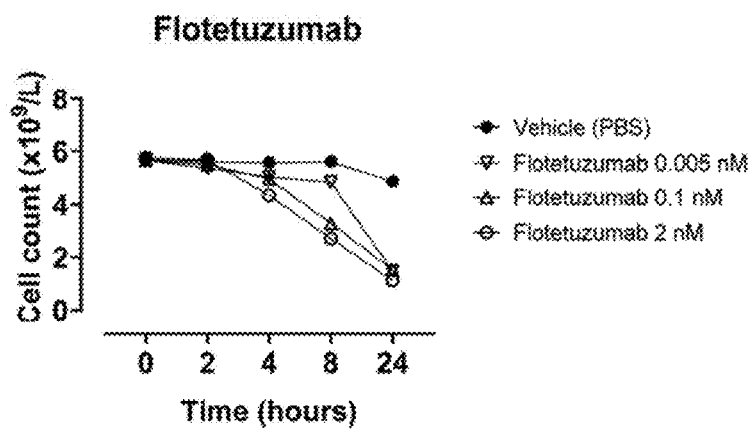
FIG. 50 (A-H). White blood cell count. Blood samples were extracted from the blood loop system at time 0 (zero) and at 2-, 4-, 8- and 24 hours and white blood cells were automatically counted using a Sysmex XN-L350 Hematology Analyzer. Each point represents the mean (and the error bar the SD) of three donors: Flotetuzumab FIG. 50A, DARPin® protein #58 FIG. 50B, DARPin® protein #59 FIG. 50C, DARPin® protein #57 FIG. 50D, DARPin® protein #60 FIG. 50E, DARPin® protein #56 FIG. 50F, DARPin® protein #61 FIG. 50G, DARPin® protein #74 FIG. 50H. Calculated LLOQ is marked with a dotted line.
Figure 50B:
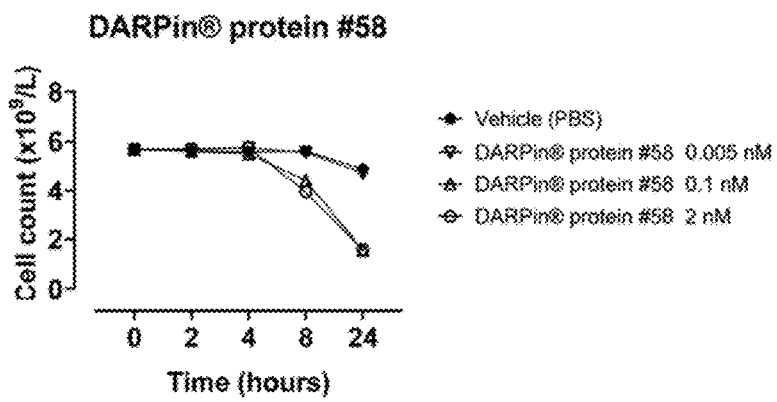
Figure 50C:
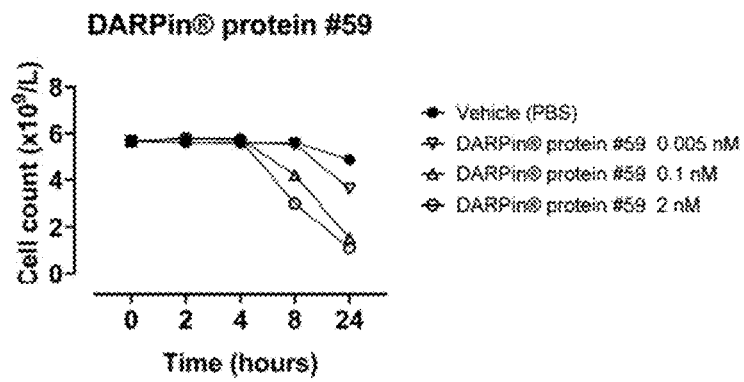
Figure 50D:
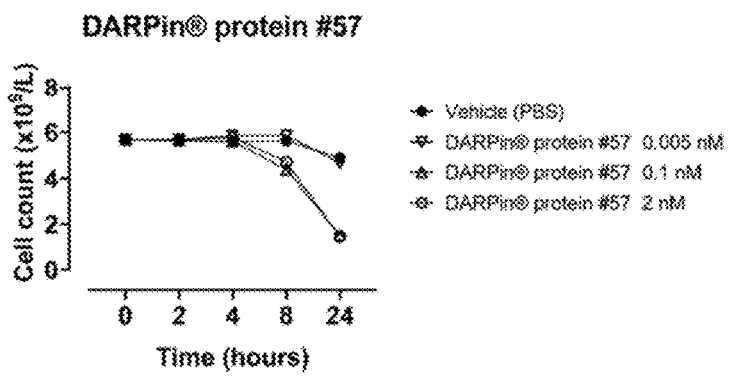
Figure 50E:
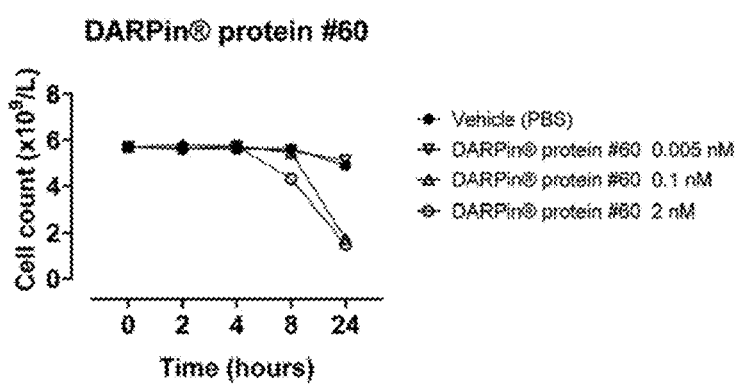
Figure 50F:
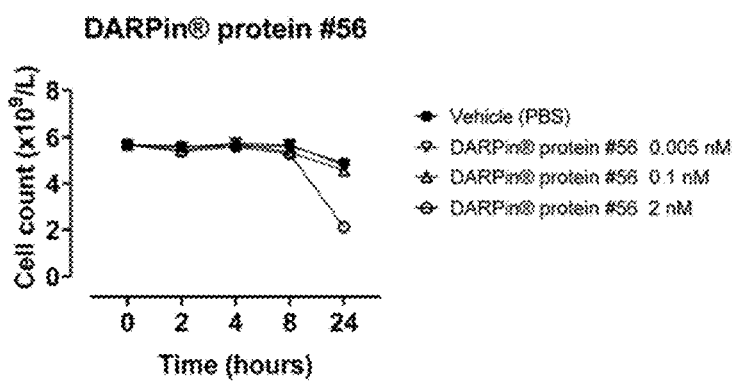
Figure 50G:
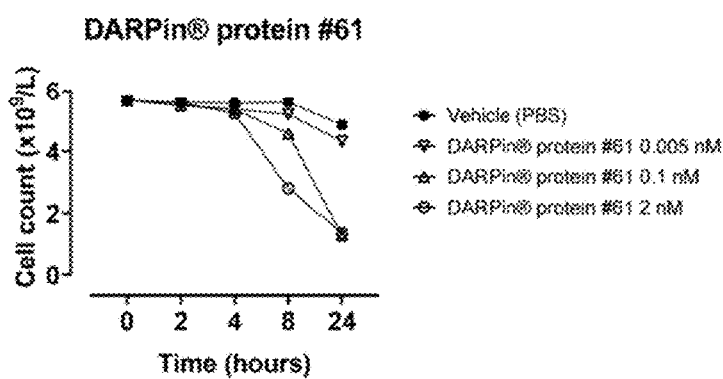
Figure 50H:
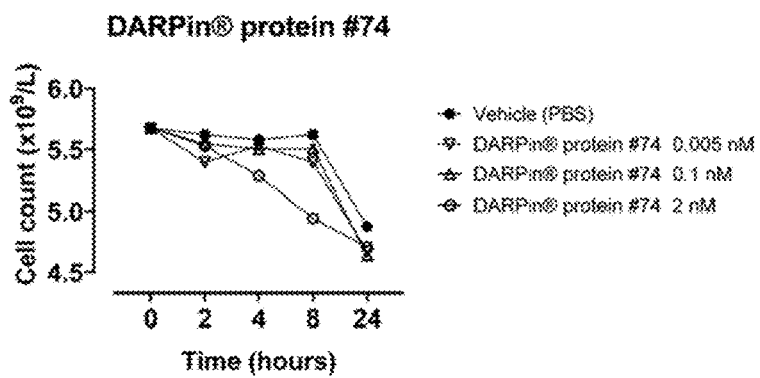

As it can be seen in FIG. 38 the CD123 binding domains showed a faster on rate to its target than CD33 binding domains, FIG. 37 ($k_{on}$ of $7E^6$ $M^{-1}s^{-1}$ for CD123, approximately 5-folds faster than the $k_{on}$ of CD33, equal to $1.3E^6$ $M^{-1}s^{-1}$). For DARPin® protein #20 two off rates were observed: one fast ($3E^2$ $s^{-1}$) which is related to the affinity binding and one slower ($1.5E^3$ $s^{-1}$), own of the avidity effect.). Accordingly, two $K_D$ can be determined for DARPin® protein #20: $K_{D,1}$, which is higher and related to the affinity binding, around 17.6 nM for CD33 and 4.9 nM CD123, respectively. And $K_{D,2}$ which is lower and related to the avidity (simultaneous binding of CD33 and CD123) in the pM range (FIGS. 39 and 40).

Figure 15A:
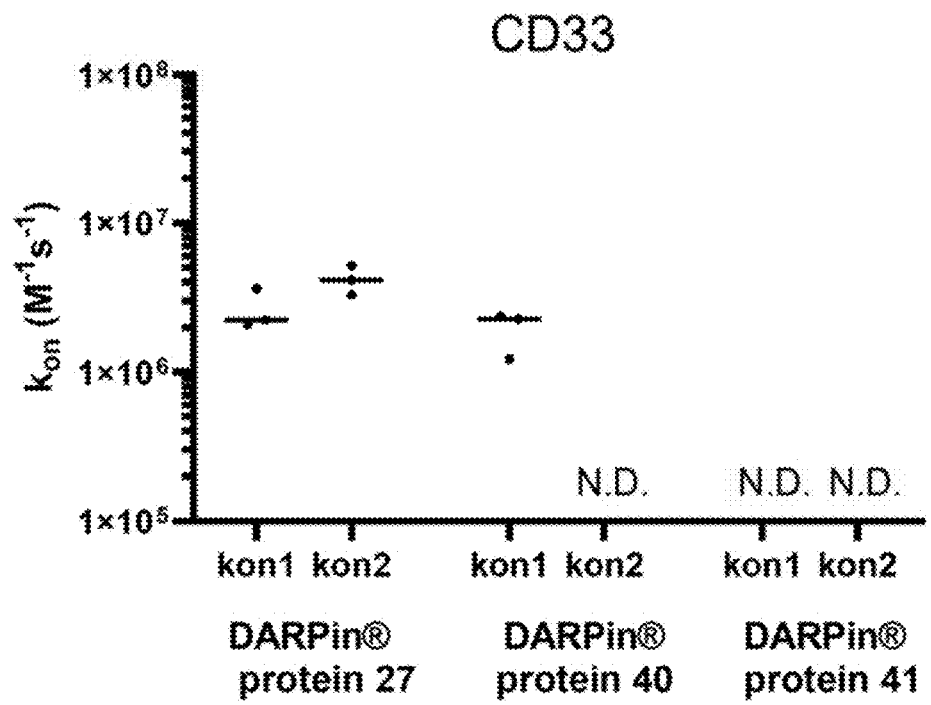
FIG. 15(A-B). On rate/off rate constants for CD33 target, measured for selected recombinant proteins DARPin® protein 27, DARPin® protein 40 and DARPin® protein 41.
Figure 15B:
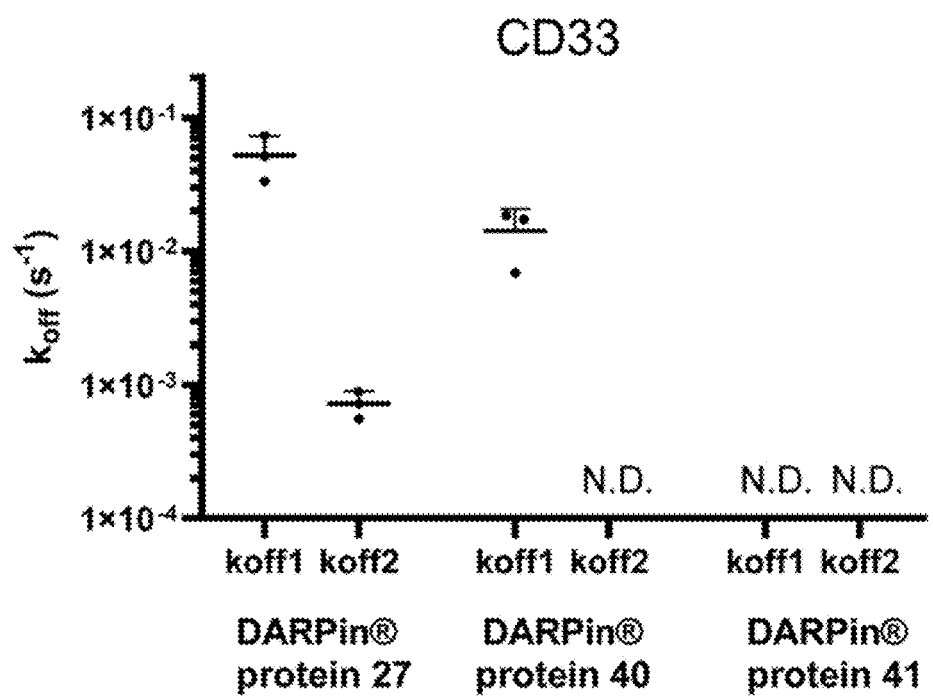
Figure 16A:
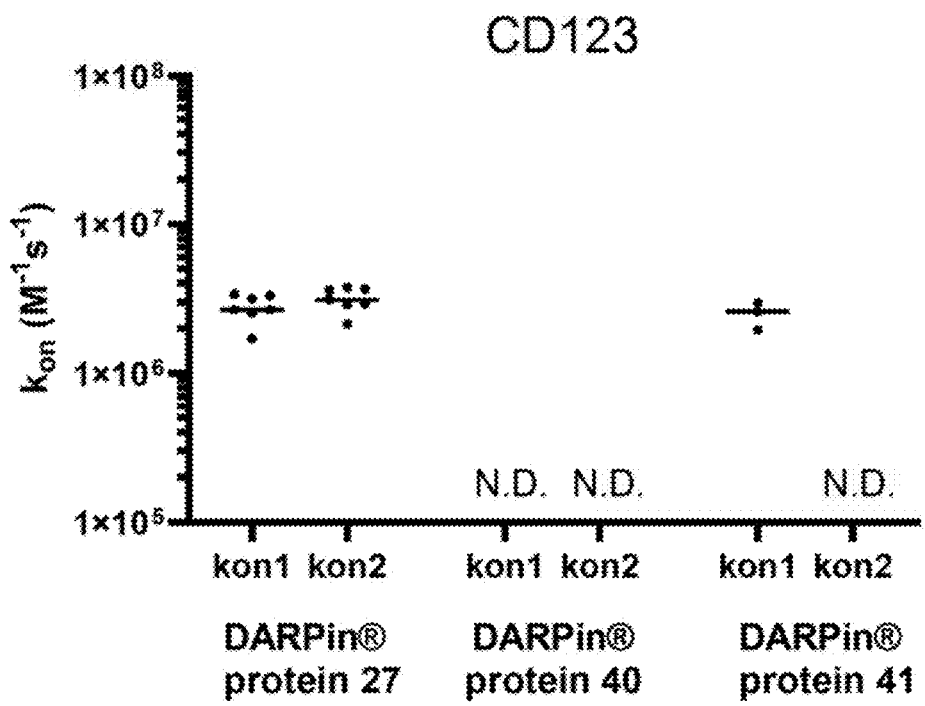
FIG. 16 (A-B). On rate/off rate constants for CD123 target, measured for selected recombinant proteins DARPin® protein 27, DARPin® protein 40 and DARPin® protein 41.
Figure 16B:
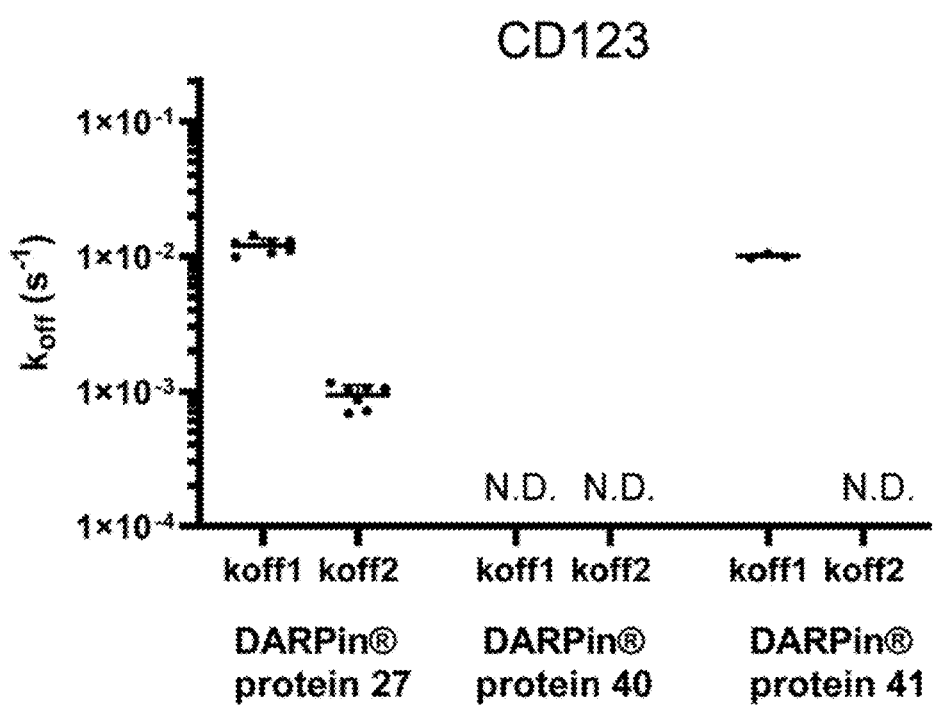

Multi-specific recombinant protein DARPin® protein #27 showed a biphasic dissociation, representing two interactions on the chip: affinity (faster off rates) in the order of $1E^{-2}$ $s^{-1}$ and avidity (slower off rates where the analyte is interacting with both ligands) in the order of $1E's^{-1}$. In addition, the association rate for CD123 seems slightly higher ($1E^7$ $M^{-1}s^{-1}$), compared to CD33 ($1E^6$ $M^{-1}s^{-1}$). For both DARPin® protein #40 and DARPin® protein #41 controls only binding interactions to one of the targets was observed. For example, DARPin® protein #15 interacts only with CD123, as expected, since it does not possess the CD33 subunit. Therefore, it shows a monophasic association and dissociation with a $k_{off}$ of $6E's^{-1}$. No interaction between DARPin® protein #41 and CD33 is observed. Analogously, DARPin® protein #40 interacts only with CD33, as expected, since it does not possess the CD123 subunit. Therefore, it shows a monophasic association and dissociation with a $k_{off}$ of $1E^{-2}$ $s^{-1}$. No interaction between DARPin® protein #40 and CD123 is observed. (FIGS. 15 and 16)

Figure 17:
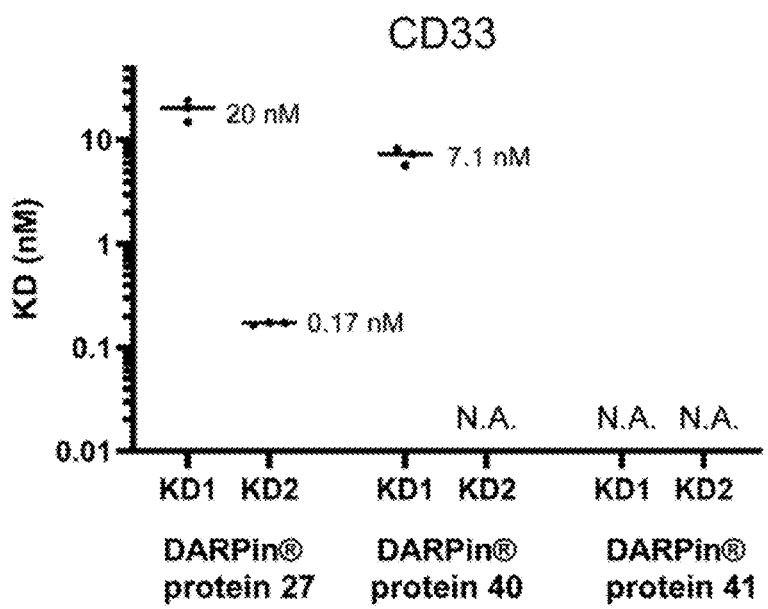
FIG. 17. $K_D$ values of recombinant proteins-human CD33 interactions.
Figure 18:
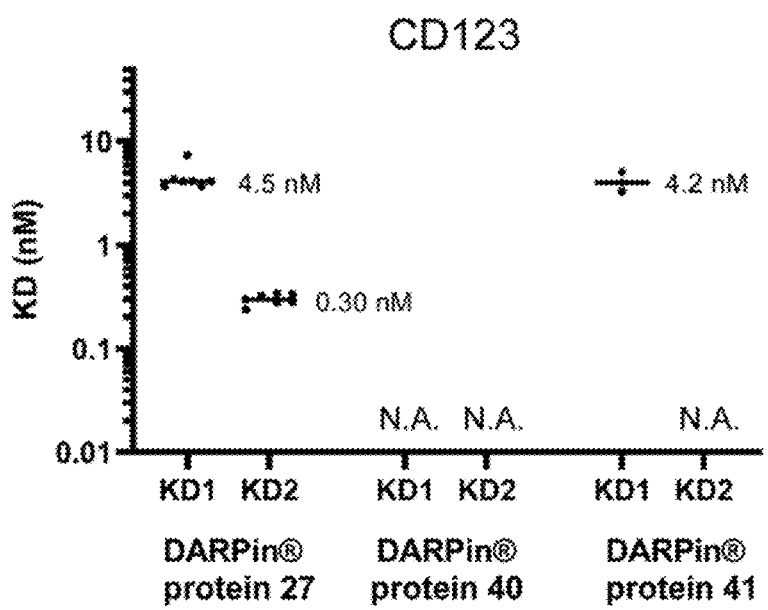
FIG. 18. $K_D$ values of recombinant proteins-human CD123 interactions.

Overall, it is shown that DARPin® protein #27 comprising both a CD33 specific and a CD123 specific binding domain (αCD33-αCD123) can bind to simultaneously to both targets attached to the surface of the chip, and they show affinity and avidity, while the designed ankyrin repeat proteins with either a CD33 specific binding domain or CD123 specific binding domain show only affinity to CD33 or CD123, respectively. Accordingly, two $K_D$ can be determined for DARPin® protein #27: $K_{D,1}$, which is higher and related to the affinity binding, around 20 nM for CD33 and 4.5 nM CD123, respectively. And $K_{D,2}$ which is lower and related to the avidity (simultaneous binding of CD33 and CD123) was determined in 0.2-0.3 nM range (FIGS. 17 and 18), at least 14 fold lower than the measured affinity.

Example 11: Assessment of Target-Specific Short-Term T Cell Activation and IFNγ Secretion Specificity and potency of previously described recombinant multi-specific ankyrin repeat proteins were assessed in an in vitro short-term T cell activation assay by FACS measuring CD25 activation marker on CD8+ T cells and by ELISA measuring IFNγ secretion.

Therefore, 100,000 purified pan-T effector cells and 100,000 Molm-13 target cells per well were co-incubated (E:T ratio 1:1) with serial dilutions of selected DARPin® proteins or control benchmark molecules in duplicates in presence of 600 μM human serum albumin for 24 hours at 37° C. After 24 hours, 100 μl supernatant per well were transferred for measurement of IFNγ secretion by human IFNγ Standard ABTS ELISA Development Kit (PeproTech) according to manufactures protocol. Cell were washed and stained with 1:1,000 Live/Dead Aqua (Thermo Fisher), 1:250 mouse anti-human CD8 Pacific Blue (BD), and 1:100 mouse anti-human-CD25 PerCP-Cy5.5 (eBiosciences) antibodies for 30 min at 4° C. After washing and fixation, cells were analyzed on a FACS Canto II (BD) machine. T cell activation was assessed by measuring CD25+ cells on Live/Dead-negative and CD8+ gated T cells. FACS data was analyzed using FlowJo software and data was plotted using GraphPad Prism 8.

Figure 23A:
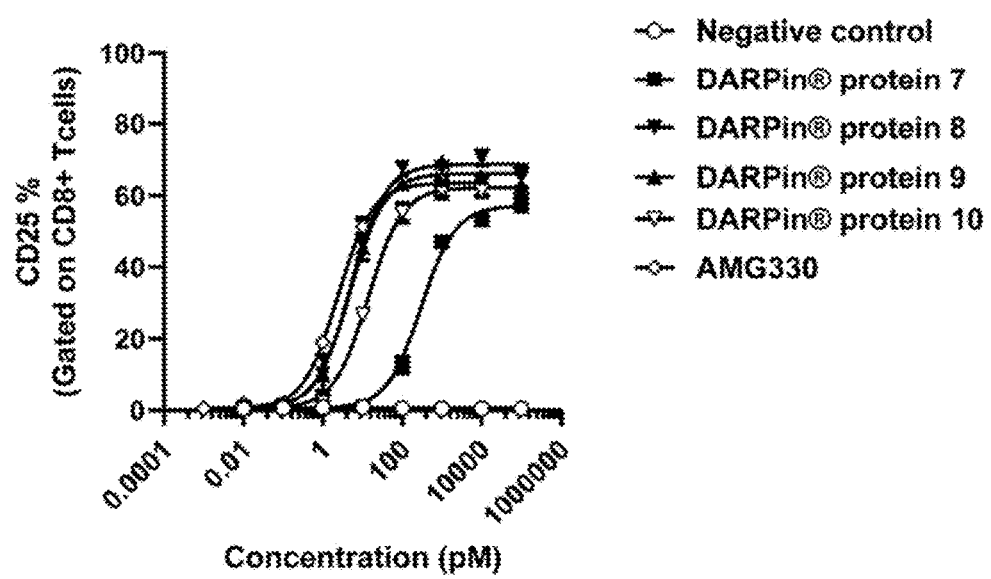
(FIG. 23A) Without half-life extension, T-cell activation induced by DARPin® protein 8 and DARPin® protein 9 is comparable to the benchmark, whereas DARPin® protein 10 and DARPin® protein 7 show lower potencies.
Figure 23B:
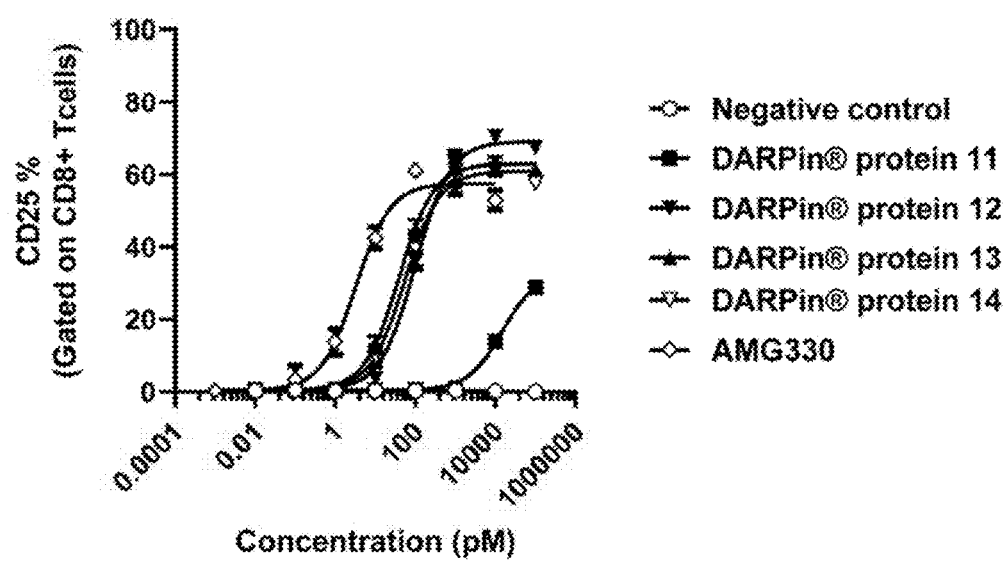
(FIG. 23B) Half-life extended proteins show 4-100-fold reduction in potency compared to the corresponding non-HLE molecules shown in (A). Pan-T cells from 7 different donors were tested, one representative donor is shown here. (*Negative control: a designed ankyrin repeat protein with binding specificity for CD33 and CD123 only, with or without half-life extension respectively).
Figure 24A:
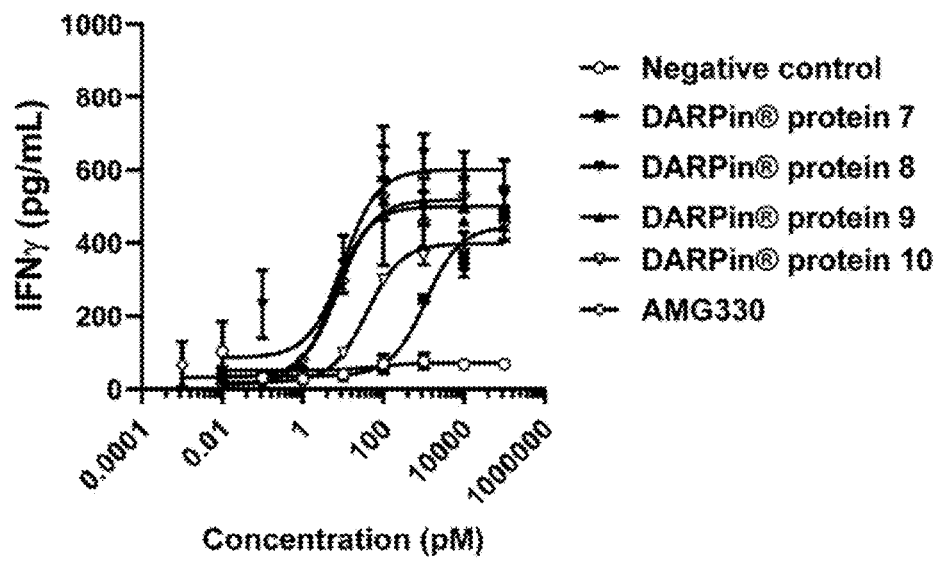
FIG. 24A-B. Short term T cell activation measured by IFNγ secretion. Pan-T and Molm-13 cells were incubated at an E:T ratio of 1:1. After 24 hours co-culture in the presence of serial dilutions of indicated molecules, IFNγ secretion in culture supernatants was analyzed by ELISA. Shown are benchmark control molecule (known benchmark T cell engager, AMG330 with binding specificity for CD33) and selected ankyrin repeat proteins DARPin® protein 7, DARPin® protein 8, DARPin® protein 9 and DARPin® protein 10 without (FIG. 24A) or DARPin® protein 11, DARPin® protein 12, DARPin® protein 13 and DARPin® protein 14 with (FIG. 24B) half-life extension (HLE).
Figure 24B:
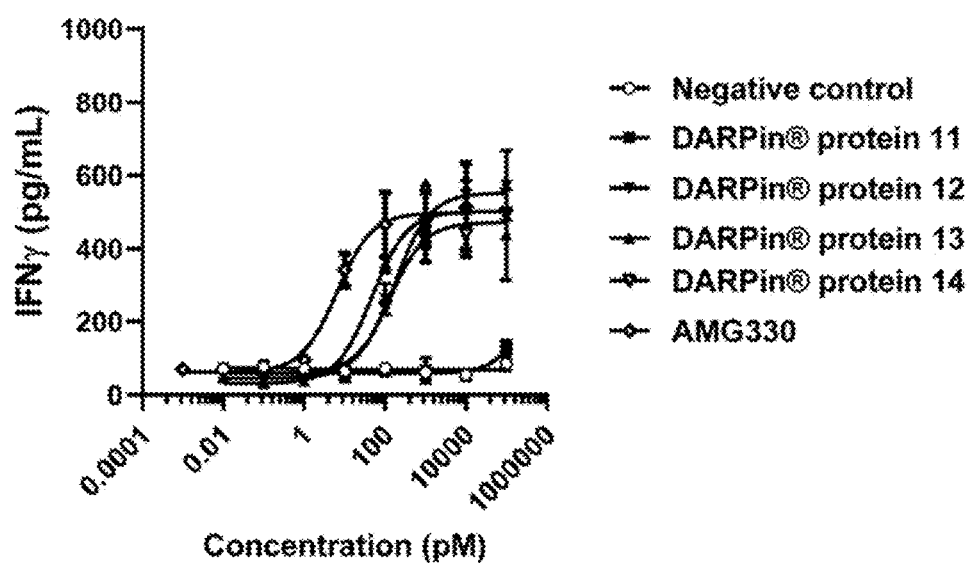

As shown in FIGS. 23A and 24A, for DARPin® proteins without half-life extension, #8 and #9 induced specific short-term T-cell activation comparable to benchmark molecules (known benchmark T cell engager, AMG330 with binding specificity for CD33), whereas DARPin® #7 and DARPin® #10 showed 10 to 100-fold reduction in potency. Half-life extended DARPin® proteins 11-14 (see FIGS. 23B and 24B) showed about 3 to 100-fold reduction in potency compared to the corresponding non-half-life extended molecules.

Example 12: Assessment of Target-Specific Long-Term Tumor Cell Killing by IncuCyte Specificity and potency of the recombinant multi-specific ankyrin repeat proteins described above were assessed by an in-vitro long-term killing assay using the IncuCyte S3 platform.

Molm-13 cells were first transduced with NucLight Red (NLR) lentiviral particles (Sartorius), and red-fluorescent cells selected by 0.7 μg/ml puromycin and/or FACS sorting. Long-term tumor cell killing was then assessed with the IncuCyte S3 system (Sartorius). Effector and target cells were co-incubated in duplicates on 0.01% poly-L-ornithine-coated 96-well plates with an E:T ratio of 5:1 in presence of 1:200 Annexin V green (Sartorius) and 600 μM human serum albumin (to mimic physiological concentration). 50,000 purified (Miltenyi) pan-T cells (isolated form healthy donor PBMCs)+10,000 Molm-13 NLR cells per well were incubated up to 6 days at 37° C. together with serial dilutions of the selected ankyrin repeat proteins or control benchmark molecules (. Images were taken every 2 h to assess for cell proliferation (red fluorescence from NLR) and cell death (green fluorescence from Annexin V). Total cell proliferation and tumor cell killing was analyzed by calculating the area under the curve after 6 days of co-culture using GraphPad Prism 8.

Figure 25:
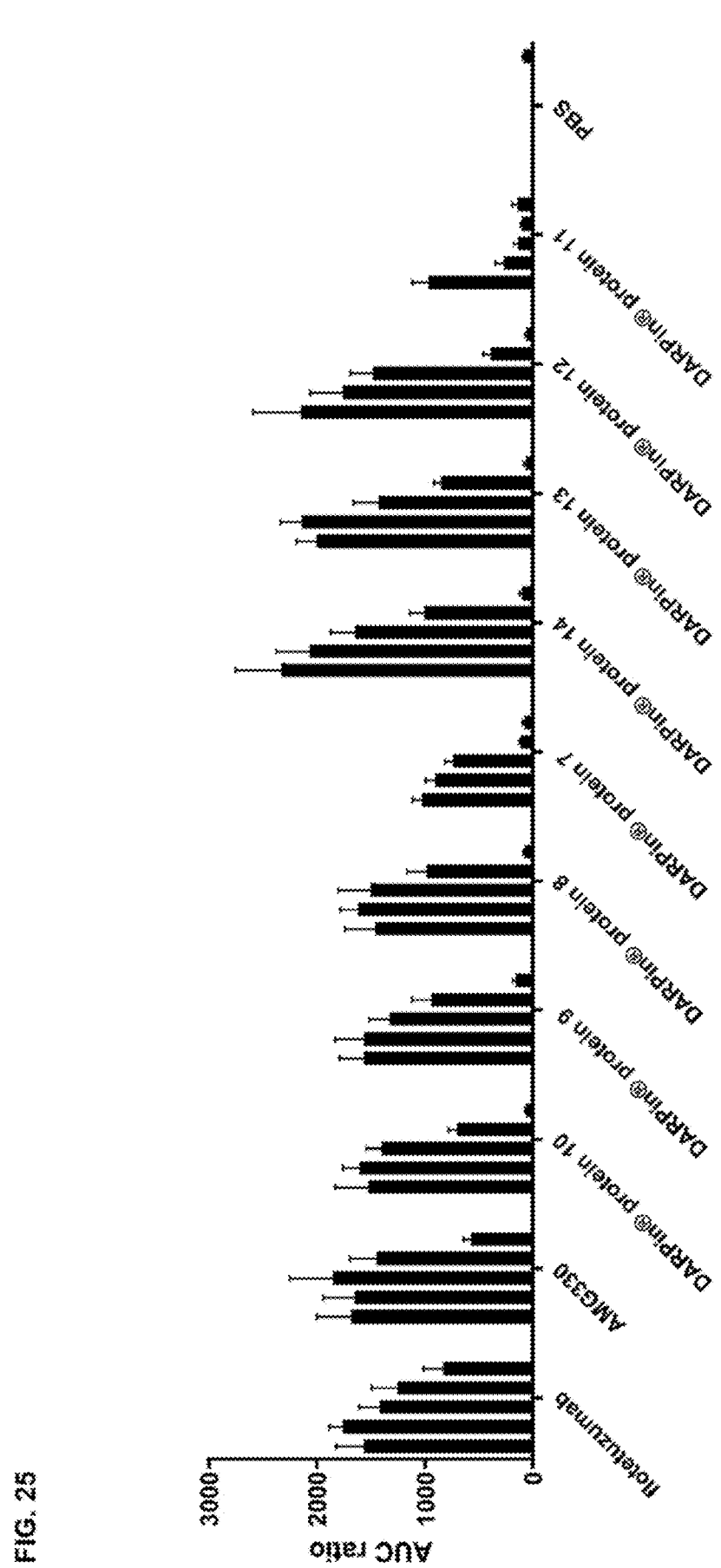
FIG. 25. Long-term tumor cell killing. Pan-T and Molm-13 cells were incubated at an E:T ratio of 5:1 and tumor cell killing assessed with an IncuCyte over 6 days of co-culture in the presence of serial dilutions of indicated molecules. Tumor cell killing is calculated as the ratio between area under the curve of Annexin V staining and cell proliferation. Shown are two benchmark control molecules (known benchmark T cell engagers, AMG330 with binding specificity for CD33 and flotetuzumab with binding specificity for CD123) and selected ankyrin repeat proteins DARPin® protein 7, DARPin® protein 8, DARPin® protein 9 and DARPin® protein 10, without or DARPin® protein 11, DARPin® protein 12, DARPin® protein 13 AND DARPin® protein 14 with half-life extension (HLE). Data shows potent and specific tumor cell killing, comparable to benchmark molecules, with most tested proteins, independent of half-life extension. Only the lower-affinity DARPin® protein 7 shows a marked reduction of killing potency. Concentrations are, left to right, 2 nM diluted ⅒ for benchmark and tested proteins, and 20 nM diluted ⅒ for half-life extended molecules. Pan-T cells from 5 different donors were used, one representative donor is shown here.

As shown in FIG. 25, tested DARPin® proteins #8, #9, #10 show potent and specific tumor cell killing, comparable to benchmark molecules (known benchmark T cell engagers, AMG330 with binding specificity for CD33 and flotetuzumab with binding specificity for CD123), independent of half-life extension. Only the lower-affinity DARPin® protein #7 shows a reduction of killing potency.

Example 13: Assessment of Target-Specific Long-Term T-Cell Activation and Proliferation by FACS Specificity and potency of the recombinant multi-specific ankyrin repeat proteins (described in Examples 5, 6, 7 and 8) were assessed by a FACS-based in-vitro long-term T-cell activation assay.

To assess drug- and target-specific T-cell activation and proliferation, effector and target cells were co-incubated in duplicates with an E:T ratio of 1:1 in presence of serial dilutions of selected molecules. Purified (Miltenyi) pan-T cells (isolated form healthy donor PBMCs) were first labelled with 5 μM CellTrace Violet (CTV) (Thermo Fischer) for 20 min at 37° C. 50,000 CTV-labelled pan-T cells+50,000 Molm-13 per well were then incubated at 37° C. together with serial dilutions of the selected CD3 specific ankyrin repeat proteins or control benchmark molecules TCE1 and TCE2) in presence of 600 μM human serum albumin (to mimic physiological concentration). After 5 days, cells were washed with PBS and stained with 1:5,000 Live/Dead Green (Thermo Fisher), 1:100 mouse anti-human CD8 PE (BD), and 1:100 mouse anti-human-CD25 PerCP-Cy5.5 (eBiosciences) antibodies for 30 min at 4° C. After 2 washes with PBS, cells were fixed using CellFIX (BD) for 20 min at 4° C., and finally the buffer replaced with PBS. Stained cells were analyzed on a FACS Canto II (BD) machine. T cell activation was assessed by measuring CD25+ cells on Live/Dead-negative and CD8+ gated T cells. T-cell proliferation was assessed by gating Live/Dead-negative and CTV-positive cells. FACS data was analyzed using FlowJo software; data was plotted using Graph Pad Prism 8.

Figure 26A:
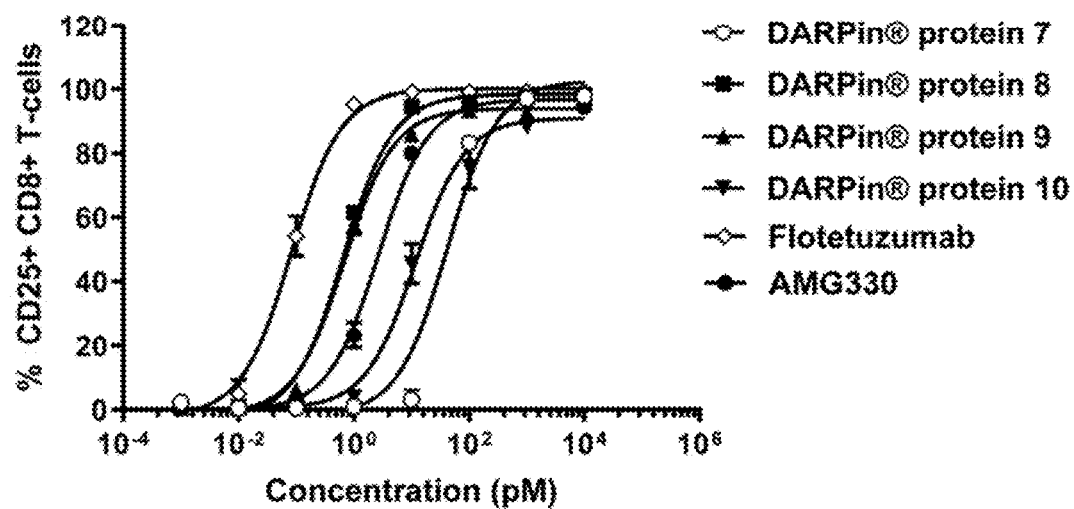
(FIG. 26A) Without half-life extension, T-cell activation induced by DARPin® protein 8 and DARPin® protein 9 is comparable to benchmark molecules, whereas DARPin® protein 7 and DARPin® protein 10 show >100-fold reduction in potency.
Figure 26B:
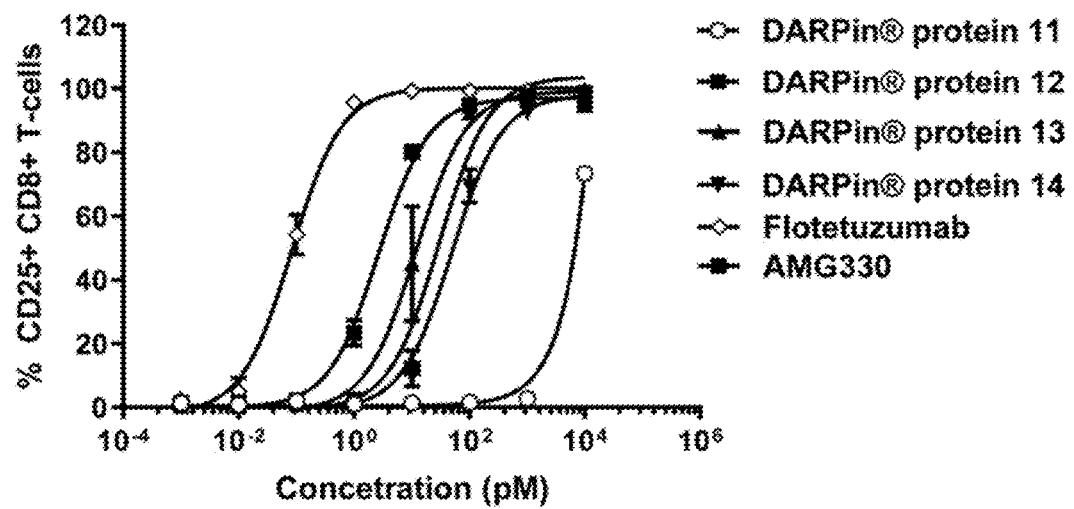
(FIG. 26B) Half-life extended proteins show >10-fold reduction in potency compared to the corresponding non-HLE molecules shown in (A). Pan-T cells from 2 different donors were used, one representative donor is shown here.

As shown in FIGS. 26 and 27, for DARPin® #8 and #9, without half-life extension, induced long term T-cell activation and proliferation comparable to benchmark molecules (known benchmark T cell engagers AMG330 with binding specificity for CD33 and flotetuzumab with binding specificity for CD123), whereas DARPin® proteins #7 and #10 show 10 to 100-fold reduction in potency. Half-life extended DARPin® proteins #11-14 show about 5 to 30-fold reduction in potency compared to the corresponding non-half-life extended molecules.

Example 14: In Vivo Efficacy Evaluation of Exemplary Multi-Specific Binding Proteins in PBMC Humanized Mice and MOLM-13 Tumor Model Experiment A. Four different designed ankyrin repeat proteins with binding specificity for CD33, CD123 and CD3—DARPin® protein #8, DARPin® protein #12, DARPin® protein #13 and DARPin® protein #14—were tested in a Peripheral Blood Mononuclear Cell (PBMC) humanized mouse model bearing the tumor cell line MOLM-13 as solid subcutaneous tumor and compared to AMG330, a known CD33 targeted T cell engager molecule currently tested in clinical trials.

DARPin® protein #12, DARPin® protein #13 and DARPin® protein #14 additionally include a designed ankyrin repeat domain with binding specificity for human serum albumin, as a half-life extending moiety. DARPin® protein #8 is the non half-life extended format of DARPin® protein #12.

Materials and Methods

Animals: 60 female NOG mice, age of animals at study initiation 65 days (provider Taconic Biosciences)

Test and control molecules: DARPin® protein #8, DARPin® protein #12, DARPin® protein #13 and DARPin® protein #14 were produced as described previously in a concentration of 5 mg/ml; control, AMG330 0.59 mg/ml: provided by Evitria AG Treatment groups: 60 mice were enrolled in the study. All animals were randomly allocated to the 8 different study groups). The date of tumor cell inoculation is denoted as day 0.

Method: Two days before the start of the experiment body weight was recorded and mice were randomized in order to have equal mean weight and similar standard deviation in each group. The mean weight was 19.6 g.

At day −2 mice have been injected intraperitoneally with $5 \times 10^6$ PBMC

At day 0 mice were injected with $10^6$ MOLM-13 cells subcutaneously in the right flank At day 5 treatment was started with intraperitoneal injections according to Table 8. The last treatment was at day 16.

Tumor measurement and weighting were performed at days 7, 10, 12, 14, 17, 19. Tumor volume was calculated according to following formula: $[\text{Length} \times (\text{width})^2 \times \pi]/6$.

Tumor volume data were analyzed by comparing growth curves by Anova and following non-parametric Kruskal-Wallis test corrected for multiple comparison (Dunn's Test).

Tumor volumes of treatment groups has been compared to the volumes of the control group. Data from the two different PBMC donors were analyzed together and separately.

TABLE 7

Allocation of Treatment Groups and Treatment Scheme

| Group | Sub-group donor | No of mice | Treatment | Dose | Frequency |
|---|---|---|---|---|---|
| 1 | A | 5 | Vehicle PBS | — | 3x week |
|   | B | 5 | 0.05% Tween |   | MON/WED/FRI |
| 2 | A | 5 | AMG330 | 200 µg/kg | daily |
|   | B | 5 |   |   |   |
| 3 | A | 5 | DARPin ® | 200 µg/kg | daily |
|   | B | 5 | protein #8 |   |   |

TABLE 7-continued

Allocation of Treatment Groups and Treatment Scheme

| Group | Sub-group donor | No of mice | Treatment | Dose | Frequency |
|---|---|---|---|---|---|
| 4 | A | 5 | DARPin ® | 200 µg/kg | 3x week |
|   | B | 5 | protein #12 |   | MON/WED/FRI |
| 5 | A | 5 | DARPin ® | 200 µg/kg | 3x week |
|   | B | 5 | protein #13 |   | MON/WED/FRI |
| 6 | A | 5 | DARPin ® | 200 µg/kg | 3x week |
|   | B | 5 | protein #14 |   | MON/WED/FRI |

Results

Tumor Growth Inhibition

The tumor growth curves upon exposure to the tested multi-specific binding proteins and the known benchmark T cell engager is summarized in FIG. 25A-C, including both donors together and separately. FIG. 26A-L shows the individual growth curves of all mice

TABLES 8

(both donors), 9 (Donor A) & 10 (Donor B): Statistics of tumor growth

Both Donors together

| Days after initiation of Treatment | Vehicle mean | AMG330 mean | p | DARPin ® protein #8 mean | p | DARPin ® protein #12 mean | p | DARPin ® protein #13 mean | p | DARPin ® protein #14 mean | p |
|---|---|---|---|---|---|---|---|---|---|---|---|
| 2 | 52.1 | 55.0 | ns | 46.1 | ns | 27.4 | ns | 36.7 | ns | 34.4 | ns |
| 5 | 443.4 | 93.0 | ++ | 197.7 | ns | 109.0 | + | 154.1 | ns | 150.9 | ns |
| 7 | 546.3 | 124.8 | ++ | 287.2 | ns | 142.3 | + | 122.1 | ++ | 118.3 | ++ |
| 9 | 706.8 | 135.6 | +++ | 376.8 | ns | 240.5 | + | 121.1 | +++ | 150.6 | ++ |
| 12 | 923.4 | 263.0 | ns | 450.3 | ns | 250.2 | ++ | 69.9 | ++++ | 204.6 | ++ |

Donor A

| Days after initiation of Treatment | Vehicle mean | AMG330 mean | p | DARPin ® protein #8 mean | p | DARPin ® protein #12 mean | p | DARPin ® protein #13 mean | p | DARPin ® protein #14 mean | p |
|---|---|---|---|---|---|---|---|---|---|---|---|
| 2 | 86.1 | 53.0 | ns | 26.8 | ns | 41.0 | ns | 43.1 | ns | 43.2 | ns |
| 5 | 704.6 | 149.5 | +++ | 172.0 | ++ | 100.3 | +++ | 169.1 | ++ | 88.6 | +++ |
| 7 | 634.0 | 183.0 | ++ | 300.5 | + | 153.2 | ++ | 124.0 | +++ | 69.2 | +++ |
| 9 | 815.7 | 197.8 | ++ | 296.7 | + | 156.4 | ++ | 119.5 | +++ | 93.7 | +++ |
| 12 | 895.1 | 389.3 | ns | 418.1 | ns | 67.6 | ++ | 57.4 | ++ | 91.8 | + |

Donor B

| Days after initiation of Treatment | Vehicle mean | AMG330 mean | p | DARPin ® protein #8 mean | p | DARPin ® protein #12 mean | p | DARPin ® protein #13 mean | p | DARPin ® protein 14 mean | p |
|---|---|---|---|---|---|---|---|---|---|---|---|
| 2 | 18.1 | 57.1 | ns | 65.5 | ns | 13.8 | ns | 30.4 | ns | 25.7 | ns |
| 5 | 182.1 | 36.6 | ns | 223.5 | ns | 117.8 | ns | 139.1 | ns | 213.1 | ns |
| 7 | 458.7 | 66.6 | + | 273.9 | ns | 131.4 | ns | 120.2 | + | 167.5 | ns |
| 9 | 597.9 | 73.5 | + | 456.8 | ns | 324.6 | ns | 122.7 | + | 207.6 | ns |
| 12 | 951.8 | 136.7 | ns | 482.5 | ns | 432.8 | ns | 82.3 | ++ | 317.3 | ns |

+ = p < 0.1;

** = p < 0.05;

+++ = p < 0-01;

++++ = p < 0.001;

ns = not significant

PBMC from Donor B led to lower amounts of CD8 positive lymphocytes in mouse blood. In general, antitumoral effect was observed in all tested molecules. In contrast DARPin® protein #12 and AMG330 showed an effect starting from 5 days after initiation of the treatment whereas the effect of DARPin® protein #13 and DARPin® protein #14 was significant and relevant starting from 7 days after initiation of the treatment. When only subgroups A where compared, a statistically significant effect was observed for all tested molecules starting from day 5 after initiation of the treatment. The effect of DARPin® protein #12, DARPin® protein #13 and DARPin® protein #14 was stronger than that of AMG330 and DARPin® protein #8. When subgroups B were compared, a significant antitumoral effect was observed for DARPin® protein #13 and the benchmark AMG330.

The result obtained with the benchmark validated the model used. At the same time, a less pronounced effect of the benchmark observed in mice humanized with PBMC from donor B indicates that the sensitivity of mice belonging to this subgroup is lower. This is also reflected by the significantly lower amounts of human CD8 positive lymphocytes found at the end of the experiment in mice humanized with PBMC from donor B.

Thus, more relevance should be attributed to the data raised from mice humanized with PBMC from donor A.

The high variability in tumor size is due to the fact that no randomization and range selection has been performed in mice, because the treatment was initiated before tumors were recognizable in all mice. Despite this high variability, statistical analysis could be performed without need of normalization to the initial tumor volume.

We confirmed that all multi-specific binding proteins tested show antitumoral activity and the half-life extended molecules, DARPin® protein #12, DARPin® protein #13 and DARPin® protein #14, at the doses and application regimen used have stronger antitumoral activity than the not half-life extended DARPin® protein #8. Without wishing to be bound by theory, it is thought that the exposure of DARPin® protein #8 may be lower due to the shorter half-life of this molecule.

Overall, all four tested multi-specific binding proteins show in vivo antitumoral activity comparable or stronger to that of the benchmark AMG330 T cell engager.

Experiment B. In a similar experimental set up and procedure as in Experiment A, an additional designed ankyrin repeat protein with binding specificity for CD70, CD33, CD123 and CD3, i.e. DARPin® protein #56, was tested in a Peripheral Blood Mononuclear Cell (PBMC) humanized mouse model bearing the tumor cell line MOLM-13 as solid subcutaneous tumor and compared to AMG330.

In brief, the in vivo experiments were performed in six 9-week-old female immunodeficient NXG mice (provided by Janvier Labs). Mice were maintained under standardized environment conditions in standard rodent micro-isolator cages (20+/−1° C. room temperature, 50+/−10% relative humidity and 12 hours light dark cycle). Mice received irradiated food and bedding and 0.22 um filtered drinking water. All experiments were done according to the Swiss Animal Protection Law with authorization from the cantonal and federal veterinary authorities.

As in Experiment A, mice were injected intraperitoneally with hPBMC two days before the xenograft of the cancer cells. MOLM-13 cells were xenografted subcutaneously (s.c.) on the right flank area into the mice. Two hPBMC donors were used. Treatments were injected intravenously (i.v.) starting four days after cancer cell implantation. Treatments were administrated as follows:

DARPin® protein #56 was administrated i.v. three times per week for 2 weeks at 0.5 mg/kg AMG330 was administrated i.v. daily for 2 weeks at 0.5 mg/kg Tumor size was evaluated by calliper measurement. Tumor volumes were calculated using the following formula: tumor volume $(mm^3)=0.5 \times length \times width^2$.

Figure 58A:
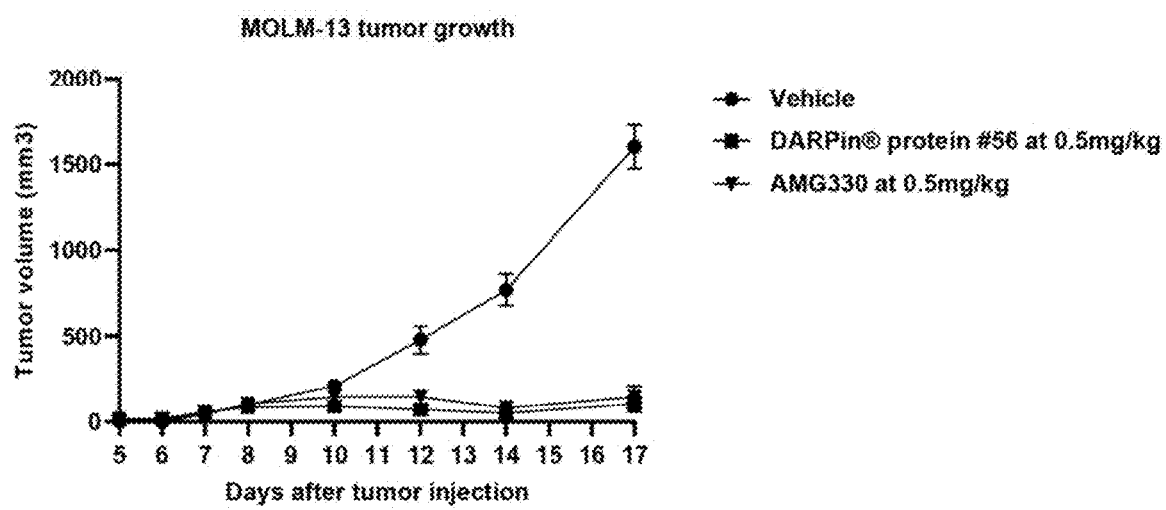
FIG. 58A. Tumor growth over time in mice injected intraperitoneally with hPBMC (n=5 mice per donor/2 hPBMC donors used), xenografted subcutaneously with MOLM-13 tumor cells two days after hPBMC injection, and treated with PBS 1× (black circle), DARPin® protein #56 at 0.5 mg/kg (black square) or AMG330 at 0.5 mg/kg (black triangle). Treatments were started at day 4 after tumor cell xenograft. Data are presented in average+SEM.
Figure 58B:
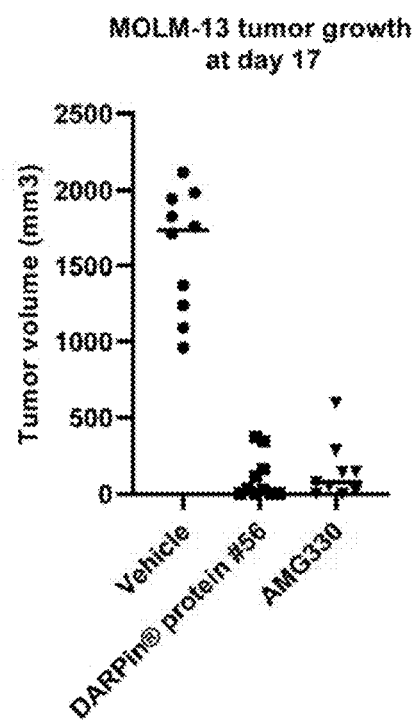
FIG. 58B. Evaluation of tumor volume at day 17 after tumor cell xenograft in the mice described in FIG. 58A.
Figure 59A:
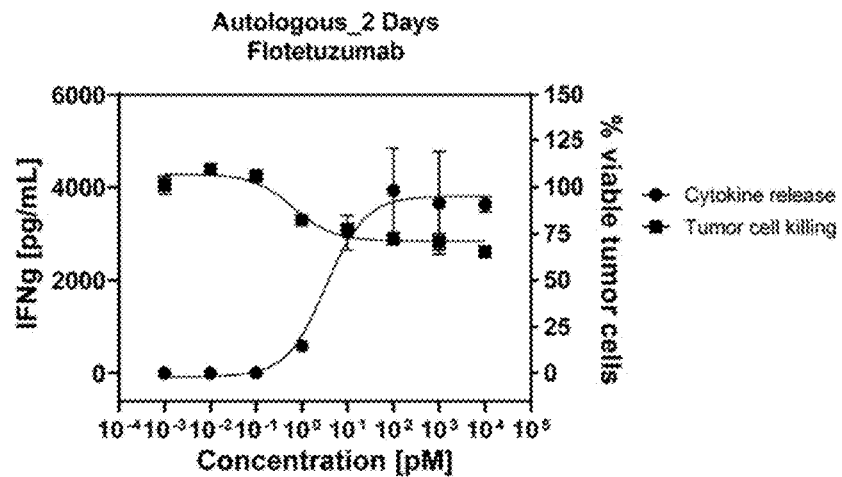
FIG. 59A. Impact of flotetuzumab similar on cell killing and IFNγ release.
Figure 59B:
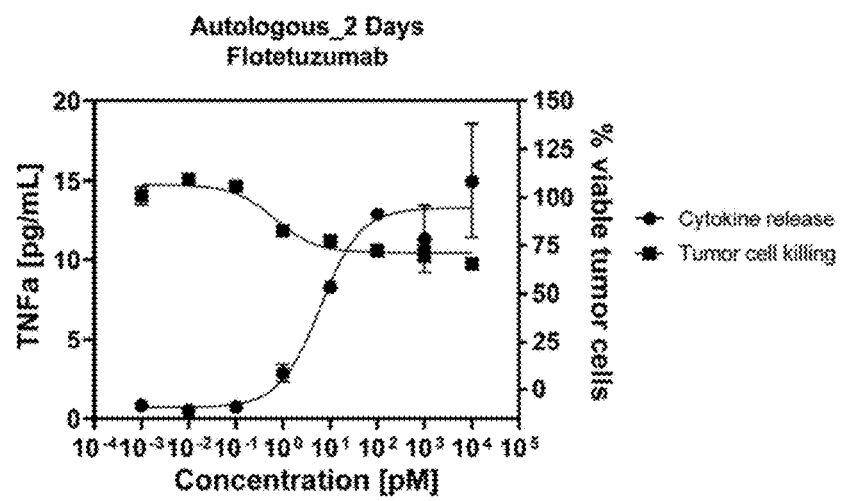
FIG. 59B. Impact of flotetuzumab similar on cell killing and TNFα release.
Figure 59C:
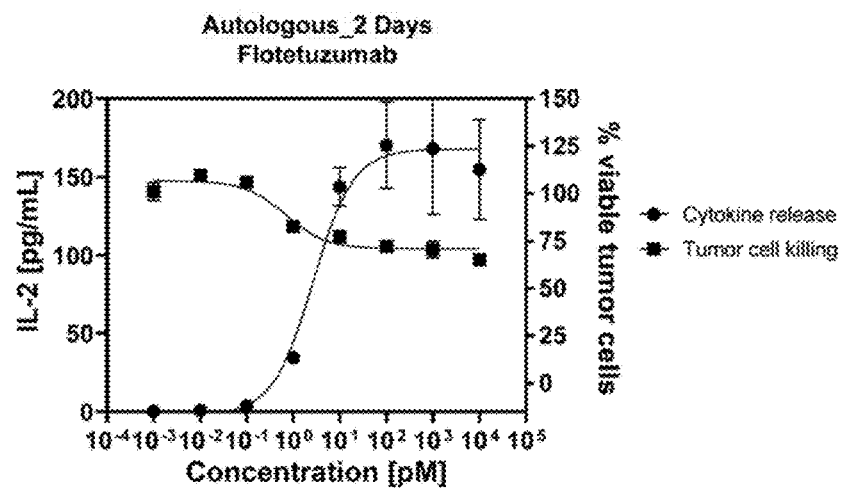
FIG. 59C. Impact of flotetuzumab similar on cell killing and IL-2 release.
Figure 59D:
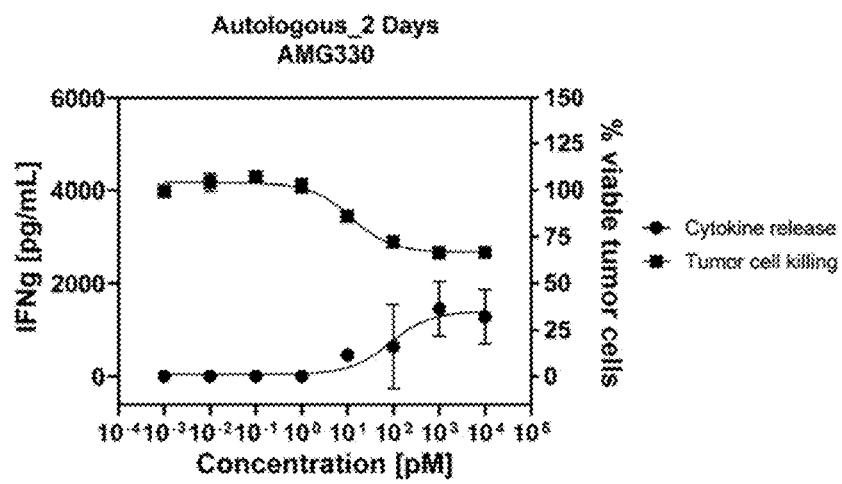
FIG. 59D. Impact of AMG330 similar on cell killing and IFNγ release.
Figure 59E:
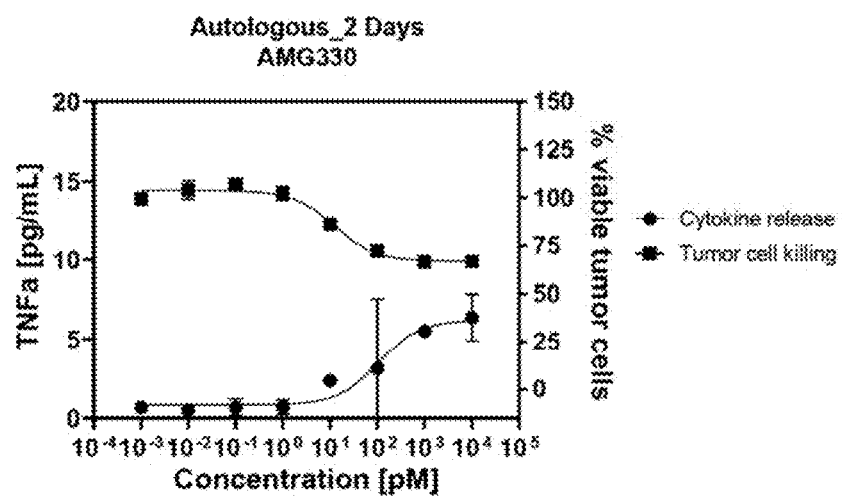
FIG. 59E. Impact of AMG330 similar on cell killing and TNFα release.
Figure 59F:
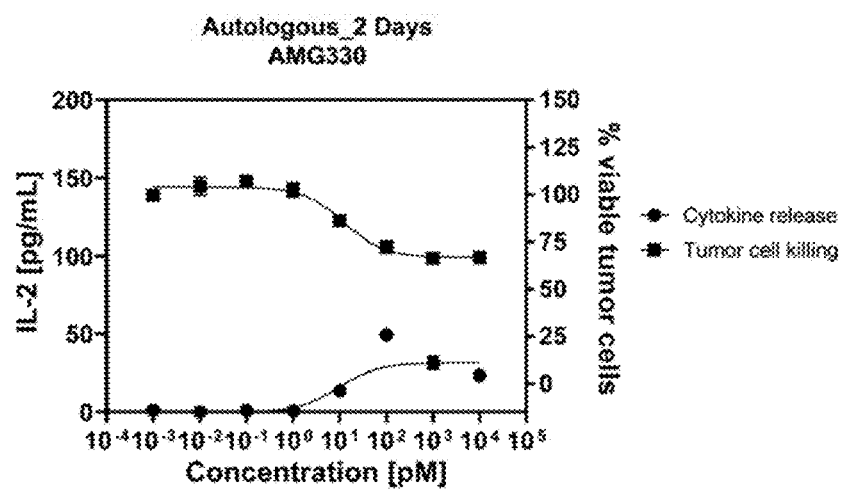
FIG. 59F. Impact of AMG330 similar on cell killing and IL-2 release.
Figure 59G:
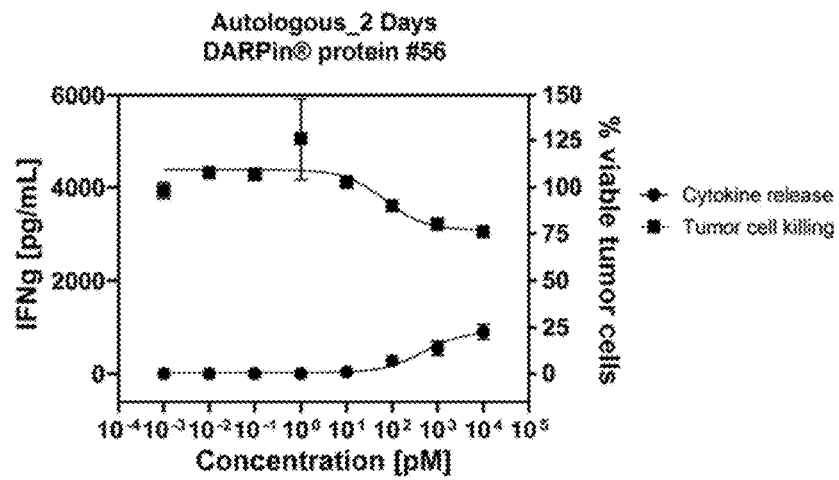
FIG. 59G. Impact of DARPin® protein #56 on cell killing and IFNγ release.
Figure 59H:
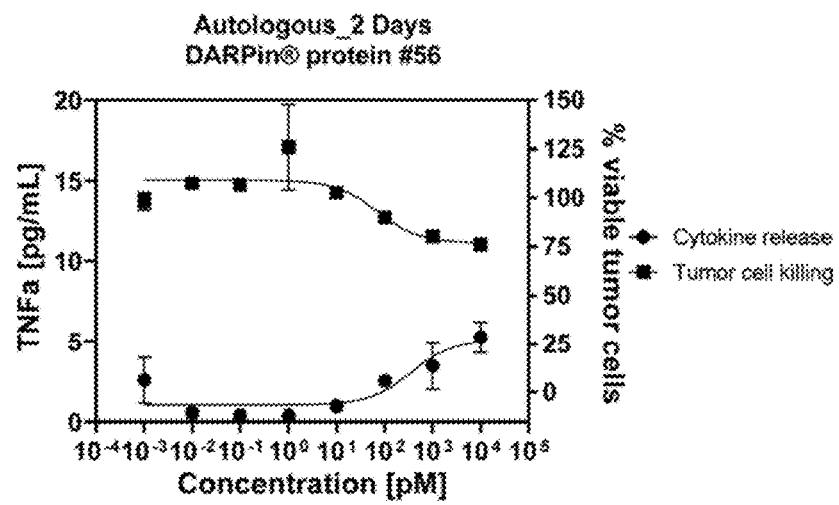
FIG. 59H. Impact of DARPin® protein #56 on cell killing and TNFα release.
Figure 59I:
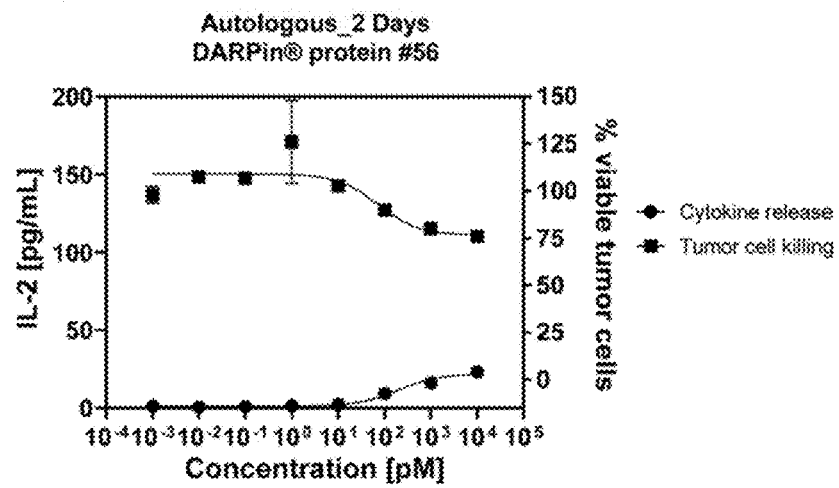
FIG. 59I. Impact of DARPin® protein #56 on cell killing and IL-2 release.
Figure 59J:
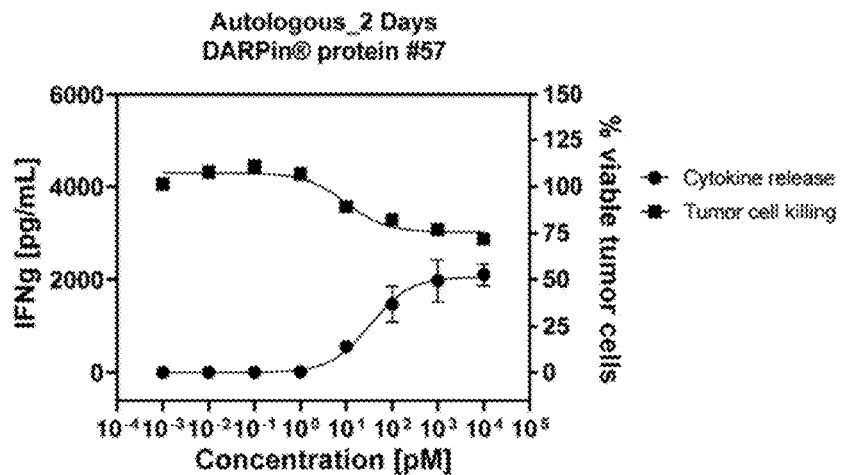
FIG. 59J. Impact of DARPin® protein #57 on cell killing and IFNγ release.
Figure 59K:
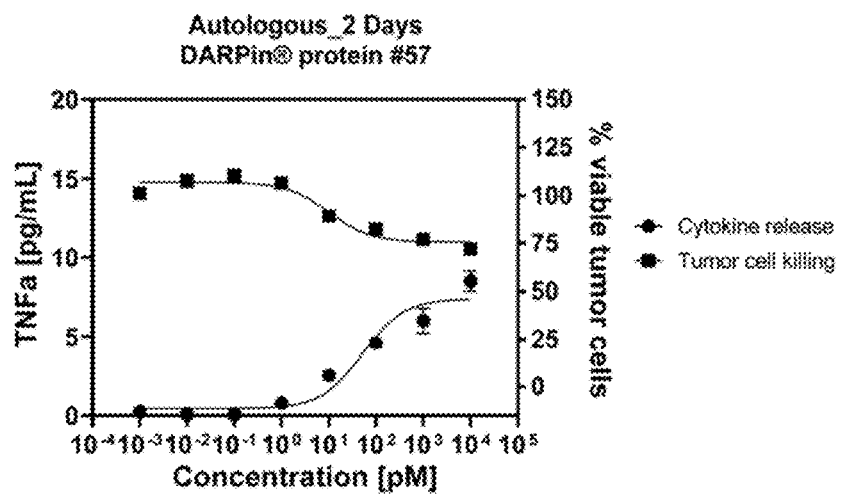
FIG. 59K. Impact of DARPin® protein #57 on cell killing and TNFα release.
Figure 59L:
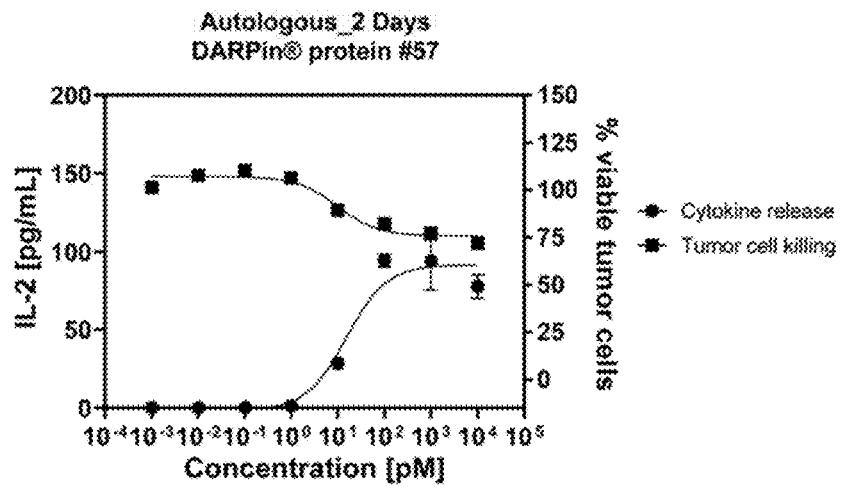
FIG. 59L. Impact of DARPin® protein #57 on cell killing and IL-2 release.
Figure 60A:
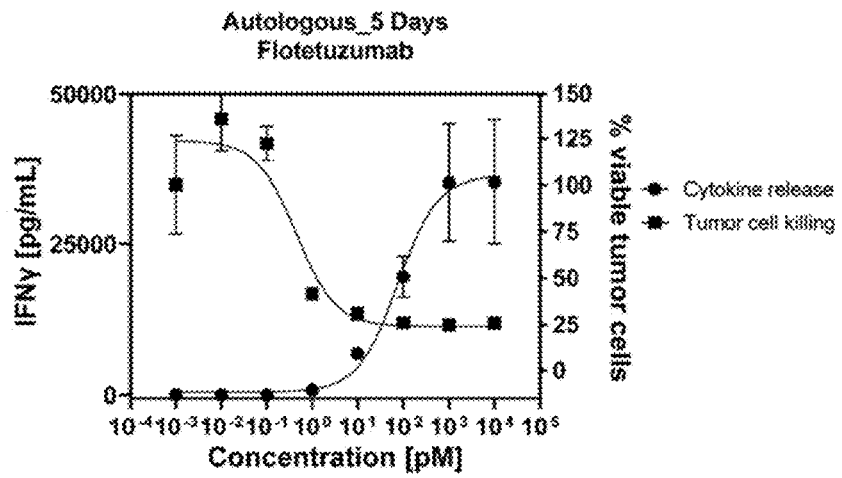
FIG. 60A. Impact of flotetuzumab similar on cell killing and IFNγ release.
Figure 60B:
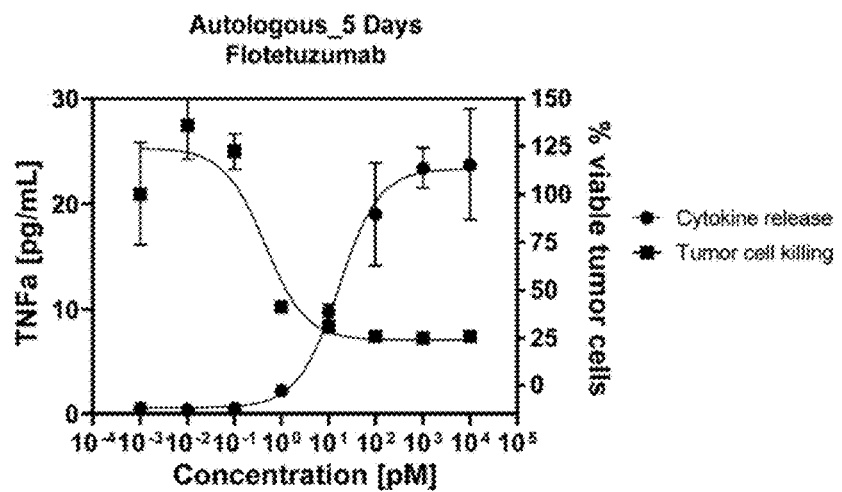
FIG. 60B. Impact of flotetuzumab similar on cell killing and TNFα release.
Figure 60C:
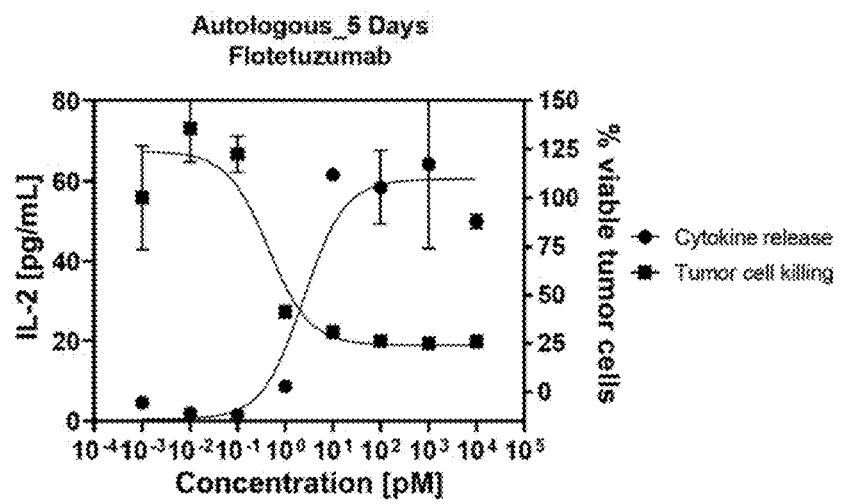
FIG. 60C Impact of flotetuzumab similar on cell killing and IL-2 release.
Figure 60D:
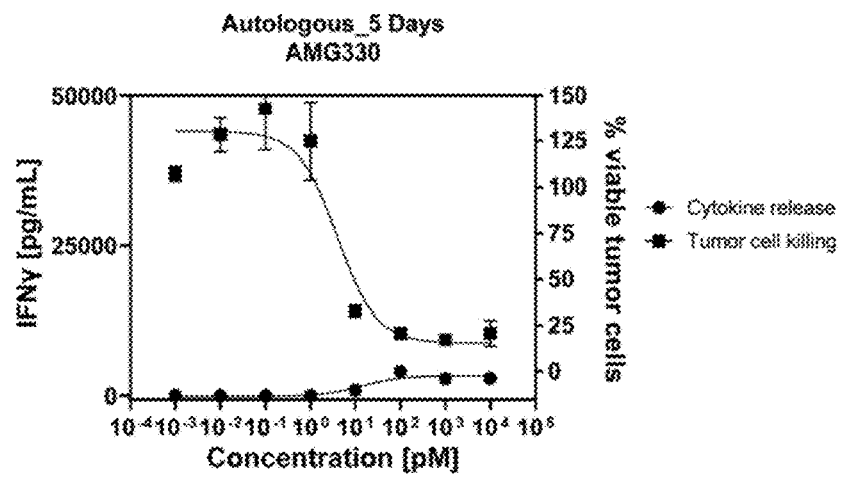
FIG. 60D. Impact of AMG330 similar on cell killing and IFNγ release.
Figure 60E:
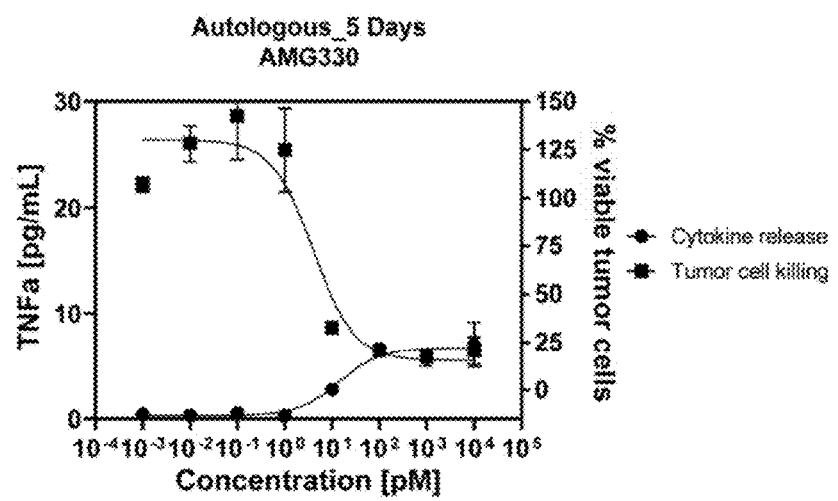
FIG. 60E. Impact of AMG330 similar on cell killing and TNFα release.
Figure 60F:
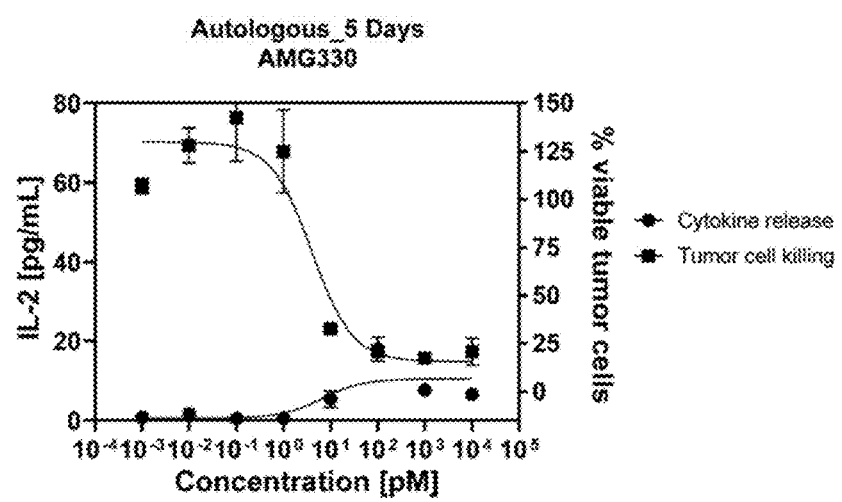
FIG. 60F. Impact of AMG330 similar on cell killing and IL-2 release.
Figure 60G:
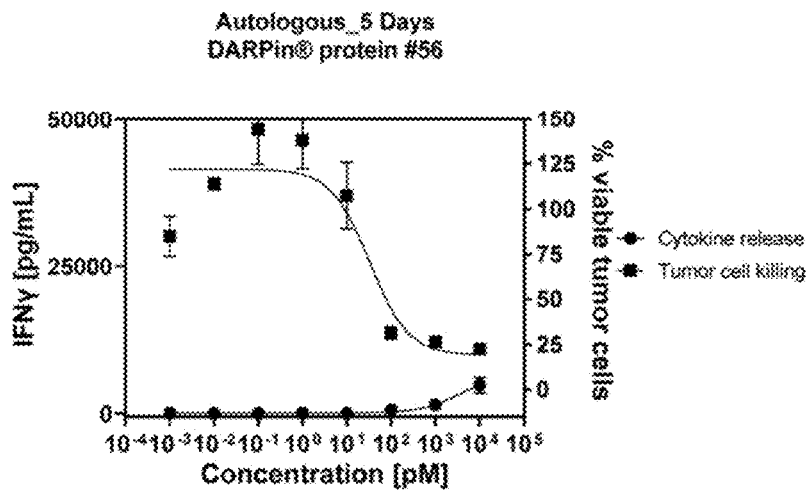
FIG. 60G. Impact of DARPin® protein #56 on cell killing and IFNγ release.
Figure 60H:
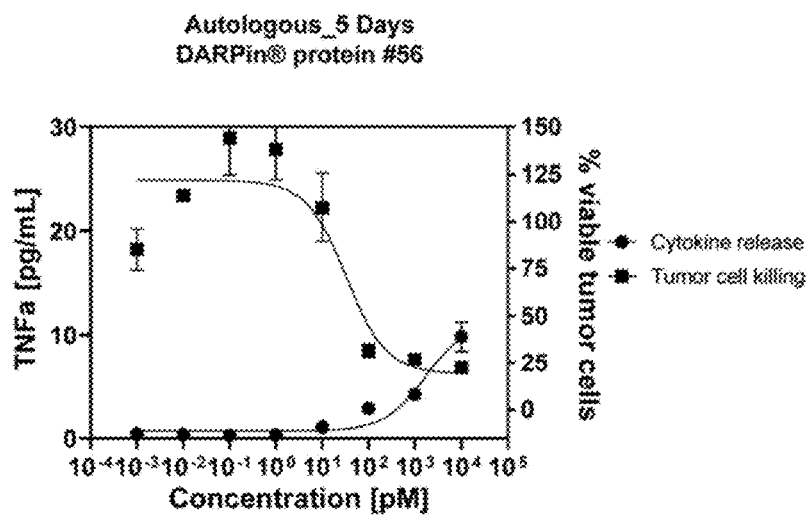
FIG. 60H. Impact of DARPin® protein #56 on cell killing and TNFα release.
Figure 60I:
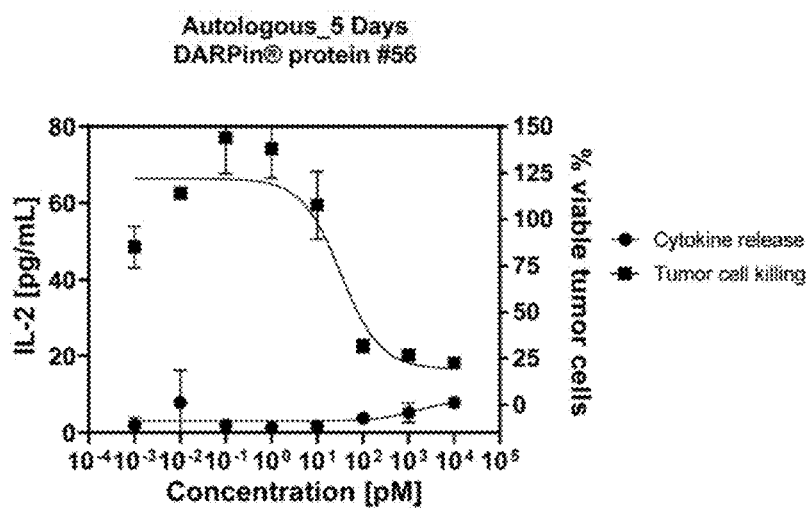
FIG. 60I. Impact of DARPin® protein #56 on cell killing and IL-2 release.
Figure 60J:
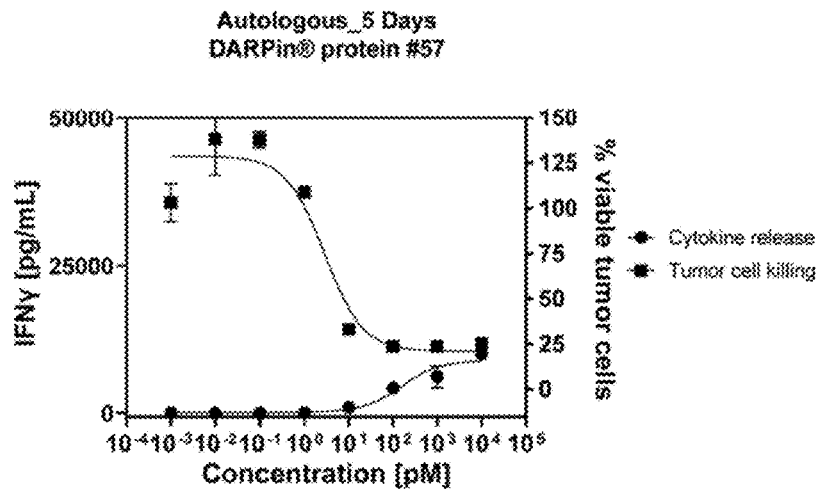
FIG. 60J. Impact of DARPin® protein #57 on cell killing and IFNγ release.
Figure 60K:
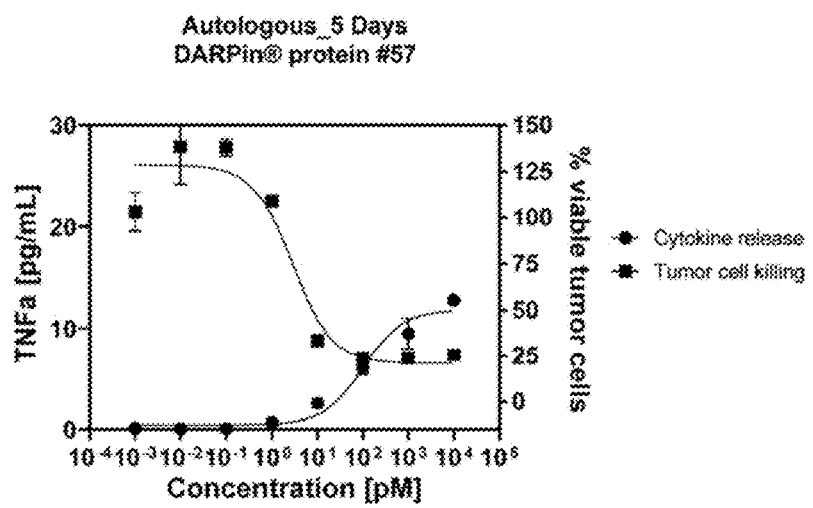
FIG. 60K. Impact of DARPin® protein #57 on cell killing and TNFα release.
Figure 60L:
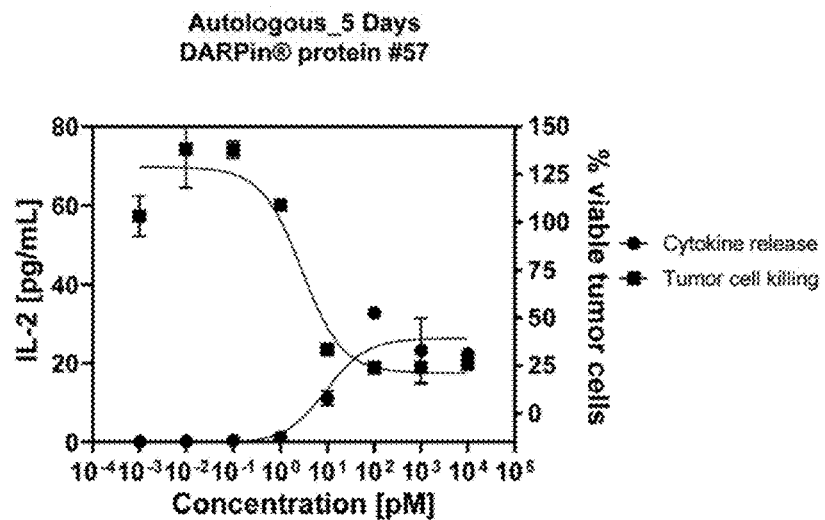
FIG. 60L. Impact of DARPin® protein #57 on cell killing and IL-2 release.
Figure 61A:
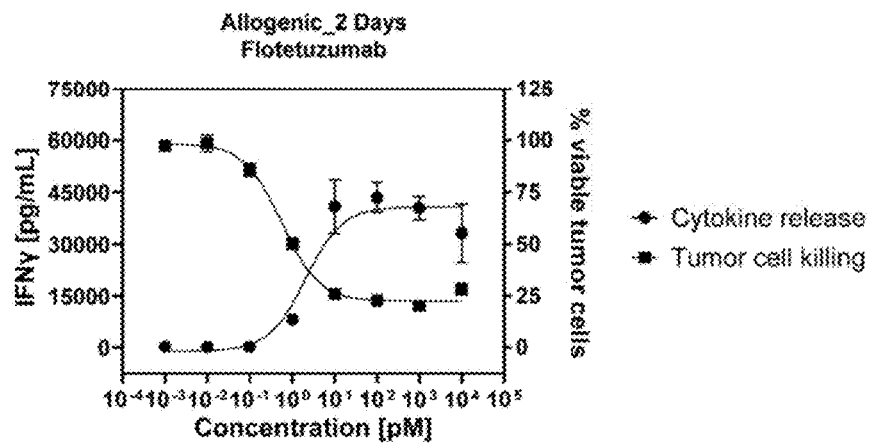
FIG. 61A. Impact of flotetuzumab similar on cell killing and IFNγ release.
Figure 61B:
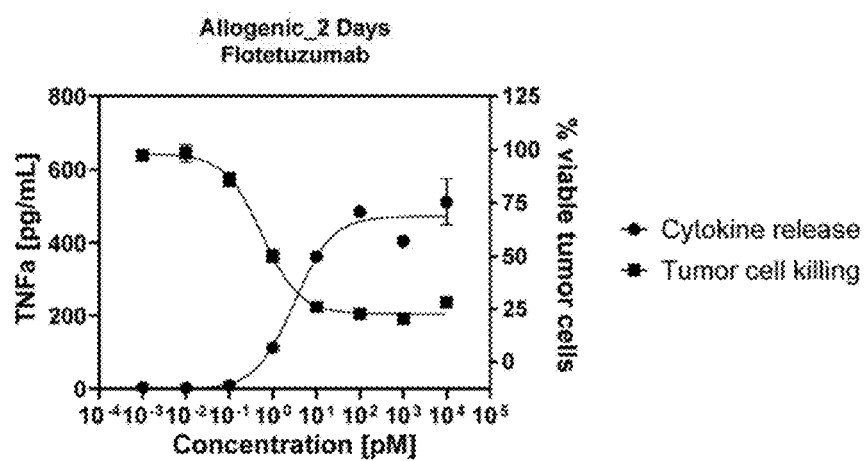
FIG. 61B. Impact of flotetuzumab similar on cell killing and TNFα release.
Figure 61C:
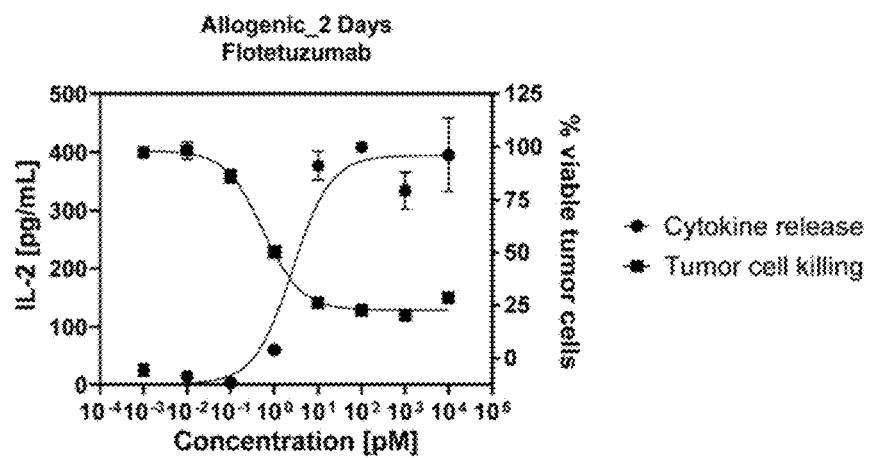
FIG. 61C Impact of flotetuzumab similar on cell killing and IL-2 release.
Figure 61D:
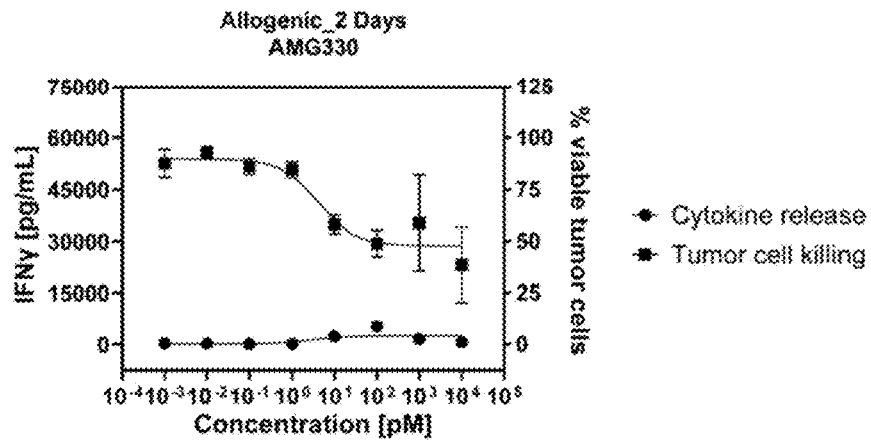
FIG. 61D. Impact of AMG330 similar on cell killing and IFNγ release.
Figure 61E:
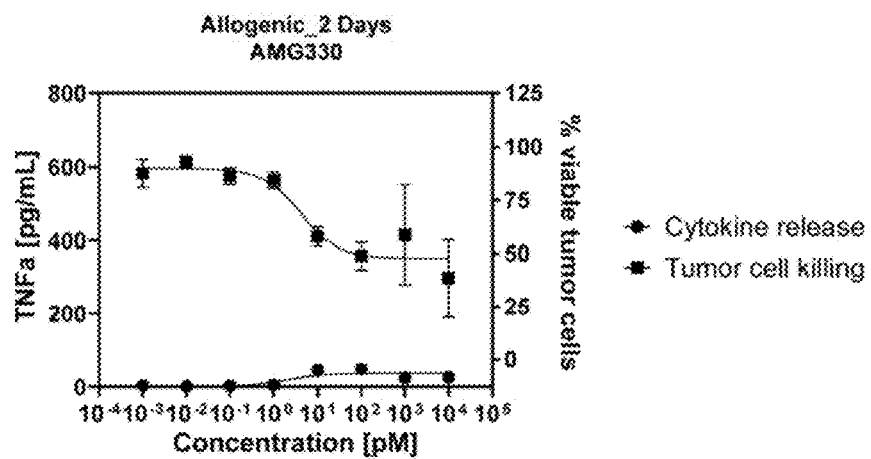
FIG. 61E. Impact of AMG330 similar on cell killing and TNFα release.
Figure 61F:
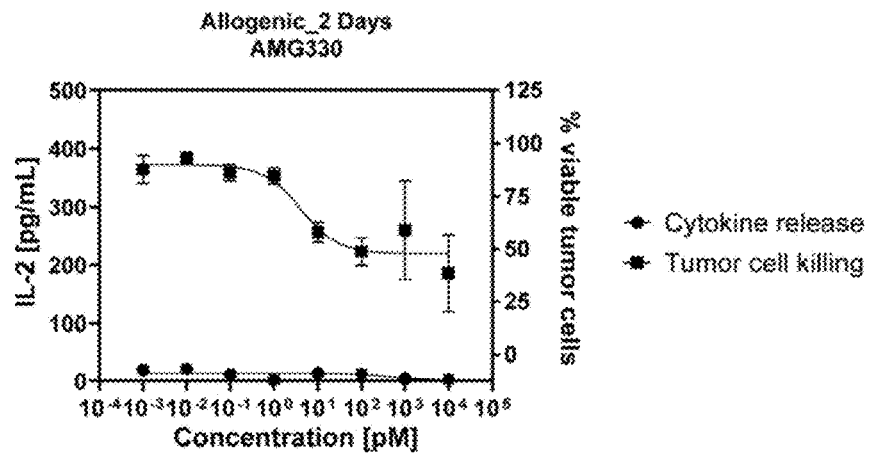
FIG. 61F. Impact of AMG330 similar on cell killing and IL-2 release.
Figure 61G:
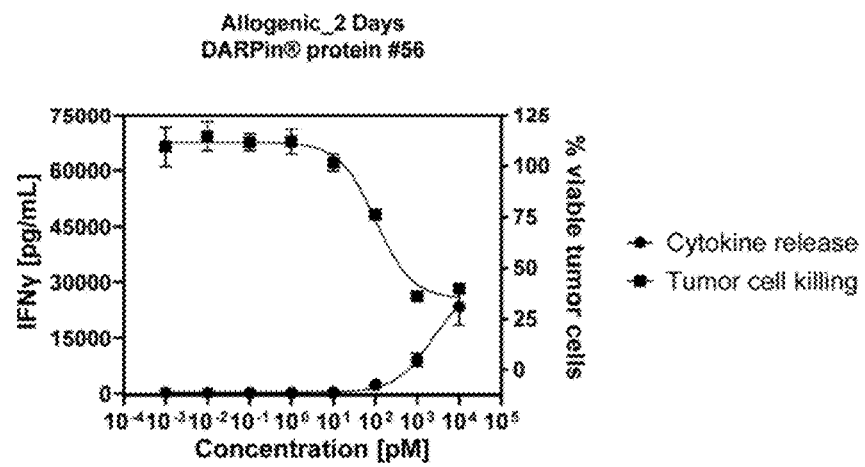
FIG. 61G. Impact of DARPin® protein #56 on cell killing and IFNγ release.
Figure 61H:
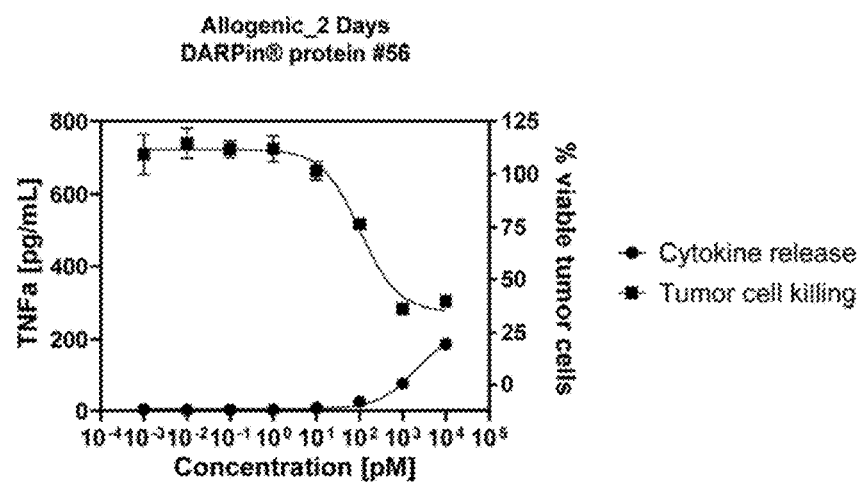
FIG. 61H. Impact of DARPin® protein #56 on cell killing and TNFα release.
Figure 61I:
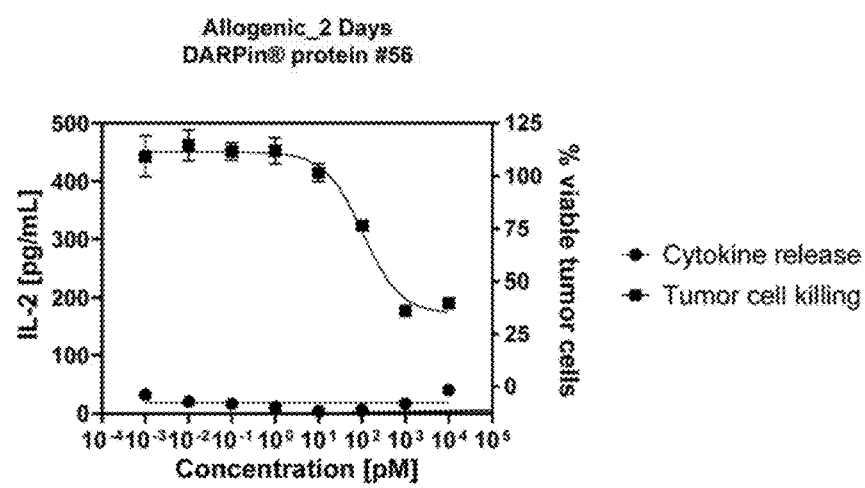
FIG. 61I. Impact of DARPin® protein #56 on cell killing and IL-2 release.
Figure 61J:
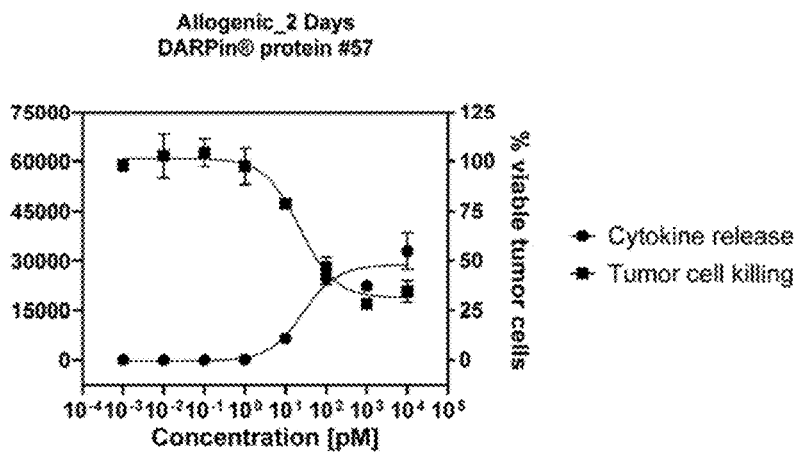
FIG. 61J. Impact of DARPin® protein #57 on cell killing and IFNγ release.
Figure 61K:
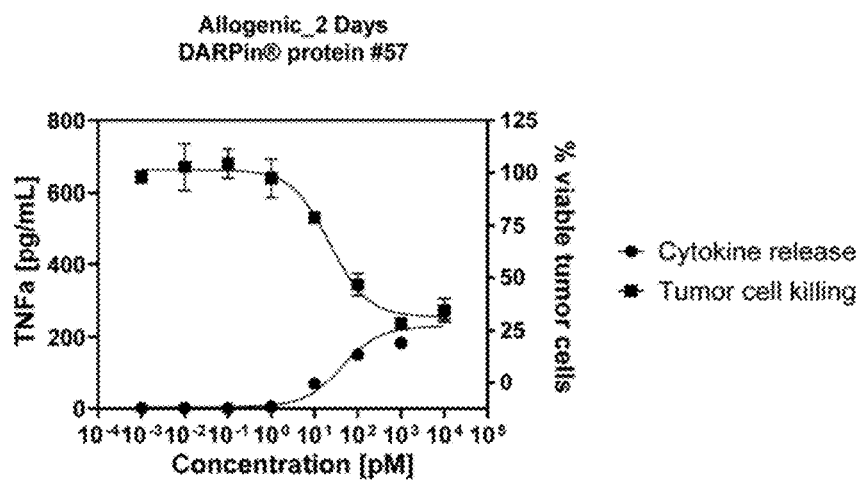
FIG. 61K. Impact of DARPin® protein #57 on cell killing and TNFα release.
Figure 61L:
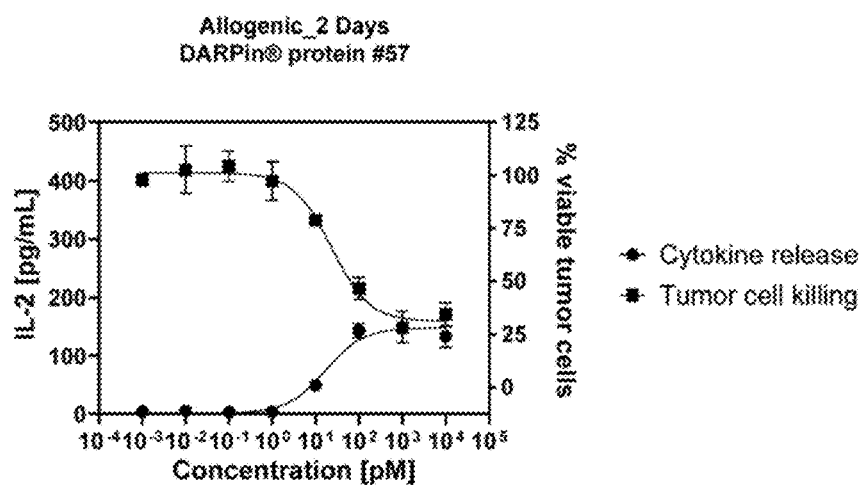
FIG. 61L. Impact of DARPin® protein #57 on cell killing and IL-2 release.
Figure 62A:
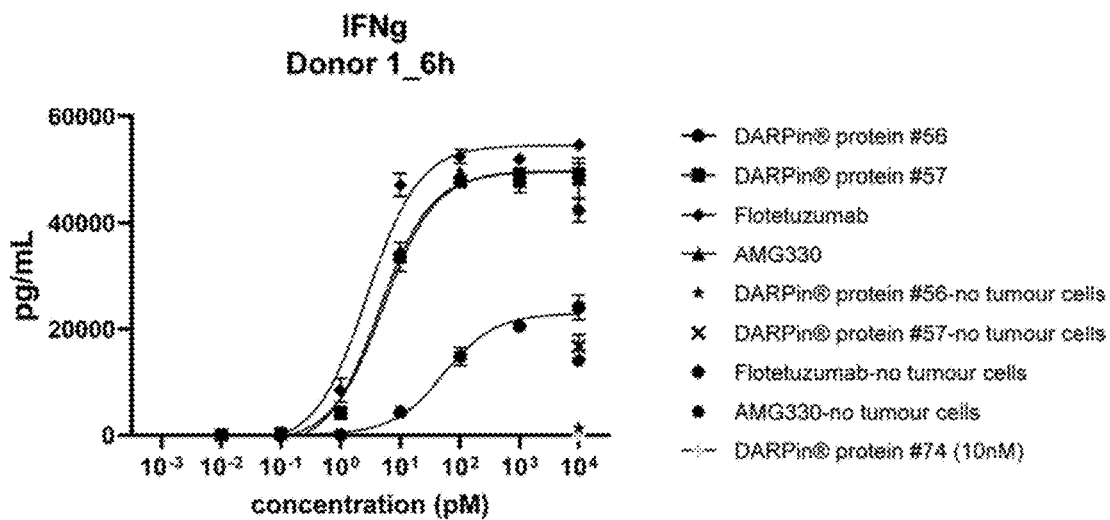
FIG. 62A. IFN release in Donor 1 blood.
Figure 62B:
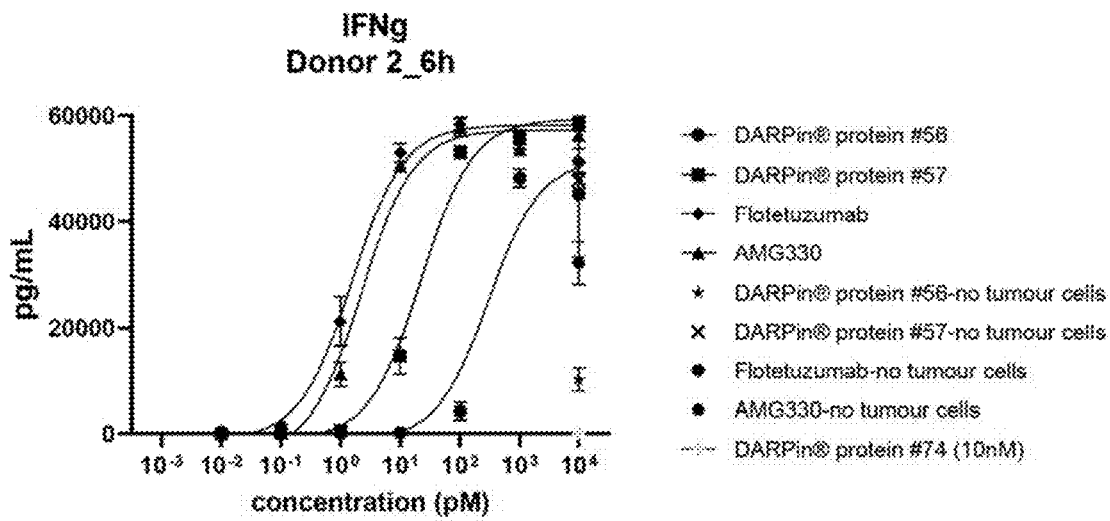
FIG. 62B. IFN release in Donor 2 blood.
Figure 62C:
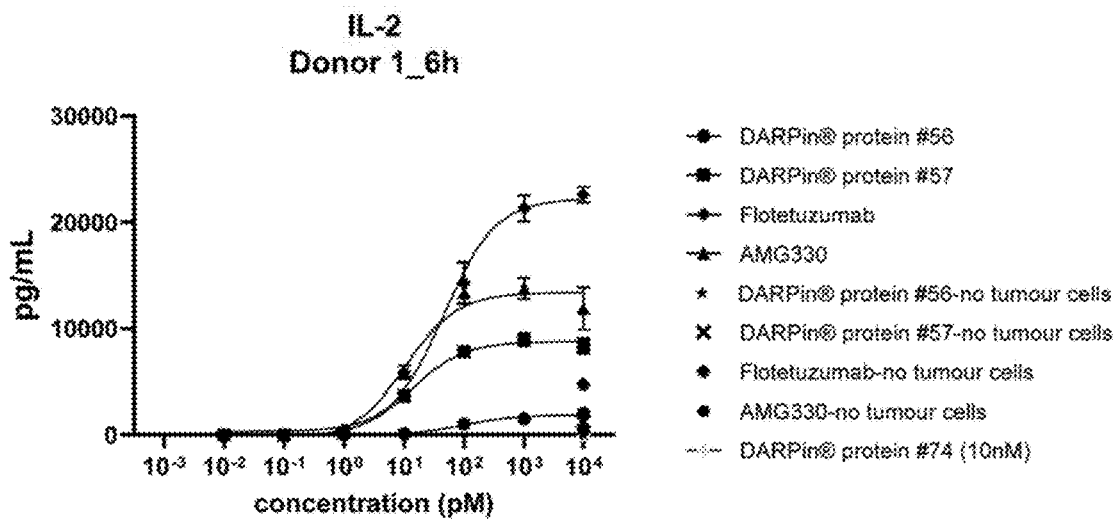
FIG. 62C. IL-2 release in Donor 1 blood.
Figure 62D:
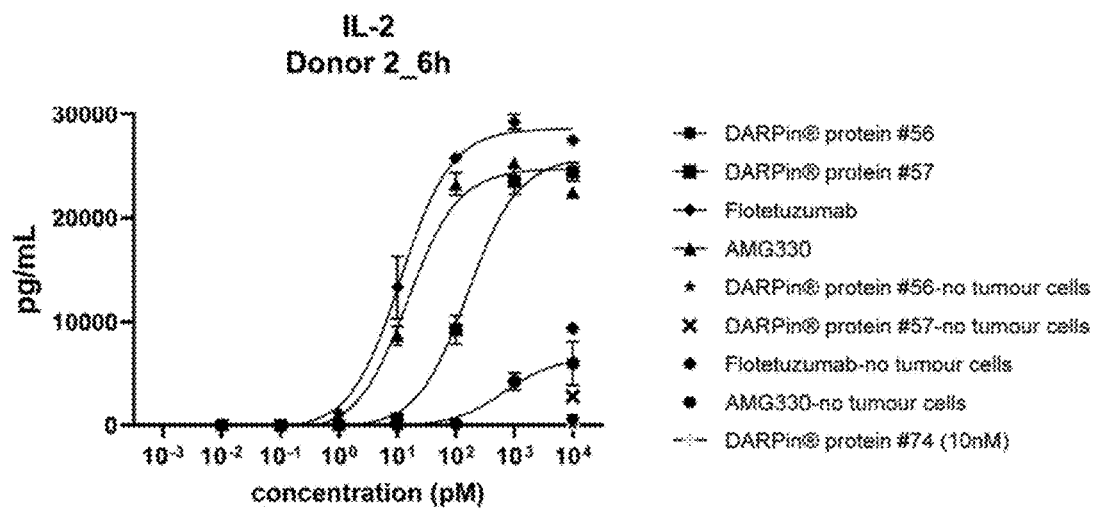
FIG. 62D. IL-2 release in Donor 2 blood.
Figure 62E:
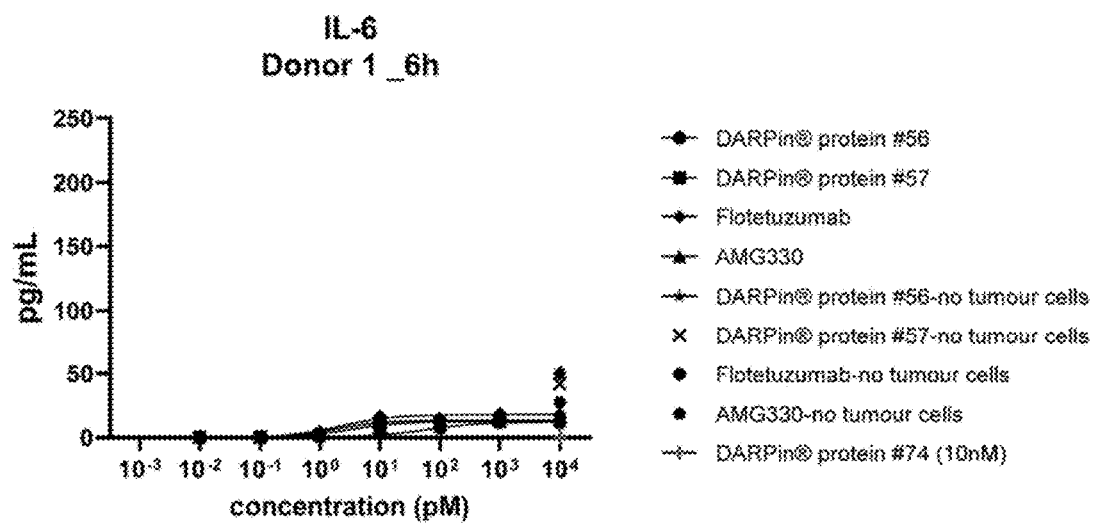
FIG. 62E. IL-6 release in Donor 1 blood.
Figure 62F:
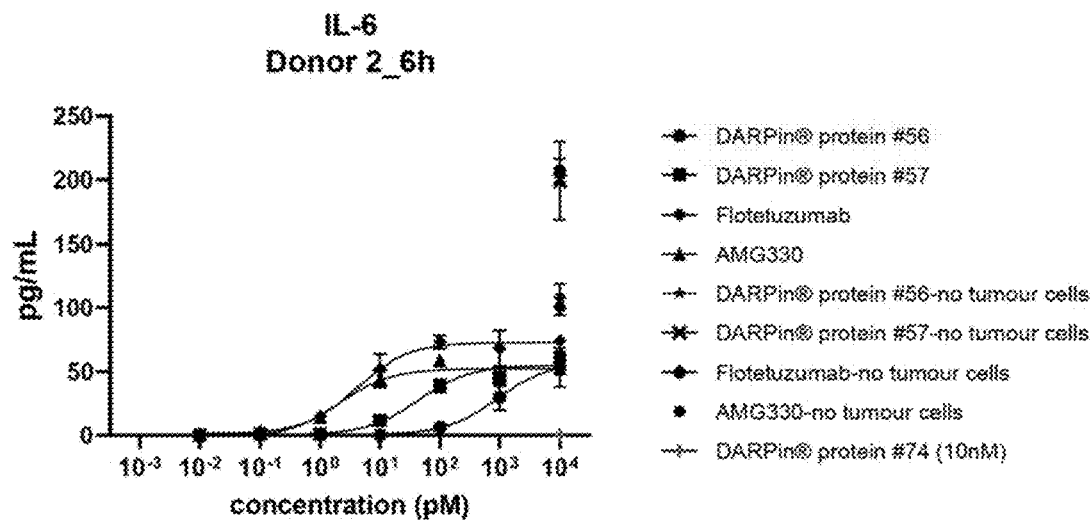
FIG. 62F. IL-6 release in Donor 2 blood.
Figure 62G:
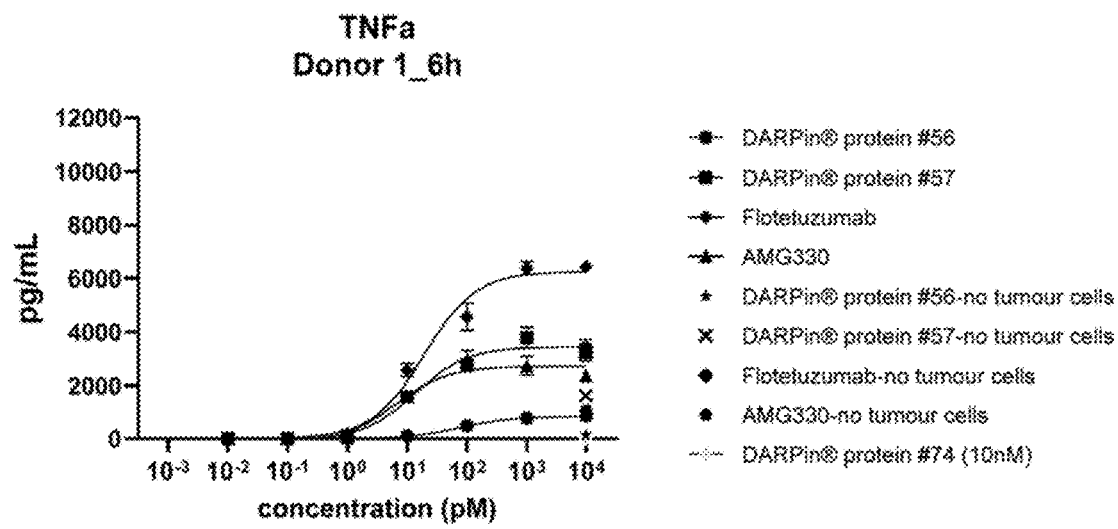
FIG. 62G. TNFα release in Donor 1 blood.
Figure 62H:
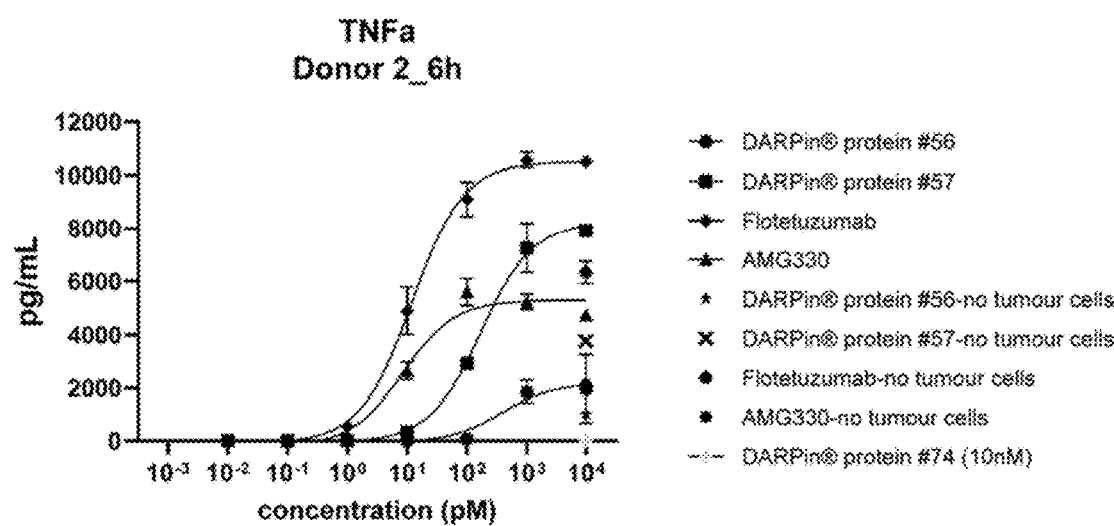
FIG. 62H. TNFα release in Donor 2 blood.

As it can be seen in FIG. 58 (A-B), DARPin® protein #56 shows good efficacy in terms of inhibition of tumor growth and tumor volume over the entire time of the experiment (FIG. 58A) and at 17 days after the first injection (FIG. 58B).

Experiment C. In a similar experimental setup and procedure as in Experiments A and B, two designed ankyrin repeat proteins with binding specificity for CD70, CD33, CD123 and CD3, i.e. DARPin® protein #56 and DARPin® protein #57, were tested in a Peripheral Blood Mononuclear Cell (PBMC) humanized mouse model bearing the tumor cell line MOLM-13 as solid subcutaneous tumor and compared to AMG330 and flotetuzumab as positive controls and DARPin® protein #74 (a CD3 specific binding protein) and DARPin® protein #75 (a CD33/CD70/CD123 specific binding protein) as negative controls.

As in Experiment B, NXG mice were injected intraperitoneally with hPBMC two days before the xenograft of the cancer cells. MOLM-13 cells were xenografted subcutaneously (s.c.) on the right flank area into NXG mice. Two to six hPBMC donors were used depending on the treatment. Treatments were injected intravenously (i.v.) starting eight days after cancer cell implantation (therapeutic treatment). All tumors were established at this time point. The average of tumor volume was around 150 $mm^3$.

Figure 65:
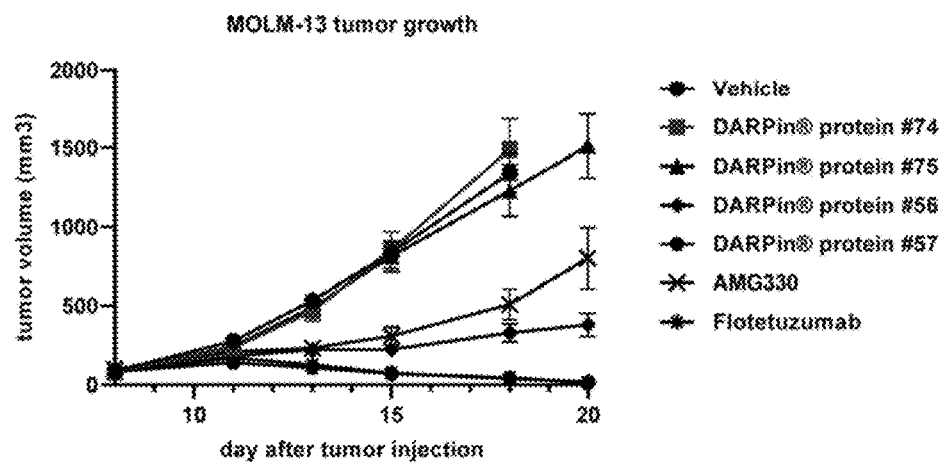
FIG. 65: Tumor growth over time in mice injected intraperitoneally with hPBMC (n=5 mice per donor/2 to 6 hPBMC donors used depending of the treatment), xenografted subcutaneously with MOLM-13 cells and treated with PBS 1× (vehicle), DARPin® protein #74 at 0.5 mg/kg, DARPin® protein #75 at 0.5 mg/kg, DARPin® protein #56 at 0.5 mg/kg, DARPin® protein #57 at 0.5 mg/kg, AMG330 similar at 0.5 mg/kg and Flotetuzumab similar at 0.5 mg/kg eight days after tumor cell injection.
Figure 66:
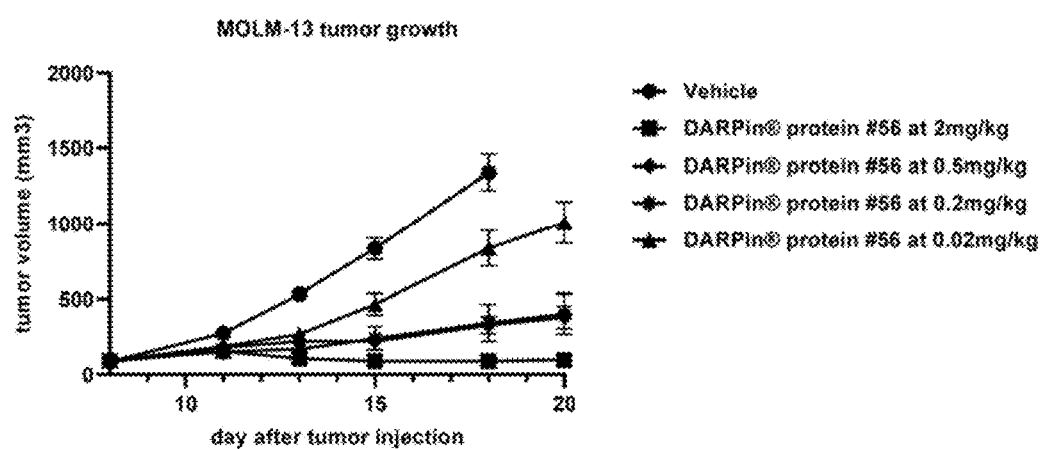
FIG. 66: Tumor growth over time in mice injected intraperitoneally with hPBMC (n=5 mice per donor/2 to 6 hPBMC donors used depending of the treatment), xenografted subcutaneously with MOLM-13 cells and treated with PBS 1× (vehicle). DARPin® protein #56 at 2 mg/kg, DARPin® protein #56 at 0.5 mg/kg, DARPin® protein #56 at 0.2 mg/kg and DARPin® protein #56 at 0.02 mg/kg eight days after tumor cell injection.

FIG. 65 shows the effect of the tested proteins on the tumor volume over time after treatment. As it can be seen, both tested multi-specific proteins, DARPin® protein #56 and DARPin® protein #57, provided effective inhibition of tumor growth. FIG. 66 shows the effect of different treatment amounts of DARPin® protein #56 (0.02 to 2 mg/kg) on tumor growth. Tumor growth inhibition became more potent with increasing amounts of administered DARPin® protein #56.

Treatments were administrated as follow:

DARPin® protein #56, DARPin® protein #74, DARPin® protein #75 and DARPin® protein #57 were administrated i.v. three times per week for 2 weeks. All molecules were administrated at 0.5 mg/kg. DARPin® protein #56 was also tested at several other doses (0.02 mg/kg, 0.2 mg/kg and 2 mg/kg).

Flotetuzumab similar and AMG similar were administrated i.v. daily for 2 weeks at 0.5 mg/kg Tumor size was evaluated by calliper measurement. Tumor volumes were calculated using the following formula: tumor volume $(mm^3)=0.5 \times length \times width^2$.

Figure 67A:
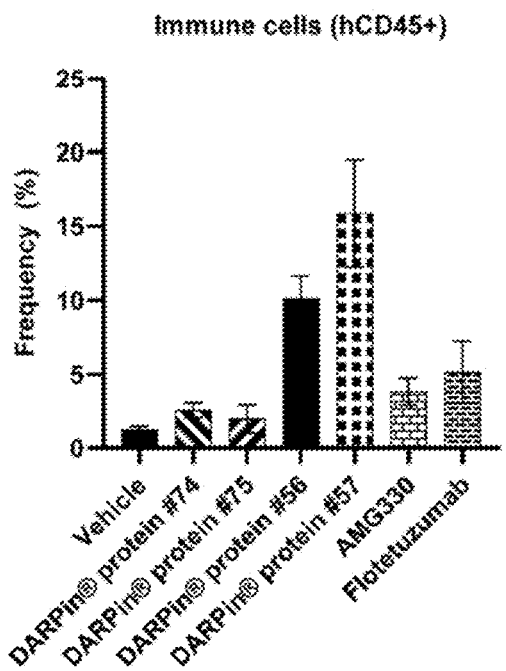
FIG. 67 (A-C): Frequency of human immune cells expressing CD45 (i.e. CD45+) (FIG. 67A) and of activated human T cells (CD4-expressing, FIG. 67B; or CD8-expressing, FIG. 67C) (measured by T cell activation markers CD25 and CD69) in dissociated MOLM-13 tumors after treatment. Activated T-cells were gated as living CD4+/CD25+/CD69+ cells (FIG. 67B) and as living CD8+/CD25+/CD69+ cells (FIG. 67C).
Figure 67B:
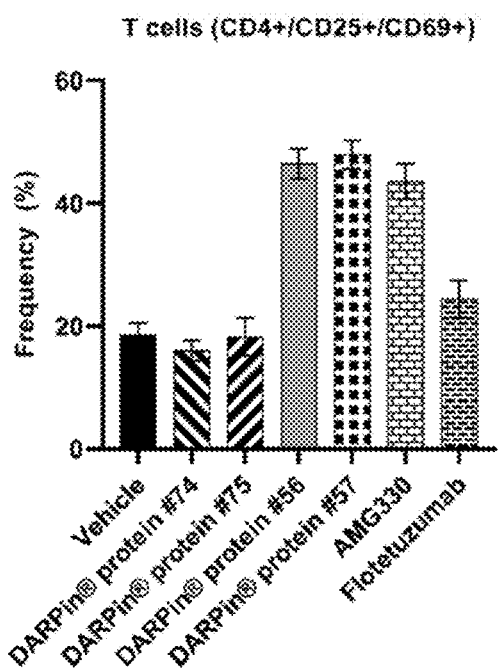
Figure 67C:
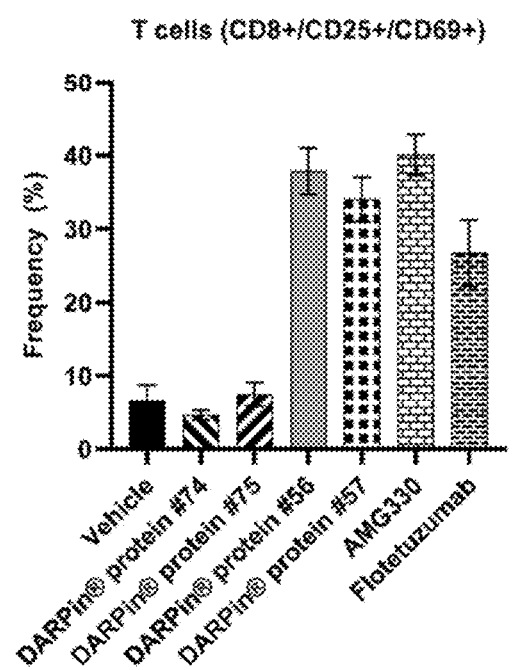
Figure 68A:
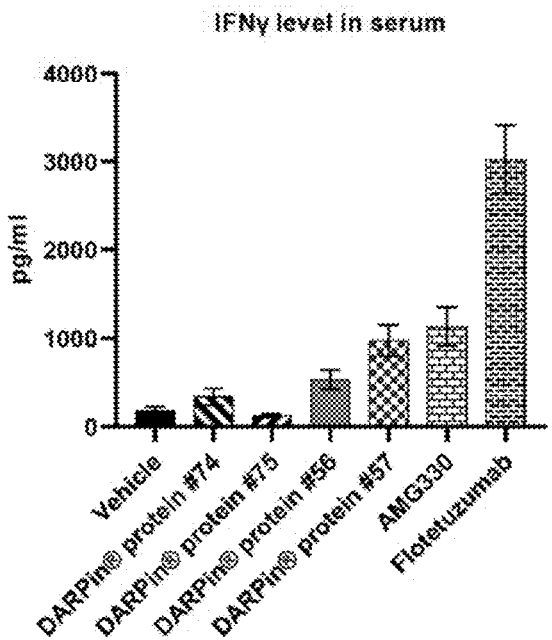
FIG. 68A. Levels of IFNγ, FIG. 68B. Levels of IL-6, FIG. 68C. Levels of IL-2, and FIG. 68D. Levels of TNFα.
Figure 68B:
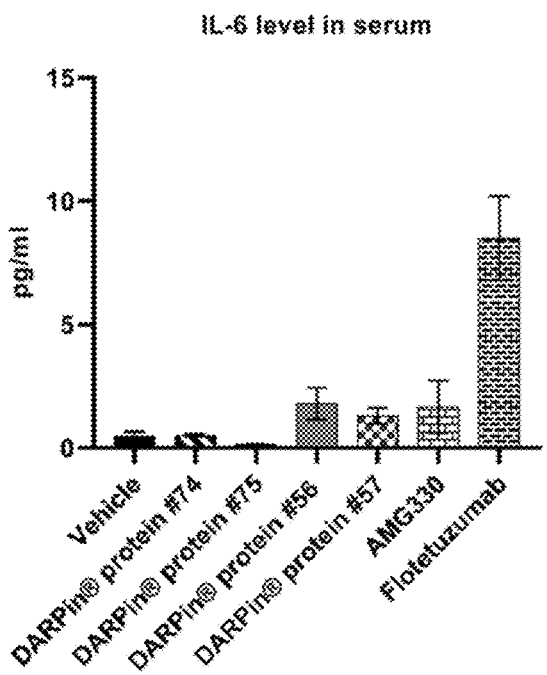
FIG. 68 (A-D). Cytokine and chemokine release in mouse serum after treatment.
Figure 68C:
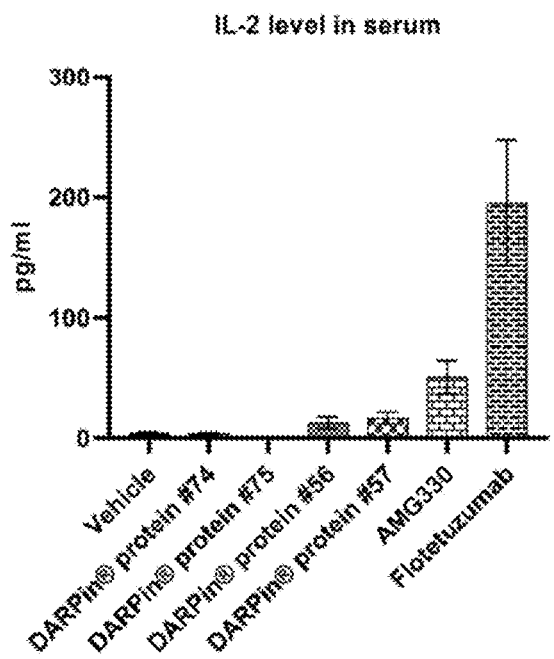
Figure 68D:
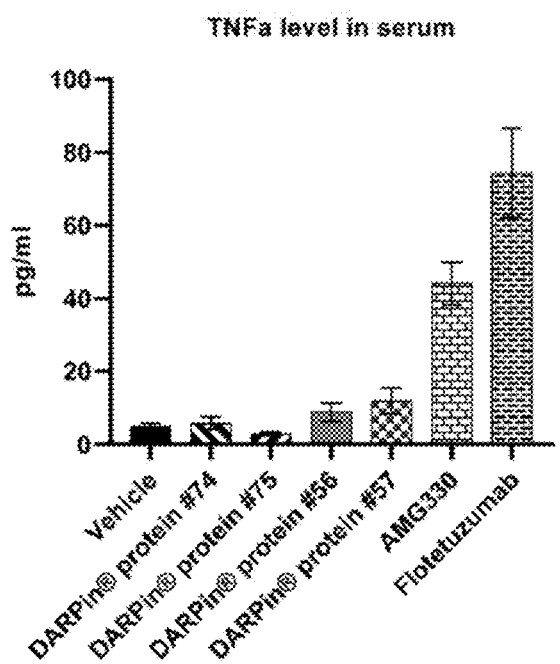

In order to correlate in vivo efficacy with the mode of action of the tested multi-specific proteins, ex vivo assays were performed in parallel to the in vivo model. For this purpose, NXG mice were injected intraperitoneally with hPBMC from the same donors and treated as described above. More particularly, T cell activation was assessed by FACS and cytokine/chemokine release was determined in mouse serum and mouse tumor supernatant by Luminex™ and Meso Scale Discovery (MSD) assays, respectively. In brief, for the T cell activation evaluation, three days after the first injection with the tested proteins, part of the mice were sacrificed. Tumors were dissociated by gentleMACS™ according to the provider's protocol and FACS assays were performed on cell suspensions. FIG. 67 shows the frequency of human immune cells (hCD45+) and activated T cells (CD4+/CD25+/CD69+ and CD8+/CD25+/CD69+) in dissociated MOLM-13 tumors. Data are presented in average and SEM (Standard Error of the Mean).

For the evaluation of cytokine and chemokine release in serum, a Luminex™ assay was performed in mouse serum from mouse blood collected four hours after the first injection with the tested proteins. The Luminex™ assay is a human custom multiplex-4 bead array assay purchased from R&D Systems.

More specifically, levels of IFN-gamma, IL-6, IL-2, and TNF-alpha were measured according to the manufacturer's recommendations using a Luminex™ MAGPIX instrument. All test samples were thawed on ice, centrifuged at 2000 rpm for 3 minutes, and then diluted 1:2 in a calibrator diluent. Each test sample was assayed as duplicates. In addition, four QC (quality control) samples were diluted 1:2 in calibrator diluent from various cytokine standard samples (S2, S3, S5, S6—namely of IFN-gamma, IL-6, IL-2, and TNF-alpha) in duplicates, according to the manufacturer's instructions. Cytokine standards supplied by the manufacturer were assayed in duplicates and used to calculate the concentrations of the test samples as well as the QC samples. Cytokine levels were measured in serum samples taken 4 hours after 1st injection. FIG. 68 shows the levels of INFgamma, IL-6, IL-2 and TNFalpha in mouse serum. Data are presented in average and SEM.

Figure 69A:
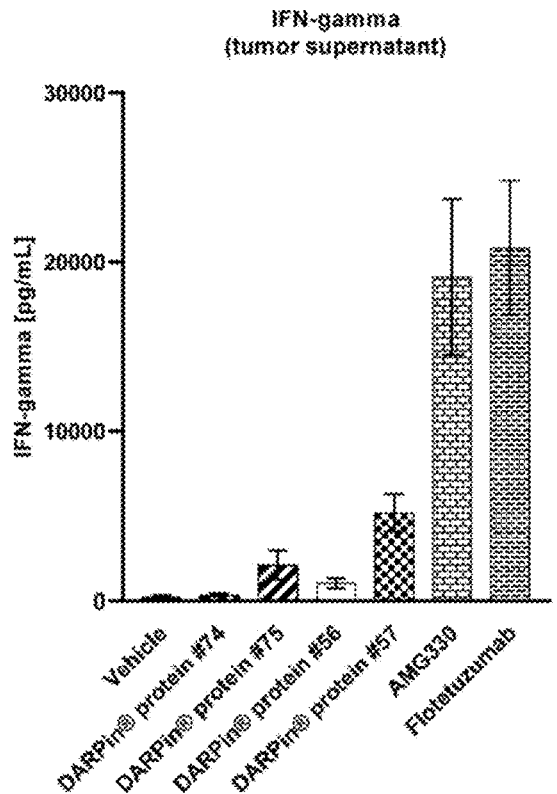
FIG. 69A. Level of IFNγ.
Figure 69B:
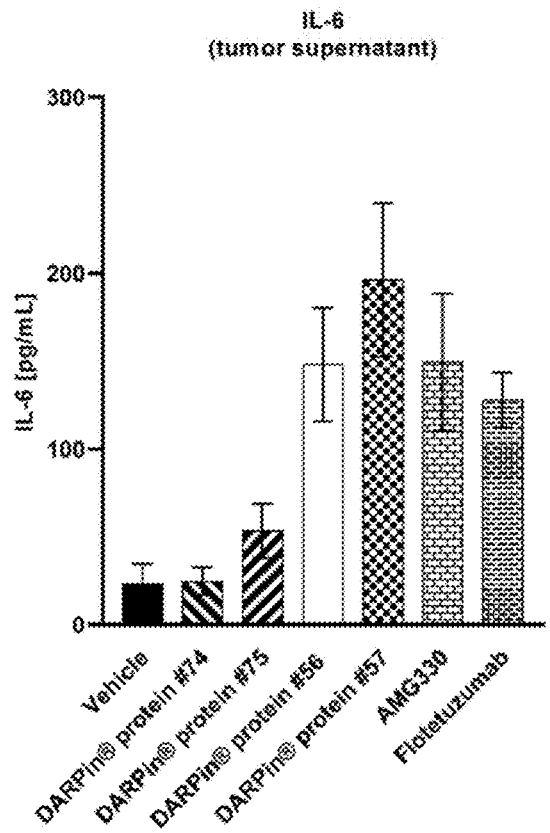
FIG. 69B. Level of IL-6.

Additionally, three days after the first injection with the tested proteins, mice were sacrificed and tumors were harvested. Tumors were dissociated by gentleMACS™ according to the provider's protocol. Cytokine levels in tumor supernatant were measured using Meso Scale Discovery (MSD) Multi-Spot Assay System's VPlex Proinflammatory Panel 1 (human) Kit (K151A9H-4)-customized for IFN-gamma, IL-2, IL-6 and TNFalpha. The assay protocol followed is described in more detail in Examples 18 and 19. FIG. 69 shows the levels of IFNγ and IL-6 in mouse tumor supernatant as examples.

In this experimental setup of Experiment C, DARPin® protein #74 and DARPin® protein #75 did not show any efficacy in vivo (FIG. 65). These data demonstrate that the presence of both a T cell engaging binding domain and tumor associated antigen-specific binding domains in the same molecule (as, e.g., in DARPin® protein #56 and DARPin® protein #57) is required to induce anti-tumor efficacy in vivo. Both tested T cell engager DARPin proteins, DARPin® protein #56 and DARPin® protein #57, showed good anti-tumor efficacy in vivo (FIG. 65). This anti-tumor efficacy was concentration dependent (FIG. 66). The in vivo anti-tumor activity of the TCE proteins of the invention is thought to be due to increased numbers of immune cells and T cell activation in the tumor tissue (FIG. 67). TCE proteins of the invention trigger cytokine/chemokine release in tumor tissue (FIG. 69), but much less or insignificantly in the serum (FIG. 68), which is consistent with a beneficial safety profile.

Example 15: Assessment of Target-Specific Short-Term Autologous and Allogenic T Cell Activation, and Tumor Cell Killing in Co-Culture with AML Patient BMMC Tumor Cells Specificity and potency of DARPin® protein #56 were assessed in an in vitro short-term T cell activation assay by FACS measuring CD25 activation marker on CD8+ T cells in presence of AML patient cells, and in an in vitro tumor cell killing assay by FACS.

Therefore, 120,000 purified pan-T effector cells were labelled with cell trace violet (CTV) according to manufacturer protocol (Thermofisher) and co-cultured with 30,000 AML tumor cells (BMMC, type M4) per well (E:T ratio 4:1) with serial dilutions of DARPin® protein #56 in duplicates in presence of 200 μM human serum albumin for 48 hours at 37° C. After 48 hours, cells were washed and stained with 1:3,000 Live/Dead Green (Thermo Fisher), 1:400 mouse anti-human CD8 Pacific Blue (BD), and 1:100 mouse anti-human-CD25 PerCP-Cy5.5 (eBiosciences) antibodies for 30 min at 4° C. After washing and fixation, cells were analyzed on a FACS Canto II (BD) machine. Allogenic T cell activation was assessed by measuring CD25+ cells on Live/Dead-negative and CD8+ gated T cells, positive for CTV. Autologous T cell activation was assessed by measuring CD25+ cells on Live/Dead-negative and CD8+ gated T cells, negative for CTV violet staining. FACS data was analyzed using FlowJo software and data was plotted using GraphPad Prism 8 (3-PL-fit).

Figure 53A:
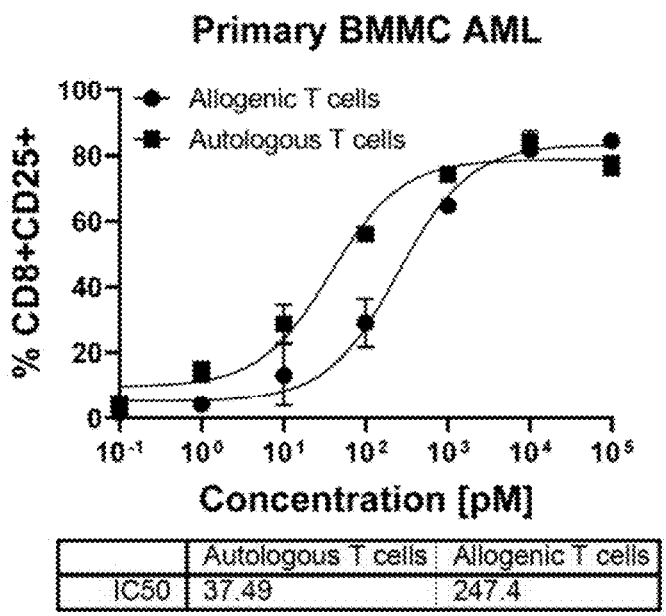
FIG. 53A. Potency Titration curves (allogenic and autologous Tcell activation) of DARPin® protein #56 targeting CD123-CD33-CD70 on AML patient BMMC tumor cells. EC50 values are shown in pM.

As shown in FIG. 53A tested DARPin® protein #56 with binding specificity for CD3, CD33, CD123 and CD70 (thus binding 3 tumor specific targets) induced potent and specific allogenic Tcell activation. In addition upregulation of CD25 Marker on autologous T cells could be shown.

To assess drug- and target-specific tumor cell killing, effector and target cells were co-incubated in duplicates with an E:T ratio of 4:1 in presence of serial dilutions of DARPin® protein #56, negative control DARPin® protein #74, Flotetuzumab-similar and AMG330-similar. Purified (Miltenyi) pan-T cells (isolated form healthy donor PBMCs) were first labelled with Celltrace violet (Thermofisher) according to manufacturer protocol. 120,000 CTV-labelled pan-T cells+30,000 AML tumor cells (BMMC, type M4) per well were then incubated at 37° C. together with serial dilutions of the selected CD3 specific ankyrin repeat proteins or control molecules in presence of 200 μM human serum albumin (to mimic physiological concentration). After 48 hours, cells were washed with PBS and stained with 1:3,000 Live/Dead Green (Thermo Fisher) for 20 min at 4° C. After washing and fixation, cells were analyzed on a FACS Canto II (BD) machine. Tumor cell killing was assessed by gating on CTV negative, single, Live/Dead negative cells. FACS data was analyzed using FlowJo software; data was normalised to background of co-culture only and was plotted using GraphPad Prism 8 (3PL-Fit).

Figure 53B:
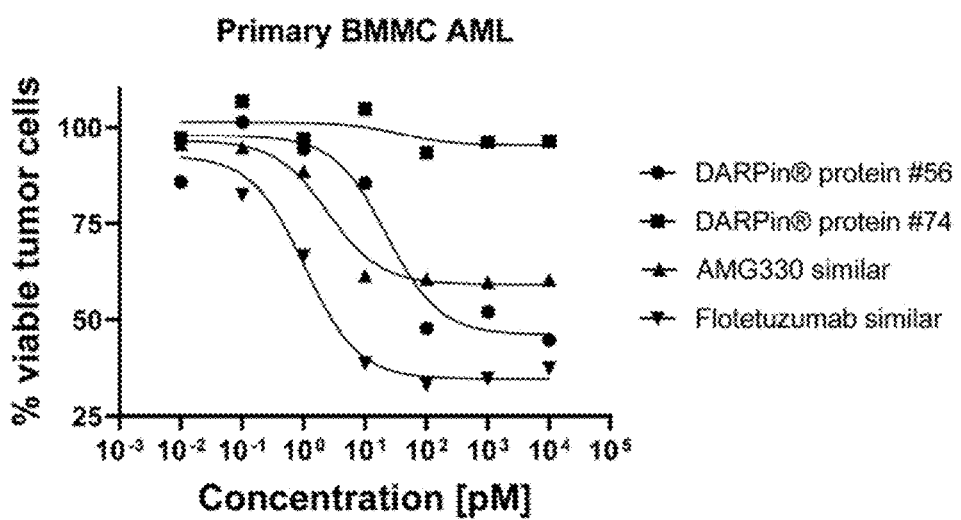
FIG. 53B. Potency Titration curves (cell Killing) of DARPin® protein #56 targeting CD123-CD33-CD70 on AML patient BMMC tumor cells compared to Flotetuzumab and AMG330.

As shown in FIG. 53B, DARPin® protein #56 shows potent and specific tumor cell killing of AML patient derived cells, with efficacy lying in between the compared AMG330-similar and flotetuzumab-similar. Negative control barely leads to tumor cell killing.

Example 16: Effect of Multi-Specific Binding Proteins in Autologous Killing of Ex Vivo AML Cells The effect of selected multi-specific binding proteins in autologous killing of ex vivo AML cells was assessed by an ex vivo personalized medicine testing in native environment provided by Vivia Biotech, using a proprietary automated flow cytometry-based technology (PharmaFlow™), in order to perform a complete pharmacological characterization of drugs in ex vivo patients' samples. In addition, Vivia can streamline clinical development by generating predictive ex vivo native environment assays and identifying reliable and robust predictive biomarkers in parallel to the drug profiling and characterization, providing high content, reliable, clinically actionable and predictive data of the activity of compounds.

The objectives of this study were to:
1. Evaluate cell surface expression of targets of molecules (CD123, CD33 and CD70) at baseline by flow cytometry.
2. Perform ex vivo pharmacological activity of different tested proteins together with Flotetuzumab, as single agents, in Vivia's Native Environment Immuno-Oncology assay.
3. Preserve the supernatant of each well, condition and time point for post-assay measurement of soluble cytokines.
4. Perform an evaluation of different cytokines levels in the preserved supernatants.

The experimental design was performed as follows:
Quantification of molecule targets expression (CD123, CD33 and CD70), using beads, on pathological cells, in triplicate, at baseline.
Measure depletion and activation simultaneously on both pathological and T-cells by dose response curves:
8 different concentrations (50 nM, 10 nM, 2 nM, 0.4 nM, 0.08 nM, 0.016 nM, 0.0032 nM and 0.00064 nM) of tested proteins DARPin® protein #56 (SEQ ID NO:95), DARPin® protein #57 (SEQ ID NO:96), DARPin® protein #58 (SEQ ID NO:97), DARPin® protein #59 (SEQ ID NO:98), DARPin® protein #60 (SEQ ID NO:99) and DARPin® protein #61 (SEQ ID NO:100)
8 different concentrations (as above) of one benchmark molecule (Flotetuzumab (MPEXT118)) in monotherapy.
1 high concentration in triplicate of DARPin® protein #74 as negative control.
1 negative control in triplicate (Negative controls means no compound, these wells only contain the solvent).
2 incubation time points (72 h and 120 h).
Supernatant preservation for future measurement of soluble cytokines:
Store the supernatants from all experimental conditions at −80° C., after each incubation time (72 h and 120 h).
Measure different cytokines levels in supernatant.
Sample Collection Vivia used for this project 5 frozen bone marrow samples from adult AML patients that co-express CD123 and CD33 (samples ID: 13043, 13045, 13271, 13272, 15131). Samples were extracted into Vacutainer™ tubes containing heparin as an anticoagulant, at the respective hospital centers within the patient's regular treatment schemes, following clinical practice at the center. A portion of sample was sent to Vivia Biotech laboratory, under Center's Ethical Committees approved research study protocols and signed patient's informed consent.

A small fraction of the sample was stained with specific monoclonal antibodies (MoAb) to identify pathological cells and cell viability. Once live cell numbers were established and considered to be enough for analysis, a second staining was performed in a different fraction of the sample to determine the expression of target proteins (CD123, CD33, CD70), compared to isotype control. Expression of the targets were quantified using QuantiBRITE PE kit (Becton Dickinson), following the manufacturer's recommendations. All 5 samples show expression of CD33 and CD123, CD33 being the strongest TAA expressed. CD70 expression is below the limit of detection of the kit.

Figure 54A:
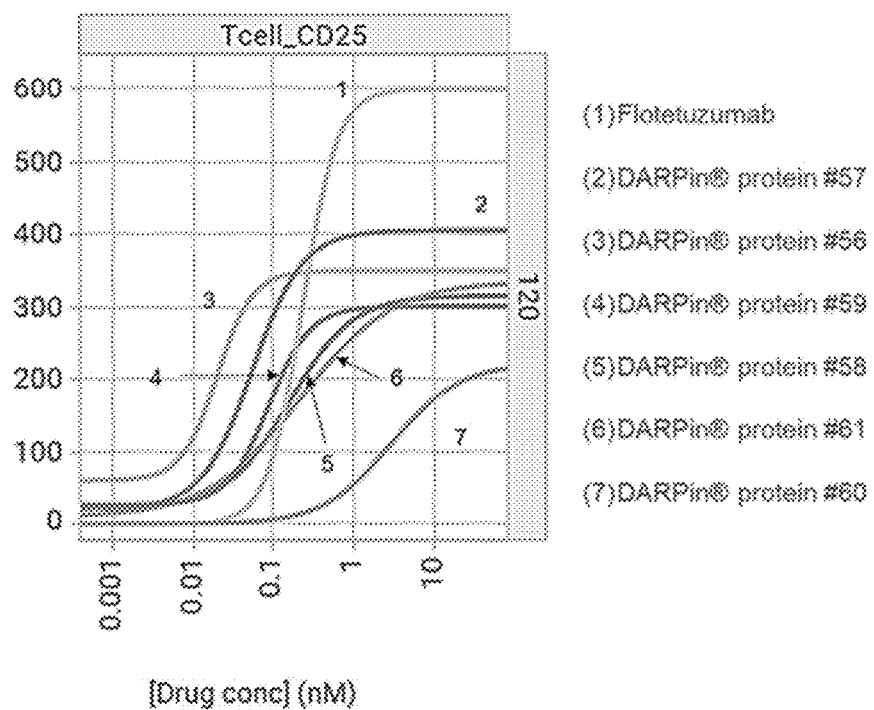
FIG. 54 (A-B)
FIG. 54B. Potency Titration curves (tumor cell killing) of selected multi-specific DARPin® proteins targeting CD123-CD33-CD70 on AML patient BMMC tumor cells compared to Flotetuzumab.
Figure 54B:
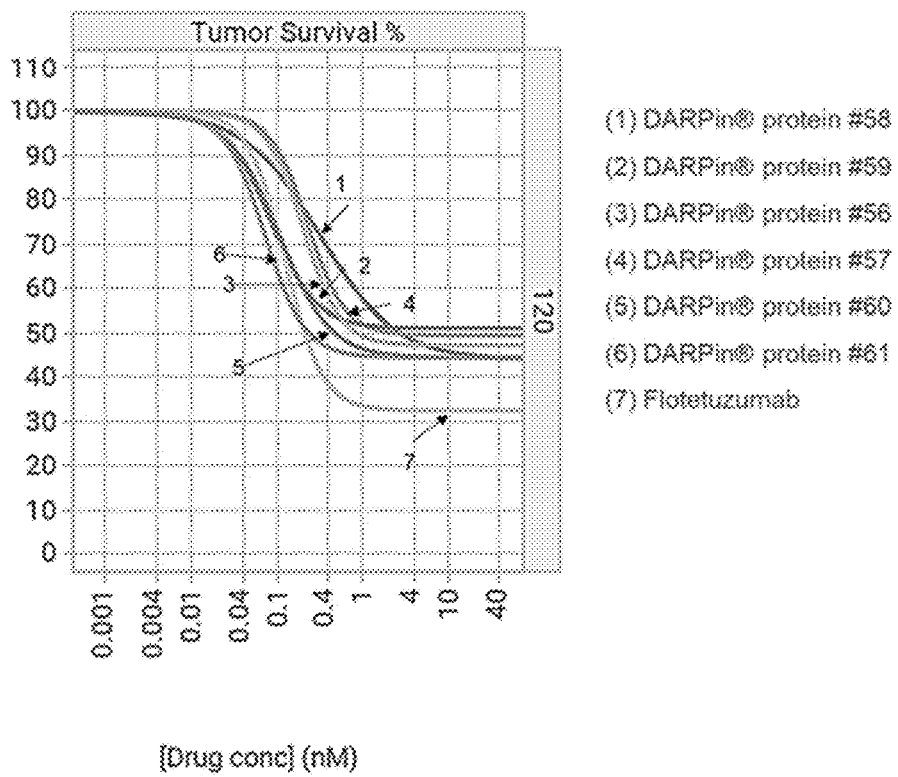

To perform the killing assay each sample was diluted in appropriate volume of IMDM/L-Glutamine 4 mM, supplemented with 20% (v/v) FBS and 1% antibiotics ("Vivia medium") to a final volume of 60 μL per well. The mixture was dispensed into 96-wells plates containing the compounds, previously prepared using an automated Echo 550 Liquid Handler. The plates containing the sample were incubated for 72 h and 120 h at 37° C. in humidified air containing 5% CO2. At final endpoints, the cells were stained with the mAb that better discriminated pathological cells according to baseline characterization plus Annexin V to measure cell death, and CD25 to measure T cell activation. Finally, plates were analyzed at Vivia's PharmaFlow platform. Killing fit-curves are shown on FIG. 54B as median of the individual donor fits. T cell activation is shown on FIG. 54A as % of CD25-positive T cells. Both killing and T cell activation data shows that all tested proteins could induce killing of AML cells and T cell activation in autologous setting.

Example 17: Effect of Multi-Specific Binding Proteins on Killing of CD34+ Sorted LSC and HSC To test efficacy and selectivity of selected multi-specific binding proteins in killing leukemic stem cells (LSC) and hematopoietic stem cells (HSC), frozen AML (peripheral blood and/or bone marrow) and healthy donor bone marrow samples were FACS-sorted for CD34+ cells.

Figure 55:
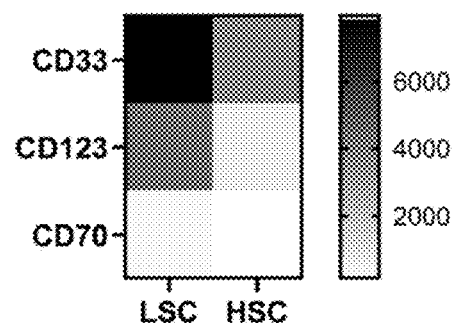
FIG. 55. Median expression across the different LSC and HSC samples, represented as delta MFI.

At the beginning of the experiment (day 0), part of the CD34+ sorted cells were stained (CD70 PE, CD123 BV421 and CD33 APC) and measured by flow cytometry (BD LSR Fortessa Analyzer) to quantify target expression by calculating the delta median fluorescence intensity (MFI) over isotype control. FIG. 55 shows the median expression across the different LSC and HSC samples, represented as delta MFI.

Figure 56:
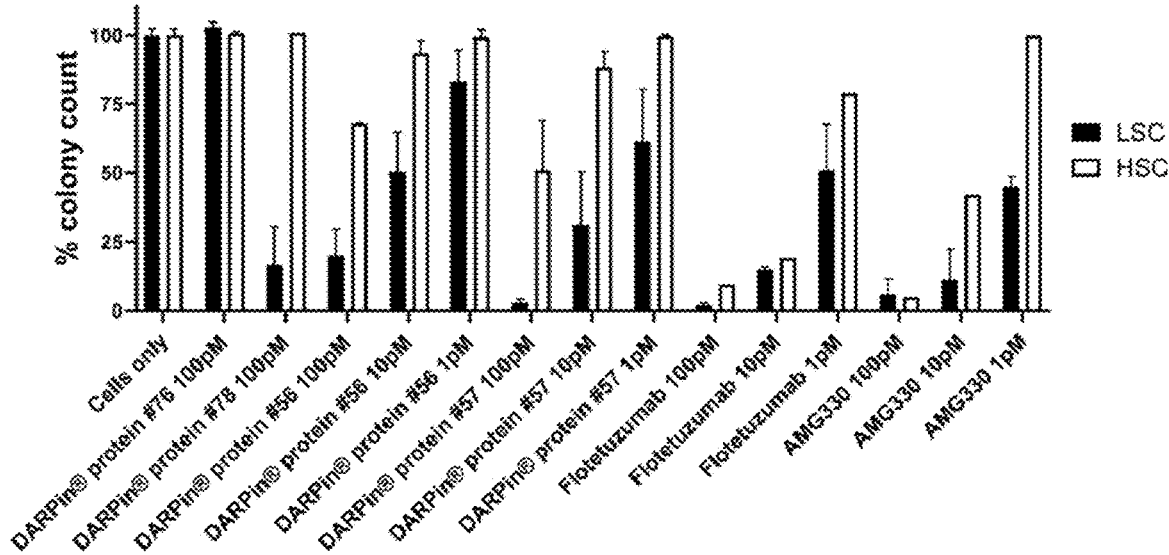
FIG. 56. Preferential killing of LSC (solid bars) over HSC (empty bars) with DARPin® protein #56 and DARPin® protein #57, confirming the presence of a window of opportunity between LSC and HSC FIG. 57 (A-F). Killing of Molm-13 cells vs release of IFNgamma. Killing of Molm-13 cells is shown by the black squares/curves, and concentration of IFNgamma by the black circles/curves.
Figure 57A:
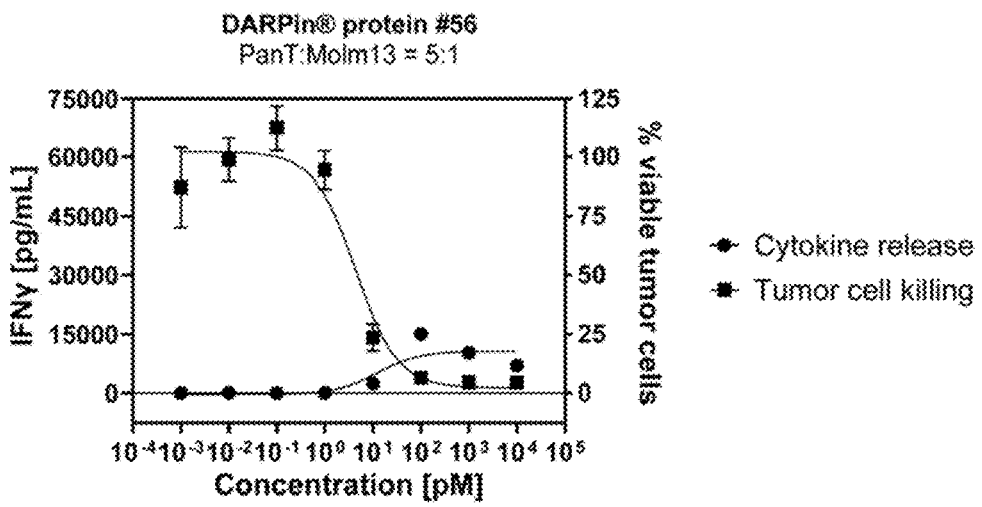
FIG. 57A. Impact of DARPin® protein #56 on cell killing and cytokine release.
Figure 57B:
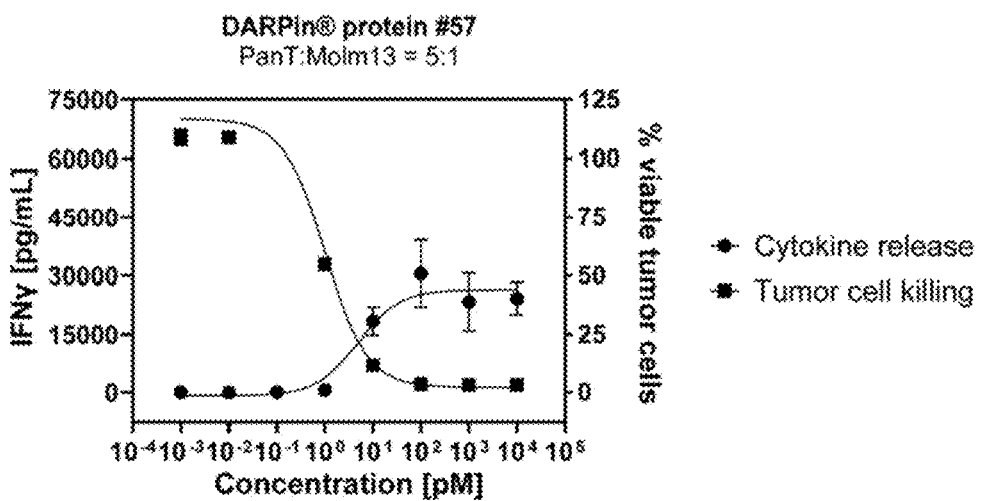
FIG. 57B. Impact of DARPin® protein #57 on cell killing and cytokine release.
Figure 57C:
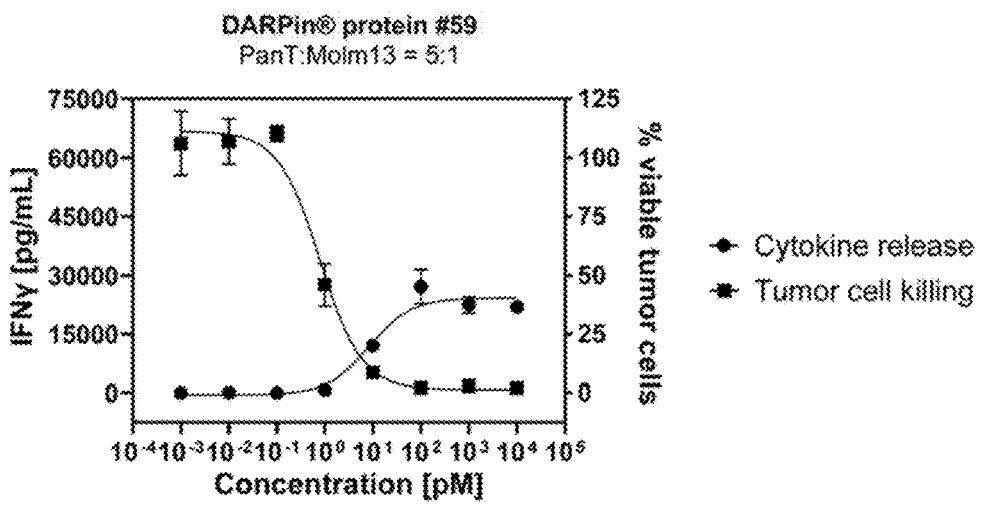
FIG. 57C. Impact of DARPin® protein #59 on cell killing and cytokine release.
Figure 57D:
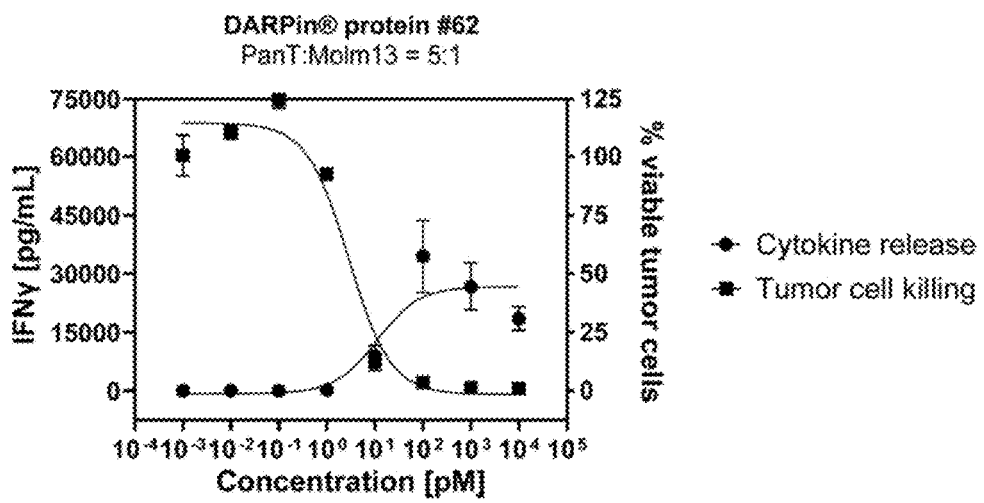
FIG. 57D. Impact of DARPin® protein #62 on cell killing and cytokine release.
Figure 57E:
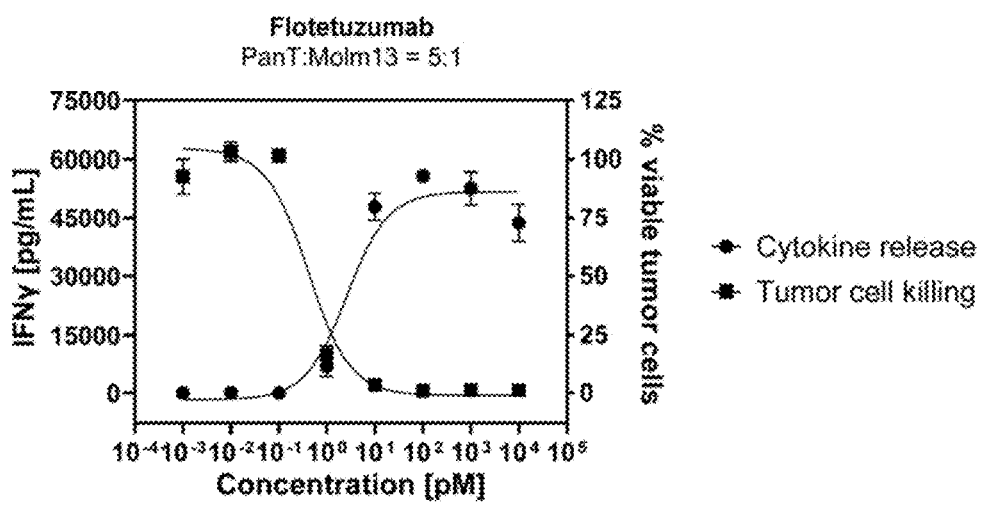
FIG. 57E. Impact of flotetuzumab on cell killing and cytokine release.
Figure 57F:
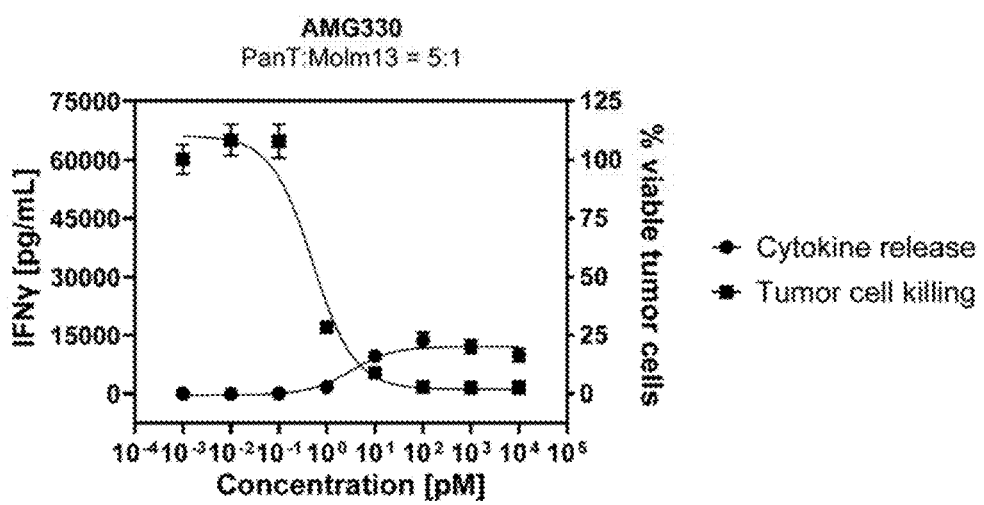
FIG. 57F. Impact of AMG330 on cell killing and cytokine release.

For the LSC/HSC killing assay, sorted CD34+ AML LSC or healthy donor HSC were first co-cultured with allogenic T-cells (isolated from buffy coats of healthy donors) at ratio of 1:1, in the presence of 100 pM, 10 pM or 1 pM DARPin® protein #56, DARPin® protein #57, DARPin® protein #58, DARPin® protein #59, DARPin® protein #60 and DARPin® protein #61 or benchmark molecules (Flotetuzumab-similar and AMG330-similar) for 4 days in a 96-well U-bottom plate. The StemSpan media used also contained a cytokine mix (SCF, IL-6, IL-3, Flt3) and 10 μM human serum albumin (HSA). After four days incubation, cells were resuspended and transferred into semi-solid methylcellulose media to check for colony forming capacity after two weeks of additional culture. Colony count was finally normalized to the untreated control (=100%, i.e. no killing). FIG. 56 shows the preferential killing of LSC (solid bars) over HSC (empty bars) with DARPin® protein #56 and DARPin® protein #57, confirming the presence of a window of opportunity between LSC and HSC. Furthermore, two benchmark compounds (Flotetuzumab-similar and AMG330-similar) were included to show the specificity difference of the selected DARPin proteins compared to those two molecules. FIG. 56 shows that both benchmark molecules are potent against LSC, but also that Flotetuzumab is killing equally well HSC. AMG330 shows some window as well, but with potent killing of HSC at low pM concentration. DARPin® protein #76, a non-TAA binding but CD3-binding protein, was used as negative control. DARPin® protein #78, a CD70-CD3 specific binding protein, was used as a positive control, also to prove that killing by targeting CD70 only is possible (and specific for LSC) even if the expression of CD70 is very low.

Example 18: Effect of Multi-Specific Binding Proteins on Killing AML Molm-13 Cells and Inducing Cytokine Release Specificity and potency of DARPin® protein #56, DARPin® protein #57, DARPin® protein #59, and DARPin® protein #62 along with benchmark molecules (Flotetuzumab-similar and AMG330-similar) were assessed by a FACS-based in-vitro tumor cell killing assay in presence of AML cell line Molm-13. To assess drug- and target-specific tumor cell killing, effector and target cells were co-incubated in duplicates with an E:T ratio of 5:1 in presence of serial dilutions of selected molecules. Purified (Miltenyi) pan-T cells (isolated form healthy donor PBMCs) were first labelled with CellTrace violet (Thermofisher) according to manufacturer protocol. 100,000 CTV-labelled pan-T+20,000 Molm-13 cells per well were then incubated at 37° C. together with serial dilutions of the selected multi-specific proteins or control molecules in presence of 20 µM human serum albumin (to provide saturation of the HSA-binding domains). After 48 h, supernatants were collected and stored at −80° C. for cytokine measurements, and cells were washed with PBS and stained with 1:3,000 Live/Dead Green (Thermo Fisher) for 20 min at 4° C. After washing and fixation, cells were analyzed on a FACS Canto II (BD) machine. Tumor cell killing was assessed by gating on CTV negative, single, Live/Dead negative cells. FACS data was analyzed using FlowJo software; data was normalized to background of co-culture only and was plotted using GraphPad Prism 8 (3PL-Fit).

Cytokine levels in the supernatants were measured using Meso Scale Discovery (MSD) Multi-Spot Assay System's VPlex Proinflammatory Panel 1 (human) Kit (K151A9H-4)-customized for IFNgamma, IL-2, IL-6 and TNFalpha. MSD instruments use Electro chemiluminescent (ECL) signals generated in the wells of MSD plates, using detection antibodies labeled with MSD Sulfo-TAG, to provide a quantitative measure of analytes present in each sample. The signal is reported as actual photon counts from each assay 'spot' layered over the working electrode. The experiment was performed as directed in the manufacturer's guide. Briefly, all supernatants were defrosted at room temperature (RT) and diluted 5-fold in Diluent 2 before addition to the MSD plates. Lyophilized calibrator blend was reconstituted in Diluent 2 (4-fold higher than standard protocol) and a series of 5-fold dilutions was performed to obtain 7 calibrators and an 8th zero calibrator (Diluent 2). SulfoTag antibodies for each of the 4 analytes were combined together by a 50-fold dilution in Diluent 3. 2× Read buffer was prepared by diluting 4× Read Buffer T 2-fold with deionized water. Wash buffer for washing MSD plates was PBS +0.05% Tween-20. Plates were washed 3 times with 150 µ/well of Wash buffer followed by addition of 50 µL per well of samples/Calibrators and incubated for 2 h at room temperature on an orbital shaker at 700 rpm. This was followed by washing 3 times with 150 µL/well of Wash buffer, then 25 µ/well detection antibody solution was added. Antibody incubation was also performed at room temperature for 2 h on an orbital shaker at 700 rpm followed by 3 washes with 150 µ/well of wash buffer. After the last wash, 150 µL/well of 2× Read Buffer T was added and plates were read using MSD MESO QuickPlex SQ. All data files were analyzed using the MSD discovery workbench software by assigning assay analytes, plate layouts and dilutions to each plate measured. The software provided calculated concentrations in pg/mL by back-fitting to 4 parameter logistic fits of the calibration curves for all 4 analytes from each plate (lot specific). The output values were plotted as non-linear regression graphs using GraphPad Prism.

As shown in FIG. 57 (A-H), tested proteins DARPin® protein #56, DARPin® protein #57, DARPin® protein #59 and DARPin® protein #62 show potent killing of Molm-13 cells (EC50 DARPin® protein #56 4.4 pM, DARPin® protein #57 1.0 pM, DARPin® protein #59 1.4 pM, DARPin® protein #62 2.9 pM, Flotetuzumab 0.4 pM, AMG330 0.5 pM). Quantification of IFNgamma in the supernatants also shows that DARPin® protein #56 shows the best safety profile, inducing the lowest release of IFNgamma.

Example 19: Effect of Multi-Specific Binding Proteins on Killing of Patient Derived AML Cells and Inducing Cytokine Release Specificity and potency of DARPin® protein #56 and DARPin® protein #57, along with benchmark molecules (Flotetuzumab-similar and AMG330-similar) used as positive controls, were assessed by a FACS-based ex vivo tumor cell killing assay in presence of AML donor patient cells. To assess drug- and target-specific tumor cell killing, AML patient derived cells were either incubated alone (autologous setup), or co-incubated with Pan-T cells (allogenic setup) from a healthy donor, in duplicates and in presence of serial dilutions of selected molecules. In the allogenic setup, an Effector cell (E) (i.e. T cell): Target cell (T) (i.e. AML cell) ratio of about 4:1 was achieved. In the autologous setup, the E:T ratio was much lower because of the limited number of T cells in the AML donor patient cell samples.

For the autologous set-up, 25,000 AML patient cells per well were incubated at 37° C. together with serial dilutions of the selected CD3 specific DARPin compounds or control molecules in presence of 20 µM human serum albumin (to provide saturation of the HSA-binding domains) and 40 ng/ml of each cytokine (IL-6, GM-CSF, SCF, TPO, Flt3L, G-CSF). After 48 and 120 h, supernatants were collected and stored at −80° C. for cytokine measurements, and cells were washed with PBS and stained with 1:3000 Live/Dead Green (Thermo Fisher) for 20 min at 4° C. After washing and fixation, cells were analyzed on a FACS Canto II (BD) machine. Tumor cell killing was assessed by gating on single, Live/Dead negative cells. FACS data was analyzed using FlowJo software; data was normalized to background of co-culture only and was plotted using GraphPad Prism 8 (3PL-Fit).

For the allogenic set-up, purified (Miltenyi) pan-T cells (isolated form healthy donor PBMCs) were first labelled with CellTrace violet (purchased from Thermofisher) according to manufacturer protocol. 100,000 CTV-labelled pan-T+25,000 AML patient cells per well were then incubated at 37° C. together with serial dilutions of the selected CD3-specific DARPin compounds or control molecules in presence of 20 µM human serum albumin (to provide saturation of the HSA-binding domains) and 40 ng/ml of each cytokine (IL-6, GM-CSF, SCF, TPO, Flt3L, G-CSF). After 48 h, supernatants were collected and stored at −80° C. for cytokine measurements, and cells were washed with PBS and stained with 1:3000 Live/Dead Green (purchased from Thermo Fisher) for 20 min at 4° C. After washing and fixation, cells were analyzed on a FACS Canto II (BD) machine. Tumor cell killing was assessed by gating on CTV negative, single, Live/Dead negative cells. FACS data was analyzed using FlowJo software; data was normalized to background of co-culture only and was plotted using GraphPad Prism 8 (3PL-Fit).

Cytokine levels in the supernatants were measured using Meso Scale Discovery (MSD) Multi-Spot Assay System's VPlex Proinflammatory Panel 1 (human) Kit (K151A9H-4)-customized for IFNgamma, IL-2 and TNFalpha. MSD instruments use Electro chemiluminescent (ECL) signals generated in the wells of MSD plates, using detection antibodies labeled with MSD Sulfo-TAG, to provide a quantitative measure of analytes present in each sample. The signal is reported as actual photon counts from each assay 'spot' layered over the working electrode. The experiment was performed as directed in the manufacturer's guide. Briefly, all supernatants were defrosted at room temperature (RT) and diluted 5-fold in Diluent 2 before addition to the MSD plates. Lyophilized calibrator blend was reconstituted in Diluent 2 (4-fold higher than standard protocol) and a series of 5-fold dilutions was performed to obtain 7 calibrators and an 8th zero calibrator (Diluent 2). SulfoTag antibodies for each of the 4 analytes were combined together by a 50-fold dilution in Diluent 3. 2× Read buffer was prepared by diluting 4× Read Buffer T 2-fold with deionized water. Wash buffer for washing MSD plates was PBS+0.05% Tween-20. Plates were washed 3 times with 150 µL/well of Wash buffer followed by addition of 504 per well of samples/Calibrators and incubated for 2 h at room temperature on an orbital shaker at 700 rpm. This was followed by washing 3 times with 150 µL/well of Wash buffer, then 25 µ/well detection antibody solution was added. Antibody incubation was also performed at room temperature for 2 h on an orbital shaker at 700 rpm followed by 3 washes with 150 µL/well of wash buffer. After the last wash, 150 µL/well of 2× Read Buffer T was added and plates were read using MSD MESO QuickPlex SQ. All data files were analyzed using the MSD discovery workbench software by assigning assay analytes, plate layouts and dilutions to each plate measured. The software provided calculated concentrations in pg/mL by back-fitting to 4 parameter logistic fits of the calibration curves for all 4 analytes from each plate (lot specific). The output values were plotted as non-linear regression graphs using GraphPad Prism.

As shown in FIGS. 59 (A-L) and 60 (A-L), tested proteins DARPin® protein #56 and DARPin® protein #57 showed potent autologous killing of AML patient cells over 5 days in a concentration-dependent manner (EC50 values: DARPin® protein #56: 33 pM, DARPin® protein #57: 2.9 pM, Flotetuzumab-similar: 0.4 pM, AMG330-similar: 4 pM). Comparison of cytokine release induction to patient AML cell killing data indicates the potentially best safety profile at efficacious concentrations for DARPin® protein #56, as it induced the lowest levels of cytokines. Also DARPin® protein #57 induced less cytokines than the benchmark Flotetuzumab-similar.

Similarly, as it can be seen in FIG. 61 (A-L), tested proteins DARPin® protein #56 and DARPin® protein #57 also showed potent killing of tumor cells in an allogenic setup (EC50: DARPin® protein #56: 103 pM, DARPin® protein #57: 22.7 pM, Flotetuzumab-similar: 0.6 pM, AMG330-similar: 4.1 pM). Also in this experimental setup, DARPin® protein #56 and DARPin® protein #57 induced less cytokines than the benchmark Flotetuzumab-similar.

Example 20: Effect on Cytokine Release Upon Spiking Whole Blood with Molm-13 Cells in the Presence of Multi-Specific Binding Proteins Cytokine release was assessed for DARPin® protein #56 and DARPin® protein #57 using whole blood from two healthy donors spiked with Molm13 cells. 400,000 Molm13 cells were incubated together with whole blood of healthy donors in the presence of serial dilutions of selected molecules. The number of Molm13 cells was chosen to achieve an E:T ratio of 1:2 and to obtain in each well about 20-25% tumour burden (since the average white blood cell count in 180 µL blood is nearly 1.3 million leucocytes, with about 200,000 total T cells). The Molm13 cells were incubated together with the molecules and whole blood of healthy donors at 37° C. for 30 min and 6 hours. Supernatants from each donor plates were collected at 2 different time points, 30 min and 6 h, and stored at −80° C. until ready for cytokine measurement assay. No significant cytokine release was observed after 30 min of incubation time.

Cytokine levels in the supernatants were measured using Meso Scale Discovery (MSD) Multi-Spot Assay System's VPlex Proinflammatory Panel 1 (human) Kit (K151A9H-4)-customized for IFNgamma, IL-2, IL-6 and TNFalpha, following the same protocol as described in Example 19.

As shown in FIG. 62 (A-H), quantification of IFNγ, IL-2, IL-6 and TNFalpha in the supernatants demonstrated that DARPin® protein #56 induced the lowest release of the four tested cytokines in both donors, indicating that DARPin® protein #56 likely has the best safety profile among the tested molecules. Also DARPin® protein #57 displayed overall lower cytokine induction than the benchmark molecules.

Example 21: Determination of Simultaneous Binding of DARPin® Protein #56 to CD33, CD123, CD70, CD3 and Serum Albumin by Surface Plasmon Resonance (SPR)

The simultaneous binding of DARPin® protein #56 to human CD33, human CD123, human CD70, and human CD3 targets as well as human serum albumin was assessed by surface plasmon resonance (SPR).

SPR measurements were performed on a Sierra SPR®-32 instrument (Bruker). PBS pH 7.4 containing 0.005% Tween 20 was used as running buffer. 2600 RU of 300 nM human serum albumin (HSA) was immobilized on an HCA sensor chip. To the HSA immobilized chip successively 1 µM DARPin® protein #56 (association 60 s, dissociation 0 s), 200 nM hCD70 (association 40 s, dissociation 0 s), and 500 nM hCD123 (association 120 s, dissociation 0 s) were applied as independent analyte injection steps. Immediately after, a dual injection step was performed injecting 150 nM hCD33 (association 150 s, dissociation 0 s) followed by 1.35 µM scCD3 (association 150 s, dissociation 180 s). More particularly, DARPin® protein #56 injection led to a response of 750 RUs. Then, 300 RUs of hCD70 were bound to DARPin® protein #56. Following, hCD123 was injected and binding to DARPin® protein #56 could be shown due to an increase of 700 RUs. Using dual injection, hCD33 binding gave a response of another 800 RUs, which was followed by subsequent binding of scCD3 upon injection stop of hCD33 with a further increase of 150 RUs. Notably, the decrease in RUs during the injection phase of hCD3 is indicative of ongoing dissociation of hCD33 during the scCD3 injection phase.

The setup allowed binding of hCD70, hCD123, hCD33 and scCD3 only if DARPin® protein #56 was already bound to HSA. A requirement for this set-up was that DARPin® protein #56 binds HSA with high avidity and hCD70/hCD123 with high affinity to prevent rapid signal loss before applying the last targets. To overcome the faster dissociation rates of hCD33 and scCD3, a dual injection was used for these targets to shorten the time between hCD33 injection stop and scCD3 injection start. In short, dual injection is conducted by separation of both target solutions in one syringe by an air bubble. Furthermore, single injections control runs have been conducted by injecting no target (PBST) or only one of the targets (Analyte 2-5) as described in injection scheme in Table 11. The signals were referenced to an empty control spot on the same channel. All steps have been performed at a flow rate of 10 μl/min, except for the dual injection at 20 μl/min.

Figure 63:
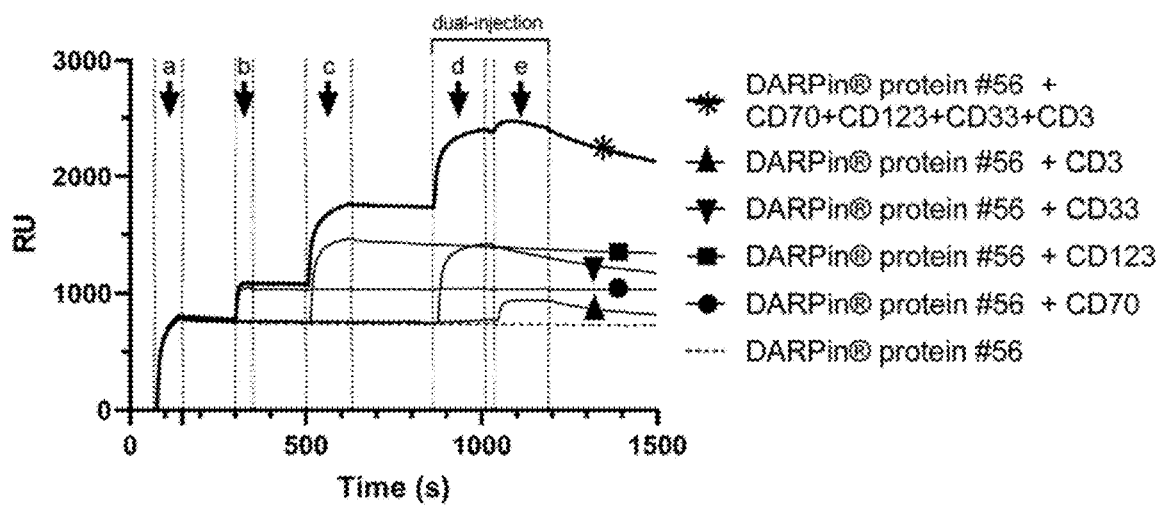
FIG. 63. SPR trace of simultaneous binding of DARPin® protein #56 to serum albumin, CD70, CD123, CD33 and CD3. (a) Binding of DARPin® protein #56 to immobilized HSA. (b) Association of hCD70 to HSA/DARPin® protein #56 complex (*/●), or PBST injections, respectively. (c) Binding of hCD123 to HSA/DARPin® protein #56/hCD70 complex (*), or to HSA/DARPin® protein #56 complex (■) or PBST injections, respectively. (d) Binding of hCD33 to HSA/DARPin® protein #56/hCD70/hCD123 complex (*), or to HSA/DARPin® protein #56 complex (▼), or PBST injections, respectively. (e) Binding of scCD3 to HAS/DARPin® protein #56/hCD70/hCD123/hCD33 complex (*), or to HSA/DARPin® protein #56 complex (▲), or PBST injections followed by a 180 s dissociation phase. The injection scheme is described in Table 11.

FIG. 63 shows SPR traces of simultaneous binding of DARPin® protein #56 to CD70, CD123, CD33 and CD3. Simultaneous binding of DARPin® protein #56 to CD70, CD123, CD33 and CD3 occurred on DARPin® protein #56 bound to the plate-immobilized serum albumin. These findings indicate that DARPin® protein #56 is capable of simultaneously binding to all five of its targets.

TABLE 11

Injection scheme of the SPR measurement

| Analyte | Symbol | Immobilization | Analyte 1 | Analyte 2 | Analyte 3 | Analyte 4 | Analyte 5 |
|---|---|---|---|---|---|---|---|
| A1 | * | HSA | DARPin® protein #56 | hCD70 | hCD123 | hCD33 | scCD3 |
| A2 | ● | HSA | DARPin® protein #56 | hCD70 | PBST | PBST | PBST |
| A3 | ■ | HSA | DARPin® protein #56 | PBST | hCD123 | PBST | PBST |
| A4 | ▲ | HSA | DARPin® protein #56 | PBST | PBST | hCD33 | PBST |
| A5 | ▼ | HSA | DARPin® protein #56 | PBST | PBST | PBST | scCD3 |
| A6 | dashed line | HSA | DARPin® protein #56 | PBST | PBST | PBST | PBST |

Figure 64:
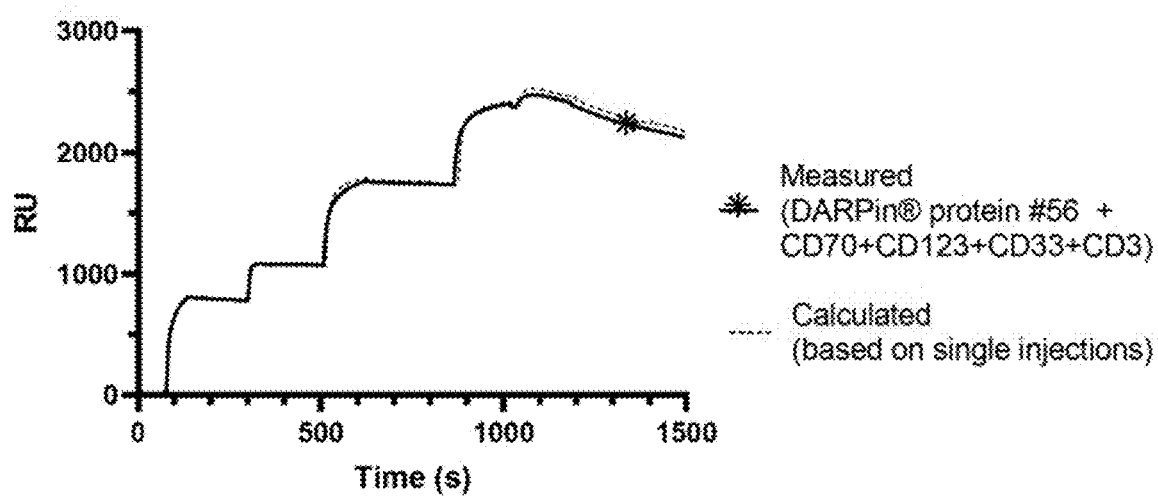
FIG. 64. Comparison of SPR traces of "Measured" vs. "Calculated" simultaneous binding of DARPin® protein #56 to all targets. "Measured" binding trace, taken from FIG. 63 (*). The "Calculated" trace was generated by combining individual single control injection SPR traces of DARPin® protein #56 binding to serum albumin, CD70, CD123, CD33 or CD3, respectively.

Additionally, a theoretical sensorgram of simultaneous binding was calculated by adding up the values of the single injections of all targets (controlling for redundant DARPin® protein #56 additions is achieved by subtracting DARPin® protein #56 single injection three times). Superposition of "Measured" and "Calculated" sensorgrams confirms that DARPin® protein #56 can bind all of its five targets simultaneously (FIG. 64). FIG. 64 shows the comparison of "Measured" and "Calculated" SPR traces.

The specification is most thoroughly understood in light of the teachings of the references cited within the specification. The aspects within the specification provide an illustration of aspects of the invention and should not be construed to limit the scope of the invention. The skilled artisan readily recognizes that many other aspects are encompassed by the invention. All publications, patents, and GenBank sequences cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize or be able to ascertain using no more than routine experimentation, many equivalents to the specific aspects of the invention described herein. Such equivalents are intended to be encompassed by the following claims.

SEQUENCE TABLE

| SEQ ID NO | Description | DARPin protein | Sequence (an X represents any amino acid) |
|---|---|---|---|
| 1 | Ankyrin repeat domain specific for CD3 | DARPin® protein #1 | DLGQKLLEAAWAGQDDEVRELLKAGADVNAKDSQGWTPLHTAAQTGHLEIFEVLLKAGADVNAKDDKGVTPLHLAAALGHLEIVEVLLKAGADVNAQDSWGTTPADLAAKYGHEDIAEVLQKAA |
| 2 | Ankyrin repeat domain specific for CD3 | DARPin® protein #2 | DLGQKLLEAAWAGQDDEVRELLKAGADVNAKNSRGWTPLHTAAQTGHLEIFEVLLKAGADVNAKDDKGVTPLHLAAALGHLEIVEVLLKAGADVNAQDSWGTTPADLAAKYGHEDIAEVLQKAA |

SEQUENCE TABLE

| SEQ ID NO | Description | DARPin protein | Sequence (an X represents any amino acid) |
|---|---|---|---|
| 3 | Ankyrin repeat domain specific for CD3 | DARPin® protein #3 | DLGQKLLEAAWAGQDDEVRELLKAGADVNAKNSRGWTPLHTAAQTGHLEIFEVLLKAGA DVNAKNDKRVTPLHLAAALGHLEIVEVLLKAGADVNARDSWGTTPADLAAKYGHQDIAE VLQKAA |
| 4 | Ankyrin repeat domain specific for CD3 | DARPin® protein #4 | DLGQKLLEAAWAGQLDEVRILLKAGADVNAKNSRGVVTPLHTAAQTGHLEIFEVLLKAG ADVNAKTNKRVTPLHLAAALGHLEIVEVLLKAGADVNARDTWGTTPADLAAKYGHRDIA EVLQKAA |
| 5 | Ankyrin repeat domain specific for CD3 | DARPin® protein #5 | DLGQKLLEAAWAGQDDEVRILLAAGADVNAKNSRGWTPLHTAAQTGHLEIFEVLLKAGA DVNAKNDKRVTPLHLAAALGHLEIVEVLLKAGADVNARDSWGTTPADLAAKYGHGDIAE VLQKLN |
| 6 | Ankyrin repeat domain specific for CD123 | DARPin® protein #6 | DLGKKLLEAARAGQDDEVRILMANGADVNALDWLGHTPLHLAAYEGHLEIVEVLLKNGA DVNAIDDNNGFTPLHLAAIDGHLEIVEVLLKNGADVNAQDKFGKTAFDISIDNGNEDLA EILQKAA |
| 7 | Ankyrin repeat protein specific for CD123-CD33-CD3 | DARPin® protein #7 | DLGKKLLEAARAGQDDEVRILMANGADVNALDWLGHTPLHLAAYEGHLEIVEVLLKNGA DVNAIDDNNGFTPLHLAAIDGHLEIVEVLLKNGADVNAQDKFGKTAFDISIDNGNEDLA EILQKAAGSPTPTPTTPTPTPTTPTPTPTGSDLGDKLLLAATSGQDDEVRILLAAGADV NAKDYDGDTPLHLAADEGHLEIVEVLLKAGADVNAKDYSGSTPLHAAAAYGHLEIVEVL LKAGADVNAQDVFGYTPADLAAYVGHEDIAEVLQKAAGSPTPTPTTPTPTPTTPTPTPT GSDLGQKLLEAAWAGQDDEVRELLKAGADVNAKDSQGWTPLHTAAQTGHLEIFEVLLKA GADVNAKDDKGVTPLHLAAALGHLEIVEVLLKAGADVNAQDSWGTTPADLAAKYGHEDI AEVLQKAA |
| 8 | Ankyrin repeat protein specific for CD123-CD33-CD3 | DARPin® protein #8 | DLGKKLLEAARAGQDDEVRILMANGADVNALDWLGHTPLHLAAYEGHLEIVEVLLKNGA DVNAIDDNNGFTPLHLAAIDGHLEIVEVLLKNGADVNAQDKFGKTAFDISIDNGNEDLA EILQKAAGSPTPTPTTPTPTPTTPTPTPTGSDLGDKLLLAATSGQDDEVRILLAAGADV NAKDYDGDTPLHLAADEGHLEIVEVLLKAGADVNAKDYSGSTPLHAAAAYGHLEIVEVL LKAGADVNAQDVFGYTPADLAAYVGHEDIAEVLQKAAGSPTPTPTTPTPTPTTPTPTPT GSDLGQKLLEAAWAGQDDEVRELLKAGADVNAKNSRGWTPLHTAAQTGHLEIFEVLLKA GADVNAKDDKGVTPLHLAAALGHLEIVEVLLKAGADVNAQDSWGTTPADLAAKYGHEDI AEVLQKAA |
| 9 | Ankyrin repeat protein specific for CD123-CD33-CD3 | DARPin® protein #9 | DLGKKLLEAARAGQDDEVRILMANGADVNALDWLGHTPLHLAAYEGHLEIVEVLLKNGA DVNAIDDNNGFTPLHLAAIDGHLEIVEVLLKNGADVNAQDKFGKTAFDISIDNGNEDLA EILQKAAGSPTPTPTTPTPTPTTPTPTPTGSDLGDKLLLAATSGQDDEVRILLAAGADV NAKDYDGDTPLHLAADEGHLEIVEVLLKAGADVNAKDYSGSTPLHAAAAYGHLEIVEVL LKAGADVNAQDVFGYTPADLAAYVGHEDIAEVLQKAAGSPTPTPTTPTPTPTTPTPTPT GSDLGQKLLEAAWAGQDDEVRELLKAGADVNAKNSRGWTPLHTAAQTGHLEIFEVLLKA GADVNAKNDKRVTPLHLAAALGHLEIVEVLLKAGADVNARDSWGTTPADLAAKYGHQDI AEVLQKAA |
| 10 | Ankyrin repeat protein specific for CD123-CD33-CD3 | DARPin® protein #10 | DLGKKLLEAARAGQDDEVRILMANGADVNALDWLGHTPLHLAAYEGHLEIVEVLLKNGA DVNAIDDNNGFTPLHLAAIDGHLEIVEVLLKNGADVNAQDKFGKTAFDISIDNGNEDLA EILQKAAGSPTPTPTTPTPTPTTPTPTPTGSDLGDKLLLAATSGQDDEVRILLAAGADV NAKDYDGDTPLHLAADEGHLEIVEVLLKAGADVNAKDYSGSTPLHAAAAYGHLEIVEVL LKAGADVNAQDVFGYTPADLAAYVGHEDIAEVLQKAAGSPTPTPTTPTPTPTTPTPTPT GSDLGQKLLEAAWAGQLDEVRILLKAGADVNAKNSRGWTPLHTAAQTGHLEIFEVLLKA GADVNAKTNKRVTPLHLAAALGHLEIVEVLLKAGADVNARDTWGTTPADLAAKYGHRDI AEVLQKAA |
| 11 | Ankyrin repeat protein specific for HSA-CD123-CD33-CD3 | DARPin® protein #11 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTPTGSDLGKKLLEAARAGQDDEVRILMANGADVN ALDWLGHTPLHLAAYEGHLEIVEVLLKNGADVNAIDDNNGFTPLHLAAIDGHLEIVEVL LKNGADVNAQDKFGKTAFDISIDNGNEDLAEILQKAAGSPTPTPTTPTPTPTTPTPTPT GSDLGDKLLLAATSGQDDEVRILLAAGADVNAKDYDGDTPLHLAADEGHLEIVEVLLKA GADVNAKDYSGSTPLHAAAAYGHLEIVEVLLKAGADVNAQDVFGYTPADLAAYVGHEDI AEVLQKAAGSPTPTPTTPTPTPTTPTPTPTGSDLGQKLLEAAWAGQDDEVRELLKAGAD VNAKDSQGWTPLHTAAQTGHLEIFEVLLKAGADVNAKDDKGVTPLHLAAALGHLEIVEV LLKAGADVNAQDSWGTTPADLAAKYGHEDIAEVLQKAA |
| 12 | Ankyrin repeat protein specific for HSA-CD123-CD33-CD3 | DARPin® protein #12 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTPTGSDLGKKLLEAARAGQDDEVRILMANGADVN ALDWLGHTPLHLAAYEGHLEIVEVLLKNGADVNAIDDNNGFTPLHLAAIDGHLEIVEVL LKNGADVNAQDKFGKTAFDISIDNGNEDLAEILQKAAGSPTPTPTTPTPTPTTPTPTPT GSDLGDKLLLAATSGQDDEVRILLAAGADVNAKDYDGDTPLHLAADEGHLEIVEVLLKA GADVNAKDYSGSTPLHAAAAYGHLEIVEVLLKAGADVNAQDVFGYTPADLAAYVGHEDI AEVLQKAAGSPTPTPTTPTPTPTTPTPTPTGSDLGQKLLEAAWAGQDDEVRELLKAGAD VNAKNSRGWTPLHTAAQTGHLEIFEVLLKAGADVNAKDDKGVTPLHLAAALGHLEIVEV LLKAGADVNAQDSWGTTPADLAAKYGHEDIAEVLQKAA |

| SEQUENCE TABLE | | | |
|---|---|---|---|
| SEQ ID NO | Description | DARPin protein | Sequence (an X represents any amino acid) |
| 13 | Ankyrin repeat protein specific for HSA-CD123-CD33-CD3 | DARPin® protein #13 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTPTGSDLGKKLLEAARADDEVRILMANGADVNAL DWLGHTPLHLAAYEGHLEIVEVLLKNGADVNAIDDNNGFTPLHLAAIDGHLEIVEVLLK NGADVNAQDKFGKTAFDISIDNGNEDLAEILQKAAGSPTPTPTTPTPTTPTPTPTGS DLGDKLLLAATSGQDDEVRILLAAGADVNAKDYDGDTPLHLAADEGHLEIVEVLLKAGA DVNAKDYSGSTPLHAAAAYGHLEIVEVLLKAGADVNAQDVFGYTPADLAAYVGHEDIAE VLQKAAGSPTPTPTTPTPTTPTPTPTGSDLGQKLLEAAWAGQDDEVRELLKAGADVN AKNSRGWTPLHTAAQTGHLEIFEVLLKAGADVNAKNDKRVTPLHLAAALGHLEIVEVLL KAGADVNARDSWGTTPADLAAKYGHQDIAEVLQKAA |
| 14 | Ankyrin repeat protein specific for HSA-CD123-CD33-CD3 | DARPin® protein #14 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTPTGSDLGKKLLEAARAGQDDEVRILMANGADVN ALDWLGHTPLHLAAYEGHLEIVEVLLKNGADVNAIDDNNGFTPLHLAAIDGHLEIVEVL LKNGADVNAQDKFGKTAFDISIDNGNEDLAEILQKAAGSPTPTPTTPTPTPTPTPTPT GSDLGDKLLLAATSGQDDEVRILLAAGADVNAKDYDGDTPLHLAADEGHLEIVEVLLKA GADVNAKDYSGSTPLHAAAAYGHLEIVEVLLKAGADVNAQDVFGYTPADLAAYVGHEDI AEVLQKAAGSPTPTPTTPTPTTPTPTPTGSDLGQKLLEAAWAGQLDEVRILLKAGAD VNAKNSRGVVTPLHTAAQTGHLEIFEVLLKAGADVNAKTNKRVTPLHLAAALGHLEIVE VLLKAGADVNARDTWGTTPADLAAKYGHRDIAEVLQKAA |
| 15 | Ankyrin repeat domain specific for CD33 | DARPin® protein #15 | DLGDKLLLAATSGQDDEVRILLAAGADVNAKDYDGDTPLHLAADEGHLEIVEVLLKAGA DVNAKDYSGSTPLHAAAAYGHLEIVEVLLKAGADVNAQDVFGYTPADLAAYVGHEDIAE VLQKAA |
| 16 | N-terminal capping module | | DLGQKLLEAAWAGQDDEVRELLKAGADVNA |
| 17 | N-terminal capping module | | DLGQKLLEAAWAGQLDEVRILLKAGADVNA |
| 18 | N-terminal capping module | | DLGQKLLEAAWAGQDDEVRILLKAGADVNA |
| 19 | N-terminal capping module | | DLGQKLLEAAWAGQDDEVRILLAAGADVNA |
| 20 | N-terminal capping module | | DLGQKLLEAAWAGQLDEVRELLKAGADVNA |
| 21 | N-terminal capping module | | DLGQKLLEAAWAGQLDEVRILLAAGADVNA |
| 22 | N-terminal capping module | | DLGxxLLQAAxxGQLDxVRxLxxxGADVNA |
| 23 | C-terminal capping module | | QDSWGTTPADLAAKYGHEDIAEVLQKAA |
| 24 | C-terminal capping module | | RDSWGTTPADLAAKYGHQDIAEVLQKAA |
| 25 | C-terminal capping module | | RDTWGTTPADLAAKYGHRDIAEVLQKAA |
| 26 | C-terminal capping module | | QDSWGTTPADLAAKYGHEDIAEVLQKLA |
| 27 | C-terminal capping module | | QDSWGTTPADLAAKYGHEDIAEVLQKLN |
| 28 | C-terminal capping module | | RDSWGTTPADLAAKYGHQDIAEVLQKLA |
| 29 | C-terminal capping module | | RDSWGTTPADLAAKYGHQDIAEVLQKLN |
| 30 | C-terminal capping module | | RDTWGTTPADLAAKYGHRDIAEVLQKLA |
| 31 | C-terminal capping module | | RDTWGTTPADLAAKYGHRDIAEVLQKLN |

SEQUENCE TABLE

| SEQ ID NO | Description | DARPin protein | Sequence (an X represents any amino acid) |
|---|---|---|---|
| 32 | C-terminal capping module | | xDxxGxTPADxAARxGHQxIAxVLQxAA |
| 33 | His Tag | | MRGSHHHHHH |
| 34 | Ankyrin repeat domain specific for human serum albumin | | DLGKKLLEAARAGQDDEVRELLKAGADVNAKDYFSHTPLHLAARNGHLKIVEVLLKAGA<br>DVNAKDFAGKTPLHLAANEGHLEIVEVLLKAGADVNAQDIFGKTPADIAADAGHEDIAE<br>VLQKAA |
| 35 | Ankyrin repeat domain specific for human serum albumin | | DLGKKLLEAARAGQDDEVRELLKAGADVNAKDYFSHTPLHLAARNGHLKIVEVLLKAGA<br>DVNAKDFAGKTPLHLAAADGHLEIVEVLLKAGADVNAQDIFGKTPADIAADAGHEDIAE<br>VLQKAA |
| 36 | Ankyrin repeat domain specific for human serum albumin | | DLGKKLLEAARAGQDDEVRELLKAGADVNAKDYFSHTPLHLAARNGHLKIVEVLLKAGA<br>DVNAKDFAGKTPLHLAADAGHLEIVEVLLKAGADVNAQDIFGKTPADIAADAGHEDIAE<br>VLQKAA |
| 37 | PT linker | | GSPTPTPTTPTPTPTTPTPTPT |
| 38 | scCD3εγ_Avi-Bio | | MQDGNEEMGGITQTPYKVSISGTTVILTCPQYPGSEILWQHNDKNIGGDEDDKNIGSDE<br>DHLSLKEFSELEQSGYYVCYPRGSKPEDANFYLYLRARVGSADDAKKDDAAKKDDAKKDD<br>AKKDGSQSIKGNHLVKVYDYQEDGSVLLTCDAEAKNITWFKDGKMIGFLTEDKKKWNLG<br>SNAKDPRGMYQCKGSQNKSKPLQVYYRMGGGLNDIFEAQKIEWHE |
| 39 | Ankyrin repeat protein specific for CD3 and human serum albumin | DARPin® protein #16 | DLGKKLLEAARAGQDDEVRELLKAGADVNAKDYFSHTPLHLAARNGHLKIVEVLLKAGA<br>DVNAKDFAGKTPLHLAAADGHLEIVEVLLKAGADVNAQDIFGKTPADIAADAGHEDIAE<br>VLQKAAGSPTPTPTTPTPTPTTPTPTPTGSDLGQKLLEAAWAGQDDEVRELLKAGADVN<br>AKDSQGWTPLHTAAQTGHLEIFEVLLKAGADVNAKDDKGVTPLHLAAALGHLEIVEVLL<br>KAGADVNAQDSWGTTPADLAAKYGHEDIAEVLQKAA |
| 40 | Ankyrin repeat protein specific for CD3 and human serum albumin | DARPin® protein #17 | DLGKKLLEAARAGQDDEVRELLKAGADVNAKDYFSHTPLHLAARNGHLKIVEVLLKAGA<br>DVNAKDFAGKTPLHLAAADGHLEIVEVLLKAGADVNAQDIFGKTPADIAADAGHEDIAE<br>VLQKAAGSPTPTPTTPTPTPTTPTPTPTGSDLGQKLLEAAWAGQDDEVRELLKAGADVN<br>AKNSRGVVTPLHTAAQTGHLEIFEVLLKAGADVNAKDDKGVTPLHLAAALGHLEIVEVL<br>LKAGADVNAQDSWGTTPADLAAKYGHEDIAEVLQKAA |
| 41 | Ankyrin repeat protein specific for CD3 and human serum albumin | DARPin® protein #18 | DLGKKLLEAARAGQDDEVRELLKAGADVNAKDYFSHTPLHLAARNGHLKIVEVLLKAGA<br>DVNAKDFAGKTPLHLAAADGHLEIVEVLLKAGADVNAQDIFGKTPADIAADAGHEDIAE<br>VLQKAAGSPTPTPTTPTPTPTTPTPTPTGSDLGQKLLEAAWAGQDDEVRELLKAGADVN<br>AKNSRGVVTPLHTAAQTGHLEIFEVLLKAGADVNAKNDKRVTPLHLAAALGHLEIVEVL<br>LKAGADVNARDSWGTTPADLAAKYGHQDIAEVLQKAA |
| 42 | Ankyrin repeat protein specific for CD3 and human serum albumin | DARPin® protein #19 | DLGKKLLEAARAGQDDEVRELLKAGADVNAKDYFSHTPLHLAARNGHLKIVEVLLKAGA<br>DVNAKDFAGKTPLHLAAADGHLEIVEVLLKAGADVNAQDIFGKTPADIAADAGHEDIAE<br>VLQKAAGSPTPTPTTPTPTPTTPTPTPTGSDLGQKLLEAAWAGQLDEVRILLKAGADVN<br>AKNSRGWTPLHTAAQTGHLEIFEVLLKAGADVNAKTNKRVTPLHLAAALGHLEIVEVLL<br>KAGADVNARDTWGTTPADLAAKYGHRDIAEVLQKAA |
| 43 | Nucleic acid encoding domain of SEQ ID NO 1 | | ATGAGAGGATCGCATCACCATCACCATCACGGCTCAGATCTGGGTCAAAAGTTATTGGA<br>GGCAGCTTGGGCTGGACAAGATGACGAAGTACGTGAATTGTTAAAAGCGGGAGCAGATG<br>TAAACGCAAAAGATAGTCAAGGTTGGACTCCGTTACACACAGCAGCGCAAACCGGCCAC<br>CTGGAAATTTTCGAGGTGTTATTGAAGGCTGGAGCAGATGTGAATGCAAAAGACGACAA<br>AGGGGTGACTCCGCTGCATCTGGCAGCGGCGTTGGGGCACTTGGAAATCGTTGAGGTCC<br>TTCTGAAAGCAGGCGCTGATGTGAATGCGCAAGACTCCTGGGGAACCACACCAGCGGAC<br>CTGGCGGCTAAGTACGGCCACGAAGATATTGCTGAAGTTCTGCAGAAGGCAGCATAATG<br>ATAG |
| 44 | Nlucleic acid encoding domain of SEQ ID NO 2 | | ATGAGAGGATCGCATCACCATCACCATCACGGCTCAGATCTGGGTCAAAAGTTGTTGGA<br>AGCTGCCTGGGCGGACAGGATGATGAGGTGCGCGAATTACTTAAGGCGGGAGCAGACG<br>TGAATGCGAAAAACTCTCGTGGCTGGACACCACTGCACACGGCCGCGCAAACTGGTCAC<br>CTTGAAATTTTCGAGTGCTTCTGAAGGCAGGCGCAGATGTAAACGCCAAGGATGACAA<br>AGGGGTAACACCGCTTCATCTGGCTGCTGCACTGGGACATCTTGAGATTGTCGAAGTAC<br>TGCTTAAGGCAGGTGCTGACGTAAACGCTCAGGATTCATGGGGACCACACCGGCGGAC<br>CTGGCGGCTAAATACGGACATGAAGATATTGCTGAAGTTCTGCAGAAGGCAGCATAATG<br>ATAG |
| 45 | Nucleic acid encoding domain of SEQ ID NO 3 | | ATGAGAGGATCGCATCACCATCACCATCACGGCTCAGATCTGGGTCAAAAGCTGTTGGA<br>AGCCGCGTGGGCGGGTCAGGACGATGAAGTCCGTGAGCTGCTTAAAGCAGGAGCCGACG<br>TGAACGCGAAGAACTCACGCGGGTGGACGCCACTTCACACGGCCGCGCAGACAGGTCAC<br>CTTGAAATCTTTGAGGTTCTTCTGAAGGCAGGAGCAGACGTTAACGCCAAAAACGACAA |

-continued

SEQUENCE TABLE

| SEQ ID NO | Description | DARPin protein | Sequence (an X represents any amino acid) |
|---|---|---|---|
| | | | GCGCGTGACTCCGTTGCACCTTGCCGCAGCTCTGGGGCATTTGGAGATCGTTGAGGTAC TGTTGAAAGCGGGAGCAGATGTTAATGCTCGCGACAGTTGGGGGACGACACCAGCAGAC CTGGCCGCAAAATACGGACACCAAGACATTGCTGAAGTTCTGCAGAAGGCAGCATAATG ATAG |
| 46 | Nucleic acid encoding domain of SEQ ID NO 4 | | ATGAGAGGATCGCATCACCATCACCATCACGGCTCAGATCTGGGTCAAAAATTGTTAGA GGCAGCCTGGGCGGGACAGTTAGACGAGGTTCGTATTCTTTTGAAAGCTGGTGCGGATG TGAACGCAAAGAATTCTCGTGGATGGACTCCGTTGCACACCGCCGCACAGACTGGGCAC TTGGAAATCTTTTGAGGTTCTGTTAAAAGCAGGGGCAGATGTTAACGCTAAAACTAATAA ACGTGTCACCCCCCTTCACCTGGCTGCGGCTTTAGGCCATTTAGAAATCGTGGAAGTAT TACTTAAAGCCGGGGCTGACGTTAACGCCCGTGACACTTGGGGGACAACCCCTGCGGAT CTGGCCGCCAAATATGGTCACCGCGACATTGCTGAAGTTCTGCAGAAGGCAGCATAATG ATAG |
| 47 | Ankyrin repeat protein specific for CD123-CD33-CD3 | DARPin® protein #20 | DLGKKLLEAARAGQDDEVRILMANGADVNALDWLGHTPLHLAAYEGHLEIVEVLLKNGA DVNAIDDNNGFTPLHLAAIDGHLEIVEVLLKNGADVNAQDKFGKTAFDISIDNGNEDLA EILQKAAGSPTPTPTTPTPTPTTPTPTPTGSDLGDKLLLAATSGQDDEVRILLAAGADV NAKDYDGDTPLHLAADEGHLEIVEVLLKAGADVNAKDYSGSTPLHAAAAYGHLEIVEVL LKAGADVNAQDVFGYTPADLAAYVGHEDIAEVLQKAAGSPTPTPTTPTPTPTTPTPTPT GSDLGQKLLEAAWAGQDDEVRILLAAGADVNAKNSRGWTPLHTAAQTGHLEIFEVLLKA GADVNAKNDKRVTPLHLAAALGHLEIVEVLLKAGADVNARDSWGTTPADLAAKYGHGDI AEVLQKLA |
| 48 | Ankyrin repeat protein specific for CD123-CD3 | DARPin® protein #21 | DLGKKLLEAARAGQDDEVRILMANGADVNALDWLGHTPLHLAAYEGHLEIVEVLLKNGA DVNAIDDNNGFTPLHLAAIDGHLEIVEVLLKNGADVNAQDKFGKTAFDISIDNGNEDLA EILQKAAGSPTPTPTTPTPTPTTPTPTPTGSDLGKKLLEAARAGQDDEVRELLKAGADV NAKDKDGYTPLHLAAREGHLEIVEVLLKAGADVNAKDKDGYTPLHLAAREGHLEIVEVL LKAGADVNAQDKSGKTPADLAADAGHEDIAEVLQKAAGSPTPTPTTPTPTPTTPTPTPT GSDLGQKLLEAAWAGQDDEVRILLAAGADVNAKNSRGWTPLHTAAQTGHLEIFEVLLKA GADVNAKNDKRVTPLHLAAALGHLEIVEVLLKAGADVNARDSWGTTPADLAAKYGHGDI AEVLQKLA |
| 49 | Ankyrin repeat protein specific for CD33-CD3 | DARPin® protein #22 | DLGKKLLEAARAGQDDEVRELLKAGADVNAKDKDGYTPLHLAAREGHLEIVEVLLKAGA DVNAKDKDGYTPLHLAAREGHLEIVEVLLKAGADVNAQDKSGKTPADLAADAGHEDIAE VLQKAAGSPTPTPTTPTPTPTTPTPTPTGSDLGDKLLLAATSGQDDEVRILLAAGADVN AKDYDGDTPLHLAADEGHLEIVEVLLKAGADVNAKDYSGSTPLHAAAAYGHLEIVEVLL KAGADVNAQDVFGYTPADLAAYVGHEDIAEVLQKAAGSPTPTPTTPTPTPTTPTPTPTG SDLGQKLLEAAWAGQDDEVRILLAAGADVNAKNSRGWTPLHTAAQTGHLEIFEVLLKAG ADVNAKNDKRVTPLHLAAALGHLEIVEVLLKAGADVNARDSWGTTPADLAAKYGHGDIA EVLQKLA |
| 50 | Ankyrin repeat protein specific for CD33-CD3 | DARPin® protein #23 | DLGDKLLLAATSGQDDEVRILLAAGADVNAKDYDGDTPLHLAADEGHLEIVEVLLKAGA DVNAKDYSGSTPLHAAAAYGHLEIVEVLLKAGADVNAQDVFGYTPADLAAYVGHEDIAE VLQKAAGSPTPTPTTPTPTPTTPTPTPTGSDLGQKLLEAAWAGQDDEVRELLKAGADVN AKNSRGWTPLHTAAQTGHLEIFEVLLKAGADVNAKDDKGVTPLHLAAALGHLEIVEVLL KAGADVNAQDSWGTTPADLAAKYGHEDIAEVLQKAA |
| 51 | Ankyrin repeat protein specific for CD123-CD3 | DARPin® protein #24 | DLGKKLLEAARAGQDDEVRILMANGADVNALDWLGHTPLHLAAYEGHLEIVEVLLKNGA DVNAIDDNNGFTPLHLAAIDGHLEIVEVLLKNGADVNAQDKFGKTAFDISIDNGNEDLA EILQKAAGSPTPTPTTPTPTPTTPTPTPTGSDLGQKLLEAAWAGQDDEVRELLKAGADV NAKNSRGVVTPLHTAAQTGHLEIFEVLLKAGADVNAKDDKGVTPLHLAAALGHLEIVEV LLKAGADVNAQDSWGTTPADLAAKYGHEDIAEVLQKAA |
| 52 | Nucleic acid encoding protein of SEQ ID NO 7 | | ATGAGAGGATCGCATCACCATCACCATCACGGATCCGACCTGGGTAAAAAGCTGCTTGA GGCTGCCCGTGCAGGTCAAGATGACGAAGTCCGCATCCTTATGGCAAATGGTGCCGATG TAAATGCACTGGACTGGCTTGGCCACACACCCCTTCATCTGGCAGCCTACGAGGGGCAC TTGGAGATTGTCGAAGTTTTGTTAAAAAACGGCGCGGATGTAAACGCGATTGATGACAA CAACGGATTTACTCCACTTCACTTGGCGGCTATCGACGGTCACTTAGAAATTGTAGAGG TGTTGTTGAAGAACGGGGCAGACGTTAATGCACAAGATAAGTTCGGCAAAACGGCATTC GATATCTCCATTGATAATGGTAATGAAGATTTAGCTGAAATCCTGCAGAAGGCAGCAGG CTCGCCGACTCCGACCCCGACCACCCCAACTCCAACACCGACCACCCCGACCCCTACCC CAACAGGATCCGACCTGGGTGACAAACTGCTGCTGGCTGCTACTTCGGTCAGGACGAC GAAGTTCGTATCCTGCTGGCTGCTGGCGCCGACGTTAATGCTAAAGACTACGACGGTGA CACTCCGCTGCACCTGGCTGCTGACGAAGGTCACCTGGAAATCGTTGAAGTTCTGCTGA AGGCTGGTGCTGACGTTAATGCTAAAGACTACTCTGGTTCTACTCCGCTGCACGCTGCT GCTGCTTACGGTCACCTGGAAATCGTTGAAGTTCTGCTGAAGGCTGGTGCTGACGTTAA CGCTCAGGACGTTTTCGGTTACACTCCGGCTGATCTGGCTGCTTACGTTGGTCACGAGG ATATCGCTGAAGTTCTGCAGAAGGCTGCGGGGAGTCCAACCCCGACGCCAACCACACCC ACTCCTACGCCTACAACTCCAACTCCGACGCCTACCGGATCAGATCGGGTCAAAAGTT ATTGGAGGCAGCTTGGGCTGGACAAGATGACGAAGTACGTGAATTGTTAAAAGCGGGAG CAGATGTAAACGCAAAAGATAGTCAAGGTTGGACTCCGTTACACACAGCAGCGCAAACC |

SEQUENCE TABLE

| SEQ ID NO | Description | DARPin protein | Sequence (an X represents any amino acid) |
|---|---|---|---|
| | | | GGCCACCTGGAAATTTTCGAGGTGTTATTGAAGGCTGGAGCAGATGTGAATGCAAAAGA<br>CGACAAAGGGGTGACTCCGCTGCATCTGGCAGCGGCGTTGGGGCACTTGGAAATCGTTG<br>AGGTCCTTCTGAAAGCAGGCGCTGATGTGAATGCGCAAGACTCCTGGGGAACCACACCA<br>GCGGACCTGCGGCTAAGTACGGCCACGAAGATATTGCTGAAGTTCTGCAGAAGGCAGC<br>ATAATGATAG |
| 53 | Nucleic acid encoding protein of SEQ ID NO 8 | | ATGAGAGGATCGCATCACCATCACCATCACGGATCCGACCTGGGTAAAAAGCTGCTTGA<br>GGCTGCCCGTGCAGGTCAAGATGACGAAGTCCGCATCCTTATGGCAAATGGTGCCGATG<br>TAAATGCACTGGACTGGCTTGGCCACACACCCCTTCATCTGGCAGCCTACGAGGGGCAC<br>TTGGAGATTGTCGAAGTTTTGTTAAAAAACGGCGCGGATGTAAACGCGATTGATGACAA<br>CAACGGATTTACTCCACTTCACTTGGCGGCTATCGACGGTCACTTAGAAATTGTAGAGG<br>TGTTGTTGAAGAACGGGGCAGACGTTAATGCACAAGATAAGTTCGGCAAAACGGCATTC<br>GATATCTCCATTGATAATGGTAATGAAGATTTAGCTGAAATCCTGCAGAAGGCAGCAGG<br>CTCGCCGACTCCGACCCCGACCACCCCAACTCCAACACCGACCACCCCGACCCCTACCC<br>CAACAGGATCCGACCTGGGTGACAAACTGCTGCTGGCTGCTACTTCTGGTCAGGACGAC<br>GAAGTTCGTATCCTGCTGGCTGCTGGCGCCGACGTTAATGCTAAAGACTACGACGGTGA<br>CACTCCGCTGCACCTGGCTGCTGACGAAGGTCACCTGGAAATCGTTGAAGTTCTGCTGA<br>AGGCTGGTGCTGACGTTAATGCTAAAGACTACTCTGGTTCTACTCCGCTGCACGCTGCT<br>GCTGCTTACGGTCACCTGGAAATCGTTGAAGTTCTGCTGAAGGCTGGTGCTGACGTTAA<br>CGCTCAGGACGTTTTCGGTTACACTCCGGCTGATCTGGCTGCTTACGTTGGTCACGAGG<br>ATATCGCTGAAGTTCTGCAGAAGGCTGCGGGGAGTCCAACCCCGACGCCAACCACACCC<br>ACTCCTACGCCTACAACTCCAACTCCGACGCCTACCGGATCAGATCTGGGTCAAAAGTT<br>GTTGGAAGCTGCCTGGGCGGGACAGGATGATGAGGTGCGCGAATTACTTAAGGCGGGAG<br>CAGACGTGAATGCGAAAAACTCTCGTGGCTGGACACCACTGCACACGGCCGCGCAAACT<br>GGTCACCTTGAAATTTTCGAAGTGCTTCTGAAGGCAGGCGCAGATGTAAACGCCAAGGA<br>TGACAAAGGGGTAACACCGCTTCATCTGGCTGCTGCACTGGGACATCTTGAGATTGTCG<br>AAGTACTGCTTAAGGCAGGTGCTGACGTAAACGCTCAGGATTCATGGGGGACCACACCG<br>GCGGACCTGCGGCTAAATACGGACATGAAGATATTGCTGAAGTTCTGCAGAAGGCAGC<br>ATAATGATAG |
| 54 | Nucleic acid encoding protein of SEQ ID NO 9 | | ATGAGAGGATCGCATCACCATCACCATCACGGATCCGACCTGGGTAAAAAGCTGCTTGA<br>GGCTGCCCGTGCAGGTCAAGATGACGAAGTCCGCATCCTTATGGCAAATGGTGCCGATG<br>TAAATGCACTGGACTGGCTTGGCCACACACCCCTTCATCTGGCAGCCTACGAGGGGCAC<br>TTGGAGATTGTCGAAGTTTTGTTAAAAAACGGCGCGGATGTAAACGCGATTGATGACAA<br>CAACGGATTTACTCCACTTCACTTGGCGGCTATCGACGGTCACTTAGAAATTGTAGAGG<br>TGTTGTTGAAGAACGGGGCAGACGTTAATGCACAAGATAAGTTCGGCAAAACGGCATTC<br>GATATCTCCATTGATAATGGTAATGAAGATTTAGCTGAAATCCTGCAGAAGGCAGCAGG<br>CTCGCCGACTCCGACCCCGACCACCCCAACTCCAACACCGACCACCCCGACCCCTACCC<br>CAACAGGATCCGACCTGGGTGACAAACTGCTGCTGGCTGCTACTTCTGGTCAGGACGAC<br>GAAGTTCGTATCCTGCTGGCTGCTGGCGCCGACGTTAATGCTAAAGACTACGACGGTGA<br>CACTCCGCTGCACCTGGCTGCTGACGAAGGTCACCTGGAAATCGTTGAAGTTCTGCTGA<br>AGGCTGGTGCTGACGTTAATGCTAAAGACTACTCTGGTTCTACTCCGCTGCACGCTGCT<br>GCTGCTTACGGTCACCTGGAAATCGTTGAAGTTCTGCTGAAGGCTGGTGCTGACGTTAA<br>CGCTCAGGACGTTTTCGGTTACACTCCGGCTGATCTGGCTGCTTACGTTGGTCACGAGG<br>ATATCGCTGAAGTTCTGCAGAAGGCTGCGGGGAGTCCAACCCCGACGCCAACCACACCC<br>ACTCCTACGCCTACAACTCCAACTCCGACGCGCTACCGGATCAGATCTGGGTCAAAAGCT<br>GTTGGAAGCCGCGTGGGCGGGTCAGGACGATGAAGTCCGTGAGCTGCTTAAAGCAGGAG<br>CCGACGTGAACGCGAAGAACTCACGCGGGTGGACGCCACTTCACACGGCCGCGCAGACA<br>GGTCACCTTGAAATCTTTGAGGTTCTTCTGAAGGCAGGAGCAGACGTTAACGCCAAAAA<br>CGACAAGCGCGTGACTCCGTTGCACCTTGCCGCAGCTCTGGGGCATTTGGAGATCGTTG<br>AGGTACTGTTGAAAGCGGGAGCAGATGTTAATGCTCGCGACAGTTGGGGGACGACACCA<br>GCAGACCTGGCCGCAAAATACGGACACCAAGACATTGCTGAAGTTCTGCAGAAGGCAGC<br>ATAATGATAG |
| 55 | Nucleic acid encoding protein of SEQ ID NO 10 | | ATGAGAGGATCGCATCACCATCACCATCACGGATCCGACCTGGGTAAAAAGCTGCTTGA<br>GGCTGCCCGTGCAGGTCAAGATGACGAAGTCCGCATCCTTATGGCAAATGGTGCCGATG<br>TAAATGCACTGGACTGGCTTGGCCACACACCCCTTCATCTGGCAGCCTACGAGGGGCAC<br>TTGGAGATTGTCGAAGTTTTGTTAAAAAACGGCGCGGATGTAAACGCGATTGATGACAA<br>CAACGGATTTACTCCACTTCACTTGGCGGCTATCGACGGTCACTTAGAAATTGTAGAGG<br>TGTTGTTGAAGAACGGGGCAGACGTTAATGCACAAGATAAGTTCGGCAAAACGGCATTC<br>GATATCTCCATTGATAATGGTAATGAAGATTTAGCTGAAATCCTGCAGAAGGCAGCAGG<br>CTCGCCGACTCCGACCCCGACCACCCCAACTCCAACACCGACCACCCCGACCCCTACCC<br>CAACAGGATCCGACCTGGGTGACAAACTGCTGCTGGCTGCTACTTCTGGTCAGGACGAC<br>GAAGTTCGTATCCTGCTGGCTGCTGGCGCCGACGTTAATGCTAAAGACTACGACGGTGA<br>CACTCCGCTGCACCTGGCTGCTGACGAAGGTCACCTGGAAATCGTTGAAGTTCTGCTGA<br>AGGCTGGTGCTGACGTTAATGCTAAAGACTACTCTGGTTCTACTCCGCTGCACGCTGCT<br>GCTGCTTACGGTCACCTGGAAATCGTTGAAGTTCTGCTGAAGGCTGGTGCTGACGTTAA<br>CGCTCAGGACGTTTTCGGTTACACTCCGGCTGATCTGGCTGCTTACGTTGGTCACGAGG<br>ATATCGCTGAAGTTCTGCAGAAGGCTGCGGGGAGTCCAACCCCGACGCCAACCACACCC<br>ACTCCTACGCCTACAACTCCAACTCCGACGCCTACCGGATCAGATCTGGGTCAAAAATT<br>GTTAGAGGCAGCCTGGGCGGGACAGTTAGACGAGGTTCGTATTCTTTTGAAAGCTGGTG<br>CGGATGTGAACGCAAAGAATTCTCGTGGATGGACTCCGTTGCACACCGCCGCACAGACT<br>GGGCACTTGGAAATCTTTGAGGTTCTGTTAAAAGCAGGGGCAGATGTTAACGCTAAAAC<br>TAATAAACGTGTCACCCCCCTTCACCTGGCTGCGGCTTTAGGCCATTTAGAAATCGTGG |

SEQUENCE TABLE

| SEQ ID NO | Description | DARPin protein | Sequence (an X represents any amino acid) |
|---|---|---|---|
| | | | AAGTATTACTTAAAGCCGGGGCTGACGTTAACGCCCGTGACACTTGGGGACAACCCCT GCGGATCTGGCCGCCAAATATGGTCACCGCGACATTGCTGAAGTTCTGCAGAAGGCAGC ATAATGATAG |
| 56 | Ankyrin repeat protein specific for CD33-CD3 | DARPin® protein #25 | DLGDKLLLAATSGQDDEVRILLAAGADVNAKDYDGDTPLHLAADEGHLEIVEVLLKAGA DVNAKDYSGSTPLHAAAAYGHLEIVEVLLKAGADVNAQDVFGYTPADLAAYVGHEDIAE VLQKAAGSPTPTPTTPTPTPTPTPTPTGSDLGQKLLEAAWAGQDDEVRILLAAGADVN AKNSRGWTPLHTAAQTGHLEIFEVLLKAGADVNAKNDKRVTPLHLAAALGHLEIVEVLL KAGADVNARDSWGTTPADLAAKYGHGDIAEVLQKLN |
| 57 | Ankyrin repeat protein specific for CD123-CD3 | DARPin® protein #26 | DLGKKLLEAARAGQDDEVRILMANGADVNALDWLGHTPLHLAAYEGHLEIVEVLLKNGA DVNAIDDNNGFTPLHLAAIDGHLEIVEVLLKAGADVNAQDKFGKTAFDISIDNGNEDLA EILQKAAGSPTPTPTTPTPTTPTPTPTGSDLGQKLLEAAWAGQDDEVRILLAAGADV NAKNSRGVVTPLHTAAQTGHLEIFEVLLKAGADVNAKNDKRVTPLHLAAALGHLEIVEV LLKAGADVNARDSWGTTPADLAAKYGHGDIAEVLQKLN |
| 58 | Ankyrin repeat protein specific for CD123-CD33-CD3 | DARPin® protein #27 | DLGKKLLEAALEGQLDEVRELLKAGADVNAKDQEGYTPLHLAAALGHLEIVEVLLKAGA DVNAKDSIGRTPLHAAYKGHLEIVEVLLKAGADVNAQDLLGETPADLAAEQGHQDIAE VLQKAAGSPTPTPTTPTPTPTPTPTPTGSDLGVKLLLAASRGQLDEVRILLKAGADVN AKDIDEGYTPLHIAAYYGHLEIVEVLLKAGADVNAKDRYGKTPLHAAISGHLEIVEVL LKAGADVNAQDDKGDTPADLAADYGHQDIAEVLQKAAGSPTPTPTTPTPTTPTPTPT GSDLGQKLLEAAWAGQDDEVRELLKAGADVNAKNSRGWTPLHTAAQTGHLEIFEVLLKA GADVNAKDDKGVTPLHLAAALGHLEIVEVLLKAGADVNAQDSWGTTPADLAAKYGHEDI AEVLQKAA |
| 59 | Ankyrin repeat protein specific for CD70-CD33-CD3 | DARPin® protein #28 | DLGYKLLQAAYDGQLDEVRILLKAGADVNAKDSRGQTPLHYAASIGHLEIVEVLLKAGA DVNAKDDHGWTPLHLAAWSGHLEIVEVLLKAGADVNAQDQEGTTPADLAAVQGHQDIAE VLQKAAGSPTPTPTTPTPTPTPTPTPTGSDLGWKLLLAASRGQDDEVRILLAAGADVN AKDIDEGYTPLHIAAYYGHLEIVEVLLKAGADVNAKDRYGKTPLHAAISGHEDIAEVL LKAGADVNAQDDKGDTPADLAADYGHEDIAEVLQKAAGSPTPTPTTPTPTTPTPTPT GSDLGQKLLEAAWAGQDDEVRELLKAGADVNAKNSRGWTPLHTAAQTGHLEIFEVLLKA GADVNAKDDKGVTPLHLAAALGHLEIVEVLLKAGADVNAQDSWGTTPADLAAKYGHEDI AEVLQKAA |
| 60 | Ankyrin repeat protein specific for CD70-CD33-CD3 | DARPin® protein #29 | DLGYKLLQAAYDGQLDEVRILLKAGADVNAKDSRGQTPLHYAASIGHLEIVEVLLKAGA DVNAKDDHGWTPLHLAAWSGHLEIVEVLLKAGADVNAQDQEGTTPADLAAVQGHQDIAE VLQKAAGSPTPTPTTPTPTPTPTPTPTGSDLGVKLLLAASRGQLDEVRILLKAGADVN AKDIDEGYTPLHIAAYYGHLEIVEVLLKAGADVNAKDRYGKTPLHAAISGHLEIVEVL LKAGADVNAQDDKGDTPADLAADYGHQDIAEVLQKAAGSPTPTPTTPTPTTPTPTPT GSDLGQKLLEAAWAGQDDEVRELLKAGADVNAKNSRGWTPLHTAAQTGHLEIFEVLLKA GADVNAKDDKGVTPLHLAAALGHLEIVEVLLKAGADVNAQDSWGTTPADLAAKYGHEDI AEVLQKAA |
| 61 | Ankyrin repeat protein specific for CD70-CD123-CD33-CD3 | DARPin® protein #30 | DLGYKLLQAAYDGQLDEVRILLKAGADVNAKDSRGQTPLHYAASIGHLEIVEVLLKAGA DVNAKDDHGWTPLHLAAWSGHLEIVEVLLKAGADVNAQDQEGTTPADLAAVQGHQDIAE VLQKAAGSPTPTPTTPTPTPTPTPTPTGSDLGKKLLEAALEGQDDEVRELLKAGADVN AKDQEGYTPLHLAAALGHLEIVEVLLKAGADVNAKDSIGRTPLHLAAYKGHLEIVEVLL KAGADVNAQDLLGETPADLAAEQGHEDIAEVLQKAAGSPTPTPTTPTPTTPTPTPTG SDLGVKLLRAAFHGQDDEVRILLAAGADVNAKDTDGETPLHYAAQFGHLEIVEVLLKAG ADVNAKDAYGATPLHWAAWHGHLEIVEVLLKAGADVNAQDVSGATPADLAAKVGHEDIA EVLQKAAGSPTPTPTTPTPTTPTPTPTGSDLGQKLLEAAWAGQDDEVRELLKAGADV NAKNSRGWTPLHTAAQTGHLEIFEVLLKAGADVNAKDDKGVTPLHLAAALGHLEIVEVL LKAGADVNAQDSWGTTPADLAAKYGHEDIAEVLQKAA |
| 62 | Ankyrin repeat protein specific for CD70-CD123-CD33-CD3 | DARPin® protein #31 | DLGYKLLQAAYDGQLDEVRILLKAGADVNAKDSRGQTPLHYAASIGHLEIVEVLLKAGA DVNAKDDHGWTPLHLAAWSGHLEIVEVLLKAGADVNAQDQEGTTPADLAAVQGHQDIAE VLQKAAGSPTPTPTTPTPTPTPTPTPTGSDLGKKLLEAALEGQLDEVRELLKAGADVN AKDQEGYTPLHLAAALGHLEIVEVLLKAGADVNAKDSIGRTPLHLAAYKGHLEIVEVLL KAGADVNAQDLLGETPADLAAEQGHQDIAEVLQKAAGSPTPTPTTPTPTTPTPTPTG SDLGVKLLRAAVHGQLDEVRILLKAGADVNAKDTDGETPLHYAAQFGHLEIVEVLLKAG ADVNAKDAYGATPLHWAAWHGHLEIVEVLLKAGADVNAQDVSGATPADLAAKVGHQDIA EVLQKAAGSPTPTPTTPTPTTPTPTPTGSDLGQKLLEAAWAGQDDEVRELLKAGADV NAKNSRGWTPLHTAAQTGHLEIFEVLLKAGADVNAKDDKGVTPLHLAAALGHLEIVEVL LKAGADVNAQDSWGTTPADLAAKYGHEDIAEVLQKAA |
| 63 | Consensus GS linker | | Gly-Gly-Gly-Gly-Serin, wherein n is 1, 2, 3, 4, 5, or 6 |
| 64 | Ankyrin repeat domain specific for CD70 | DARPin® protein #33 | DLGYKLLQAAYDGQLDEVRILLKAGADVNAKDSRGQTPLHYAASIGHLEIVEVLLKAGA DVNAKDDHGWTPLHLAAWSGHLEIVEVLLKAGADVNAQDQEGTTPADLAAVQGHQDIAE VLQKAA |
| 65 | Ankyrin repeat domain specific for CD123 | DARPin® protein #34 | DLGKKLLEAALEGQLDEVRELLKAGADVNAKDQEGYTPLHLAAALGHLEIVEVLLKAGA DVNAKDSIGRTPLHLAAYKGHLEIVEVLLKAGADVNAQDLLGETPADLAAEQGHQDIAE VLQKAA |

| SEQ ID NO | Description | DARPin protein | Sequence (an X represents any amino acid) |
|---|---|---|---|
| 66 | Ankyrin repeat domain specific for CD123 | DARPin® protein #35 | DLGKKLLEAALEGQDDEVRELLKAGADVNAKDQEGYTPLHLAAALGHLEIVEVLLKAGA DVNAKDSIGRTPLHLAAYKGHLEIVEVLLKAGADVNAQDLLGETPADLAAEQGHEDIAE VLQKAA |
| 67 | Ankyrin repeat domain specific for CD33 | DARPin® protein #36 | DLGVKLLLAASRGQLDEVRILLKAGADVNAKDIDEGYTPLHIAAYYGHLEIVEVLLKAG ADVNAKDRYGKTPLHLAAISGHLEIVEVLLKAGADVNAQDDKGDTPADLAADYGHQDIA EVLQKAA |
| 68 | Ankyrin repeat domain specific for CD33 | DARPin® protein #37 | DLGWKLLLAASRGQDDEVRILLAAGADVNAKDIDEGYTPLHIAAYYGHLEIVEVLLKAG ADVNAKDRYGKTPLHLAAISGHEDIAEVLLKAGADVNAQDDKGDTPADLAADYGHEDIA EVLQKAA |
| 69 | Ankyrin repeat domain specific for CD33 | DARPin® protein #38 | DLGVKLLRAAFHGQDDEVRILLAAGADVNAKDTDGETPLHYAAQFGHLEIVEVLLKAGA DVNAKDAYGATPLHWAAWHGHLEIVEVLLKAGADVNAQDVSGATPADLAAKVGHEDIAE VLQKAA |
| 70 | Ankyrin repeat domain specific for CD33 | DARPin® protein #39 | DLGVKLLRAAVHGQLDEVRILLKAGADVNAKDTDGETPLHYAAQFGHLEIVEVLLKAGA DVNAKDAYGATPLHWAAWHGHLEIVEVLLKAGADVNAQDVSGATPADLAAKVGHQDIAE VLQKAA |
| 71 | Ankyrin repeat protein specific for CD33-CD3 | DARPin® protein #40 | DLGKKLLEAARAGQDDEVRELLKAGADVNAKDKDGYTPLHLAAREGHLEIVEVLLKAGA DVNAKDKDGYTPLHLAAREGHLEIVEVLLKAGADVNAQDKSGKTPADLAADAGHEDIAE VLQKAAGSPTPTPTTPTPTPTTPTPTPTGSDLGVKLLLLAASRGQLDEVRILLKAGADVN AKDIDEGYTPLHIAAYYGHLEIVEVLLKAGADVNAKDRYGKTPLHLAAISGHLEIVEVL LKAGADVNAQDDKGDTPADLAADYGHQDIAEVLQKAAGSPTPTPTTPTPTPTTPTPTPT GSDLGQKLLEAAWAGQDDEVRELLKAGADVNAKNSRGWTPLHTAAQTGHLEIFEVLLKA GADVNAKDDKGVTPLHLAAALGHLEIVEVLLKAGADVNAQDSWGTTPADLAAKYGHEDI AEVLQKAA |
| 72 | Ankyrin repeat protein specific for CD123-CD3 | DARPin® protein #41 | DLGKKLLEAALEGQLDEVRELLKAGADVNAKDQEGYTPLHLAAALGHLEIVEVLLKAGA DVNAKDSIGRTPLHLAAYKGHLEIVEVLLKAGADVNAQDLLGETPADLAAEQGHQDIAE VLQKAAGSPTPTPTTPTPTPTTPTPTPTGSDLGKKLLEAARAGQDDEVRELLKAGADVN AKDKDGYTPLHLAAREGHLEIVEVLLKAGADVNAKDKDGYTPLHLAAREGHLEIVEVLL KAGADVNAQDKSGKTPADLAADAGHEDIAEVLQKAAGSPTPTPTTPTPTPTTPTPTPTG SDLGQKLLEAAWAGQDDEVRELLKAGADVNAKNSRGWTPLHTAAQTGHLEIFEVLLKAG ADVNAKDDKGVTPLHLAAALGHLEIVEVLLKAGADVNAQDSWGTTPADLAAKYGHEDIA EVLQKAA |
| 73 | Ankyrin repeat protein specific for CD33-CD3 | DARPin® protein #42 | DLGKKLLEAARAGQDDEVRELLKAGADVNAKDKDGYTPLHLAAREGHLEIVEVLLKAGA DVNAKDKDGYTPLHLAAREGHLEIVEVLLKAGADVNAQDKSGKTPADLAADAGHEDIAE VLQKAAGSPTPTPTTPTPTPTTPTPTPTGSDLGVKLLLAASRGQLDEVRILLKAGADVN AKDIDEGYTPLHIAAYYGHLEIVEVLLKAGADVNAKDRYGKTPLHLAAISGHLEIVEVL LKAGADVNAQDDKGDTPADLAADYGHQDIAEVLQKAAGSPTPTPTTPTPTPTTPTPTPT GSDLGQKLLEAAWAGQDDEVRELLKAGADVNAKNSRGWTPLHTAAQTGHLEIFEVLLKA GADVNAKDDKGVTPLHLAAALGHLEIVEVLLKAGADVNAQDSWGTTPADLAAKYGHEDI AEVLQKAA |
| 74 | Ankyrin repeat protein specific for CD70-CD3 | DARPin® protein #43 | DLGYKLLQAAYDGQLDEVRILLKAGADVNAKDSRGQTPLHYAASIGHLEIVEVLLKAGA DVNAKDDHGWTPLHLAAWSGHLEIVEVLLKAGADVNAQDQEGTTPADLAAVQGHQDIAE VLQKAAGSPTPTPTTPTPTPTTPTPTPTGSDLGKKLLEAARAGQDDEVRELLKAGADVN AKDKDGYTPLHLAAREGHLEIVEVLLKAGADVNAKDKDGYTPLHLAAREGHLEIVEVLL KAGADVNAQDKSGKTPADLAADAGHEDIAEVLQKAAGSPTPTPTTPTPTPTTPTPTPTG SDLGQKLLEAAWAGQDDEVRELLKAGADVNAKNSRGWTPLHTAAQTGHLEIFEVLLKAG ADVNAKDDKGVTPLHLAAALGHLEIVEVLLKAGADVNAQDSWGTTPADLAAKYGHEDIA EVLQKAA |
| 75 | Ankyrin repeat protein specific for CD33-CD3 | DARPin® protein #44 | DLGKKLLEAARAGQDDEVRELLKAGADVNAKDKDGYTPLHLAAREGHLEIVEVLLKAGA DVNAKDKDGYTPLHLAAREGHLEIVEVLLKAGADVNAQDKSGKTPADLAADAGHEDIAE VLQKAAGSPTPTPTTPTPTPTTPTPTPTGSDLGKKLLEAARAGQDDEVRELLKAGADVN AKDKDGYTPLHLAAREGHLEIVEVLLKAGADVNAKDKDGYTPLHLAAREGHLEIVEVLL KAGADVNAQDKSGKTPADLAADAGHEDIAEVLQKAAGSPTPTPTTPTPTPTTPTPTPTG SDLGVKLLRAAVHGQLDEVRILLKAGADVNAKDTDGETPLHYAAQFGHLEIVEVLLKAG ADVNAKDAYGATPLHWAAWHGHLEIVEVLLKAGADVNAQDVSGATPADLAAKVGHQDIA EVLQKAAGSPTPTPTTPTPTPTTPTPTPTGSDLGQKLLEAAWAGQDDEVRELLKAGADV NAKNSRGWTPLHTAAQTGHLEIFEVLLKAGADVNAKDDKGVTPLHLAAALGHLEIVEVL LKAGADVNAQDSWGTTPADLAAKYGHEDIAEVLQKAA |
| 76 | Ankyrin repeat protein specific for CD70-CD3 | DARPin® protein #45 | DLGYKLLQAAYDGQLDEVRILLKAGADVNAKDSRGQTPLHYAASIGHLEIVEVLLKAGA DVNAKDDHGWTPLHLAAWSGHLEIVEVLLKAGADVNAQDQEGTTPADLAAVQGHQDIAE VLQKAAGSPTPTPTTPTPTPTTPTPTPTGSDLGKKLLEAARAGQDDEVRELLKAGADVN AKDKDGYTPLHLAAREGHLEIVEVLLKAGADVNAKDKDGYTPLHLAAREGHLEIVEVLL KAGADVNAQDKSGKTPADLAADAGHEDIAEVLQKAAGSPTPTPTTPTPTPTTPTPTPTG SDLGKKLLEAARAGQDDEVRELLKAGADVNAKDKDGYTPLHLAAREGHLEIVEVLLKAG |

| SEQ ID NO | Description | DARPin protein | Sequence (an X represents any amino acid) |
|---|---|---|---|
| | | | ADVNAKDKDGYTPLHLAAREGHLEIVEVLLKAGADVNAQDKSGKTPADLAADAGHEDIA EVLQKAAGSPTPTPTTPTPTPTTPTPTPTGSDLGQKLLEAAWAGQDDEVRELLKAGADV NAKNSRGWTPLHTAAQTGHLEIFEVLLKAGADVNAKDDKGVTPLHLAAALGHLEIVEVL LKAGADVNAQDSWGTTPADLAAKYGHEDIAEVLQKAA |
| 77 | Ankyrin repeat protein specific for CD123-CD3 | DARPin® protein #46 | DLGKKLLEAARAGQDDEVRELLKAGADVNAKDKDGYTPLHLAAREGHLEIVEVLLKAGA DVNAKDKDGYTPLHLAAREGHLEIVEVLLKAGADVNAQDKSGKTPADLAADAGHEDIAE VLQKAAGSPTPTPTTPTPTPTTPTPTPTGSDLGKKLLEAARAGQDDEVRELLKAGADVN AKDQEGYTPLHLAAALGHLEIVEVLLKAGADVNAKDSIGRTPLHLAAYKGHLEIVEVLL KAGADVNAQDLLGETPADLAAEQGHQDIAEVLQKAAGSPTPTPTTPTPTPTTPTPTPTG SDLGKKLLEAARAGQDDEVRELLKAGADVNAKDKDGYTPLHLAAREGHLEIVEVLLKAG ADVNAKDKDGYTPLHLAAREGHLEIVEVLLKAGADVNAQDKSGKTPADLAADAGHEDIA EVLQKAAGSPTPTPTTPTPTPTTPTPTPTGSDLGQKLLEAAWAGQDDEVRELLKAGADV NAKNSRGWTPLHTAAQTGHLEIFEVLLKAGADVNAKDDKGVTPLHLAAALGHLEIVEVL LKAGADVNAQDSWGTTPADLAAKYGHEDIAEVLQKAA |
| 78 | Ankyrin repeat protein with binding specificity for HSA-CD123-CD33-CD3 | DARPin® protein #47 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTPTGSDLGKKLLEAALEGQLDEVRELLKAGADVN AKDQEGYTPLHLAAALGHLEIVEVLLKAGADVNAKDSIGRTPLHLAAYKGHLEIVEVLL KAGADVNAQDLLGETPADLAAEQGHQDIAEVLQKAAGSPTPTPTTPTPTPTTPTPTPTG SDLGVKLLLAASRGQLDEVRILLKAGADVNAKDIDEGYTPLHIAAYYGHLEIVEVLLKA GADVNAKDRYGKTPLHLAAISGHLEIVEVLLKAGADVNAQDDKGDTPADLAADYGHQDI AEVLQKAAGSPTPTPTTPTPTPTTPTPTPTGSDLGQKLLEAAWAGQDDEVRELLKAGAD VNAKNSRGWTPLHTAAQTGHLEIFEVLLKAGADVNAKDDKGVTPLHLAAALGHLEIVEV LLKAGADVNAQDSWGTTPADLAAKYGHEDIAEVLQKAA |
| 79 | Ankyrin repeat protein with binding specificity for HSA-HSA-CD123-CD33-CD3 | DARPin® protein #48 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTPTGSDLGKKLLEAARAGQDDEVRELLKAGADVN AKDYFSHTPLHLAARNGHLKIVEVLLKAGADVNAKDFAGKTPLHLAAADGHLEIVEVLL KAGADVNAQDIFGKTPADIAADAGHEDIAEVLQKAAGSPTPTPTTPTPTPTTPTPTPTG SDLGKKLLEAALEGQLDEVRELLKAGADVNAKDQEGYTPLHLAAALGHLEIVEVLLKAG ADVNAKDSIGRTPLHLAAYKGHLEIVEVLLKAGADVNAQDLLGETPADLAAEQGHQDIA EVLQKAAGSPTPTPTTPTPTPTTPTPTPTGSDLGVKLLLAASRGQLDEVRILLKAGADV NAKDIDEGYTPLHIAAYYGHLEIVEVLLKAGADVNAKDRYGKTPLHLAAISGHLEIVEV LLKAGADVNAQDDKGDTPADLAADYGHQDIAEVLQKAAGSPTPTPTTPTPTPTTPTPTP TGSDLGQKLLEAAWAGQDDEVRELLKAGADVNAKNSRGWTPLHTAAQTGHLEIFEVLLK AGADVNAKDDKGVTPLHLAAALGHLEIVEVLLKAGADVNAQDSWGTTPADLAAKYGHED IAEVLQKAA |
| 80 | Ankyrin repeat protein with binding specificity for CD123-CD33-CD3-HSA | DARPin® protein #49 | DLGKKLLEAALEGQLDEVRELLKAGADVNAKDQEGYTPLHLAAALGHLEIVEVLLKAGA DVNAKDSIGRTPLHLAAYKGHLEIVEVLLKAGADVNAQDLLGETPADLAAEQGHQDIAE VLQKAAGSPTPTPTTPTPTPTTPTPTPTGSDLGVKLLLAASRGQLDEVRILLKAGADVN AKDIDEGYTPLHIAAYYGHLEIVEVLLKAGADVNAKDRYGKTPLHLAAISGHLEIVEVL LKAGADVNAQDDKGDTPADLAADYGHQDIAEVLQKAAGSPTPTPTTPTPTPTTPTPTPT GSDLGQKLLEAAWAGQDDEVRELLKAGADVNAKNSRGWTPLHTAAQTGHLEIFEVLLKA GADVNAKDDKGVTPLHLAAALGHLEIVEVLLKAGADVNAQDSWGTTPADLAAKYGHEDI AEVLQKAAGSPTPTPTTPTPTPTTPTPTPTGSDLGKKLLEAARAGQDDEVRELLKAGAD VNAKDYFSHTPLHLAARNGHLKIVEVLLKAGADVNAKDFAGKTPLHLAAADGHLEIVEV LLKAGADVNAQDIFGKTPADIAADAGHEDIAEVLQKAA |
| 81 | Ankyrin repeat protein with binding specificity for HSA-CD70-CD33-CD3 | DARPin® protein #50 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTPTGSDLGYKLLQAAYDGQLDEVRILLKAGADVN AKDSRGQTPLHYAASIGHLEIVEVLLKAGADVNAKDDHGWTPLHLAAWSGHLEIVEVLL KAGADVNAQDQEGTTPADLAAVQGHQDIAEVLQKAAGSPTPTPTTPTPTPTTPTPTPTG SDLGVKLLLAASRGQLDEVRILLKAGADVNAKDIDEGYTPLHIAAYYGHLEIVEVLLKA GADVNAKDRYGKTPLHLAAISGHLEIVEVLLKAGADVNAQDDKGDTPADLAADYGHQDI AEVLQKAAGSPTPTPTTPTPTPTTPTPTPTGSDLGQKLLEAAWAGQDDEVRELLKAGAD VNAKNSRGWTPLHTAAQTGHLEIFEVLLKAGADVNAKDDKGVTPLHLAAALGHLEIVEV LLKAGADVNAQDSWGTTPADLAAKYGHEDIAEVLQKAA |
| 82 | Ankyrin repeat protein with binding specificity for HSA-HSA-CD70-CD33-CD3 | DARPin® Protein #51 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTPTGSDLGKKLLEAARAGQDDEVRELLKAGADVN AKDYFSHTPLHLAARNGHLKIVEVLLKAGADVNAKDFAGKTPLHLAAADGHLEIVEVLL KAGADVNAQDIFGKTPADIAADAGHEDIAEVLQKAAGSPTPTPTTPTPTPTTPTPTPTG SDLGYKLLQAAYDGQLDEVRILLKAGADVNAKDSRGQTPLHYAASIGHLEIVEVLLKAG ADVNAKDDHGWTPLHLAAWSGHLEIVEVLLKAGADVNAQDQEGTTPADLAAVQGHQDIA EVLQKAAGSPTPTPTTPTPTPTTPTPTPTGSDLGVKLLLAASRGQLDEVRILLKAGADV NAKDIDEGYTPLHIAAYYGHLEIVEVLLKAGADVNAKDRYGKTPLHLAAISGHLEIVEV |

| SEQ ID NO | Description | DARPin protein | Sequence (an X represents any amino acid) |
|---|---|---|---|
| | | | LLKAGADVNAQDDKGDTPADLAADYGHQDIAEVLQKAAGSPTPTPTTPTPTPTPTPTP TGSDLGQKLLEAAWAGQDDEVRELLKAGADVNAKNSRGWTPLHTAAQTGHLEIFEVLLK AGADVNAKDDKGVTPLHLAAALGHLEIVEVLLKAGADVNAQDSWGTTPADLAAKYGHED IAEVLQKAA |
| 83 | Ankyrin repeat protein with binding specificity for CD70-CD33-CD3 | DARPin® protein #52 | DLGYKLLQAAYDGQLDEVRILLKAGADVNAKDSRGQTPLHYAASIGHLEIVEVLLKAGA DVNAKDDHGWTPLHLAAWSGHLEIVEVLLKAGADVNAQDQEGTTPADLAAVQGHQDIAE VLQKAAGSPTPTPTTPTPTPTPTPTGSDLGKKLLEAALEGQLDEVRELLKAGADVN AKDIDEGYTPLHIAAYYGHLEIVEVLLKAGADVNAKDRYGKTPLHLAAISGHLEIVEVL LKAGADVNAQDDKGDTPADLAADYGHQDIAEVLQKAAGSPTPTPTTPTPTTPTPTPT GSDLGQKLLEAAWAGQDDEVRELLKAGADVNAKNSRGWTPLHTAAQTGHLEIFEVLLKA GADVNAKDDKGVTPLHLAAALGHLEIVEVLLKAGADVNAQDSWGTTPADLAAKYGHEDI AEVLQKAAGSPTPTPTTPTPTPTPTPTGSDLGKKLLEAARAGQDDEVRELLKAGAD VNAKDYFSHTPLHLAARNGHLKIVEVLLKAGADVNAKDFAGKTPLHLAAADGHLEIVEV LLKAGADVNAQDIFGKTPADIAADAGHEDIAEVLQKAA |
| 84 | Ankyrin repeat protein with binding specificity for HSA-CD70-CD123-CD33-CD3 | DARPin® protein #53 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTPTPTGSDLGYKLLQAAYDGQLDEVRILLKAGADVN AKDSRGQTPLHYAASIGHLEIVEVLLKAGADVNAKDDHGWTPLHLAAWSGHLEIVEVLL KAGADVNAQDQEGTTPADLAAVQGHQDIAEVLQKAAGSPTPTPTTPTPTPTPTPTG SDLGKKLLEAALEGQLDEVRELLKAGADVNAKDQEGYTPLHLAAALGHLEIVEVLLKAG ADVNAKDSIGRTPLHLAAYKGHLEIVEVLLKAGADVNAQDLLGETPADLAAEQGHQDIA EVLQKAAGSPTPTPTTPTPTTPTPTPTGSDLGVKLLRAAVHGQLDEVRILLKAGADV NAKDTDGETPLHYAAQFGHLEIVEVLLKAGADVNAKDAYGATPLHWAAWHGHLEIVEVL LKAGADVNAQDVSGATPADLAAKVGHQDIAEVLQKAAGSPTPTPTTPTPTTPTPTPT GSDLGQKLLEAAWAGQDDEVRELLKAGADVNAKNSRGVVTPLHTAAQTGHLEIFEVLLK AGADVNAKDDKGVTPLHLAAALGHLEIVEVLLKAGADVNAQDSWGTTPADLAAKYGHED IAEVLQKAA |
| 85 | Ankyrin repeat protein with binding specificity for HSA-HSA-CD70-CD123-CD33-CD3 | DARPin® protein #54 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTPTPTGSDLGKKLLEAARAGQDDEVRELLKAGADVN AKDYFSHTPLHLAARNGHLKIVEVLLKAGADVNAKDFAGKTPLHLAAADGHLEIVEVLL KAGADVNAQDIFGKTPADIAADAGHEDIAEVLQKAAGSPTPTPTTPTPTPTPTPTG SDLGYKLLQAAYDGQLDEVRILLKAGADVNAKDSRGQTPLHYAASIGHLEIVEVLLKAG ADVNAKDDHGWTPLHLAAWSGHLEIVEVLLKAGADVNAQDQEGTTPADLAAVQGHQDIA EVLQKAAGSPTPTPTTPTPTPTPTPTGSDLGKKLLEAALEGQLDEVRELLKAGADV NAKDQEGYTPLHLAAALGHLEIVEVLLKAGADVNAKDSIGRTPLHLAAYKGHLEIVEVL LKAGADVNAQDLLGETPADLAAEQGHQDIAEVLQKAAGSPTPTPTTPTPTTPTPTPT GSDLGVKLLRAAVHGQLDEVRILLKAGADVNAKDTDGETPLHYAAQFGHLEIVEVLLKA GADVNAKDAYGATPLHWAAWHGHLEIVEVLLKAGADVNAQDVSGATPADLAAKVGHQDI AEVLQKAAGSPTPTPTTPTPTTPTPTPTGSDLGQKLLEAAWAGQDDEVRELLKAGAD VNAKNSRGVVTPLHTAAQTGHLEIFEVLLKAGADVNAKDDKGVTPLHLAAALGHLEIVE VLLKAGADVNAQDSWGTTPADLAAKYGHEDIAEVLQKAA |
| 86 | Ankyrin repeat protein with binding specificity for CD70-CD123-CD33-CD3-HSA | DARPin® protein #55 | DLGYKLLQAAYDGQLDEVRILLKAGADVNAKDSRGQTPLHYAASIGHLEIVEVLLKAGA DVNAKDDHGWTPLHLAAWSGHLEIVEVLLKAGADVNAQDQEGTTPADLAAVQGHQDIAE VLQKAAGSPTPTPTTPTPTPTPTPTGSDLGKKLLEAALEGQLDEVRELLKAGADVN AKDQEGYTPLHLAAALGHLEIVEVLLKAGADVNAKDSIGRTPLHLAAYKGHLEIVEVLL KAGADVNAQDLLGETPADLAAEQGHQDIAEVLQKAAGSPTPTPTTPTPTPTPTPTG SDLGVKLLRAAVHGQLDEVRILLKAGADVNAKDTDGETPLHYAAQFGHLEIVEVLLKAG ADVNAKDAYGATPLHWAAWHGHLEIVEVLLKAGADVNAQDVSGATPADLAAKVGHQDIA EVLQKAAGSPTPTPTTPTPTPTPTPTGSDLGQKLLEAAWAGQDDEVRELLKAGADV NAKNSRGWTPLHTAAQTGHLEIFEVLLKAGADVNAKDDKGVTPLHLAAALGHLEIVEVL LKAGADVNAQDSWGTTPADLAAKYGHEDIAEVLQKAAGSPTPTPTTPTPTTPTPTPT GSDLGKKLLEAARAGQDDEVRELLKAGADVNAKDYFSHTPLHLAARNGHLKIVEVLLKA GADVNAKDFAGKTPLHLAAADGHLEIVEVLLKAGADVNAQDIFGKTPADIAADAGHEDI AEVLQKAA |
| 87 | biotinylated extracellular domain of human CD33 | | DPNFWLQVQESVTVQEGLCVLVPCTFFHPIPYYDKNSPVHGYWFREGAIISGDSPVATN KLDQEVQEETQGRFRLLGDPSRNNCSLSIVDARRRDNGSYFFRMERGSTKYSYKSPQLS VHVTDLTHRPKILIPGTLEPGHSKNLTCSVSWACEQGTPPIFSWLSAAPTSLGPRTTHS SVLIITPRPQDHGTNLTCQVKFAGAGVTTERTIQLNVTYVPQNPTTGIFPGDGSGKQET RAGVVH |
| 88 | biotinylated extracellular domain of human CD123 | | TKEDPNPPITNLRMKAKAQQLTWDLNRNVTDIECVKDADYSMPAVNNSYCQFGAISLCE VTNYTVRVANPPFSTWILFPENSGKPWAGAENLTCWIHDVDFLSCSWAVGPGAPADVQY DLYLNVANRQQYECLHYKTDAQGTRIGCRFDDISRLSSGSQSSHILVRGRSAAFGIPC TDKFVVFSQIEILTPPNMTAKCNKTHSFMHWKMRSHFNRKFRYELQIQKRMQPVITEQV RDRTSFOLLNPGTYTVQ1RARERVYEFLSAWSTPQRFECDQEEGANTRA |

SEQUENCE TABLE

| SEQ ID NO | Description | DARPin protein | Sequence (an X represents any amino acid) |
|---|---|---|---|
| 89 | biotinylated extracellular domain of human CD70 | | SLGWDVAELQLNHTGPQQDPRLYWQGGPALGRSFLHGPELDKGQLRIHRDGIYMVHIQV TLAICSSTTASRHHPTTLAVGICSPASRSISLLRLSFHQGCTIASQRLTPLARGDTLCT NLTGTLLPSRNTDETFFGVQWVRP |
| 90 | Nucleic acid encoding domain of SEQ ID NO 58 | | ATGAGAGGATCGCATCACCATCACCATCACGGTTCCGACCTGGGTAAAAAGCTGTTGGA GGCCGCGTTAGAGGGTCAATTGGATGAAGTTCGTGAACTGTTAAAAGCGGGCGCCGATG TAAACGCTAAAGACCAGGAGGGGTACACTCCTTTGCATCTGGCAGCAGCTCTTGGTCAT CTGGAAATTGTCGAGGTGCTGTTAAAGGCAGGAGCAGATGTAAATGCAAAGGACTCTAT TGGACGTACACCACTGCACTTGGCTGCCTACAAAGGTCACCTGGAAATTGTGGAAGTCT TACTGAAAGCGGGCGCTGACGTTAACGCCCAAGACCTGCTGGGGGAAACGCCAGCCGAC CTGGCCGCCGAGCAGGGACATCAGGATATTGCTGAAGTTCTGCAAAAGGCAGCAGGCTC GCCGACTCCGACCCCGACCACCCCAACTCCAACACCGACCACCCCGACCCCTACCCCAA CAGGATCCGACCTGGGTGTTAAACTTTTGTTAGCTGCATCTCGTGGTCAACTGGATGAG GTGCGTATTTTGCTGAAAGCGGGTGCAGATGTTAACGCAAAGGACATCGATGAAGGATA TACGCCATTACACATTGCAGCATATTATGGTCATTTAGAGATCGTAGAGGTTCTTTTGA AGGCAGGAGCCGATGTTAACGCCAAGGACCGTTATGGAAAGACCCCGTTACATTTAGCC GCAATTAGTGGGCATCTTGAAATTGTCGAAGTTTTATTAAAGGCTGGGGCTGATGTAAA TGCTCAGGATGACAAGGGCGACACTCCCGCAGATCTGGCGGCAGACTATGGGCACCAGG ATATTGCTGAAGTTCTGCAGAAGGCTGCGGGGAGTCCAACCCCGACGCCAACCACACCC ACTCCTACGCCTACAACTCCAACTCCGACGCCTACCGGATCAGATCTGGGTCAAAAGTT GTTGGAAGCTGCCTGGGCGGGACAGGATGATGAGGTGCGCGAATTACTTAAGGCGGGAG CAGACGTGAATGCGAAAAACTCTCGTGGCTGGACACCACTGCACACGGCCGCGCAAACT GGTCACCTTGAAATTTTCGAAGTGCTTCTGAAGGCAGGCGCAGATGTAAACGCCAAGGA TGACAAAGGGGTAACACCGCTTCATCTGGCTGCTGCACTGGGACATCTTGAGATTGTCG AAGTACTGCTTAAGGCAGGTGCTGACGTAAACGCTCAGGATTCATGGGGGACCACACCG GCGGACCTGGCGGCTAAATACGGACATGAAGATATTGCTGAAGTTCTTCAGAAGGCAGC ATAATGATAG |
| 91 | Nucleic acid encoding domain of SEQ ID NO 59 | | ATGAGAGGATCGCATCACCATCACCATCACGGATCCGACCTGGGTTATAAACTTCTTCA AGCGGCCTATGATGGGCAGCTTGATGAGGTACGCATTTTGTTAAAGGCCGGCGCAGATG TCAACGCGAAAGATAGTCGCGGACAGACGCCCCTTCATTACGCCGCATCAATCGGCCAT CTGGAAATTGTAGAGGTACTGCTTAAAGCCGGTGCTGATGTAAACGCTAAGGACGACCA CGGATGGACGCCACTTCATCTTGCCGCGTGGAGTGGACACTTGGAGATTGTCGAAGTCT TGTTAAAAGCGGGCGCTGACGTTAACGCACAAGACCAGGAAGGTACGACGCCAGCAGAC TTGGCTGCTGTCCAAGGGCACCAGGACATTGCTGAAGTTCTGCAGAAGGCAGCAGGCAG CCCTACACCTACGCCGACTACGCCTACGCCGACTCCGACTACCCCGACTCCGACCCCGA CCGGATCAGACCTGGGTTGGAAACTGCTGCTGGCTGCTTCTCGTGGTCAGGACGACGAA GTTCGTATCCTGCTGGCTGCTGGCGCCGACGTTAATGCTAAAGACATCGACGAAGGTTA CACTCCGCTGCACATCGCTGCTTACTACGGTCACCTGGAAATCGTTGAAGTTCTGCTGA AGGCTGGTGCTGACGTTAATGCTAAAGACCGTTACGGTAAAACTCCGCTGCACCTGGCT GCTATCTCTGGTCACGAGGATATCGCTGAAGTTCTGCTGAAGGCTGGTGCTGACGTTAA CGCTCAGGACGACAAAGGTGACACTCCGGCTGATCTGGCTGCTGACTACGGTCACGAGG ATATCGCTGAAGTTCTGCAGAAGGCAGCAGGTTCCCCGACCCCTACGCCAACGACTCCG ACCCCAACTCCAACGACCCCTACCCCGACCCCGACCGGATCAGACCTGGGTCAAAAGTT GTTGGAAGCTGCCTGGGCGGGACAGGATGATGAGGTGCGCGAATTACTTAAGGCGGGAG CAGACGTGAATGCGAAAAACTCTCGTGGCTGGACACCACTGCACACGGCCGCGCAAACT GGTCACCTTGAAATTTTCGAAGTGCTTCTGAAGGCAGGCGCAGATGTAAACGCCAAGGA TGACAAAGGGGTAACACCGCTTCATCTGGCTGCTGCACTGGGACATCTTGAGATTGTCG AAGTACTGCTTAAGGCAGGTGCTGACGTAAACGCTCAGGATTCATGGGGGACCACACCG GCGGACCTGGCGGCTAAATACGGACATGAAGATATTGCTGAAGTTCTGCAGAAGGCGGC ATAATGATAG |
| 92 | Nucleic acid encoding domain of SEQ ID NO 60 | | ATGAGAGGATCGCATCACCATCACCATCACGGATCCGACCTGGGTTATAAACTTCTTCA AGCGGCCTATGATGGGCAGCTTGATGAGGTACGCATTTTGTTAAAGGCCGGCGCAGATG TCAACGCGAAAGATAGTCGCGGACAGACGCCCCTTCATTACGCCGCATCAATCGGCCAT CTGGAAATTGTAGAGGTACTGCTTAAAGCCGGTGCTGATGTAAACGCTAAGGACGACCA CGGATGGACGCCACTTCATCTTGCCGCGTGGAGTGGACACTTGGAGATTGTCGAAGTCT TGTTAAAAGCGGGCGCTGACGTTAACGCACAAGACCAGGAAGGTACGACGCCAGCAGAC TTGGCTGCTGTCCAAGGGCACCAGGACATTGCTGAAGTTCTGCAGAAGGCAGCAGGCAG CCCTACACCTACGCCGACTACGCCTACGCCGACTCCGACTACCCCGACTCCGACCCCGA CCGGATCAGACCTGGGTGTTAAACTTTTGTTAGCTGCATCTCGTGGTCAACTGGATGAG GTGCGTATTTTGCTGAAAGCGGGTGCAGATGTTAACGCAAAGGACATCGATGAAGGATA TACGCCATTACACATTGCAGCATATTATGGTCATTTAGAGATCGTAGAGGTTCTTTTGA AGGCAGGAGCCGATGTTAACGCCAAGGACCGTTATGGAAAGACCCCGTTACATTTAGCC GCAATTAGTGGGCATCTTGAAATTGTCGAAGTTTTATTAAAGGCTGGGGCTGATGTAAA TGCTCAGGATGACAAGGGCGACACTCCCGCAGATCTGGCGGCAGACTATGGGCACCAGG ATATTGCTGAAGTTCTGCAGAAGGCAGGTTCCCCGACCCCTACGCCAACGACTCCG ACCCCAACTCCAACGACCCCTACCCCGACCCCGACCGGATCAGACCTGGGTCAAAAGTT GTTGGAAGCTGCCTGGGCGGGACAGGATGATGAGGTGCGCGAATTACTTAAGGCGGGAG CAGACGTGAATGCGAAAAACTCTCGTGGCTGGACACCACTGCACACGGCCGCGCAAACT GGTCACCTTGAAATTTTCGAAGTGCTTCTGAAGGCAGGCGCAGATGTAAACGCCAAGGA TGACAAAGGGGTAACACCGCTTCATCTGGCTGCTGCACTGGGACATCTTGAGATTGTCG AAGTACTGCTTAAGGCAGGTGCTGACGTAAACGCTCAGGATTCATGGGGGACCACACCG |

SEQUENCE TABLE

| SEQ ID NO | Description | DARPin protein | Sequence (an X represents any amino acid) |
|---|---|---|---|
| | | | GCGGACCTGGCGGCTAAATACGGACATGAAGATATTGCTGAAGTTCTGCAGAAGGCGGC<br>ATAATGATAG |
| 93 | Nucleic acid encoding domain of SEQ ID NO 61 | | ATGAGAGGATCGCATCACCATCACCATCACGGATCCGACCTGGGTTATAAACTTCTTCA<br>AGCGGCCTATGATGGGCAGCTTGATGAGGTACGCATTTTGTTAAAGGCCGGCGCAGATG<br>TCAACGCGAAAGATAGTCGCGGACAGACGCCCCTTCATTACGCCGCATCAATCGGCCAT<br>CTGGAAATTGTAGAGGTACTGCTTAAAGCCGGTGCTGATGTAAACGCTAAGGACGACCA<br>CGGATGGACGCCACTTCATCTTGCCGCGTGGAGTGGACACTTGGAGATTGTCGAAGTCT<br>TGTTAAAAGCGGGCGCTGACGTTAACGCACAAGACCAGGAAGGTACGACGCCAGCAGAC<br>TTGGCTGCTGTCCAAGGGCACCAGGACATTGCTGAAGTTCTGCAGAAGGCAGCAGGCTC<br>GCCGACTCCGACCCCGACCACCCCAACTCCAACACCGACCACCCCGACCCCTACCCCAA<br>CAGGATCCGACCTGGGTAAGAAGCTGCTGGAAGCTGCTCTGGAAGGTCAGGATGATGAA<br>GTTCGTGAACTGCTGAAAGCAGGCGCCGATGTTAATGCAAAAGATCAAGAGGGCTACAC<br>CCCACTGCATCTGGCTGCTGCTCTGGGTCACCTGGAAATTGTTGAAGTTCTGCTGAAAG<br>CCGGTGCAGATGTTAATGCAAAAGATTCTATCGGCAGAACCCCGCTGCATCTGGCTGCT<br>TACAAGGGTCACCTGGAAATTGTTGAAGTTCTGCTGAAAGCCGGTGCAGATGTTAACGC<br>ACAGGATCTGCTGGGCGAAACCCTGCCGATCTGGCAGCTGAACAAGGTCATGAAGATA<br>TTGCAGAAGTGCTGCAGAAGGCAGCAGGCAGCCCTACACCTACGCCGACTACGCCTACG<br>CCGACTCCGACTACCCCGACTCCGACCCCGACCGGATCAGACCTGGGTGTTAAACTGCT<br>GCGTGCTGCTTTCCATGGTCAGGACGACGAAGTTCGTATCCTGCTGGCTGCTGGCGCTG<br>ACGTTAATGCTAAAGACACTGACGGTGAAACTCCGCTGCACTACGCTGCTCAGTTCGGT<br>CACCTGGAAATCGTTGAAGTTCTGCTGAAGGCTGGTGCTGACGTTAATGCTAAAGACGC<br>TTACGGTGCTACTCCGCTGCACTGGGCTGCTTGGCATGGTCACCTGGAAATCGTTGAAG<br>TTCTGCTGAAGGCTGGTGCTGACGTTAACGCTCAGGACGTTTCTGGTGCTACTCCGGCT<br>GATCTGGCTGCTAAAGTTGGTCACGAGGATATCGCTGAAGTTCTGCAGAAGGCAGCAGG<br>TTCCCCGACCCCTACGCCAACGACTCCGACCCCAACTCCAACGACCCCTACCCCGACCC<br>CGACCGGATCAGACCTGGGTCAAAAGTTGTTGGAAGCTGCCTGGGCGGGACAGGATGAT<br>GAGGTGCGCGAATTACTTAAGGCGGGAGCAGACGTGAATGCGAAAAACTCTCGTGGCTG<br>GACACCACTGCACACGGCCGCGCAAACTGGTCACCTTGAAATTTTCGAAGTGCTTCTGA<br>AGGCAGGCGCAGATGTAAACGCCAAGGATGACAAAGGGGTAACACCGCTTCATCTGGCT<br>GCTGCACTGGGACATCTTGAGATTGTCGAAGTACTGCTTAAGGCAGGTGCTGACGTAAA<br>CGCTCAGGATTCATGGGGACCACACCGGCGGACCTGGCGGCTAAATACGGACATGAAG<br>ATATTGCTGAAGTTCTGCAGAAGGCGGCATAATGATAG |
| 94 | Nucleic acid encoding domain of SEQ ID NO 62 | | ATGAGAGGATCGCATCACCATCACCATCACGGATCCGACCTGGGTTATAAACTTCTTCA<br>AGCGGCCTATGATGGGCAGCTTGATGAGGTACGCATTTTGTTAAAGGCCGGCGCAGATG<br>TCAACGCGAAAGATAGTCGCGGACAGACGCCCCTTCATTACGCCGCATCAATCGGCCAT<br>CTGGAAATTGTAGAGGTACTGCTTAAAGCCGGTGCTGATGTAAACGCTAAGGACGACCA<br>CGGATGGACGCCACTTCATCTTGCCGCGTGGAGTGGACACTTGGAGATTGTCGAAGTCT<br>TGTTAAAAGCGGGCGCTGACGTTAACGCACAAGACCAGGAAGGTACGACGCCAGCAGAC<br>TTGGCTGCTGTCCAAGGGCACCAGGACATTGCTGAAGTTCTGCAGAAGGCAGCAGGCAG<br>CCCTACACCTACGCCGACTACGCCTACGCCGACTCCGACTACCCCGACTCCGACCCCGA<br>CCGGATCAGACCTGGGTAAAAAGCTGTTGGAGGCCGCGTTAGAGGGTCAATTGGATGAA<br>GTTCGTGAACTGTTAAAAGCGGGCGCCGATGTAAACGCTAAAGACCAGGAGGGGTACAC<br>TCCTTTGCATCTGGCAGCAGCTCTTGGTCATCTGGAAATTGTCGAGGTGCTGTTAAAGG<br>CAGGAGCAGATGTAAATGCAAAGGACTCTATTGGACGTACACCACTGCACTTGGCTGCC<br>TACAAAGGTCACCTGGAAATTGTGGAAGTCTTACTGAAAGCGGGCGCTGACGTTAACGC<br>CCAAGACCTGCTGGGGGAAACGCCAGCCGACCTGGCCGCCGAGCAGGGACATCAGGATA<br>TTGCTGAAGTTCTGCAGAAGGCAGCAGGCTCGCCAACGCCGACCCCTACAACGCCAACC<br>CCGACACCAACTACACCGACCCCCACACCAACGGGATCAGACCTGGGTGTTAAGTTGCT<br>TCGTGCTGCCGTCCACGGTCAATTGGATGAAGTACGCATCCTTCTGAAGGCTGGTGCAG<br>ACGTGAACGCGAAAGACACTGACGGCGAAACCCCCCTTCATTACGCGGCACAATTCGGC<br>CACTTGGAGATCGTTGAGGTCCTTCTGAAAGCCGGCGCAGACGTGAATGCAAAGGATGC<br>TTATGGGGCTACGCCGTTACATTGGGCTGCTTGGCACGGCCATCTTGAGATTGTTGAGG<br>TCCTGTTGAAAGCGGGGCGGATGTAAACGCTCAGGACGTATCCGGCGCGACACCTGCT<br>GACTTAGCAGCTAAAGTCGGACACCAGGATATTGCTGAAGTTCTGCAGAAGGCAGCAGG<br>TTCCCCGACCCCTACGCCAACGACTCCGACCCCAACTCCAACGACCCCTACCCCGACCC<br>CGACCGGATCAGACCTGGGTCAAAAGTTGTTGGAAGCTGCCTGGGCGGGACAGGATGAT<br>GAGGTGCGCGAATTACTTAAGGCGGGAGCAGACGTGAATGCGAAAAACTCTCGTGGCTG<br>GACACCACTGCACACGGCCGCGCAAACTGGTCACCTTGAAATTTTCGAAGTGCTTCTGA<br>AGGCAGGCGCAGATGTAAACGCCAAGGATGACAAAGGGGTAACACCGCTTCATCTGGCT<br>GCTGCACTGGGACATCTTGAGATTGTCGAAGTACTGCTTAAGGCAGGTGCTGACGTAAA<br>CGCTCAGGATTCATGGGGACCACACCGGCGGACCTGGCGGCTAAATACGGACATGAAG<br>ATATTGCTGAAGTTCTGCAGAAGGCGGCATAATGATAG |
| 95 | Ankyrin repeat protein with binding specificity for HSA-HSA-CD33-CD123-CD70-CD3 | DARPin® protein #56 | DLGKKLLEAARAGQDDEVRELLKAGADVNAKDYFSHTPLHLAARNGHLKIVEVLLKAGA<br>DVNAKDFAGKTPLHLAAADGHLEIVEVLLKAGADVNAQDIFGKTPADIAADAGHEDIAE<br>VLQKAAGSPTPTPTTPTPTTPTPTGSDLGKKLLEAARAGQDDEVRELLKAGADVN<br>AKDYFSHTPLHLAARNGHLKIVEVLLKAGADVNAKDFAGKTPLHLAAADGHLEIVEVLL<br>KAGADVNAQDIFGKTPADIAADAGHEDIAEVLQKAAGSPTPTPTTPTPTTPTPTPTG<br>SDLGVKLLLAAERGQLDEVRILLKAGADVNAKDIAEGYTPLHIAAYQGHLEIVEVLLKA<br>GADVNAKDRYGKTPLHLAAIGGHLEIVEVLLKAGADVNAQDNKGSTPADLAADYGHQDI<br>AEVLQKAAGSPTPTPTTPTPTTPTPTPTGSDLGKKLLEAALEGQLDEVRELLKAGAD<br>VNAKDQEGYTPLHLAAALGHLEIVEVLLKAGADVNAKDQIGRTPLHLAAYKGHLEIVEV |

| SEQ ID NO | Description | DARPin protein | Sequence (an X represents any amino acid) |
|---|---|---|---|
| | | | LLKAGADVNAQDIIGQTPADLAAQRGHQDIAEVLQKAAGSPTPTPTTPTPTPTTPTPTP TGSDLGIKLLTAAYDGQLDEVRILLKAGADVNAKDLRGQTPLHYAAGLGHLEIVEVLLK AGADVNAKDLHGVVTPLHLAAWSGHLEIVEVLLKAGADVNAQDVEGVTPADLAAVQGHQ DIAEVLQKAAGSPTPTPTTPTPTPTTPTPTGSDLGQKLLEAAWAGQDDEVRELLKAG ADVNAKNSRGWTPLHTAAQTGHLEIFEVLLKAGADVNAKNDKRVTPLHLAAALGHLEIV EVLLKAGADVNARDSWGTTPADLAAKYGHQDIAEVLQKAA |
| 96 | Ankyrin repeat protein with binding specificity for HSA-HSA-CD70-CD123-CD33-CD3 | DARPin® protein #57 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTGSDLGKKLLEAARAGQDDEVRELLKAGADVN AKDYFSHTPLHLAARNGHLKIVEVLLKAGADVNAKDFAGKTPLHLAAADGHLEIVEVLL KAGADVNAQDIFGKTPADIAADAGHEDIAEVLQKAAGSPTPTPTTPTPTPTTPTPTG SDLGIKLLTAAYDGQLDEVRILLKAGADVNAKDLRGQTPLHYAAGLGHLEIVEVLLKAG ADVNAKDLHGWTPLHLAAWSGHLEIVEVLLKAGADVNAQDVEGVTPADLAAVQGHQDIA EVLQKAAGSPTPTPTTPTPTTPTPTGSDLGKKLLQAALEGQLDEVRELLKAGADV NAKDIFGYTPLHLAAALGHLEIVEVLLKAGADVNAKDQIGRTPLHLAAYKGHLEIVEVL LKAGADVNAQDIIGQTPADLAAQRGHQDIAEVLQKAAGSPTPTPTTPTPTPTTPTPT GSDLGKKLLLAAERGQLDEVRILLKAGADVNAKDRAEGYTPLHIAAYQGHLEIVEVLLK AGADVNAKDRYGKTPLHLAAISGHLFIVEVLLKAGADVNAQDNKGSTPADLAADYGHQD IAEVLQKAAGSPTGSDLGQKLLEAAWAGQDDEVRELLKAGADVNAKNSRGWTPLHTAAQ TGHLEIFEVLLKAGADVNAKNDKRVTPLHLAAALGHLEIVEVLLKAGADVNARDSWGTT PADLAAKYGHQDIAEVLQKAA |
| 97 | Ankyrin repeat protein with binding specificity for HSA-HSA-CD70-CD123-CD33-CD3 | DARPin® protein #58 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTGSDLGKKLLEAARAGQDDEVRELLKAGADVN AKDYFSHTPLHLAARNGHLKIVEVLLKAGADVNAKDFAGKTPLHLAAADGHLEIVEVLL KAGADVNAQDIFGKTPADIAADAGHEDIAEVLQKAAGSPTPTPTTPTPTPTTPTPTG SDLGIKLLTAAYDGQLDEVRILLKAGADVNAKDLRGQTPLHYAAGLGHLEIVEVLLKAG ADVNAKDLHGWTPLHLAAWSGHLEIVEVLLKAGADVNAQDVEGVTPADLAAVQGHQDIA EVLQKAAGSPTPTPTTPTPTTPTPTGSDLGWKLLDAAEIGQLDEVRILLKAGADV NAKDKQGITPLHIAAAHGHLEIVEVLLKAGADVNAKDEIGRTPLHLAAFKGHLEIVEVL LKAGADVNAQDIIGETPADLAAVRGHQDIAEVLQKAAGSPTPTPTTPTPTPTTPTPT GSDLGVKLLLLAAERGQLDEVRILLKAGADVNAKDIAEGYTPLHIAAYQGHLEIVEVLLK AGADVNAKDRYGKTPLHLAAIGGHLEIVEVLLKAGADVNAQDNKGSTPADLAADYGHQD IAEVLQKAAGSPTGSDLGQKLLEAAWAGQDDEVRELLKAGADVNAKNSRGVVTPLHTAA QTGHLEIFEVLLKAGADVNAKNDKRVTPLHLAAALGHLEIVEVLLKAGADVNARDSWGT TPADLAAKYGHQDIAEVLQKAA |
| 98 | Ankyrin repeat protein with binding specificity for HSA-HSA-CD70-CD123-CD33-CD3 | DARPin® protein #59 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTGSDLGKKLLEAARAGQDDEVRELLKAGADVN AKDYFSHTPLHLAARNGHLKIVEVLLKAGADVNAKDFAGKTPLHLAAADGHLEIVEVLL KAGADVNAQDIFGKTPADIAADAGHEDIAEVLQKAAGSPTPTPTTPTPTPTTPTPTG SDLGIKLLTAAYDGQLDEVRILLKAGADVNAKDLRGQTPLHYAAGLGHLEIVEVLLKAG ADVNAKDLHGWTPLHLAAWSGHLEIVEVLLKAGADVNAQDVEGVTPADLAAVQGHQDIA EVLQKAAGSPTPTPTTPTPTTPTPTGSDLGKKLLEAALEGQLDEVRELLKAGADV NAKDQEGYTPLHLAAALGHLEIVEVLLKAGADVNAKDQIGRTPLHLAAYKGHLEIVEVL LKAGADVNAQDIIGQTPADLAAQRGHQDIAEVLQKAAGSPTPTPTTPTPTPTTPTPT GSDLGVKLLLLAAERGQLDEVRILLKAGADVNAKDIAEGYTPLHIAAYQGHLEIVEVLLK AGADVNAKDRYGKTPLHLAAIGGHLEIVEVLLKAGADVNAQDNKGSTPADLAADYGHQD IAEVLQKAAGSPTGSDLGQKLLEAAWAGQDDEVRELLKAGADVNAKNSRGWTPLHTAAQ TGHLEIFEVLLKAGADVNAKNDKRVTPLHLAAALGHLEIVEVLLKAGADVNARDSWGTT PADLAAKYGHQDIAEVLQKAA |
| 99 | Ankyrin repeat protein with binding specificity for HSA-HSA-CD70-CD123-CD33-CD3 | DARPin® protein #60 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTGSDLGKKLLEAARAGQDDEVRELLKAGADVN AKDYFSHTPLHLAARNGHLKIVEVLLKAGADVNAKDFAGKTPLHLAAADGHLEIVEVLL KAGADVNAQDIFGKTPADIAADAGHEDIAEVLQKAAGSPTPTPTTPTPTPTTPTPTG SDLGIKLLTAAYDGQLDEVRILLKAGADVNAKDLRGQTPLHYAAGLGHLEIVEVLLKAG ADVNAKDLHGWTPLHLAAWSGHLEIVEVLLKAGADVNAQDVEGVTPADLAAVQGHQDIA EVLQKAAGSPTPTPTTPTPTTPTPTGSDLGKKLLQAARAGQDEVRELLKAGADV NAKDQYGRTPLHLAAIKGHLEIVEVLLKAGADVNAKDSLGYTPLHLAAVEGPLEIVEVL LKAGADVNAKDAYGQTPLHIAAAWGHLEIVEVLLKAVADVNAQDKSGKTPADLAARAGH QDIAEVLQKAAGSPTPTPTTPTPTPTTPTPTGSDLGVKLLLLAAERGQLDEVRILLKA GADVNAKDIAEGYTPLHIAAYQGHLEIVEVLLKAGADVNAKDRYGKTPLHLAAIGGHLE IVEVLLKAGADVNAQDNKGSTPADLAADYGHQDIAEVLQKAAGSPTGSDLGQKLLEAAW AGQDDEVRELLKAGADVNAKNSRGVVTPLHTAAQTGHLEIFEVLLKAGADVNAKNDKRV TPLHLAAALGHLEIVEVLLKAGADVNARDSWGTTPADLAAKYGHQDIAEVLQKAA |
| 100 | Ankyrin repeat protein with binding | DARPin® protein #61 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTGSDLGKKLLEAARAGQDDEVRELLKAGADVN |

SEQUENCE TABLE

| SEQ ID NO | Description | DARPin protein | Sequence (an X represents any amino acid) |
|---|---|---|---|
| | specificity for HSA-HSA-CD70-CD123-CD33-CD3 | | AKDYFSHTPLHLAARNGHLKIVEVLLKAGADVNAKDFAGKTPLHLAAADGHLEIVEVLL KAGADVNAQDIFGKTPADIAADAGHEDIAEVLQKAAGSPTPTPTTPTPTPTTPTPTPTG SDLGKKLLQAARAGQLDEVRELLKAGADVNAKDQQGLTPLHIAANLGHLEIVEVLLKAG ADVNAKDLFGLTPLHLAAFEGHLEIVEVLLKAGADVNAKDQHGATPLHAAWVGHLEIV EVLLKAGADVNAQDKSGKTPADLAARAGHQDIAEVLQKAAGSPTPTPTTPTPTTPTP TPTGSDLGKKLLQAALEGQLDEVRELLKAGADVNAKDIEGYTPLHLAAALGHLEIVEVL LKAGADVNAKDQIGRTPLHLAAYKGHLEIVEVLLKAGADVNAQDIIGQTPADLAAQRGH QDIAEVLQKAAGSPTPTPTTPTPTTPTPTPTGSDLGKKLLLAAERGQLDEVRILLKA GADVNAKDRAEGYTPLHIAAYQGHLEIVEVLLKAGADVNAKDRYGKTPLHLAAISGHLE IVEVLLKAGADVNAQDNKGSTPADLAADYGHQDIAEVLQKAAGSPTGSDLGQKLLEAAW AGQDDEVRELLKAGADVNAKNSRGWTPLHTAAQTGHLEIFEVLLKAGADVNAKNDKRVT PLHLAAALGHLEIVEVLLKAGADVNARDSWGTTPADLAAKYGHQDIAEVLQKAA |
| 101 | Ankyrin repeat protein with binding specificity for HSA-HSA-CD70-CD33-CD123-CD3 | DARPin® protein #62 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTPTGSDLGKKLLEAARAGQDDEVRELLKAGADVN AKDYFSHTPLHLAARNGHLKIVEVLLKAGADVNAKDFAGKTPLHLAAADGHLEIVEVLL KAGADVNAQDIFGKTPADIAADAGHEDIAEVLQKAAGSPTPTPTTPTPTPTTPTPTPTG SDLGIKLLTAAYDGQLDEVRILLKAGADVNAKDLRGQTPLHYAAGLGHLEIVEVLLKAG ADVNAKDLHGWTPLHLAAWSGHLEIVEVLLKAGADVNAQDVEGVTPADLAAVQGHQDIA EVLQKAAGSPTPTPTTPTPTTPTPTPTGSDLGVKLLLLAAERGQLDEVRILLKAGADV NAKDIAEGYTPLHIAAYQGHLEIVEVLLKAGADVNAKDRYGKTPLHLAAIGGHLEIVEV LLKAGADVNAQDNKGSTPADLAADYGHQDIAEVLQKAAGSPTPTPTTPTPTTPTPTP TGSDLGKKLLEAALEGQLDEVRELLKAGADVNAKDQEGYTPLHLAAALGHLEIVEVLLK AGADVNAKDQIGRTPLHLAAYKGHLEIVEVLLKAGADVNAQDIIGQTPADLAAQRGHQD IAEVLQKAAGSPTPTPTTPTPTTPTPTPTGSDLGQKLLEAAWAGQDDEVRELLKAGA DVNAKNSRGWTPLHTAAQTGHLEIFEVLLKAGADVNAKNDKRVTPLHLAAALGHLEIVE VLLKAGADVNARDSWGTTPADLAAKYGHQDIAEVLQKAA |
| 102 | Ankyrin repeat domain specific for CD123 | DARPin® protein #63 | DLGKKLLQAARAGQLDEVRELLKAGADVNAKDQYGRTPLHLAAIKGHLEIVEVLLKAGA DVNAKDSLGYTPLHLAAVEGPLEIVEVLLKAGADVNAKDAYGQTPLHIAAAWGHLEIVE VLLKAVADVNAQDKSGKTPADLAARAGHQDIAEVLQKAA |
| 103 | Ankyrin repeat domain specific for CD123 | DARPin® protein #64 | DLGWKLLDAAEIGQDDEVRILLAAGADVNAKDKQGITPLHIAAAHGHLEIVEVLLKAGA DVNAKDEIGRTPLHLAAFKGHLEIVEVLLKAGADVNAQDIIGETPADLAAVRGHEDIAE VLQKAA |
| 104 | Ankyrin repeat domain specific for CD123 | DARPin® protein #65 | DLGWKLLDAAEIGQLDEVRILLAAGADVNAKDKQGITPLHIAAAHGHLEIVEVLLKAGA DVNAKDEIGRTPLHLAAFKGHLEIVEVLLKAGADVNAQDIIGETPADLAAVRGHQDIAE VLQKAA |
| 105 | Ankyrin repeat domain specific for CD123 | DARPin® protein #66 | DLGKKLLEAALEGQLDEVRELLKAGADVNAKDQEGYTPLHLAAALGHLEIVEVLLKAGA DVNAKDQIGRTPLHLAAYKGHLEIVEVLLKAGADVNAQDIIGQTPADLAAQRGHQDIAE VLQKAA |
| 106 | Ankyrin repeat domain specific for CD123 | DARPin® protein #67 | DLGKKLLQAALEGQLDEVRELLKAGADVNAKDIEGYTPLHLAAALGHLEIVEVLLKAGA DVNAKDQIGRTPLHLAAYKGHLEIVEVLLKAGADVNAQDIIGQTPADLAAQRGHQDIAE VLQKAA |
| 107 | Ankyrin repeat domain specific for CD70 | DARPin® protein #68 | DLGKKLLQAARAGQLDEVRELLKAGADVNAKDQAGLTPLHIAAATGHLEIVEVLLKAGA DVNAKDFSGLTPLHLAAFEGHLEIVEVLLKAGADVNAKDQHGQTPLHAAWTGHLEIVE VLLKAGADVNAQDKSGKTPADLAARAGHQDIAEVLQKAA |
| 108 | Ankyrin repeat domain specific for CD70 | DARPin® protein #69 | DLGYKLLQAAYDGQDDEVRILLAAGADVNAKDSRGQTPLHYAASIGHLEIVEVLLKAGA DVNAKDDHGWTPLHLAAWSGHLEIVEVLLKAGADVNAQDQEGTTPADLAAVQSHEDIAE VLQKAA |
| 109 | Ankyrin repeat domain specific for CD70 | DARPin® protein #70 | DLGIKLLTAAYDGQLDEVRILLKAGADVNAKDLRGQTPLHYAAGLGHLEIVEVLLKAGA DVNAKDLHGWTPLHLAAWSGHLEIVEVLLKAGADVNAQDVEGVTPADLAAVQGHQDIAE VLQKAA |
| 110 | Ankyrin repeat domain specific for CD70 | DARPin® protein #71 | DLGKKLLQAARAGQLDEVRELLKAGADVNAKDQQGLTPLHIAANLGHLEIVEVLLKAGA DVNAKDLFGLTPLHLAAFEGHLEIVEVLLKAGADVNAKDQHGATPLHAAWVGHLEIVE VLLKAGADVNAQDKSGKTPADLAARAGHQDIAEVLQKAA |
| 111 | Ankyrin repeat domain specific for CD33 | DARPin® protein #72 | DLGVKLLLAAERGQLDEVRILLKAGADVNAKDIAEGYTPLHIAAYQGHLEIVEVLLKAG ADVNAKDRYGKTPLHLAAIGGHLEIVEVLLKAGADVNAQDNKGSTPADLAADYGHQDIA EVLQKAA |
| 112 | Ankyrin repeat domain specific for CD33 | DARPin® protein #73 | DLGKKLLLAAERGQLDEVRILLKAGADVNAKDRAEGYTPLHIAAYQGHLEIVEVLLKAG ADVNAKDRYGKTPLHLAAISGHLEIVEVLLKAGADVNAQDNKGSTPADLAADYGHQDIA EVLQKAA |

| SEQUENCE TABLE | | |
|---|---|---|
| SEQ ID NO / Description | DARPin protein | Sequence (an X represents any amino acid) |
| 113 Ankyrin repeat protein with binding specificity to HSA-three non binding domains-CD3 | DARPin® protein #74 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTPTGSDLGKKLLEAARAGQDDEVRELLKAGADVN AKDYFSHTPLHLAARNGHLKIVEVLLKAGADVNAKDFAGKTPLHLAAADGHLEIVEVLL KAGADVNAQDIFGKTPADIAADAGHEDIAEVLQKAAGSPTPTPTTPTPTPTTPTPTPTG SDLGKKLLEAARAGQDDEVRELLKAGADVNAKDKDGYTPLHLAAREGHLEIVEVLLKAG ADVNAKDKDGYTPLHLAAREGHLEIVEVLLKAGADVNAQDKSGKTPADLAADAGHEDIA EVLQKAAGSPTPTPTTPTPTPTTPTPTPTGSDLGKKLLEAARAGQDDEVRELLKAGADV NAKDKDGYTPLHLAAREGHLEIVEVLLKAGADVNAKDKDGYTPLHLAAREGHLEIVEVL LKAGADVNAQDKSGKTPADLAADAGHEDIAEVLQKAAGSPTPTPTTPTPTPTTPTPTPT GSDLGKKLLEAARAGQDDEVRELLKAGADVNAKDKDGYTPLHLAAREGHLEIVEVLLKA GADVNAKDKDGYTPLHLAAREGHLEIVEVLLKAGADVNAQDKSGKTPADLAADAGHEDI AEVLQKAAGSPTPTPTTPTPTPTTPTPTGSDLGQKLLEAAWAGQDDEVRELLKAGAD VNAKNSRGWTPLHTAAQTGHLEIFEVLLKAGADVNAKNDKRVTPLHLAAALGHLEIVEV LLKAGADVNARDSWGTTPADLAAKYGHQDIAEVLQKAA |
| 114 Ankyrin repeat protein with binding specificity to HSA-HSA-CD33-CD123-CD70-non binding domain | DARPin® protein #75 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTPTGSDLGKKLLEAARAGQDDEVRELLKAGADVN AKDYFSHTPLHLAARNGHLKIVEVLLKAGADVNAKDFAGKTPLHLAAADGHLEIVEVLL KAGADVNAQDIFGKTPADIAADAGHEDIAEVLQKAAGSPTPTPTTPTPTPTTPTPTPTG SDLGVKLLLAAERGQLDEVRILLKAGADVNAKDIAEGYTPLHIAAYQGHLEIVEVLLKA GADVNAKDRYGKTPLHLAAIGGHLEIVEVLLKAGADVNAQDNKGSTPADLAADYGHQDI AEVLQKAAGSPTPTPTTPTPTTPTPTPTGSDLGKKLLEAALEGQLDEVRELLKAGAD VNAKDQEGYTPLHLAAALGHLEIVEVLLKAGADVNAKDQIGRTPLHLAAYKGHLEIVEV LLKAGADVNAQDIIGQTPADLAAQRGHQDIAEVLQKAAGSPTPTPTTPTPTTPTPTP TGSDLGIKLLTAAYDGQLDEVRILLKAGADVNAKDLRGQTPLHYAAGLGHLEIVEVLLK AGADVNAKDLHGVVTPLHLAAWSGHLEIVEVLLKAGADVNAQDVEGVTPADLAAVQGHQ DIAEVLQKAAGSPTPTPTTPTPTPTTPTPTPTGSDLGKKLLEAARAGQDDEVRELLKAG ADVNAKDKDGYTPLHLAAREGHLEIVEVLLKAGADVNAKDKDGYTPLHLAAREGHLEIV EVLLKAGADVNAQDKSGKTPADLAADAGHEDIAEVLQKAA |
| 115 Ankyrin repeat protein with binding specificity to HSA-HSA-three nonbinding domains-CD3 | DARPin® protein #76 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTPTGSDLGKKLLEAARAGQDDEVRELLKAGADVN AKDYFSHTPLHLAARNGHLKIVEVLLKAGADVNAKDFAGKTPLHLAAADGHLEIVEVLL KAGADVNAQDIFGKTPADIAADAGHEDIAEVLQKAAGSPTPTPTTPTPTPTTPTPTPTG SDLGKKLLEAARAGQDDEVRELLKAGADVNAKDKDGYTPLHLAAREGHLEIVEVLLKAG ADVNAKDKDGYTPLHLAAREGHLEIVEVLLKAGADVNAQDKSGKTPADLAADAGHEDIA EVLQKAAGSPTPTPTTPTPTPTTPTPTPTGSDLGKKLLEAARAGQDDEVRELLKAGADV NAKDKDGYTPLHLAAREGHLEIVEVLLKAGADVNAKDKDGYTPLHLAAREGHLEIVEVL LKAGADVNAQDKSGKTPADLAADAGHEDIAEVLQKAAGSPTPTPTTPTPTPTTPTPTPT GSDLGKKLLEAARAGQDDEVRELLKAGADVNAKDKDGYTPLHLAAREGHLEIVEVLLKA GADVNAKDKDGYTPLHLAAREGHLEIVEVLLKAGADVNAQDKSGKTPADLAADAGHEDI AEVLQKAAGSPTGSDLGQKLLEAAWAGQDDEVRELLKAGADVNAKNSRGWTPLHTAAQT GHLEIFEVLLKAGADVNAKNDKRVTPLHLAAALGHLEIVEVLLKAGADVNARDSWGTTP ADLAAKYGHQDIAEVLQKAA |
| 116 Ankyrin repeat protein with binding specificity to HSA-HSA-CD70-CD123-CD33 | DARPin® protein #77 | DLGKKLLEAARAGQDDEVRELLKAGADVNAKDYFSHTPLHLAARNGHLKIVEVLLKAGA DVNAKDFAGKTPLHLAAADGHLEIVEVLLKAGADVNAQDIFGKTPADIAADAGHEDIAE VLQKAAGSPTPTPTTPTPTPTTPTPTPTGSDLGKKLLEAARAGQDDEVRELLKAGADVN AKDYFSHTPLHLAARNGHLKIVEVLLKAGADVNAKDFAGKTPLHLAAADGHLEIVEVLL KAGADVNAQDIFGKTPADIAADAGHEDIAEVLQKAAGSPTPTPTTPTPTPTTPTPTPTG SDLGIKLLTAAYDGQLDEVRILLKAGADVNAKDLRGQTPLHYAAGLGHLEIVEVLLKAG ADVNAKDLHGWTPLHLAAWSGHLEIVEVLLKAGADVNAQDVEGVTPADLAAVQGHQDIA EVLQKAAGSPTPTPTTPTPTPTTPTPTPTGSDLGKKLLQAALEGQLDEVRELLKAGADV NAKDIEGYTPLHLAAALGHLEIVEVLLKAGADVNAKDQIGRTPLHLAAYKGHLEIVEVL LKAGADVNAQDIIGQTPADLAAQRGHQDIAEVLQKAAGSPTPTPTTPTPTPTTPTPTPT GSDLGKKLLLAAERGQLDEVRILLKAGADVNAKDRAEGYTPLHIAAYQGHLEIVEVLLK AGADVNAKDRYGKTPLHLAAISGHLEIVEVLLKAGADVNAQDNKGSTPADLAADYGHQD IAEVLQKAAGSPTGSDLGKKLLEAARAGQDDEVRELLKAGADVNAKDKDGYTPLHLAAR EGHLEIVEVLLKAGADVNAKDKDGYTPLHLAAREGHLEIVEVLLKAGADVNAQDKSGKT PADLAADAGHEDIAEVLQKAA |
| 117 Ankyrin repeat protein specific for CD70-CD3 | DARPin® protein #78 | DLGIKLLTAAYDGQLDEVRILLKAGADVNAKDLRGQTPLHYAAGLGHLEIVEVLLKAGA DVNAKDLHGWTPLHLAAWSGHLEIVEVLLKAGADVNAQDVEGVTPADLAAVQGHQDIAE VLQKAAGSPTPTPTTPTPTPTTPTPTPTGSDLGQKLLEAAWAGQDDEVRELLKAGADVN AKNSRGVVTPLHTAAQTGHLEIFEVLLKAGADVNAKNDKRVTPLHLAAALGHLEIVEVL LKAGADVNARDSWGTTPADLAAKYGHQDIAEVLQKAA |
| 118 Nucleic acid encoding protein of SEQ ID NO:95 | | ATGAGAGGATCGCATCACCATCACCATCACGGATCCGACCTGGGTAAAAAGCTGCTGGA GGCAGCGCGTGCCGGTCAAGACGACGAGGTTCGCGAATTGCTTAAAGCGGGTGCAGACG TCAACGCCAAAGATTATTTCTCTCATACCCCGTTGCATTTAGCCGCGCGTAATGGCCAT CTGAAGATCGTCGAGGTCCTCTTGAAGGCAGGCGCGGATGTCAATGCGAAGGATTTTGC |

SEQUENCE TABLE

| SEQ ID NO | Description | DARPin protein | Sequence (an X represents any amino acid) |
|---|---|---|---|
| | | | GGGCAAAACGCCGCTGCACTTAGCGGCGGCGGACGGTCATTTAGAAATCGTTGAAGTCC<br>TGTTAAAAGCGGGCGCCGATGTGAATGCGCAGGATATTTTCGGTAAAACGCCGGCGGAC<br>ATTGCGGCAGATGCGGGTCATGAAGATATCGCAGAAGTCCTGCAGAAGGCAGCAGGCAG<br>CCCTACACCTACGCCGACTACGCCTACGCCGACTCCGACTACCCCGACTCCGACCCCGA<br>CCGGATCAGACCTGGGTAAAAAGCTGCTGGAGGCAGCGCGTGCCGGTCAAGACGACGAG<br>GTTCGCGAATTGCTTAAAGCGGGTGCAGACGTCAACGCCAAAGATTATTTCTCTCATAC<br>CCCGTTGCATTTAGCCGCGCGTAATGGCCATCTGAAGATCGTCGAGGTCCTCTTGAAGG<br>CAGGCGCGGATGTCAATGCGAAGGATTTTGCGGGCAAAACGCCCGCTGCACTTAGCGGCG<br>GCGGACGGTCATTTAGAAATCGTTGAAGTCCTGTTAAAAGCGGGCGCCGATGTGAATGC<br>GCAGGATATTTTCGGTAAAACGCCGGCGGACATTGCGGCAGATGCGGGTCATGAAGATA<br>TCGCAGAAGTCCTGCAGAAGGCAGCAGGCTCGCCAACGCCGACCCCTACAACGCCAACC<br>CCGACACCAACTACACCGACCCCCACACCAACGGGATCAGACCTGGGTGTTAAGCTGTT<br>GCTTGCAGCCGAGCGTGGGCAGCTTGATGAAGTACGCATTCTTCTTAAAGCGGGGGCTG<br>ATGTGAACGCGAAAGATATTGCTGAGGGTTACACACCGCTTCACATTGCCGCCTACCAG<br>GGTCATCTGGAGATTGTTGAAGTATTACTGAAAGCGGGAGCAGATGTTAATGCCAAAGA<br>TCGCTATGGAAAAACTCCTTTGCATTTAGCTGCAATGGAGGACACCTGGAAATCGTCG<br>AAGTGTTATTAAAAGCTGGAGCGGACGTAAACGCACAAGATAACAAGGGCTCAACTCCC<br>GCGGACCTTGCCGCAGATTACGGTCATCAGGACATTGCTGAAGTTCTGCAGAAGGCAGC<br>AGGTTCCCGACCCCTACGCCAACGACTCCGACCCCAACTCCAACGACCCCTACCCCGA<br>CCCCGACCGGATCAGACCTGGGTAAAAAATTGCTTGAAGCCGCGTTGGAAGGACAATTA<br>GACGAGGTACGTGAGCTGTTAAAAGCAGGGGCCGATGTGAATGCTAAAGACCAGGAGGG<br>ATACACCCCCTTGCACCTGGCTGCCGCGTTGGGCCACTTAGAGATTGTAGAGGTTCTTC<br>TTAAGGCGGGGGCAGACGTGAATGCAAAGGACCAAATTGGACGTACTCCTTTGCATCTG<br>GCAGCCTATAAGGGGCACTTGGAGATTGTCGAGGTCTTGTTAAAGGCGGGTGCCGATGT<br>AAATGCCCAGGACATCATTGGGCAGACTCCGGCAGATTTGGCCGCCAACGTGGCCACC<br>AAGATATTGCTGAAGTTCTGCAGAAGGCAGCAGGCAGCCCCACGCCAACTCCTACAACC<br>CCCACACCTACACCGACGACGCCGACACCGACTCCAACCGGATCAGACCTGGGTATTAA<br>ACTGTTGACAGCCGCTTACGACGGGCAATTAGACGAAGTGCGTATTCTGCTTAAAGCTG<br>GAGCTGACGTGAACGCGAAAGACTTACGCGGCCAAACGCCTTTACATTACGCGGCGGGA<br>CTGGGCCATCTTGAGATTGTTGAGGTGCTTCTGAAGGCAGGCGCGGATGTCAATGCAAA<br>AGACCTGCACGGATGGACACCTCTTCACTTAGCTGCTTGGTCTGGGCATTTGGAGATTG<br>TAGAGGTTTTATTGAAAGCAGGGGCGGATGTGAATGCGCAAGACGTAGAAGGAGTCACC<br>CCAGCTGACCTGGCAGCGGTTCAAGGGCATCAAGACATTGCTGAAGTTCTGCAGAAGGC<br>AGCAGGTTCGCCGACCCCAACCCCTACCACTCCAACGCCGACGCCTACCACTCCAACAC<br>CAACACCAACGGGATCAGACCTGGGTCAAAAGCTGTTGGAAGCCGCGTGGGCGGGTCAG<br>GACGATGAAGTCCGTGAGCTGCTTAAAGCAGGAGCCGACGTGAACGCGAAGAACTCACG<br>CGGGTGGACGCCACTTCACACGGCCGCGCAGACAGGTCACCTTGAAATCTTTGAGGTTC<br>TTCTGAAGGCAGGAGCAGACGTTAACGCCAAAAACGACAAGCGCGTGACTCCGTTGCAC<br>CTTGCCGCAGCTCTGGGGCATTTGGAGATCGTTGAGGTACTGTTGAAAGCGGGAGCAGA<br>TGTTAATGCTCGCGACAGTTGGGGGACGACACCAGCAGACCTGGCCGCAAAATACGGAC<br>ACCAAGACATTGCTGAAGTTCTGCAGAAGGCGGCA |
| 119 | Nucleic acid encoding protein of SEQ ID NO:96 | | ATGAGAGGATCGCATCACCATCACCATCACGGATCCGACCTGGGTAAGAAACTGTTGGA<br>AGCAGCACGTGCGGGTCAAGACGATGAAGTTCGTGAGCTGTTAAAGGCTGGCGCCGACG<br>TGAACGCGAAGGACTACTTTAGCCACACCCCGCTGCACTTGGCAGCGCGCAACGGTCAC<br>CTGAAAATTGTCGAGGTCCTGTTGAAGGCTGGTGCGGATGTGAACGCAAAAGATTTTGC<br>GGGTAAGACGCCGCTGCATCTGGCGGCGGCTGATGGTCACTTAGAGATCGTAGAGGTTC<br>TGTTGAAAGCGGGCGCCGATGTGAATGCCCAGGACATCTTCGGCAAGACCCCGGCAGAC<br>ATTGCCGCGGATGCTGGTCACGAAGATATCGCAGAGGTCCTGCAAAAAGCGGCAGGCAG<br>CCCGACCCCGACGCCGACCACTCCGACCCCCAACCACCCCGACTCCGACTCCGA<br>CCGGATCTGACCTGGGTAAAAAACTGCTGGAAGCAGCACGTGCCGGCAGGATGATGAA<br>GTTCGTGAACTGCTGAAAGCAGGCGCCGATGTTAATGCAAAGGATTATTTTAGCCACAC<br>ACCGCTGCATCTGGCAGCCCGTAATGGTCACCTAAAGATTGTTGAAGTTCTGCTGAAGG<br>CTGGTGCAGAGTTAACGCCAAAGATTTCGCGGGCAAAACCCTCTGCATTTAGCCGCA<br>GCGGACGGTCACCTGGAGATCGTAGAGGTGCTGCTTAAGGCGGGTGCGGATGTTAATGC<br>ACAGGATATTTTCGGTAAAACCCTGCCGATATTGCAGCTGATGCCGGTCATGAAGATA<br>TCGCAGAAGTCTGCAGAAGGCAGCAGGATCACCAACACCAACCCCGACCACCCCAACT<br>CCAACACCGACCACCCCGACCCCTACCCCAACAGGATCCGACCTGGGTATTAAACTGTT<br>GACAGCCGCTTACGACGGGCAATTAGACGAAGTGCGTATTCTGCTTAAAGCTGGAGCTG<br>ACGTGAACGCGAAAGACTTACGCGGCCAAACGCCTTTACATTACGCGGCGGGACTGGGC<br>CATCTTGAGATTGTTGAGGTGCTTCTGAAGGCAGGCGCGGATGTCAATGCAAAAGACCT<br>GCACGGATGGACACCTCTTCACTTAGCTGCTTGGTCTGGGCATTTGGAGATTGTAGAGG<br>TTTTATTGAAAGCAGGGGCGGATGTGAATGCGCAAGACGTAGAAGGAGTCACCCCAGCT<br>GACCTGGCAGCGGTTCAAGGGCATCAAGACATTGCTGAAGTTCTGCAGAAGGCAGCAGG<br>CTCGCCGACTCCGACCCCGACCACCCCAACTCCAACACCGACCACCCCGACCCCTACCC<br>AACAGGATCTGACCTGGGTAAAAAGTTGTTACAGGCAGCATTGGAGGGCAACTTGAC<br>GAGGTGCGCGAGTTACTGAAAGCTGGTGCAGATGTCAACGCGAAGGACATTGAAGGATA<br>TACTCCGCTGCACCTTGCCGCGGCTTTGGGGCATCTTGAGATTGTGGAGGTGCTTCTTA<br>AGGCGGGAGCTGATGTCAATGCTAAAGACCAAATCGGGCGCACACCGTTACACTTGGCT<br>GCGTACAAAGGTCACTTAGAAATCGTGGAAGTGCTTCTGAAGGCTGGCGCTGATGTCAA<br>CGCCCAAGACATTATCGGCCAGACACCGGCGGACCTGGCAGCGCAACGTGGGCATCAGG<br>ATATTGCTGAAGTTCTGCAGAAGGCAGCAGGCTCGCCGACTCCGACCCCGACCACCCCA<br>ACTCCAACACCGACCACCCCGACCCCTACCCCAACAGGATCTGACCTGGGTAAAAAGTT<br>GTTATTAGCTGCGGAGCGCGGGCAGTTAGACGAAGTGCGTATTCTGCTGAAGGCCGGGG |

SEQUENCE TABLE

| SEQ ID NO | Description | DARPin protein | Sequence (an X represents any amino acid) |
|---|---|---|---|
| | | | CCGACGTTAACGCAAAGGATCGTGCAGAGGGTTACACCCCCTGCACATCGCCGCTTAT<br>CAAGGTCACTTGGAGATTGTTGAGGTCTTACTGAAAGCGGGGGCCGACGTGAATGCCAA<br>AGATCGCTATGGAAAAACACCGTTACACTTAGCAGCTATTTCGGGGCATCTGGAGATCG<br>TGGAAGTCCTGTTAAAGGCTGGTGCCGATGTTAATGCACAAGATAATAAAGGCAGCACT<br>CCAGCCGATCTGGCCGCTGATTATGGGCACCAGGACATTGCTGAAGTTCTGCAGAAGGC<br>AGCAGGCTCGCCAACCGGATCAGATCTGGGTCAAAAGCTGTTGGAAGCCGCGTGGGCGG<br>GTCAGGACGATGAAGTCCGTGAGCTGCTTAAAGCAGGAGCCGACGTGAACGCGAAGAAC<br>TCACGCGGGTGGACGCCACTTCACACGGCCGCGCAGACAGGTCACCTTGAAATCTTTGA<br>GGTTCTTCTGAAGGCAGGAGCAGACGTTAACGCCAAAAACGACAAGCGCGTGACTCCGT<br>TGCACCTTGCCGCAGCTCTGGGGCATTTGGAGATCGTTGAGGTACTGTTGAAAGCGGGA<br>GCAGATGTTAATGCTCGCGACAGTTGGGGGACGACACCAGCAGACCTGGCCGCAAAATA<br>CGGACACCAAGACATTGCTGAAGTTCTGCAAAAGGCAGCA |
| 120 | Nucleic acid encoding protein of SEQ ID NO:97 | | ATGAGAGGATCGCATCACCATCACCATCACGGATCCGACCTGGGTAAGAAACTGTTGGA<br>AGCAGCACGTGCGGGTCAAGACGATGAAGTTCGTGAGCTGTTAAAGGCTGGCGCCGACG<br>TGAACGCGAAGGACTACTTTAGCCACACCCCGCTGCACTTGGCAGCGCGCAACGGTCAC<br>CTGAAAATTGTCGAGGTCCTGTTGAAGGCTGGTGCCGATGTGAACGCAAAAGATTTTGC<br>GGGTAAGACGCCGCTGCATCTGGCGGCGGCTGATGGTCACTTAGAGATCGTAGAGGTTC<br>TGTTGAAAGCGGGCGCCGATGTGAATGCCCAGGACATCTTCGGCAAGACCCCGGCAGAC<br>ATTGCCGCGGATGCTGGTCACGAAGATATCGCAGAGGTCCTGCAAAAAGCGGCAGGCAG<br>CCCGACCCCGACGCCGACCACTCCGACCCCGACCCCAACCACCCCGACTCCGACTCCGA<br>CCGGATCTGACCTGGGTAAAAAACTGCTGGAAGCAGCACGTGCCGGCCAGGATGATGAA<br>GTTCGTGAACTGCTGAAAGCAGGCGCCGATGTTAATGCAAAGGATTATTTTAGCCACAC<br>ACCGCTGCATCTGGCAGCCCGTAATGGTCACCTAAAGATTGTTGAAGTTCTGCTGAAGG<br>CTGGTGCAGACGTTAACGCCAAAGATTTCGCGGGCAAAACCCCTCTGCATTTAGCCGCA<br>GCGGACGGTCACCTGGAGATCGTAGAGGTGCTGCTTAAGGCGGGTGCGGATGTTAATGC<br>ACAGGATATTTTCGGTAAAACCCCTGCCGATATTGCAGCTGATGCCGGTCATGAAGATA<br>TCGCAGAAGTGCTGCAGAAGGCAGCAGGATCACCAACACCAACCCCGACCACCCCAACT<br>CCAACACCGACCACCCCGACCCCTACCCCAACAGGATCGACCTGGGTATTAAACTGTT<br>GACAGCCGCTTACGACGGGCAATTAGACGAAGTGCGTATTCTGCTTAAAGCTGGAGCTG<br>ACGTGAACGCGAAAGACTTACGCGGCCAAACGCCTTTACATTACGCGGCGGGACTGGGC<br>CATCTTGAGATTGTTGAGGTGCTTCTGAAGGCAGGCGCGGATGTCAATGCAAAAGACCT<br>GCACGGATGGACACCTCTTCACTTAGCTGCTTGGTCTGGGCATTTGGAGATTGTAGAGG<br>TTTTATTGAAAGCAGGGGCGGATGTGAATGCGCAAGACGTAGAAGGAGTCACCCCAGCT<br>GACCTGGCAGCGGTTCAAGGGCATCAAGACATTGCTGAAGTTCTGCAGAAGGCAGCAGG<br>CTCGCCGACTCCGACCCCGACCACCCCAACTCCAACACCGACCACCCCGACCCCTACCC<br>CAACAGGATCTGACCTGGGTTGGAAACTGCTTGATGCCGCCGAGATTGGTCAGCTTGAC<br>GAAGTCCGTATTCTTTTGAAGGCAGGGGCCGACGTTAATGCCAAAGACAAACAGGGTAT<br>CACGCCGTTACATATTGCCGCAGCGCATGGTCACTTAGAGATCGTAGAAGTACTTCTGA<br>AAGCAGGTGCTGACGTTAATGCAAAGGATGAGATCGGCCGCACCCCGCTTCATCTTGCT<br>GCCTTTAAGGGCCATTTGGAAATCGTAGAGGTGCTGTTAAAGGCTGGCGCTGATGTCAA<br>TGCACACAAGACATCATCGGGGAGAGCGCTGCCGACCTGGCGGCGGTACGCGGGCATCAGG<br>ATATTGCTGAAGTTCTGCAGAAGGCAGCAGGCTCGCCGACTCCGACCCCGACCACCCCA<br>ACTCCAACACCGACCACCCCGACCCCTACCCCAACAGGATCTGACCTGGGTGTTAAGCT<br>GTTGCTTGCAGCCGAGCGTGGGCAGCTTGATGAAGTACGCATTCTTCTTAAAGCGGGGG<br>CTGATGTGAACGCGAAAGATATTGCTGAGGGTTACACACCGCTTCACATTGCCGCCTAC<br>CAGGGTCATCTGGAGATTGTTGAAGTATTACTGAAAGCGGGAGCAGATGTTAATGCCAA<br>AGATCGCTATGGAAAAACTCCTTTGCATTTAGCTGCAATCGGAGGACACCTGGAAATCG<br>TCGAAGTGTTATTAAAAGCTGGAGCGGACGTAAACGCACAAGATAACAAGGGCTCAACT<br>CCCGCGGACCTTGCCGCAGATTACGGTCATCAGGACATTGCTGAAGTTCTGCAGAAGGC<br>AGCAGGCTCGCCAACCGGATCAGATCTGGGTCAAAAGCTGTTGGAAGCCGCGTGGGCGG<br>GTCAGGACGATGAAGTCCGTGAGCTGCTTAAAGCAGGAGCCGACGTGAACGCGAAGAAC<br>TCACGCGGGTGGACGCCACTTCACACGGCCGCGCAGACAGGTCACCTTGAAATCTTTGA<br>GGTTCTTCTGAAGGCAGGAGCAGACGTTAACGCCAAAAACGACAAGCGCGTGACTCCGT<br>TGCACCTTGCCGCAGCTCTGGGGCATTTGGAGATCGTTGAGGTACTGTTGAAAGCGGGA<br>GCAGATGTTAATGCTCGCGACAGTTGGGGGACGACACCAGCAGACCTGGCCGCAAAATA<br>CGGACACCAAGACATTGCTGAAGTTCTGCAAAAGGCAGCATAATGATAG |
| 121 | Nucleic acid encoding protein of SEQ ID NO:98 | | ATGAGAGGATCGCATCACCATCACCATCACGGATCCGACCTGGGTAAGAAACTGTTGGA<br>AGCAGCACGTGCGGGTCAAGACGATGAAGTTCGTGAGCTGTTAAAGGCTGGCGCCGACG<br>TGAACGCGAAGGACTACTTTAGCCACACCCCGCTGCACTTGGCAGCGCGCAACGGTCAC<br>CTGAAAATTGTCGAGGTCCTGTTGAAGGCTGGTGCCGATGTGAACGCAAAAGATTTTGC<br>GGGTAAGACGCCGCTGCATCTGGCGGCGGCTGATGGTCACTTAGAGATCGTAGAGGTTC<br>TGTTGAAAGCGGGCGCCGATGTGAATGCCCAGGACATCTTCGGCAAGACCCCGGCAGAC<br>ATTGCCGCGGATGCTGGTCACGAAGATATCGCAGAGGTCCTGCAAAAAGCGGCAGGCAG<br>CCCGACCCCGACGCCGACCACTCCGACCCCGACCCCAACCACCCCGACTCCGACTCCGA<br>CCGGATCTGACCTGGGTAAAAAACTGCTGGAAGCAGCACGTGCCGGCCAGGATGATGAA<br>GTTCGTGAACTGCTGAAAGCAGGCGCCGATGTTAATGCAAAGGATTATTTTAGCCACAC<br>ACCGCTGCATCTGGCAGCCCGTAATGGTCACCTAAAGATTGTTGAAGTTCTGCTGAAGG<br>CTGGTGCAGACGTTAACGCCAAAGATTTCGCGGGCAAAACCCCTCTGCATTTAGCCGCA<br>GCGGACGGTCACCTGGAGATCGTAGAGGTGCTGCTTAAGGCGGGTGCGGATGTTAATGC<br>ACAGGATATTTTCGGTAAAACCCCTGCCGATATTGCAGCTGATGCCGGTCATGAAGATA<br>TCGCAGAAGTGCTGCAGAAGGCAGCAGGATCACCAACACCAACCCCGACCACCCCAACT<br>CCAACACCGACCACCCCGACCCCTACCCCAACAGGATCCGACCTGGGTATTAAACTGTT |

SEQUENCE TABLE

| SEQ ID NO | Description | DARPin protein | Sequence (an X represents any amino acid) |
|---|---|---|---|
| | | | GACAGCCGCTTACGACGGGCAATTAGACGAAGTGCGTATTCTGCTTAAAGCTGGAGCTG<br>ACGTGAACGCGAAAGACTTACGCGGCCAAACGCCTTTACATTACGCGGCGGGACTGGGC<br>CATCTTGAGATTGTTGAGGTGCTTCTGAAGGCAGGCGCGGATGTCAATGCAAAAGACCT<br>GCACGGATGGACACCTCTTCACTTAGCTGCTTGGTCTGGGCATTTGGAGATTGTAGAGG<br>TTTTATTGAAAGCAGGGGCGGATGTGAATGCGCAAGACGTAGAAGGAGTCACCCCAGCT<br>GACCTGGCAGCGGTTCAAGGGCATCAAGACATTGCTGAAGTTCTGCAGAAGGCAGCAGG<br>CTCGCCGACTCCGACCCCGACCACCCCAACTCCAACACCGACCACCCCGACCCCTACCC<br>CAACAGGATCTGACCTGGGTAAAAAATTGCTTGAAGCCGCGTTGGAAGGACAATTAGAC<br>GAGGTACGTGAGCTGTTAAAAGCAGGGGCCGATGTGAATGCTAAAGACCAGGAGGGATA<br>CACCCCCTTGCACCTGGCTGCCGCGTTGGGCCACTTAGAGATTGTAGAGGTTCTTCTTA<br>AGGCGGGGGCAGACGTGAATGCAAAGGACCAAATTGGACGTACTCCTTTGCATCTGGCA<br>GCCTATAAGGGGCACTTGGAGATTGTCGAGGTCTTGTTAAAGGCGGGTGCCGATGTAAA<br>TGCCCAGGACATCATTGGGCAGACTCCGGCAGATTTGGCCGCCCAACGTGGCCACCAAG<br>ATATTGCTGAAGTTCTGCAGAAGGCAGCAGGCTCGCCGACTCCGACCCCGACCACCCCA<br>ACTCCAACACCGACCACCCCGACCCCTACCCCAACAGGATCTGACCTGGGTGTTAAGCT<br>GTTGCTTGCAGCCGAGCGTGGGCAGCTTGATGAAGTACGCATTCTTCTTAAAGCGGGGG<br>CTGATGTGAACGCGAAAGATATTGCTGAGGGTTACACACCGTTCACATTGCCGCCTAC<br>CAGGGTCATCTGGAGATTGTTGAAGTATTACTGAAAGCGGGAGCAGATGTTAATGCCAA<br>AGATCGCTATGGAAAAACTCCTTTGCATTTAGCTGCAATCGGAGGACACCTGGAAATCG<br>TCGAAGTGTTATTAAAAGCTGGAGCGGACGTAAACGCACAAGATAACAAGGGCTCAACT<br>CCCGCGGACCTTGCCGCAGATTACGGTCATCAGGACATTGCTGAAGTTCTGCAGAAGGC<br>AGCAGGCTCGCCAACCGGATCAGATCTGGGTCAAAAGCTGTTGGAAGCCGCGTGGGCGG<br>GTCAGGACGATGAAGTCCGTGAGCTGCTTAAAGCAGGAGCCGACGTGAACGCGAAGAAC<br>TCACGCGGGTGGACGCCACTTCACACGGCCGCGCAGACAGGTCACCTTGAAATCTTTGA<br>GGTTCTTCTGAAGGCAGGAGCAGACGTTAACGCCAAAAACGACAAGCGCGTGACTCCGT<br>TGCACCTTGCCGCAGCTCTGGGGCATTTGGAGATCGTTGAGGTACTGTTGAAAGCGGGA<br>GCAGATGTTAATGCTCGCGACAGTTGGGGGACGACACCAGCAGACCTGGCCGCAAAATA<br>CGGACACCAAGACATTGCTGAAGTTCTGCAAAAGGCAGCATAATGATAG |
| 122 | Nucleic acid encoding protein of SEQ ID NO:99 | | ATGAGAGGATCGCATCACCATCACCATCACGGATCCGACCTGGGTAAGAAACTGTTGGA<br>AGCAGCACGTGCGGGTCAAGACGATGAAGTTCGTGAGCTGTTAAAGGCTGGCGCCGACG<br>TGAACGCGAAGGACTACTTTAGCCACACCCCGCTGCACTTGGCAGCGCGCAACGGTCAC<br>CTGAAAATTGTCGAGGTCCTGTTGAAGGCTGGTGCGGATGTGAACGCAAAAGATTTTGC<br>GGGTAAGACGCCGCTGCATCTGGCGGCGGCTGATGGTCACTTAGAGATCGTAGAGGTTC<br>TGTTGAAAGCGGGCGCCGATGTGAATGCCCAGGACATCTTCGGCAAGACCCCGGCAGAC<br>ATTGCCGCGGATGCTGGTCACGAAGATATCGCAGAGGTCCTGCAAAAAGCGGCAGGCAG<br>CCCGACCCCGACGCCGACCACTCCGACCCCGACCCCAACCACCCCGACTCCGACTCCGA<br>CCGGATCTGACCTGGGTAAAAAACTGCTGGAAGCAGCACGTGCCGGCCAGGATGATGAA<br>GTTCGTGAACTGCTGAAAGCAGGCGCCGATGTTAATGCAAAGGATTATTTTAGCCACAC<br>ACCGCTGCATCTGGCAGCCCGTAATGGTCACCTAAAGATTGTTGAAGTTCTGCTGAAGG<br>CTGGTGCAGACGTTAACGCCAAAGATTTCGCGGGCAAAACCCCTCTGCATTTAGCCGCA<br>GCGGACGGTCACCTGGAGATCGTAGAGGTGCTGCTTAAGGCGGGTGCGGATGTTAATGC<br>ACAGGATATTTTCGGTAAAACCCCTGCCGATATTGCAGCTGATGCCGGTCATGAAGATA<br>TCGCAGAAGTGCTGCAGAAGGCAGCAGGATCACCAACACCAACCCCGACCACCCCAACT<br>CCAACACCGACCACCCCGACCCCTACCCCAACAGGATCGACCTGGGTATTAAACTGTT<br>GACAGCCGCTTACGACGGGCAATTAGACGAAGTGCGTATTCTGCTTAAAGCTGGAGCTG<br>ACGTGAACGCGAAAGACTTACGCGGCCAAACGCCTTTACATTACGCGGCGGGACTGGGC<br>CATCTTGAGATTGTTGAGGTGCTTCTGAAGGCAGGCGCGGATGTCAATGCAAAAGACCT<br>GCACGGATGGACACCTCTTCACTTAGCTGCTTGGTCTGGGCATTTGGAGATTGTAGAGG<br>TTTTATTGAAAGCAGGGGCGGATGTGAATGCGCAAGACGTAGAAGGAGTCACCCCAGCT<br>GACCTGGCAGCGGTTCAAGGGCATCAAGACATTGCTGAAGTTCTGCAGAAGGCAGCAGG<br>CTCGCCGACTCCGACCCCGACCACCCCAACTCCAACACCGACCACCCCGACCCCTACCC<br>CAACAGGATCTGACCTGGGTAAAAAACTGCTGCAAGCAGCACGTGCAGGTCAGCTGGAT<br>GAAGTTCGTGAACTGCTGAAAGCAGGCGCCGATGTTAATGCAAAAGATCAATACGGCAG<br>AACCCCGCTGCATCTGGCTGCTATCAAGGGTCACCTGGAAATTGTTGAAGTTCTGCTGA<br>AGCCGGTGCAGATGTTAATGCAAAAGATTCTCTGGGCTACACCCCGCTGCATCTGGCT<br>GCTGTGGAGGGTCCCCTGGAAATTGTTGAAGTTCTGCTGAAAGCCGGTGCAGATGTTAA<br>TGCAAAAGATGCTTACGGCCAAACCCCGCTGCATATCGCTGCTGCTTGGGGTCACCTGG<br>AAATTGTTGAAGTTCTGCTGAAAGCCGTTGCAGATGTTAACGCACAGGATAAAAGCGGT<br>AAAACCCCTGCCGATCTGGCAGCTCGCGCCGGTCATCAAGATATTGCTGAAGTGCTGCA<br>GAAGGCAGCAGGCTCGCCGACTCCGACCCCGACCACCCCAACTCCAACACCGACCACCC<br>CGACCCCTACCCCAACAGGATCTGACCTGGGTGTTAAGCTGTTGCTTGCAGCCGAGCGT<br>GGGCAGCTTGATGAAGTACGCATTCTTCTTAAAGCGGGGGCTGATGTGAACGCGAAAGA<br>TATTGCTGAGGGTTACACACCGCTTCACATTGCCGCCTACCAGGGTCATCTGGAGATTG<br>TTGAAGTATTACTGAAAGCGGGAGCAGATGTTAATGCCAAAGATCGCTATGGAAAAACT<br>CCTTTGCATTTAGCTGCAATCGGAGGACACCTGGAAATCGTCGAAGTGTTATTAAAAGC<br>TGGAGCGGACGTAAACGCACAAGATAACAAGGGCTCAACTCCCGCGGACCTTGCCGCAG<br>ATTACGGTCATCAGGACATTGCTGAAGTTCTGCAGAAGGCAGCAGGCTCGCCAACCGGA<br>TCAGATCTGGGTCAAAAGCTGTTGGAAGCCGCGTGGGCGGGTCAGGACGATGAAGTCCG<br>TGAGCTGCTTAAAGCAGGAGCCGACGTGAACGCGAAGAACTCACGCGGGTGGACGCCAC |

SEQUENCE TABLE

| SEQ ID NO | Description | DARPin protein | Sequence (an X represents any amino acid) |
|---|---|---|---|
| | | | TTCACACGGCCGCGCAGACAGGTCACCTTGAAATCTTTGAGGTTCTTCTGAAGGCAGGA<br>GCAGACGTTAACGCCAAAAACGACAAGCGCGTGACTCCGTTGCACCTTGCCGCAGCTCT<br>GGGGCATTTGGAGATCGTTGAGGTACTGTTGAAAGCGGGAGCAGATGTTAATGCTCGCG<br>ACAGTTGGGGGACGACACCAGCAGACCTGGCCGCAAAATACGGACACCAAGACATTGCT<br>GAAGTTCTGCAAAAGGCAGCA |
| 123 | Nucleic acid encoding protein of SEQ ID NO:100 | | ATGAGAGGATCGCATCACCATCACCATCACGGATCCGACCTGGGTAAGAAACTGTTGGA<br>AGCAGCACGTGCGGGTCAAGACGATGAAGTTCGTGAGCTGTTAAAGGCTGGCGCCGACG<br>TGAACGCGAAGGACTACTTTAGCCACACCCCGCTGCACTTGGCAGCGCGCAACGGTCAC<br>CTGAAAATTGTCGAGGTCCTGTTGAAGGCTGGTGCGGATGTGAACGCAAAGATTTTGC<br>GGGTAAGACGCCGCTGCATCTGGCGGCGGCTGATGGTCACTTAGAGATCGTAGAGGTTC<br>TGTTGAAAGCGGGCGCCGATGTGAATGCCCAGGACATCTTCGGCAAGACCCCGGCAGAC<br>ATTGCCGCGGATGCTGGTCACGAAGATATCGCAGAGGTCCTGCAAAAAGCGGCAGGCAG<br>CCCGACCCCGACGCCGACCACTCCGACCCCGACCCCAACCACCCCGACTCCGACTCCGA<br>CCGGATCTGACCTGGGTAAAAAACTGCTGGAAGCAGCACGTGCCGGCCAGGATGATGAA<br>GTTCGTGAACTGCTGAAAGCAGGCGCCGATGTTAATGCAAAGGATTATTTTAGCCACAC<br>ACCGCTGCATCTGGCAGCCCGTAATGGTCACCTAAAGATTGTTGAAGTTCTGCTGAAGG<br>CTGGTGCAGACGTTAACGCCAAAGATTTCGCGGGCAAAACCCCTCTGCATTTAGCCGCA<br>GCGGACGGTCACCTGGAGATCGTAGAGGTGCTGCTTAAGGCGGGTGCGGATGTTAATGC<br>ACAGGATATTTTCGGTAAAACCCCTGCCGATATTGCAGCTGATGCCGGTCATGAAGATA<br>TCGCAGAAGTGCTGCAGAAGGCAGCAGGATCACCAACACCAACCCCGACCACCCCAACT<br>CCAACACCGACCACCCCGACCCCTACCCCAACAGGATCCGACCTGGGTAAAAAATTGCT<br>TCAGGCCGCTCGCGCCGGGCAACTTGACGAAGTACGTGAATTACTGAAAGCAGGCGCAG<br>ACGTGAACGCTAAGGATCAGCAGGGCTTAACTCCGTTACACATCGCCGCTAATCTGGGT<br>CATCTGGAGATTGTTGAAGTATTATTAAAGGCCGGAGCGGATGTAAATGCCAAGGATCT<br>GTTTGGACTTACGCCGCTTCATCTGGCCGCTTTTGAGGGTCACTTAGAAATTGTGGAGG<br>TCTTACTTAAGGCGGGGGCTGACGTAAATGCGAAAGATCAGCATGGTGCCACGCCTCTT<br>CATTTGGCTGCTTGGGTCGGACATTTGGAAATTGTGGAAGTGTTATTGAAAGCTGGAGC<br>AGATGTGAACGCGAGGACAAGTCAGGTAAAACCCCGGCGGATCTGGCGGCACGCGCAG<br>GACATCAAGATATTGCTGAAGTTCTGCAGAAGGCAGCAGGCTCGCCGACTCCGACCCCG<br>ACCACCCCAACTCCAACACCGACCACCCCGACCCCTACCCCAACAGGATCTGACCTGGG<br>TAAAAAGTTGTTACAGGCAGCATTGGAGGGCAACTTGACGAGGTGCGCGAGTTACTGA<br>AAGCTGGTGCAGATGTCAACGCGAAGGACATTGAAGGATATACTCCGCTGCACCTTGCC<br>GCGGCTTTGGGGCATCTTGAGATTGTGGAGGTGCTTCTTAAGGCGGGAGCTGATGTCAA<br>TGCTAAAGACCAAATCGGGCGCACACCGTTACACTTGGCTGCGTACAAAGGTCACTTAG<br>AAATCGTGGAAGTGCTTCTGAAGGCTGGCGCTGATGTCAACGCCCAAGACATTATCGGC<br>CAGACACCGGCGGACCTGGCAGCGCAACGTGGGCATCAGGATATTGCTGAAGTTCTGCA<br>GAAGGCAGCAGGCTCGCCGACTCCGACCCCGACCACCCCAACTCCAACACCGACCACCC<br>CGACCCCTACCCCAACAGGATCTGACCTGGGTAAAAAGTTGTTATTAGCTGCGGAGCGC<br>GGGCAGTTAGACGAAGTGCGTATTCTGCTGAAGGCCGGGGCCGACGTTAACGCAAAGGA<br>TCGTGCAGAGGGTTACACCCCCCTGCACATCGCCGCTTATCAAGGTCACTTGGAGATTG<br>TTGAGGTCTTACTGAAAGCGGGGGCCGACGTGAATGCCAAAGATCGCTATGGAAAAACA<br>CCGTTACACTTAGCAGCTATTTCGGGGCATCTGGAGATCGTGGAAGTCCTGTTAAAGGC<br>TGGTGCCGATGTTAATGCACAAGATAATAAAGGCAGCACTCCAGCCGATCTGGCCGCTG<br>ATTATGGGCACCAGGACATTGCTGAAGTTCTGCAGAAGGCAGCAGGCTCGCCAACCGGA<br>TCAGATCTGGGTCAAAAGCTGTTGGAAGCCGCGTGGGCGGGTCAGGACGATGAAGTCCG<br>TGAGCTGCTTAAAGCAGGAGCCGACGTGAACGCGAAGAACTCACGCGGGTGGACGCCAC<br>TTCACACGGCCGCGCAGACAGGTCACCTTGAAATCTTTGAGGTTCTTCTGAAGGCAGGA<br>GCAGACGTTAACGCCAAAAACGACAAGCGCGTGACTCCGTTGCACCTTGCCGCAGCTCT<br>GGGGCATTTGGAGATCGTTGAGGTACTGTTGAAAGCGGGAGCAGATGTTAATGCTCGCG<br>ACAGTTGGGGGACGACACCAGCAGACCTGGCCGCAAAATACGGACACCAAGACATTGCT<br>GAAGTTCTGCAAAAGGCAGCA |
| 124 | Nucleic acid encoding protein of SEQ ID NO:101 | | ATGAGAGGATCGCATCACCATCACCATCACGGATCCGACCTGGGTAAAAAGCTGCTGGA<br>GGCAGCGCGTGCCGGTCAAGACGACGAGGTTCGCGAATTGCTTAAAGCGGGTGCAGACG<br>TCAACGCCAAAGATTATTTCTCTCATACCCCGTTGCATTTAGCCGCGCGTAATGGCCAT<br>CTGAAGATCGTCGAGGTCCTCTTGAAGGCAGGCGCGGATGTCAATGCGAAGGATTTTGC<br>GGGGCAAAACGCCGCTGCACTTAGCGGCGGCGGACGGTCATTTAGAAATCGTTGAAGTCC<br>TGTTAAAAGCGGGCGCCGATGTGAATGCGCAGGATATTTCGGTAAAACGCCGGCGGAC<br>ATTGCCGCAGATGCGGGTCATGAAGATATCGCAGAAGTCCTGCAGAAGGCAGCAGGCAG<br>CCCTACACCTACGCCGACTACGCCTACGCCGACTCCGACTACCCCGACTCCGACCCCGA<br>CCGGATCAGACCTGGGTAAAAAGCTGCTGGAGGCAGCGCGTGCCGGTCAAGACGACGAG<br>GTTCGCGAATTGCTTAAAGCGGGTGCAGACGTCAACGCCAAAGATTATTTCTCTCATAC<br>CCCGTTGCATTTAGCCGCGCGTAATGGCCATCTGAAGATCGTCGAGGTCCTCTTGAAGG<br>CAGGCGCGGATGTCAATGCGAAGGATTTTGCGGGCAAAACGCCGCTGCACTTAGCGGCG<br>GCGGACGGTCATTTAGAAATCGTTGAAGTCCTGTTAAAAGCGGGCGCCGATGTGAATGC<br>GCAGGATATTTTCGGTAAAACGCCGGCGGACATTGCGGCAGATGCGGGTCATGAAGATA<br>TCGCAGAAGTCCTGCAGAAGGCAGCAGGCTCGCCAACGCCGACCCCTACAACGCCAACC<br>CCGACACCAACTACGACCGACCCCACACCAACGGGATCAGACCTGGGTATTAAACTGTT<br>GACAGCCGCTTACGACGGGCAATTAGACGAAGTGCGTATTCTGCTTAAAGCTGGAGCTG<br>ACGTGAACGCGAAAGACTTACGCGGCCAAACGCCTTTACATTACGCGGCGGGACTGGGC<br>CATCTTGAGATTGTTGAGGTGCTTCTGAAGGCAGGCGCGGATGTCAATGCAAAAGACCT<br>GCACGGATGGACACCTCTTCACTTAGCTGCTTGGTCTGGGCATTTGGAGATTGTAGAGG<br>TTTTATTGAAAGCAGGGCGGATGTGAATGCGCAAGACGTAGAAGGAGTCACCCCCAGCT |

| SEQUENCE TABLE | | |
|---|---|---|
| SEQ ID NO Description | DARPin protein | Sequence (an X represents any amino acid) |
| | | GACCTGGCAGCGGTTCAAGGGCATCAAGACATTGCTGAAGTTCTGCAGAAGGCAGCAGG<br>TTCCCCGACCCCTACGCCAACGACTCCGACCCCAACTCCAACGACCCCTACCCCGACCC<br>CGACCGGATCAGACCTGGGTGTTAAGCTGTTGCTTGCAGCCGAGCGTGGGCAGCTTGAT<br>GAAGTACGCATTCTTCTTAAAGCGGGGGCTGATGTGAACGCGAAAGATATTGCTGAGGG<br>TTACACACCGCTTCACATTGCCGCCTACCAGGGTCATCTGGAGATTGTTGAAGTATTAC<br>TGAAAGCGGGAGCAGATGTTAATGCCAAAGATCGCTATGGAAAAACTCCTTTGCATTTA<br>GCTGCAATCGGAGGACACCTGGAAATCGTCGAAGTGTTATTAAAAGCTGGAGCGGACGT<br>AAACGCACAAGATAACAAGGGCTCAACTCCCGCGGACCTTGCCGCAGATTACGGTCATC<br>AGGACATTGCTGAAGTTCTGCAGAAGGCAGCAGGCAGCCCCACGCCAACTCCTACAACC<br>CCCACACCTACACCGACGACGCCGACACCGACTCCAACCGGATCAGACCTGGGTAAAAA<br>ATTGCTTGAAGCCGCGTTGGAAGGACAATTAGACGAGGTACGTGAGCTGTTAAAAGCAG<br>GGGCCGATGTGAATGCTAAAGACCAGGAGGGATACACCCCCTTGCACCTGGCTGCCGCG<br>TTGGGCCACTTAGAGATTGTAGAGGTTCTTCTTAAGGCGGGGGCAGACGTGAATGCAAA<br>GGACCAAATTGGACGTACTCCTTTGCATCTGGCAGCCTATAAGGGGCACTTGGAGATTG<br>TCGAGGTCTTGTTAAAGGCGGGTGCCGATGTAAATGCCCAGGACATCATTGGGCAGACT<br>CCGGCAGATTTGGCCGCCCAACGTGGCCACCAAGATATTGCTGAAGTTCTGCAGAAGGC<br>AGCAGGTTCGCCGACCCCAACCCCTACCACTCCAACGCCGACGCCTACCACTCCAACAC<br>CAACACCAACGGGATCAGACCTGGGTCAAAAGCTGTTGGAAGCCGCGTGGGCGGGTCAG<br>GACGATGAAGTCCGTGAGCTGCTTAAAGCAGGAGCCGACGTGAACGCGAAGAACTCACG<br>CGGGTGGACGCCACTTCACACGGCCGCGCAGACAGGTCACCTTGAAATCTTTGAGGTTC<br>TTCTGAAGGCAGGAGCAGACGTTAACGCCAAAAACGACAAGCGCGTGACTCCGTTGCAC<br>CTTGCCGCAGCTCTGGGGCATTTGGAGATCGTTGAGGTACTGTTGAAAGCGGGAGCAGA<br>TGTTAATGCTCGCGACAGTTGGGGGACGACACCAGCAGACCTGGCCGCAAAATACGGAC<br>ACCAAGACATTGCTGAAGTTCTGCAGAAGGCGGCA |

---

The invention claimed is:

1. A recombinant protein comprising (1) a first binding agent that specifically binds to a protein expressed on the surface of an immune cell, and (2) at least two binding agents that specifically bind to a tumor-associated antigen, wherein said two binding agents specifically bind to different tumor-associated antigens, and wherein said first binding agent is a designed ankyrin repeat domain with binding specificity for CD3, and wherein said ankyrin repeat domain with binding specificity for CD3 comprises an amino acid sequence that is at least 85% identical to any one of the amino acid sequences of SEQ ID NOs: 1 to 5.

2. The recombinant protein of claim 1, wherein said protein comprises at least three binding agents that specifically bind to a tumor-associated antigen, wherein said three binding agents specifically bind to different tumor-associated antigens.

3. The recombinant protein of claim 1, wherein said recombinant protein is capable of binding with a lower dissociation constant ($K_D$) to a surface displaying said tumor-associated antigens, when compared to a recombinant protein comprising only one of said binding agents that specifically bind to a tumor-associated antigen.

4. The recombinant protein of claim 3, wherein said surface displaying said tumor-associated antigens is the surface of a tumor cell.

5. The recombinant protein of claim 1, wherein said protein expressed on the surface of an immune cell is CD3.

6. The recombinant protein of claim 1, wherein said ankyrin repeat domain with binding specificity for CD3 comprises any one of the amino acid sequences of SEQ ID NOs: 1 to 5.

7. The recombinant protein of claim 1, wherein said recombinant protein binds human CD3 in PBS with a dissociation constant ($K_D$) below $10^{-6}$ M.

8. The recombinant protein of claim 1, wherein said recombinant protein binds human CD3 with an $EC_{50}$ ranging from 1 to 400 nM.

9. The recombinant protein of claim 1, wherein said recombinant protein comprises a polypeptide having an amino acid sequence that is at least 80% identical to any one of the amino acid sequences of SEQ ID NOs: 11 to 14, 78 to 86 and 95 to 101.

10. The recombinant protein of claim 1, wherein said recombinant protein comprises a polypeptide having an amino acid sequence that is at least 80% identical to any one of the amino acid sequences of SEQ ID NOs: 95 to 101.

11. The recombinant protein of claim 1, wherein said recombinant protein comprises a polypeptide having an amino acid sequence that is at least 80% identical to the amino acid sequence of SEQ ID NO: 95.

12. The recombinant protein of claim 1, wherein said recombinant protein comprises a polypeptide having an amino acid sequence that is at least 80% identical to the amino acid sequence of SEQ ID NO: 96.

13. The recombinant protein of claim 1, wherein said recombinant protein is capable of binding simultaneously to said protein expressed on the surface of an immune cell, which is specifically bound by said first binding agent, and to said tumor-associated antigens, which are specifically bound by said at least two binding agents that specifically bind to a tumor-associated antigen.

14. The recombinant protein of claim 1, wherein said recombinant protein comprises a polypeptide having the amino acid sequence of any one of SEQ ID NOs: 11 to 14, 78 to 86 and 95 to 101.

15. The recombinant protein of claim 1, wherein said recombinant protein comprises a polypeptide having the amino acid sequence of any one of SEQ ID NOs: 95 to 101.

16. The recombinant protein of claim 1, wherein said recombinant protein comprises a polypeptide having the amino acid sequence of SEQ ID NO: 95.

17. The recombinant protein of claim 1, wherein said recombinant protein comprises a polypeptide having the amino acid sequence of SEQ ID NO: 96.

18. A recombinant protein comprising a polypeptide having the amino acid sequence of SEQ ID NO: 95 or SEQ ID NO: 96.

19. A nucleic acid encoding the recombinant protein of claim 1.

20. A pharmaceutical composition comprising the recombinant protein of claim 1, and a pharmaceutically acceptable carrier and/or diluent.

21. A method of treating a cancer, the method comprising the step of administering to a patient in need thereof a therapeutically effective amount of the recombinant protein of claim 1.

* * * * *

SEQUENCE LISTING

<160> NUMBER OF SEQ ID NOS: 124

<210> SEQ ID NO 1
<211> LENGTH: 124
<212> TYPE: PRT
<213> ORGANISM: Artificial Sequence
<220> FEATURE:
<223> OTHER INFORMATION: DARPin protein 1

<400> SEQUENCE: 1

Asp Leu Gly Gln Lys Leu Leu Glu Ala Ala Trp Ala Gly Gln Asp Asp
1               5                   10                  15

Glu Val Arg Glu Leu Leu Lys Ala Gly Ala Asp Val Asn Ala Lys Asp
                20                  25                  30

Ser Gln Gly Trp Thr Pro Leu His Thr Ala Ala Gln Thr Gly His Leu
            35                  40                  45

Glu Ile Phe Glu Val Leu Leu Lys Ala Gly Ala Asp Val Asn Ala Lys
        50                  55                  60

Asp Asp Lys Gly Val Thr Pro Leu His Leu Ala Ala Ala Leu Gly His
65                  70                  75                  80

Leu Glu Ile Val Glu Val Leu Leu Lys Ala Gly Ala Asp Val Asn Ala
                85                  90                  95

Gln Asp Ser Trp Gly Thr Thr Pro Ala Asp Leu Ala Ala Lys Tyr Gly
                100                 105                 110

His Glu Asp Ile Ala Glu Val Leu Gln Lys Ala Ala
                115                 120

<210> SEQ ID NO 2
<211> LENGTH: 124
<212> TYPE: PRT
<213> ORGANISM: Artificial Sequence
<220> FEATURE:
<223> OTHER INFORMATION: DARPin protein 2

```
<400> SEQUENCE: 2

Asp Leu Gly Gln Lys Leu Leu Glu Ala Ala Trp Ala Gly Gln Asp Asp
1               5                   10                  15

Glu Val Arg Glu Leu Leu Lys Ala Gly Ala Asp Val Asn Ala Lys Asn
            20                  25                  30

Ser Arg Gly Trp Thr Pro Leu His Thr Ala Ala Gln Thr Gly His Leu
        35                  40                  45

Glu Ile Phe Glu Val Leu Leu Lys Ala Gly Ala Asp Val Asn Ala Lys
    50                  55                  60

Asp Asp Lys Gly Val Thr Pro Leu His Leu Ala Ala Leu Gly His
65                  70                  75                  80

Leu Glu Ile Val Glu Val Leu Leu Lys Ala Gly Ala Asp Val Asn Ala
                85                  90                  95

Gln Asp Ser Trp Gly Thr Thr Pro Ala Asp Leu Ala Ala Lys Tyr Gly
            100                 105                 110

His Glu Asp Ile Ala Glu Val Leu Gln Lys Ala Ala
            115                 120

<210> SEQ ID NO 3
<211> LENGTH: 124
<212> TYPE: PRT
<213> ORGANISM: Artificial Sequence
<220> FEATURE:
<223> OTHER INFORMATION: DARPin protein 3

<400> SEQUENCE: 3

Asp Leu Gly Gln Lys Leu Leu Glu Ala Ala Trp Ala Gly Gln Asp Asp
1               5                   10                  15

Glu Val Arg Glu Leu Leu Lys Ala Gly Ala Asp Val Asn Ala Lys Asn
            20                  25                  30

Ser Arg Gly Trp Thr Pro Leu His Thr Ala Ala Gln Thr Gly His Leu
        35                  40                  45

Glu Ile Phe Glu Val Leu Leu Lys Ala Gly Ala Asp Val Asn Ala Lys
    50                  55                  60

Asn Asp Lys Arg Val Thr Pro Leu His Leu Ala Ala Leu Gly His
65                  70                  75                  80

Leu Glu Ile Val Glu Val Leu Leu Lys Ala Gly Ala Asp Val Asn Ala
                85                  90                  95

Arg Asp Ser Trp Gly Thr Thr Pro Ala Asp Leu Ala Ala Lys Tyr Gly
            100                 105                 110

His Gln Asp Ile Ala Glu Val Leu Gln Lys Ala Ala
            115                 120

<210> SEQ ID NO 4
<211> LENGTH: 124
<212> TYPE: PRT
<213> ORGANISM: Artificial Sequence
<220> FEATURE:
<223> OTHER INFORMATION: DARPin protein 4

<400> SEQUENCE: 4

Asp Leu Gly Gln Lys Leu Leu Glu Ala Ala Trp Ala Gly Gln Leu Asp
1               5                   10                  15

Glu Val Arg Ile Leu Leu Lys Ala Gly Ala Asp Val Asn Ala Lys Asn
            20                  25                  30

Ser Arg Gly Trp Thr Pro Leu His Thr Ala Ala Gln Thr Gly His Leu
        35                  40                  45
```

```
Glu Ile Phe Glu Val Leu Leu Lys Ala Gly Ala Asp Val Asn Ala Lys
 50                  55                  60

Thr Asn Lys Arg Val Thr Pro Leu His Leu Ala Ala Leu Gly His
 65                  70                  75                  80

Leu Glu Ile Val Glu Val Leu Lys Ala Gly Ala Asp Val Asn Ala
                 85                  90                  95

Arg Asp Thr Trp Gly Thr Thr Pro Ala Asp Leu Ala Ala Lys Tyr Gly
                100                 105                 110

His Arg Asp Ile Ala Glu Val Leu Gln Lys Ala Ala
            115                 120
```

<210> SEQ ID NO 5
<211> LENGTH: 124
<212> TYPE: PRT
<213> ORGANISM: Artificial Sequence
<220> FEATURE:
<223> OTHER INFORMATION: DARPin protein 5

<400> SEQUENCE: 5

```
Asp Leu Gly Gln Lys Leu Leu Glu Ala Ala Trp Ala Gly Gln Asp Asp
  1                   5                  10                  15

Glu Val Arg Ile Leu Leu Ala Ala Gly Ala Asp Val Asn Ala Lys Asn
                 20                  25                  30

Ser Arg Gly Trp Thr Pro Leu His Thr Ala Ala Gln Thr Gly His Leu
             35                  40                  45

Glu Ile Phe Glu Val Leu Leu Lys Ala Gly Ala Asp Val Asn Ala Lys
 50                  55                  60

Asn Asp Lys Arg Val Thr Pro Leu His Leu Ala Ala Leu Gly His
 65                  70                  75                  80

Leu Glu Ile Val Glu Val Leu Leu Lys Ala Gly Ala Asp Val Asn Ala
                 85                  90                  95

Arg Asp Ser Trp Gly Thr Thr Pro Ala Asp Leu Ala Ala Lys Tyr Gly
                100                 105                 110

His Gly Asp Ile Ala Glu Val Leu Gln Lys Leu Asn
            115                 120
```

<210> SEQ ID NO 6
<211> LENGTH: 125
<212> TYPE: PRT
<213> ORGANISM: Artificial Sequence
<220> FEATURE:
<223> OTHER INFORMATION: DARPin protein 6

<400> SEQUENCE: 6

```
Asp Leu Gly Lys Lys Leu Leu Glu Ala Ala Arg Ala Gly Gln Asp Asp
  1                   5                  10                  15

Glu Val Arg Ile Leu Met Ala Asn Gly Ala Asp Val Asn Ala Leu Asp
                 20                  25                  30

Trp Leu Gly His Thr Pro Leu His Leu Ala Ala Tyr Glu Gly His Leu
             35                  40                  45

Glu Ile Val Glu Val Leu Leu Lys Asn Gly Ala Asp Val Asn Ala Ile
 50                  55                  60

Asp Asp Asn Asn Gly Phe Thr Pro Leu His Leu Ala Ala Ile Asp Gly
 65                  70                  75                  80

His Leu Glu Ile Val Glu Val Leu Leu Lys Asn Gly Ala Asp Val Asn
                 85                  90                  95

Ala Gln Asp Lys Phe Gly Lys Thr Ala Phe Asp Ile Ser Ile Asp Asn
                100                 105                 110
```

```
Gly Asn Glu Asp Leu Ala Glu Ile Leu Gln Lys Ala Ala
        115                 120                 125

<210> SEQ ID NO 7
<211> LENGTH: 421
<212> TYPE: PRT
<213> ORGANISM: Artificial Sequence
<220> FEATURE:
<223> OTHER INFORMATION: DARPin protein 7

<400> SEQUENCE: 7

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Leu Asp
            20                  25                  30

Trp Leu Gly His Thr Pro Leu His Leu Ala Ala Tyr Glu Gly His Leu
        35                  40                  45

Glu Ile Val Glu Val Leu Leu Lys Asn Gly Ala Asp Val Asn Ala Ile
    50                  55                  60

Asp Asp Asn Asn Gly Phe Thr Pro Leu His Leu Ala Ala Ile Asp Gly
65                  70                  75                  80

His Leu Glu Ile Val Glu Val Leu Leu Lys Asn Gly Ala Asp Val Asn
                85                  90                  95

Ala Gln Asp Lys Phe Gly Lys Thr Ala Phe Asp Ile Ser Ile Asp Asn
            100                 105                 110

Gly Asn Glu Asp Leu Ala Glu Ile Leu Gln Lys Ala Ala Gly Ser Pro
        115                 120                 125

Thr Pro Thr Pro Thr Thr Pro Thr Pro Thr Thr Pro Thr Pro Thr Pro
    130                 135                 140

Thr Pro Thr Gly Ser Asp Leu Gly Asp Lys Leu Leu Leu Ala Ala Thr
145                 150                 155                 160

Ser Gly Gln Asp Asp Glu Val Arg Ile Leu Leu Ala Ala Gly Ala Asp
                165                 170                 175

Val Asn Ala Lys Asp Tyr Asp Gly Asp Thr Pro Leu His Leu Ala Ala
            180                 185                 190

Asp Glu Gly His Leu Glu Ile Val Glu Val Leu Leu Lys Ala Gly Ala
        195                 200                 205

Asp Val Asn Ala Lys Asp Tyr Ser Gly Ser Thr Pro Leu His Ala Ala
    210                 215                 220

Ala Ala Tyr Gly His Leu Glu Ile Val Glu Val Leu Leu Lys Ala Gly
225                 230                 235                 240

Ala Asp Val Asn Ala Gln Asp Val Phe Gly Tyr Thr Pro Ala Asp Leu
                245                 250                 255

Ala Ala Tyr Val Gly His Glu Asp Ile Ala Glu Val Leu Gln Lys Ala
            260                 265                 270

Ala Gly Ser Pro Thr Pro Thr Pro Thr Thr Pro Thr Pro Thr Pro Thr
        275                 280                 285

Thr Pro Thr Pro Thr Pro Thr Gly Ser Asp Leu Gly Gln Lys Leu Leu
    290                 295                 300

Glu Ala Ala Trp Ala Gly Gln Asp Asp Glu Val Arg Glu Leu Leu Lys
305                 310                 315                 320

Ala Gly Ala Asp Val Asn Ala Lys Asp Ser Gln Gly Trp Thr Pro Leu
                325                 330                 335

His Thr Ala Ala Gln Thr Gly His Leu Glu Ile Phe Glu Val Leu Leu
            340                 345                 350
```

```
Lys Ala Gly Ala Asp Val Asn Ala Lys Asp Asp Lys Gly Val Thr Pro
            355                 360                 365

Leu His Leu Ala Ala Ala Leu Gly His Leu Glu Ile Val Glu Val Leu
    370                 375                 380

Leu Lys Ala Gly Ala Asp Val Asn Ala Gln Asp Ser Trp Gly Thr Thr
385                 390                 395                 400

Pro Ala Asp Leu Ala Ala Lys Tyr Gly His Glu Asp Ile Ala Glu Val
            405                 410                 415

Leu Gln Lys Ala Ala
            420

<210> SEQ ID NO 8
<211> LENGTH: 421
<212> TYPE: PRT
<213> ORGANISM: Artificial Sequence
<220> FEATURE:
<223> OTHER INFORMATION: DARPin protein 8

<400> SEQUENCE: 8

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Leu Asp
                20                  25                  30

Trp Leu Gly His Thr Pro Leu His Leu Ala Ala Tyr Glu Gly His Leu
            35                  40                  45

Glu Ile Val Glu Val Leu Leu Lys Asn Gly Ala Asp Val Asn Ala Ile
        50                  55                  60

Asp Asp Asn Asn Gly Phe Thr Pro Leu His Leu Ala Ala Ile Asp Gly
65                  70                  75                  80

His Leu Glu Ile Val Glu Val Leu Leu Lys Asn Gly Ala Asp Val Asn
                85                  90                  95

Ala Gln Asp Lys Phe Gly Lys Thr Ala Phe Asp Ile Ser Ile Asp Asn
            100                 105                 110

Gly Asn Glu Asp Leu Ala Glu Ile Leu Gln Lys Ala Ala Gly Ser Pro
        115                 120                 125

Thr Pro Thr Pro Thr Pro Thr Pro Thr Pro Thr Pro Thr Pro Thr Pro
    130                 135                 140

Thr Pro Thr Gly Ser Asp Leu Gly Asp Lys Leu Leu Leu Ala Ala Thr
145                 150                 155                 160

Ser Gly Gln Asp Asp Glu Val Arg Ile Leu Leu Ala Ala Gly Ala Asp
                165                 170                 175

Val Asn Ala Lys Asp Tyr Asp Gly Asp Thr Pro Leu His Leu Ala Ala
            180                 185                 190

Asp Glu Gly His Leu Glu Ile Val Glu Val Leu Leu Lys Ala Gly Ala
        195                 200                 205

Asp Val Asn Ala Lys Asp Tyr Ser Gly Ser Thr Pro Leu His Ala Ala
    210                 215                 220

Ala Ala Tyr Gly His Leu Glu Ile Val Glu Val Leu Leu Lys Ala Gly
225                 230                 235                 240

Ala Asp Val Asn Ala Gln Asp Val Phe Gly Tyr Thr Pro Ala Asp Leu
                245                 250                 255

Ala Ala Tyr Val Gly His Glu Asp Ile Ala Glu Val Leu Gln Lys Ala
            260                 265                 270

Ala Gly Ser Pro Thr Pro Thr Pro Thr Pro Thr Pro Thr Pro Thr Pro Thr
        275                 280                 285
```

```
Thr Pro Thr Pro Thr Pro Thr Gly Ser Asp Leu Gly Gln Lys Leu Leu
    290                 295                 300

Glu Ala Ala Trp Ala Gly Gln Asp Asp Glu Val Arg Glu Leu Leu Lys
305                 310                 315                 320

Ala Gly Ala Asp Val Asn Ala Lys Asn Ser Arg Gly Trp Thr Pro Leu
            325                 330                 335

His Thr Ala Ala Gln Thr Gly His Leu Glu Ile Phe Glu Val Leu Leu
            340                 345                 350

Lys Ala Gly Ala Asp Val Asn Ala Lys Asp Asp Lys Gly Val Thr Pro
            355                 360                 365

Leu His Leu Ala Ala Ala Gly His Leu Glu Ile Val Glu Val Leu
    370                 375                 380

Leu Lys Ala Gly Ala Asp Val Asn Ala Gln Asp Ser Trp Gly Thr Thr
385                 390                 395                 400

Pro Ala Asp Leu Ala Ala Lys Tyr Gly His Glu Asp Ile Ala Glu Val
            405                 410                 415

Leu Gln Lys Ala Ala
            420

<210> SEQ ID NO 9
<211> LENGTH: 421
<212> TYPE: PRT
<213> ORGANISM: Artificial Sequence
<220> FEATURE:
<223> OTHER INFORMATION: DARPin protein 9

<400> SEQUENCE: 9

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Leu Asp
            20                  25                  30

Trp Leu Gly His Thr Pro Leu His Leu Ala Ala Tyr Glu Gly His Leu
        35                  40                  45

Glu Ile Val Glu Val Leu Leu Lys Asn Gly Ala Asp Val Asn Ala Ile
    50                  55                  60

Asp Asp Asn Asn Gly Phe Thr Pro Leu His Leu Ala Ala Ile Asp Gly
65                  70                  75                  80

His Leu Glu Ile Val Glu Val Leu Leu Lys Asn Gly Ala Asp Val Asn
                85                  90                  95

Ala Gln Asp Lys Phe Gly Lys Thr Ala Phe Asp Ile Ser Ile Asp Asn
            100                 105                 110

Gly Asn Glu Asp Leu Ala Glu Ile Leu Gln Lys Ala Ala Gly Ser Pro
        115                 120                 125

Thr Pro Thr Pro Thr Thr Pro Thr Pro Thr Pro Thr Pro Thr Pro Thr Pro
    130                 135                 140

Thr Pro Thr Gly Ser Asp Leu Gly Asp Lys Leu Leu Ala Ala Thr
145                 150                 155                 160

Ser Gly Gln Asp Asp Glu Val Arg Ile Leu Leu Ala Ala Gly Ala Asp
                165                 170                 175

Val Asn Ala Lys Asp Tyr Asp Gly Asp Thr Pro Leu His Leu Ala Ala
            180                 185                 190

Asp Glu Gly His Leu Glu Ile Val Glu Val Leu Leu Lys Ala Gly Ala
        195                 200                 205

Asp Val Asn Ala Lys Asp Tyr Ser Gly Ser Thr Pro Leu His Ala Ala
    210                 215                 220
```

```
Ala Ala Tyr Gly His Leu Glu Ile Val Glu Val Leu Leu Lys Ala Gly
225                 230                 235                 240

Ala Asp Val Asn Ala Gln Asp Val Phe Gly Tyr Thr Pro Ala Asp Leu
            245                 250                 255

Ala Ala Tyr Val Gly His Glu Asp Ile Ala Glu Val Leu Gln Lys Ala
            260                 265                 270

Ala Gly Ser Pro Thr Pro Thr Pro Thr Thr Pro Thr Pro Thr Pro Thr
            275                 280                 285

Thr Pro Thr Pro Thr Pro Thr Gly Ser Asp Leu Gly Gln Lys Leu Leu
        290                 295                 300

Glu Ala Ala Trp Ala Gly Gln Asp Asp Glu Val Arg Glu Leu Leu Lys
305                 310                 315                 320

Ala Gly Ala Asp Val Asn Ala Lys Asn Ser Arg Gly Trp Thr Pro Leu
                325                 330                 335

His Thr Ala Ala Gln Thr Gly His Leu Glu Ile Phe Glu Val Leu Leu
            340                 345                 350

Lys Ala Gly Ala Asp Val Asn Ala Lys Asn Asp Lys Arg Val Thr Pro
            355                 360                 365

Leu His Leu Ala Ala Ala Leu Gly His Leu Glu Ile Val Glu Val Leu
370                 375                 380

Leu Lys Ala Gly Ala Asp Val Asn Ala Arg Asp Ser Trp Gly Thr Thr
385                 390                 395                 400

Pro Ala Asp Leu Ala Ala Lys Tyr Gly His Gln Asp Ile Ala Glu Val
            405                 410                 415

Leu Gln Lys Ala Ala
            420

<210> SEQ ID NO 10
<211> LENGTH: 421
<212> TYPE: PRT
<213> ORGANISM: Artificial Sequence
<220> FEATURE:
<223> OTHER INFORMATION: DARPin protein 10

<400> SEQUENCE: 10

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Leu Asp
            20                  25                  30

Trp Leu Gly His Thr Pro Leu His Leu Ala Ala Tyr Glu Gly His Leu
        35                  40                  45

Glu Ile Val Glu Val Leu Leu Lys Asn Gly Ala Asp Val Asn Ala Ile
50                  55                  60

Asp Asp Asn Asn Gly Phe Thr Pro Leu His Leu Ala Ala Ile Asp Gly
65                  70                  75                  80

His Leu Glu Ile Val Glu Val Leu Leu Lys Asn Gly Ala Asp Val Asn
            85                  90                  95

Ala Gln Asp Lys Phe Gly Lys Thr Ala Phe Asp Ile Ser Ile Asp Asn
            100                 105                 110

Gly Asn Glu Asp Leu Ala Glu Ile Leu Gln Lys Ala Ala Gly Ser Pro
        115                 120                 125

Thr Pro Thr Pro Thr Thr Pro Thr Pro Thr Thr Pro Thr Pro Thr Pro
        130                 135                 140

Thr Pro Thr Gly Ser Asp Leu Gly Asp Lys Leu Leu Leu Ala Ala Thr
145                 150                 155                 160
```

-continued

```
Ser Gly Gln Asp Asp Glu Val Arg Ile Leu Leu Ala Ala Gly Ala Asp
                165                 170                 175

Val Asn Ala Lys Asp Tyr Asp Gly Asp Thr Pro Leu His Leu Ala Ala
            180                 185                 190

Asp Glu Gly His Leu Glu Ile Val Glu Val Leu Leu Lys Ala Gly Ala
        195                 200                 205

Asp Val Asn Ala Lys Asp Tyr Ser Gly Ser Thr Pro Leu His Ala Ala
    210                 215                 220

Ala Ala Tyr Gly His Leu Glu Ile Val Glu Val Leu Leu Lys Ala Gly
225                 230                 235                 240

Ala Asp Val Asn Ala Gln Asp Val Phe Gly Tyr Thr Pro Ala Asp Leu
                245                 250                 255

Ala Ala Tyr Val Gly His Glu Asp Ile Ala Glu Val Leu Gln Lys Ala
            260                 265                 270

Ala Gly Ser Pro Thr Pro Thr Pro Thr Thr Pro Thr Pro Thr Pro Thr
        275                 280                 285

Thr Pro Thr Pro Thr Pro Thr Gly Ser Asp Leu Gly Gln Lys Leu Leu
    290                 295                 300

Glu Ala Ala Trp Ala Gly Gln Leu Asp Glu Val Arg Ile Leu Leu Lys
305                 310                 315                 320

Ala Gly Ala Asp Val Asn Ala Lys Asn Ser Arg Gly Trp Thr Pro Leu
                325                 330                 335

His Thr Ala Ala Gln Thr Gly His Leu Glu Ile Phe Glu Val Leu Leu
            340                 345                 350

Lys Ala Gly Ala Asp Val Asn Ala Lys Thr Asn Lys Arg Val Thr Pro
        355                 360                 365

Leu His Leu Ala Ala Ala Leu Gly His Leu Glu Ile Val Glu Val Leu
    370                 375                 380

Leu Lys Ala Gly Ala Asp Val Asn Ala Arg Asp Thr Trp Gly Thr Thr
385                 390                 395                 400

Pro Ala Asp Leu Ala Ala Lys Tyr Gly His Arg Asp Ile Ala Glu Val
                405                 410                 415

Leu Gln Lys Ala Ala
            420

<210> SEQ ID NO 11
<211> LENGTH: 569
<212> TYPE: PRT
<213> ORGANISM: Artificial Sequence
<220> FEATURE:
<223> OTHER INFORMATION: DARPin protein 11

<400> SEQUENCE: 11

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95
```

```
Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Thr Pro Thr Pro Thr
        130                 135                 140

Pro Thr Gly Ser Asp Leu Gly Lys Lys Leu Leu Glu Ala Ala Arg Ala
145                 150                 155                 160

Gly Gln Asp Asp Glu Val Arg Ile Leu Met Ala Asn Gly Ala Asp Val
                165                 170                 175

Asn Ala Leu Asp Trp Leu Gly His Thr Pro Leu His Leu Ala Ala Tyr
            180                 185                 190

Glu Gly His Leu Glu Ile Val Glu Val Leu Leu Lys Asn Gly Ala Asp
        195                 200                 205

Val Asn Ala Ile Asp Asp Asn Gly Phe Thr Pro Leu His Leu Ala
    210                 215                 220

Ala Ile Asp Gly His Leu Glu Ile Val Glu Val Leu Leu Lys Asn Gly
225                 230                 235                 240

Ala Asp Val Asn Ala Gln Asp Lys Phe Gly Lys Thr Ala Phe Asp Ile
                245                 250                 255

Ser Ile Asp Asn Gly Asn Glu Asp Leu Ala Glu Ile Leu Gln Lys Ala
            260                 265                 270

Ala Gly Ser Pro Thr Pro Thr Pro Thr Thr Pro Thr Pro Thr Pro Thr
        275                 280                 285

Thr Pro Thr Pro Thr Pro Gly Ser Asp Leu Gly Asp Lys Leu Leu
        290                 295                 300

Leu Ala Ala Thr Ser Gly Gln Asp Asp Glu Val Arg Ile Leu Leu Ala
305                 310                 315                 320

Ala Gly Ala Asp Val Asn Ala Lys Asp Tyr Asp Gly Asp Thr Pro Leu
                325                 330                 335

His Leu Ala Ala Asp Glu Gly His Leu Glu Ile Val Glu Val Leu Leu
            340                 345                 350

Lys Ala Gly Ala Asp Val Asn Ala Lys Asp Tyr Ser Gly Ser Thr Pro
        355                 360                 365

Leu His Ala Ala Ala Tyr Gly His Leu Glu Ile Val Glu Val Leu
        370                 375                 380

Leu Lys Ala Gly Ala Asp Val Asn Ala Gln Asp Val Phe Gly Tyr Thr
385                 390                 395                 400

Pro Ala Asp Leu Ala Ala Tyr Val Gly His Glu Asp Ile Ala Glu Val
                405                 410                 415

Leu Gln Lys Ala Ala Gly Ser Pro Thr Pro Thr Pro Thr Thr Pro Thr
            420                 425                 430

Pro Thr Pro Thr Thr Pro Thr Pro Thr Pro Thr Gly Ser Asp Leu Gly
        435                 440                 445

Gln Lys Leu Leu Glu Ala Ala Trp Ala Gly Gln Asp Asp Glu Val Arg
        450                 455                 460

Glu Leu Leu Lys Ala Gly Ala Asp Val Asn Ala Lys Asp Ser Gln Gly
465                 470                 475                 480

Trp Thr Pro Leu His Thr Ala Ala Gln Thr Gly His Leu Glu Ile Phe
                485                 490                 495

Glu Val Leu Leu Lys Ala Gly Ala Asp Val Asn Ala Lys Asp Asp Lys
            500                 505                 510
```

```
Gly Val Thr Pro Leu His Leu Ala Ala Leu Gly His Leu Glu Ile
            515                 520                 525

Val Glu Val Leu Leu Lys Ala Gly Ala Asp Val Asn Ala Gln Asp Ser
    530                 535                 540

Trp Gly Thr Thr Pro Ala Asp Leu Ala Ala Lys Tyr Gly His Glu Asp
545                 550                 555                 560

Ile Ala Glu Val Leu Gln Lys Ala Ala
                565

<210> SEQ ID NO 12
<211> LENGTH: 569
<212> TYPE: PRT
<213> ORGANISM: Artificial Sequence
<220> FEATURE:
<223> OTHER INFORMATION: DARPin protein 12

<400> SEQUENCE: 12

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr
    130                 135                 140

Pro Thr Gly Ser Asp Leu Gly Lys Lys Leu Leu Glu Ala Ala Arg Ala
145                 150                 155                 160

Gly Gln Asp Asp Glu Val Arg Ile Leu Met Ala Asn Gly Ala Asp Val
                165                 170                 175

Asn Ala Leu Asp Trp Leu Gly His Thr Pro Leu His Leu Ala Ala Tyr
            180                 185                 190

Glu Gly His Leu Glu Ile Val Glu Val Leu Leu Lys Asn Gly Ala Asp
        195                 200                 205

Val Asn Ala Ile Asp Asp Asn Gly Phe Thr Pro Leu His Leu Ala
    210                 215                 220

Ala Ile Asp Gly His Leu Glu Ile Val Glu Val Leu Leu Lys Asn Gly
225                 230                 235                 240

Ala Asp Val Asn Ala Gln Asp Lys Phe Gly Lys Thr Ala Phe Asp Ile
                245                 250                 255

Ser Ile Asp Asn Gly Asn Glu Asp Leu Ala Glu Ile Leu Gln Lys Ala
            260                 265                 270

Ala Gly Ser Pro Thr Pro Thr Pro Thr Thr Pro Thr Pro Thr Pro Thr
        275                 280                 285

Thr Pro Thr Pro Thr Pro Thr Gly Ser Asp Leu Gly Asp Lys Leu Leu
    290                 295                 300
```

```
Leu Ala Ala Thr Ser Gly Gln Asp Asp Glu Val Arg Ile Leu Leu Ala
305                 310                 315                 320

Ala Gly Ala Asp Val Asn Ala Lys Asp Tyr Asp Gly Asp Thr Pro Leu
                325                 330                 335

His Leu Ala Ala Asp Glu Gly His Leu Glu Ile Val Glu Val Leu Leu
                340                 345                 350

Lys Ala Gly Ala Asp Val Asn Ala Lys Asp Tyr Ser Gly Ser Thr Pro
                355                 360                 365

Leu His Ala Ala Ala Tyr Gly His Leu Glu Ile Val Glu Val Leu
370                 375                 380

Leu Lys Ala Gly Ala Asp Val Asn Ala Gln Asp Val Phe Gly Tyr Thr
385                 390                 395                 400

Pro Ala Asp Leu Ala Ala Tyr Val Gly His Glu Asp Ile Ala Glu Val
                405                 410                 415

Leu Gln Lys Ala Ala Gly Ser Pro Thr Pro Thr Pro Thr Thr Pro Thr
                420                 425                 430

Pro Thr Pro Thr Thr Pro Thr Pro Thr Pro Thr Gly Ser Asp Leu Gly
                435                 440                 445

Gln Lys Leu Leu Glu Ala Ala Trp Ala Gly Gln Asp Asp Glu Val Arg
                450                 455                 460

Glu Leu Leu Lys Ala Gly Ala Asp Val Asn Ala Lys Asn Ser Arg Gly
465                 470                 475                 480

Trp Thr Pro Leu His Thr Ala Ala Gln Thr Gly His Leu Glu Ile Phe
                485                 490                 495

Glu Val Leu Leu Lys Ala Gly Ala Asp Val Asn Ala Lys Asp Asp Lys
                500                 505                 510

Gly Val Thr Pro Leu His Leu Ala Ala Ala Leu Gly His Leu Glu Ile
                515                 520                 525

Val Glu Val Leu Leu Lys Ala Gly Ala Asp Val Asn Ala Gln Asp Ser
530                 535                 540

Trp Gly Thr Thr Pro Ala Asp Leu Ala Ala Lys Tyr Gly His Glu Asp
545                 550                 555                 560

Ile Ala Glu Val Leu Gln Lys Ala Ala
                565

<210> SEQ ID NO 13
<211> LENGTH: 569
<212> TYPE: PRT
<213> ORGANISM: Artificial Sequence
<220> FEATURE:
<223> OTHER INFORMATION: DARPin protein 13

<400> SEQUENCE: 13

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Ser His Thr Pro Leu His Leu Ala Ala Arg Asn Gly His Leu
                35                  40                  45

Lys Ile Val Glu Val Leu Leu Lys Ala Gly Ala Asp Val Asn Ala Lys
50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95
```

-continued

```
Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Thr Pro Thr Pro Thr
        130                 135                 140

Pro Thr Gly Ser Asp Leu Gly Lys Lys Leu Leu Glu Ala Ala Arg Ala
145                 150                 155                 160

Gly Gln Asp Asp Glu Val Arg Ile Leu Met Ala Asn Gly Ala Asp Val
                165                 170                 175

Asn Ala Leu Asp Trp Leu Gly His Thr Pro Leu His Leu Ala Ala Tyr
            180                 185                 190

Glu Gly His Leu Glu Ile Val Glu Val Leu Leu Lys Asn Gly Ala Asp
        195                 200                 205

Val Asn Ala Ile Asp Asp Asn Gly Phe Thr Pro Leu His Leu Ala
210                 215                 220

Ala Ile Asp Gly His Leu Glu Ile Val Glu Val Leu Leu Lys Asn Gly
225                 230                 235                 240

Ala Asp Val Asn Ala Gln Asp Lys Phe Gly Lys Thr Ala Phe Asp Ile
            245                 250                 255

Ser Ile Asp Asn Gly Asn Glu Asp Leu Ala Glu Ile Leu Gln Lys Ala
        260                 265                 270

Ala Gly Ser Pro Thr Pro Thr Pro Thr Thr Pro Thr Pro Thr Pro Thr
        275                 280                 285

Thr Pro Thr Pro Thr Pro Thr Gly Ser Asp Leu Gly Asp Lys Leu Leu
        290                 295                 300

Leu Ala Ala Thr Ser Gly Gln Asp Asp Glu Val Arg Ile Leu Leu Ala
305                 310                 315                 320

Ala Gly Ala Asp Val Asn Ala Lys Asp Tyr Asp Gly Asp Thr Pro Leu
            325                 330                 335

His Leu Ala Ala Asp Glu Gly His Leu Glu Ile Val Glu Val Leu Leu
        340                 345                 350

Lys Ala Gly Ala Asp Val Asn Ala Lys Asp Tyr Ser Gly Ser Thr Pro
        355                 360                 365

Leu His Ala Ala Ala Tyr Gly His Leu Glu Ile Val Glu Val Leu
        370                 375                 380

Leu Lys Ala Gly Ala Asp Val Asn Ala Gln Asp Val Phe Gly Tyr Thr
385                 390                 395                 400

Pro Ala Asp Leu Ala Ala Tyr Val Gly His Glu Asp Ile Ala Glu Val
            405                 410                 415

Leu Gln Lys Ala Ala Gly Ser Pro Thr Pro Thr Pro Thr Thr Pro Thr
        420                 425                 430

Pro Thr Pro Thr Thr Pro Thr Pro Thr Pro Thr Gly Ser Asp Leu Gly
        435                 440                 445

Gln Lys Leu Leu Glu Ala Ala Trp Ala Gly Gln Asp Asp Glu Val Arg
        450                 455                 460

Glu Leu Leu Lys Ala Gly Ala Asp Val Asn Ala Lys Asn Ser Arg Gly
465                 470                 475                 480

Trp Thr Pro Leu His Thr Ala Ala Gln Thr Gly His Leu Glu Ile Phe
            485                 490                 495

Glu Val Leu Leu Lys Ala Gly Ala Asp Val Asn Ala Lys Asn Asp Lys
        500                 505                 510

Arg Val Thr Pro Leu His Leu Ala Ala Ala Leu Gly His Leu Glu Ile
```

```
                515                 520                 525
Val Glu Val Leu Leu Lys Ala Gly Ala Asp Val Asn Ala Arg Asp Ser
530                 535                 540

Trp Gly Thr Thr Pro Ala Asp Leu Ala Ala Lys Tyr Gly His Gln Asp
545                 550                 555                 560

Ile Ala Glu Val Leu Gln Lys Ala Ala
                565

<210> SEQ ID NO 14
<211> LENGTH: 569
<212> TYPE: PRT
<213> ORGANISM: Artificial Sequence
<220> FEATURE:
<223> OTHER INFORMATION: DARPin protein 14

<400> SEQUENCE: 14

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr
    130                 135                 140

Pro Thr Gly Ser Asp Leu Gly Lys Lys Leu Leu Glu Ala Ala Arg Ala
145                 150                 155                 160

Gly Gln Asp Asp Glu Val Arg Ile Leu Met Ala Asn Gly Ala Asp Val
                165                 170                 175

Asn Ala Leu Asp Trp Leu Gly His Thr Pro Leu His Leu Ala Ala Tyr
            180                 185                 190

Glu Gly His Leu Glu Ile Val Glu Val Leu Leu Lys Asn Gly Ala Asp
        195                 200                 205

Val Asn Ala Ile Asp Asp Asn Gly Phe Thr Pro Leu His Leu Ala
    210                 215                 220

Ala Ile Asp Gly His Leu Glu Ile Val Glu Val Leu Leu Lys Asn Gly
225                 230                 235                 240

Ala Asp Val Asn Ala Gln Asp Lys Phe Gly Lys Thr Ala Phe Asp Ile
                245                 250                 255

Ser Ile Asp Asn Gly Asn Glu Asp Leu Ala Glu Ile Leu Gln Lys Ala
            260                 265                 270

Ala Gly Ser Pro Thr Pro Thr Pro Thr Pro Thr Pro Thr Pro Thr
        275                 280                 285

Thr Pro Thr Pro Thr Pro Thr Gly Ser Asp Leu Gly Asp Lys Leu Leu
    290                 295                 300

Leu Ala Ala Thr Ser Gly Gln Asp Asp Glu Val Arg Ile Leu Leu Ala
```

```
                305                 310                 315                 320
Ala Gly Ala Asp Val Asn Ala Lys Asp Tyr Asp Gly Asp Thr Pro Leu
                    325                 330                 335

His Leu Ala Ala Asp Glu Gly His Leu Glu Ile Val Glu Val Leu Leu
                    340                 345                 350

Lys Ala Gly Ala Asp Val Asn Ala Lys Asp Tyr Ser Gly Ser Thr Pro
                    355                 360                 365

Leu His Ala Ala Ala Tyr Gly His Leu Glu Ile Val Glu Val Leu
            370                 375                 380

Leu Lys Ala Gly Ala Asp Val Asn Ala Gln Asp Val Phe Gly Tyr Thr
385                 390                 395                 400

Pro Ala Asp Leu Ala Ala Tyr Val Gly His Glu Asp Ile Ala Glu Val
                    405                 410                 415

Leu Gln Lys Ala Ala Gly Ser Pro Thr Pro Thr Pro Thr Pro Thr Thr
                    420                 425                 430

Pro Thr Pro Thr Thr Pro Thr Pro Thr Pro Thr Gly Ser Asp Leu Gly
                    435                 440                 445

Gln Lys Leu Leu Glu Ala Ala Trp Ala Gly Gln Leu Asp Glu Val Arg
    450                 455                 460

Ile Leu Leu Lys Ala Gly Ala Asp Val Asn Ala Lys Asn Ser Arg Gly
465                 470                 475                 480

Trp Thr Pro Leu His Thr Ala Ala Gln Thr Gly His Leu Glu Ile Phe
                    485                 490                 495

Glu Val Leu Leu Lys Ala Gly Ala Asp Val Asn Ala Lys Thr Asn Lys
                    500                 505                 510

Arg Val Thr Pro Leu His Leu Ala Ala Ala Leu Gly His Leu Glu Ile
                    515                 520                 525

Val Glu Val Leu Leu Lys Ala Gly Ala Asp Val Asn Ala Arg Asp Thr
                    530                 535                 540

Trp Gly Thr Thr Pro Ala Asp Leu Ala Ala Lys Tyr Gly His Arg Asp
545                 550                 555                 560

Ile Ala Glu Val Leu Gln Lys Ala Ala
                    565

<210> SEQ ID NO 15
<211> LENGTH: 124
<212> TYPE: PRT
<213> ORGANISM: Artificial Sequence
<220> FEATURE:
<223> OTHER INFORMATION: DARPin protein 15

<400> SEQUENCE: 15

Asp Leu Gly Asp Lys Leu Leu Ala Ala Thr Ser Gly Gln Asp Asp
1               5                   10                  15

Glu Val Arg Ile Leu Leu Ala Ala Gly Ala Asp Val Asn Ala Lys Asp
                20                  25                  30

Tyr Asp Gly Asp Thr Pro Leu His Leu Ala Ala Asp Glu Gly His Leu
            35                  40                  45

Glu Ile Val Glu Val Leu Leu Lys Ala Gly Ala Asp Val Asn Ala Lys
        50                  55                  60

Asp Tyr Ser Gly Ser Thr Pro Leu His Ala Ala Ala Tyr Gly His
65                  70                  75                  80

Leu Glu Ile Val Glu Val Leu Leu Lys Ala Gly Ala Asp Val Asn Ala
                    85                  90                  95

Gln Asp Val Phe Gly Tyr Thr Pro Ala Asp Leu Ala Ala Tyr Val Gly
```

```
            100                 105                 110
His Glu Asp Ile Ala Glu Val Leu Gln Lys Ala Ala
        115                 120

<210> SEQ ID NO 16
<211> LENGTH: 30
<212> TYPE: PRT
<213> ORGANISM: Artificial Sequence
<220> FEATURE:
<223> OTHER INFORMATION: N-terminal capping module

<400> SEQUENCE: 16

Asp Leu Gly Gln Lys Leu Leu Glu Ala Ala Trp Ala Gly Gln Asp Asp
1               5                   10                  15

Glu Val Arg Glu Leu Leu Lys Ala Gly Ala Asp Val Asn Ala
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: N-terminal capping module

<400> SEQUENCE: 17

Asp Leu Gly Gln Lys Leu Leu Glu Ala Ala Trp Ala Gly Gln Leu Asp
1               5                   10                  15

Glu Val Arg Ile Leu Leu Lys Ala Gly Ala Asp Val Asn Ala
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: N-terminal capping module

<400> SEQUENCE: 18

Asp Leu Gly Gln Lys Leu Leu Glu Ala Ala Trp Ala Gly Gln Asp Asp
1               5                   10                  15

Glu Val Arg Ile Leu Leu Lys Ala Gly Ala Asp Val Asn Ala
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: N-terminal capping module

<400> SEQUENCE: 19

Asp Leu Gly Gln Lys Leu Leu Glu Ala Ala Trp Ala Gly Gln Asp Asp
1               5                   10                  15

Glu Val Arg Ile Leu Leu Ala Ala Gly Ala Asp Val Asn Ala
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: N-terminal capping module

<400> SEQUENCE: 20
```

```
Asp Leu Gly Gln Lys Leu Leu Glu Ala Ala Trp Ala Gly Gln Leu Asp
1               5                   10                  15

Glu Val Arg Glu Leu Leu Lys Ala Gly Ala Asp Val Asn Ala
            20                  25                  30
```

<210> SEQ ID NO 21
<211> LENGTH: 30
<212> TYPE: PRT
<213> ORGANISM: Artificial Sequence
<220> FEATURE:
<223> OTHER INFORMATION: N-terminal capping module

<400> SEQUENCE: 21

```
Asp Leu Gly Gln Lys Leu Leu Glu Ala Ala Trp Ala Gly Gln Leu Asp
1               5                   10                  15

Glu Val Arg Ile Leu Leu Ala Ala Gly Ala Asp Val Asn Ala
            20                  25                  30
```

<210> SEQ ID NO 22
<211> LENGTH: 30
<212> TYPE: PRT
<213> ORGANISM: Artificial Sequence
<220> FEATURE:
<223> OTHER INFORMATION: N-terminal capping module
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 5
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
    Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid

<400> SEQUENCE: 22

```
Asp Leu Gly Xaa Xaa Leu Leu Gln Ala Ala Xaa Xaa Gly Gln Leu Asp
1               5                   10                  15

Xaa Val Arg Xaa Leu Xaa Xaa Xaa Gly Ala Asp Val Asn Ala
            20                  25                  30
```

<210> SEQ ID NO 23
<211> LENGTH: 28
<212> TYPE: PRT

```
<213> ORGANISM: Artificial Sequence
<220> FEATURE:
<223> OTHER INFORMATION: C-terminal capping module

<400> SEQUENCE: 23

Gln Asp Ser Trp Gly Thr Thr Pro Ala Asp Leu Ala Ala Lys Tyr Gly
1               5                   10                  15

His Glu Asp Ile Ala Glu Val Leu Gln Lys Ala Ala
            20                  25

<210> SEQ ID NO 24
<211> LENGTH: 28
<212> TYPE: PRT
<213> ORGANISM: Artificial Sequence
<220> FEATURE:
<223> OTHER INFORMATION: C-terminal capping module

<400> SEQUENCE: 24

Arg Asp Ser Trp Gly Thr Thr Pro Ala Asp Leu Ala Ala Lys Tyr Gly
1               5                   10                  15

His Gln Asp Ile Ala Glu Val Leu Gln Lys Ala Ala
            20                  25

<210> SEQ ID NO 25
<211> LENGTH: 28
<212> TYPE: PRT
<213> ORGANISM: Artificial Sequence
<220> FEATURE:
<223> OTHER INFORMATION: C-terminal capping module

<400> SEQUENCE: 25

Arg Asp Thr Trp Gly Thr Thr Pro Ala Asp Leu Ala Ala Lys Tyr Gly
1               5                   10                  15

His Arg Asp Ile Ala Glu Val Leu Gln Lys Ala Ala
            20                  25

<210> SEQ ID NO 26
<211> LENGTH: 28
<212> TYPE: PRT
<213> ORGANISM: Artificial Sequence
<220> FEATURE:
<223> OTHER INFORMATION: C-terminal capping module

<400> SEQUENCE: 26

Gln Asp Ser Trp Gly Thr Thr Pro Ala Asp Leu Ala Ala Lys Tyr Gly
1               5                   10                  15

His Glu Asp Ile Ala Glu Val Leu Gln Lys Leu Ala
            20                  25

<210> SEQ ID NO 27
<211> LENGTH: 28
<212> TYPE: PRT
<213> ORGANISM: Artificial Sequence
<220> FEATURE:
<223> OTHER INFORMATION: C-terminal capping module

<400> SEQUENCE: 27

Gln Asp Ser Trp Gly Thr Thr Pro Ala Asp Leu Ala Ala Lys Tyr Gly
1               5                   10                  15

His Glu Asp Ile Ala Glu Val Leu Gln Lys Leu Asn
            20                  25

<210> SEQ ID NO 28
<211> LENGTH: 28
```

```
<212> TYPE: PRT
<213> ORGANISM: Artificial Sequence
<220> FEATURE:
<223> OTHER INFORMATION: C-terminal capping module

<400> SEQUENCE: 28

Arg Asp Ser Trp Gly Thr Thr Pro Ala Asp Leu Ala Ala Lys Tyr Gly
 1               5                  10                  15
His Gln Asp Ile Ala Glu Val Leu Gln Lys Leu Ala
            20                  25

<210> SEQ ID NO 29
<211> LENGTH: 28
<212> TYPE: PRT
<213> ORGANISM: Artificial Sequence
<220> FEATURE:
<223> OTHER INFORMATION: C-terminal capping module

<400> SEQUENCE: 29

Arg Asp Ser Trp Gly Thr Thr Pro Ala Asp Leu Ala Ala Lys Tyr Gly
 1               5                  10                  15
His Gln Asp Ile Ala Glu Val Leu Gln Lys Leu Asn
            20                  25

<210> SEQ ID NO 30
<211> LENGTH: 28
<212> TYPE: PRT
<213> ORGANISM: Artificial Sequence
<220> FEATURE:
<223> OTHER INFORMATION: C-terminal capping module

<400> SEQUENCE: 30

Arg Asp Thr Trp Gly Thr Thr Pro Ala Asp Leu Ala Ala Lys Tyr Gly
 1               5                  10                  15
His Arg Asp Ile Ala Glu Val Leu Gln Lys Leu Ala
            20                  25

<210> SEQ ID NO 31
<211> LENGTH: 28
<212> TYPE: PRT
<213> ORGANISM: Artificial Sequence
<220> FEATURE:
<223> OTHER INFORMATION: C-terminal capping module

<400> SEQUENCE: 31

Arg Asp Thr Trp Gly Thr Thr Pro Ala Asp Leu Ala Ala Lys Tyr Gly
 1               5                  10                  15
His Arg Asp Ile Ala Glu Val Leu Gln Lys Leu Asn
            20                  25

<210> SEQ ID NO 32
<211> LENGTH: 28
<212> TYPE: PRT
<213> ORGANISM: Artificial Sequence
<220> FEATURE:
<223> OTHER INFORMATION: C-terminal capping module
<220> FEATURE:
<221> NAME/KEY: VARIANT
<222> LOCATION: 1
<223> OTHER INFORMATION: Xaa is any naturally occuring amino acid
<220> FEATURE:
<221> NAME/KEY: VARIANT
<222> LOCATION: 3
<223> OTHER INFORMATION: Xaa is any naturally occuring amino acid
<220> FEATURE:
<221> NAME/KEY: VARIANT
<222> LOCATION: 4
```

```
<223> OTHER INFORMATION: Xaa is any naturally occuring amino acid
<220> FEATURE:
<221> NAME/KEY: VARIANT
<222> LOCATION: 6
<223> OTHER INFORMATION: Xaa is any naturally occuring amino acid
<220> FEATURE:
<221> NAME/KEY: VARIANT
<222> LOCATION: 11
<223> OTHER INFORMATION: Xaa is any naturally occuring amino acid
<220> FEATURE:
<221> NAME/KEY: VARIANT
<222> LOCATION: 15
<223> OTHER INFORMATION: Xaa is any naturally occuring amino acid
<220> FEATURE:
<221> NAME/KEY: VARIANT
<222> LOCATION: 19
<223> OTHER INFORMATION: Xaa is any naturally occuring amino acid
<220> FEATURE:
<221> NAME/KEY: VARIANT
<222> LOCATION: 22
<223> OTHER INFORMATION: Xaa is any naturally occuring amino acid
<220> FEATURE:
<221> NAME/KEY: VARIANT
<222> LOCATION: 26
<223> OTHER INFORMATION: Xaa is any naturally occuring amino acid

<400> SEQUENCE: 32

Xaa Asp Xaa Xaa Gly Xaa Thr Pro Ala Asp Xaa Ala Ala Arg Xaa Gly
1               5                   10                  15

His Gln Xaa Ile Ala Xaa Val Leu Gln Xaa Ala Ala
            20                  25

<210> SEQ ID NO 33
<211> LENGTH: 10
<212> TYPE: PRT
<213> ORGANISM: Artificial Sequence
<220> FEATURE:
<223> OTHER INFORMATION: His Tag

<400> SEQUENCE: 33

Met Arg Gly Ser His His His His His His
1               5                   10

<210> SEQ ID NO 34
<211> LENGTH: 124
<212> TYPE: PRT
<213> ORGANISM: Artificial Sequence
<220> FEATURE:
<223> OTHER INFORMATION: Ankyrin repeat domain specific for human serum
      albumin

<400> SEQUENCE: 34

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110
```

His Glu Asp Ile Ala Glu Val Leu Gln Lys Ala Ala
        115                 120

<210> SEQ ID NO 35
<211> LENGTH: 124
<212> TYPE: PRT
<213> ORGANISM: Artificial Sequence
<220> FEATURE:
<223> OTHER INFORMATION: Ankyrin repeat domain specific for human serum
      albumin

<400> SEQUENCE: 35

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Ala Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala
        115                 120

<210> SEQ ID NO 36
<211> LENGTH: 124
<212> TYPE: PRT
<213> ORGANISM: Artificial Sequence
<220> FEATURE:
<223> OTHER INFORMATION: Ankyrin repeat domain specific for human serum
      albumin

<400> SEQUENCE: 36

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Ala Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala
        115                 120

<210> SEQ ID NO 37
<211> LENGTH: 22
<212> TYPE: PRT
<213> ORGANISM: Artificial Sequence
<220> FEATURE:

<223> OTHER INFORMATION: PT linker

<400> SEQUENCE: 37

Gly Ser Pro Thr Pro Thr Pro Thr Thr Pro Thr Pro Thr Pro Thr Thr
1               5                   10                  15

Pro Thr Pro Thr Pro Thr
            20

<210> SEQ ID NO 38
<211> LENGTH: 222
<212> TYPE: PRT
<213> ORGANISM: Artificial Sequence
<220> FEATURE:
<223> OTHER INFORMATION: scCD3eg_Avi-Bio

<400> SEQUENCE: 38

Met Gln Asp Gly Asn Glu Glu Met Gly Gly Ile Thr Gln Thr Pro Tyr
1               5                   10                  15

Lys Val Ser Ile Ser Gly Thr Thr Val Ile Leu Thr Cys Pro Gln Tyr
            20                  25                  30

Pro Gly Ser Glu Ile Leu Trp Gln His Asn Asp Lys Asn Ile Gly Gly
        35                  40                  45

Asp Glu Asp Asp Lys Asn Ile Gly Ser Asp Glu Asp His Leu Ser Leu
    50                  55                  60

Lys Glu Phe Ser Glu Leu Glu Gln Ser Gly Tyr Tyr Val Cys Tyr Pro
65              70                  75                  80

Arg Gly Ser Lys Pro Glu Asp Ala Asn Phe Tyr Leu Tyr Leu Arg Ala
                85                  90                  95

Arg Val Gly Ser Ala Asp Asp Ala Lys Lys Asp Ala Ala Lys Lys Asp
            100                 105                 110

Asp Ala Lys Lys Asp Asp Ala Lys Lys Asp Gly Ser Gln Ser Ile Lys
        115                 120                 125

Gly Asn His Leu Val Lys Val Tyr Asp Tyr Gln Glu Asp Gly Ser Val
    130                 135                 140

Leu Leu Thr Cys Asp Ala Glu Ala Lys Asn Ile Thr Trp Phe Lys Asp
145             150                 155                 160

Gly Lys Met Ile Gly Phe Leu Thr Glu Asp Lys Lys Lys Trp Asn Leu
                165                 170                 175

Gly Ser Asn Ala Lys Asp Pro Arg Gly Met Tyr Gln Cys Lys Gly Ser
            180                 185                 190

Gln Asn Lys Ser Lys Pro Leu Gln Val Tyr Tyr Arg Met Gly Gly Gly
        195                 200                 205

Leu Asn Asp Ile Phe Glu Ala Gln Lys Ile Glu Trp His Glu
    210                 215                 220

<210> SEQ ID NO 39
<211> LENGTH: 272
<212> TYPE: PRT
<213> ORGANISM: Artificial Sequence
<220> FEATURE:
<223> OTHER INFORMATION: DARPin protein 16

<400> SEQUENCE: 39

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu

```
            35                  40                  45
Lys Ile Val Glu Val Leu Leu Lys Ala Gly Ala Asp Val Asn Ala Lys
 50                  55                  60

Asp Phe Ala Gly Lys Thr Pro Leu His Leu Ala Ala Asp Gly His
 65                  70                  75                  80

Leu Glu Ile Val Glu Val Leu Leu Lys Ala Gly Ala Asp Val Asn Ala
                 85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
                115                 120                 125

Pro Thr Pro Thr Thr Pro Thr Pro Thr Thr Pro Thr Pro Thr
130                 135                 140

Pro Thr Gly Ser Asp Leu Gly Gln Lys Leu Leu Glu Ala Ala Trp Ala
145                 150                 155                 160

Gly Gln Asp Asp Glu Val Arg Glu Leu Leu Lys Ala Gly Ala Asp Val
                165                 170                 175

Asn Ala Lys Asp Ser Gln Gly Trp Thr Pro Leu His Thr Ala Ala Gln
                180                 185                 190

Thr Gly His Leu Glu Ile Phe Glu Val Leu Leu Lys Ala Gly Ala Asp
                195                 200                 205

Val Asn Ala Lys Asp Asp Lys Gly Val Thr Pro Leu His Leu Ala Ala
210                 215                 220

Ala Leu Gly His Leu Glu Ile Val Glu Val Leu Leu Lys Ala Gly Ala
225                 230                 235                 240

Asp Val Asn Ala Gln Asp Ser Trp Gly Thr Thr Pro Ala Asp Leu Ala
                245                 250                 255

Ala Lys Tyr Gly His Glu Asp Ile Ala Glu Val Leu Gln Lys Ala Ala
                260                 265                 270

<210> SEQ ID NO 40
<211> LENGTH: 272
<212> TYPE: PRT
<213> ORGANISM: Artificial Sequence
<220> FEATURE:
<223> OTHER INFORMATION: DARPin protein 17

<400> SEQUENCE: 40

Asp Leu Gly Lys Lys Leu Leu Glu Ala Ala Arg Ala Gly Gln Asp Asp
 1               5                  10                  15

Glu Val Arg Glu Leu Leu Lys Ala Gly Ala Asp Val Asn Ala Lys Asp
                 20                  25                  30

Tyr Phe Ser His Thr Pro Leu His Leu Ala Ala Arg Asn Gly His Leu
                 35                  40                  45

Lys Ile Val Glu Val Leu Leu Lys Ala Gly Ala Asp Val Asn Ala Lys
 50                  55                  60

Asp Phe Ala Gly Lys Thr Pro Leu His Leu Ala Ala Asp Gly His
 65                  70                  75                  80

Leu Glu Ile Val Glu Val Leu Leu Lys Ala Gly Ala Asp Val Asn Ala
                 85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
                115                 120                 125

Pro Thr Pro Thr Thr Pro Thr Pro Thr Thr Pro Thr Pro Thr Pro Thr
```

```
                   130                 135                 140
Pro Thr Gly Ser Asp Leu Gly Gln Lys Leu Leu Glu Ala Ala Trp Ala
145                 150                 155                 160

Gly Gln Asp Asp Glu Val Arg Glu Leu Leu Lys Ala Gly Ala Asp Val
                    165                 170                 175

Asn Ala Lys Asn Ser Arg Gly Trp Thr Pro Leu His Thr Ala Ala Gln
                180                 185                 190

Thr Gly His Leu Glu Ile Phe Glu Val Leu Leu Lys Ala Gly Ala Asp
            195                 200                 205

Val Asn Ala Lys Asp Asp Lys Gly Val Thr Pro Leu His Leu Ala Ala
        210                 215                 220

Ala Leu Gly His Leu Glu Ile Val Glu Val Leu Leu Lys Ala Gly Ala
225                 230                 235                 240

Asp Val Asn Ala Gln Asp Ser Trp Gly Thr Thr Pro Ala Asp Leu Ala
                    245                 250                 255

Ala Lys Tyr Gly His Glu Asp Ile Ala Glu Val Leu Gln Lys Ala Ala
                260                 265                 270
```

<210> SEQ ID NO 41
<211> LENGTH: 272
<212> TYPE: PRT
<213> ORGANISM: Artificial Sequence
<220> FEATURE:
<223> OTHER INFORMATION: DARPin protein 18

<400> SEQUENCE: 41

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Thr Pro Thr Pro Thr
130                 135                 140

Pro Thr Gly Ser Asp Leu Gly Gln Lys Leu Leu Glu Ala Ala Trp Ala
145                 150                 155                 160

Gly Gln Asp Asp Glu Val Arg Glu Leu Leu Lys Ala Gly Ala Asp Val
                    165                 170                 175

Asn Ala Lys Asn Ser Arg Gly Trp Thr Pro Leu His Thr Ala Ala Gln
                180                 185                 190

Thr Gly His Leu Glu Ile Phe Glu Val Leu Leu Lys Ala Gly Ala Asp
            195                 200                 205

Val Asn Ala Lys Asn Asp Lys Arg Val Thr Pro Leu His Leu Ala Ala
        210                 215                 220

Ala Leu Gly His Leu Glu Ile Val Glu Val Leu Leu Lys Ala Gly Ala
```

```
                225                 230                 235                 240

Asp Val Asn Ala Arg Asp Ser Trp Gly Thr Thr Pro Ala Asp Leu Ala
                245                 250                 255

Ala Lys Tyr Gly His Gln Asp Ile Ala Glu Val Leu Gln Lys Ala Ala
                260                 265                 270

<210> SEQ ID NO 42
<211> LENGTH: 272
<212> TYPE: PRT
<213> ORGANISM: Artificial Sequence
<220> FEATURE:
<223> OTHER INFORMATION: DARPin protein 19

<400> SEQUENCE: 42

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Pro Thr Pro Thr
    130                 135                 140

Pro Thr Gly Ser Asp Leu Gly Gln Lys Leu Leu Glu Ala Ala Trp Ala
145                 150                 155                 160

Gly Gln Leu Asp Glu Val Arg Ile Leu Leu Lys Ala Gly Ala Asp Val
                165                 170                 175

Asn Ala Lys Asn Ser Arg Gly Trp Thr Pro Leu His Thr Ala Ala Gln
                180                 185                 190

Thr Gly His Leu Glu Ile Phe Glu Val Leu Leu Lys Ala Gly Ala Asp
            195                 200                 205

Val Asn Ala Lys Thr Asn Lys Arg Val Thr Pro Leu His Leu Ala Ala
    210                 215                 220

Ala Leu Gly His Leu Glu Ile Val Glu Val Leu Leu Lys Ala Gly Ala
225                 230                 235                 240

Asp Val Asn Ala Arg Asp Thr Trp Gly Thr Thr Pro Ala Asp Leu Ala
                245                 250                 255

Ala Lys Tyr Gly His Arg Asp Ile Ala Glu Val Leu Gln Lys Ala Ala
                260                 265                 270

<210> SEQ ID NO 43
<211> LENGTH: 417
<212> TYPE: DNA
<213> ORGANISM: Artificial Sequence
<220> FEATURE:
<223> OTHER INFORMATION: Nucleic acid encoding domain of SEQ ID NO 1

<400> SEQUENCE: 43
```

```
atgagaggat cgcatcacca tcaccatcac ggctcagatc tgggtcaaaa gttattggag    60
gcagcttggg ctggacaaga tgacgaagta cgtgaattgt taaaagcggg agcagatgta   120
aacgcaaaag atagtcaagg ttggactccg ttacacacag cagcgcaaac cggccacctg   180
gaaattttcg aggtgttatt gaaggctgga gcagatgtga atgcaaaaga cgacaaaggg   240
gtgactccgc tgcatctggc agcggcgttg gggcacttgg aaatcgttga ggtccttctg   300
aaagcaggcg ctgatgtgaa tgcgcaagac tcctggggaa ccacaccagc ggacctggcg   360
gctaagtacg gccacgaaga tattgctgaa gttctgcaga aggcagcata atgatag     417

<210> SEQ ID NO 44
<211> LENGTH: 417
<212> TYPE: DNA
<213> ORGANISM: Artificial Sequence
<220> FEATURE:
<223> OTHER INFORMATION: Nucleic acid encoding domain of SEQ ID NO 2

<400> SEQUENCE: 44
atgagaggat cgcatcacca tcaccatcac ggctcagatc tgggtcaaaa gttgttggaa    60
gctgcctggg cgggacagga tgatgaggtg cgcgaattac ttaaggcggg agcagacgtg   120
aatgcgaaaa actctcgtgg ctggacacca ctgcacacgg ccgcgcaaac tggtcacctt   180
gaaattttcg aagtgcttct gaaggcaggc gcagatgtaa acgccaagga tgacaaaggg   240
gtaacaccgc ttcatctggc tgctgcactg ggacatcttg agattgtcga agtactgctt   300
aaggcaggtg ctgacgtaaa cgctcaggat tcatggggga ccacaccggc ggacctggcg   360
gctaaatacg gacatgaaga tattgctgaa gttctgcaga aggcagcata atgatag     417

<210> SEQ ID NO 45
<211> LENGTH: 417
<212> TYPE: DNA
<213> ORGANISM: Artificial Sequence
<220> FEATURE:
<223> OTHER INFORMATION: Nucleic acid encoding domain of SEQ ID NO 3

<400> SEQUENCE: 45
atgagaggat cgcatcacca tcaccatcac ggctcagatc tgggtcaaaa gctgttggaa    60
gccgcgtggg cgggtcagga cgatgaagtc cgtgagctgc ttaaagcagg agccgacgtg   120
aacgcgaaga actcacgcgg gtggacgcca cttcacacgg ccgcgcagac aggtcacctt   180
gaaatctttg aggttcttct gaaggcagga gcagacgtta acgccaaaaa cgacaagcgc   240
gtgactccgt tgcaccttgc cgcagctctg gggcatttgg agatcgttga ggtactgttg   300
aaagcgggag cagatgttaa tgctcgcgac agttggggga cgacaccagc agacctggcc   360
gcaaaatacg gacaccaaga cattgctgaa gttctgcaga aggcagcata atgatag     417

<210> SEQ ID NO 46
<211> LENGTH: 417
<212> TYPE: DNA
<213> ORGANISM: Artificial Sequence
<220> FEATURE:
<223> OTHER INFORMATION: Nucleic acid encoding domain of SEQ ID NO 4

<400> SEQUENCE: 46
atgagaggat cgcatcacca tcaccatcac ggctcagatc tgggtcaaaa attgttagag    60
gcagcctggg cgggacagtt agacgaggtt cgtattcttt tgaaagctgg tgcggatgtg   120
aacgcaaaga attctcgtgg atggactccg ttgcacaccg ccgcacagac tgggcacttg   180
gaaatctttg aggttctgtt aaaagcaggg gcagatgtta acgctaaaac taataaacgt   240
```

```
gtcaccccccc ttcacctggc tgcggcttta ggccatttag aaatcgtgga agtattactt    300
aaagccgggg ctgacgttaa cgcccgtgac acttgggga caaccctgc ggatctggcc       360 gccaaatatg gtcaccgcga cattgctgaa gttctgcaga aggcagcata atgatag         417
```

<210> SEQ ID NO 47
<211> LENGTH: 421
<212> TYPE: PRT
<213> ORGANISM: Artificial Sequence
<220> FEATURE:
<223> OTHER INFORMATION: DARPin protein 20

<400> SEQUENCE: 47

| | | | | | | | | | | | | | | |
|---|---|---|---|---|---|---|---|---|---|---|---|---|---|---|
| Asp | Leu | Gly | Lys | Lys | Leu | Leu | Glu | Ala | Ala | Arg | Ala | Gly | Gln | Asp | Asp |
| 1 | | | | 5 | | | | | 10 | | | | | 15 | |
| Glu | Val | Arg | Ile | Leu | Met | Ala | Asn | Gly | Ala | Asp | Val | Asn | Ala | Leu | Asp |
| | | | 20 | | | | | 25 | | | | | 30 | | |
| Trp | Leu | Gly | His | Thr | Pro | Leu | His | Leu | Ala | Ala | Tyr | Glu | Gly | His | Leu |
| | | 35 | | | | | 40 | | | | | 45 | | | |
| Glu | Ile | Val | Glu | Val | Leu | Leu | Lys | Asn | Gly | Ala | Asp | Val | Asn | Ala | Ile |
| | 50 | | | | | 55 | | | | | 60 | | | | |
| Asp | Asp | Asn | Asn | Gly | Phe | Thr | Pro | Leu | His | Leu | Ala | Ala | Ile | Asp | Gly |
| 65 | | | | | 70 | | | | | 75 | | | | | 80 |
| His | Leu | Glu | Ile | Val | Glu | Val | Leu | Leu | Lys | Asn | Gly | Ala | Asp | Val | Asn |
| | | | | 85 | | | | | 90 | | | | | 95 | |
| Ala | Gln | Asp | Lys | Phe | Gly | Lys | Thr | Ala | Phe | Asp | Ile | Ser | Ile | Asp | Asn |
| | | | 100 | | | | | 105 | | | | | 110 | | |
| Gly | Asn | Glu | Asp | Leu | Ala | Glu | Ile | Leu | Gln | Lys | Ala | Ala | Gly | Ser | Pro |
| | | 115 | | | | | 120 | | | | | 125 | | | |
| Thr | Pro | Thr | Pro | Thr | Thr | Pro | Thr | Pro | Thr | Pro | Thr | Thr | Pro | Thr | Pro |
| | 130 | | | | | 135 | | | | | 140 | | | | |
| Thr | Pro | Thr | Gly | Ser | Asp | Leu | Gly | Asp | Lys | Leu | Leu | Leu | Ala | Ala | Thr |
| 145 | | | | | 150 | | | | | 155 | | | | | 160 |
| Ser | Gly | Gln | Asp | Asp | Glu | Val | Arg | Ile | Leu | Leu | Ala | Ala | Gly | Ala | Asp |
| | | | | 165 | | | | | 170 | | | | | 175 | |
| Val | Asn | Ala | Lys | Asp | Tyr | Asp | Gly | Asp | Thr | Pro | Leu | His | Leu | Ala | Ala |
| | | | 180 | | | | | 185 | | | | | 190 | | |
| Asp | Glu | Gly | His | Leu | Glu | Ile | Val | Glu | Val | Leu | Leu | Lys | Ala | Gly | Ala |
| | | 195 | | | | | 200 | | | | | 205 | | | |
| Asp | Val | Asn | Ala | Lys | Asp | Tyr | Ser | Gly | Ser | Thr | Pro | Leu | His | Ala | Ala |
| | 210 | | | | | 215 | | | | | 220 | | | | |
| Ala | Ala | Tyr | Gly | His | Leu | Glu | Ile | Val | Glu | Val | Leu | Leu | Lys | Ala | Gly |
| 225 | | | | | 230 | | | | | 235 | | | | | 240 |
| Ala | Asp | Val | Asn | Ala | Gln | Asp | Val | Phe | Gly | Tyr | Thr | Pro | Ala | Asp | Leu |
| | | | | 245 | | | | | 250 | | | | | 255 | |
| Ala | Ala | Tyr | Val | Gly | His | Glu | Asp | Ile | Ala | Glu | Val | Leu | Gln | Lys | Ala |
| | | | 260 | | | | | 265 | | | | | 270 | | |
| Ala | Gly | Ser | Pro | Thr | Pro | Thr | Pro | Thr | Thr | Pro | Thr | Pro | Thr | Pro | Thr |
| | | 275 | | | | | 280 | | | | | 285 | | | |
| Thr | Pro | Thr | Pro | Thr | Pro | Thr | Gly | Ser | Asp | Leu | Gly | Gln | Lys | Leu | Leu |
| | 290 | | | | | 295 | | | | | 300 | | | | |
| Glu | Ala | Ala | Trp | Ala | Gly | Gln | Asp | Asp | Glu | Val | Arg | Ile | Leu | Leu | Ala |
| 305 | | | | | 310 | | | | | 315 | | | | | 320 |
| Ala | Gly | Ala | Asp | Val | Asn | Ala | Lys | Asn | Ser | Arg | Gly | Trp | Thr | Pro | Leu |
| | | | | 325 | | | | | 330 | | | | | 335 | |

```
His Thr Ala Ala Gln Thr Gly His Leu Glu Ile Phe Glu Val Leu Leu
                340                 345                 350

Lys Ala Gly Ala Asp Val Asn Ala Lys Asn Asp Lys Arg Val Thr Pro
                355                 360                 365

Leu His Leu Ala Ala Leu Gly His Leu Glu Ile Val Glu Val Leu
    370                 375                 380

Leu Lys Ala Gly Ala Asp Val Asn Ala Arg Asp Ser Trp Gly Thr Thr
385                 390                 395                 400

Pro Ala Asp Leu Ala Ala Lys Tyr Gly His Gly Asp Ile Ala Glu Val
                405                 410                 415

Leu Gln Lys Leu Ala
                420

<210> SEQ ID NO 48
<211> LENGTH: 421
<212> TYPE: PRT
<213> ORGANISM: Artificial Sequence
<220> FEATURE:
<223> OTHER INFORMATION: DARPin protein 21

<400> SEQUENCE: 48

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Leu Asp
                20                  25                  30

Trp Leu Gly His Thr Pro Leu His Leu Ala Ala Tyr Glu Gly His Leu
                35                  40                  45

Glu Ile Val Glu Val Leu Leu Lys Asn Gly Ala Asp Val Asn Ala Ile
    50                  55                  60

Asp Asp Asn Asn Gly Phe Thr Pro Leu His Leu Ala Ala Ile Asp Gly
65                  70                  75                  80

His Leu Glu Ile Val Glu Val Leu Leu Lys Asn Gly Ala Asp Val Asn
                85                  90                  95

Ala Gln Asp Lys Phe Gly Lys Thr Ala Phe Asp Ile Ser Ile Asp Asn
                100                 105                 110

Gly Asn Glu Asp Leu Ala Glu Ile Leu Gln Lys Ala Ala Gly Ser Pro
            115                 120                 125

Thr Pro Thr Pro Thr Thr Pro Thr Pro Thr Pro Thr Thr Pro Thr Pro
        130                 135                 140

Thr Pro Thr Gly Ser Asp Leu Gly Lys Lys Leu Leu Glu Ala Ala Arg
145                 150                 155                 160

Ala Gly Gln Asp Asp Glu Val Arg Glu Leu Leu Lys Ala Gly Ala Asp
                165                 170                 175

Val Asn Ala Lys Asp Lys Asp Gly Tyr Thr Pro Leu His Leu Ala Ala
                180                 185                 190

Arg Glu Gly His Leu Glu Ile Val Glu Val Leu Leu Lys Ala Gly Ala
            195                 200                 205

Asp Val Asn Ala Lys Asp Lys Asp Gly Tyr Thr Pro Leu His Leu Ala
        210                 215                 220

Ala Arg Glu Gly His Leu Glu Ile Val Glu Val Leu Leu Lys Ala Gly
225                 230                 235                 240

Ala Asp Val Asn Ala Gln Asp Lys Ser Gly Lys Thr Pro Ala Asp Leu
                245                 250                 255

Ala Ala Asp Ala Gly His Glu Asp Ile Ala Glu Val Leu Gln Lys Ala
                260                 265                 270
```

```
Ala Gly Ser Pro Thr Pro Thr Pro Thr Thr Pro Thr Pro Thr
        275                 280                 285

Thr Pro Thr Pro Thr Pro Thr Gly Ser Asp Leu Gly Gln Lys Leu Leu
290                 295                 300

Glu Ala Ala Trp Ala Gly Gln Asp Asp Glu Val Arg Ile Leu Leu Ala
305                 310                 315                 320

Ala Gly Ala Asp Val Asn Ala Lys Asn Ser Arg Gly Trp Thr Pro Leu
            325                 330                 335

His Thr Ala Ala Gln Thr Gly His Leu Glu Ile Phe Glu Val Leu Leu
        340                 345                 350

Lys Ala Gly Ala Asp Val Asn Ala Lys Asn Asp Lys Arg Val Thr Pro
            355                 360                 365

Leu His Leu Ala Ala Ala Leu Gly His Leu Glu Ile Val Glu Val Leu
        370                 375                 380

Leu Lys Ala Gly Ala Asp Val Asn Ala Arg Asp Ser Trp Gly Thr Thr
385                 390                 395                 400

Pro Ala Asp Leu Ala Ala Lys Tyr Gly His Gly Asp Ile Ala Glu Val
            405                 410                 415

Leu Gln Lys Leu Ala
            420

<210> SEQ ID NO 49
<211> LENGTH: 420
<212> TYPE: PRT
<213> ORGANISM: Artificial Sequence
<220> FEATURE:
<223> OTHER INFORMATION: DARPin protein 22

<400> SEQUENCE: 49

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Lys Asp Gly Tyr Thr Pro Leu His Leu Ala Ala Arg Glu Gly His Leu
        35                  40                  45

Glu Ile Val Glu Val Leu Leu Lys Ala Gly Ala Asp Val Asn Ala Lys
50                  55                  60

Asp Lys Asp Gly Tyr Thr Pro Leu His Leu Ala Ala Arg Glu Gly His
65                  70                  75                  80

Leu Glu Ile Val Glu Val Leu Leu Lys Ala Gly Ala Asp Val Asn Ala
                85                  90                  95

Gln Asp Lys Ser Gly Lys Thr Pro Ala Asp Leu Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Thr Pro Thr Pro Thr Pro Thr
        130                 135                 140

Pro Thr Gly Ser Asp Leu Gly Asp Lys Leu Leu Leu Ala Ala Thr Ser
145                 150                 155                 160

Gly Gln Asp Asp Glu Val Arg Ile Leu Leu Ala Ala Gly Ala Asp Val
                165                 170                 175

Asn Ala Lys Asp Tyr Asp Gly Asp Thr Pro Leu His Leu Ala Ala Asp
            180                 185                 190

Glu Gly His Leu Glu Ile Val Glu Val Leu Leu Lys Ala Gly Ala Asp
        195                 200                 205
```

```
Val Asn Ala Lys Asp Tyr Ser Gly Ser Thr Pro Leu His Ala Ala Ala
    210                 215                 220

Ala Tyr Gly His Leu Glu Ile Val Glu Val Leu Leu Lys Ala Gly Ala
225                 230                 235                 240

Asp Val Asn Ala Gln Asp Val Phe Gly Tyr Thr Pro Ala Asp Leu Ala
                245                 250                 255

Ala Tyr Val Gly His Glu Asp Ile Ala Glu Val Leu Gln Lys Ala Ala
            260                 265                 270

Gly Ser Pro Thr Pro Thr Pro Thr Pro Thr Pro Thr Pro Thr Pro Thr
        275                 280                 285

Pro Thr Pro Thr Pro Thr Gly Ser Asp Leu Gly Gln Lys Leu Leu Glu
    290                 295                 300

Ala Ala Trp Ala Gly Gln Asp Asp Glu Val Arg Ile Leu Leu Ala Ala
305                 310                 315                 320

Gly Ala Asp Val Asn Ala Lys Asn Ser Arg Gly Trp Thr Pro Leu His
                325                 330                 335

Thr Ala Ala Gln Thr Gly His Leu Glu Ile Phe Glu Val Leu Leu Lys
            340                 345                 350

Ala Gly Ala Asp Val Asn Ala Lys Asn Asp Lys Arg Val Thr Pro Leu
                355                 360                 365

His Leu Ala Ala Ala Leu Gly His Leu Glu Ile Val Glu Val Leu Leu
370                 375                 380

Lys Ala Gly Ala Asp Val Asn Ala Arg Asp Ser Trp Gly Thr Thr Pro
385                 390                 395                 400

Ala Asp Leu Ala Ala Lys Tyr Gly His Gly Asp Ile Ala Glu Val Leu
                405                 410                 415

Gln Lys Leu Ala
        420

<210> SEQ ID NO 50
<211> LENGTH: 272
<212> TYPE: PRT
<213> ORGANISM: Artificial Sequence
<220> FEATURE:
<223> OTHER INFORMATION: DARPin protein 23

<400> SEQUENCE: 50

Asp Leu Gly Asp Lys Leu Leu Leu Ala Ala Thr Ser Gly Gln Asp Asp
1               5                   10                  15

Glu Val Arg Ile Leu Leu Ala Ala Gly Ala Asp Val Asn Ala Lys Asp
                20                  25                  30

Tyr Asp Gly Asp Thr Pro Leu His Leu Ala Ala Asp Glu Gly His Leu
            35                  40                  45

Glu Ile Val Glu Val Leu Leu Lys Ala Gly Ala Asp Val Asn Ala Lys
50                  55                  60

Asp Tyr Ser Gly Ser Thr Pro Leu His Ala Ala Ala Tyr Gly His
65                  70                  75                  80

Leu Glu Ile Val Glu Val Leu Leu Lys Ala Gly Ala Asp Val Asn Ala
                85                  90                  95

Gln Asp Val Phe Gly Tyr Thr Pro Ala Asp Leu Ala Ala Tyr Val Gly
            100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Thr Pro Thr Pro Thr
130                 135                 140
```

```
Pro Thr Gly Ser Asp Leu Gly Gln Lys Leu Leu Glu Ala Ala Trp Ala
145                 150                 155                 160

Gly Gln Asp Asp Glu Val Arg Glu Leu Leu Lys Ala Gly Ala Asp Val
            165                 170                 175

Asn Ala Lys Asn Ser Arg Gly Trp Thr Pro Leu His Thr Ala Ala Gln
        180                 185                 190

Thr Gly His Leu Glu Ile Phe Glu Val Leu Leu Lys Ala Gly Ala Asp
            195                 200                 205

Val Asn Ala Lys Asp Asp Lys Gly Val Thr Pro Leu His Leu Ala Ala
    210                 215                 220

Ala Leu Gly His Leu Glu Ile Val Glu Val Leu Leu Lys Ala Gly Ala
225                 230                 235                 240

Asp Val Asn Ala Gln Asp Ser Trp Gly Thr Thr Pro Ala Asp Leu Ala
                245                 250                 255

Ala Lys Tyr Gly His Glu Asp Ile Ala Glu Val Leu Gln Lys Ala Ala
            260                 265                 270

<210> SEQ ID NO 51
<211> LENGTH: 273
<212> TYPE: PRT
<213> ORGANISM: Artificial Sequence
<220> FEATURE:
<223> OTHER INFORMATION: DARPin protein 24

<400> SEQUENCE: 51

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Leu Asp
            20                  25                  30

Trp Leu Gly His Thr Pro Leu His Leu Ala Ala Tyr Glu Gly His Leu
            35                  40                  45

Glu Ile Val Glu Val Leu Leu Lys Asn Gly Ala Asp Val Asn Ala Ile
        50                  55                  60

Asp Asp Asn Asn Gly Phe Thr Pro Leu His Leu Ala Ala Ile Asp Gly
65                  70                  75                  80

His Leu Glu Ile Val Glu Val Leu Leu Lys Asn Gly Ala Asp Val Asn
                85                  90                  95

Ala Gln Asp Lys Phe Gly Lys Thr Ala Phe Asp Ile Ser Ile Asp Asn
            100                 105                 110

Gly Asn Glu Asp Leu Ala Glu Ile Leu Gln Lys Ala Ala Gly Ser Pro
        115                 120                 125

Thr Pro Thr Pro Thr Thr Pro Thr Pro Thr Pro Thr Thr Pro Thr Pro
    130                 135                 140

Thr Pro Thr Gly Ser Asp Leu Gly Gln Lys Leu Leu Glu Ala Ala Trp
145                 150                 155                 160

Ala Gly Gln Asp Asp Glu Val Arg Glu Leu Leu Lys Ala Gly Ala Asp
                165                 170                 175

Val Asn Ala Lys Asn Ser Arg Gly Trp Thr Pro Leu His Thr Ala Ala
            180                 185                 190

Gln Thr Gly His Leu Glu Ile Phe Glu Val Leu Leu Lys Ala Gly Ala
        195                 200                 205

Asp Val Asn Ala Lys Asp Asp Lys Gly Val Thr Pro Leu His Leu Ala
    210                 215                 220

Ala Ala Leu Gly His Leu Glu Ile Val Glu Val Leu Leu Lys Ala Gly
225                 230                 235                 240
```

Ala Asp Val Asn Ala Gln Asp Ser Trp Gly Thr Thr Pro Ala Asp Leu
            245                 250                 255

Ala Ala Lys Tyr Gly His Glu Asp Ile Ala Glu Val Leu Gln Lys Ala
        260                 265                 270

Ala

<210> SEQ ID NO 52
<211> LENGTH: 1308
<212> TYPE: DNA
<213> ORGANISM: Artificial Sequence
<220> FEATURE:
<223> OTHER INFORMATION: Nucleic acid encoding protein of SEQ ID NO 7

<400> SEQUENCE: 52

```
atgagaggat cgcatcacca tcaccatcac ggatccgacc tgggtaaaaa gctgcttgag    60
gctgcccgtg caggtcaaga tgacgaagtc cgcatcctta tggcaaatgg tgccgatgta   120
aatgcactgg actggcttgg ccacacaccc cttcatctgg cagcctacga ggggcacttg   180
gagattgtcg aagttttgtt aaaaaacggc gcggatgtaa acgcgattga tgacaacaac   240
ggatttactc cacttcactt ggcggctatc gacggtcact tagaaattgt agaggtgttg   300
ttgaagaacg gggcagacgt taatgcacaa gataagttcg gcaaaacggc attcgatatc   360
tccattgata atggtaatga agatttagct gaaatcctgc agaaggcagc aggctcgccg   420
actccgaccc cgaccacccc aactccaaca ccgaccaccc cgaccctac cccaacagga   480
tccgacctgg gtgacaaact gctgctggct gctacttctg gtcaggacga cgaagttcgt   540
atcctgctgg ctgctggcgc cgacgttaat gctaaagact acgacggtga cactccgctg   600
cacctggctg ctgacgaagg tcacctggaa atcgttgaag ttctgctgaa ggctggtgct   660
gacgttaatg ctaaagacta ctctggttct actccgctgc acgctgctgc tgcttacggt   720
cacctggaaa tcgttgaagt tctgctgaag gctggtgctg acgttaacgc tcaggacgtt   780
tcggttaca ctccggctga tctggctgct tacgttggtc acgaggatat cgctgaagtt   840
ctgcagaagg ctgcggggag tccaaccccg acgccaacca cacccactcc tacgcctaca   900
actccaactc cgacgcctac cggatcagat ctgggtcaaa agttattgga ggcagcttgg   960
gctggacaag atgacgaagt acgtgaattg ttaaaagcgg agcagatgt aaacgcaaaa  1020
gatagtcaag gttggactcc gttacacaca gcagcgcaaa ccggccacct ggaaattttc  1080
gaggtgttat tgaaggctgg agcagatgtg aatgcaaaag acgacaaagg ggtgactccg  1140
ctgcatctgg cagcggcgtt ggggcacttg gaaatcgttg aggtccttct gaaagcaggc  1200
gctgatgtga atgcgcaaga ctcctgggga accacaccag cggacctggc ggctaagtac  1260
ggccacgaaa atattgctga agttctgcag aaggcagcat aatgatag               1308
```

<210> SEQ ID NO 53
<211> LENGTH: 1308
<212> TYPE: DNA
<213> ORGANISM: Artificial Sequence
<220> FEATURE:
<223> OTHER INFORMATION: Nucleic acid encoding protein of SEQ ID NO 8

<400> SEQUENCE: 53

```
atgagaggat cgcatcacca tcaccatcac ggatccgacc tgggtaaaaa gctgcttgag    60
gctgcccgtg caggtcaaga tgacgaagtc cgcatcctta tggcaaatgg tgccgatgta   120
aatgcactgg actggcttgg ccacacaccc cttcatctgg cagcctacga ggggcacttg   180
```

```
gagattgtcg aagttttgtt aaaaaacggc gcggatgtaa acgcgattga tgacaacaac    240
ggatttactc cacttcactt ggcggctatc gacggtcact tagaaattgt agaggtgttg    300
ttgaagaacg gggcagacgt taatgcacaa gataagttcg gcaaaacggc attcgatatc    360
tccattgata atggtaatga agatttagct gaaatcctgc agaaggcagc aggctcgccg    420
actccgaccc cgaccacccc aactccaaca ccgaccaccc cgacccctac cccaacagga    480
tccgacctgg gtgacaaact gctgctggct gctacttctg gtcaggacga cgaagttcgt    540
atcctgctgg ctgctggcgc cgacgttaat gctaaagact acgacggtga cactccgctg    600
cacctggctg ctgacgaagg tcacctggaa atcgttgaag ttctgctgaa ggctggtgct    660
gacgttaatg ctaaagacta ctctggttct actccgctgc acgctgctgc tgcttacggt    720
cacctggaaa tcgttgaagt tctgctgaag gctggtgctg acgttaacgc tcaggacgtt    780
ttcggttaca ctccggctga tctggctgct tacgttggtc acgaggatat cgctgaagtt    840
ctgcagaagg ctgcggggag tccaaccccg acgccaacca cacccactcc tacgcctaca    900
actccaactc cgacgcctac cggatcagat ctgggtcaaa agttgttgga agctgcctgg    960
gcgggacagg atgatgaggt gcgcgaatta cttaaggcgg gagcagacgt gaatgcgaaa   1020
aactctcgtg gctggacacc actgcacacg gccgcgcaaa ctggtcacct tgaaatttc    1080 gaagtgcttc tgaaggcagg cgcagatgta acgccaagg atgacaaagg ggtaacaccg    1140
cttcatctgg ctgctgcact gggacatctt gagattgtcg aagtactgct taaggcaggt    1200
gctgacgtaa acgctcagga ttcatggggg accacaccgg cggacctggc ggctaaatac    1260
ggacatgaag atattgctga agttctgcag aaggcagcat aatgatag                 1308
```

<210> SEQ ID NO 54
<211> LENGTH: 1308
<212> TYPE: DNA
<213> ORGANISM: Artificial Sequence
<220> FEATURE:
<223> OTHER INFORMATION: Nucleic acid encoding protein of SEQ ID NO 9

<400> SEQUENCE: 54

```
atgagaggat cgcatcacca tcaccatcac ggatccgacc tgggtaaaaa gctgcttgag     60
gctgcccgtg caggtcaaga tgacgaagtc cgcatcctta tggcaaatgg tgccgatgta    120
aatgcactgg actggcttgg ccacacaccc cttcatctgg cagcctacga ggggcacttg    180
gagattgtcg aagttttgtt aaaaaacggc gcggatgtaa acgcgattga tgacaacaac    240
ggatttactc cacttcactt ggcggctatc gacggtcact tagaaattgt agaggtgttg    300
ttgaagaacg gggcagacgt taatgcacaa gataagttcg gcaaaacggc attcgatatc    360
tccattgata atggtaatga agatttagct gaaatcctgc agaaggcagc aggctcgccg    420
actccgaccc cgaccacccc aactccaaca ccgaccaccc cgacccctac cccaacagga    480
tccgacctgg gtgacaaact gctgctggct gctacttctg gtcaggacga cgaagttcgt    540
atcctgctgg ctgctggcgc cgacgttaat gctaaagact acgacggtga cactccgctg    600
cacctggctg ctgacgaagg tcacctggaa atcgttgaag ttctgctgaa ggctggtgct    660
gacgttaatg ctaaagacta ctctggttct actccgctgc acgctgctgc tgcttacggt    720
cacctggaaa tcgttgaagt tctgctgaag gctggtgctg acgttaacgc tcaggacgtt    780
ttcggttaca ctccggctga tctggctgct tacgttggtc acgaggatat cgctgaagtt    840
ctgcagaagg ctgcggggag tccaaccccg acgccaacca cacccactcc tacgcctaca    900
actccaactc cgacgcctac cggatcagat ctgggtcaaa agctgttgga agccgcgtgg    960
```

-continued

```
gcgggtcagg acgatgaagt ccgtgagctg cttaaagcag gagccgacgt gaacgcgaag      1020
aactcacgcg ggtggacgcc acttcacacg gccgcgcaga caggtcacct tgaaatcttt      1080
gaggttcttc tgaaggcagg agcagacgtt aacgccaaaa acgacaagcg cgtgactccg      1140
ttgcaccttg ccgcagctct ggggcatttg agatcgttg aggtactgtt gaaagcggga       1200
gcagatgtta atgctcgcga cagttggggg acgacaccag cagacctggc cgcaaaatac      1260
ggacaccaag acattgctga agttctgcag aaggcagcat aatgatag                  1308
```

<210> SEQ ID NO 55
<211> LENGTH: 1308
<212> TYPE: DNA
<213> ORGANISM: Artificial Sequence
<220> FEATURE:
<223> OTHER INFORMATION: Nucleic acid encoding protein of SEQ ID NO 10

<400> SEQUENCE: 55

```
atgagaggat cgcatcacca tcaccatcac ggatccgacc tgggtaaaaa gctgcttgag       60
gctgcccgtg caggtcaaga tgacgaagtc cgcatcctta tggcaaatgg tgccgatgta      120
aatgcactgg actggcttgg ccacacaccc cttcatctgg cagcctacga ggggcacttg      180
gagattgtcg aagttttgtt aaaaaacggc gcggatgtaa acgcgattga tgacaacaac      240
ggatttactc cacttcactt ggcggctatc gacggtcact tagaaattgt agaggtgttg      300
ttgaagaacg gggcagacgt taatgcacaa gataagttcg gcaaaacggc attcgatatc      360
tccattgata atggtaatga agatttagct gaaatcctgc agaaggcagc aggctcgccg      420
actccgaccc cgaccacccc aactccaaca ccgaccaccc cgacccctac cccaacagga      480
tccgacctgg gtgacaaaact gctgctggct gctacttctg gtcaggacga cgaagttcgt      540
atcctgctgg ctgctggcgc cgacgttaat gctaaagact acgacggtga cactccgctg      600
cacctggctg ctgacgaagg tcacctggaa atcgttgaag ttctgctgaa ggctggtgct      660
gacgttaatg ctaaagacta ctctggttct actccgctgc acgctgctgc tgcttacggt      720
cacctggaaa tcgttgaagt tctgctgaag gctggtgctg acgttaacgc tcaggacgtt      780
ttcggttaca ctccggctga tctggctgct tacgttggtc acgaggatat cgctgaagtt      840
ctgcagaagg ctgcggggag tccaaccccg acgccaacca cacccactcc tacgcctaca      900
actccaactc cgacgcctac cggatcagat ctgggtcaaa aattgttaga ggcagcctgg      960
gcgggacagt tagacgaggt tcgtattctt ttgaaagctg gtgcggatgt gaacgcaaag     1020
aattctcgtg gatggactcc gttgcacacc gccgcacaga ctgggcactt ggaaatcttt     1080
gaggttctgt taaaagcagg ggcagatgtt aacgctaaaa ctaataaacg tgtcaccccc     1140
cttcacctgg ctgcggcttt aggccattta gaaatcgtgg aagtattact aaagccggg      1200 gctgacgtta acgccgtga cacttggggg acaaccctg cggatctggc cgccaaatat      1260
ggtcaccgcg acattgctga agttctgcag aaggcagcat aatgatag                 1308
```

<210> SEQ ID NO 56
<211> LENGTH: 272
<212> TYPE: PRT
<213> ORGANISM: Artificial Sequence
<220> FEATURE:
<223> OTHER INFORMATION: DARPin protein 25

<400> SEQUENCE: 56

```
Asp Leu Gly Asp Lys Leu Leu Leu Ala Ala Thr Ser Gly Gln Asp Asp
1               5                   10                  15
```

```
Glu Val Arg Ile Leu Ala Ala Gly Ala Asp Val Asn Ala Lys Asp
            20                  25                  30

Tyr Asp Gly Asp Thr Pro Leu His Leu Ala Ala Asp Glu Gly His Leu
        35                  40                  45

Glu Ile Val Glu Val Leu Leu Lys Ala Gly Ala Asp Val Asn Ala Lys
 50                  55                  60

Asp Tyr Ser Gly Ser Thr Pro Leu His Ala Ala Ala Tyr Gly His
 65                  70                  75                  80

Leu Glu Ile Val Glu Val Leu Leu Lys Ala Gly Ala Asp Val Asn Ala
                85                  90                  95

Gln Asp Val Phe Gly Tyr Thr Pro Ala Asp Leu Ala Ala Tyr Val Gly
            100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Thr Pro Thr Pro Thr
 130                 135                 140

Pro Thr Gly Ser Asp Leu Gly Gln Lys Leu Leu Glu Ala Ala Trp Ala
 145                 150                 155                 160

Gly Gln Asp Asp Glu Val Arg Ile Leu Leu Ala Ala Gly Ala Asp Val
            165                 170                 175

Asn Ala Lys Asn Ser Arg Gly Trp Thr Pro Leu His Thr Ala Ala Gln
            180                 185                 190

Thr Gly His Leu Glu Ile Phe Glu Val Leu Leu Lys Ala Gly Ala Asp
            195                 200                 205

Val Asn Ala Lys Asn Asp Lys Arg Val Thr Pro Leu His Leu Ala Ala
            210                 215                 220

Ala Leu Gly His Leu Glu Ile Val Glu Val Leu Leu Lys Ala Gly Ala
225                 230                 235                 240

Asp Val Asn Ala Arg Asp Ser Trp Gly Thr Thr Pro Ala Asp Leu Ala
            245                 250                 255

Ala Lys Tyr Gly His Gly Asp Ile Ala Glu Val Leu Gln Lys Leu Asn
            260                 265                 270

<210> SEQ ID NO 57
<211> LENGTH: 273
<212> TYPE: PRT
<213> ORGANISM: Artificial Sequence
<220> FEATURE:
<223> OTHER INFORMATION: DARPin protein 26

<400> SEQUENCE: 57

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Leu Asp
            20                  25                  30

Trp Leu Gly His Thr Pro Leu His Leu Ala Ala Tyr Glu Gly His Leu
        35                  40                  45

Glu Ile Val Glu Val Leu Leu Lys Asn Gly Ala Asp Val Asn Ala Ile
 50                  55                  60

Asp Asp Asn Asn Gly Phe Thr Pro Leu His Leu Ala Ala Ile Asp Gly
 65                  70                  75                  80

His Leu Glu Ile Val Glu Val Leu Leu Lys Asn Gly Ala Asp Val Asn
                85                  90                  95

Ala Gln Asp Lys Phe Gly Lys Thr Ala Phe Asp Ile Ser Ile Asp Asn
            100                 105                 110
```

-continued

Gly Asn Glu Asp Leu Ala Glu Ile Leu Gln Lys Ala Ala Gly Ser Pro
            115                 120                 125

Thr Pro Thr Pro Thr Thr Pro Thr Pro Thr Thr Pro Thr Pro
130                 135                 140

Thr Pro Thr Gly Ser Asp Leu Gly Gln Lys Leu Leu Glu Ala Ala Trp
145                 150                 155                 160

Ala Gly Gln Asp Asp Glu Val Arg Ile Leu Ala Ala Gly Ala Asp
            165                 170                 175

Val Asn Ala Lys Asn Ser Arg Gly Trp Thr Pro Leu His Thr Ala Ala
            180                 185                 190

Gln Thr Gly His Leu Glu Ile Phe Glu Val Leu Leu Lys Ala Gly Ala
            195                 200                 205

Asp Val Asn Ala Lys Asn Asp Lys Arg Val Thr Pro Leu His Leu Ala
            210                 215                 220

Ala Ala Leu Gly His Leu Glu Ile Val Glu Val Leu Leu Lys Ala Gly
225                 230                 235                 240

Ala Asp Val Asn Ala Arg Asp Ser Trp Gly Thr Thr Pro Ala Asp Leu
            245                 250                 255

Ala Ala Lys Tyr Gly His Gly Asp Ile Ala Glu Val Leu Gln Lys Leu
            260                 265                 270

Asn

<210> SEQ ID NO 58
<211> LENGTH: 421
<212> TYPE: PRT
<213> ORGANISM: Artificial Sequence
<220> FEATURE:
<223> OTHER INFORMATION: DARPin protein 27

<400> SEQUENCE: 58

Asp Leu Gly Lys Lys Leu Leu Glu Ala Ala Leu Glu Gly Gln Leu Asp
1               5                   10                  15

Glu Val Arg Glu Leu Leu Lys Ala Gly Ala Asp Val Asn Ala Lys Asp
                20                  25                  30

Gln Glu Gly Tyr Thr Pro Leu His Leu Ala Ala Ala Leu Gly His Leu
            35                  40                  45

Glu Ile Val Glu Val Leu Leu Lys Ala Gly Ala Asp Val Asn Ala Lys
50                  55                  60

Asp Ser Ile Gly Arg Thr Pro Leu His Leu Ala Ala Tyr Lys Gly His
65                  70                  75                  80

Leu Glu Ile Val Glu Val Leu Leu Lys Ala Gly Ala Asp Val Asn Ala
                85                  90                  95

Gln Asp Leu Leu Gly Glu Thr Pro Ala Asp Leu Ala Ala Glu Gln Gly
            100                 105                 110

His Gln Asp Ile Ala Glu Val Leu Gln Lys Ala Ala Gly Ser Pro Thr
            115                 120                 125

Pro Thr Pro Thr Thr Pro Thr Pro Thr Thr Pro Thr Pro Thr
        130                 135                 140

Pro Thr Gly Ser Asp Leu Gly Val Lys Leu Leu Leu Ala Ala Ser Arg
145                 150                 155                 160

Gly Gln Leu Asp Glu Val Arg Ile Leu Leu Lys Ala Gly Ala Asp Val
            165                 170                 175

Asn Ala Lys Asp Ile Asp Glu Gly Tyr Thr Pro Leu His Ile Ala Ala
            180                 185                 190

```
Tyr Tyr Gly His Leu Glu Ile Val Glu Val Leu Leu Lys Ala Gly Ala
            195                 200                 205

Asp Val Asn Ala Lys Asp Arg Tyr Gly Lys Thr Pro Leu His Leu Ala
210                 215                 220

Ala Ile Ser Gly His Leu Glu Ile Val Glu Val Leu Leu Lys Ala Gly
225                 230                 235                 240

Ala Asp Val Asn Ala Gln Asp Lys Gly Asp Thr Pro Ala Asp Leu
            245                 250                 255

Ala Ala Asp Tyr Gly His Gln Asp Ile Ala Glu Val Leu Gln Lys Ala
            260                 265                 270

Ala Gly Ser Pro Thr Pro Thr Pro Thr Thr Pro Thr Pro Thr Pro Thr
            275                 280                 285

Thr Pro Thr Pro Thr Pro Thr Gly Ser Asp Leu Gly Gln Lys Leu Leu
            290                 295                 300

Glu Ala Ala Trp Ala Gly Gln Asp Asp Glu Val Arg Glu Leu Leu Lys
305                 310                 315                 320

Ala Gly Ala Asp Val Asn Ala Lys Asn Ser Arg Gly Trp Thr Pro Leu
            325                 330                 335

His Thr Ala Ala Gln Thr Gly His Leu Glu Ile Phe Glu Val Leu Leu
            340                 345                 350

Lys Ala Gly Ala Asp Val Asn Ala Lys Asp Lys Gly Val Thr Pro
355                 360                 365

Leu His Leu Ala Ala Ala Leu Gly His Leu Glu Ile Val Glu Val Leu
            370                 375                 380

Leu Lys Ala Gly Ala Asp Val Asn Ala Gln Asp Ser Trp Gly Thr Thr
385                 390                 395                 400

Pro Ala Asp Leu Ala Ala Lys Tyr Gly His Glu Asp Ile Ala Glu Val
            405                 410                 415

Leu Gln Lys Ala Ala
            420

<210> SEQ ID NO 59
<211> LENGTH: 421
<212> TYPE: PRT
<213> ORGANISM: Artificial Sequence
<220> FEATURE:
<223> OTHER INFORMATION: DARPin protein 28

<400> SEQUENCE: 59

Asp Leu Gly Tyr Lys Leu Leu Gln Ala Ala Tyr Asp Gly Gln Leu Asp
1               5                   10                  15

Glu Val Arg Ile Leu Leu Lys Ala Gly Ala Asp Val Asn Ala Lys Asp
            20                  25                  30

Ser Arg Gly Gln Thr Pro Leu His Tyr Ala Ala Ser Ile Gly His Leu
        35                  40                  45

Glu Ile Val Glu Val Leu Leu Lys Ala Gly Ala Asp Val Asn Ala Lys
    50                  55                  60

Asp Asp His Gly Trp Thr Pro Leu His Leu Ala Ala Trp Ser Gly His
65                  70                  75                  80

Leu Glu Ile Val Glu Val Leu Leu Lys Ala Gly Ala Asp Val Asn Ala
                85                  90                  95

Gln Asp Gln Glu Gly Thr Thr Pro Ala Asp Leu Ala Ala Val Gln Gly
            100                 105                 110

His Gln Asp Ile Ala Glu Val Leu Gln Lys Ala Ala Gly Ser Pro Thr
        115                 120                 125
```

Pro Thr Pro Thr Thr Pro Thr Pro Thr Thr Pro Thr Pro Thr
            130                 135                 140

Pro Thr Gly Ser Asp Leu Gly Trp Lys Leu Leu Leu Ala Ala Ser Arg
145                 150                 155                 160

Gly Gln Asp Asp Glu Val Arg Ile Leu Leu Ala Ala Gly Ala Asp Val
                165                 170                 175

Asn Ala Lys Asp Ile Asp Glu Gly Tyr Thr Pro Leu His Ile Ala Ala
            180                 185                 190

Tyr Tyr Gly His Leu Glu Ile Val Glu Val Leu Leu Lys Ala Gly Ala
                195                 200                 205

Asp Val Asn Ala Lys Asp Arg Tyr Gly Lys Thr Pro Leu His Leu Ala
210                 215                 220

Ala Ile Ser Gly His Glu Asp Ile Ala Glu Val Leu Leu Lys Ala Gly
225                 230                 235                 240

Ala Asp Val Asn Ala Gln Asp Lys Gly Asp Thr Pro Ala Asp Leu
                245                 250                 255

Ala Ala Asp Tyr Gly His Glu Asp Ile Ala Glu Val Leu Gln Lys Ala
            260                 265                 270

Ala Gly Ser Pro Thr Pro Thr Pro Thr Thr Pro Thr Pro Thr Pro Thr
            275                 280                 285

Thr Pro Thr Pro Thr Pro Thr Gly Ser Asp Leu Gly Gln Lys Leu Leu
290                 295                 300

Glu Ala Ala Trp Ala Gly Gln Asp Asp Glu Val Arg Glu Leu Leu Lys
305                 310                 315                 320

Ala Gly Ala Asp Val Asn Ala Lys Asn Ser Arg Gly Trp Thr Pro Leu
                325                 330                 335

His Thr Ala Ala Gln Thr Gly His Leu Glu Ile Phe Glu Val Leu Leu
            340                 345                 350

Lys Ala Gly Ala Asp Val Asn Ala Lys Asp Asp Lys Gly Val Thr Pro
            355                 360                 365

Leu His Leu Ala Ala Ala Leu Gly His Leu Glu Ile Val Glu Val Leu
            370                 375                 380

Leu Lys Ala Gly Ala Asp Val Asn Ala Gln Asp Ser Trp Gly Thr Thr
385                 390                 395                 400

Pro Ala Asp Leu Ala Ala Lys Tyr Gly His Glu Asp Ile Ala Glu Val
                405                 410                 415

Leu Gln Lys Ala Ala
            420

<210> SEQ ID NO 60
<211> LENGTH: 421
<212> TYPE: PRT
<213> ORGANISM: Artificial Sequence
<220> FEATURE:
<223> OTHER INFORMATION: DARPin protein 29

<400> SEQUENCE: 60

Asp Leu Gly Tyr Lys Leu Leu Gln Ala Ala Tyr Asp Gly Gln Leu Asp
1               5                   10                  15

Glu Val Arg Ile Leu Leu Lys Ala Gly Ala Asp Val Asn Ala Lys Asp
                20                  25                  30

Ser Arg Gly Gln Thr Pro Leu His Tyr Ala Ala Ser Ile Gly His Leu
            35                  40                  45

Glu Ile Val Glu Val Leu Leu Lys Ala Gly Ala Asp Val Asn Ala Lys
        50                  55                  60

```
Asp Asp His Gly Trp Thr Pro Leu His Leu Ala Ala Trp Ser Gly His
 65                  70                  75                  80

Leu Glu Ile Val Glu Val Leu Leu Lys Ala Gly Ala Asp Val Asn Ala
                 85                  90                  95

Gln Asp Gln Glu Gly Thr Thr Pro Ala Asp Leu Ala Ala Val Gln Gly
            100                 105                 110

His Gln Asp Ile Ala Glu Val Leu Gln Lys Ala Gly Ser Pro Thr
        115                 120                 125

Pro Thr Pro Thr Thr Pro Thr Pro Thr Pro Thr Pro Thr Pro Thr
    130                 135                 140

Pro Thr Gly Ser Asp Leu Gly Val Lys Leu Leu Leu Ala Ala Ser Arg
145                 150                 155                 160

Gly Gln Leu Asp Glu Val Arg Ile Leu Leu Lys Ala Gly Ala Asp Val
                165                 170                 175

Asn Ala Lys Asp Ile Asp Glu Gly Tyr Thr Pro Leu His Ile Ala Ala
            180                 185                 190

Tyr Tyr Gly His Leu Glu Ile Val Glu Val Leu Leu Lys Ala Gly Ala
        195                 200                 205

Asp Val Asn Ala Lys Asp Arg Tyr Gly Lys Thr Pro Leu His Leu Ala
210                 215                 220

Ala Ile Ser Gly His Leu Glu Ile Val Glu Val Leu Leu Lys Ala Gly
225                 230                 235                 240

Ala Asp Val Asn Ala Gln Asp Lys Gly Asp Thr Pro Ala Asp Leu
                245                 250                 255

Ala Ala Asp Tyr Gly His Gln Asp Ile Ala Glu Val Leu Gln Lys Ala
            260                 265                 270

Ala Gly Ser Pro Thr Pro Thr Pro Thr Thr Pro Thr Pro Thr Pro Thr
        275                 280                 285

Thr Pro Thr Pro Thr Pro Thr Gly Ser Asp Leu Gly Gln Lys Leu Leu
    290                 295                 300

Glu Ala Ala Trp Ala Gly Gln Asp Asp Glu Val Arg Glu Leu Leu Lys
305                 310                 315                 320

Ala Gly Ala Asp Val Asn Ala Lys Asn Ser Arg Gly Trp Thr Pro Leu
                325                 330                 335

His Thr Ala Ala Gln Thr Gly His Leu Glu Ile Phe Glu Val Leu Leu
            340                 345                 350

Lys Ala Gly Ala Asp Val Asn Ala Lys Asp Lys Gly Val Thr Pro
        355                 360                 365

Leu His Leu Ala Ala Leu Gly His Leu Glu Ile Val Glu Val Leu
    370                 375                 380

Leu Lys Ala Gly Ala Asp Val Asn Ala Gln Asp Ser Trp Gly Thr Thr
385                 390                 395                 400

Pro Ala Asp Leu Ala Ala Lys Tyr Gly His Glu Asp Ile Ala Glu Val
                405                 410                 415

Leu Gln Lys Ala Ala
            420
```

<210> SEQ ID NO 61
<211> LENGTH: 568
<212> TYPE: PRT
<213> ORGANISM: Artificial Sequence
<220> FEATURE:
<223> OTHER INFORMATION: DARPin protein 30

<400> SEQUENCE: 61

-continued

```
Asp Leu Gly Tyr Lys Leu Leu Gln Ala Ala Tyr Asp Gly Gln Leu Asp
1               5                   10                  15

Glu Val Arg Ile Leu Leu Lys Ala Gly Ala Asp Val Asn Ala Lys Asp
            20                  25                  30

Ser Arg Gly Gln Thr Pro Leu His Tyr Ala Ala Ser Ile Gly His Leu
        35                  40                  45

Glu Ile Val Glu Val Leu Leu Lys Ala Gly Ala Asp Val Asn Ala Lys
    50                  55                  60

Asp His Gly Trp Thr Pro Leu His Leu Ala Ala Trp Ser Gly His
65                  70                  75                  80

Leu Glu Ile Val Glu Val Leu Leu Lys Ala Gly Ala Asp Val Asn Ala
                85                  90                  95

Gln Asp Gln Glu Gly Thr Thr Pro Ala Asp Leu Ala Ala Val Gln Gly
            100                 105                 110

His Gln Asp Ile Ala Glu Val Leu Gln Lys Ala Ala Gly Ser Pro Thr
        115                 120                 125

Pro Thr Pro Thr Pro Thr Pro Thr Pro Thr Pro Thr Pro Thr Pro Thr
    130                 135                 140

Pro Thr Gly Ser Asp Leu Gly Lys Lys Leu Leu Glu Ala Ala Leu Glu
145                 150                 155                 160

Gly Gln Asp Asp Glu Val Arg Glu Leu Leu Lys Ala Gly Ala Asp Val
                165                 170                 175

Asn Ala Lys Asp Gln Glu Gly Tyr Thr Pro Leu His Leu Ala Ala Ala
            180                 185                 190

Leu Gly His Leu Glu Ile Val Glu Val Leu Leu Lys Ala Gly Ala Asp
        195                 200                 205

Val Asn Ala Lys Asp Ser Ile Gly Arg Thr Pro Leu His Leu Ala Ala
    210                 215                 220

Tyr Lys Gly His Leu Glu Ile Val Glu Val Leu Leu Lys Ala Gly Ala
225                 230                 235                 240

Asp Val Asn Ala Gln Asp Leu Leu Gly Glu Thr Pro Ala Asp Leu Ala
                245                 250                 255

Ala Glu Gln Gly His Glu Asp Ile Ala Glu Val Leu Gln Lys Ala Ala
            260                 265                 270

Gly Ser Pro Thr Pro Thr Pro Thr Thr Pro Thr Pro Thr Pro Thr Thr
        275                 280                 285

Pro Thr Pro Thr Pro Thr Gly Ser Asp Leu Gly Val Lys Leu Leu Arg
    290                 295                 300

Ala Ala Phe His Gly Gln Asp Glu Val Arg Ile Leu Leu Ala Ala
305                 310                 315                 320

Gly Ala Asp Val Asn Ala Lys Asp Thr Asp Gly Glu Thr Pro Leu His
                325                 330                 335

Tyr Ala Ala Gln Phe Gly His Leu Glu Ile Val Glu Val Leu Leu Lys
            340                 345                 350

Ala Gly Ala Asp Val Asn Ala Lys Asp Ala Tyr Gly Ala Thr Pro Leu
        355                 360                 365

His Trp Ala Ala Trp His Gly His Leu Glu Ile Val Glu Val Leu Leu
    370                 375                 380

Lys Ala Gly Ala Asp Val Asn Ala Gln Asp Val Ser Gly Ala Thr Pro
385                 390                 395                 400

Ala Asp Leu Ala Ala Lys Val Gly His Glu Asp Ile Ala Glu Val Leu
                405                 410                 415

Gln Lys Ala Ala Gly Ser Pro Thr Pro Thr Pro Thr Thr Pro Thr Pro
```

```
               420             425             430
Thr Pro Thr Thr Pro Thr Pro Thr Pro Thr Gly Ser Asp Leu Gly Gln
            435             440             445
Lys Leu Leu Glu Ala Ala Trp Ala Gly Gln Asp Asp Glu Val Arg Glu
        450             455             460
Leu Leu Lys Ala Gly Ala Asp Val Asn Ala Lys Asn Ser Arg Gly Trp
465             470             475             480
Thr Pro Leu His Thr Ala Ala Gln Thr Gly His Leu Glu Ile Phe Glu
            485             490             495
Val Leu Leu Lys Ala Gly Ala Asp Val Asn Ala Lys Asp Asp Lys Gly
        500             505             510
Val Thr Pro Leu His Leu Ala Ala Leu Gly His Leu Glu Ile Val
        515             520             525
Glu Val Leu Leu Lys Ala Gly Ala Asp Val Asn Ala Gln Asp Ser Trp
        530             535             540
Gly Thr Thr Pro Ala Asp Leu Ala Ala Lys Tyr Gly His Glu Asp Ile
545             550             555             560
Ala Glu Val Leu Gln Lys Ala Ala
                565

<210> SEQ ID NO 62
<211> LENGTH: 568
<212> TYPE: PRT
<213> ORGANISM: Artificial Sequence
<220> FEATURE:
<223> OTHER INFORMATION: DARPin protein 31

<400> SEQUENCE: 62

Asp Leu Gly Tyr Lys Leu Leu Gln Ala Ala Tyr Asp Gly Gln Leu Asp
1               5               10              15
Glu Val Arg Ile Leu Leu Lys Ala Gly Ala Asp Val Asn Ala Lys Asp
            20              25              30
Ser Arg Gly Gln Thr Pro Leu His Tyr Ala Ala Ser Ile Gly His Leu
        35              40              45
Glu Ile Val Glu Val Leu Leu Lys Ala Gly Ala Asp Val Asn Ala Lys
    50              55              60
Asp Asp His Gly Trp Thr Pro Leu His Leu Ala Ala Trp Ser Gly His
65              70              75              80
Leu Glu Ile Val Glu Val Leu Leu Lys Ala Gly Ala Asp Val Asn Ala
            85              90              95
Gln Asp Gln Glu Gly Thr Thr Pro Ala Asp Leu Ala Ala Val Gln Gly
        100             105             110
His Gln Asp Ile Ala Glu Val Leu Gln Lys Ala Ala Gly Ser Pro Thr
    115             120             125
Pro Thr Pro Thr Thr Pro Thr Pro Thr Pro Thr Thr Pro Thr Pro Thr
130             135             140
Pro Thr Gly Ser Asp Leu Gly Lys Lys Leu Leu Glu Ala Ala Leu Glu
145             150             155             160
Gly Gln Leu Asp Glu Val Arg Glu Leu Leu Lys Ala Gly Ala Asp Val
            165             170             175
Asn Ala Lys Asp Gln Glu Gly Tyr Thr Pro Leu His Leu Ala Ala Ala
        180             185             190
Leu Gly His Leu Glu Ile Val Glu Val Leu Leu Lys Ala Gly Ala Asp
    195             200             205
Val Asn Ala Lys Asp Ser Ile Gly Arg Thr Pro Leu His Leu Ala Ala
```

```
                    210                 215                 220
Tyr Lys Gly His Leu Glu Ile Val Glu Val Leu Leu Lys Ala Gly Ala
225                 230                 235                 240

Asp Val Asn Ala Gln Asp Leu Leu Gly Glu Thr Pro Ala Asp Leu Ala
                245                 250                 255

Ala Glu Gln Gly His Gln Asp Ile Ala Glu Val Leu Gln Lys Ala Ala
                260                 265                 270

Gly Ser Pro Thr Pro Thr Pro Thr Thr Pro Thr Pro Thr Pro Thr Thr
            275                 280                 285

Pro Thr Pro Thr Pro Thr Gly Ser Asp Leu Gly Val Lys Leu Leu Arg
            290                 295                 300

Ala Ala Val His Gly Gln Leu Asp Glu Val Arg Ile Leu Leu Lys Ala
305                 310                 315                 320

Gly Ala Asp Val Asn Ala Lys Asp Thr Asp Gly Glu Thr Pro Leu His
                325                 330                 335

Tyr Ala Ala Gln Phe Gly His Leu Glu Ile Val Glu Val Leu Leu Lys
                340                 345                 350

Ala Gly Ala Asp Val Asn Ala Lys Asp Ala Tyr Gly Ala Thr Pro Leu
            355                 360                 365

His Trp Ala Ala Trp His Gly His Leu Glu Ile Val Glu Val Leu Leu
            370                 375                 380

Lys Ala Gly Ala Asp Val Asn Ala Gln Asp Val Ser Gly Ala Thr Pro
385                 390                 395                 400

Ala Asp Leu Ala Ala Lys Val Gly His Gln Asp Ile Ala Glu Val Leu
                405                 410                 415

Gln Lys Ala Ala Gly Ser Pro Thr Pro Thr Pro Thr Thr Pro Thr Pro
            420                 425                 430

Thr Pro Thr Thr Pro Thr Pro Thr Pro Thr Gly Ser Asp Leu Gly Gln
            435                 440                 445

Lys Leu Leu Glu Ala Ala Trp Ala Gly Gln Asp Asp Glu Val Arg Glu
450                 455                 460

Leu Leu Lys Ala Gly Ala Asp Val Asn Ala Lys Asn Ser Arg Gly Trp
465                 470                 475                 480

Thr Pro Leu His Thr Ala Ala Gln Thr Gly His Leu Glu Ile Phe Glu
                485                 490                 495

Val Leu Leu Lys Ala Gly Ala Asp Val Asn Ala Lys Asp Asp Lys Gly
            500                 505                 510

Val Thr Pro Leu His Leu Ala Ala Ala Leu Gly His Leu Glu Ile Val
            515                 520                 525

Glu Val Leu Leu Lys Ala Gly Ala Asp Val Asn Ala Gln Asp Ser Trp
530                 535                 540

Gly Thr Thr Pro Ala Asp Leu Ala Ala Lys Tyr Gly His Glu Asp Ile
545                 550                 555                 560

Ala Glu Val Leu Gln Lys Ala Ala
                565

<210> SEQ ID NO 63
<211> LENGTH: 5
<212> TYPE: PRT
<213> ORGANISM: Artificial Sequence
<220> FEATURE:
<223> OTHER INFORMATION: Consensus GS linker
<220> FEATURE:
<221> NAME/KEY: VARIANT
<222> LOCATION: 1..5
<223> OTHER INFORMATION: Gly-Gly-Gly-Gly-Ser]n, wherein n is 1, 2, 3, 4,
```

5, or 6

<400> SEQUENCE: 63

Gly Gly Gly Gly Ser
1               5

<210> SEQ ID NO 64
<211> LENGTH: 124
<212> TYPE: PRT
<213> ORGANISM: Artificial Sequence
<220> FEATURE:
<223> OTHER INFORMATION: DARPin protein 33

<400> SEQUENCE: 64

Asp Leu Gly Tyr Lys Leu Leu Gln Ala Ala Tyr Asp Gly Gln Leu Asp
1               5                   10                  15

Glu Val Arg Ile Leu Leu Lys Ala Gly Ala Asp Val Asn Ala Lys Asp
                20                  25                  30

Ser Arg Gly Gln Thr Pro Leu His Tyr Ala Ala Ser Ile Gly His Leu
            35                  40                  45

Glu Ile Val Glu Val Leu Leu Lys Ala Gly Ala Asp Val Asn Ala Lys
        50                  55                  60

Asp Asp His Gly Trp Thr Pro Leu His Leu Ala Ala Trp Ser Gly His
65                  70                  75                  80

Leu Glu Ile Val Glu Val Leu Leu Lys Ala Gly Ala Asp Val Asn Ala
                85                  90                  95

Gln Asp Gln Glu Gly Thr Thr Pro Ala Asp Leu Ala Ala Val Gln Gly
            100                 105                 110

His Gln Asp Ile Ala Glu Val Leu Gln Lys Ala Ala
        115                 120

<210> SEQ ID NO 65
<211> LENGTH: 124
<212> TYPE: PRT
<213> ORGANISM: Artificial Sequence
<220> FEATURE:
<223> OTHER INFORMATION: DARPin protein 34

<400> SEQUENCE: 65

Asp Leu Gly Lys Lys Leu Leu Glu Ala Ala Leu Glu Gly Gln Leu Asp
1               5                   10                  15

Glu Val Arg Glu Leu Leu Lys Ala Gly Ala Asp Val Asn Ala Lys Asp
                20                  25                  30

Gln Glu Gly Tyr Thr Pro Leu His Leu Ala Ala Ala Leu Gly His Leu
            35                  40                  45

Glu Ile Val Glu Val Leu Leu Lys Ala Gly Ala Asp Val Asn Ala Lys
        50                  55                  60

Asp Ser Ile Gly Arg Thr Pro Leu His Leu Ala Ala Tyr Lys Gly His
65                  70                  75                  80

Leu Glu Ile Val Glu Val Leu Leu Lys Ala Gly Ala Asp Val Asn Ala
                85                  90                  95

Gln Asp Leu Leu Gly Glu Thr Pro Ala Asp Leu Ala Ala Glu Gln Gly
            100                 105                 110

His Gln Asp Ile Ala Glu Val Leu Gln Lys Ala Ala
        115                 120

<210> SEQ ID NO 66
<211> LENGTH: 124
<212> TYPE: PRT

```
<213> ORGANISM: Artificial Sequence
<220> FEATURE:
<223> OTHER INFORMATION: DARPin protein 35

<400> SEQUENCE: 66

Asp Leu Gly Lys Lys Leu Leu Glu Ala Ala Leu Glu Gly Gln Asp Asp
1               5                   10                  15

Glu Val Arg Glu Leu Leu Lys Ala Gly Ala Asp Val Asn Ala Lys Asp
                20                  25                  30

Gln Glu Gly Tyr Thr Pro Leu His Leu Ala Ala Ala Leu Gly His Leu
            35                  40                  45

Glu Ile Val Glu Val Leu Leu Lys Ala Gly Ala Asp Val Asn Ala Lys
        50                  55                  60

Asp Ser Ile Gly Arg Thr Pro Leu His Leu Ala Ala Tyr Lys Gly His
65                  70                  75                  80

Leu Glu Ile Val Glu Val Leu Leu Lys Ala Gly Ala Asp Val Asn Ala
                85                  90                  95

Gln Asp Leu Leu Gly Thr Pro Ala Asp Leu Ala Ala Glu Gln Gly
            100                 105                 110

His Glu Asp Ile Ala Glu Val Leu Gln Lys Ala Ala
        115                 120

<210> SEQ ID NO 67
<211> LENGTH: 125
<212> TYPE: PRT
<213> ORGANISM: Artificial Sequence
<220> FEATURE:
<223> OTHER INFORMATION: DARPin protein 36

<400> SEQUENCE: 67

Asp Leu Gly Val Lys Leu Leu Ala Ala Ser Arg Gly Gln Leu Asp
1               5                   10                  15

Glu Val Arg Ile Leu Leu Lys Ala Gly Ala Asp Val Asn Ala Lys Asp
                20                  25                  30

Ile Asp Glu Gly Tyr Thr Pro Leu His Ile Ala Ala Tyr Tyr Gly His
            35                  40                  45

Leu Glu Ile Val Glu Val Leu Leu Lys Ala Gly Ala Asp Val Asn Ala
        50                  55                  60

Lys Asp Arg Tyr Gly Lys Thr Pro Leu His Leu Ala Ala Ile Ser Gly
65                  70                  75                  80

His Leu Glu Ile Val Glu Val Leu Leu Lys Ala Gly Ala Asp Val Asn
                85                  90                  95

Ala Gln Asp Asp Lys Gly Asp Thr Pro Ala Asp Leu Ala Ala Asp Tyr
            100                 105                 110

Gly His Gln Asp Ile Ala Glu Val Leu Gln Lys Ala Ala
        115                 120                 125

<210> SEQ ID NO 68
<211> LENGTH: 125
<212> TYPE: PRT
<213> ORGANISM: Artificial Sequence
<220> FEATURE:
<223> OTHER INFORMATION: DARPin protein 37

<400> SEQUENCE: 68

Asp Leu Gly Trp Lys Leu Leu Leu Ala Ala Ser Arg Gly Gln Asp Asp
1               5                   10                  15

Glu Val Arg Ile Leu Leu Ala Ala Gly Ala Asp Val Asn Ala Lys Asp
                20                  25                  30
```

```
Ile Asp Glu Gly Tyr Thr Pro Leu His Ile Ala Ala Tyr Tyr Gly His
        35                  40                  45

Leu Glu Ile Val Glu Val Leu Leu Lys Ala Gly Ala Asp Val Asn Ala
50                  55                  60

Lys Asp Arg Tyr Gly Lys Thr Pro Leu His Leu Ala Ala Ile Ser Gly
65                  70                  75                  80

His Glu Asp Ile Ala Glu Val Leu Leu Lys Ala Gly Ala Asp Val Asn
                85                  90                  95

Ala Gln Asp Asp Lys Gly Asp Thr Pro Ala Asp Leu Ala Ala Asp Tyr
            100                 105                 110

Gly His Glu Asp Ile Ala Glu Val Leu Gln Lys Ala Ala
        115                 120                 125

<210> SEQ ID NO 69
<211> LENGTH: 124
<212> TYPE: PRT
<213> ORGANISM: Artificial Sequence
<220> FEATURE:
<223> OTHER INFORMATION: DARPin protein 38

<400> SEQUENCE: 69

Asp Leu Gly Val Lys Leu Leu Arg Ala Ala Phe His Gly Gln Asp Asp
1               5                   10                  15

Glu Val Arg Ile Leu Leu Ala Ala Gly Ala Asp Val Asn Ala Lys Asp
                20                  25                  30

Thr Asp Gly Glu Thr Pro Leu His Tyr Ala Ala Gln Phe Gly His Leu
        35                  40                  45

Glu Ile Val Glu Val Leu Leu Lys Ala Gly Ala Asp Val Asn Ala Lys
50                  55                  60

Asp Ala Tyr Gly Ala Thr Pro Leu His Trp Ala Ala Trp His Gly His
65                  70                  75                  80

Leu Glu Ile Val Glu Val Leu Leu Lys Ala Gly Ala Asp Val Asn Ala
                85                  90                  95

Gln Asp Val Ser Gly Ala Thr Pro Ala Asp Leu Ala Ala Lys Val Gly
            100                 105                 110

His Glu Asp Ile Ala Glu Val Leu Gln Lys Ala Ala
        115                 120

<210> SEQ ID NO 70
<211> LENGTH: 124
<212> TYPE: PRT
<213> ORGANISM: Artificial Sequence
<220> FEATURE:
<223> OTHER INFORMATION: DARPin protein 39

<400> SEQUENCE: 70

Asp Leu Gly Val Lys Leu Leu Arg Ala Ala Val His Gly Gln Leu Asp
1               5                   10                  15

Glu Val Arg Ile Leu Leu Lys Ala Gly Ala Asp Val Asn Ala Lys Asp
                20                  25                  30

Thr Asp Gly Glu Thr Pro Leu His Tyr Ala Ala Gln Phe Gly His Leu
        35                  40                  45

Glu Ile Val Glu Val Leu Leu Lys Ala Gly Ala Asp Val Asn Ala Lys
50                  55                  60

Asp Ala Tyr Gly Ala Thr Pro Leu His Trp Ala Ala Trp His Gly His
65                  70                  75                  80

Leu Glu Ile Val Glu Val Leu Leu Lys Ala Gly Ala Asp Val Asn Ala
```

```
                    85                  90                  95
Gln Asp Val Ser Gly Ala Thr Pro Ala Asp Leu Ala Ala Lys Val Gly
                100                 105                 110

His Gln Asp Ile Ala Glu Val Leu Gln Lys Ala Ala
            115                 120
```

<210> SEQ ID NO 71
<211> LENGTH: 421
<212> TYPE: PRT
<213> ORGANISM: Artificial Sequence
<220> FEATURE:
<223> OTHER INFORMATION: DARPin protein 40

<400> SEQUENCE: 71

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Lys Asp Gly Tyr Thr Pro Leu His Leu Ala Ala Arg Glu Gly His Leu
            35                  40                  45

Glu Ile Val Glu Val Leu Leu Lys Ala Gly Ala Asp Val Asn Ala Lys
        50                  55                  60

Asp Lys Asp Gly Tyr Thr Pro Leu His Leu Ala Ala Arg Glu Gly His
65                  70                  75                  80

Leu Glu Ile Val Glu Val Leu Leu Lys Ala Gly Ala Asp Val Asn Ala
                85                  90                  95

Gln Asp Lys Ser Gly Lys Thr Pro Ala Asp Leu Ala Ala Asp Ala Gly
                100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Pro Thr Pro Thr
130                 135                 140

Pro Thr Gly Ser Asp Leu Gly Val Lys Leu Leu Leu Ala Ala Ser Arg
145                 150                 155                 160

Gly Gln Leu Asp Glu Val Arg Ile Leu Leu Lys Ala Gly Ala Asp Val
                165                 170                 175

Asn Ala Lys Asp Ile Asp Glu Gly Tyr Thr Pro Leu His Ile Ala Ala
            180                 185                 190

Tyr Tyr Gly His Leu Glu Ile Val Glu Val Leu Leu Lys Ala Gly Ala
        195                 200                 205

Asp Val Asn Ala Lys Asp Arg Tyr Gly Lys Thr Pro Leu His Leu Ala
210                 215                 220

Ala Ile Ser Gly His Leu Glu Ile Val Glu Val Leu Leu Lys Ala Gly
225                 230                 235                 240

Ala Asp Val Asn Ala Gln Asp Lys Gly Asp Thr Pro Ala Asp Leu
                245                 250                 255

Ala Ala Asp Tyr Gly His Gln Asp Ile Ala Glu Val Leu Gln Lys Ala
            260                 265                 270

Ala Gly Ser Pro Thr Pro Thr Pro Thr Thr Pro Thr Pro Thr Pro Thr
        275                 280                 285

Thr Pro Thr Pro Thr Pro Gly Ser Asp Leu Gly Gln Lys Leu Leu
            290                 295                 300

Glu Ala Ala Trp Ala Gly Gln Asp Asp Glu Val Arg Glu Leu Leu Lys
305                 310                 315                 320

Ala Gly Ala Asp Val Asn Ala Lys Asn Ser Arg Gly Trp Thr Pro Leu
```

His Thr Ala Ala Gln Thr Gly His Leu Glu Ile Phe Glu Val Leu Leu
                325                 330                 335

Lys Ala Gly Ala Asp Val Asn Ala Lys Asp Asp Lys Gly Val Thr Pro
        340                 345                 350

Leu His Leu Ala Ala Ala Leu Gly His Leu Glu Ile Val Glu Val Leu
    355                 360                 365

Leu Lys Ala Gly Ala Asp Val Asn Ala Gln Asp Ser Trp Gly Thr Thr
385                 390                 395                 400

Pro Ala Asp Leu Ala Ala Lys Tyr Gly His Glu Asp Ile Ala Glu Val
                405                 410                 415

Leu Gln Lys Ala Ala
            420

<210> SEQ ID NO 72
<211> LENGTH: 420
<212> TYPE: PRT
<213> ORGANISM: Artificial Sequence
<220> FEATURE:
<223> OTHER INFORMATION: DARPin protein 41

<400> SEQUENCE: 72

Asp Leu Gly Lys Lys Leu Leu Glu Ala Ala Leu Glu Gly Gln Leu Asp
1               5                   10                  15

Glu Val Arg Glu Leu Leu Lys Ala Gly Ala Asp Val Asn Ala Lys Asp
            20                  25                  30

Gln Glu Gly Tyr Thr Pro Leu His Leu Ala Ala Ala Leu Gly His Leu
        35                  40                  45

Glu Ile Val Glu Val Leu Leu Lys Ala Gly Ala Asp Val Asn Ala Lys
    50                  55                  60

Asp Ser Ile Gly Arg Thr Pro Leu His Leu Ala Ala Tyr Lys Gly His
65                  70                  75                  80

Leu Glu Ile Val Glu Val Leu Leu Lys Ala Gly Ala Asp Val Asn Ala
                85                  90                  95

Gln Asp Leu Leu Gly Glu Thr Pro Ala Asp Leu Ala Ala Glu Gln Gly
            100                 105                 110

His Gln Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr Pro
    130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Lys Asp Gly Tyr Thr Pro Leu His Leu Ala Ala Arg
            180                 185                 190

Glu Gly His Leu Glu Ile Val Glu Val Leu Leu Lys Ala Gly Ala Asp
        195                 200                 205

Val Asn Ala Lys Asp Lys Asp Gly Tyr Thr Pro Leu His Leu Ala Ala
    210                 215                 220

Arg Glu Gly His Leu Glu Ile Val Glu Val Leu Leu Lys Ala Gly Ala
225                 230                 235                 240

Asp Val Asn Ala Gln Asp Lys Ser Gly Lys Thr Pro Ala Asp Leu Ala
                245                 250                 255

Ala Asp Ala Gly His Glu Asp Ile Ala Glu Val Leu Gln Lys Ala Ala

```
                260                 265                 270
Gly Ser Pro Thr Pro Thr Pro Thr Pro Thr Pro Thr Thr
        275                 280                 285
Pro Thr Pro Thr Pro Thr Gly Ser Asp Leu Gly Gln Lys Leu Leu Glu
        290                 295                 300
Ala Ala Trp Ala Gly Gln Asp Asp Glu Val Arg Glu Leu Leu Lys Ala
305                 310                 315                 320
Gly Ala Asp Val Asn Ala Lys Asn Ser Arg Gly Trp Thr Pro Leu His
                325                 330                 335
Thr Ala Ala Gln Thr Gly His Leu Glu Ile Phe Glu Val Leu Leu Lys
                340                 345                 350
Ala Gly Ala Asp Val Asn Ala Lys Asp Asp Lys Gly Val Thr Pro Leu
                355                 360                 365
His Leu Ala Ala Ala Leu Gly His Leu Glu Ile Val Glu Val Leu Leu
        370                 375                 380
Lys Ala Gly Ala Asp Val Asn Ala Gln Asp Ser Trp Gly Thr Thr Pro
385                 390                 395                 400
Ala Asp Leu Ala Ala Lys Tyr Gly His Glu Asp Ile Ala Glu Val Leu
                405                 410                 415
Gln Lys Ala Ala
        420

<210> SEQ ID NO 73
<211> LENGTH: 421
<212> TYPE: PRT
<213> ORGANISM: Artificial Sequence
<220> FEATURE:
<223> OTHER INFORMATION: DARPin protein 42

<400> SEQUENCE: 73

Asp Leu Gly Lys Lys Leu Leu Glu Ala Ala Arg Ala Gly Gln Asp Asp
1               5                   10                  15
Glu Val Arg Glu Leu Leu Lys Ala Gly Ala Asp Val Asn Ala Lys Asp
            20                  25                  30
Lys Asp Gly Tyr Thr Pro Leu His Leu Ala Ala Arg Glu Gly His Leu
        35                  40                  45
Glu Ile Val Glu Val Leu Leu Lys Ala Gly Ala Asp Val Asn Ala Lys
    50                  55                  60
Asp Lys Asp Gly Tyr Thr Pro Leu His Leu Ala Ala Arg Glu Gly His
65                  70                  75                  80
Leu Glu Ile Val Glu Val Leu Leu Lys Ala Gly Ala Asp Val Asn Ala
                85                  90                  95
Gln Asp Lys Ser Gly Lys Thr Pro Ala Asp Leu Ala Ala Asp Ala Gly
            100                 105                 110
His Glu Asp Ile Ala Glu Val Leu Gln Lys Ala Ala Gly Ser Pro Thr
        115                 120                 125
Pro Thr Pro Thr Thr Pro Thr Pro Thr Pro Thr Pro Thr Pro Thr
        130                 135                 140
Pro Thr Gly Ser Asp Leu Gly Val Lys Leu Leu Leu Ala Ala Ser Arg
145                 150                 155                 160
Gly Gln Leu Asp Glu Val Arg Ile Leu Leu Lys Ala Gly Ala Asp Val
                165                 170                 175
Asn Ala Lys Asp Ile Asp Glu Gly Tyr Thr Pro Leu His Ile Ala Ala
            180                 185                 190
Tyr Tyr Gly His Leu Glu Ile Val Glu Val Leu Leu Lys Ala Gly Ala
```

```
                195                 200                 205
Asp Val Asn Ala Lys Asp Arg Tyr Gly Lys Thr Pro Leu His Leu Ala
        210                 215                 220

Ala Ile Ser Gly His Leu Glu Ile Val Glu Val Leu Leu Lys Ala Gly
225                 230                 235                 240

Ala Asp Val Asn Ala Gln Asp Lys Gly Asp Thr Pro Ala Asp Leu
            245                 250                 255

Ala Ala Asp Tyr Gly His Gln Asp Ile Ala Glu Val Leu Gln Lys Ala
            260                 265                 270

Ala Gly Ser Pro Thr Pro Thr Pro Thr Thr Pro Thr Pro Thr Pro Thr
            275                 280                 285

Thr Pro Thr Pro Thr Pro Thr Gly Ser Asp Leu Gly Gln Lys Leu Leu
        290                 295                 300

Glu Ala Ala Trp Ala Gly Gln Asp Asp Glu Val Arg Glu Leu Leu Lys
305                 310                 315                 320

Ala Gly Ala Asp Val Asn Ala Lys Asn Ser Arg Gly Trp Thr Pro Leu
                325                 330                 335

His Thr Ala Ala Gln Thr Gly His Leu Glu Ile Phe Glu Val Leu Leu
            340                 345                 350

Lys Ala Gly Ala Asp Val Asn Ala Lys Asp Asp Lys Gly Val Thr Pro
            355                 360                 365

Leu His Leu Ala Ala Leu Gly His Leu Glu Ile Val Glu Val Leu
        370                 375                 380

Leu Lys Ala Gly Ala Asp Val Asn Ala Gln Asp Ser Trp Gly Thr Thr
385                 390                 395                 400

Pro Ala Asp Leu Ala Ala Lys Tyr Gly His Glu Asp Ile Ala Glu Val
                405                 410                 415

Leu Gln Lys Ala Ala
            420

<210> SEQ ID NO 74
<211> LENGTH: 420
<212> TYPE: PRT
<213> ORGANISM: Artificial Sequence
<220> FEATURE:
<223> OTHER INFORMATION: DARPin protein 43

<400> SEQUENCE: 74

Asp Leu Gly Tyr Lys Leu Leu Gln Ala Ala Tyr Asp Gly Gln Leu Asp
1               5                   10                  15

Glu Val Arg Ile Leu Leu Lys Ala Gly Ala Asp Val Asn Ala Lys Asp
                20                  25                  30

Ser Arg Gly Gln Thr Pro Leu His Tyr Ala Ala Ser Ile Gly His Leu
            35                  40                  45

Glu Ile Val Glu Val Leu Leu Lys Ala Gly Ala Asp Val Asn Ala Lys
        50                  55                  60

Asp Asp His Gly Trp Thr Pro Leu His Leu Ala Ala Trp Ser Gly His
65                  70                  75                  80

Leu Glu Ile Val Glu Val Leu Leu Lys Ala Gly Ala Asp Val Asn Ala
                85                  90                  95

Gln Asp Gln Glu Gly Thr Thr Pro Ala Asp Leu Ala Ala Val Gln Gly
            100                 105                 110

His Gln Asp Ile Ala Glu Val Leu Gln Lys Ala Ala Gly Ser Pro Thr
            115                 120                 125

Pro Thr Pro Thr Thr Pro Thr Pro Thr Pro Thr Thr Pro Thr Pro Thr
```

```
          130                 135                 140
Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Lys Asp Gly Tyr Thr Pro Leu His Leu Ala Ala Arg
            180                 185                 190

Glu Gly His Leu Glu Ile Val Glu Val Leu Leu Lys Ala Gly Ala Asp
        195                 200                 205

Val Asn Ala Lys Asp Lys Asp Gly Tyr Thr Pro Leu His Leu Ala Ala
    210                 215                 220

Arg Glu Gly His Leu Glu Ile Val Glu Val Leu Leu Lys Ala Gly Ala
225                 230                 235                 240

Asp Val Asn Ala Gln Asp Lys Ser Gly Lys Thr Pro Ala Asp Leu Ala
                245                 250                 255

Ala Asp Ala Gly His Glu Asp Ile Ala Glu Val Leu Gln Lys Ala Ala
            260                 265                 270

Gly Ser Pro Thr Pro Thr Pro Thr Thr Pro Thr Pro Thr Pro Thr Thr
        275                 280                 285

Pro Thr Pro Thr Pro Thr Gly Ser Asp Leu Gly Gln Lys Leu Leu Glu
    290                 295                 300

Ala Ala Trp Ala Gly Gln Asp Asp Glu Val Arg Glu Leu Leu Lys Ala
305                 310                 315                 320

Gly Ala Asp Val Asn Ala Lys Asn Ser Arg Gly Trp Thr Pro Leu His
                325                 330                 335

Thr Ala Ala Gln Thr Gly His Leu Glu Ile Phe Glu Val Leu Leu Lys
            340                 345                 350

Ala Gly Ala Asp Val Asn Ala Lys Asp Lys Gly Val Thr Pro Leu
        355                 360                 365

His Leu Ala Ala Ala Leu Gly His Leu Glu Ile Val Glu Val Leu Leu
    370                 375                 380

Lys Ala Gly Ala Asp Val Asn Ala Gln Asp Ser Trp Gly Thr Thr Pro
385                 390                 395                 400

Ala Asp Leu Ala Ala Lys Tyr Gly His Glu Asp Ile Ala Glu Val Leu
                405                 410                 415

Gln Lys Ala Ala
        420

<210> SEQ ID NO 75
<211> LENGTH: 568
<212> TYPE: PRT
<213> ORGANISM: Artificial Sequence
<220> FEATURE:
<223> OTHER INFORMATION: DARPin protein 44

<400> SEQUENCE: 75

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Lys Asp Gly Tyr Thr Pro Leu His Leu Ala Ala Arg Glu Gly His Leu
        35                  40                  45

Glu Ile Val Glu Val Leu Leu Lys Ala Gly Ala Asp Val Asn Ala Lys
    50                  55                  60

Asp Lys Asp Gly Tyr Thr Pro Leu His Leu Ala Ala Arg Glu Gly His
```

```
                65                  70                  75                  80
Leu Glu Ile Val Glu Val Leu Leu Lys Ala Gly Ala Asp Val Asn Ala
                    85                  90                  95
Gln Asp Lys Ser Gly Lys Thr Pro Ala Asp Leu Ala Ala Asp Ala Gly
                    100                 105                 110
His Glu Asp Ile Ala Glu Val Leu Gln Lys Ala Ala Gly Ser Pro Thr
                    115                 120                 125
Pro Thr Pro Thr Thr Pro Thr Pro Thr Pro Thr Thr Pro Thr Pro Thr
                    130                 135                 140
Pro Thr Gly Ser Asp Leu Gly Lys Lys Leu Leu Glu Ala Ala Arg Ala
145                 150                 155                 160
Gly Gln Asp Asp Glu Val Arg Glu Leu Leu Lys Ala Gly Ala Asp Val
                    165                 170                 175
Asn Ala Lys Asp Lys Asp Gly Tyr Thr Pro Leu His Leu Ala Ala Arg
                    180                 185                 190
Glu Gly His Leu Glu Ile Val Glu Val Leu Leu Lys Ala Gly Ala Asp
                    195                 200                 205
Val Asn Ala Lys Asp Lys Asp Gly Tyr Thr Pro Leu His Leu Ala Ala
                    210                 215                 220
Arg Glu Gly His Leu Glu Ile Val Glu Val Leu Leu Lys Ala Gly Ala
225                 230                 235                 240
Asp Val Asn Ala Gln Asp Lys Ser Gly Lys Thr Pro Ala Asp Leu Ala
                    245                 250                 255
Ala Asp Ala Gly His Glu Asp Ile Ala Glu Val Leu Gln Lys Ala Ala
                    260                 265                 270
Gly Ser Pro Thr Pro Thr Pro Thr Thr Pro Thr Pro Thr Pro Thr Thr
                    275                 280                 285
Pro Thr Pro Thr Pro Thr Gly Ser Asp Leu Gly Val Lys Leu Leu Arg
                    290                 295                 300
Ala Ala Val His Gly Gln Leu Asp Glu Val Arg Ile Leu Leu Lys Ala
305                 310                 315                 320
Gly Ala Asp Val Asn Ala Lys Asp Thr Asp Gly Glu Thr Pro Leu His
                    325                 330                 335
Tyr Ala Ala Gln Phe Gly His Leu Glu Ile Val Glu Val Leu Leu Lys
                    340                 345                 350
Ala Gly Ala Asp Val Asn Ala Lys Asp Ala Tyr Gly Ala Thr Pro Leu
                    355                 360                 365
His Trp Ala Ala Trp His Gly His Leu Glu Ile Val Glu Val Leu Leu
                    370                 375                 380
Lys Ala Gly Ala Asp Val Asn Ala Gln Asp Val Ser Gly Ala Thr Pro
385                 390                 395                 400
Ala Asp Leu Ala Ala Lys Val Gly His Gln Asp Ile Ala Glu Val Leu
                    405                 410                 415
Gln Lys Ala Ala Gly Ser Pro Thr Pro Thr Pro Thr Thr Pro Thr Pro
                    420                 425                 430
Thr Pro Thr Thr Pro Thr Pro Thr Pro Thr Gly Ser Asp Leu Gly Gln
                    435                 440                 445
Lys Leu Leu Glu Ala Ala Trp Ala Gly Gln Asp Asp Glu Val Arg Glu
                    450                 455                 460
Leu Leu Lys Ala Gly Ala Asp Val Asn Ala Lys Asn Ser Arg Gly Trp
465                 470                 475                 480
Thr Pro Leu His Thr Ala Ala Gln Thr Gly His Leu Glu Ile Phe Glu
                    485                 490                 495
```

```
Val Leu Leu Lys Ala Gly Ala Asp Val Asn Ala Lys Asp Lys Gly
            500                 505                 510

Val Thr Pro Leu His Leu Ala Ala Leu Gly His Leu Glu Ile Val
            515                 520                 525

Glu Val Leu Leu Lys Ala Gly Ala Asp Val Asn Ala Gln Asp Ser Trp
            530                 535                 540

Gly Thr Thr Pro Ala Asp Leu Ala Ala Lys Tyr Gly His Glu Asp Ile
545                 550                 555                 560

Ala Glu Val Leu Gln Lys Ala Ala
                565

<210> SEQ ID NO 76
<211> LENGTH: 568
<212> TYPE: PRT
<213> ORGANISM: Artificial Sequence
<220> FEATURE:
<223> OTHER INFORMATION: DARPin protein 45

<400> SEQUENCE: 76

Asp Leu Gly Tyr Lys Leu Leu Gln Ala Ala Tyr Asp Gly Gln Leu Asp
1               5                   10                  15

Glu Val Arg Ile Leu Leu Lys Ala Gly Ala Asp Val Asn Ala Lys Asp
            20                  25                  30

Ser Arg Gly Gln Thr Pro Leu His Tyr Ala Ala Ser Ile Gly His Leu
            35                  40                  45

Glu Ile Val Glu Val Leu Leu Lys Ala Gly Ala Asp Val Asn Ala Lys
            50                  55                  60

Asp Asp His Gly Trp Thr Pro Leu His Leu Ala Ala Trp Ser Gly His
65                  70                  75                  80

Leu Glu Ile Val Glu Val Leu Leu Lys Ala Gly Ala Asp Val Asn Ala
                85                  90                  95

Gln Asp Gln Glu Gly Thr Thr Pro Ala Asp Leu Ala Ala Val Gln Gly
            100                 105                 110

His Gln Asp Ile Ala Glu Val Leu Gln Lys Ala Ala Gly Ser Pro Thr
            115                 120                 125

Pro Thr Pro Thr Thr Pro Thr Pro Thr Pro Thr Thr Pro Thr Pro Thr
            130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
            165                 170                 175

Asn Ala Lys Asp Lys Asp Gly Tyr Thr Pro Leu His Leu Ala Ala Arg
            180                 185                 190

Glu Gly His Leu Glu Ile Val Glu Val Leu Leu Lys Ala Gly Ala Asp
            195                 200                 205

Val Asn Ala Lys Asp Lys Asp Gly Tyr Thr Pro Leu His Leu Ala Ala
            210                 215                 220

Arg Glu Gly His Leu Glu Ile Val Glu Val Leu Leu Lys Ala Gly Ala
225                 230                 235                 240

Asp Val Asn Ala Gln Asp Lys Ser Gly Lys Thr Pro Ala Asp Leu Ala
            245                 250                 255

Ala Asp Ala Gly His Glu Asp Ile Ala Glu Val Leu Gln Lys Ala Ala
            260                 265                 270

Gly Ser Pro Thr Pro Thr Pro Thr Thr Pro Thr Pro Thr Pro Thr Thr
            275                 280                 285
```

```
Pro Thr Pro Thr Pro Thr Gly Ser Asp Leu Gly Lys Lys Leu Leu Glu
        290                 295                 300

Ala Ala Arg Ala Gly Gln Asp Asp Glu Val Arg Glu Leu Leu Lys Ala
305                 310                 315                 320

Gly Ala Asp Val Asn Ala Lys Asp Lys Asp Gly Tyr Thr Pro Leu His
                325                 330                 335

Leu Ala Ala Arg Glu Gly His Leu Glu Ile Val Glu Val Leu Leu Lys
                340                 345                 350

Ala Gly Ala Asp Val Asn Ala Lys Asp Lys Asp Gly Tyr Thr Pro Leu
                355                 360                 365

His Leu Ala Ala Arg Glu Gly His Leu Glu Ile Val Glu Val Leu Leu
        370                 375                 380

Lys Ala Gly Ala Asp Val Asn Ala Gln Asp Lys Ser Gly Lys Thr Pro
385                 390                 395                 400

Ala Asp Leu Ala Ala Asp Ala Gly His Glu Asp Ile Ala Glu Val Leu
                405                 410                 415

Gln Lys Ala Ala Gly Ser Pro Thr Pro Thr Pro Thr Pro Thr Pro Thr Pro
                420                 425                 430

Thr Pro Thr Thr Pro Thr Pro Thr Pro Thr Gly Ser Asp Leu Gly Gln
        435                 440                 445

Lys Leu Leu Glu Ala Ala Trp Ala Gly Gln Asp Asp Glu Val Arg Glu
450                 455                 460

Leu Leu Lys Ala Gly Ala Asp Val Asn Ala Lys Asn Ser Arg Gly Trp
465                 470                 475                 480

Thr Pro Leu His Thr Ala Ala Gln Thr Gly His Leu Glu Ile Phe Glu
                485                 490                 495

Val Leu Leu Lys Ala Gly Ala Asp Val Asn Ala Lys Asp Asp Lys Gly
                500                 505                 510

Val Thr Pro Leu His Leu Ala Ala Leu Gly His Leu Glu Ile Val
                515                 520                 525

Glu Val Leu Leu Lys Ala Gly Ala Asp Val Asn Ala Gln Asp Ser Trp
        530                 535                 540

Gly Thr Thr Pro Ala Asp Leu Ala Ala Lys Tyr Gly His Glu Asp Ile
545                 550                 555                 560

Ala Glu Val Leu Gln Lys Ala Ala
                565

<210> SEQ ID NO 77
<211> LENGTH: 568
<212> TYPE: PRT
<213> ORGANISM: Artificial Sequence
<220> FEATURE:
<223> OTHER INFORMATION: DARPin protein 46

<400> SEQUENCE: 77

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Lys Asp Gly Tyr Thr Pro Leu His Leu Ala Ala Arg Glu Gly His Leu
        35                  40                  45

Glu Ile Val Glu Val Leu Leu Lys Ala Gly Ala Asp Val Asn Ala Lys
    50                  55                  60

Asp Lys Asp Gly Tyr Thr Pro Leu His Leu Ala Ala Arg Glu Gly His
65                  70                  75                  80
```

```
Leu Glu Ile Val Glu Val Leu Leu Lys Ala Gly Ala Asp Val Asn Ala
                85                  90                  95

Gln Asp Lys Ser Gly Lys Thr Pro Ala Asp Leu Ala Ala Asp Ala Gly
            100                 105                 110

His Glu Asp Ile Ala Glu Val Leu Gln Lys Ala Gly Ser Pro Thr
        115                 120                 125

Pro Thr Pro Thr Thr Pro Thr Pro Thr Pro Thr Thr Pro Thr Pro Thr
130                 135                 140

Pro Thr Gly Ser Asp Leu Gly Lys Lys Leu Leu Glu Ala Ala Leu Glu
145                 150                 155                 160

Gly Gln Leu Asp Glu Val Arg Glu Leu Leu Lys Ala Gly Ala Asp Val
                165                 170                 175

Asn Ala Lys Asp Gln Glu Gly Tyr Thr Pro Leu His Leu Ala Ala
                180                 185                 190

Leu Gly His Leu Glu Ile Val Glu Val Leu Leu Lys Ala Gly Ala Asp
                195                 200                 205

Val Asn Ala Lys Asp Ser Ile Gly Arg Thr Pro Leu His Leu Ala Ala
210                 215                 220

Tyr Lys Gly His Leu Glu Ile Val Glu Val Leu Leu Lys Ala Gly Ala
225                 230                 235                 240

Asp Val Asn Ala Gln Asp Leu Leu Gly Glu Thr Pro Ala Asp Leu Ala
                245                 250                 255

Ala Glu Gln Gly His Gln Asp Ile Ala Glu Val Leu Gln Lys Ala Ala
                260                 265                 270

Gly Ser Pro Thr Pro Thr Pro Thr Pro Thr Pro Thr Pro Thr Thr
        275                 280                 285

Pro Thr Pro Thr Pro Thr Gly Ser Asp Leu Gly Lys Lys Leu Leu Glu
        290                 295                 300

Ala Ala Arg Ala Gly Gln Asp Glu Val Arg Glu Leu Leu Lys Ala
305                 310                 315                 320

Gly Ala Asp Val Asn Ala Lys Asp Lys Asp Gly Tyr Thr Pro Leu His
                325                 330                 335

Leu Ala Ala Arg Glu Gly His Leu Glu Ile Val Glu Val Leu Leu Lys
            340                 345                 350

Ala Gly Ala Asp Val Asn Ala Lys Asp Lys Asp Gly Tyr Thr Pro Leu
            355                 360                 365

His Leu Ala Ala Arg Glu Gly His Leu Glu Ile Val Glu Val Leu Leu
    370                 375                 380

Lys Ala Gly Ala Asp Val Asn Ala Gln Asp Lys Ser Gly Lys Thr Pro
385                 390                 395                 400

Ala Asp Leu Ala Ala Asp Ala Gly His Glu Asp Ile Ala Glu Val Leu
                405                 410                 415

Gln Lys Ala Ala Gly Ser Pro Thr Pro Thr Pro Thr Thr Pro Thr Pro
            420                 425                 430

Thr Pro Thr Thr Pro Thr Pro Thr Pro Thr Gly Ser Asp Leu Gly Gln
        435                 440                 445

Lys Leu Leu Glu Ala Ala Trp Ala Gly Gln Asp Asp Glu Val Arg Glu
    450                 455                 460

Leu Leu Lys Ala Gly Ala Asp Val Asn Ala Lys Asn Ser Arg Gly Trp
465                 470                 475                 480

Thr Pro Leu His Thr Ala Ala Gln Thr Gly His Leu Glu Ile Phe Glu
                485                 490                 495
```

Val Leu Leu Lys Ala Gly Ala Asp Val Asn Ala Lys Asp Lys Gly
                500                 505                 510

Val Thr Pro Leu His Leu Ala Ala Ala Leu Gly His Leu Glu Ile Val
        515                 520                 525

Glu Val Leu Leu Lys Ala Gly Ala Asp Val Asn Ala Gln Asp Ser Trp
        530                 535                 540

Gly Thr Thr Pro Ala Asp Leu Ala Ala Lys Tyr Gly His Glu Asp Ile
545                 550                 555                 560

Ala Glu Val Leu Gln Lys Ala Ala
                565

<210> SEQ ID NO 78
<211> LENGTH: 569
<212> TYPE: PRT
<213> ORGANISM: Artificial Sequence
<220> FEATURE:
<223> OTHER INFORMATION: DARPin protein 47

<400> SEQUENCE: 78

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr Thr
    130                 135                 140

Pro Thr Gly Ser Asp Leu Gly Lys Lys Leu Leu Glu Ala Ala Leu Glu
145                 150                 155                 160

Gly Gln Leu Asp Glu Val Arg Glu Leu Leu Lys Ala Gly Ala Asp Val
                165                 170                 175

Asn Ala Lys Asp Gln Glu Gly Tyr Thr Pro Leu His Leu Ala Ala Ala
            180                 185                 190

Leu Gly His Leu Glu Ile Val Glu Val Leu Leu Lys Ala Gly Ala Asp
        195                 200                 205

Val Asn Ala Lys Asp Ser Ile Gly Arg Thr Pro Leu His Leu Ala Ala
    210                 215                 220

Tyr Lys Gly His Leu Glu Ile Val Glu Val Leu Leu Lys Ala Gly Ala
225                 230                 235                 240

Asp Val Asn Ala Gln Asp Leu Leu Gly Glu Thr Pro Ala Asp Leu Ala
                245                 250                 255

Ala Glu Gln Gly His Gln Asp Ile Ala Glu Val Leu Gln Lys Ala Ala
            260                 265                 270

Gly Ser Pro Thr Pro Thr Pro Thr Thr Pro Thr Pro Thr Pro Thr Thr
        275                 280                 285

```
Pro Thr Pro Thr Pro Thr Gly Ser Asp Leu Gly Val Lys Leu Leu Leu
            290                 295                 300
Ala Ala Ser Arg Gly Gln Leu Asp Glu Val Arg Ile Leu Leu Lys Ala
305                 310                 315                 320
Gly Ala Asp Val Asn Ala Lys Asp Ile Asp Glu Gly Tyr Thr Pro Leu
                325                 330                 335
His Ile Ala Ala Tyr Tyr Gly His Leu Glu Ile Val Glu Val Leu Leu
            340                 345                 350
Lys Ala Gly Ala Asp Val Asn Ala Lys Asp Arg Tyr Gly Lys Thr Pro
355                 360                 365
Leu His Leu Ala Ala Ile Ser Gly His Leu Glu Ile Val Glu Val Leu
370                 375                 380
Leu Lys Ala Gly Ala Asp Val Asn Ala Gln Asp Lys Gly Asp Thr
385                 390                 395                 400
Pro Ala Asp Leu Ala Ala Asp Tyr Gly His Gln Asp Ile Ala Glu Val
                405                 410                 415
Leu Gln Lys Ala Ala Gly Ser Pro Thr Pro Thr Pro Thr Thr Pro Thr
            420                 425                 430
Pro Thr Pro Thr Thr Pro Thr Pro Thr Pro Gly Ser Asp Leu Gly
            435                 440                 445
Gln Lys Leu Leu Glu Ala Ala Trp Ala Gly Gln Asp Asp Glu Val Arg
450                 455                 460
Glu Leu Leu Lys Ala Gly Ala Asp Val Asn Ala Lys Asn Ser Arg Gly
465                 470                 475                 480
Trp Thr Pro Leu His Thr Ala Ala Gln Thr Gly His Leu Glu Ile Phe
                485                 490                 495
Glu Val Leu Leu Lys Ala Gly Ala Asp Val Asn Ala Lys Asp Asp Lys
            500                 505                 510
Gly Val Thr Pro Leu His Leu Ala Ala Ala Leu Gly His Leu Glu Ile
            515                 520                 525
Val Glu Val Leu Leu Lys Ala Gly Ala Asp Val Asn Ala Gln Asp Ser
530                 535                 540
Trp Gly Thr Thr Pro Ala Asp Leu Ala Ala Lys Tyr Gly His Glu Asp
545                 550                 555                 560
Ile Ala Glu Val Leu Gln Lys Ala Ala
                565

<210> SEQ ID NO 79
<211> LENGTH: 717
<212> TYPE: PRT
<213> ORGANISM: Artificial Sequence
<220> FEATURE:
<223> OTHER INFORMATION: DARPin protein 48

<400> SEQUENCE: 79

Asp Leu Gly Lys Lys Leu Leu Glu Ala Ala Arg Ala Gly Gln Asp Asp
1               5                   10                  15
Glu Val Arg Glu Leu Leu Lys Ala Gly Ala Asp Val Asn Ala Lys Asp
                20                  25                  30
Tyr Phe Ser His Thr Pro Leu His Leu Ala Ala Arg Asn Gly His Leu
            35                  40                  45
Lys Ile Val Glu Val Leu Leu Lys Ala Gly Ala Asp Val Asn Ala Lys
        50                  55                  60
Asp Phe Ala Gly Lys Thr Pro Leu His Leu Ala Ala Asp Gly His
65                  70                  75                  80
```

-continued

```
Leu Glu Ile Val Glu Val Leu Leu Lys Ala Gly Ala Asp Val Asn Ala
             85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Thr Pro Thr Pro Thr
130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Tyr Phe Ser His Thr Pro Leu His Leu Ala Ala Arg
            180                 185                 190

Asn Gly His Leu Lys Ile Val Glu Val Leu Leu Lys Ala Gly Ala Asp
            195                 200                 205

Val Asn Ala Lys Asp Phe Ala Gly Lys Thr Pro Leu His Leu Ala Ala
            210                 215                 220

Ala Asp Gly His Leu Glu Ile Val Glu Val Leu Leu Lys Ala Gly Ala
225                 230                 235                 240

Asp Val Asn Ala Gln Asp Ile Phe Gly Lys Thr Pro Ala Asp Ile Ala
                245                 250                 255

Ala Asp Ala Gly His Glu Asp Ile Ala Glu Val Leu Gln Lys Ala Ala
            260                 265                 270

Gly Ser Pro Thr Pro Thr Pro Thr Thr Pro Thr Pro Thr Pro Thr Thr
            275                 280                 285

Pro Thr Pro Thr Pro Thr Gly Ser Asp Leu Gly Lys Lys Leu Leu Glu
            290                 295                 300

Ala Ala Leu Glu Gly Gln Leu Asp Glu Val Arg Glu Leu Leu Lys Ala
305                 310                 315                 320

Gly Ala Asp Val Asn Ala Lys Asp Gln Glu Gly Tyr Thr Pro Leu His
            325                 330                 335

Leu Ala Ala Ala Leu Gly His Leu Glu Ile Val Glu Val Leu Leu Lys
            340                 345                 350

Ala Gly Ala Asp Val Asn Ala Lys Asp Ser Ile Gly Arg Thr Pro Leu
            355                 360                 365

His Leu Ala Ala Tyr Lys Gly His Leu Glu Ile Val Glu Val Leu Leu
            370                 375                 380

Lys Ala Gly Ala Asp Val Asn Ala Gln Asp Leu Leu Gly Glu Thr Pro
385                 390                 395                 400

Ala Asp Leu Ala Ala Glu Gln Gly His Gln Asp Ile Ala Glu Val Leu
                405                 410                 415

Gln Lys Ala Ala Gly Ser Pro Thr Pro Thr Pro Thr Thr Pro Thr Pro
            420                 425                 430

Thr Pro Thr Pro Thr Pro Thr Pro Thr Gly Ser Asp Leu Gly Val
            435                 440                 445

Lys Leu Leu Leu Ala Ala Ser Arg Gly Gln Leu Asp Glu Val Arg Ile
            450                 455                 460

Leu Leu Lys Ala Gly Ala Asp Val Asn Ala Lys Asp Ile Asp Glu Gly
465                 470                 475                 480

Tyr Thr Pro Leu His Ile Ala Ala Tyr Tyr Gly His Leu Glu Ile Val
                485                 490                 495

Glu Val Leu Leu Lys Ala Gly Ala Asp Val Asn Ala Lys Asp Arg Tyr
```

```
                500                 505                 510
Gly Lys Thr Pro Leu His Leu Ala Ala Ile Ser Gly His Leu Glu Ile
            515                 520                 525

Val Glu Val Leu Leu Lys Ala Gly Ala Asp Val Asn Ala Gln Asp Asp
        530                 535                 540

Lys Gly Asp Thr Pro Ala Asp Leu Ala Ala Asp Tyr Gly His Gln Asp
545                 550                 555                 560

Ile Ala Glu Val Leu Gln Lys Ala Ala Gly Ser Pro Thr Pro Thr Pro
                565                 570                 575

Thr Thr Pro Thr Pro Thr Pro Thr Pro Thr Pro Thr Pro Thr Gly
            580                 585                 590

Ser Asp Leu Gly Gln Lys Leu Leu Glu Ala Ala Trp Ala Gly Gln Asp
        595                 600                 605

Asp Glu Val Arg Glu Leu Leu Lys Ala Gly Ala Asp Val Asn Ala Lys
            610                 615                 620

Asn Ser Arg Gly Trp Thr Pro Leu His Thr Ala Ala Gln Thr Gly His
625                 630                 635                 640

Leu Glu Ile Phe Glu Val Leu Leu Lys Ala Gly Ala Asp Val Asn Ala
                645                 650                 655

Lys Asp Asp Lys Gly Val Thr Pro Leu His Leu Ala Ala Leu Gly
            660                 665                 670

His Leu Glu Ile Val Glu Val Leu Leu Lys Ala Gly Ala Asp Val Asn
        675                 680                 685

Ala Gln Asp Ser Trp Gly Thr Thr Pro Ala Asp Leu Ala Ala Lys Tyr
            690                 695                 700

Gly His Glu Asp Ile Ala Glu Val Leu Gln Lys Ala Ala
705                 710                 715

<210> SEQ ID NO 80
<211> LENGTH: 569
<212> TYPE: PRT
<213> ORGANISM: Artificial Sequence
<220> FEATURE:
<223> OTHER INFORMATION: DARPin protein 49

<400> SEQUENCE: 80

Asp Leu Gly Lys Lys Leu Leu Glu Ala Ala Leu Glu Gly Gln Leu Asp
1               5                   10                  15

Glu Val Arg Glu Leu Leu Lys Ala Gly Ala Asp Val Asn Ala Lys Asp
            20                  25                  30

Gln Glu Gly Tyr Thr Pro Leu His Leu Ala Ala Ala Leu Gly His Leu
        35                  40                  45

Glu Ile Val Glu Val Leu Leu Lys Ala Gly Ala Asp Val Asn Ala Lys
    50                  55                  60

Asp Ser Ile Gly Arg Thr Pro Leu His Leu Ala Ala Tyr Lys Gly His
65                  70                  75                  80

Leu Glu Ile Val Glu Val Leu Leu Lys Ala Gly Ala Asp Val Asn Ala
                85                  90                  95

Gln Asp Leu Leu Gly Glu Thr Pro Ala Asp Leu Ala Ala Glu Gln Gly
            100                 105                 110

His Gln Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr
    130                 135                 140

Pro Thr Gly Ser Asp Leu Gly Val Lys Leu Leu Leu Ala Ala Ser Arg
```

```
            145                 150                 155                 160
        Gly Gln Leu Asp Glu Val Arg Ile Leu Leu Lys Ala Gly Ala Asp Val
                        165                 170                 175
        Asn Ala Lys Asp Ile Asp Glu Gly Tyr Thr Pro Leu His Ile Ala Ala
                        180                 185                 190
        Tyr Tyr Gly His Leu Glu Ile Val Glu Val Leu Leu Lys Ala Gly Ala
                        195                 200                 205
        Asp Val Asn Ala Lys Asp Arg Tyr Gly Lys Thr Pro Leu His Leu Ala
            210                 215                 220
        Ala Ile Ser Gly His Leu Glu Ile Val Glu Val Leu Leu Lys Ala Gly
        225                 230                 235                 240
        Ala Asp Val Asn Ala Gln Asp Lys Gly Asp Thr Pro Ala Asp Leu
                        245                 250                 255
        Ala Ala Asp Tyr Gly His Gln Asp Ile Ala Glu Val Leu Gln Lys Ala
                        260                 265                 270
        Ala Gly Ser Pro Thr Pro Thr Pro Thr Thr Pro Thr Pro Thr Pro Thr
                        275                 280                 285
        Thr Pro Thr Pro Thr Pro Thr Gly Ser Asp Leu Gly Gln Lys Leu Leu
                        290                 295                 300
        Glu Ala Ala Trp Ala Gly Gln Asp Asp Glu Val Arg Glu Leu Leu Lys
        305                 310                 315                 320
        Ala Gly Ala Asp Val Asn Ala Lys Asn Ser Arg Gly Trp Thr Pro Leu
                        325                 330                 335
        His Thr Ala Ala Gln Thr Gly His Leu Glu Ile Phe Glu Val Leu Leu
                        340                 345                 350
        Lys Ala Gly Ala Asp Val Asn Ala Lys Asp Asp Lys Gly Val Thr Pro
                        355                 360                 365
        Leu His Leu Ala Ala Ala Leu Gly His Leu Glu Ile Val Glu Val Leu
                        370                 375                 380
        Leu Lys Ala Gly Ala Asp Val Asn Ala Gln Asp Ser Trp Gly Thr Thr
        385                 390                 395                 400
        Pro Ala Asp Leu Ala Ala Lys Tyr Gly His Glu Asp Ile Ala Glu Val
                        405                 410                 415
        Leu Gln Lys Ala Ala Gly Ser Pro Thr Pro Thr Pro Thr Thr Pro Thr
                        420                 425                 430
        Pro Thr Pro Thr Thr Pro Thr Pro Thr Pro Thr Gly Ser Asp Leu Gly
                        435                 440                 445
        Lys Lys Leu Leu Glu Ala Ala Arg Ala Gly Gln Asp Asp Glu Val Arg
        450                 455                 460
        Glu Leu Leu Lys Ala Gly Ala Asp Val Asn Ala Lys Asp Tyr Phe Ser
        465                 470                 475                 480
        His Thr Pro Leu His Leu Ala Ala Arg Asn Gly His Leu Lys Ile Val
                        485                 490                 495
        Glu Val Leu Leu Lys Ala Gly Ala Asp Val Asn Ala Lys Asp Phe Ala
                        500                 505                 510
        Gly Lys Thr Pro Leu His Leu Ala Ala Ala Asp Gly His Leu Glu Ile
                        515                 520                 525
        Val Glu Val Leu Leu Lys Ala Gly Ala Asp Val Asn Ala Gln Asp Ile
                        530                 535                 540
        Phe Gly Lys Thr Pro Ala Asp Ile Ala Ala Asp Ala Gly His Glu Asp
        545                 550                 555                 560
        Ile Ala Glu Val Leu Gln Lys Ala Ala
                        565
```

<210> SEQ ID NO 81
<211> LENGTH: 569
<212> TYPE: PRT
<213> ORGANISM: Artificial Sequence
<220> FEATURE:
<223> OTHER INFORMATION: DARPin protein 50

<400> SEQUENCE: 81

| | | | | | | | | | | | | | | |
|---|---|---|---|---|---|---|---|---|---|---|---|---|---|---|
| Asp | Leu | Gly | Lys | Lys | Leu | Leu | Glu | Ala | Ala | Arg | Ala | Gly | Gln | Asp | Asp |
| 1 | | | | 5 | | | | | 10 | | | | | 15 | |
| Glu | Val | Arg | Glu | Leu | Leu | Lys | Ala | Gly | Ala | Asp | Val | Asn | Ala | Lys | Asp |
| | | | 20 | | | | | 25 | | | | | 30 | | |
| Tyr | Phe | Ser | His | Thr | Pro | Leu | His | Leu | Ala | Ala | Arg | Asn | Gly | His | Leu |
| | | | 35 | | | | | 40 | | | | | 45 | | |
| Lys | Ile | Val | Glu | Val | Leu | Leu | Lys | Ala | Gly | Ala | Asp | Val | Asn | Ala | Lys |
| | 50 | | | | | 55 | | | | | 60 | | | | |
| Asp | Phe | Ala | Gly | Lys | Thr | Pro | Leu | His | Leu | Ala | Ala | Asp | Gly | His | |
| 65 | | | | | 70 | | | | | 75 | | | | | 80 |
| Leu | Glu | Ile | Val | Glu | Val | Leu | Leu | Lys | Ala | Gly | Ala | Asp | Val | Asn | Ala |
| | | | | 85 | | | | | 90 | | | | | 95 | |
| Gln | Asp | Ile | Phe | Gly | Lys | Thr | Pro | Ala | Asp | Ile | Ala | Ala | Asp | Ala | Gly |
| | | | | 100 | | | | | 105 | | | | | 110 | |
| His | Glu | Asp | Ile | Ala | Glu | Val | Leu | Gln | Lys | Ala | Ala | Gly | Ser | Pro | Thr |
| | | | 115 | | | | | 120 | | | | | 125 | | |
| Pro | Thr | Pro | Thr | Thr | Pro | Thr | Pro | Thr | Pro | Thr | Thr | Pro | Thr | Pro | Thr |
| | | 130 | | | | | 135 | | | | | 140 | | | |
| Pro | Thr | Gly | Ser | Asp | Leu | Gly | Tyr | Lys | Leu | Leu | Gln | Ala | Ala | Tyr | Asp |
| 145 | | | | | 150 | | | | | 155 | | | | | 160 |
| Gly | Gln | Leu | Asp | Glu | Val | Arg | Ile | Leu | Leu | Lys | Ala | Gly | Ala | Asp | Val |
| | | | | 165 | | | | | 170 | | | | | 175 | |
| Asn | Ala | Lys | Asp | Ser | Arg | Gly | Gln | Thr | Pro | Leu | His | Tyr | Ala | Ala | Ser |
| | | | 180 | | | | | 185 | | | | | 190 | | |
| Ile | Gly | His | Leu | Glu | Ile | Val | Glu | Val | Leu | Leu | Lys | Ala | Gly | Ala | Asp |
| | | 195 | | | | | 200 | | | | | 205 | | | |
| Val | Asn | Ala | Lys | Asp | Asp | His | Gly | Trp | Thr | Pro | Leu | His | Leu | Ala | Ala |
| | 210 | | | | | 215 | | | | | 220 | | | | |
| Trp | Ser | Gly | His | Leu | Glu | Ile | Val | Glu | Val | Leu | Leu | Lys | Ala | Gly | Ala |
| 225 | | | | | 230 | | | | | 235 | | | | | 240 |
| Asp | Val | Asn | Ala | Gln | Asp | Gln | Glu | Gly | Thr | Thr | Pro | Ala | Asp | Leu | Ala |
| | | | 245 | | | | | 250 | | | | | 255 | | |
| Ala | Val | Gln | Gly | His | Gln | Asp | Ile | Ala | Glu | Val | Leu | Gln | Lys | Ala | Ala |
| | | | 260 | | | | | 265 | | | | | 270 | | |
| Gly | Ser | Pro | Thr | Pro | Thr | Pro | Thr | Thr | Pro | Thr | Pro | Thr | Pro | Thr | Thr |
| | | 275 | | | | | 280 | | | | | 285 | | | |
| Pro | Thr | Pro | Thr | Pro | Thr | Gly | Ser | Asp | Leu | Gly | Val | Lys | Leu | Leu | Leu |
| | | 290 | | | | | 295 | | | | | 300 | | | |
| Ala | Ala | Ser | Arg | Gly | Gln | Leu | Asp | Glu | Val | Arg | Ile | Leu | Leu | Lys | Ala |
| 305 | | | | | 310 | | | | | 315 | | | | | 320 |
| Gly | Ala | Asp | Val | Asn | Ala | Lys | Asp | Ile | Asp | Glu | Gly | Tyr | Thr | Pro | Leu |
| | | | 325 | | | | | 330 | | | | | 335 | | |
| His | Ile | Ala | Ala | Tyr | Tyr | Gly | His | Leu | Glu | Ile | Val | Glu | Val | Leu | Leu |
| | | | 340 | | | | | 345 | | | | | 350 | | |
| Lys | Ala | Gly | Ala | Asp | Val | Asn | Ala | Lys | Asp | Arg | Tyr | Gly | Lys | Thr | Pro |
| | | 355 | | | | | 360 | | | | | 365 | | | |

```
Leu His Leu Ala Ala Ile Ser Gly His Leu Glu Ile Val Glu Val Leu
    370                 375                 380

Leu Lys Ala Gly Ala Asp Val Asn Ala Gln Asp Asp Lys Gly Asp Thr
385                 390                 395                 400

Pro Ala Asp Leu Ala Ala Asp Tyr Gly His Gln Asp Ile Ala Glu Val
                405                 410                 415

Leu Gln Lys Ala Ala Gly Ser Pro Thr Pro Thr Pro Thr Thr Pro Thr
            420                 425                 430

Pro Thr Pro Thr Thr Pro Thr Pro Thr Pro Thr Gly Ser Asp Leu Gly
                435                 440                 445

Gln Lys Leu Leu Glu Ala Ala Trp Ala Gly Gln Asp Asp Glu Val Arg
    450                 455                 460

Glu Leu Leu Lys Ala Gly Ala Asp Val Asn Ala Lys Asn Ser Arg Gly
465                 470                 475                 480

Trp Thr Pro Leu His Thr Ala Ala Gln Thr Gly His Leu Glu Ile Phe
                485                 490                 495

Glu Val Leu Leu Lys Ala Gly Ala Asp Val Asn Ala Lys Asp Asp Lys
            500                 505                 510

Gly Val Thr Pro Leu His Leu Ala Ala Ala Leu Gly His Leu Glu Ile
                515                 520                 525

Val Glu Val Leu Leu Lys Ala Gly Ala Asp Val Asn Ala Gln Asp Ser
            530                 535                 540

Trp Gly Thr Thr Pro Ala Asp Leu Ala Ala Lys Tyr Gly His Glu Asp
545                 550                 555                 560

Ile Ala Glu Val Leu Gln Lys Ala Ala
                565

<210> SEQ ID NO 82
<211> LENGTH: 717
<212> TYPE: PRT
<213> ORGANISM: Artificial Sequence
<220> FEATURE:
<223> OTHER INFORMATION: DARPin protein 51

<400> SEQUENCE: 82

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Pro Thr Pro Thr
                130                 135                 140

Pro Thr Gly Ser Asp Leu Gly Lys Lys Leu Leu Glu Ala Ala Arg Ala
145                 150                 155                 160
```

-continued

Gly Gln Asp Asp Glu Val Arg Glu Leu Leu Lys Ala Gly Ala Asp Val
            165                 170                 175

Asn Ala Lys Asp Tyr Phe Ser His Thr Pro Leu His Leu Ala Ala Arg
            180                 185                 190

Asn Gly His Leu Lys Ile Val Glu Val Leu Leu Lys Ala Gly Ala Asp
            195                 200                 205

Val Asn Ala Lys Asp Phe Ala Gly Lys Thr Pro Leu His Leu Ala Ala
210                 215                 220

Ala Asp Gly His Leu Glu Ile Val Glu Val Leu Leu Lys Ala Gly Ala
225                 230                 235                 240

Asp Val Asn Ala Gln Asp Ile Phe Gly Lys Thr Pro Ala Asp Ile Ala
            245                 250                 255

Ala Asp Ala Gly His Glu Asp Ile Ala Glu Val Leu Gln Lys Ala Ala
            260                 265                 270

Gly Ser Pro Thr Pro Thr Pro Thr Thr Pro Thr Pro Thr Pro Thr Thr
            275                 280                 285

Pro Thr Pro Thr Pro Thr Gly Ser Asp Leu Gly Tyr Lys Leu Leu Gln
            290                 295                 300

Ala Ala Tyr Asp Gly Gln Leu Asp Glu Val Arg Ile Leu Leu Lys Ala
305                 310                 315                 320

Gly Ala Asp Val Asn Ala Lys Asp Ser Arg Gly Gln Thr Pro Leu His
            325                 330                 335

Tyr Ala Ala Ser Ile Gly His Leu Glu Ile Val Glu Val Leu Leu Lys
            340                 345                 350

Ala Gly Ala Asp Val Asn Ala Lys Asp His Gly Trp Thr Pro Leu
            355                 360                 365

His Leu Ala Ala Trp Ser Gly His Leu Glu Ile Val Glu Val Leu Leu
            370                 375                 380

Lys Ala Gly Ala Asp Val Asn Ala Gln Asp Gln Glu Gly Thr Thr Pro
385                 390                 395                 400

Ala Asp Leu Ala Ala Val Gln Gly His Gln Asp Ile Ala Glu Val Leu
            405                 410                 415

Gln Lys Ala Ala Gly Ser Pro Thr Pro Thr Pro Thr Thr Pro Thr Pro
            420                 425                 430

Thr Pro Thr Thr Pro Thr Pro Thr Pro Thr Gly Ser Asp Leu Gly Val
            435                 440                 445

Lys Leu Leu Leu Ala Ala Ser Arg Gly Gln Leu Asp Glu Val Arg Ile
            450                 455                 460

Leu Leu Lys Ala Gly Ala Asp Val Asn Ala Lys Asp Ile Asp Glu Gly
465                 470                 475                 480

Tyr Thr Pro Leu His Ile Ala Ala Tyr Tyr Gly His Leu Glu Ile Val
            485                 490                 495

Glu Val Leu Leu Lys Ala Gly Ala Asp Val Asn Ala Lys Asp Arg Tyr
            500                 505                 510

Gly Lys Thr Pro Leu His Leu Ala Ala Ile Ser Gly His Leu Glu Ile
            515                 520                 525

Val Glu Val Leu Leu Lys Ala Gly Ala Asp Val Asn Ala Gln Asp Asp
            530                 535                 540

Lys Gly Asp Thr Pro Ala Asp Leu Ala Ala Asp Tyr Gly His Gln Asp
545                 550                 555                 560

Ile Ala Glu Val Leu Gln Lys Ala Ala Gly Ser Pro Thr Pro Thr Pro
            565                 570                 575

-continued

```
Thr Thr Pro Thr Pro Thr Pro Thr Thr Pro Thr Pro Thr Pro Thr Gly
            580             585             590

Ser Asp Leu Gly Gln Lys Leu Leu Glu Ala Ala Trp Ala Gly Gln Asp
        595                 600                 605

Asp Glu Val Arg Glu Leu Leu Lys Ala Gly Ala Asp Val Asn Ala Lys
    610                 615                 620

Asn Ser Arg Gly Trp Thr Pro Leu His Thr Ala Ala Gln Thr Gly His
625                 630                 635                 640

Leu Glu Ile Phe Glu Val Leu Leu Lys Ala Gly Ala Asp Val Asn Ala
                645                 650                 655

Lys Asp Asp Lys Gly Val Thr Pro Leu His Leu Ala Ala Ala Leu Gly
            660                 665                 670

His Leu Glu Ile Val Glu Val Leu Leu Lys Ala Gly Ala Asp Val Asn
        675                 680                 685

Ala Gln Asp Ser Trp Gly Thr Thr Pro Ala Asp Leu Ala Ala Lys Tyr
    690                 695                 700

Gly His Glu Asp Ile Ala Glu Val Leu Gln Lys Ala Ala
705                 710                 715

<210> SEQ ID NO 83
<211> LENGTH: 569
<212> TYPE: PRT
<213> ORGANISM: Artificial Sequence
<220> FEATURE:
<223> OTHER INFORMATION: DARPin protein 52

<400> SEQUENCE: 83

Asp Leu Gly Tyr Lys Leu Leu Gln Ala Ala Tyr Asp Gly Gln Leu Asp
1               5                   10                  15

Glu Val Arg Ile Leu Leu Lys Ala Gly Ala Asp Val Asn Ala Lys Asp
            20                  25                  30

Ser Arg Gly Gln Thr Pro Leu His Tyr Ala Ala Ser Ile Gly His Leu
        35                  40                  45

Glu Ile Val Glu Val Leu Leu Lys Ala Gly Ala Asp Val Asn Ala Lys
    50                  55                  60

Asp Asp His Gly Trp Thr Pro Leu His Leu Ala Ala Trp Ser Gly His
65                  70                  75                  80

Leu Glu Ile Val Glu Val Leu Leu Lys Ala Gly Ala Asp Val Asn Ala
                85                  90                  95

Gln Asp Gln Glu Gly Thr Thr Pro Ala Asp Leu Ala Ala Val Gln Gly
            100                 105                 110

His Gln Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr
    130                 135                 140

Pro Thr Gly Ser Asp Leu Gly Val Lys Leu Leu Leu Ala Ala Ser Arg
145                 150                 155                 160

Gly Gln Leu Asp Glu Val Arg Ile Leu Leu Lys Ala Gly Ala Asp Val
                165                 170                 175

Asn Ala Lys Asp Ile Asp Glu Gly Tyr Thr Pro Leu His Ile Ala Ala
            180                 185                 190

Tyr Tyr Gly His Leu Glu Ile Val Glu Val Leu Leu Lys Ala Gly Ala
        195                 200                 205

Asp Val Asn Ala Lys Asp Arg Tyr Gly Lys Thr Pro Leu His Leu Ala
    210                 215                 220
```

```
Ala Ile Ser Gly His Leu Glu Ile Val Glu Val Leu Leu Lys Ala Gly
225                 230                 235                 240

Ala Asp Val Asn Ala Gln Asp Asp Lys Gly Asp Thr Pro Ala Asp Leu
            245                 250                 255

Ala Ala Asp Tyr Gly His Gln Asp Ile Ala Glu Val Leu Gln Lys Ala
        260                 265                 270

Ala Gly Ser Pro Thr Pro Thr Pro Thr Thr Pro Thr Pro Thr Pro Thr
    275                 280                 285

Thr Pro Thr Pro Thr Pro Thr Gly Ser Asp Leu Gly Gln Lys Leu Leu
290                 295                 300

Glu Ala Ala Trp Ala Gly Gln Asp Asp Glu Val Arg Glu Leu Leu Lys
305                 310                 315                 320

Ala Gly Ala Asp Val Asn Ala Lys Asn Ser Arg Gly Trp Thr Pro Leu
            325                 330                 335

His Thr Ala Ala Gln Thr Gly His Leu Glu Ile Phe Glu Val Leu Leu
        340                 345                 350

Lys Ala Gly Ala Asp Val Asn Ala Lys Asp Asp Lys Gly Val Thr Pro
    355                 360                 365

Leu His Leu Ala Ala Ala Leu Gly His Leu Glu Ile Val Glu Val Leu
370                 375                 380

Leu Lys Ala Gly Ala Asp Val Asn Ala Gln Asp Ser Trp Gly Thr Thr
385                 390                 395                 400

Pro Ala Asp Leu Ala Ala Lys Tyr Gly His Glu Asp Ile Ala Glu Val
            405                 410                 415

Leu Gln Lys Ala Ala Gly Ser Pro Thr Pro Thr Pro Thr Thr Pro Thr
        420                 425                 430

Pro Thr Pro Thr Thr Pro Thr Pro Thr Pro Thr Gly Ser Asp Leu Gly
    435                 440                 445

Lys Lys Leu Leu Glu Ala Ala Arg Ala Gly Gln Asp Asp Glu Val Arg
450                 455                 460

Glu Leu Leu Lys Ala Gly Ala Asp Val Asn Ala Lys Asp Tyr Phe Ser
465                 470                 475                 480

His Thr Pro Leu His Leu Ala Ala Arg Asn Gly His Leu Lys Ile Val
            485                 490                 495

Glu Val Leu Leu Lys Ala Gly Ala Asp Val Asn Ala Lys Asp Phe Ala
        500                 505                 510

Gly Lys Thr Pro Leu His Leu Ala Ala Ala Asp Gly His Leu Glu Ile
    515                 520                 525

Val Glu Val Leu Leu Lys Ala Gly Ala Asp Val Asn Ala Gln Asp Ile
530                 535                 540

Phe Gly Lys Thr Pro Ala Asp Ile Ala Ala Asp Ala Gly His Glu Asp
545                 550                 555                 560

Ile Ala Glu Val Leu Gln Lys Ala Ala
                565

<210> SEQ ID NO 84
<211> LENGTH: 716
<212> TYPE: PRT
<213> ORGANISM: Artificial Sequence
<220> FEATURE:
<223> OTHER INFORMATION: DARPin protein 53

<400> SEQUENCE: 84

Asp Leu Gly Lys Lys Leu Leu Glu Ala Ala Arg Ala Gly Gln Asp Asp
1               5                   10                  15
```

```
Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Pro Thr Pro Thr
        130                 135                 140

Pro Thr Gly Ser Asp Leu Gly Tyr Lys Leu Leu Gln Ala Ala Tyr Asp
145                 150                 155                 160

Gly Gln Leu Asp Glu Val Arg Ile Leu Leu Lys Ala Gly Ala Asp Val
                165                 170                 175

Asn Ala Lys Asp Ser Arg Gly Gln Thr Pro Leu His Tyr Ala Ala Ser
            180                 185                 190

Ile Gly His Leu Glu Ile Val Glu Val Leu Leu Lys Ala Gly Ala Asp
        195                 200                 205

Val Asn Ala Lys Asp Asp His Gly Trp Thr Pro Leu His Leu Ala Ala
        210                 215                 220

Trp Ser Gly His Leu Glu Ile Val Glu Val Leu Leu Lys Ala Gly Ala
225                 230                 235                 240

Asp Val Asn Ala Gln Asp Gln Glu Gly Thr Thr Pro Ala Asp Leu Ala
                245                 250                 255

Ala Val Gln Gly His Gln Asp Ile Ala Glu Val Leu Gln Lys Ala Ala
            260                 265                 270

Gly Ser Pro Thr Pro Thr Pro Thr Thr Pro Thr Pro Thr Pro Thr Thr
        275                 280                 285

Pro Thr Pro Thr Pro Thr Gly Ser Asp Leu Gly Lys Lys Leu Leu Glu
        290                 295                 300

Ala Ala Leu Glu Gly Gln Leu Asp Glu Val Arg Glu Leu Leu Lys Ala
305                 310                 315                 320

Gly Ala Asp Val Asn Ala Lys Asp Gln Glu Gly Tyr Thr Pro Leu His
                325                 330                 335

Leu Ala Ala Ala Leu Gly His Leu Glu Ile Val Glu Val Leu Leu Lys
            340                 345                 350

Ala Gly Ala Asp Val Asn Ala Lys Asp Ser Ile Gly Arg Thr Pro Leu
        355                 360                 365

His Leu Ala Ala Tyr Lys Gly His Leu Glu Ile Val Glu Val Leu Leu
    370                 375                 380

Lys Ala Gly Ala Asp Val Asn Ala Gln Asp Leu Leu Gly Glu Thr Pro
385                 390                 395                 400

Ala Asp Leu Ala Ala Glu Gln Gly His Gln Asp Ile Ala Glu Val Leu
                405                 410                 415

Gln Lys Ala Ala Gly Ser Pro Thr Pro Thr Pro Thr Thr Pro Thr Pro
            420                 425                 430

Thr Pro Thr Thr Pro Thr Pro Thr Pro Thr Gly Ser Asp Leu Gly Val
```

-continued

```
            435                 440                 445
Lys Leu Leu Arg Ala Ala Val His Gly Gln Leu Asp Glu Val Arg Ile
            450                 455                 460
Leu Leu Lys Ala Gly Ala Asp Val Asn Ala Lys Asp Thr Asp Gly Glu
465                 470                 475                 480
Thr Pro Leu His Tyr Ala Ala Gln Phe Gly His Leu Glu Ile Val Glu
                    485                 490                 495
Val Leu Leu Lys Ala Gly Ala Asp Val Asn Ala Lys Asp Ala Tyr Gly
                500                 505                 510
Ala Thr Pro Leu His Trp Ala Ala Trp His Gly His Leu Glu Ile Val
                515                 520                 525
Glu Val Leu Leu Lys Ala Gly Ala Asp Val Asn Ala Gln Asp Val Ser
            530                 535                 540
Gly Ala Thr Pro Ala Asp Leu Ala Ala Lys Val Gly His Gln Asp Ile
545                 550                 555                 560
Ala Glu Val Leu Gln Lys Ala Ala Gly Ser Pro Thr Pro Thr Pro Thr
                565                 570                 575
Thr Pro Thr Pro Thr Pro Thr Thr Pro Thr Pro Thr Pro Thr Gly Ser
                580                 585                 590
Asp Leu Gly Gln Lys Leu Leu Glu Ala Ala Trp Ala Gly Gln Asp Asp
            595                 600                 605
Glu Val Arg Glu Leu Leu Lys Ala Gly Ala Asp Val Asn Ala Lys Asn
            610                 615                 620
Ser Arg Gly Trp Thr Pro Leu His Thr Ala Ala Gln Thr Gly His Leu
625                 630                 635                 640
Glu Ile Phe Glu Val Leu Leu Lys Ala Gly Ala Asp Val Asn Ala Lys
                645                 650                 655
Asp Asp Lys Gly Val Thr Pro Leu His Leu Ala Ala Ala Leu Gly His
                660                 665                 670
Leu Glu Ile Val Glu Val Leu Leu Lys Ala Gly Ala Asp Val Asn Ala
            675                 680                 685
Gln Asp Ser Trp Gly Thr Thr Pro Ala Asp Leu Ala Ala Lys Tyr Gly
            690                 695                 700
His Glu Asp Ile Ala Glu Val Leu Gln Lys Ala Ala
705                 710                 715

<210> SEQ ID NO 85
<211> LENGTH: 864
<212> TYPE: PRT
<213> ORGANISM: Artificial Sequence
<220> FEATURE:
<223> OTHER INFORMATION: DARPin protein 54

<400> SEQUENCE: 85

Asp Leu Gly Lys Lys Leu Leu Glu Ala Ala Arg Ala Gly Gln Asp Asp
1               5                   10                  15
Glu Val Arg Glu Leu Leu Lys Ala Gly Ala Asp Val Asn Ala Lys Asp
            20                  25                  30
Tyr Phe Ser His Thr Pro Leu His Leu Ala Ala Arg Asn Gly His Leu
            35                  40                  45
Lys Ile Val Glu Val Leu Leu Lys Ala Gly Ala Asp Val Asn Ala Lys
        50                  55                  60
Asp Phe Ala Gly Lys Thr Pro Leu His Leu Ala Ala Asp Gly His
65                  70                  75                  80
Leu Glu Ile Val Glu Val Leu Leu Lys Ala Gly Ala Asp Val Asn Ala
```

-continued

|     |     |     |     | 85  |     |     |     |     | 90  |     |     |     |     | 95  |     |
| --- | --- | --- | --- | --- | --- | --- | --- | --- | --- | --- | --- | --- | --- | --- | --- |

Gln Asp Ile Phe Gly Lys Thr Pro Ala Asp Ile Ala Ala Asp Ala Gly
                            100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Thr Pro Thr Pro Thr
        130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
            165                 170                 175

Asn Ala Lys Asp Tyr Phe Ser His Thr Pro Leu His Leu Ala Ala Arg
            180                 185                 190

Asn Gly His Leu Lys Ile Val Glu Val Leu Leu Lys Ala Gly Ala Asp
            195                 200                 205

Val Asn Ala Lys Asp Phe Ala Gly Lys Thr Pro Leu His Leu Ala Ala
210                 215                 220

Ala Asp Gly His Leu Glu Ile Val Glu Val Leu Leu Lys Ala Gly Ala
225                 230                 235                 240

Asp Val Asn Ala Gln Asp Ile Phe Gly Lys Thr Pro Ala Asp Ile Ala
                245                 250                 255

Ala Asp Ala Gly His Glu Asp Ile Ala Glu Val Leu Gln Lys Ala Ala
                260                 265                 270

Gly Ser Pro Thr Pro Thr Pro Thr Thr Pro Thr Pro Thr Thr
            275                 280                 285

Pro Thr Pro Thr Pro Thr Gly Ser Asp Leu Gly Tyr Lys Leu Leu Gln
        290                 295                 300

Ala Ala Tyr Asp Gly Gln Leu Asp Glu Val Arg Ile Leu Leu Lys Ala
305                 310                 315                 320

Gly Ala Asp Val Asn Ala Lys Asp Ser Arg Gly Gln Thr Pro Leu His
                325                 330                 335

Tyr Ala Ala Ser Ile Gly His Leu Glu Ile Val Glu Val Leu Leu Lys
            340                 345                 350

Ala Gly Ala Asp Val Asn Ala Lys Asp Asp His Gly Trp Thr Pro Leu
            355                 360                 365

His Leu Ala Ala Trp Ser Gly His Leu Glu Ile Val Glu Val Leu Leu
        370                 375                 380

Lys Ala Gly Ala Asp Val Asn Ala Gln Asp Gln Glu Gly Thr Thr Pro
385                 390                 395                 400

Ala Asp Leu Ala Ala Val Gln Gly His Gln Asp Ile Ala Glu Val Leu
                405                 410                 415

Gln Lys Ala Ala Gly Ser Pro Thr Pro Thr Pro Thr Thr Pro Thr Pro
                420                 425                 430

Thr Pro Thr Thr Pro Thr Pro Thr Pro Thr Gly Ser Asp Leu Gly Lys
            435                 440                 445

Lys Leu Leu Glu Ala Ala Leu Glu Gly Gln Leu Asp Glu Val Arg Glu
        450                 455                 460

Leu Leu Lys Ala Gly Ala Asp Val Asn Ala Lys Asp Gln Glu Gly Tyr
465                 470                 475                 480

Thr Pro Leu His Leu Ala Ala Ala Leu Gly His Leu Glu Ile Val Glu
                485                 490                 495

Val Leu Leu Lys Ala Gly Ala Asp Val Asn Ala Lys Asp Ser Ile Gly
            500                 505                 510

```
Arg Thr Pro Leu His Leu Ala Ala Tyr Lys Gly His Leu Glu Ile Val
            515                 520                 525

Glu Val Leu Leu Lys Ala Gly Ala Asp Val Asn Ala Gln Asp Leu Leu
        530                 535                 540

Gly Glu Thr Pro Ala Asp Leu Ala Ala Glu Gln Gly His Gln Asp Ile
545                 550                 555                 560

Ala Glu Val Leu Gln Lys Ala Ala Gly Ser Pro Thr Pro Thr Pro Thr
                565                 570                 575

Thr Pro Thr Pro Thr Pro Thr Thr Pro Thr Pro Thr Pro Thr Gly Ser
            580                 585                 590

Asp Leu Gly Val Lys Leu Leu Arg Ala Ala Val His Gly Gln Leu Asp
        595                 600                 605

Glu Val Arg Ile Leu Leu Lys Ala Gly Ala Asp Val Asn Ala Lys Asp
        610                 615                 620

Thr Asp Gly Glu Thr Pro Leu His Tyr Ala Ala Gln Phe Gly His Leu
625                 630                 635                 640

Glu Ile Val Glu Val Leu Leu Lys Ala Gly Ala Asp Val Asn Ala Lys
                645                 650                 655

Asp Ala Tyr Gly Ala Thr Pro Leu His Trp Ala Ala Trp His Gly His
            660                 665                 670

Leu Glu Ile Val Glu Val Leu Leu Lys Ala Gly Ala Asp Val Asn Ala
        675                 680                 685

Gln Asp Val Ser Gly Ala Thr Pro Ala Asp Leu Ala Ala Lys Val Gly
        690                 695                 700

His Gln Asp Ile Ala Glu Val Leu Gln Lys Ala Ala Gly Ser Pro Thr
705                 710                 715                 720

Pro Thr Pro Thr Thr Pro Thr Pro Thr Pro Thr Thr Pro Thr Pro Thr
                725                 730                 735

Pro Thr Gly Ser Asp Leu Gly Gln Lys Leu Leu Glu Ala Ala Trp Ala
            740                 745                 750

Gly Gln Asp Asp Glu Val Arg Glu Leu Leu Lys Ala Gly Ala Asp Val
        755                 760                 765

Asn Ala Lys Asn Ser Arg Gly Trp Thr Pro Leu His Thr Ala Ala Gln
        770                 775                 780

Thr Gly His Leu Glu Ile Phe Glu Val Leu Leu Lys Ala Gly Ala Asp
785                 790                 795                 800

Val Asn Ala Lys Asp Asp Lys Gly Val Thr Pro Leu His Leu Ala Ala
                805                 810                 815

Ala Leu Gly His Leu Glu Ile Val Glu Val Leu Leu Lys Ala Gly Ala
            820                 825                 830

Asp Val Asn Ala Gln Asp Ser Trp Gly Thr Thr Pro Ala Asp Leu Ala
        835                 840                 845

Ala Lys Tyr Gly His Glu Asp Ile Ala Glu Val Leu Gln Lys Ala Ala
        850                 855                 860

<210> SEQ ID NO 86
<211> LENGTH: 716
<212> TYPE: PRT
<213> ORGANISM: Artificial Sequence
<220> FEATURE:
<223> OTHER INFORMATION: DARPin protein 55

<400> SEQUENCE: 86

Asp Leu Gly Tyr Lys Leu Leu Gln Ala Ala Tyr Asp Gly Gln Leu Asp
1               5                   10                  15
```

```
Glu Val Arg Ile Leu Leu Lys Ala Gly Ala Asp Val Asn Ala Lys Asp
            20                  25                  30

Ser Arg Gly Gln Thr Pro Leu His Tyr Ala Ala Ser Ile Gly His Leu
        35                  40                  45

Glu Ile Val Glu Val Leu Leu Lys Ala Gly Ala Asp Val Asn Ala Lys
50                  55                  60

Asp Asp His Gly Trp Thr Pro Leu His Leu Ala Ala Trp Ser Gly His
65              70                  75                  80

Leu Glu Ile Val Glu Val Leu Leu Lys Ala Gly Ala Asp Val Asn Ala
                85                  90                  95

Gln Asp Gln Glu Gly Thr Thr Pro Ala Asp Leu Ala Ala Val Gln Gly
                100                 105                 110

His Gln Asp Ile Ala Glu Val Leu Gln Lys Ala Ala Gly Ser Pro Thr
        115                 120                 125

Pro Thr Pro Thr Thr Pro Thr Pro Thr Pro Thr Thr Pro Thr Pro Thr
        130                 135                 140

Pro Thr Gly Ser Asp Leu Gly Lys Lys Leu Leu Glu Ala Ala Leu Glu
145                 150                 155                 160

Gly Gln Leu Asp Glu Val Arg Glu Leu Leu Lys Ala Gly Ala Asp Val
                165                 170                 175

Asn Ala Lys Asp Gln Glu Gly Tyr Thr Pro Leu His Leu Ala Ala Ala
            180                 185                 190

Leu Gly His Leu Glu Ile Val Glu Val Leu Leu Lys Ala Gly Ala Asp
        195                 200                 205

Val Asn Ala Lys Asp Ser Ile Gly Arg Thr Pro Leu His Leu Ala Ala
210                 215                 220

Tyr Lys Gly His Leu Glu Ile Val Glu Val Leu Leu Lys Ala Gly Ala
225                 230                 235                 240

Asp Val Asn Ala Gln Asp Leu Leu Gly Glu Thr Pro Ala Asp Leu Ala
                245                 250                 255

Ala Glu Gln Gly His Gln Asp Ile Ala Glu Val Leu Gln Lys Ala Ala
            260                 265                 270

Gly Ser Pro Thr Pro Thr Pro Thr Thr Pro Thr Pro Thr Pro Thr Thr
        275                 280                 285

Pro Thr Pro Thr Pro Thr Gly Ser Asp Leu Gly Val Lys Leu Leu Arg
290                 295                 300

Ala Ala Val His Gly Gln Leu Asp Glu Val Arg Ile Leu Leu Lys Ala
305                 310                 315                 320

Gly Ala Asp Val Asn Ala Lys Asp Thr Asp Gly Glu Thr Pro Leu His
                325                 330                 335

Tyr Ala Ala Gln Phe Gly His Leu Glu Ile Val Glu Val Leu Leu Lys
            340                 345                 350

Ala Gly Ala Asp Val Asn Ala Lys Asp Ala Tyr Gly Ala Thr Pro Leu
        355                 360                 365

His Trp Ala Ala Trp His Gly His Leu Glu Ile Val Glu Val Leu Leu
        370                 375                 380

Lys Ala Gly Ala Asp Val Asn Ala Gln Asp Val Ser Gly Ala Thr Pro
385                 390                 395                 400

Ala Asp Leu Ala Ala Lys Val Gly His Gln Asp Ile Ala Glu Val Leu
                405                 410                 415

Gln Lys Ala Ala Gly Ser Pro Thr Pro Thr Pro Thr Thr Pro Thr Pro
            420                 425                 430
```

```
Thr Pro Thr Thr Pro Thr Pro Thr Pro Thr Gly Ser Asp Leu Gly Gln
            435                 440                 445
Lys Leu Leu Glu Ala Ala Trp Ala Gly Gln Asp Asp Glu Val Arg Glu
    450                 455                 460
Leu Leu Lys Ala Gly Ala Asp Val Asn Ala Lys Asn Ser Arg Gly Trp
465                 470                 475                 480
Thr Pro Leu His Thr Ala Ala Gln Thr Gly His Leu Glu Ile Phe Glu
                485                 490                 495
Val Leu Leu Lys Ala Gly Ala Asp Val Asn Ala Lys Asp Lys Gly
            500                 505                 510
Val Thr Pro Leu His Leu Ala Ala Leu Gly His Leu Glu Ile Val
            515                 520                 525
Glu Val Leu Leu Lys Ala Gly Ala Asp Val Asn Ala Gln Asp Ser Trp
        530                 535                 540
Gly Thr Thr Pro Ala Asp Leu Ala Ala Lys Tyr Gly His Glu Asp Ile
545                 550                 555                 560
Ala Glu Val Leu Gln Lys Ala Ala Gly Ser Pro Thr Pro Thr Pro Thr
                565                 570                 575
Thr Pro Thr Pro Thr Pro Thr Thr Pro Thr Pro Thr Pro Thr Gly Ser
            580                 585                 590
Asp Leu Gly Lys Lys Leu Leu Glu Ala Ala Arg Ala Gly Gln Asp Asp
                595                 600                 605
Glu Val Arg Glu Leu Leu Lys Ala Gly Ala Asp Val Asn Ala Lys Asp
            610                 615                 620
Tyr Phe Ser His Thr Pro Leu His Leu Ala Ala Arg Asn Gly His Leu
625                 630                 635                 640
Lys Ile Val Glu Val Leu Leu Lys Ala Gly Ala Asp Val Asn Ala Lys
                645                 650                 655
Asp Phe Ala Gly Lys Thr Pro Leu His Leu Ala Ala Ala Asp Gly His
                660                 665                 670
Leu Glu Ile Val Glu Val Leu Leu Lys Ala Gly Ala Asp Val Asn Ala
            675                 680                 685
Gln Asp Ile Phe Gly Lys Thr Pro Ala Asp Ile Ala Ala Asp Ala Gly
        690                 695                 700
His Glu Asp Ile Ala Glu Val Leu Gln Lys Ala Ala
705                 710                 715

<210> SEQ ID NO 87
<211> LENGTH: 242
<212> TYPE: PRT
<213> ORGANISM: Artificial Sequence
<220> FEATURE:
<223> OTHER INFORMATION: biotinylated extracellular domain of human CD33

<400> SEQUENCE: 87

Asp Pro Asn Phe Trp Leu Gln Val Gln Glu Ser Val Thr Val Gln Glu
1               5                   10                  15
Gly Leu Cys Val Leu Val Pro Cys Thr Phe Phe His Pro Ile Pro Tyr
            20                  25                  30
Tyr Asp Lys Asn Ser Pro Val His Gly Tyr Trp Phe Arg Glu Gly Ala
        35                  40                  45
Ile Ile Ser Gly Asp Ser Pro Val Ala Thr Asn Lys Leu Asp Gln Glu
    50                  55                  60
Val Gln Glu Glu Thr Gln Gly Arg Phe Arg Leu Leu Gly Asp Pro Ser
65                  70                  75                  80
```

```
Arg Asn Asn Cys Ser Leu Ser Ile Val Asp Ala Arg Arg Arg Asp Asn
                85                  90                  95

Gly Ser Tyr Phe Phe Arg Met Glu Arg Gly Ser Thr Lys Tyr Ser Tyr
            100                 105                 110

Lys Ser Pro Gln Leu Ser Val His Val Thr Asp Leu Thr His Arg Pro
            115                 120                 125

Lys Ile Leu Ile Pro Gly Thr Leu Glu Pro Gly His Ser Lys Asn Leu
            130                 135                 140

Thr Cys Ser Val Ser Trp Ala Cys Glu Gln Gly Thr Pro Pro Ile Phe
145                 150                 155                 160

Ser Trp Leu Ser Ala Ala Pro Thr Ser Leu Gly Pro Arg Thr Thr His
                165                 170                 175

Ser Ser Val Leu Ile Ile Thr Pro Arg Pro Gln Asp His Gly Thr Asn
                180                 185                 190

Leu Thr Cys Gln Val Lys Phe Ala Gly Ala Gly Val Thr Thr Glu Arg
                195                 200                 205

Thr Ile Gln Leu Asn Val Thr Tyr Val Pro Gln Asn Pro Thr Thr Gly
            210                 215                 220

Ile Phe Pro Gly Asp Gly Ser Gly Lys Gln Glu Thr Arg Ala Gly Val
225                 230                 235                 240

Val His

<210> SEQ ID NO 88
<211> LENGTH: 285
<212> TYPE: PRT
<213> ORGANISM: Artificial Sequence
<220> FEATURE:
<223> OTHER INFORMATION: biotinylated extracellular domain of human
      CD123

<400> SEQUENCE: 88

Thr Lys Glu Asp Pro Asn Pro Pro Ile Thr Asn Leu Arg Met Lys Ala
1               5                   10                  15

Lys Ala Gln Gln Leu Thr Trp Asp Leu Asn Arg Asn Val Thr Asp Ile
            20                  25                  30

Glu Cys Val Lys Asp Ala Asp Tyr Ser Met Pro Ala Val Asn Asn Ser
            35                  40                  45

Tyr Cys Gln Phe Gly Ala Ile Ser Leu Cys Glu Val Thr Asn Tyr Thr
        50                  55                  60

Val Arg Val Ala Asn Pro Pro Phe Ser Thr Trp Ile Leu Phe Pro Glu
65                  70                  75                  80

Asn Ser Gly Lys Pro Trp Ala Gly Ala Glu Asn Leu Thr Cys Trp Ile
                85                  90                  95

His Asp Val Asp Phe Leu Ser Cys Ser Trp Ala Val Gly Pro Gly Ala
            100                 105                 110

Pro Ala Asp Val Gln Tyr Asp Leu Tyr Leu Asn Val Ala Asn Arg Arg
            115                 120                 125

Gln Gln Tyr Glu Cys Leu His Tyr Lys Thr Asp Ala Gln Gly Thr Arg
        130                 135                 140

Ile Gly Cys Arg Phe Asp Asp Ile Ser Arg Leu Ser Ser Gly Ser Gln
145                 150                 155                 160

Ser Ser His Ile Leu Val Arg Gly Arg Ser Ala Ala Phe Gly Ile Pro
                165                 170                 175

Cys Thr Asp Lys Phe Val Val Phe Ser Gln Ile Glu Ile Leu Thr Pro
            180                 185                 190
```

```
Pro Asn Met Thr Ala Lys Cys Asn Lys Thr His Ser Phe Met His Trp
        195                 200                 205

Lys Met Arg Ser His Phe Asn Arg Lys Phe Arg Tyr Glu Leu Gln Ile
        210                 215                 220

Gln Lys Arg Met Gln Pro Val Ile Thr Glu Gln Val Arg Asp Arg Thr
225                 230                 235                 240

Ser Phe Gln Leu Leu Asn Pro Gly Thr Tyr Thr Val Gln Ile Arg Ala
                245                 250                 255

Arg Glu Arg Val Tyr Glu Phe Leu Ser Ala Trp Ser Thr Pro Gln Arg
            260                 265                 270

Phe Glu Cys Asp Gln Glu Glu Gly Ala Asn Thr Arg Ala
            275                 280                 285

<210> SEQ ID NO 89
<211> LENGTH: 142
<212> TYPE: PRT
<213> ORGANISM: Artificial Sequence
<220> FEATURE:
<223> OTHER INFORMATION: biotinylated extracellular domain of human CD70

<400> SEQUENCE: 89

Ser Leu Gly Trp Asp Val Ala Glu Leu Gln Leu Asn His Thr Gly Pro
1               5                   10                  15

Gln Gln Asp Pro Arg Leu Tyr Trp Gln Gly Gly Pro Ala Leu Gly Arg
            20                  25                  30

Ser Phe Leu His Gly Pro Glu Leu Asp Lys Gly Gln Leu Arg Ile His
        35                  40                  45

Arg Asp Gly Ile Tyr Met Val His Ile Gln Val Thr Leu Ala Ile Cys
    50                  55                  60

Ser Ser Thr Thr Ala Ser Arg His His Pro Thr Thr Leu Ala Val Gly
65                  70                  75                  80

Ile Cys Ser Pro Ala Ser Arg Ser Ile Ser Leu Leu Arg Leu Ser Phe
                85                  90                  95

His Gln Gly Cys Thr Ile Ala Ser Gln Arg Leu Thr Pro Leu Ala Arg
            100                 105                 110

Gly Asp Thr Leu Cys Thr Asn Leu Thr Gly Thr Leu Leu Pro Ser Arg
        115                 120                 125

Asn Thr Asp Glu Thr Phe Phe Gly Val Gln Trp Val Arg Pro
    130                 135                 140

<210> SEQ ID NO 90
<211> LENGTH: 1308
<212> TYPE: DNA
<213> ORGANISM: Artificial Sequence
<220> FEATURE:
<223> OTHER INFORMATION: Nucleic acid encoding domain of SEQ ID NO 58

<400> SEQUENCE: 90
atgagaggat cgcatcacca tcaccatcac ggttccgacc tgggtaaaaa gctgttggag      60
gccgcgttag agggtcaatt ggatgaagtt cgtgaactgt aaaagcggg cgccgatgta     120 aacgctaaag accaggaggg gtacactcct ttgcatctgg cagcagctct tggtcatctg     180
gaaattgtcg aggtgctgtt aaaggcagga gcagatgtaa atgcaaagga ctctattgga     240
cgtacaccac tgcacttggc tgcctacaaa ggtcacctgg aaattgtgga agtcttactg     300
aaagcgggcg ctgacgttaa cgcccaagac ctgctggggg aaacgccagc cgacctggcc     360
gccgagcagg gacatcagga tattgctgaa gttctgcaaa aggcagcagg ctcgccgact     420
```

```
ccgaccccga ccaccccaac tccaacaccg accaccccga cccctacccc aacaggatcc    480
gacctgggtg ttaaactttt gttagctgca tctcgtggtc aactggatga ggtgcgtatt    540
ttgctgaaag cgggtgcaga tgttaacgca aaggacatcg atgaaggata tacgccatta    600
cacattgcag catattatgg tcatttagag atcgtagagg ttcttttgaa ggcaggagcc    660
gatgttaacg ccaaggaccg ttatggaaag accccgttac atttagccgc aattagtggg    720
catcttgaaa ttgtcgaagt tttattaaag gctgggctg atgtaaatgc tcaggatgac    780
aagggcgaca ctcccgcaga tctggcggca gactatgggc accaggatat tgctgaagtt    840
ctgcagaagg ctgcggggag tccaaccccg acgccaacca cacccactcc tacgcctaca    900
actccaactc cgacgcctac cggatcagat ctgggtcaaa agttgttgga agctgcctgg    960
gcgggacagg atgatgaggt gcgcgaatta cttaaggcgg gagcagacgt gaatgcgaaa   1020
aactctcgtg gctggacacc actgcacacg gccgcgcaaa ctggtcacct tgaaattttc   1080
gaagtgcttc tgaaggcagg cgcagatgta aacgccaagg atgacaaagg ggtaacaccg   1140
cttcatctgg ctgctgcact gggacatctt gagattgtcg aagtactgct taaggcaggt   1200
gctgacgtaa acgctcagga ttcatggggg accacaccgg cggacctggc ggctaaatac   1260
ggacatgaag atattgctga agttcttcag aaggcagcat aatgatag               1308
```

<210> SEQ ID NO 91
<211> LENGTH: 1308
<212> TYPE: DNA
<213> ORGANISM: Artificial Sequence
<220> FEATURE:
<223> OTHER INFORMATION: Nucleic acid encoding domain of SEQ ID NO 59

<400> SEQUENCE: 91

```
atgagaggat cgcatcacca tcaccatcac ggatccgacc tgggttataa acttcttcaa     60
gcggcctatg atgggcagct tgatgaggta cgcattttgt taaaggccgg cgcagatgtc    120
aacgcgaaag atagtcgcgg acagacgccc cttcattacg ccgcatcaat cggccatctg    180
gaaattgtag aggtactgct taaagccggt gctgatgtaa acgctaagga cgaccacgga    240
tggacgccac ttcatcttgc cgcgtggagt ggacacttgg agattgtcga agtcttgtta    300
aaagcgggcg ctgacgttaa cgcacaagac caggaaggta cgacgccagc agacttggct    360
gctgtccaag gcaccaggac cattgctgaa gttctgcaga aggcagcagg cagccctaca    420
cctacgccga ctacgcctac gccgactccg actaccccga ctccgacccc gaccggatca    480
gacctgggtt ggaaactgct gctggctgct tctcgtggtc aggacgacga agttcgtatc    540
ctgctggctg ctggcgccga cgttaatgct aaagacatcg acgaaggtta cactccgctg    600
cacatcgctg cttactacgg tcacctggaa atcgttgaag ttctgctgaa ggctggtgct    660
gacgttaatg ctaaagaccg ttacggtaaa actccgctgc acctggctgc tatctctggt    720
cacgaggata tcgctgaagt tctgctgaag gctggtgctg acgttaacgc tcaggacgac    780
aaaggtgaca ctccggctga tctggctgct gactacggtc acgaggatat cgctgaagtt    840
ctgcagaagg cagcaggttc cccgaccccc acgccaacga ctccgacccc aactccaacg    900
accccctacc cgaccccgac cggatcagac ctgggtcaaa agttgttgga agctgcctgg    960
gcgggacagg atgatgaggt gcgcgaatta cttaaggcgg gagcagacgt gaatgcgaaa   1020
aactctcgtg gctggacacc actgcacacg gccgcgcaaa ctggtcacct tgaaattttc   1080
gaagtgcttc tgaaggcagg cgcagatgta aacgccaagg atgacaaagg ggtaacaccg   1140
cttcatctgg ctgctgcact gggacatctt gagattgtcg aagtactgct taaggcaggt   1200
```

```
gctgacgtaa acgctcagga ttcatgggg accacaccgg cggacctggc ggctaaatac    1260
ggacatgaag atattgctga agttctgcag aaggcggcat aatgatag               1308

<210> SEQ ID NO 92
<211> LENGTH: 1308
<212> TYPE: DNA
<213> ORGANISM: Artificial Sequence
<220> FEATURE:
<223> OTHER INFORMATION: Nucleic acid encoding domain of SEQ ID NO 60

<400> SEQUENCE: 92
atgagaggat cgcatcacca tcaccatcac ggatccgacc tgggttataa acttcttcaa    60
gcggcctatg atgggcagct tgatgaggta cgcattttgt taaaggccgg cgcagatgtc   120
aacgcgaaag atagtcgcgg acagacgccc cttcattacg ccgcatcaat cggccatctg   180
gaaattgtag aggtactgct taaagccggt gctgatgtaa acgctaagga cgaccacgga   240
tggacgccac ttcatcttgc cgcgtggagt ggacacttgg agattgtcga agtcttgtta   300
aaagcgggcg ctgacgttaa cgcacaagac caggaaggta cgacgccagc agacttggct   360
gctgtccaag gcaccagga cattgctgaa gttctgcaga aggcagcagg cagccctaca   420
cctacgccga ctacgcctac gccgactccg actaccccga ctccgacccc gaccggatca   480
gacctgggtg ttaaactttt gttagctgca tctcgtggtc aactggatga ggtgcgtatt   540
ttgctgaaag cgggtgcaga tgttaacgca aaggacatcg atgaaggata tacgccatta   600
cacattgcag catattatgg tcatttagag atcgtagagg ttcttttgaa ggcaggagcc   660
gatgttaacg ccaaggaccg ttatggaaag accccgttac atttagccgc aattagtggg   720
catcttgaaa ttgtcgaagt tttattaaag gctggggctg atgtaaatgc tcaggatgac   780
aagggcgaca ctcccgcaga tctggcggca gactatgggc accaggatat tgctgaagtt   840
ctgcagaagg cagcaggttc cccgacccct acgccaacga ctccgacccc aactccaacg   900 accccctaccc cgaccccgac cggatcagac ctgggtcaaa agttgttgga agctgcctgg   960
gcgggacagg atgatgaggt gcgcgaatta cttaaggcgg gagcagacgt gaatgcgaaa  1020
aactctcgtg gctggacacc actgcacacg gccgcgcaaa ctggtcacct tgaaattttc  1080
gaagtgcttc tgaaggcagg cgcagatgta aacgccaagg atgacaaagg ggtaacaccg  1140
cttcatctgg ctgctgcact gggacatctt gagattgtcg aagtactgct taaggcaggt  1200
gctgacgtaa acgctcagga ttcatgggg accacaccgg cggacctggc ggctaaatac  1260
ggacatgaag atattgctga agttctgcag aaggcggcat aatgatag               1308

<210> SEQ ID NO 93
<211> LENGTH: 1749
<212> TYPE: DNA
<213> ORGANISM: Artificial Sequence
<220> FEATURE:
<223> OTHER INFORMATION: Nucleic acid encoding domain of SEQ ID NO 61

<400> SEQUENCE: 93
atgagaggat cgcatcacca tcaccatcac ggatccgacc tgggttataa acttcttcaa    60
gcggcctatg atgggcagct tgatgaggta cgcattttgt taaaggccgg cgcagatgtc   120
aacgcgaaag atagtcgcgg acagacgccc cttcattacg ccgcatcaat cggccatctg   180
gaaattgtag aggtactgct taaagccggt gctgatgtaa acgctaagga cgaccacgga   240
tggacgccac ttcatcttgc cgcgtggagt ggacacttgg agattgtcga agtcttgtta   300
```

| | |
|---|---:|
| aaagcgggcg ctgacgttaa cgcacaagac caggaaggta cgacgccagc agacttggct | 360 |
| gctgtccaag ggcaccagga cattgctgaa gttctgcaga aggcagcagg ctcgccgact | 420 |
| ccgaccccga ccaccccaac tccaacaccg accaccccga ccctaccccc aacaggatcc | 480 |
| gacctgggta agaagctgct ggaagctgct ctggaaggtc aggatgatga agttcgtgaa | 540 |
| ctgctgaaag caggcgccga tgttaatgca aaagatcaag agggctacac cccactgcat | 600 |
| ctggctgctg ctctgggtca cctggaaatt gttgaagttc tgctgaaagc cggtgcagat | 660 |
| gttaatgcaa aagattctat cggcagaacc ccgctgcatc tggctgctta aagggtcac | 720 |
| ctggaaattg ttgaagttct gctgaaagcc ggtgcagatg ttaacgcaca ggatctgctg | 780 |
| ggcgaaaccc ctgccgatct ggcagctgaa caaggtcatg aagatattgc agaagtgctg | 840 |
| cagaaggcag caggcagccc tacacctacg ccgactacgc ctacgccgac tccgactacc | 900 |
| ccgactccga ccccgaccgg atcagacctg ggtgttaaac tgctgcgtgc tgctttccat | 960 |
| ggtcaggacg acgaagttcg tatcctgctg gctgctggcg ctgacgttaa tgctaaagac | 1020 |
| actgacggtg aaactccgct gcactacgct gctcagttcg gtcacctgga aatcgttgaa | 1080 |
| gttctgctga aggctggtgc tgacgttaat gctaaagacg cttacggtgc tactccgctg | 1140 |
| cactgggctg cttggcatgg tcacctggaa atcgttgaag ttctgctgaa ggctggtgct | 1200 |
| gacgtcaacg ctcaggacgt ttctggtgct actccggctg atctggctgc taaagttggt | 1260 |
| cacgaggata tcgctgaagt tctgcagaag gcagcaggtt ccccgacccc tacgccaacg | 1320 |
| actccgaccc caactccaac gacccctacc ccgacccga ccggatcaga cctgggtcaa | 1380 |
| aagttgttgg aagctgcctg gcgggacagg atgatgagg tgcgcgaatt acttaaggcg | 1440 |
| ggagcagacg tgaatgcgaa aaactctcgt ggctggacac cactgcacac ggccgcgcaa | 1500 |
| actggtcacc ttgaaatttt cgaagtgctt ctgaaggcag cgcagatgt aaacgccaag | 1560 |
| gatgacaaag gggtaacacc gcttcatctg gctgctgcac tgggacatct tgagattgtc | 1620 |
| gaagtactgc ttaaggcagg tgctgacgta aacgctcagg attcatgggg gaccacaccg | 1680 |
| gcggacctgg cggctaaata cggacatgaa gatattgctg aagttctgca gaaggcggca | 1740 |
| taatgatag | 1749 |

<210> SEQ ID NO 94
<211> LENGTH: 1749
<212> TYPE: DNA
<213> ORGANISM: Artificial Sequence
<220> FEATURE:
<223> OTHER INFORMATION: Nucleic acid encoding domain of SEQ ID NO 62

<400> SEQUENCE: 94

| | |
|---|---:|
| atgagaggat cgcatcacca tcaccatcac ggatccgacc tgggttataa acttcttcaa | 60 |
| gcggcctatg atgggcagct tgatgaggta cgcattttgt taaaggccgg cgcagatgtc | 120 |
| aacgcgaaag atagtcgcgg acagacgccc cttcattacg ccgcatcaat cggccatctg | 180 |
| gaaattgtag aggtactgct taaagccggt gctgatgtaa acgctaagga cgaccacgga | 240 |
| tggacgccac ttcatcttgc cgcgtggagt ggacacttgg agattgtcga agtcttgtta | 300 |
| aaagcgggcg ctgacgttaa cgcacaagac caggaaggta cgacgccagc agacttggct | 360 |
| gctgtccaag ggcaccagga cattgctgaa gttctgcaga aggcagcagg cagccctaca | 420 |
| cctacgccga ctacgcctac gccgactccg actaccccga ctccgacccc gaccggatca | 480 |
| gacctgggta aaagctgtt ggaggccgcg ttagagggtc aattggatga agttcgtgaa | 540 |
| ctgttaaaag cgggcgccga tgtaaacgct aaagaccagg aggggtacac tcctttgcat | 600 |

-continued

```
ctggcagcag ctcttggtca tctggaaatt gtcgaggtgc tgttaaaggc aggagcagat    660
gtaaatgcaa aggactctat tggacgtaca ccactgcact ggctgcctaa caaaggtcac    720
ctggaaattg tggaagtctt actgaaagcg ggcgctgacg ttaacgccca agacctgctg    780
ggggaaacgc cagccgacct ggccgccgag cagggacatc aggatattgc tgaagttctg    840
cagaaggcag caggctcgcc aacgccgacc cctacaacgc caaccccgac accaactaca    900
ccgaccccca caccaacggg atcagacctg gtgttaagt  tgcttcgtgc tgccgtccac    960
ggtcaattgg atgaagtacg catccttctg aaggctggtg cagacgtgaa cgcgaaagac   1020
actgacggca aaccccccct tcattacgcg gcacaattcg ccacttgga  gatcgttgag   1080 gtccttctga agccggcgc  agacgtgaat gcaaaggatg cttatgggc  tacgccgtta   1140 cattgggctg cttggcacgg ccatcttgag attgttgagg tcctgttgaa agcggggcg    1200 gatgtaaacg ctcaggacgt atccggcgcg acacctgctg acttagcagc taaagtcgga   1260
caccaggata ttgctgaagt tctgcagaag gcagcaggtt ccccgacccc tacgccaacg   1320
actccgaccc caactccaac gacccctacc ccgaccccga ccggatcaga cctgggtcaa   1380
aagttgttgg aagctgcctg gcgggacaca gatgatgagg tgcgcgaatt acttaaggcg   1440
ggagcagacg tgaatgcgaa aaactctcgt ggctggacac cactgcacac ggccgcgcaa   1500
actggtcacc ttgaaatttt cgaagtgctt ctgaaggcag gcgcagatgt aaacgccaag   1560
gatgacaaag gggtaacacc gcttcatctg gctgctgcac tgggacatct tgagattgtc   1620
gaagtactgc ttaaggcagg tgctgacgta aacgctcagg attcatgggg gaccacaccg   1680
gcggacctgg cggctaaata cggacatgaa gatattgctg aagttctgca gaaggcggca   1740
taatgatag                                                           1749
```

```
<210> SEQ ID NO 95
<211> LENGTH: 865
<212> TYPE: PRT
<213> ORGANISM: Artificial Sequence
<220> FEATURE:
<223> OTHER INFORMATION: DARPin protein 56

<400> SEQUENCE: 95

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr
    130                 135                 140

Pro Thr Gly Ser Asp Leu Gly Lys Lys Leu Leu Glu Ala Ala Arg Ala
```

```
145                 150                 155                 160
Gly Gln Asp Asp Glu Val Arg Glu Leu Leu Lys Ala Gly Ala Asp Val
                165                 170                 175

Asn Ala Lys Asp Tyr Phe Ser His Thr Pro Leu His Leu Ala Ala Arg
            180                 185                 190

Asn Gly His Leu Lys Ile Val Glu Val Leu Leu Lys Ala Gly Ala Asp
        195                 200                 205

Val Asn Ala Lys Asp Phe Ala Gly Lys Thr Pro Leu His Leu Ala Ala
    210                 215                 220

Ala Asp Gly His Leu Glu Ile Val Glu Val Leu Leu Lys Ala Gly Ala
225                 230                 235                 240

Asp Val Asn Ala Gln Asp Ile Phe Gly Lys Thr Pro Ala Asp Ile Ala
                245                 250                 255

Ala Asp Ala Gly His Glu Asp Ile Ala Glu Val Leu Gln Lys Ala Ala
            260                 265                 270

Gly Ser Pro Thr Pro Thr Pro Thr Thr Pro Thr Pro Thr Pro Thr Thr
        275                 280                 285

Pro Thr Pro Thr Pro Thr Gly Ser Asp Leu Gly Val Lys Leu Leu Leu
    290                 295                 300

Ala Ala Glu Arg Gly Gln Leu Asp Glu Val Arg Ile Leu Leu Lys Ala
305                 310                 315                 320

Gly Ala Asp Val Asn Ala Lys Asp Ile Ala Glu Gly Tyr Thr Pro Leu
                325                 330                 335

His Ile Ala Ala Tyr Gln Gly His Leu Glu Ile Val Glu Val Leu Leu
            340                 345                 350

Lys Ala Gly Ala Asp Val Asn Ala Lys Asp Arg Tyr Gly Lys Thr Pro
        355                 360                 365

Leu His Leu Ala Ala Ile Gly Gly His Leu Glu Ile Val Glu Val Leu
    370                 375                 380

Leu Lys Ala Gly Ala Asp Val Asn Ala Gln Asp Asn Lys Gly Ser Thr
385                 390                 395                 400

Pro Ala Asp Leu Ala Ala Asp Tyr Gly His Gln Asp Ile Ala Glu Val
                405                 410                 415

Leu Gln Lys Ala Ala Gly Ser Pro Thr Pro Thr Pro Thr Thr Pro Thr
            420                 425                 430

Pro Thr Pro Thr Thr Pro Thr Pro Thr Gly Ser Asp Leu Gly
        435                 440                 445

Lys Lys Leu Leu Glu Ala Ala Leu Glu Gly Gln Leu Asp Glu Val Arg
    450                 455                 460

Glu Leu Leu Lys Ala Gly Ala Asp Val Asn Ala Lys Asp Gln Glu Gly
465                 470                 475                 480

Tyr Thr Pro Leu His Leu Ala Ala Ala Leu Gly His Leu Glu Ile Val
                485                 490                 495

Glu Val Leu Leu Lys Ala Gly Ala Asp Val Asn Ala Lys Asp Gln Ile
            500                 505                 510

Gly Arg Thr Pro Leu His Leu Ala Ala Tyr Lys Gly His Leu Glu Ile
        515                 520                 525

Val Glu Val Leu Leu Lys Ala Gly Ala Asp Val Asn Ala Gln Asp Ile
    530                 535                 540

Ile Gly Gln Thr Pro Ala Asp Leu Ala Ala Gln Arg Gly His Gln Asp
545                 550                 555                 560

Ile Ala Glu Val Leu Gln Lys Ala Ala Gly Ser Pro Thr Pro Thr Pro
                565                 570                 575
```

Thr Thr Pro Thr Pro Thr Pro Thr Thr Pro Thr Pro Thr Gly
            580              585              590

Ser Asp Leu Gly Ile Lys Leu Leu Thr Ala Ala Tyr Asp Gly Gln Leu
        595                 600                 605

Asp Glu Val Arg Ile Leu Leu Lys Ala Gly Ala Asp Val Asn Ala Lys
610                 615                 620

Asp Leu Arg Gly Gln Thr Pro Leu His Tyr Ala Ala Gly Leu Gly His
625                 630                 635                 640

Leu Glu Ile Val Glu Val Leu Leu Lys Ala Gly Ala Asp Val Asn Ala
                645                 650                 655

Lys Asp Leu His Gly Trp Thr Pro Leu His Leu Ala Ala Trp Ser Gly
            660                 665                 670

His Leu Glu Ile Val Glu Val Leu Leu Lys Ala Gly Ala Asp Val Asn
        675                 680                 685

Ala Gln Asp Val Glu Gly Val Thr Pro Ala Asp Leu Ala Ala Val Gln
    690                 695                 700

Gly His Gln Asp Ile Ala Glu Val Leu Gln Lys Ala Ala Gly Ser Pro
705                 710                 715                 720

Thr Pro Thr Pro Thr Thr Pro Thr Pro Thr Pro Thr Thr Pro Thr Pro
                725                 730                 735

Thr Pro Thr Gly Ser Asp Leu Gly Gln Lys Leu Leu Glu Ala Ala Trp
            740                 745                 750

Ala Gly Gln Asp Asp Glu Val Arg Glu Leu Leu Lys Ala Gly Ala Asp
        755                 760                 765

Val Asn Ala Lys Asn Ser Arg Gly Trp Thr Pro Leu His Thr Ala Ala
770                 775                 780

Gln Thr Gly His Leu Glu Ile Phe Glu Val Leu Leu Lys Ala Gly Ala
785                 790                 795                 800

Asp Val Asn Ala Lys Asn Asp Lys Arg Val Thr Pro Leu His Leu Ala
                805                 810                 815

Ala Ala Leu Gly His Leu Glu Ile Val Glu Val Leu Leu Lys Ala Gly
            820                 825                 830

Ala Asp Val Asn Ala Arg Asp Ser Trp Gly Thr Thr Pro Ala Asp Leu
        835                 840                 845

Ala Ala Lys Tyr Gly His Gln Asp Ile Ala Glu Val Leu Gln Lys Ala
    850                 855                 860

Ala
865

<210> SEQ ID NO 96
<211> LENGTH: 847
<212> TYPE: PRT
<213> ORGANISM: Artificial Sequence
<220> FEATURE:
<223> OTHER INFORMATION: DARPin protein 57

<400> SEQUENCE: 96

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

```
Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
            85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Thr Pro Thr Pro Thr
            130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Tyr Phe Ser His Thr Pro Leu His Leu Ala Ala Arg
            180                 185                 190

Asn Gly His Leu Lys Ile Val Glu Val Leu Leu Lys Ala Gly Ala Asp
            195                 200                 205

Val Asn Ala Lys Asp Phe Ala Gly Lys Thr Pro Leu His Leu Ala Ala
210                 215                 220

Ala Asp Gly His Leu Glu Ile Val Glu Val Leu Leu Lys Ala Gly Ala
225                 230                 235                 240

Asp Val Asn Ala Gln Asp Ile Phe Gly Lys Thr Pro Ala Asp Ile Ala
            245                 250                 255

Ala Asp Ala Gly His Glu Asp Ile Ala Glu Val Leu Gln Lys Ala Ala
            260                 265                 270

Gly Ser Pro Thr Pro Thr Pro Thr Thr Pro Thr Pro Thr Pro Thr Thr
            275                 280                 285

Pro Thr Pro Thr Pro Thr Gly Ser Asp Leu Gly Ile Lys Leu Leu Thr
            290                 295                 300

Ala Ala Tyr Asp Gly Gln Leu Asp Glu Val Arg Ile Leu Leu Lys Ala
305                 310                 315                 320

Gly Ala Asp Val Asn Ala Lys Asp Leu Arg Gly Gln Thr Pro Leu His
            325                 330                 335

Tyr Ala Ala Gly Leu Gly His Leu Glu Ile Val Glu Val Leu Leu Lys
            340                 345                 350

Ala Gly Ala Asp Val Asn Ala Lys Asp Leu His Gly Trp Thr Pro Leu
            355                 360                 365

His Leu Ala Ala Trp Ser Gly His Leu Glu Ile Val Glu Val Leu Leu
            370                 375                 380

Lys Ala Gly Ala Asp Val Asn Ala Gln Asp Val Glu Gly Val Thr Pro
385                 390                 395                 400

Ala Asp Leu Ala Ala Val Gln Gly His Gln Asp Ile Ala Glu Val Leu
            405                 410                 415

Gln Lys Ala Ala Gly Ser Pro Thr Pro Thr Pro Thr Thr Pro Thr Pro
            420                 425                 430

Thr Pro Thr Thr Pro Thr Pro Thr Pro Thr Gly Ser Asp Leu Gly Lys
            435                 440                 445

Lys Leu Leu Gln Ala Ala Leu Glu Gly Gln Leu Asp Glu Val Arg Glu
            450                 455                 460

Leu Leu Lys Ala Gly Ala Asp Val Asn Ala Lys Asp Ile Glu Gly Tyr
465                 470                 475                 480
```

Thr Pro Leu His Leu Ala Ala Leu Gly His Leu Glu Ile Val Glu
            485                 490                 495

Val Leu Leu Lys Ala Gly Ala Asp Val Asn Ala Lys Asp Gln Ile Gly
        500                 505                 510

Arg Thr Pro Leu His Leu Ala Ala Tyr Lys Gly His Leu Glu Ile Val
        515                 520                 525

Glu Val Leu Leu Lys Ala Gly Ala Asp Val Asn Ala Gln Asp Ile Ile
        530                 535                 540

Gly Gln Thr Pro Ala Asp Leu Ala Ala Gln Arg Gly His Gln Asp Ile
545                 550                 555                 560

Ala Glu Val Leu Gln Lys Ala Ala Gly Ser Pro Thr Pro Thr Pro Thr
                565                 570                 575

Thr Pro Thr Pro Thr Pro Thr Thr Pro Thr Pro Thr Pro Thr Gly Ser
            580                 585                 590

Asp Leu Gly Lys Lys Leu Leu Leu Ala Ala Glu Arg Gly Gln Leu Asp
            595                 600                 605

Glu Val Arg Ile Leu Leu Lys Ala Gly Ala Asp Val Asn Ala Lys Asp
        610                 615                 620

Arg Ala Glu Gly Tyr Thr Pro Leu His Ile Ala Ala Tyr Gln Gly His
625                 630                 635                 640

Leu Glu Ile Val Glu Val Leu Leu Lys Ala Gly Ala Asp Val Asn Ala
                645                 650                 655

Lys Asp Arg Tyr Gly Lys Thr Pro Leu His Leu Ala Ala Ile Ser Gly
            660                 665                 670

His Leu Glu Ile Val Glu Val Leu Leu Lys Ala Gly Ala Asp Val Asn
        675                 680                 685

Ala Gln Asp Asn Lys Gly Ser Thr Pro Ala Asp Leu Ala Ala Asp Tyr
690                 695                 700

Gly His Gln Asp Ile Ala Glu Val Leu Gln Lys Ala Ala Gly Ser Pro
705                 710                 715                 720

Thr Gly Ser Asp Leu Gly Gln Lys Leu Leu Glu Ala Ala Trp Ala Gly
            725                 730                 735

Gln Asp Asp Glu Val Arg Glu Leu Leu Lys Ala Gly Ala Asp Val Asn
        740                 745                 750

Ala Lys Asn Ser Arg Gly Trp Thr Pro Leu His Thr Ala Ala Gln Thr
755                 760                 765

Gly His Leu Glu Ile Phe Glu Val Leu Leu Lys Ala Gly Ala Asp Val
        770                 775                 780

Asn Ala Lys Asn Asp Lys Arg Val Thr Pro Leu His Leu Ala Ala Ala
785                 790                 795                 800

Leu Gly His Leu Glu Ile Val Glu Val Leu Leu Lys Ala Gly Ala Asp
                805                 810                 815

Val Asn Ala Arg Asp Ser Trp Gly Thr Thr Pro Ala Asp Leu Ala Ala
            820                 825                 830

Lys Tyr Gly His Gln Asp Ile Ala Glu Val Leu Gln Lys Ala Ala
        835                 840                 845

<210> SEQ ID NO 97
<211> LENGTH: 847
<212> TYPE: PRT
<213> ORGANISM: Artificial Sequence
<220> FEATURE:
<223> OTHER INFORMATION: DARPin protein 58

<400> SEQUENCE: 97

-continued

```
Asp Leu Gly Lys Lys Leu Leu Glu Ala Ala Arg Ala Gly Gln Asp Asp
1               5                   10                  15
Glu Val Arg Glu Leu Leu Lys Ala Gly Ala Asp Val Asn Ala Lys Asp
            20                  25                  30
Tyr Phe Ser His Thr Pro Leu His Leu Ala Ala Arg Asn Gly His Leu
            35                  40                  45
Lys Ile Val Glu Val Leu Leu Lys Ala Gly Ala Asp Val Asn Ala Lys
50                  55                  60
Asp Phe Ala Gly Lys Thr Pro Leu His Leu Ala Ala Asp Gly His
65                  70                  75                  80
Leu Glu Ile Val Glu Val Leu Leu Lys Ala Gly Ala Asp Val Asn Ala
                85                  90                  95
Gln Asp Ile Phe Gly Lys Thr Pro Ala Asp Ile Ala Ala Asp Ala Gly
                100                 105                 110
His Glu Asp Ile Ala Glu Val Leu Gln Lys Ala Ala Gly Ser Pro Thr
            115                 120                 125
Pro Thr Pro Thr Pro Thr Pro Thr Pro Thr Pro Thr Pro Thr Pro Thr
            130                 135                 140
Pro Thr Gly Ser Asp Leu Gly Lys Lys Leu Leu Glu Ala Ala Arg Ala
145                 150                 155                 160
Gly Gln Asp Asp Glu Val Arg Glu Leu Leu Lys Ala Gly Ala Asp Val
                165                 170                 175
Asn Ala Lys Asp Tyr Phe Ser His Thr Pro Leu His Leu Ala Ala Arg
                180                 185                 190
Asn Gly His Leu Lys Ile Val Glu Val Leu Leu Lys Ala Gly Ala Asp
            195                 200                 205
Val Asn Ala Lys Asp Phe Ala Gly Lys Thr Pro Leu His Leu Ala Ala
            210                 215                 220
Ala Asp Gly His Leu Glu Ile Val Glu Val Leu Leu Lys Ala Gly Ala
225                 230                 235                 240
Asp Val Asn Ala Gln Asp Ile Phe Gly Lys Thr Pro Ala Asp Ile Ala
                245                 250                 255
Ala Asp Ala Gly His Glu Asp Ile Ala Glu Val Leu Gln Lys Ala Ala
                260                 265                 270
Gly Ser Pro Thr Pro Thr Pro Thr Pro Thr Pro Thr Pro Thr Pro Thr
            275                 280                 285
Pro Thr Pro Thr Pro Thr Gly Ser Asp Leu Gly Ile Lys Leu Leu Thr
            290                 295                 300
Ala Ala Tyr Asp Gly Gln Leu Asp Glu Val Arg Ile Leu Leu Lys Ala
305                 310                 315                 320
Gly Ala Asp Val Asn Ala Lys Asp Leu Arg Gly Gln Thr Pro Leu His
                325                 330                 335
Tyr Ala Ala Gly Leu Gly His Leu Glu Ile Val Glu Val Leu Leu Lys
            340                 345                 350
Ala Gly Ala Asp Val Asn Ala Lys Asp Leu His Gly Trp Thr Pro Leu
            355                 360                 365
His Leu Ala Ala Trp Ser Gly His Leu Glu Ile Val Glu Val Leu Leu
            370                 375                 380
Lys Ala Gly Ala Asp Val Asn Ala Gln Asp Val Gly Val Thr Pro
385                 390                 395                 400
Ala Asp Leu Ala Ala Val Gln Gly His Gln Asp Ile Ala Glu Val Leu
                405                 410                 415
Gln Lys Ala Ala Gly Ser Pro Thr Pro Thr Pro Thr Thr Pro Thr Pro
```

-continued

```
            420                 425                 430
Thr Pro Thr Pro Thr Pro Thr Pro Thr Gly Ser Asp Leu Gly Trp
        435                 440                 445
Lys Leu Leu Asp Ala Ala Glu Ile Gly Gln Leu Asp Glu Val Arg Ile
    450                 455                 460
Leu Leu Lys Ala Gly Ala Asp Val Asn Ala Lys Asp Lys Gln Gly Ile
465                 470                 475                 480
Thr Pro Leu His Ile Ala Ala His Gly His Leu Glu Ile Val Glu
            485                 490                 495
Val Leu Leu Lys Ala Gly Ala Asp Val Asn Ala Lys Asp Glu Ile Gly
        500                 505                 510
Arg Thr Pro Leu His Leu Ala Ala Phe Lys Gly His Leu Glu Ile Val
        515                 520                 525
Glu Val Leu Leu Lys Ala Gly Ala Asp Val Asn Ala Gln Asp Ile Ile
        530                 535                 540
Gly Glu Thr Pro Ala Asp Leu Ala Ala Val Arg Gly His Gln Asp Ile
545                 550                 555                 560
Ala Glu Val Leu Gln Lys Ala Ala Gly Ser Pro Thr Pro Thr Pro Thr
                565                 570                 575
Thr Pro Thr Pro Thr Pro Thr Thr Pro Thr Pro Thr Pro Thr Gly Ser
            580                 585                 590
Asp Leu Gly Val Lys Leu Leu Ala Ala Glu Arg Gly Gln Leu Asp
        595                 600                 605
Glu Val Arg Ile Leu Leu Lys Ala Gly Ala Asp Val Asn Ala Lys Asp
        610                 615                 620
Ile Ala Glu Gly Tyr Thr Pro Leu His Ile Ala Ala Tyr Gln Gly His
625                 630                 635                 640
Leu Glu Ile Val Glu Val Leu Leu Lys Ala Gly Ala Asp Val Asn Ala
                645                 650                 655
Lys Asp Arg Tyr Gly Lys Thr Pro Leu His Leu Ala Ala Ile Gly Gly
            660                 665                 670
His Leu Glu Ile Val Glu Val Leu Leu Lys Ala Gly Ala Asp Val Asn
        675                 680                 685
Ala Gln Asp Asn Lys Gly Ser Thr Pro Ala Asp Leu Ala Ala Asp Tyr
        690                 695                 700
Gly His Gln Asp Ile Ala Glu Val Leu Gln Lys Ala Ala Gly Ser Pro
705                 710                 715                 720
Thr Gly Ser Asp Leu Gly Gln Lys Leu Leu Glu Ala Ala Trp Ala Gly
            725                 730                 735
Gln Asp Asp Glu Val Arg Glu Leu Leu Lys Ala Gly Ala Asp Val Asn
        740                 745                 750
Ala Lys Asn Ser Arg Gly Trp Thr Pro Leu His Thr Ala Ala Gln Thr
        755                 760                 765
Gly His Leu Glu Ile Phe Glu Val Leu Leu Lys Ala Gly Ala Asp Val
        770                 775                 780
Asn Ala Lys Asn Asp Lys Arg Val Thr Pro Leu His Leu Ala Ala Ala
785                 790                 795                 800
Leu Gly His Leu Glu Ile Val Glu Val Leu Leu Lys Ala Gly Ala Asp
                805                 810                 815
Val Asn Ala Arg Asp Ser Trp Gly Thr Thr Pro Ala Asp Leu Ala Ala
            820                 825                 830
Lys Tyr Gly His Gln Asp Ile Ala Glu Val Leu Gln Lys Ala Ala
        835                 840                 845
```

<210> SEQ ID NO 98
<211> LENGTH: 847
<212> TYPE: PRT
<213> ORGANISM: Artificial Sequence
<220> FEATURE:
<223> OTHER INFORMATION: DARPin protein 59

<400> SEQUENCE: 98

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Thr Pro Thr Pro Thr
    130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Tyr Phe Ser His Thr Pro Leu His Leu Ala Ala Arg
            180                 185                 190

Asn Gly His Leu Lys Ile Val Glu Val Leu Leu Lys Ala Gly Ala Asp
        195                 200                 205

Val Asn Ala Lys Asp Phe Ala Gly Lys Thr Pro Leu His Leu Ala Ala
    210                 215                 220

Ala Asp Gly His Leu Glu Ile Val Glu Val Leu Leu Lys Ala Gly Ala
225                 230                 235                 240

Asp Val Asn Ala Gln Asp Ile Phe Gly Lys Thr Pro Ala Asp Ile Ala
                245                 250                 255

Ala Asp Ala Gly His Glu Asp Ile Ala Glu Val Leu Gln Lys Ala Ala
            260                 265                 270

Gly Ser Pro Thr Pro Thr Pro Thr Thr Pro Thr Pro Thr Pro Thr Thr
        275                 280                 285

Pro Thr Pro Thr Pro Thr Gly Ser Asp Leu Gly Ile Lys Leu Leu Thr
    290                 295                 300

Ala Ala Tyr Asp Gly Gln Leu Asp Glu Val Arg Ile Leu Leu Lys Ala
305                 310                 315                 320

Gly Ala Asp Val Asn Ala Lys Asp Leu Arg Gly Gln Thr Pro Leu His
                325                 330                 335

Tyr Ala Ala Gly Leu Gly His Leu Glu Ile Val Glu Val Leu Leu Lys
            340                 345                 350

Ala Gly Ala Asp Val Asn Ala Lys Asp Leu His Gly Trp Thr Pro Leu
        355                 360                 365
```

```
His Leu Ala Ala Trp Ser Gly His Leu Glu Ile Val Glu Val Leu Leu
    370                 375                 380

Lys Ala Gly Ala Asp Val Asn Ala Gln Asp Val Glu Gly Val Thr Pro
385                 390                 395                 400

Ala Asp Leu Ala Ala Val Gln Gly His Gln Asp Ile Ala Glu Val Leu
                405                 410                 415

Gln Lys Ala Ala Gly Ser Pro Thr Pro Thr Pro Thr Thr Pro Thr Pro
            420                 425                 430

Thr Pro Thr Thr Pro Thr Pro Thr Pro Thr Gly Ser Asp Leu Gly Lys
            435                 440                 445

Lys Leu Leu Glu Ala Ala Leu Glu Gly Gln Leu Asp Glu Val Arg Glu
450                 455                 460

Leu Leu Lys Ala Gly Ala Asp Val Asn Ala Lys Asp Gln Glu Gly Tyr
465                 470                 475                 480

Thr Pro Leu His Leu Ala Ala Leu Gly His Leu Glu Ile Val Glu
            485                 490                 495

Val Leu Leu Lys Ala Gly Ala Asp Val Asn Ala Lys Asp Gln Ile Gly
            500                 505                 510

Arg Thr Pro Leu His Leu Ala Ala Tyr Lys Gly His Leu Glu Ile Val
            515                 520                 525

Glu Val Leu Leu Lys Ala Gly Ala Asp Val Asn Ala Gln Asp Ile Ile
            530                 535                 540

Gly Gln Thr Pro Ala Asp Leu Ala Ala Gln Arg Gly His Gln Asp Ile
545                 550                 555                 560

Ala Glu Val Leu Gln Lys Ala Ala Gly Ser Pro Thr Pro Thr Pro Thr
                565                 570                 575

Thr Pro Thr Pro Thr Pro Thr Thr Pro Thr Pro Thr Pro Thr Gly Ser
            580                 585                 590

Asp Leu Gly Val Lys Leu Leu Ala Ala Glu Arg Gly Gln Leu Asp
            595                 600                 605

Glu Val Arg Ile Leu Leu Lys Ala Gly Ala Asp Val Asn Ala Lys Asp
            610                 615                 620

Ile Ala Glu Gly Tyr Thr Pro Leu His Ile Ala Ala Tyr Gln Gly His
625                 630                 635                 640

Leu Glu Ile Val Glu Val Leu Leu Lys Ala Gly Ala Asp Val Asn Ala
            645                 650                 655

Lys Asp Arg Tyr Gly Lys Thr Pro Leu His Leu Ala Ala Ile Gly Gly
            660                 665                 670

His Leu Glu Ile Val Glu Val Leu Lys Ala Gly Ala Asp Val Asn
            675                 680                 685

Ala Gln Asp Asn Lys Gly Ser Thr Pro Ala Asp Leu Ala Ala Asp Tyr
            690                 695                 700

Gly His Gln Asp Ile Ala Glu Val Leu Gln Lys Ala Ala Gly Ser Pro
705                 710                 715                 720

Thr Gly Ser Asp Leu Gly Gln Lys Leu Leu Glu Ala Ala Trp Ala Gly
            725                 730                 735

Gln Asp Asp Glu Val Arg Glu Leu Leu Lys Ala Gly Ala Asp Val Asn
            740                 745                 750

Ala Lys Asn Ser Arg Gly Trp Thr Pro Leu His Thr Ala Ala Gln Thr
            755                 760                 765

Gly His Leu Glu Ile Phe Glu Val Leu Leu Lys Ala Gly Ala Asp Val
            770                 775                 780
```

```
Asn Ala Lys Asn Asp Lys Arg Val Thr Pro Leu His Leu Ala Ala Ala
785                 790                 795                 800

Leu Gly His Leu Glu Ile Val Glu Val Leu Leu Lys Ala Gly Ala Asp
            805                 810                 815

Val Asn Ala Arg Asp Ser Trp Gly Thr Thr Pro Ala Asp Leu Ala Ala
        820                 825                 830

Lys Tyr Gly His Gln Asp Ile Ala Glu Val Leu Gln Lys Ala Ala
            835                 840                 845

<210> SEQ ID NO 99
<211> LENGTH: 880
<212> TYPE: PRT
<213> ORGANISM: Artificial Sequence
<220> FEATURE:
<223> OTHER INFORMATION: DARPin protein 60

<400> SEQUENCE: 99

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Thr Pro Thr Pro Thr
    130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
            165                 170                 175

Asn Ala Lys Asp Tyr Phe Ser His Thr Pro Leu His Leu Ala Ala Arg
        180                 185                 190

Asn Gly His Leu Lys Ile Val Glu Val Leu Leu Lys Ala Gly Ala Asp
    195                 200                 205

Val Asn Ala Lys Asp Phe Ala Gly Lys Thr Pro Leu His Leu Ala Ala
210                 215                 220

Ala Asp Gly His Leu Glu Ile Val Glu Val Leu Leu Lys Ala Gly Ala
225                 230                 235                 240

Asp Val Asn Ala Gln Asp Ile Phe Gly Lys Thr Pro Ala Asp Ile Ala
            245                 250                 255

Ala Asp Ala Gly His Glu Asp Ile Ala Glu Val Leu Gln Lys Ala Ala
        260                 265                 270

Gly Ser Pro Thr Pro Thr Pro Thr Thr Pro Thr Pro Thr Thr
    275                 280                 285

Pro Thr Pro Thr Pro Thr Gly Ser Asp Leu Gly Ile Lys Leu Leu Thr
290                 295                 300
```

```
Ala Ala Tyr Asp Gly Gln Leu Asp Glu Val Arg Ile Leu Leu Lys Ala
305                 310                 315                 320
Gly Ala Asp Val Asn Ala Lys Asp Leu Arg Gly Gln Thr Pro Leu His
            325                 330                 335
Tyr Ala Ala Gly Leu Gly His Leu Glu Ile Val Glu Val Leu Leu Lys
        340                 345                 350
Ala Gly Ala Asp Val Asn Ala Lys Asp Leu His Gly Trp Thr Pro Leu
    355                 360                 365
His Leu Ala Ala Trp Ser Gly His Leu Glu Ile Val Glu Val Leu Leu
    370                 375                 380
Lys Ala Gly Ala Asp Val Asn Ala Gln Asp Val Glu Gly Val Thr Pro
385                 390                 395                 400
Ala Asp Leu Ala Ala Val Gln Gly His Gln Asp Ile Ala Glu Val Leu
                405                 410                 415
Gln Lys Ala Ala Gly Ser Pro Thr Pro Thr Pro Thr Thr Pro Thr Pro
            420                 425                 430
Thr Pro Thr Thr Pro Thr Pro Thr Pro Thr Gly Ser Asp Leu Gly Lys
        435                 440                 445
Lys Leu Leu Gln Ala Ala Arg Ala Gly Gln Leu Asp Glu Val Arg Glu
    450                 455                 460
Leu Leu Lys Ala Gly Ala Asp Val Asn Ala Lys Asp Gln Tyr Gly Arg
465                 470                 475                 480
Thr Pro Leu His Leu Ala Ala Ile Lys Gly His Leu Glu Ile Val Glu
                485                 490                 495
Val Leu Leu Lys Ala Gly Ala Asp Val Asn Ala Lys Asp Ser Leu Gly
            500                 505                 510
Tyr Thr Pro Leu His Leu Ala Ala Val Glu Gly Pro Leu Glu Ile Val
        515                 520                 525
Glu Val Leu Leu Lys Ala Gly Ala Asp Val Asn Ala Lys Asp Ala Tyr
    530                 535                 540
Gly Gln Thr Pro Leu His Ile Ala Ala Ala Trp Gly His Leu Glu Ile
545                 550                 555                 560
Val Glu Val Leu Leu Lys Ala Val Ala Asp Val Asn Ala Gln Asp Lys
                565                 570                 575
Ser Gly Lys Thr Pro Ala Asp Leu Ala Ala Arg Ala Gly His Gln Asp
            580                 585                 590
Ile Ala Glu Val Leu Gln Lys Ala Ala Gly Ser Pro Thr Pro Thr Pro
        595                 600                 605
Thr Thr Pro Thr Pro Thr Pro Thr Thr Pro Thr Pro Thr Pro Thr Gly
    610                 615                 620
Ser Asp Leu Gly Val Lys Leu Leu Ala Ala Glu Arg Gly Gln Leu
625                 630                 635                 640
Asp Glu Val Arg Ile Leu Leu Lys Ala Gly Ala Asp Val Asn Ala Lys
                645                 650                 655
Asp Ile Ala Glu Gly Tyr Thr Pro Leu His Ile Ala Ala Tyr Gln Gly
            660                 665                 670
His Leu Glu Ile Val Glu Val Leu Leu Lys Ala Gly Ala Asp Val Asn
        675                 680                 685
Ala Lys Asp Arg Tyr Gly Lys Thr Pro Leu His Leu Ala Ala Ile Gly
    690                 695                 700
Gly His Leu Glu Ile Val Glu Val Leu Leu Lys Ala Gly Ala Asp Val
705                 710                 715                 720
Asn Ala Gln Asp Asn Lys Gly Ser Thr Pro Ala Asp Leu Ala Ala Asp
```

Tyr Gly His Gln Asp Ile Ala Glu Val Leu Gln Lys Ala Ala Gly Ser
            725                 730                 735

Pro Thr Gly Ser Asp Leu Gly Gln Lys Leu Leu Glu Ala Ala Trp Ala
        740                 745                 750

Gly Gln Asp Asp Glu Val Arg Glu Leu Leu Lys Ala Gly Ala Asp Val
    755                 760                 765

Asn Ala Lys Asn Ser Arg Gly Trp Thr Pro Leu His Thr Ala Ala Gln
770                 775                 780

Thr Gly His Leu Glu Ile Phe Glu Val Leu Leu Lys Ala Gly Ala Asp
            785                 790                 795                 800

Val Asn Ala Lys Asn Asp Lys Arg Val Thr Pro Leu His Leu Ala Ala
            805                 810                 815

Ala Leu Gly His Leu Glu Ile Val Glu Val Leu Leu Lys Ala Gly Ala
        820                 825                 830

Asp Val Asn Ala Arg Asp Ser Trp Gly Thr Thr Pro Ala Asp Leu Ala
    835                 840                 845

Ala Lys Tyr Gly His Gln Asp Ile Ala Glu Val Leu Gln Lys Ala Ala
865                 870                 875                 880

<210> SEQ ID NO 100
<211> LENGTH: 880
<212> TYPE: PRT
<213> ORGANISM: Artificial Sequence
<220> FEATURE:
<223> OTHER INFORMATION: DARPin protein 61

<400> SEQUENCE: 100

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr
    130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Tyr Phe Ser His Thr Pro Leu His Leu Ala Ala Arg
            180                 185                 190

Asn Gly His Leu Lys Ile Val Glu Val Leu Leu Lys Ala Gly Ala Asp
        195                 200                 205

Val Asn Ala Lys Asp Phe Ala Gly Lys Thr Pro Leu His Leu Ala Ala

-continued

```
            210                 215                 220
Ala Asp Gly His Leu Glu Ile Val Glu Val Leu Leu Lys Ala Gly Ala
225                 230                 235                 240

Asp Val Asn Ala Gln Asp Ile Phe Gly Lys Thr Pro Ala Asp Ile Ala
                245                 250                 255

Ala Asp Ala Gly His Glu Asp Ile Ala Glu Val Leu Gln Lys Ala Ala
                260                 265                 270

Gly Ser Pro Thr Pro Thr Pro Thr Thr Pro Thr Pro Thr Pro Thr Thr
            275                 280                 285

Pro Thr Pro Thr Pro Thr Gly Ser Asp Leu Gly Lys Lys Leu Leu Gln
            290                 295                 300

Ala Ala Arg Ala Gly Gln Leu Asp Glu Val Arg Glu Leu Leu Lys Ala
305                 310                 315                 320

Gly Ala Asp Val Asn Ala Lys Asp Gln Gln Gly Leu Thr Pro Leu His
                325                 330                 335

Ile Ala Ala Asn Leu Gly His Leu Glu Ile Val Glu Val Leu Leu Lys
            340                 345                 350

Ala Gly Ala Asp Val Asn Ala Lys Asp Leu Phe Gly Leu Thr Pro Leu
            355                 360                 365

His Leu Ala Ala Phe Glu Gly His Leu Glu Ile Val Glu Val Leu Leu
            370                 375                 380

Lys Ala Gly Ala Asp Val Asn Ala Lys Asp Gln His Gly Ala Thr Pro
385                 390                 395                 400

Leu His Leu Ala Ala Trp Val Gly His Leu Glu Ile Val Glu Val Leu
                405                 410                 415

Leu Lys Ala Gly Ala Asp Val Asn Ala Gln Asp Lys Ser Gly Lys Thr
                420                 425                 430

Pro Ala Asp Leu Ala Ala Arg Ala Gly His Gln Asp Ile Ala Glu Val
            435                 440                 445

Leu Gln Lys Ala Ala Gly Ser Pro Thr Pro Thr Pro Thr Thr Pro Thr
450                 455                 460

Pro Thr Pro Thr Thr Pro Thr Pro Thr Pro Thr Gly Ser Asp Leu Gly
465                 470                 475                 480

Lys Lys Leu Leu Gln Ala Ala Leu Glu Gly Gln Leu Asp Glu Val Arg
                485                 490                 495

Glu Leu Leu Lys Ala Gly Ala Asp Val Asn Ala Lys Asp Ile Glu Gly
                500                 505                 510

Tyr Thr Pro Leu His Leu Ala Ala Leu Gly His Leu Glu Ile Val
            515                 520                 525

Glu Val Leu Leu Lys Ala Gly Ala Asp Val Asn Ala Lys Asp Gln Ile
530                 535                 540

Gly Arg Thr Pro Leu His Leu Ala Ala Tyr Lys Gly His Leu Glu Ile
545                 550                 555                 560

Val Glu Val Leu Leu Lys Ala Gly Ala Asp Val Asn Ala Gln Asp Ile
                565                 570                 575

Ile Gly Gln Thr Pro Ala Asp Leu Ala Ala Gln Arg Gly His Gln Asp
                580                 585                 590

Ile Ala Glu Val Leu Gln Lys Ala Ala Gly Ser Pro Thr Pro Thr Pro
            595                 600                 605

Thr Thr Pro Thr Pro Thr Pro Thr Thr Pro Thr Pro Thr Pro Thr Gly
            610                 615                 620

Ser Asp Leu Gly Lys Lys Leu Leu Leu Ala Ala Glu Arg Gly Gln Leu
625                 630                 635                 640
```

Asp Glu Val Arg Ile Leu Leu Lys Ala Gly Ala Asp Val Asn Ala Lys
            645                 650                 655

Asp Arg Ala Glu Gly Tyr Thr Pro Leu His Ile Ala Ala Tyr Gln Gly
            660                 665                 670

His Leu Glu Ile Val Glu Val Leu Leu Lys Ala Gly Ala Asp Val Asn
            675                 680                 685

Ala Lys Asp Arg Tyr Gly Lys Thr Pro Leu His Leu Ala Ala Ile Ser
690                 695                 700

Gly His Leu Glu Ile Val Glu Val Leu Leu Lys Ala Gly Ala Asp Val
705                 710                 715                 720

Asn Ala Gln Asp Asn Lys Gly Ser Thr Pro Ala Asp Leu Ala Ala Asp
            725                 730                 735

Tyr Gly His Gln Asp Ile Ala Glu Val Leu Gln Lys Ala Ala Gly Ser
            740                 745                 750

Pro Thr Gly Ser Asp Leu Gly Gln Lys Leu Leu Glu Ala Ala Trp Ala
            755                 760                 765

Gly Gln Asp Asp Glu Val Arg Glu Leu Leu Lys Ala Gly Ala Asp Val
            770                 775                 780

Asn Ala Lys Asn Ser Arg Gly Trp Thr Pro Leu His Thr Ala Ala Gln
785                 790                 795                 800

Thr Gly His Leu Glu Ile Phe Glu Val Leu Leu Lys Ala Gly Ala Asp
            805                 810                 815

Val Asn Ala Lys Asn Asp Lys Arg Val Thr Pro Leu His Leu Ala Ala
            820                 825                 830

Ala Leu Gly His Leu Glu Ile Val Glu Val Leu Leu Lys Ala Gly Ala
            835                 840                 845

Asp Val Asn Ala Arg Asp Ser Trp Gly Thr Thr Pro Ala Asp Leu Ala
            850                 855                 860

Ala Lys Tyr Gly His Gln Asp Ile Ala Glu Val Leu Gln Lys Ala Ala
865                 870                 875                 880

<210> SEQ ID NO 101
<211> LENGTH: 865
<212> TYPE: PRT
<213> ORGANISM: Artificial Sequence
<220> FEATURE:
<223> OTHER INFORMATION: DARPin protein 62

<400> SEQUENCE: 101

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
            50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
            85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
            115                 120                 125

```
Pro Thr Pro Thr Thr Pro Thr Pro Thr Thr Pro Thr Pro Thr
    130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Tyr Phe Ser His Thr Pro Leu His Leu Ala Ala Arg
            180                 185                 190

Asn Gly His Leu Lys Ile Val Glu Val Leu Leu Lys Ala Gly Ala Asp
        195                 200                 205

Val Asn Ala Lys Asp Phe Ala Gly Lys Thr Pro Leu His Leu Ala Ala
    210                 215                 220

Ala Asp Gly His Leu Glu Ile Val Glu Val Leu Leu Lys Ala Gly Ala
225                 230                 235                 240

Asp Val Asn Ala Gln Asp Ile Phe Gly Lys Thr Pro Ala Asp Ile Ala
                245                 250                 255

Ala Asp Ala Gly His Glu Asp Ile Ala Glu Val Leu Gln Lys Ala Ala
            260                 265                 270

Gly Ser Pro Thr Pro Thr Pro Thr Thr Pro Thr Pro Thr Pro Thr Thr
        275                 280                 285

Pro Thr Pro Thr Pro Thr Gly Ser Asp Leu Gly Ile Lys Leu Leu Thr
    290                 295                 300

Ala Ala Tyr Asp Gly Gln Leu Asp Glu Val Arg Ile Leu Leu Lys Ala
305                 310                 315                 320

Gly Ala Asp Val Asn Ala Lys Asp Leu Arg Gly Gln Thr Pro Leu His
                325                 330                 335

Tyr Ala Ala Gly Leu Gly His Leu Glu Ile Val Glu Val Leu Leu Lys
            340                 345                 350

Ala Gly Ala Asp Val Asn Ala Lys Asp Leu His Gly Trp Thr Pro Leu
        355                 360                 365

His Leu Ala Ala Trp Ser Gly His Leu Glu Ile Val Glu Val Leu Leu
    370                 375                 380

Lys Ala Gly Ala Asp Val Asn Ala Gln Asp Val Glu Gly Val Thr Pro
385                 390                 395                 400

Ala Asp Leu Ala Ala Val Gln Gly His Gln Asp Ile Ala Glu Val Leu
                405                 410                 415

Gln Lys Ala Ala Gly Ser Pro Thr Pro Thr Pro Thr Pro Thr Pro Thr
            420                 425                 430

Thr Pro Thr Thr Pro Thr Pro Thr Pro Thr Gly Ser Asp Leu Gly Val
    435                 440                 445

Lys Leu Leu Leu Ala Ala Glu Arg Gly Gln Leu Asp Glu Val Arg Ile
450                 455                 460

Leu Leu Lys Ala Gly Ala Asp Val Asn Ala Lys Asp Ile Ala Glu Gly
465                 470                 475                 480

Tyr Thr Pro Leu His Ile Ala Ala Tyr Gln Gly His Leu Glu Ile Val
                485                 490                 495

Glu Val Leu Leu Lys Ala Gly Ala Asp Val Asn Ala Lys Asp Arg Tyr
            500                 505                 510

Gly Lys Thr Pro Leu His Leu Ala Ala Ile Gly Gly His Leu Glu Ile
        515                 520                 525

Val Glu Val Leu Leu Lys Ala Gly Ala Asp Val Asn Ala Gln Asp Asn
    530                 535                 540
```

```
Lys Gly Ser Thr Pro Ala Asp Leu Ala Ala Asp Tyr Gly His Gln Asp
545                 550                 555                 560

Ile Ala Glu Val Leu Gln Lys Ala Ala Gly Ser Pro Thr Pro Thr Pro
                565                 570                 575

Thr Thr Pro Thr Pro Thr Pro Thr Thr Pro Thr Pro Thr Pro Thr Gly
            580                 585                 590

Ser Asp Leu Gly Lys Lys Leu Leu Glu Ala Ala Leu Glu Gly Gln Leu
            595                 600                 605

Asp Glu Val Arg Glu Leu Leu Lys Ala Gly Ala Asp Val Asn Ala Lys
        610                 615                 620

Asp Gln Glu Gly Tyr Thr Pro Leu His Leu Ala Ala Leu Gly His
625                 630                 635                 640

Leu Glu Ile Val Glu Val Leu Leu Lys Ala Gly Ala Asp Val Asn Ala
                645                 650                 655

Lys Asp Gln Ile Gly Arg Thr Pro Leu His Leu Ala Ala Tyr Lys Gly
                660                 665                 670

His Leu Glu Ile Val Glu Val Leu Leu Lys Ala Gly Ala Asp Val Asn
            675                 680                 685

Ala Gln Asp Ile Ile Gly Gln Thr Pro Ala Asp Leu Ala Ala Gln Arg
        690                 695                 700

Gly His Gln Asp Ile Ala Glu Val Leu Gln Lys Ala Ala Gly Ser Pro
705                 710                 715                 720

Thr Pro Thr Pro Thr Thr Pro Thr Pro Thr Pro Thr Thr Pro Thr Pro
                725                 730                 735

Thr Pro Thr Gly Ser Asp Leu Gly Gln Lys Leu Leu Glu Ala Ala Trp
            740                 745                 750

Ala Gly Gln Asp Asp Glu Val Arg Glu Leu Leu Lys Ala Gly Ala Asp
        755                 760                 765

Val Asn Ala Lys Asn Ser Arg Gly Trp Thr Pro Leu His Thr Ala Ala
        770                 775                 780

Gln Thr Gly His Leu Glu Ile Phe Glu Val Leu Leu Lys Ala Gly Ala
785                 790                 795                 800

Asp Val Asn Ala Lys Asn Asp Lys Arg Val Thr Pro Leu His Leu Ala
                805                 810                 815

Ala Leu Gly His Leu Glu Ile Val Glu Val Leu Leu Lys Ala Gly
            820                 825                 830

Ala Asp Val Asn Ala Arg Asp Ser Trp Gly Thr Thr Pro Ala Asp Leu
        835                 840                 845

Ala Ala Lys Tyr Gly His Gln Asp Ile Ala Glu Val Leu Gln Lys Ala
    850                 855                 860

Ala
865

<210> SEQ ID NO 102
<211> LENGTH: 157
<212> TYPE: PRT
<213> ORGANISM: Artificial Sequence
<220> FEATURE:
<223> OTHER INFORMATION: DARPin protein 63

<400> SEQUENCE: 102

Asp Leu Gly Lys Lys Leu Leu Gln Ala Ala Arg Ala Gly Gln Leu Asp
1               5                   10                  15

Glu Val Arg Glu Leu Leu Lys Ala Gly Ala Asp Val Asn Ala Lys Asp
            20                  25                  30
```

```
Gln Tyr Gly Arg Thr Pro Leu His Leu Ala Ala Ile Lys Gly His Leu
            35                  40                  45

Glu Ile Val Glu Val Leu Leu Lys Ala Gly Ala Asp Val Asn Ala Lys
 50                  55                  60

Asp Ser Leu Gly Tyr Thr Pro Leu His Leu Ala Ala Val Glu Gly Pro
 65                  70                  75                  80

Leu Glu Ile Val Glu Val Leu Leu Lys Ala Gly Ala Asp Val Asn Ala
                 85                  90                  95

Lys Asp Ala Tyr Gly Gln Thr Pro Leu His Ile Ala Ala Ala Trp Gly
            100                 105                 110

His Leu Glu Ile Val Glu Val Leu Leu Lys Ala Val Ala Asp Val Asn
            115                 120                 125

Ala Gln Asp Lys Ser Gly Lys Thr Pro Ala Asp Leu Ala Ala Arg Ala
    130                 135                 140

Gly His Gln Asp Ile Ala Glu Val Leu Gln Lys Ala Ala
145                 150                 155

<210> SEQ ID NO 103
<211> LENGTH: 124
<212> TYPE: PRT
<213> ORGANISM: Artificial Sequence
<220> FEATURE:
<223> OTHER INFORMATION: DARPin protein 64

<400> SEQUENCE: 103

Asp Leu Gly Trp Lys Leu Leu Asp Ala Ala Glu Ile Gly Gln Asp Asp
1               5                   10                  15

Glu Val Arg Ile Leu Leu Ala Ala Gly Ala Asp Val Asn Ala Lys Asp
            20                  25                  30

Lys Gln Gly Ile Thr Pro Leu His Ile Ala Ala Ala His Gly His Leu
        35                  40                  45

Glu Ile Val Glu Val Leu Leu Lys Ala Gly Ala Asp Val Asn Ala Lys
 50                  55                  60

Asp Glu Ile Gly Arg Thr Pro Leu His Leu Ala Ala Phe Lys Gly His
 65                  70                  75                  80

Leu Glu Ile Val Glu Val Leu Leu Lys Ala Gly Ala Asp Val Asn Ala
                85                  90                  95

Gln Asp Ile Ile Gly Glu Thr Pro Ala Asp Leu Ala Ala Val Arg Gly
            100                 105                 110

His Glu Asp Ile Ala Glu Val Leu Gln Lys Ala Ala
            115                 120

<210> SEQ ID NO 104
<211> LENGTH: 124
<212> TYPE: PRT
<213> ORGANISM: Artificial Sequence
<220> FEATURE:
<223> OTHER INFORMATION: DARPin protein 65

<400> SEQUENCE: 104

Asp Leu Gly Trp Lys Leu Leu Asp Ala Ala Glu Ile Gly Gln Leu Asp
1               5                   10                  15

Glu Val Arg Ile Leu Leu Lys Ala Gly Ala Asp Val Asn Ala Lys Asp
            20                  25                  30

Lys Gln Gly Ile Thr Pro Leu His Ile Ala Ala Ala His Gly His Leu
        35                  40                  45

Glu Ile Val Glu Val Leu Leu Lys Ala Gly Ala Asp Val Asn Ala Lys
 50                  55                  60
```

Asp Glu Ile Gly Arg Thr Pro Leu His Leu Ala Ala Phe Lys Gly His
65                  70                  75                  80

Leu Glu Ile Val Glu Val Leu Leu Lys Ala Gly Ala Asp Val Asn Ala
                85                  90                  95

Gln Asp Ile Ile Gly Glu Thr Pro Ala Asp Leu Ala Ala Val Arg Gly
            100                 105                 110

His Gln Asp Ile Ala Glu Val Leu Gln Lys Ala Ala
        115                 120

<210> SEQ ID NO 105
<211> LENGTH: 124
<212> TYPE: PRT
<213> ORGANISM: Artificial Sequence
<220> FEATURE:
<223> OTHER INFORMATION: DARPin protein 66

<400> SEQUENCE: 105

Asp Leu Gly Lys Lys Leu Leu Glu Ala Ala Leu Glu Gly Gln Leu Asp
1               5                   10                  15

Glu Val Arg Glu Leu Leu Lys Ala Gly Ala Asp Val Asn Ala Lys Asp
            20                  25                  30

Gln Glu Gly Tyr Thr Pro Leu His Leu Ala Ala Ala Leu Gly His Leu
        35                  40                  45

Glu Ile Val Glu Val Leu Leu Lys Ala Gly Ala Asp Val Asn Ala Lys
    50                  55                  60

Asp Gln Ile Gly Arg Thr Pro Leu His Leu Ala Ala Tyr Lys Gly His
65                  70                  75                  80

Leu Glu Ile Val Glu Val Leu Leu Lys Ala Gly Ala Asp Val Asn Ala
                85                  90                  95

Gln Asp Ile Ile Gly Gln Thr Pro Ala Asp Leu Ala Ala Gln Arg Gly
            100                 105                 110

His Gln Asp Ile Ala Glu Val Leu Gln Lys Ala Ala
        115                 120

<210> SEQ ID NO 106
<211> LENGTH: 123
<212> TYPE: PRT
<213> ORGANISM: Artificial Sequence
<220> FEATURE:
<223> OTHER INFORMATION: DARPin protein 67

<400> SEQUENCE: 106

Asp Leu Gly Lys Lys Leu Leu Gln Ala Ala Leu Glu Gly Gln Leu Asp
1               5                   10                  15

Glu Val Arg Glu Leu Leu Lys Ala Gly Ala Asp Val Asn Ala Lys Asp
            20                  25                  30

Ile Glu Gly Tyr Thr Pro Leu His Leu Ala Ala Ala Leu Gly His Leu
        35                  40                  45

Glu Ile Val Glu Val Leu Leu Lys Ala Gly Ala Asp Val Asn Ala Lys
    50                  55                  60

Asp Gln Ile Gly Arg Thr Pro Leu His Leu Ala Ala Tyr Lys Gly His
65                  70                  75                  80

Leu Glu Ile Val Glu Val Leu Leu Lys Ala Gly Ala Asp Val Asn Ala
                85                  90                  95

Gln Asp Ile Ile Gly Gln Thr Pro Ala Asp Leu Ala Ala Gln Arg Gly
            100                 105                 110

His Gln Asp Ile Ala Glu Val Leu Gln Lys Ala
        115                 120

```
              115                 120

<210> SEQ ID NO 107
<211> LENGTH: 157
<212> TYPE: PRT
<213> ORGANISM: Artificial Sequence
<220> FEATURE:
<223> OTHER INFORMATION: DARPin protein 68

<400> SEQUENCE: 107

Asp Leu Gly Lys Lys Leu Leu Gln Ala Ala Arg Ala Gly Gln Leu Asp
1               5                   10                  15

Glu Val Arg Glu Leu Leu Lys Ala Gly Ala Asp Val Asn Ala Lys Asp
            20                  25                  30

Gln Ala Gly Leu Thr Pro Leu His Ile Ala Ala Thr Gly His Leu
        35                  40                  45

Glu Ile Val Glu Val Leu Leu Lys Ala Gly Ala Asp Val Asn Ala Lys
    50                  55                  60

Asp Phe Ser Gly Leu Thr Pro Leu His Leu Ala Ala Phe Glu Gly His
65                  70                  75                  80

Leu Glu Ile Val Glu Val Leu Leu Lys Ala Gly Ala Asp Val Asn Ala
                85                  90                  95

Lys Asp Gln His Gly Gln Thr Pro Leu His Leu Ala Ala Trp Thr Gly
            100                 105                 110

His Leu Glu Ile Val Glu Val Leu Leu Lys Ala Gly Ala Asp Val Asn
        115                 120                 125

Ala Gln Asp Lys Ser Gly Lys Thr Pro Ala Asp Leu Ala Ala Arg Ala
    130                 135                 140

Gly His Gln Asp Ile Ala Glu Val Leu Gln Lys Ala Ala
145                 150                 155

<210> SEQ ID NO 108
<211> LENGTH: 124
<212> TYPE: PRT
<213> ORGANISM: Artificial Sequence
<220> FEATURE:
<223> OTHER INFORMATION: DARPin protein 69

<400> SEQUENCE: 108

Asp Leu Gly Tyr Lys Leu Leu Gln Ala Ala Tyr Asp Gly Gln Asp Asp
1               5                   10                  15

Glu Val Arg Ile Leu Leu Ala Ala Gly Ala Asp Val Asn Ala Lys Asp
            20                  25                  30

Ser Arg Gly Gln Thr Pro Leu His Tyr Ala Ala Ser Ile Gly His Leu
        35                  40                  45

Glu Ile Val Glu Val Leu Leu Lys Ala Gly Ala Asp Val Asn Ala Lys
    50                  55                  60

Asp Asp His Gly Trp Thr Pro Leu His Leu Ala Ala Trp Ser Gly His
65                  70                  75                  80

Leu Glu Ile Val Glu Val Leu Leu Lys Ala Gly Ala Asp Val Asn Ala
                85                  90                  95

Gln Asp Gln Glu Gly Thr Thr Pro Ala Asp Leu Ala Ala Val Gln Ser
            100                 105                 110

His Glu Asp Ile Ala Glu Val Leu Gln Lys Ala Ala
        115                 120

<210> SEQ ID NO 109
<211> LENGTH: 124
```

```
<212> TYPE: PRT
<213> ORGANISM: Artificial Sequence
<220> FEATURE:
<223> OTHER INFORMATION: DARPin protein 70

<400> SEQUENCE: 109

Asp Leu Gly Ile Lys Leu Leu Thr Ala Ala Tyr Asp Gly Gln Leu Asp
1               5                   10                  15

Glu Val Arg Ile Leu Leu Lys Ala Gly Ala Asp Val Asn Ala Lys Asp
            20                  25                  30

Leu Arg Gly Gln Thr Pro Leu His Tyr Ala Ala Gly Leu Gly His Leu
        35                  40                  45

Glu Ile Val Glu Val Leu Leu Lys Ala Gly Ala Asp Val Asn Ala Lys
    50                  55                  60

Asp Leu His Gly Trp Thr Pro Leu His Leu Ala Ala Trp Ser Gly His
65                  70                  75                  80

Leu Glu Ile Val Glu Val Leu Leu Lys Ala Gly Ala Asp Val Asn Ala
                85                  90                  95

Gln Asp Val Glu Gly Val Thr Pro Ala Asp Leu Ala Ala Val Gln Gly
            100                 105                 110

His Gln Asp Ile Ala Glu Val Leu Gln Lys Ala Ala
        115                 120

<210> SEQ ID NO 110
<211> LENGTH: 157
<212> TYPE: PRT
<213> ORGANISM: Artificial Sequence
<220> FEATURE:
<223> OTHER INFORMATION: DARPin protein 71

<400> SEQUENCE: 110

Asp Leu Gly Lys Lys Leu Leu Gln Ala Ala Arg Ala Gly Gln Leu Asp
1               5                   10                  15

Glu Val Arg Glu Leu Leu Lys Ala Gly Ala Asp Val Asn Ala Lys Asp
            20                  25                  30

Gln Gln Gly Leu Thr Pro Leu His Ile Ala Ala Asn Leu Gly His Leu
        35                  40                  45

Glu Ile Val Glu Val Leu Leu Lys Ala Gly Ala Asp Val Asn Ala Lys
    50                  55                  60

Asp Leu Phe Gly Leu Thr Pro Leu His Leu Ala Ala Phe Glu Gly His
65                  70                  75                  80

Leu Glu Ile Val Glu Val Leu Leu Lys Ala Gly Ala Asp Val Asn Ala
                85                  90                  95

Lys Asp Gln His Gly Ala Thr Pro Leu His Leu Ala Ala Trp Val Gly
            100                 105                 110

His Leu Glu Ile Val Glu Val Leu Leu Lys Ala Gly Ala Asp Val Asn
        115                 120                 125

Ala Gln Asp Lys Ser Gly Lys Thr Pro Ala Asp Leu Ala Ala Arg Ala
    130                 135                 140

Gly His Gln Asp Ile Ala Glu Val Leu Gln Lys Ala Ala
145                 150                 155

<210> SEQ ID NO 111
<211> LENGTH: 125
<212> TYPE: PRT
<213> ORGANISM: Artificial Sequence
<220> FEATURE:
<223> OTHER INFORMATION: DARPin protein 72
```

-continued

```
<400> SEQUENCE: 111

Asp Leu Gly Val Lys Leu Leu Ala Ala Glu Arg Gly Gln Leu Asp
1               5                   10                  15

Glu Val Arg Ile Leu Leu Lys Ala Gly Ala Asp Val Asn Ala Lys Asp
                20                  25                  30

Ile Ala Glu Gly Tyr Thr Pro Leu His Ile Ala Ala Tyr Gln Gly His
            35                  40                  45

Leu Glu Ile Val Glu Val Leu Leu Lys Ala Gly Ala Asp Val Asn Ala
        50                  55                  60

Lys Asp Arg Tyr Gly Lys Thr Pro Leu His Leu Ala Ala Ile Gly Gly
65                  70                  75                  80

His Leu Glu Ile Val Glu Val Leu Leu Lys Ala Gly Ala Asp Val Asn
                85                  90                  95

Ala Gln Asp Asn Lys Gly Ser Thr Pro Ala Asp Leu Ala Ala Asp Tyr
            100                 105                 110

Gly His Gln Asp Ile Ala Glu Val Leu Gln Lys Ala Ala
        115                 120                 125

<210> SEQ ID NO 112
<211> LENGTH: 125
<212> TYPE: PRT
<213> ORGANISM: Artificial Sequence
<220> FEATURE:
<223> OTHER INFORMATION: DARPin protein 73

<400> SEQUENCE: 112

Asp Leu Gly Lys Lys Leu Leu Ala Ala Glu Arg Gly Gln Leu Asp
1               5                   10                  15

Glu Val Arg Ile Leu Leu Lys Ala Gly Ala Asp Val Asn Ala Lys Asp
                20                  25                  30

Arg Ala Glu Gly Tyr Thr Pro Leu His Ile Ala Ala Tyr Gln Gly His
            35                  40                  45

Leu Glu Ile Val Glu Val Leu Leu Lys Ala Gly Ala Asp Val Asn Ala
        50                  55                  60

Lys Asp Arg Tyr Gly Lys Thr Pro Leu His Leu Ala Ala Ile Ser Gly
65                  70                  75                  80

His Leu Glu Ile Val Glu Val Leu Leu Lys Ala Gly Ala Asp Val Asn
                85                  90                  95

Ala Gln Asp Asn Lys Gly Ser Thr Pro Ala Asp Leu Ala Ala Asp Tyr
            100                 105                 110

Gly His Gln Asp Ile Ala Glu Val Leu Gln Lys Ala Ala
        115                 120                 125

<210> SEQ ID NO 113
<211> LENGTH: 864
<212> TYPE: PRT
<213> ORGANISM: Artificial Sequence
<220> FEATURE:
<223> OTHER INFORMATION: DARPin protein 74

<400> SEQUENCE: 113

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45
```

-continued

Lys Ile Val Glu Val Leu Leu Lys Ala Gly Ala Asp Val Asn Ala Lys
 50                  55                  60

Asp Phe Ala Gly Lys Thr Pro Leu His Leu Ala Ala Asp Gly His
 65                  70                  75                  80

Leu Glu Ile Val Glu Val Leu Leu Lys Ala Gly Ala Asp Val Asn Ala
                 85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Thr Pro Thr Pro Thr
130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Tyr Phe Ser His Thr Pro Leu His Leu Ala Ala Arg
            180                 185                 190

Asn Gly His Leu Lys Ile Val Glu Val Leu Leu Lys Ala Gly Ala Asp
            195                 200                 205

Val Asn Ala Lys Asp Phe Ala Gly Lys Thr Pro Leu His Leu Ala Ala
210                 215                 220

Ala Asp Gly His Leu Glu Ile Val Glu Val Leu Leu Lys Ala Gly Ala
225                 230                 235                 240

Asp Val Asn Ala Gln Asp Ile Phe Gly Lys Thr Pro Ala Asp Ile Ala
                245                 250                 255

Ala Asp Ala Gly His Glu Asp Ile Ala Glu Val Leu Gln Lys Ala Ala
            260                 265                 270

Gly Ser Pro Thr Pro Thr Pro Thr Thr Pro Thr Pro Thr Pro Thr Thr
            275                 280                 285

Pro Thr Pro Thr Pro Thr Gly Ser Asp Leu Gly Lys Lys Leu Leu Glu
290                 295                 300

Ala Ala Arg Ala Gly Gln Asp Asp Glu Val Arg Glu Leu Leu Lys Ala
305                 310                 315                 320

Gly Ala Asp Val Asn Ala Lys Asp Lys Asp Gly Tyr Thr Pro Leu His
                325                 330                 335

Leu Ala Ala Arg Glu Gly His Leu Glu Ile Val Glu Val Leu Leu Lys
            340                 345                 350

Ala Gly Ala Asp Val Asn Ala Lys Asp Lys Asp Gly Tyr Thr Pro Leu
            355                 360                 365

His Leu Ala Ala Arg Glu Gly His Leu Glu Ile Val Glu Val Leu Leu
            370                 375                 380

Lys Ala Gly Ala Asp Val Asn Ala Gln Asp Lys Ser Gly Lys Thr Pro
385                 390                 395                 400

Ala Asp Leu Ala Ala Asp Ala Gly His Glu Asp Ile Ala Glu Val Leu
                405                 410                 415

Gln Lys Ala Ala Gly Ser Pro Thr Pro Thr Pro Thr Thr Pro Thr Pro
            420                 425                 430

Thr Pro Thr Thr Pro Thr Pro Thr Pro Thr Gly Ser Asp Leu Gly Lys
            435                 440                 445

Lys Leu Leu Glu Ala Ala Arg Ala Gly Gln Asp Asp Glu Val Arg Glu
450                 455                 460

Leu Leu Lys Ala Gly Ala Asp Val Asn Ala Lys Asp Lys Asp Gly Tyr

```
             465                 470                 475                 480
        Thr Pro Leu His Leu Ala Ala Arg Glu Gly His Leu Glu Ile Val Glu
                        485                 490                 495
        Val Leu Leu Lys Ala Gly Ala Asp Val Asn Ala Lys Asp Lys Asp Gly
                        500                 505                 510
        Tyr Thr Pro Leu His Leu Ala Ala Arg Glu Gly His Leu Glu Ile Val
                        515                 520                 525
        Glu Val Leu Leu Lys Ala Gly Ala Asp Val Asn Ala Gln Asp Lys Ser
                        530                 535                 540
        Gly Lys Thr Pro Ala Asp Leu Ala Ala Asp Ala Gly His Glu Asp Ile
        545                 550                 555                 560
        Ala Glu Val Leu Gln Lys Ala Ala Gly Ser Pro Thr Pro Thr Pro Thr
                        565                 570                 575
        Thr Pro Thr Pro Thr Pro Thr Pro Thr Pro Thr Pro Thr Gly Ser
                        580                 585                 590
        Asp Leu Gly Lys Lys Leu Leu Glu Ala Ala Arg Ala Gly Gln Asp Asp
                        595                 600                 605
        Glu Val Arg Glu Leu Leu Lys Ala Gly Ala Asp Val Asn Ala Lys Asp
                        610                 615                 620
        Lys Asp Gly Tyr Thr Pro Leu His Leu Ala Ala Arg Glu Gly His Leu
        625                 630                 635                 640
        Glu Ile Val Glu Val Leu Leu Lys Ala Gly Ala Asp Val Asn Ala Lys
                        645                 650                 655
        Asp Lys Asp Gly Tyr Thr Pro Leu His Leu Ala Ala Arg Glu Gly His
                        660                 665                 670
        Leu Glu Ile Val Glu Val Leu Leu Lys Ala Gly Ala Asp Val Asn Ala
                        675                 680                 685
        Gln Asp Lys Ser Gly Lys Thr Pro Ala Asp Leu Ala Ala Asp Ala Gly
                        690                 695                 700
        His Glu Asp Ile Ala Glu Val Leu Gln Lys Ala Ala Gly Ser Pro Thr
        705                 710                 715                 720
        Pro Thr Pro Thr Thr Pro Thr Pro Thr Thr Pro Thr Pro Thr
                        725                 730                 735
        Pro Thr Gly Ser Asp Leu Gly Gln Lys Leu Leu Glu Ala Ala Trp Ala
                        740                 745                 750
        Gly Gln Asp Asp Glu Val Arg Glu Leu Leu Lys Ala Gly Ala Asp Val
                        755                 760                 765
        Asn Ala Lys Asn Ser Arg Gly Trp Thr Pro Leu His Thr Ala Ala Gln
                        770                 775                 780
        Thr Gly His Leu Glu Ile Phe Glu Val Leu Leu Lys Ala Gly Ala Asp
        785                 790                 795                 800
        Val Asn Ala Lys Asn Asp Lys Arg Val Thr Pro Leu His Leu Ala Ala
                        805                 810                 815
        Ala Leu Gly His Leu Glu Ile Val Glu Val Leu Leu Lys Ala Gly Ala
                        820                 825                 830
        Asp Val Asn Ala Arg Asp Ser Trp Gly Thr Thr Pro Ala Asp Leu Ala
                        835                 840                 845
        Ala Lys Tyr Gly His Gln Asp Ile Ala Glu Val Leu Gln Lys Ala Ala
                        850                 855                 860

<210> SEQ ID NO 114
<211> LENGTH: 865
<212> TYPE: PRT
<213> ORGANISM: Artificial Sequence
```

```
<220> FEATURE:
<223> OTHER INFORMATION: DARPin protein 75

<400> SEQUENCE: 114

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr
    130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Tyr Phe Ser His Thr Pro Leu His Leu Ala Ala Arg
            180                 185                 190

Asn Gly His Leu Lys Ile Val Glu Val Leu Leu Lys Ala Gly Ala Asp
        195                 200                 205

Val Asn Ala Lys Asp Phe Ala Gly Lys Thr Pro Leu His Leu Ala Ala
    210                 215                 220

Ala Asp Gly His Leu Glu Ile Val Glu Val Leu Leu Lys Ala Gly Ala
225                 230                 235                 240

Asp Val Asn Ala Gln Asp Ile Phe Gly Lys Thr Pro Ala Asp Ile Ala
                245                 250                 255

Ala Asp Ala Gly His Glu Asp Ile Ala Glu Val Leu Gln Lys Ala Ala
            260                 265                 270

Gly Ser Pro Thr Pro Thr Pro Thr Thr Pro Thr Pro Thr Pro Thr Thr
        275                 280                 285

Pro Thr Pro Thr Pro Thr Gly Ser Asp Leu Gly Val Lys Leu Leu Leu
    290                 295                 300

Ala Ala Glu Arg Gly Gln Leu Asp Glu Val Arg Ile Leu Leu Lys Ala
305                 310                 315                 320

Gly Ala Asp Val Asn Ala Lys Asp Ile Ala Glu Gly Tyr Thr Pro Leu
                325                 330                 335

His Ile Ala Ala Tyr Gln Gly His Leu Glu Ile Val Glu Val Leu Leu
            340                 345                 350

Lys Ala Gly Ala Asp Val Asn Ala Lys Asp Arg Tyr Gly Lys Thr Pro
        355                 360                 365

Leu His Leu Ala Ala Ile Gly Gly His Leu Glu Ile Val Glu Val Leu
    370                 375                 380

Leu Lys Ala Gly Ala Asp Val Asn Ala Gln Asp Asn Lys Gly Ser Thr
385                 390                 395                 400
```

```
Pro Ala Asp Leu Ala Ala Asp Tyr Gly His Gln Asp Ile Ala Glu Val
                405                 410                 415

Leu Gln Lys Ala Ala Gly Ser Pro Thr Pro Thr Pro Thr Thr Pro Thr
            420                 425                 430

Pro Thr Pro Thr Thr Pro Thr Pro Thr Pro Thr Gly Ser Asp Leu Gly
            435                 440                 445

Lys Lys Leu Leu Glu Ala Ala Leu Glu Gly Gln Leu Asp Glu Val Arg
        450                 455                 460

Glu Leu Leu Lys Ala Gly Ala Asp Val Asn Ala Lys Asp Gln Glu Gly
465                 470                 475                 480

Tyr Thr Pro Leu His Leu Ala Ala Ala Leu Gly His Leu Glu Ile Val
                485                 490                 495

Glu Val Leu Leu Lys Ala Gly Ala Asp Val Asn Ala Lys Asp Gln Ile
            500                 505                 510

Gly Arg Thr Pro Leu His Leu Ala Ala Tyr Lys Gly His Leu Glu Ile
            515                 520                 525

Val Glu Val Leu Leu Lys Ala Gly Ala Asp Val Asn Ala Gln Asp Ile
        530                 535                 540

Ile Gly Gln Thr Pro Ala Asp Leu Ala Ala Gln Arg Gly His Gln Asp
545                 550                 555                 560

Ile Ala Glu Val Leu Gln Lys Ala Ala Gly Ser Pro Thr Pro Thr Pro
                565                 570                 575

Thr Thr Pro Thr Pro Thr Pro Thr Thr Pro Thr Pro Thr Pro Thr Gly
            580                 585                 590

Ser Asp Leu Gly Ile Lys Leu Leu Thr Ala Ala Tyr Asp Gly Gln Leu
            595                 600                 605

Asp Glu Val Arg Ile Leu Leu Lys Ala Gly Ala Asp Val Asn Ala Lys
        610                 615                 620

Asp Leu Arg Gly Gln Thr Pro Leu His Tyr Ala Ala Gly Leu Gly His
625                 630                 635                 640

Leu Glu Ile Val Glu Val Leu Leu Lys Ala Gly Ala Asp Val Asn Ala
                645                 650                 655

Lys Asp Leu His Gly Trp Thr Pro Leu His Leu Ala Ala Trp Ser Gly
            660                 665                 670

His Leu Glu Ile Val Glu Val Leu Leu Lys Ala Gly Ala Asp Val Asn
            675                 680                 685

Ala Gln Asp Val Glu Gly Val Thr Pro Ala Asp Leu Ala Ala Val Gln
        690                 695                 700

Gly His Gln Asp Ile Ala Glu Val Leu Gln Lys Ala Ala Gly Ser Pro
705                 710                 715                 720

Thr Pro Thr Pro Thr Thr Pro Thr Pro Thr Pro Thr Thr Pro Thr Pro
                725                 730                 735

Thr Pro Thr Gly Ser Asp Leu Gly Lys Lys Leu Leu Glu Ala Ala Arg
            740                 745                 750

Ala Gly Gln Asp Asp Glu Val Arg Glu Leu Leu Lys Ala Gly Ala Asp
            755                 760                 765

Val Asn Ala Lys Asp Lys Asp Gly Tyr Thr Pro Leu His Leu Ala Ala
        770                 775                 780

Arg Glu Gly His Leu Glu Ile Val Glu Val Leu Leu Lys Ala Gly Ala
785                 790                 795                 800

Asp Val Asn Ala Lys Asp Lys Asp Gly Tyr Thr Pro Leu His Leu Ala
                805                 810                 815
```

```
Ala Arg Glu Gly His Leu Glu Ile Val Glu Val Leu Leu Lys Ala Gly
                820                 825                 830

Ala Asp Val Asn Ala Gln Asp Lys Ser Gly Lys Thr Pro Ala Asp Leu
            835                 840                 845

Ala Ala Asp Ala Gly His Glu Asp Ile Ala Glu Val Leu Gln Lys Ala
        850                 855                 860

Ala
865

<210> SEQ ID NO 115
<211> LENGTH: 846
<212> TYPE: PRT
<213> ORGANISM: Artificial Sequence
<220> FEATURE:
<223> OTHER INFORMATION: DARPin protein 76

<400> SEQUENCE: 115

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr Pro
130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Tyr Phe Ser His Thr Pro Leu His Leu Ala Ala Arg
            180                 185                 190

Asn Gly His Leu Lys Ile Val Glu Val Leu Leu Lys Ala Gly Ala Asp
        195                 200                 205

Val Asn Ala Lys Asp Phe Ala Gly Lys Thr Pro Leu His Leu Ala Ala
210                 215                 220

Ala Asp Gly His Leu Glu Ile Val Glu Val Leu Leu Lys Ala Gly Ala
225                 230                 235                 240

Asp Val Asn Ala Gln Asp Ile Phe Gly Lys Thr Pro Ala Asp Ile Ala
                245                 250                 255

Ala Asp Ala Gly His Glu Asp Ile Ala Glu Val Leu Gln Lys Ala Ala
            260                 265                 270

Gly Ser Pro Thr Pro Thr Pro Thr Thr Pro Thr Pro Thr Pro Thr Thr
        275                 280                 285

Pro Thr Pro Thr Pro Thr Gly Ser Asp Leu Gly Lys Lys Leu Leu Glu
290                 295                 300
```

-continued

Ala Ala Arg Ala Gly Gln Asp Asp Glu Val Arg Glu Leu Leu Lys Ala
305                 310                 315                 320

Gly Ala Asp Val Asn Ala Lys Asp Lys Asp Gly Tyr Thr Pro Leu His
            325                 330                 335

Leu Ala Ala Arg Glu Gly His Leu Glu Ile Val Glu Val Leu Leu Lys
        340                 345                 350

Ala Gly Ala Asp Val Asn Ala Lys Asp Lys Asp Gly Tyr Thr Pro Leu
    355                 360                 365

His Leu Ala Ala Arg Glu Gly His Leu Glu Ile Val Glu Val Leu Leu
    370                 375                 380

Lys Ala Gly Ala Asp Val Asn Ala Gln Asp Lys Ser Gly Lys Thr Pro
385                 390                 395                 400

Ala Asp Leu Ala Ala Asp Ala Gly His Glu Asp Ile Ala Glu Val Leu
            405                 410                 415

Gln Lys Ala Ala Gly Ser Pro Thr Pro Thr Pro Thr Pro Thr Pro Thr Pro
        420                 425                 430

Thr Pro Thr Thr Pro Thr Pro Thr Pro Thr Gly Ser Asp Leu Gly Lys
        435                 440                 445

Lys Leu Leu Glu Ala Ala Arg Ala Gly Gln Asp Asp Glu Val Arg Glu
    450                 455                 460

Leu Leu Lys Ala Gly Ala Asp Val Asn Ala Lys Asp Lys Asp Gly Tyr
465                 470                 475                 480

Thr Pro Leu His Leu Ala Ala Arg Glu Gly His Leu Glu Ile Val Glu
            485                 490                 495

Val Leu Leu Lys Ala Gly Ala Asp Val Asn Ala Lys Asp Lys Asp Gly
        500                 505                 510

Tyr Thr Pro Leu His Leu Ala Ala Arg Glu Gly His Leu Glu Ile Val
    515                 520                 525

Glu Val Leu Leu Lys Ala Gly Ala Asp Val Asn Ala Gln Asp Lys Ser
    530                 535                 540

Gly Lys Thr Pro Ala Asp Leu Ala Ala Asp Ala Gly His Glu Asp Ile
545                 550                 555                 560

Ala Glu Val Leu Gln Lys Ala Ala Gly Ser Pro Thr Pro Thr Pro Thr
            565                 570                 575

Thr Pro Thr Pro Thr Pro Thr Pro Thr Pro Thr Pro Thr Gly Ser
        580                 585                 590

Asp Leu Gly Lys Lys Leu Leu Glu Ala Ala Arg Ala Gly Gln Asp Asp
        595                 600                 605

Glu Val Arg Glu Leu Leu Lys Ala Gly Ala Asp Val Asn Ala Lys Asp
    610                 615                 620

Lys Asp Gly Tyr Thr Pro Leu His Leu Ala Ala Arg Glu Gly His Leu
625                 630                 635                 640

Glu Ile Val Glu Val Leu Leu Lys Ala Gly Ala Asp Val Asn Ala Lys
            645                 650                 655

Asp Lys Asp Gly Tyr Thr Pro Leu His Leu Ala Ala Arg Glu Gly His
        660                 665                 670

Leu Glu Ile Val Glu Val Leu Leu Lys Ala Gly Ala Asp Val Asn Ala
    675                 680                 685

Gln Asp Lys Ser Gly Lys Thr Pro Ala Asp Leu Ala Ala Asp Ala Gly
    690                 695                 700

His Glu Asp Ile Ala Glu Val Leu Gln Lys Ala Ala Gly Ser Pro Thr
705                 710                 715                 720

Gly Ser Asp Leu Gly Gln Lys Leu Leu Glu Ala Ala Trp Ala Gly Gln

-continued

```
                725                 730                 735
Asp Asp Glu Val Arg Glu Leu Leu Lys Ala Gly Ala Asp Val Asn Ala
                740                 745                 750

Lys Asn Ser Arg Gly Trp Thr Pro Leu His Thr Ala Ala Gln Thr Gly
            755                 760                 765

His Leu Glu Ile Phe Glu Val Leu Leu Lys Ala Gly Ala Asp Val Asn
        770                 775                 780

Ala Lys Asn Asp Lys Arg Val Thr Pro Leu His Leu Ala Ala Ala Leu
785                 790                 795                 800

Gly His Leu Glu Ile Val Glu Val Leu Leu Lys Ala Gly Ala Asp Val
                805                 810                 815

Asn Ala Arg Asp Ser Trp Gly Thr Thr Pro Ala Asp Leu Ala Ala Lys
                820                 825                 830

Tyr Gly His Gln Asp Ile Ala Glu Val Leu Gln Lys Ala Ala
            835                 840                 845

<210> SEQ ID NO 116
<211> LENGTH: 847
<212> TYPE: PRT
<213> ORGANISM: Artificial Sequence
<220> FEATURE:
<223> OTHER INFORMATION: DARPin protein 77

<400> SEQUENCE: 116

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Pro Thr Pro Thr Pro Thr Pro Thr Pro Thr Pro Thr
    130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Tyr Phe Ser His Thr Pro Leu His Leu Ala Ala Arg
            180                 185                 190

Asn Gly His Leu Lys Ile Val Glu Val Leu Leu Lys Ala Gly Ala Asp
        195                 200                 205

Val Asn Ala Lys Asp Phe Ala Gly Lys Thr Pro Leu His Leu Ala Ala
    210                 215                 220

Ala Asp Gly His Leu Glu Ile Val Glu Val Leu Leu Lys Ala Gly Ala
225                 230                 235                 240

Asp Val Asn Ala Gln Asp Ile Phe Gly Lys Thr Pro Ala Asp Ile Ala
```

-continued

```
                245                 250                 255
Ala Asp Ala Gly His Glu Asp Ile Ala Glu Val Leu Gln Lys Ala Ala
                260                 265                 270

Gly Ser Pro Thr Pro Thr Pro Thr Thr Pro Thr Pro Thr Pro Thr Thr
                275                 280                 285

Pro Thr Pro Thr Pro Thr Gly Ser Asp Leu Gly Ile Lys Leu Leu Thr
                290                 295                 300

Ala Ala Tyr Asp Gly Gln Leu Asp Glu Val Arg Ile Leu Leu Lys Ala
305                 310                 315                 320

Gly Ala Asp Val Asn Ala Lys Asp Leu Arg Gly Gln Thr Pro Leu His
                325                 330                 335

Tyr Ala Ala Gly Leu Gly His Leu Glu Ile Val Glu Val Leu Leu Lys
                340                 345                 350

Ala Gly Ala Asp Val Asn Ala Lys Asp Leu His Gly Trp Thr Pro Leu
                355                 360                 365

His Leu Ala Ala Trp Ser Gly His Leu Glu Ile Val Glu Val Leu Leu
                370                 375                 380

Lys Ala Gly Ala Asp Val Asn Ala Gln Asp Val Glu Gly Val Thr Pro
385                 390                 395                 400

Ala Asp Leu Ala Ala Val Gln Gly His Gln Asp Ile Ala Glu Val Leu
                405                 410                 415

Gln Lys Ala Ala Gly Ser Pro Thr Pro Thr Pro Thr Thr Pro Thr Pro
                420                 425                 430

Thr Pro Thr Thr Pro Thr Pro Thr Pro Thr Gly Ser Asp Leu Gly Lys
                435                 440                 445

Lys Leu Leu Gln Ala Ala Leu Glu Gly Gln Leu Asp Glu Val Arg Glu
                450                 455                 460

Leu Leu Lys Ala Gly Ala Asp Val Asn Ala Lys Asp Ile Glu Gly Tyr
465                 470                 475                 480

Thr Pro Leu His Leu Ala Ala Ala Leu Gly His Leu Glu Ile Val Glu
                485                 490                 495

Val Leu Leu Lys Ala Gly Ala Asp Val Asn Ala Lys Asp Gln Ile Gly
                500                 505                 510

Arg Thr Pro Leu His Leu Ala Ala Tyr Lys Gly His Leu Glu Ile Val
                515                 520                 525

Glu Val Leu Leu Lys Ala Gly Ala Asp Val Asn Ala Gln Asp Ile Ile
                530                 535                 540

Gly Gln Thr Pro Ala Asp Leu Ala Ala Gln Arg Gly His Gln Asp Ile
545                 550                 555                 560

Ala Glu Val Leu Gln Lys Ala Ala Gly Ser Pro Thr Pro Thr Pro Thr
                565                 570                 575

Thr Pro Thr Pro Thr Pro Thr Thr Pro Thr Pro Thr Pro Thr Gly Ser
                580                 585                 590

Asp Leu Gly Lys Lys Leu Leu Ala Ala Glu Arg Gly Gln Leu Asp
                595                 600                 605

Glu Val Arg Ile Leu Leu Lys Ala Gly Ala Asp Val Asn Ala Lys Asp
                610                 615                 620

Arg Ala Glu Gly Tyr Thr Pro Leu His Ile Ala Ala Tyr Gln Gly His
625                 630                 635                 640

Leu Glu Ile Val Glu Val Leu Leu Lys Ala Gly Ala Asp Val Asn Ala
                645                 650                 655

Lys Asp Arg Tyr Gly Lys Thr Pro Leu His Leu Ala Ala Ile Ser Gly
                660                 665                 670
```

His Leu Glu Ile Val Glu Val Leu Leu Lys Ala Gly Ala Asp Val Asn
            675                 680                 685

Ala Gln Asp Asn Lys Gly Ser Thr Pro Ala Asp Leu Ala Ala Asp Tyr
    690                 695                 700

Gly His Gln Asp Ile Ala Glu Val Leu Gln Lys Ala Ala Gly Ser Pro
705                 710                 715                 720

Thr Gly Ser Asp Leu Gly Lys Lys Leu Leu Glu Ala Ala Arg Ala Gly
            725                 730                 735

Gln Asp Asp Glu Val Arg Glu Leu Leu Lys Ala Gly Ala Asp Val Asn
            740                 745                 750

Ala Lys Asp Lys Asp Gly Tyr Thr Pro Leu His Leu Ala Ala Arg Glu
            755                 760                 765

Gly His Leu Glu Ile Val Glu Val Leu Leu Lys Ala Gly Ala Asp Val
            770                 775                 780

Asn Ala Lys Asp Lys Asp Gly Tyr Thr Pro Leu His Leu Ala Ala Arg
785                 790                 795                 800

Glu Gly His Leu Glu Ile Val Glu Val Leu Leu Lys Ala Gly Ala Asp
            805                 810                 815

Val Asn Ala Gln Asp Lys Ser Gly Lys Thr Pro Ala Asp Leu Ala Ala
            820                 825                 830

Asp Ala Gly His Glu Asp Ile Ala Glu Val Leu Gln Lys Ala Ala
            835                 840                 845

<210> SEQ ID NO 117
<211> LENGTH: 272
<212> TYPE: PRT
<213> ORGANISM: Artificial Sequence
<220> FEATURE:
<223> OTHER INFORMATION: DARPin protein 78

<400> SEQUENCE: 117

Asp Leu Gly Ile Lys Leu Leu Thr Ala Ala Tyr Asp Gly Gln Leu Asp
1               5                   10                  15

Glu Val Arg Ile Leu Leu Lys Ala Gly Ala Asp Val Asn Ala Lys Asp
            20                  25                  30

Leu Arg Gly Gln Thr Pro Leu His Tyr Ala Ala Gly Leu Gly His Leu
            35                  40                  45

Glu Ile Val Glu Val Leu Leu Lys Ala Gly Ala Asp Val Asn Ala Lys
        50                  55                  60

Asp Leu His Gly Trp Thr Pro Leu His Leu Ala Ala Trp Ser Gly His
65                  70                  75                  80

Leu Glu Ile Val Glu Val Leu Leu Lys Ala Gly Ala Asp Val Asn Ala
            85                  90                  95

Gln Asp Val Glu Gly Val Thr Pro Ala Asp Leu Ala Ala Val Gln Gly
            100                 105                 110

His Gln Asp Ile Ala Glu Val Leu Gln Lys Ala Ala Gly Ser Pro Thr
            115                 120                 125

Pro Thr Pro Thr Thr Pro Thr Pro Thr Pro Thr Pro Thr Pro Thr
130                 135                 140

Pro Thr Gly Ser Asp Leu Gly Gln Lys Leu Leu Glu Ala Ala Trp Ala
145                 150                 155                 160

Gly Gln Asp Asp Glu Val Arg Glu Leu Leu Lys Ala Gly Ala Asp Val
            165                 170                 175

Asn Ala Lys Asn Ser Arg Gly Trp Thr Pro Leu His Thr Ala Ala Gln
            180                 185                 190

```
Thr Gly His Leu Glu Ile Phe Glu Val Leu Lys Ala Gly Ala Asp
        195                 200                 205

Val Asn Ala Lys Asn Asp Lys Arg Val Thr Pro Leu His Leu Ala Ala
    210                 215                 220

Ala Leu Gly His Leu Glu Ile Val Glu Val Leu Leu Lys Ala Gly Ala
225                 230                 235                 240

Asp Val Asn Ala Arg Asp Ser Trp Gly Thr Thr Pro Ala Asp Leu Ala
                245                 250                 255

Ala Lys Tyr Gly His Gln Asp Ile Ala Glu Val Leu Gln Lys Ala Ala
            260                 265                 270

<210> SEQ ID NO 118
<211> LENGTH: 2631
<212> TYPE: DNA
<213> ORGANISM: Artificial Sequence
<220> FEATURE:
<223> OTHER INFORMATION: Nucleic acid encoding protein of SEQ ID NO 95

<400> SEQUENCE: 118
atgagaggat cgcatcacca tcaccatcac ggatccgacc tgggtaaaaa gctgctggag      60
gcagcgcgtg ccggtcaaga cgacgaggtt cgcgaattgc ttaaagcggg tgcagacgtc     120
aacgccaaag attatttctc tcatacccccg ttgcatttag ccgcgcgtaa tggccatctg    180
aagatcgtcg aggtcctctt gaaggcaggc gcggatgtca atgcgaagga ttttgcgggc    240
aaaacgccgc tgcacttagc ggcggcggac ggtcatttag aaatcgttga agtcctgtta    300
aaagcgggcg ccgatgtgaa tgcgcaggat attttcggta aaacgccggc ggacattgcg    360
gcagatgcgg gtcatgaaga tatcgcagaa gtcctgcaga aggcagcagg cagccctaca    420
cctacgccga ctacgcctac gccgactccg actaccccga ctccgacccc gaccggatca    480
gacctgggta aaagctgct ggaggcagcg cgtgccggtc aagacgacga ggttcgcgaa    540
ttgcttaaag cgggtgcaga cgtcaacgcc aaagattatt tctctcatac cccgttgcat    600
ttagccgcgc gtaatggcca tctgaagatc gtcgaggtcc tcttgaaggc aggcgcggat    660
gtcaatgcga aggattttgc gggcaaaacg ccgctgcact tagcggcggc ggacggtcat    720
ttagaaatcg ttgaagtcct gttaaaagcg gcgccgatg tgaatgcgca ggatattttc     780
ggtaaaacgc cggcggacat tgcggcagat gcgggtcatg aagatatcgc agaagtcctg    840
cagaaggcag caggctcgcc aacgccgacc cctacaacgc caaccccgac accaactaca    900
ccgaccccca caccaacggg atcagacctg gtgttaagc tgttgcttgc agccgagcgt    960
gggcagcttg atgaagtacg cattcttctt aaagcggggg ctgatgtgaa cgcgaaagat   1020
attgctgagg ttacacaccg cttcacatt gccgcctacc agggtcatct ggagattgtt    1080
gaagtattac tgaaagcggg agcagatgtt aatgccaaag atcgctatgg aaaaactcct   1140
ttgcatttag ctgcaatcgg aggacacctg gaaatcgtcg aagtgttatt aaaagctgga   1200
gcggacgtaa acgcacaaga taacaagggc tcaactcccg cggaccttgc cgcagattac   1260
ggtcatcagg acattgctga agttctgcag aaggcagcag gttccccgac ccctacgcca   1320
acgactccga ccccaactcc aacgacccct accccgaccc cgaccggatc agacctgggt   1380
aaaaaattgc ttgaagccgc gttggaagga caattagacg aggtacgtga gctgttaaaa   1440
gcaggggccg atgtgaatgc taaagaccag gagggataca ccccccttgca cctggctgcc   1500 gcgttgggcc acttagagat tgtagaggtt cttcttaagg cggggggcaga cgtgaatgca   1560 aaggaccaaa ttggacgtac tccttttgcat ctggcagcct ataaggggca cttggagatt   1620
```

```
gtcgaggtct tgttaaaggc gggtgccgat gtaaatgccc aggacatcat tgggcagact    1680
ccggcagatt tggccgccca acgtggccac caagatattg ctgaagttct gcagaaggca    1740
gcaggcagcc ccacgccaac tcctacaacc cccacaccta caccgacgac gccgacaccg    1800
actccaaccg gatcagacct gggtattaaa ctgttgacag ccgcttacga cgggcaatta    1860
gacgaagtgc gtattctgct taaagctgga gctgacgtga acgcgaaaga cttacgcggc    1920
caaacgcctt tacattacgc ggcgggactg ggccatcttg agattgttga ggtgcttctg    1980
aaggcaggcg cggatgtcaa tgcaaaagac ctgcacggat ggacacctct tcacttagct    2040
gcttggtctg gcatttgga gattgtagag gttttattga aagcagggc ggatgtgaat    2100 gcgcaagacg tagaaggagt cacccccagct gacctggcag cggttcaagg catcaagac    2160 attgctgaag ttctgcagaa ggcagcaggt tcgccgaccc caaccctac cactccaacg    2220 ccgacgccta ccactccaac accaacacca acgggatcag acctgggtca aaagctgttg    2280
gaagccgcgt gggcgggtca ggacgatgaa gtccgtgagc tgcttaaagc aggagccgac    2340
gtgaacgcga agaactcacg cgggtggacg ccacttcaca cggccgcgca gacaggtcac    2400
cttgaaatct tgaggttct tctgaaggca ggagcagacg ttaacgccaa aaacgacaag    2460
cgcgtgactc cgttgcacct gccgcagct ctggggcatt tggagatcgt tgaggtactg    2520
ttgaaagcgg gagcagatgt taatgctcgc gacagtgggg gacgacacc agcagacctg    2580 gccgcaaaat acggacacca agacattgct gaagttctgc agaaggcggc a             2631
```

<210> SEQ ID NO 119
<211> LENGTH: 2577
<212> TYPE: DNA
<213> ORGANISM: Artificial Sequence
<220> FEATURE:
<223> OTHER INFORMATION: Nucleic acid encoding protein of SEQ ID NO 96

<400> SEQUENCE: 119

```
atgagaggat cgcatcacca tcaccatcac ggatccgacc tgggtaagaa actgttggaa      60
gcagcacgtg cgggtcaaga cgatgaagtt cgtgagctgt taaaggctgg cgccgacgtg     120
aacgcgaagg actactttag ccacacccg ctgcacttgg cagcgcgcaa cggtcacctg     180
aaaattgtcg aggtcctgtt gaaggctggt gcggatgtga acgcaaaaga ttttgcgggt     240
aagacgccgc tgcatctggc ggcggctgat ggtcacttag atcgtagag ggttctgttg     300 aaagcgggcg ccgatgtgaa tgcccaggac atcttcggca agaccccggc agacattgcc     360
gcggatgctg tcacgaaga tatcgcagag gtcctgcaaa agcggcagg cagcccgacc     420 ccgacgccga ccactccgac cccgacccca accacccga ctccgactcc gaccggatct     480
gacctgggta aaaactgct ggaagcagca cgtgccggcc aggatgatga agttcgtgaa     540
ctgctgaaag caggcgccga tgttaatgca aaggattatt ttagccacac accgctgcat     600
ctggcagccc gtaatggtca cctaaagatt gttgaagttc tgctgaaggc tggtgcagac     660
gttaacgcca agatttcgc gggcaaaacc cctctgcatt tagccgcagc ggacggtcac     720
ctggagatcg tagaggtgct gcttaaggcg ggtgcggatg ttaatgcaca ggatatttc     780 ggtaaaaccc ctgccgatat tgcagctgat gccggtcatg aagatatcgc agaagtgctg     840
cagaaggcag caggatcacc aacaccaacc ccgaccaccc caactccaac accgaccacc     900
ccgaccccta cccaacagg atccgacctg gtattaaac tgttgacagc cgcttacgac     960
gggcaattag acgaagtgcg tattctgctt aaagctggag ctgacgtgaa cgcgaaagac    1020
```

| | |
|---|---|
| ttacgcggcc aaacgccttt acattacgcg gcgggactgg gccatcttga gattgttgag | 1080 |
| gtgcttctga aggcaggcgc ggatgtcaat gcaaaagacc tgcacggatg gacacctctt | 1140 |
| cacttagctg cttggtctgg gcatttggag attgtagagg ttttattgaa agcaggggcg | 1200 |
| gatgtgaatg cgcaagacgt agaaggagtc accccagctg acctggcagc ggttcaaggg | 1260 |
| catcaagaca ttgctgaagt tctgcagaag gcagcaggct cgccgactcc gaccccgacc | 1320 |
| accccaactc caacaccgac caccccgacc cctaccccaa caggatctga cctgggtaaa | 1380 |
| aagttgttac aggcagcatt ggagggccaa cttgacgagg tgcgcgagtt actgaaagct | 1440 |
| ggtgcagatg tcaacgcgaa ggacattgaa ggatatactc cgctgcacct tgccgcggct | 1500 |
| ttggggcatc ttgagattgt ggaggtgctt cttaaggcgg gagctgatgt caatgctaaa | 1560 |
| gaccaaatcg gcgcacacc gttacacttg gctgcgtaca aaggtcactt agaaatcgtg | 1620 |
| gaagtgcttc tgaaggctgg cgctgatgtc aacgcccaag acattatcgg ccagacaccg | 1680 |
| gcggacctgg cagcgcaacg tgggcatcag gatattgctg aagttctgca gaaggcagca | 1740 |
| ggctcgccga ctccgacccc gaccaccccca actccaacac cgaccaccccc gacccctacc | 1800 |
| ccaacaggat ctgacctggg taaaaagttg ttattagctg cggagcgcgg gcagttagac | 1860 |
| gaagtgcgta ttctgctgaa ggccggggcc gacgttaacg caaaggatcg tgcagagggt | 1920 |
| tacaccccc tgcacatcgc cgcttatcaa ggtcacttgg agattgttga ggtcttactg | 1980 |
| aaagcggggg ccgacgtgaa tgccaaagat cgctatggaa aaacaccgtt acacttagca | 2040 |
| gctatttcgg ggcatctgga gatcgtggaa gtcctgttaa aggctggtgc cgatgttaat | 2100 |
| gcacaagata taaaggcag cactccagcc gatctggccg ctgattatgg gcaccaggac | 2160 |
| attgctgaag ttctgcagaa ggcagcaggc tcgccaaccg gatcagatct gggtcaaaag | 2220 |
| ctgttggaag ccgcgtgggc gggtcaggac gatgaagtcc gtgagctgct taaagcagga | 2280 |
| gccgacgtga acgcgaagaa ctcacgcggg tggacgccac ttcacacggc cgcgcagaca | 2340 |
| ggtcaccttg aaatctttga ggttcttctg aaggcaggag cagacgttaa cgccaaaaac | 2400 |
| gacaagcgcg tgactccgtt gcaccttgcc gcagctctgg ggcatttgga gatcgttgag | 2460 |
| gtactgttga aagcgggagc agatgttaat gctcgcgaca gttggggac gacaccagca | 2520 |
| gacctggccg caaaatacgg acaccaagac attgctgaag ttctgcaaaa ggcagca | 2577 |

<210> SEQ ID NO 120
<211> LENGTH: 2586
<212> TYPE: DNA
<213> ORGANISM: Artificial Sequence
<220> FEATURE:
<223> OTHER INFORMATION: Nucleic acid encoding protein of SEQ ID NO 97

<400> SEQUENCE: 120

| | |
|---|---|
| atgagaggat cgcatcacca tcaccatcac ggatccgacc tgggtaagaa actgttggaa | 60 |
| gcagcacgtg cgggtcaaga cgatgaagtt cgtgagctgt taaaggctgg cgccgacgtg | 120 |
| aacgcgaagg actactttag ccacaccccg ctgcacttgg cagcgcgcaa cggtcacctg | 180 |
| aaaattgtcg aggtcctgtt gaaggctggt gcggatgtga acgcaaaaga ttttgcgggt | 240 |
| aagacgccgc tgcatctggc ggcggctgat ggtcacttag atcgtagag ggttctgttg | 300 |
| aaagcgggcg ccgatgtgaa tgcccaggac atcttcggca gaccccggc agacattgcc | 360 |
| gcggatgctg gtcacgaaga tatcgcagag gtcctgcaaa agcggcagg cagcccgacc | 420 |
| ccgacgccga ccactccgac cccgaccccca accacccccga ctccgactcc gaccggatct | 480 |
| gacctgggta aaaaactgct ggaagcagca cgtgccggcc aggatgatga agttcgtgaa | 540 |

```
ctgctgaaag caggcgccga tgttaatgca aggattatt ttagccacac accgctgcat      600
ctggcagccc gtaatggtca cctaaagatt gttgaagttc tgctgaaggc tggtgcagac      660
gttaacgcca agatttcgc gggcaaaacc cctctgcatt tagccgcagc ggacggtcac      720
ctggagatcg tagaggtgct gcttaaggcg ggtgcggatg ttaatgcaca ggatattttc      780
ggtaaaaccc ctgccgatat tgcagctgat gccggtcatg aagatatcgc agaagtgctg      840
cagaaggcag caggatcacc aacaccaacc ccgaccaccc caactccaac accgaccacc      900
ccgacccta ccccaacagg atccgacctg gtattaaac tgttgacagc cgcttacgac       960
gggcaattag acgaagtgcg tattctgctt aaagctggag ctgacgtgaa cgcgaaagac     1020
ttacgcggcc aaacgccttt acattacgcg gcgggactgg gccatcttga gattgttgag     1080
gtgcttctga aggcaggcgc ggatgtcaat gcaaaagacc tgcacggatg gacacctctt     1140
cacttagctg cttggtctgg gcatttggag attgtagagg ttttattgaa gcaggggcg     1200
gatgtgaatg cgcaagacgt agaaggagtc accccagctg acctggcagc ggttcaaggg     1260
catcaagaca ttgctgaagt tctgcagaag gcagcaggct cgccgactcc gaccccgacc     1320
accccaactc caacaccgac caccccgacc cctaccccaa caggatctga cctgggttgg     1380
aaactgcttg atgccgccga gattggtcag cttgacgaag tccgtattct tttgaaggca     1440
ggggccgacg ttaatgccaa agacaaacag ggtatcacgc cgttacatat tgccgcagcg     1500
catggtcact tagagatcgt agaagtactt ctgaaagcag gtgctgacgt taatgcaaag     1560
gatgagatcg gccgcacccc gcttcatctt gctgccttta agggccattt ggaaatcgta     1620
gaggtgctgt taaaggctgg cgctgatgtc aatgcacaag acatcatcgg ggagacgcct     1680
gccgacctgg cggcggtacg cgggcatcag gatattgctg aagttctgca gaaggcagca     1740
ggctcgccga ctccgacccc gaccaccca actccaacac cgaccaccc gaccctacc       1800
ccaacaggat ctgacctggg tgttaagctg ttgcttgcag ccgagcgtgg gcagcttgat     1860
gaagtacgca ttcttcttaa gcggggggct gatgtgaacg cgaaagatat tgctgagggt     1920
tacacaccgc ttcacattgc cgcctaccag ggtcatctgg agattgttga agtattactg     1980
aaagcgggag cagatgttaa tgccaaagat cgctatggaa aaactccttt gcatttagct     2040
gcaatcggag acacctgga aatcgtcgaa gtgttattaa agctggagc ggacgtaaac      2100
gcacaagata caagggctc aactcccgcg gaccttgccg cagattacgg tcatcaggac     2160
attgctgaag ttctgcagaa ggcagcaggc tcgccaaccg gatcagatct gggtcaaaag     2220
ctgttggaag ccgcgtgggc gggtcaggac gatgaagtcc gtgagctgct aaagcagga      2280
gccgacgtga acgcgaagaa ctcacgcggg tggacgccac ttcacacggc cgcgcagaca     2340
ggtcaccttg aaatctttga ggttcttctg aaggcaggag cagacgttaa cgccaaaaac     2400
gacaagcgcg tgactccgtt gcaccttgcc gcagctctgg ggcatttgga gatcgttgag     2460
gtactgttga aagcgggagc agatgttaat gctcgcgaca gttgggggac gacaccagca     2520
gacctggccg caaaatacgg acaccaagac attgctgaag ttctgcaaaa ggcagcataa     2580
tgatag                                                              2586
```

<210> SEQ ID NO 121
<211> LENGTH: 2586
<212> TYPE: DNA
<213> ORGANISM: Artificial Sequence
<220> FEATURE:
<223> OTHER INFORMATION: Nucleic acid encoding protein of SEQ ID NO 98

<400> SEQUENCE: 121

```
atgagaggat cgcatcacca tcaccatcac ggatccgacc tgggtaagaa actgttggaa      60
gcagcacgtg cgggtcaaga cgatgaagtt cgtgagctgt taaaggctgg cgccgacgtg     120
aacgcgaagg actactttag ccacaccccg ctgcacttgg cagcgcgcaa cggtcacctg     180
aaaattgtcg aggtcctgtt gaaggctggt gcggatgtga acgcaaaaga ttttgcgggt     240
aagacgccgc tgcatctggc ggcggctgat ggtcacttag atcgtagaa ggttctgttg     300
aaagcgggcg ccgatgtgaa tgcccaggac atcttcggca agaccccggc agacattgcc     360
gcggatgctg gtcacgaaga tatcgcgagg gtcctgcaaa agcggcagg cagcccgacc     420
ccgacgccga ccactccgac cccgacccca accaccccga ctccgactcc gaccggatct     480
gacctgggta aaaaactgct ggaagcagca cgtgccggcc aggatgatga agttcgtgaa     540
ctgctgaaag caggcgccga tgttaatgca aggattatt ttagccacac accgctgcat     600
ctggcagccc gtaatggtca cctaaagatt gttgaagttc tgctgaaggc tggtgcagac     660
gttaacgcca aagatttcgc gggcaaaacc cctctgcatt tagccgcagc ggacggtcac     720
ctggagatcg tagaggtgct gcttaaggcg ggtgcggatg ttaatgcaca ggatattttc     780
ggtaaaaccc ctgccgatat tgcagctgat gccggtcatg aagatatcgc agaagtgctg     840
cagaaggcag caggatcacc aacaccaacc ccgaccaccc caactccaac accgaccacc     900
ccgaccccta ccccaacagg atccgacctg ggtattaaac tgttgacagc cgcttacgac     960
gggcaattag acgaagtgcg tattctgctt aaagctggag ctgacgtgaa cgcgaaagac    1020
ttacgcggcc aaacgccttt acattacgcg gcgggactgg ccatcttga gattgttgag    1080
gtgcttctga aggcaggcgc ggatgtcaat gcaaaagacc tgcacggatg gacacctctt    1140
cacttagctg cttggtctgg gcatttggag attgtagagg ttttattgaa gcaggggcg    1200
gatgtgaatg cgcaagacgt agaaggagtc accccagctg acctggcagc ggttcaaggg    1260
catcaagaca ttgctgaagt tctgcagaag gcagcaggct cgccgactcc gaccccgacc    1320
accccaactc caacaccgac caccccgacc cctaccccaa caggatctga cctgggtaaa    1380
aaattgcttg aagccgcgtt ggaaggacaa ttagacgagg tacgtgagct gttaaaagca    1440
ggggccgatg tgaatgctaa agaccaggag ggatacaccc ccttgcacct ggctgccgcg    1500
ttgggccact agagattgt agaggttctt cttaaggcgg gggcagacgt gaatgcaaag    1560
gaccaaattg gacgtactcc tttgcatctg gcagcctata aggggcactt ggagattgtc    1620
gaggtcttgt taaaggcggg tgccgatgta aatgcccagg acatcattgg gcagactccg    1680
gcagatttgg ccgcccaacg tggccaccaa gatattgctg aagttctgca gaaggcagca    1740
ggctcgccga ctccgacccc gaccacccca actccaacac cgaccacccc gacccctacc    1800
ccaacaggat ctgacctggg tgttaagctg ttgcttgcag ccgagcgtgg gcagcttgat    1860
gaagtacgca ttcttcttaa gcgggggct gatgtgaacg cgaaagatat tgctgagggt    1920
tacacaccgc ttcacattgc cgcctaccag ggtcatctgg agattgttga agtattactg    1980
aaagcgggag cagatgttaa tgccaaagat cgctatggaa aaactccttt gcatttagct    2040
gcaatcggag acacctgga aatcgtcgaa gtgttattaa agctggagc ggacgtaaac    2100
gcacaagata caagggctc aactcccgcg gaccttgccg cagattacgg tcatcaggac    2160
attgctgaag ttctgcagaa ggcagcaggc tcgccaaccg gatcagatct gggtcaaaag    2220
ctgttggaag ccgcgtgggc gggtcaggac gatgaagtcc gtgagctgct taaagcagga    2280
gccgacgtga acgcgaagaa ctcacgcggg tggacgccac ttcacacggc cgcgcagaca    2340
```

```
ggtcaccttg aaatctttga ggttcttctg aaggcaggag cagacgttaa cgccaaaaac    2400
gacaagcgcg tgactccgtt gcaccttgcc gcagctctgg ggcatttgga gatcgttgag    2460
gtactgttga aagcgggagc agatgttaat gctcgcgaca gttgggggac gacaccagca    2520
gacctggccg caaaatacgg acaccaagac attgctgaag ttctgcaaaa ggcagcataa    2580
tgatag                                                               2586
```

<210> SEQ ID NO 122
<211> LENGTH: 2676
<212> TYPE: DNA
<213> ORGANISM: Artificial Sequence
<220> FEATURE:
<223> OTHER INFORMATION: Nucleic acid encoding protein of SEQ ID NO 99

<400> SEQUENCE: 122

```
atgagaggat cgcatcacca tcaccatcac ggatccgacc tgggtaagaa actgttggaa      60
gcagcacgtg cgggtcaaga cgatgaagtt cgtgagctgt taaaggctgg cgccgacgtg     120
aacgcgaagg actactttag ccacaccccg ctgcacttgg cagcgcgcaa cggtcacctg     180
aaaattgtcg aggtcctgtt gaaggctggt gcggatgtga acgcaaaaga tttttgcgggt    240 aagacgccgc tgcatctggc ggcggctgat ggtcacttag agatcgtaga ggttctgttg     300
aaagcgggcg ccgatgtgaa tgcccaggac atcttcggca agaccccggc agacattgcc     360
gcggatgctg gtcacgaaga tatcgcagag gtcctgcaaa aagcggcagg cagcccgacc     420
ccgacgccga ccactccgac cccgacccca accaccccga ctccgactcc gaccggatct     480
gacctgggta aaaaactgct ggaagcagca cgtgccggcc aggatgatga agttcgtgaa     540
ctgctgaaag caggcgccga tgttaatgca aaggattatt ttagccacac accgctgcat     600
ctggcagccc gtaatggtca cctaaagatt gttgaagttc tgctgaaggc tggtgcagac     660
gttaacgcca aagatttcgc gggcaaaacc cctctgcatt tagccgcagc ggacggtcac     720
ctggagatcg tagaggtgct gcttaaggcg ggtgcggatg ttaatgcaca ggatattttc     780
ggtaaaaccc ctgccgatat tgcagctgat gccggtcatg aagatatcgc agaagtgctg     840
cagaaggcag caggatcacc aacaccaacc ccgaccaccc caactccaac accgaccacc     900
ccgaccccta ccccaacagg atccgacctg gtattaaac tgttgacagc cgcttacgac     960
gggcaattag acgaagtgcg tattctgctt aaagctggag ctgacgtgaa cgcgaaagac    1020
ttacgcggcc aaacgccttt acattacgcg gcgggactgg ccatcttgat gattgttgag    1080
gtgcttctga aggcaggcgc ggatgtcaat gcaaagacc tgcacggatg gacacctctt    1140
cacttagctg cttggtctgg gcatttggag attgtagagg ttttattgaa agcagggcg     1200 gatgtgaatg cgcaagacgt agaaggagtc accccagctg acctggcagc ggttcaaggg    1260
catcaagaca ttgctgaagt tctgcagaag gcagcaggct cgccgactcc gaccccgacc    1320
accccaactc caacaccgac caccccgacc cctaccccaa caggatctga cctgggtaaa    1380
aaactgctgc aagcagcacg tgcaggtcag ctggatgaag ttcgtgaact gctgaaagca    1440
ggcgccgatg ttaatgcaaa agatcaatac ggcagaaccc cgctgcatct ggctgctatc    1500
aagggtcacc tggaaattgt tgaagttctg ctgaaagccg tgcagatgt taatgcaaaa    1560 gattctctgg gctacacccc gctgcatctg ctgctgtgg agggtcccct ggaaattgtt    1620
gaagttctgc tgaaagccgg tgcagatgtt aatgcaaaag atgcttacgg ccaaaccccg    1680
ctgcatatcg ctgctgcttg gggtcacctg gaaattgttg aagttctgct gaaagccgtt    1740
```

```
gcagatgtta acgcacagga taaaagcggt aaaaccctg ccgatctggc agctcgcgcc    1800
ggtcatcaag atattgctga agtgctgcag aaggcagcag gctcgccgac tccgaccccg    1860
accaccccaa ctccaacacc gaccaccccg acccctaccc aacaggatc tgacctgggt    1920
gttaagctgt tgcttgcagc cgagcgtggg cagcttgatg aagtacgcat tcttcttaaa    1980
gcgggggctg atgtgaacgc gaaagatatt gctgagggtt acacaccgct tcacattgcc    2040
gcctaccagg gtcatctgga gattgttgaa gtattactga aagcgggagc agatgttaat    2100
gccaaagatc gctatggaaa aactcctttg catttagctg caatcggagg acacctggaa    2160
atcgtcgaag tgttattaaa agctggagcg gacgtaaacg cacaagataa caagggctca    2220
actcccgcgg accttgccgc agattacggt catcaggaca ttgctgaagt tctgcagaag    2280
gcagcaggct cgccaaccgg atcagatctg ggtcaaaagc tgttggaagc cgcgtgggcg    2340
ggtcaggacg atgaagtccg tgagctgctt aaagcaggag ccgacgtgaa cgcgaagaac    2400
tcacgcgggt ggacgccact tcacacggcc gcgcagacag gtcacttga aatctttgag    2460
gttcttctga aggcaggagc agacgttaac gccaaaaacg acaagcgcgt gactccgttg    2520
caccttgccg cagctctggg gcatttggag atcgttgagg tactgttgaa agcgggagca    2580
gatgttaatg ctcgcgacag ttgggggacg acaccagcag acctggccgc aaaatacgga    2640
caccaagaca ttgctgaagt tctgcaaaag gcagca                              2676
```

<210> SEQ ID NO 123
<211> LENGTH: 2676
<212> TYPE: DNA
<213> ORGANISM: Artificial Sequence
<220> FEATURE:
<223> OTHER INFORMATION: Nucleic acid encoding protein of SEQ ID NO 100

<400> SEQUENCE: 123

```
atgagaggat cgcatcacca tcaccatcac ggatccgacc tgggtaagaa actgttggaa      60
gcagcacgtg cgggtcaaga cgatgaagtt cgtgagctgt taaaggctgg cgccgacgtg     120
aacgcgaagg actactttag ccacaccccg ctgcacttgg cagcgcgcaa cggtcacctg     180
aaaattgtcg aggtcctgtt gaaggctggt gcggatgtga acgcaaaaga ttttgcgggt     240
aagacgccgc tgcatctggc ggcggctgat ggtcacttag agatcgtaga ggttctgttg     300
aaagcgggcg ccgatgtgaa tgcccaggac atcttcggca agaccccggc agacattgcc     360
gcggatgctg gtcacgaaga tatcgcagag gtcctgcaaa aagcggcagg cagcccgacc     420
ccgacgccga ccactccgac cccgaccccca accaccccga ctccgactcc gaccggatct     480
gacctgggta aaaaactgct ggaagcagca cgtgccggcc aggatgatga agttcgtgaa     540
ctgctgaaag caggcgccga tgttaatgca aaggattatt ttagccacac accgctgcat     600
ctggcagccc gtaatggtca cctaaagatt gttgaagttc tgctgaaggc tggtgcagac     660
gttaacgcca agatttcgc gggcaaaacc cctctgcatt tagccgcagc ggacggtcac     720
ctggagatcg tagaggtgct gcttaaggcg ggtgcggatg ttaatgcaca ggatatttc     780
ggtaaaaccc ctgccgatat tgcagctgat gccggtcatg aagatatcgc agaagtgctg     840
cagaaggcag caggatcacc aacaccaacc ccgaccaccc caactccaac accgaccacc     900
ccgaccccta ccccaacagg atccgacctg gtaaaaaat gcttcaggc cgctcgcgcc     960
ggcaacttg acgaagtacg tgaattactg aaagcaggcg cagacgtgaa cgctaaggat    1020
cagcagggct taactccgtt acacatcgcc gctaatctgg gtcatctgga gattgttgaa    1080
gtattattaa aggccggagc ggatgtaaat gccaaggatc tgtttggact tacgccgctt    1140
```

```
catctggccg cttttgaggg tcacttagaa attgtggagg tcttacttaa ggcgggggct    1200
gacgtaaatg cgaaagatca gcatggtgcc acgcctcttc atttggctgc ttgggtcgga    1260
catttggaaa ttgtggaagt gttattgaaa gctggagcag atgtgaacgc gcaggacaag    1320
tcaggtaaaa ccccggcgga tctggcggca cgcgcaggac atcaagatat tgctgaagtt    1380
ctgcagaagg cagcaggctc gccgactccg accccgacca ccccaactcc aacaccgacc    1440
accccgaccc ctaccccaac aggatctgac ctgggtaaaa agttgttaca ggcagcattg    1500
gagggccaac ttgacgaggt gcgcgagtta ctgaaagctg gtgcagatgt caacgcgaag    1560
gacattgaag gatatactcc gctgcacctt gccgcggctt tggggcatct tgagattgtg    1620
gaggtgcttc ttaaggcggg agctgatgtc aatgctaaag accaaatcgg gcgcacaccg    1680
ttacacttgg ctgcgtacaa aggtcactta gaaatcgtgg aagtgcttct gaaggctggc    1740
gctgatgtca acgcccaaga cattatcggc cagacaccgg cggacctggc agcgcaacgt    1800
gggcatcagg atattgctga agttctgcag aaggcagcag gctcgccgac tccgaccccg    1860
accaccccaa ctccaacacc gaccaccccg accctaccc caacaggatc tgacctgggt    1920
aaaaagttgt tattagctgc ggagcgcggg cagttagacg aagtgcgtat tctgctgaag    1980
gccggggccg acgttaacgc aaaggatcgt gcagagggtt acacccccct gcacatcgcc    2040
gcttatcaag gtcacttgga gattgttgag gtcttactga agcggggc cgacgtgaat     2100 gccaaagatc gctatggaaa acaccgttta cacttagcag ctatttcggg gcatctggag    2160
atcgtggaag tcctgttaaa ggctggtgcc gatgttaatg cacaagataa taaaggcagc    2220
actccagccg atctggccgc tgattatggg caccaggaca ttgctgaagt tctgcagaag    2280
gcagcaggct cgccaaccgg atcagatctg ggtcaaaagc tgttggaagc cgcgtgggcg    2340
ggtcaggacg atgaagtccg tgagctgctt aaagcaggag ccgacgtgaa cgcgaagaac    2400
tcacgcgggt ggacgccact tcacacggcc gcgcagacag tcaccttga aatctttgag     2460 gttcttctga aggcaggagc agacgttaac gccaaaaacg acaagcgcgt gactccgttg    2520
caccttgccg cagctctggg gcatttggag atcgttgagg tactgttgaa agcgggagca    2580
gatgttaatg ctcgcgacag ttgggggacg acaccagcag acctggccgc aaaatacgga    2640
caccaagaca ttgctgaagt tctgcaaaag gcagca                              2676
```

<210> SEQ ID NO 124
<211> LENGTH: 2631
<212> TYPE: DNA
<213> ORGANISM: Artificial Sequence
<220> FEATURE:
<223> OTHER INFORMATION: Nucleic acid encoding protein of SEQ ID NO 101

<400> SEQUENCE: 124

```
atgagaggat cgcatcacca tcaccatcac ggatccgacc tgggtaaaaa gctgctggag     60
gcagcgcgtg ccggtcaaga cgacgaggtt cgcgaattgc ttaaagcggg tgcagacgtc    120
aacgccaaag attatttctc tcatacccg ttgcatttag ccgcgcgtaa tggccatctg     180
aagatcgtcg aggtcctctt gaaggcaggc gcggatgtca atgcgaagga ttttgcgggc    240
aaaacgccgc tgcacttagc ggcggcggac ggtcatttag aaatcgttga agtcctgtta    300 aagcgggcg ccgatgtgaa tgcgcaggat attttcggta aaacgccggc ggacattgcg     360
gcagatgcgg gtcatgaaga tatcgcagaa gtcctgcaga aggcagcagg cagccctaca    420
cctacgccga ctacgcctac gccgactccg actaccccga ctccgacccc gaccggatca    480
```

-continued

```
gacctgggta aaaagctgct ggaggcagcg cgtgccggtc aagacgacga ggttcgcgaa      540
ttgcttaaag cgggtgcaga cgtcaacgcc aaagattatt tctctcatac cccgttgcat      600
ttagccgcgc gtaatggcca tctgaagatc gtcgaggtcc tcttgaaggc aggcgcggat      660
gtcaatgcga aggattttgc gggcaaaacg ccgctgcact tagcggcggc ggacggtcat      720
ttagaaatcg ttgaagtcct gttaaaagcg ggcgccgatg tgaatgcgca ggatattttc      780
ggtaaaacgc cggcggacat tgcggcagat gcgggtcatg aagatatcgc agaagtcctg      840
cagaaggcag caggctcgcc aacgccgacc cctacaacgc caaccccgac accaactaca      900
ccgaccccca caccaacggg atcagacctg ggtattaaac tgttgacagc cgcttacgac      960
gggcaattag acgaagtgcg tattctgctt aaagctggag ctgacgtgaa cgcgaaagac     1020
ttacgcggcc aaacgccttt acattacgcg gcgggactgg gccatcttga gattgttgag     1080
gtgcttctga aggcaggcgc ggatgtcaat gcaaaagacc tgcacggatg gacacctctt     1140
cacttagctg cttggtctgg gcatttggag attgtagagg ttttattgaa agcaggggcg     1200
gatgtgaatg cgcaagacgt agaaggagtc accccagctg acctggcagc ggttcaaggg     1260
catcaagaca ttgctgaagt tctgcagaag gcagcaggtt ccccgacccc tacgccaacg     1320
actccgaccc caactccaac gacccctacc ccgaccccga ccggatcaga cctgggtgtt     1380
aagctgttgc ttgcagccga gcgtgggcag cttgatgaag tacgcattct tcttaaagcg     1440
ggggctgatg tgaacgcgaa agatattgct gagggttaca caccgcttca cattgccgcc     1500
taccagggtc atctggagat tgttgaagta ttactgaaag cgggagcaga tgttaatgcc     1560
aaagatcgct atggaaaaac tcctttgcat ttagctgcaa tcgaggacca cctggaaatc     1620
gtcgaagtgt tattaaaagc tggagcggac gtaaacgcac aagataacaa gggctcaact     1680
cccgcggacc ttgccgcaga ttacggtcat caggacattg ctgaagttct gcagaaggca     1740
gcaggcagcc ccacgccaac tcctacaacc cccacaccta caccgacgac gccgacaccg     1800
actccaaccg gatcagacct gggtaaaaaa ttgcttgaag ccgcgttgga aggacaatta     1860
gacgaggtac gtgagctgtt aaaagcaggg gccgatgtga atgctaaaga ccaggaggga     1920
tacacccct  tgcacctggc tgccgcgttg ggccacttag agattgtaga ggttcttctt     1980
aaggcggggg cagacgtgaa tgcaaaggac caaattggac gtactccttt gcatctggca     2040
gcctataagg ggcacttgga gattgtcgag gtcttgttaa aggcgggtgc cgatgtaaat     2100
gcccaggaca tcattgggca gactccggca gatttggccg cccaacgtgg ccaccaagat     2160
attgctgaag ttctgcagaa ggcagcaggt tcgccgaccc caaccc ctac cactccaacg     2220
ccgacgccta ccactccaac accaacacca acgggatcag acctgggtca aaagctgttg     2280
gaagccgcgt gggcgggtca ggacgatgaa gtccgtgagc tgcttaaagc aggagccgac     2340
gtgaacgcga agaactcacg cgggtggacg ccacttcaca cggccgcgca gacaggtcac     2400
cttgaaatct ttgaggttct tctgaaggca ggagcagacg ttaacgccaa aaacgacaag     2460
cgcgtgactc cgttgcacct tgccgcagct ctggggcatt tggagatcgt tgaggtactg     2520
ttgaaagcgg gagcagatgt taatgctcgc gacagttggg ggacgacacc agcagacctg     2580
gccgcaaaat acggacacca agacattgct gaagttctgc agaaggcggc a              2631
```